US012529083B2

(12) United States Patent
Aharoni et al.

(10) Patent No.: US 12,529,083 B2
(45) Date of Patent: *Jan. 20, 2026

(54) CYP76AD1-BETA CLADE POLYNUCLEOTIDES, POLYPEPTIDES, AND METHODS FOR PRODUCING BETALAINS

(71) Applicant: YEDA RESEARCH AND DEVELOPMENT CO. LTD., Rehovot (IL)

(72) Inventors: Asaph Aharoni, Tel Aviv (IL); Guy Polturak, Rehovot (IL)

(73) Assignee: RADA RESEARCH AND DEVELOPMENT CO. LTD., Rehovot (IL)

(*) Notice: Subject to any disclaimer, the term of this patent is extended or adjusted under 35 U.S.C. 154(b) by 0 days.

This patent is subject to a terminal disclaimer.

(21) Appl. No.: 18/436,233

(22) Filed: Feb. 8, 2024

(65) Prior Publication Data

US 2024/0263202 A1 Aug. 8, 2024

Related U.S. Application Data

(63) Continuation of application No. 16/940,666, filed on Jul. 28, 2020, now Pat. No. 11,932,887, which is a continuation of application No. 15/758,372, filed as application No. PCT/IL2016/051010 on Sep. 11, 2016, now Pat. No. 10,767,201.

(30) Foreign Application Priority Data

Sep. 10, 2015 (IL) .......................................... 241462

(51) Int. Cl.

| | |
|---|---|
| ***C12P 13/22*** | (2006.01) |
| ***A23B 2/729*** | (2025.01) |
| ***A23B 2/762*** | (2025.01) |
| ***A23B 2/771*** | (2025.01) |
| ***A23L 5/46*** | (2016.01) |
| ***C07K 14/415*** | (2006.01) |
| ***C12N 9/02*** | (2006.01) |
| ***C12N 9/12*** | (2006.01) |
| ***C12P 13/04*** | (2006.01) |
| ***C12P 17/12*** | (2006.01) |
| ***C12P 19/02*** | (2006.01) |

(52) U.S. Cl.

CPC ............ *C12P 13/225* (2013.01); *A23B 2/729* (2025.01); *A23B 2/762* (2025.01); *A23B 2/771* (2025.01); *A23L 5/46* (2016.08); *C07K 14/415* (2013.01); *C12N 9/0083* (2013.01); *C12N 9/1205* (2013.01); *C12P 13/04* (2013.01); *C12P 17/12* (2013.01); *C12P 19/02* (2013.01); *C12Y 207/01095* (2013.01); *A23V 2002/00* (2013.01)

(58) Field of Classification Search

None

See application file for complete search history.

(56) References Cited

U.S. PATENT DOCUMENTS

| | | | | |
|---|---|---|---|---|
| 5,015,580 | A | 5/1991 | Christou et al. | |
| 5,464,764 | A | 11/1995 | Capecchi et al. | |
| 5,487,992 | A | 1/1996 | Capecchi et al. | |
| 5,538,880 | A | 7/1996 | Lundquist et al. | |
| 5,550,318 | A | 8/1996 | Adams et al. | |
| 5,591,616 | A | 1/1997 | Hiei et al. | |
| 5,635,055 | A | 6/1997 | Sweet et al. | |
| 5,661,017 | A | 8/1997 | Dunahay et al. | |
| 5,824,877 | A | 10/1998 | Hinchee et al. | |
| 5,932,447 | A | 8/1999 | Siegall | |
| 5,981,840 | A | 11/1999 | Zhao et al. | |
| 6,160,208 | A | 12/2000 | Lundquist et al. | |
| 6,384,301 | B1 | 5/2002 | Martinell et al. | |
| 6,399,861 | B1 | 6/2002 | Anderson et al. | |
| 6,403,865 | B1 | 6/2002 | Koziel et al. | |
| 7,001,772 | B2 | 2/2006 | Roessler et al. | |
| 8,802,925 | B2 | 8/2014 | Luo et al. | |
| 10,167,482 | B2 | 1/2019 | Coffin | |
| 10,457,918 | B2 * | 10/2019 | Martin | C12Y 114/16002 |
| 10,767,201 | B2 | 9/2020 | Aharoni et al. | |

(Continued)

FOREIGN PATENT DOCUMENTS

| | | | |
|---|---|---|---|
| CN | 102827852 | A * | 12/2012 |
| JP | 2015192669 | A | 11/2015 |

(Continued)

OTHER PUBLICATIONS

GenBank Accession No. P87064.1 (Version 1), Nov. 24, 2017.
GenBankAccession No. AB182643.1 (Version 1), Aug. 9, 2006.
GenBank Accession No. HQ656027.1 (Version 1), Jun. 3, 2012.

(Continued)

*Primary Examiner* — Hope A Robinson

(74) *Attorney, Agent, or Firm* — The Roy Gross Law Firm, LLC; Roy D. Gross

(57) ABSTRACT

The invention provides recombinant polynucleotides comprising a nucleic acid encoding a CYP76AD6 or related gene and their use for producing L-DOPA from tyrosine. The invention also provides recombinant polynucleotides comprising a nucleic acid encoding a CYP76AD1 and/or CYP76AD6, a nucleic acid encoding a DOPA 4,5-dioxygenase (DOD) enzyme, such as *Beta vulgaris* DODA1, and, in some cases, a nucleic acid encoding betalain related glucosyltransferase, such as *Mirabilis jalapa* gene cyclo-DOPA 5-O-glucosyltransferase (cDOPA5GT), and their use for producing betalains. Finally, the invention provides chimeric polypeptides, expression vectors, cells, compositions, and organisms, including plants, and their uses in various methods of the invention.

20 Claims, 46 Drawing Sheets

Specification includes a Sequence Listing.

(56) References Cited

U.S. PATENT DOCUMENTS

| | | | |
|---|---|---|---|
| 2001/0031724 | A1 | 10/2001 | Roemer et al. |
| 2003/0028913 | A1 | 2/2003 | Hein et al. |
| 2003/0049785 | A1 | 3/2003 | Schreier et al. |
| 2003/0196219 | A1 | 10/2003 | Zhang |
| 2004/0133937 | A1 | 7/2004 | Boudreau et al. |
| 2005/0158861 | A1 | 7/2005 | Song |
| 2007/0026506 | A1 | 2/2007 | Miele et al. |
| 2007/0079396 | A1 | 4/2007 | Malvar et al. |
| 2007/0264716 | A1 | 11/2007 | Boergel et al. |
| 2008/0194029 | A1 | 8/2008 | Hegerrnann et al. |
| 2008/0307541 | A1 | 12/2008 | Hsieh |
| 2009/0264320 | A1 | 10/2009 | Hsieh et al. |
| 2009/0325247 | A1 | 12/2009 | Kodama et al. |
| 2010/0159545 | A1 | 6/2010 | Kim et al. |
| 2010/0190223 | A1 | 7/2010 | Saito et al. |
| 2010/0199371 | A1 | 8/2010 | Castle et al. |
| 2011/0113514 | A1 | 5/2011 | Malvar et al. |
| 2011/0209247 | A1 | 8/2011 | Aharoni et al. |
| 2011/0251408 | A1 | 10/2011 | Mathews et al. |
| 2011/0300633 | A1 | 12/2011 | Adachi et al. |
| 2012/0034698 | A1 | 2/2012 | Maor |
| 2012/0094385 | A1 | 4/2012 | Kuehnle et al. |
| 2013/0130389 | A1 | 5/2013 | Adachi et al. |
| 2014/0051135 | A1 | 2/2014 | Mathews et al. |
| 2014/0170753 | A1 | 6/2014 | Zhang |
| 2014/0179006 | A1 | 6/2014 | Zhang |
| 2014/0179770 | A1 | 6/2014 | Zhang et al. |
| 2014/0186843 | A1 | 7/2014 | Zhang et al. |
| 2014/0186919 | A1 | 7/2014 | Zhang et al. |
| 2014/0234972 | A1 | 8/2014 | Zhang |
| 2014/0248702 | A1 | 9/2014 | Zhang et al. |
| 2014/0283166 | A1 | 9/2014 | Chomet et al. |
| 2015/0004704 | A1 | 1/2015 | Maor |
| 2015/0011008 | A1 | 1/2015 | Fukuzawa et al. |
| 2015/0082478 | A1 | 3/2015 | Cigan et al. |
| 2015/0184139 | A1 | 7/2015 | Zhang et al. |
| 2015/0356239 | A1 | 12/2015 | Zhang et al. |
| 2016/0074535 | A1 | 3/2016 | Ranganathan et al. |
| 2016/0177304 | A1 | 6/2016 | Collingwood |
| 2016/0243251 | A1 | 8/2016 | Blainey et al. |
| 2016/0251648 | A1 | 9/2016 | Wang et al. |
| 2020/0354759 | A1 | 11/2020 | Aharoni et al. |

FOREIGN PATENT DOCUMENTS

| | | | |
|---|---|---|---|
| JP | 2016182044 | A | 10/2016 |
| JP | 2018057354 | A | 4/2018 |
| WO | 2003/104451 | A2 | 12/2003 |
| WO | 2014/013056 | A1 | 1/2014 |
| WO | 2014/104878 | A1 | 7/2014 |
| WO | 2014/194190 | A1 | 12/2014 |
| WO | 2015/048707 | A2 | 4/2015 |
| WO | 2015/131101 | A1 | 9/2015 |
| WO | 2016/033230 | A1 | 3/2016 |
| WO | 2016/049364 | A2 | 3/2016 |
| WO | 2017/034971 | A1 | 3/2017 |
| WO | 2017/122189 | A1 | 7/2017 |
| WO | 2017/222779 | A1 | 12/2017 |

OTHER PUBLICATIONS

GenBank Accession No. HQ656023.1 (Version 1), Jun. 3, 2012.

GenBank Accession No. KT962274.1 (Version 1), Mar. 29, 2016.

Gengatharan et al. "Betalains: Natural plant pigments with potential application in functional foods" LWT-Food Science and Technology. Dec. 1, 2015 :64(2):645-9. DOI:10.1016/j.lwt.2015.06.052.

Gilboa, E. "Transfer and expression of cloned genes using retroviral vectors" BioTechniques. 1986;4:504-12.

Girod et al. "Biogenesis of betalains: purification and partial characterization of DOPA 4, 5-dioxygenase from Amanita muscaria" Phytochemistry. Jan. 1, 1991; 30(1):169-74. https://doi.org/10.1016/0031-9422(91)84119-D.

Grefen et al, "A ubiquitin-10 promoter-based vector set for fluorescent protein tagging facilitates temporal stability and native protein distribution in transient and stable expression studies", 2010, The Plant Journal, vol. 64, pp. 355-365. DOI: 10.1111/j.1365-313X.2010.04322.x.

Grotewold, E. "The genetics and biochemistry of floral pigments" / Annu. Rev. Plant Biol. Jun. 2, 2006;57:761-80. DOI: 10.1146/annurev.arplant.57.032905.105248.

Gurley et al. "Upstream sequences required for efficient expression of a soybean heal shock gene" Molecular and cellular biology. HI86 Feb. 1 ;6(2):559-65. DOI: 10.1128/mcb.6.2.559-565. 1986.

Haas et al. "De novo transcript sequence reconstruction from RNA-seq using the Trinity platform for reference generation and analysis" Nature protocols. Aug. 2013:8(8):1494. DOI: 10.1038/nprot.2013.084.

Hallmann, A., "Algal Transgenic and Biotechnology" Apr. 2007, Transgenic Plant Journal, vol. 1 (1), pp. 81-98.

Harris et al., "Betalain production is possible" in anthocyanin-producing plant species given the presence of DOPA-dioxygenase and L-Dopa, BMC Plant Biology, Mar. 12, 2016, vol. 12, No. 1, pp. 1-12. DOI: 10.1186/1471-2229-12-34.

Hatlestad et al., "The beet R locus encodes a new cytochrome P450 required for red betalain production", Nature Genetics, Jun. 3, 2012, vol. 44, No. 7, pp. 816-820. DOI: 10.1038/ng.2297.

Hatlestad et al. "The beet Y locus encodes an anthocyanin MYB-like protein that activates the betalain red pigment pathway" Nature Genetics. 20• Jan. 15, 47(1):92. https://doi.org/10.1038/ng.3163.

Heid et al., "Real Time Quantitative PCR", 1996 Genome Research, vol. 6, pp. 986-994. doi: 10.1101/gr.6.10.986.

Herbach et al. "Betalain stability and degradation-structural and chromatic aspects" Journal of food science. May 2006:71(4):R41-50. https://doi.org/10.1111/j.1750-3841.2006.00022.x.

Horsch et al., "Leaf disc transformation" 1988, Plant Molecular Biology Manual AS, pp. 1-9, Kluwer Academic Publishers, Dordrecht. https://doi.org/10.1007/978-94-009-0951-9_5.

Horsch et al. "A simple and general method for transferring genes into plants" Science. 1985;227(4691):1229-31. DOI: 10.1126/science.227.4691.1229.

PCT International Search Report and Written Opinion for International Application No. PCT/IL2016/051010, mailed Nov. 27, 2016, 9pp.

Isaacson et al, "Cloning of tangerine from Tomato Reveals a Carotenoid Isomerase Essential for the Production of B Carotene and Xanthophylls in Plants", 2002, Plant Ceil vol. 14, pp. 333-342. DOI: 10.1105/tpc.010303.

Jain et. al., "Betalain induction by L-DOPA application confers photoprotection to saline-exposed leaves of Disphyma austral" 2015, New Phytologist, vol. 207, pp. 1075-1083. DOI: 10.1111/nph.13409.

Jiang et al."Virus-induced gene silencing in ornamental plants", Methods Mol Biol. 2011;744:81-96. doi: 10.1007/978-1-61779-123-9_6. PMID: 21533687.

Katre et al. "Chemical modification of recombinant interleukin 2 by polyethylene glycol increases its potency in the murine Meth A sarcoma model" Proceedings or the National Academy or Sciences. Mar. 1, 1987 ;84(6):1487-91. DOI: 10.1073/pnas.84.6.1487.

Khan et al "Plant betalains: Chemistry and biochemistry" Phytochemistry. Sep. 1, 2015;117:267-95. https://doi.org/10.1016/j.phytochem.2015.06.008.

Khan, MI. "Plant betalains: Safety, antioxidant activity, clinical efficacy, and bioavailability" Comprehensive Reviews in Food Science and Food Safety. Mar. 2016; 15(2):316-30. DOI: 10.1111/1541-4337.12185.

Killan et al., "High-efficiency homologous recombination in the oil-producing alga *Nannochloropsis* sp." PNAS 2011, 108(52), pp. 21265-21269. DOI: 10.1073/pnas.1105861108.

Komari et al. "Advances in cereal gene transfer" Current opinion in plant biology, Apr. 1, 1998 :1 (2):rn1-5. DOI: 10.1016/s1369-5266(98)80019-8.

Min et al., "Overview on the biotechnological production of L-DOPA" 2015, Appl Microbial Biotechnol, vol. 99, pp. 575-584. doi: 10.1007/s00253-014-6215-4. Epub Nov. 30, 2014. PMID: 25432672.

Liu et al. "Virus-induced gene silencing in tomato" The Plant Journal. Sep. 2002;31 (6):777-86. DOI: 10.1046/j.1365-313x.2002.01394.x.

(56) References Cited

OTHER PUBLICATIONS

Livak et al "Analysis of relative gene expression data using real-time quantitative PCR and the 2 (-Delta Delta C(T)) method" Methods 25. Dec. 1, 2001;25(4):402-8. DOI: 10.1006/meth.2001.1262.
Lu et al. Virus-induced gene silencing in plants Methods 30. Aug. 1, 2003;30(4):296-303. DOI: 10.1016/s1046-2023(03)00037-9.
Martinez-Parra et al "Characterization of betacyanin oxidation catalyzed by a peroxidase from *Beta vulgaris* L. roots" Journal of agricultural and food chemistry. Aug. 20, 2001;49(8):4064-8. https://doi.org/10.1021/jf0013555.
McCormick S. "Transformation of tomato with Agrobacteriurn tumefaciens" In: Plant tissue culture manual . 1991 (pp. 311-319). Springer. Dordrecht.
Meissner et al. "A new model system for tomato genetics", 1997, Plant J., vol. 12, pp. 1465-1472. https://doi.org/10.1046/j.1365-313x.1997.12061465.x.
Georgiev et al. "Betalain production in plant in vitro systems" Acta Physiologiae Planlarurn. Sep. 2008;30(5):581-93. DOI 10.1007/s11738-008-0170-6.
Misra et al., "Extraction of bioactive principles from Mucuna pruriens seeds" 2007, Indian Journal of Biochemistry & Biophysics, vol. 44, pp. 56-60. PMID: 17385342.
Moreno et al. "Betalains in the era of global agri-food science, technology and nutritional health" Phytochemistry Reviews. Jul. 1, 2008;7(2):261-80. https://doi.org/10.1007/s11101-007-9084-y.
Mozo et al. "Factors affecting the rate of T-DNA transfer from Agrobacterium tumefaciens to Nicotiana glauca plant cells" Plant molecular biology. Sep. 1, 1992;19(6):1019-30. DOI: 10.1007/BF00040533.
Nagatsu et al. "L-dopa therapy for Parkinson's disease: past, present, and future" Parkinsonism & related disorders. . Jan. 2009 i; 15:83-8. DOI: 10.1016/S1353-8020(09)70004-5.
Nakatsu KA et al. "Genetic engineering of yellow betalain pigments beyond the species barrier" Scientific reports. Jun. 12, 2013:3: 1970. https://doi.org/10.1038/srep01970.
Perl et al. "Regulation of lysine synthesis in transgenic potato plants expressing a bacterial dihydrodipicolinate synthase in their chloroplasts" Plant molecular biology—Aug. 1, 1992;19(5):815-23. DOI: 10.1007/BF00027077.
Podevin et al., "Site-directed nucleases: a paradigm shift in predictable, knowledge-base plant breeding", Apr. 17, 2013, Trends in Biotechnology, Elsevier Publications, Cambridge, GB, vol. 31, No. 6, pp. 375-383. DOI: 10.1016/j.tibtech.2013.03.004.
Polturak et al. "Elucidation of the first committed step in betalain biosynthesis enables the heterologous engineering of betalain pigments in plants" New Phytologlst. Apr. 1, 2016:210(1 ):269-83. DOI: 10.1111/nph.13796.
Porta et al. "Use of viral replicons for tile expression of genes in plants" Molecular Biotechnology. Jun. 1, 1996;5(3):209. DOI: 10.1007/BF02900359.
Potrykus L, "Gene Transfer to Plants: Assessment of Published Approaches and Results" 1991, Annual Review Plant Physiol, Plant Mol. Biol, vol. 42, pp. 205-225. https://doi.org/10.1146/annurev.pp.42.060191.001225.
Pribat et al., "Nonflowering plants possess a unique folate-dependent phenylalanine hydroxylase that is localized in chloroplasts" The Plant Cell. Oct. 1, 2010:22(10):34 10-22. DOI: 10.1105/tpc.110.078824.
Qi , "Chapter 3: High efficient genome modification by designed zinc finger nuclease", Jan. 1, 2015, Advances in New Technology for Targeted Modification of Plant Genomes, Springer, pp. 39-53. DOI: 10.1007/978-1-4939-2556-8_3.
Qingzhu et al. "Transcriptomic analysis reveals key genes related to betalain biosynthesis in pulp coloration of Hylocereus polyrhizus". Frontiers in plant science. Jan. 5, 2016;6:1179. DOI: 10.3389/fpls.2015.01179.
Radakovits et al., "Genetic Engineering of Algae for Enhanced Biofuel Production" Eukaryotic Cell, Apr. 2010, vol. 9(4), pp. 486-501. doi: 10.1128/EC.00364-09.
Radakovits et al., "Draft genome sequence and genetic transformation of the oleaginous alga Nannochloropsis gaditana", Feb. 21, 2012, Nat Commun., 3: 686. https://doi.org/10.1038/ncomms1688.
Ramsden "Quantitative Drug Design", Chapter 17.2, F. Choplin Pergamon Press (1990).
Sambrook, Joseph et al. "Molecular cloning: a laboratory manual." Cold Spring Harbor Laboratory Press, Cold Spring Harbor, New York 2 (2001).
Sarrion-Perdigones et al., "Design and construction of multigenic constructs for plant biotechnology using the GoldenBraid cloning strategy" 2014, Methods Mol. Biol., vol. 1116, pp. 133-151. DOI: 10.1007/978-1-62703-764-8_10.
Sarrion-Perdigones et al., "GoldenBraid 2.0: A Comprehensive DNA Assembly Framework for Plant Synthetic Biology" 2013, Plant Physiology, vol. 162, pp. 1618-1631.
Sasaki et al., "Isolation and characterization of cDNAs encoding an enzyme with glucosyltransferase activity for cyclo-DOPA from four o'clocks and feather cockscombs" 2005, Plant and Cell Physiology, vol. 46, pp. 666-670. DOI: 10.1093/pcp/pci064.
Sasaki et al. "Detection of DOPA 4,5-Dioxygenase (DOD) Activity Using Recombinant Protein Prepared from *Escherichia coli* Cells Harboring cDNA Encoding DOD from Mirabilis jalapa", Plant and Cell Physiology, vol. 50, Issue 5, May 2009, pp. 1012-1016, https://doi.org/10.1093/pcp/pcp053.
Saudek et al., "A preliminary trial of the programmable implantable medication system for insulin delivery" New England Journal of Medicine. Aug. 31, 1989 ;321 (9):574-9. DOI: 10.1056/NEJM198908313210904.
Schiml et al., "The CRISPR/Cas system can be used as nuclease for in planta gene targeting and as paired nickases for directed mutagenesis in Arabidopsis resulting in heritable progeny", Nov. 11, 2014, The Plant Journal, vol. 80, No. 6, pp. 1139-1150. DOI: 10.1111/tpj.12704.
Sefton, CR (1987) "Critical Review" in Biomedical Engineering, vol. 14. Issue.3:201-40.
Sekiguchi et al., "In Vitro Synthesis of Betaxanthins Using Recombinant DOPA 4,5-Dioxygenase and Evaluation of Their Radical Scavenging Activities" 2010, Journal of Agricultural and Food Chemistry, vol. 58, pp. 12504-12509. DOI: 10.1021/jf1030086.
Sepulveda-Jimenez et al. "A red beet (*Beta vulgaris*) UDP-glucosyltransferase gene induced by wounding, bacterial infiltration and oxidative stress" Journal of experimental botany. Dec. 6, 2004;56(412):605-11. doi: 10.1093/jxb/eri036.
Hayut et al., "Targeted recombination between homologous chromosomes for precise breeding in tomato", May 26, 2017, Nature Communications, vol. 8, pp. 15605. DOI: 10.1038/ncomms15605.
Shimamoto et al., "Fertile transgenic rice plants regenerated from transformed protoplasts" Mar. 16, 1989, Nature, vol. 338, pp. 274-276. https://doi.org/10.1038/338274a0.
Singh et al., "Co-silencing of the Mirabilis antiviral protein (MAP) permits virus-induced gene silencing (VIGS) of other genes in Four O'Clock plants (*Mirabilis jalapa*)" The Journal of Horticulture Science and Biotechnology. Jan. 1, 2012, 87(4):334-40. https://doi.org/10.1080/14620316.2012.11512873.
Soares et al., "The role of L-DOPA in plants" Plant signaling & behavior. Apr. 2014 i ;9(4): pp. e28275-1-e28275-7. DOI: 10.4161/psb.28275.
Solomon et al., "Multicopper oxidases and oxygenases" 1996, Chemical Reviews, vol. 96, pp. 2563-2605. DOI: 10.1021/cr9500460.
Sparkes et al. "Rapid, transient expression of fluorescent fusion proteins in tobacco plants and generation of stably transformed plants" Nature protocols. Nov. 2006; 1(4):2019. https://doi.org/10.1038/nprot.2006.286.
Steiner et al. Tyrosinase involved in betalain biosynthesis of higher plants Planta. Mar. 1, 1999 ;208(1):114-24. https://doi.org/10.1007/s004250050541.
Steiner et al. "Assay for tyrosine hydroxylation activity of tyrosinase from betalain-forming plants and cell cultures" Analytical biochemistry. Jun. 15, 1996;238(1):72-5. DOI: 10.1006/abio.1996.0253.
Stintzing et al. "Betalains-emerging prospects for food scientists." Trends in Food Science & Technology. Oct. 1, 2007 ;18(10):514-25. DOI: 10.1016/j.tifs.2007.04.012.

(56) References Cited

OTHER PUBLICATIONS

Stintzing et al. "Analysis of betalains. Food colorants: Chemical and functional properties" 2008:507-20.
Stintzing et al. "Evaluation of colour properties and chemical quality parameters of cactus juices" European Food Research and Technology—Apr. 1, 2003 ;216(4):303-11. https://doi.org/10.1007/s00217-002-0657-0.
Stintzing et al. "Functional properties of anthocyanins and betalains in plants, food, and in human nutrition" Trends in food science & technology. . Jan. 1, 2004:15(1): 19-38. https://doi.org/10.1016/j.tifs.2003.07.004.
Strack et al. "Recent advances in betalain research" Phytochemistry. Feb. 1, 2003,62(3):247-69. DOI: 10.1016/s0031-9422(02)00564-2.
Sunnadeniya et al., Tyrosine Hydroxylation in Betalain Pigment Biosynthesis is Performed by Cytochrome P450 Enzymes in Beets (*Beta vulgaris*) Feb. 18, 2016, PloS One, 11 (2). DOI: 10.1371/journal.pone.0149417.
Supplementary European Search Report for European Application No. 16884828.1 dated Jan. 9, 2019.
Suzuki et al. "Transposon-mediated mutation of CYP76AD3 affects betalain synthesis and produces variegated flowers in four o'clock (*Mirabilis jalapa*)" Journal of plant physiology. Nov. 20-24 • 1 : 171(17): 1586-90. DOI: 10.1016/j.jplph.2014.07.010.
Takamatsu et al •Expression of bacterial chloramphenicol acetyltransferase gene in tobacco plants mediated by TMV-RNA The EMBO journal. Feb. 1, 1987;6(2):307-11. DOI: 10.1002/j.1460-2075.1987.tb04755.x.
Tamura et al. "MEGA6: molecular evolutionary genetics analysis version 6.0" Molecular biology and evolution. Oct. 16, 2013;30(12):2725-9. https://doi.org/10.1093/molbev/mst197.
Tanaka et al. "Biosynthesis of plant pigments: anthocyanins, betalains and carotenoids" The Plant Journal. May 2008;54(4):733-49. DOI: 10.1111/j.1365-313X.2008.03447.x.
Trenchard el al., "De novo production of the key branch point benzylisoquinoline alkaloid reticuline in yeast" 2015, Elsevier Metabolic Engineering, vol. 31, pp. 74-83. DOI: 10.1016/j.ymben.2015.06.010.
Tzin et al. "Expression of a bacterial feedback-insensitive 3-deoxy-d-arabino-heptulosonate 7-phosphate synthase of the shikimate pathway in *Arabidopsis elucidates* potential metabolic bottlenecks between primary and secondary metabolism" New Phytologist. Apr. 1, 2012;194(2):430-9. DOI: 10.1111/j.1469-8137.2012.04052.x.
Van Eck et al. "Eggplant (*Solanum melongena* L)" in Agrobacterium Protocols 2006 (pp. 439-448). Humana Press. DOI: 10.1385/1-59745-130-4:439.
Vogt T. "Substrate specificity and sequence analysis define a polyphyletic origin of betanidin 5-and 6-O-glucosyltransferase from Dorotheanthus bellidiformis" Planta. Jan. 1, 2002 ;214(3):492-5. DOI: 10.1007/s00425-001-0685-1.
Vogt et al. "Cloning and expression of a cDNA encoding betanidin 5-O-glucosyltransferase, a betanidin-and flavonoid-specific enzyme with high homology to inducible glucosyltransferases from the Solanaceae" The Plant Journal Sep. 1999;19(5):509-19. DOI: 10.1046/j.1365-313x.1999.00540.x.
Von Elbe et al. "Oxygen involvement in betanine degradation-Measurement of active oxygen species and oxidation reduction potentials" Food chemistry. Jan. 1, 1985 ;16(1):49-67. https://doi.org/10.1016/0308-8146(85)90019-6.
Weissbach and Weissbach, "Methods for Plant Molecular Biology" (Eds.), Chapters 23 and 24 pp. 355-401, 1988 Academic Press, inc., San Diego, California, article by Potrykus L et al., "Protoplasts: isolation, Culture, Plant Regeneration".
Weissbach and Weissbach, "Methods for Plant Molecular Biology." Selected Methods in Enzymology (USA) Section Viii: 421-463 (1988).
Williamson et al. "Botrytis cinerea: the cause of grey mould disease" Molecular plant pathology. Sep. 2007; 8(5):561-80. https://doi.org/10.1111/j.1364-3703.2007.00417.x.
Yamamoto et al. "Isolation and purification of tyrosine hydroxylase from callus cultures of Portulaca grandiflora" Plant and Cell Physiology. Sep. 15, 2001;42(9):969-75. https://doi.org/10.1093/pcp/pce125.
Zhang et al., "Anthocyanins Double the Shelf Life of Tomatoes by Delaying Over-ripening and Reducing Susceptibility to Gray Mold." 2013, Current Biology, vol. 23, pp. 1094-1100. https://doi.org/10.1016/j.cub.2013.04.072.
Zhong et al. "High-throughput illumina strand-specific RNA sequencing library preparation" Cold spring harbor protocols. 20-1 • 1 Aug. 1, 2011 (8):pdb-rot5652. DOI: 10.1101/pdb.prot5652.
Studier, F.W. "Use of T7 Rna polymerase to direct expression of cloned genes" Methods Enzymol . . . 1990:185:60-89. DOI: 10.1016/0076-6879(90)85008-c.
Brockington, S.F. et al. Beta vulgaris subsp. maritima isolate FVXD@8922 cytochrome P450 76AD1-like protein mRNA, partial cds, KR376381.1, GenBank, 1-2, 2015.
Abuchowski et al. "Reduction of plasma urate levels in the cockerel with polyethylene glycol-uricase" Journal of Pharmacology and Experimental Therapeutics. Nov. 1, 1981 ;219(2):352-4. PMID: 7288624.
Alberti et al. "A suite of Gateway® cloning vectors for high-throughput genetic analysis in *Saccharomyces cerevisiae*" Yeast Oct. 2007;24('10):913-9. doi: 10.1002/yea.1502. PMID: 17583893; PMCID: PMC2190539.
An, G. "High efficiency transformation of cultured tobacco cells" Plant physiology. Oct. 1, 1985 ;79(2):568-70. doi: 10.1104/pp.79.2.568.
Azeredo, H.M.C. "Betalains: properties, sources, applications. and stability—a review" 2009, International Journal of Food Science & Technology, vol. 44, pp. 2365-2376. https://doi.org/10.1111/j.1365-2621.2007.01668.x.
Bak et al. "Cytochromes P450" The *Arabidopsis* Book, American Society of Plant Biologists, 2011;9:e0144. doi: 10.1199/tab.0144. Epub Oct. 6, 2011. PMID: 22303269; PMCID: PMC3268508.
Baltes et al., "DNA Replicons for Plant Genome Engineering" Jan. 2014, The Plant Cell, vol. 26, pp. 151-163. https://doi.org/10.1105/tpc.113.119792.
Bates, G.W. "Plant transformation via protoplast electroporation" in Hall, R.D. (ed) Plant Cell Culture Protocols 1999 (pp. 359-366). Methods In Molecular Biology™, vol. 111. Humana Press. https://doi.org/10.1385/1-59259-583-9:359.
Beaudoin et al. "Benzylisoquinoline alkaloid biosynthesis in opium poppy" Planta. .Jul. 1, 2014 :240(1):19-32. https://doi.org/10.1007/s00425-014-2056-8.
Behera et al., "Analyses of Ca 2+ dynamics using a ubiquitin-10 promoter-driven Yellow Cameleon 3.6 indicator reveal reliable transgene expression and differences in cytoplasmic Ca 2+ responses in *Arabidopis* and rice (*Oryza saliva*) roots", New Phytologist, vol. 206, No. 2, Jan. 5, 2015, pp. 751-760. PMID: 25641067 DOI: 10.1111/nph.13250.
Belhaj et al., "Plant genome editing made easy: targeted mutagenesis in model and crop plants using the CRISPR/Cas system", 2013, Plant Methods, 9:39. https://doi.org/10.1186/1746-4811-9-39.
"Beta subsp. *Vulgaris geraniol* 8-hydroxylase-like (LOC104904803}, mRNA", Dec. 10, 2014, URL: https://www.ncbi.nlm.nih.gov/protein/731359838.
Bitter et al. "Expression and secretion vectors for yeast" In Methods in enzymology Jan. 1, 1987 (vol. 153, pp. 516-544). Academic Press. DOI: 10.1016/0076-6879(87)53076-2.
Booth et al. "The use of a 'universal' yeast expression vector to produce an antigenic protein of *Mycobacterium* ! eprae" Immunology letters. Sep. 1, 1988 ;19(1):65-9. DOI: 10.1016/0165-2478(88)90121-6.
Brisson et al "Expression of a bacterial gene in plants by using a viral vector" Nature. Aug. 1984;310(5977):511. https://doi.org/10.1038/310511a0.
Brockington et al, "Lineage-specific gene radiations underlie the evolution of novel betalain pigmentation in Caryophyllales" 2015, New Phytologist vol. 207, Issue 4, pp. 1170-1180. doi: 10.1111/nph.13441. Epub May 13, 2015. PMID: 25966996; PMCID: PMC4557044.

(56) References Cited

OTHER PUBLICATIONS

Broglie et al. "Light-regulated expression of a pea ribulose-1, 5-bisphosphate carboxylase small subunit gene in transformed plant cells" Science. May 25, 1984;224:838-44. DOI: 10.1126/science. 6719112.

Buchwald et al. "Long-term, continuous intravenous heparin administration by an implantable infusion pump in ambulatory patients with recurrent venous thrombosis" Surgery. Oct. 1, 1980 ;88(4):507-16. PMID: 7423373.

Christinet et al. "Characterization and functional identification of a novel plant 4,5-extradiol dioxygenase involved in betalain pigment biosynthesis in Portulaca grandiflora". Plant Physiology. Jan. 1, 2004; 134(1): 265-74. doi: 10.1104/ pp. 103.031914. PMID: 14730069; PMCID: PMC316306.

Brockington et al. "Complex pigment evolution in the Caryophyllales" New Phytologist. Jun. 2011:190(4):854-64. DOI: 10.1111/j. 1469-8137.2011.03687.x.

Clifford et al. "The potential benefits of red beetroot supplementation in health and disease" Nutrients. Apr. 2015:7(4):2801-22. doi: 10.3390/nu7042801. PMID: 25875121; PMCID: PMC4425174.

Conesa et al. "Blast2GO: a universal tool for annotation, visualization and analysis in functional genomics research". Bioinforrnatics. Aug. 4, 2005;21 (18):3674-6. DOI: 10.1093/bioinformatics/bti610.

Conner et al. Transformation and regeneration of Petunia In Petunia 2009 (pp. 395-409). Springer, New York, NY.

Coruzzi et al. "Tissue-specific and light-regulated expression of a pea nuclear gene encoding the small subunit of ribulose-1, 5-bisphosphate carboxylase" The EMBO journal. Aug. 1, 1984 ;3(8): 1671-9. DOI: 10.1002/j.1460-2075.1984.tb02031.x.

Database, "Cloning vector pNIGEL16, complete sequence.", retrieved from Database EMBL [Online], Apr. 7, 2009.

Deloache et al. "An enzyme-coupled biosensor enables (S)-reticuline production in yeast from glucose", 2015, Nat Chem Biol, vol. 11, pp. 465-471. https://doi.org/10.1038/nchembio.1816.

Dohm et al. "The genome of the recently domesticated crop plant sugar beet (*Beta vulgaris*)" Nature. Jan. 2014;505(7484):546. https://doi.org/10.1038/nature12817.

Enfissi et al., The regulation of carotenoid formation in tomato fruit 2016, Plant J., vol. 89, pp. 774-788. DOI: 10.1111/tpj.13428.

Esatbeyoglu et al."Betanin—A food colorant with biological activity" Molecular nutrition & food research Jan. 2015;59(i):36-47. DOI: 10.1002/mnfr.201400484.

Gandia-Herrero et al. "Biosynthesis of betalains: yellow and violet plant pigments" 2013, Trends in Plant Science, vol. 18, pp. 334-343. https://doi.org/10.1016/j.tplants.2013.01.003.

Gandia-Herrero et al. "Characterization of recombinant Beta vulgaris 4,5-DOPA-extradiol-dioxygenase active in the biosynthesis of betalains" 2012, Planta, vol. 236, pp. 91-100. DOI: 10.1007/s00425-012-1593-2.

Gandia-Herrero et al. "Betaxanthins as pigments responsible for visible fluorescence in flowers" Planta. Nov. 1, 2005 :222(4):586-93. DOI: 10.1007/s00425-005-0004-3.

Gandia-Herrero et al. "Purification and characterization of a latent polyphenol oxidase from beet root (*Beta vulgaris* L.)" Journal of Agricultural and Food Chemistry. Feb. 11, 2004 ;52(:3):609-15. DOI: 10.1021/jf034381m.

Gandia-Herrero et al. "Biological activities of plant pigments betalains" Critical reviews in food science and nutrition. Apr. 25, 2016;56(6):937-45. DOI: 10.1080/10408398.2012.740103.

Garbarino et al., "Expression of stress-responsive ubiquitin genes in potato tubers", Plant Molecular Biology, Springer, Dordrecht, NL, vol. 20, Jan. 1, 1992, pp. 235-244. DOI: 10.1007/BF00014491.

Gardella et aL "Expression of human parathyroid hormone-(1-84) in *Escherichia coli* as a factor X-cleavabie fusion protein" Journal of Biological Chemistry. Sep. 15, 1990;265(26): 15854-9. PMID: 2168424.

GenBank Accession No. AKI33834.1 (Version 1), Sep. 9, 2015.

GenBank Accession No. AKI33838.1 (Version 1), Sep. 9, 2015.

GenBank Accession No. AKI33835.1 (Version 1), Sep. 9, 2015.

GenBank Accession No. AKI33831.1 (Version 1), Sep. 9, 2015.

GenBank Accession No. AET43289.1 (Version 1), Jun. 3, 2012.

GenBank Accession No. AET43291.1 (Version 1), Jun. 3, 2012.

GenBank Accession No. AET43292.1 (Version 1), Jun. 3, 2012.

GenBank Accession No. AGI78466.1 (Version 1), Apr. 14, 2013.

GenBank Accession No. JC233128.1 (Version 1), Feb. 3, 2014.

GenBankAccession No. HQ003815.1 (Version 1), Dec. 5, 2010.

GenBank Accession No. AJ580598.1 (Version 1), Feb. 3, 2011.

GenBank Accession No. AB435372.1 (Version 1), May 20, 2009.

GenBank Accession No. A8435373.1 (Version 1), May 20, 2009.

Clemente T. "Nicotiana (*Nicotiana tobaccum, Nicotiana bentharniana*)" In: Wang, K. (ed.) Agrobacterium Protocols. Methods in Molecular Biology, 2006, vol. 343. Humana Press. https://doi.org/10.1385/1-59745-130-4:143-154. Humana Press, Totowa, NJ.

Finer et al. "Particle bombardment mediated transformation" In: Hammond, J., McGarvey, P., Yusibov, V. (eds) Plant Biotechnology. Current Topics in Microbiology and Immunology, 2000, vol. 240. Springer, Berlin, Heidelberg. https://doi.org/10.1007/978-3-642-60234-4_3.

* cited by examiner pX11

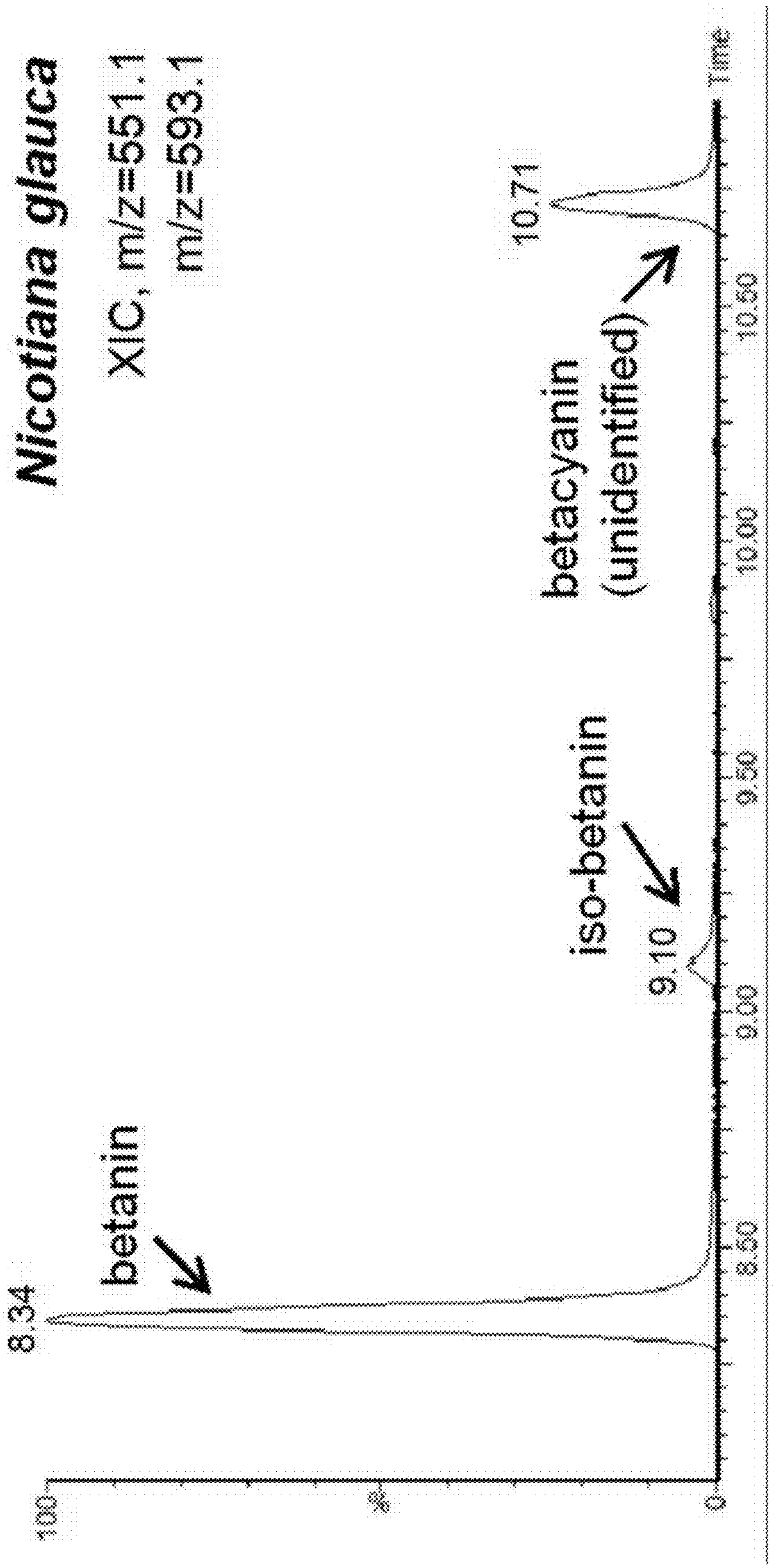
Figure 11B1

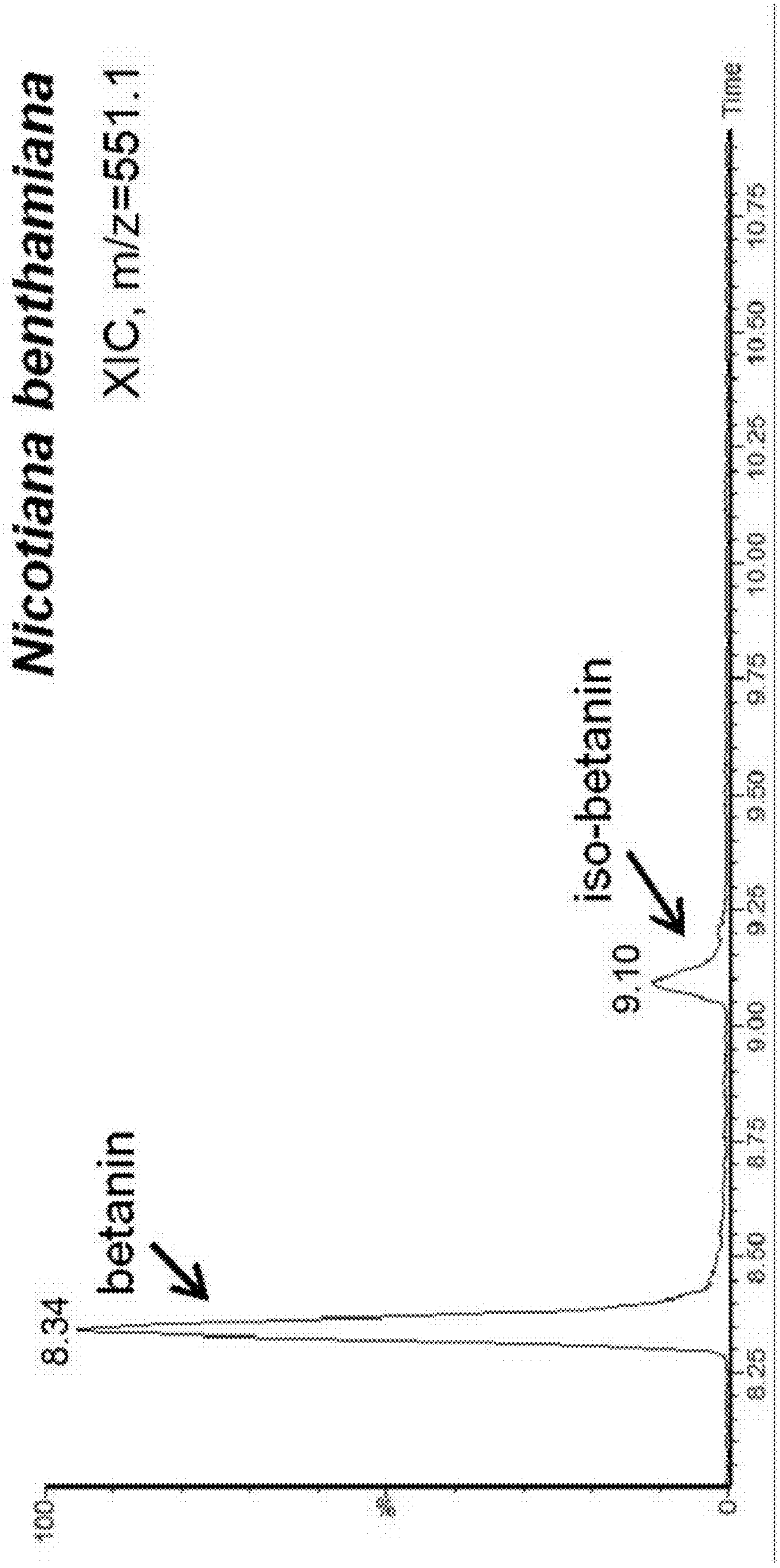
Figure 11B2

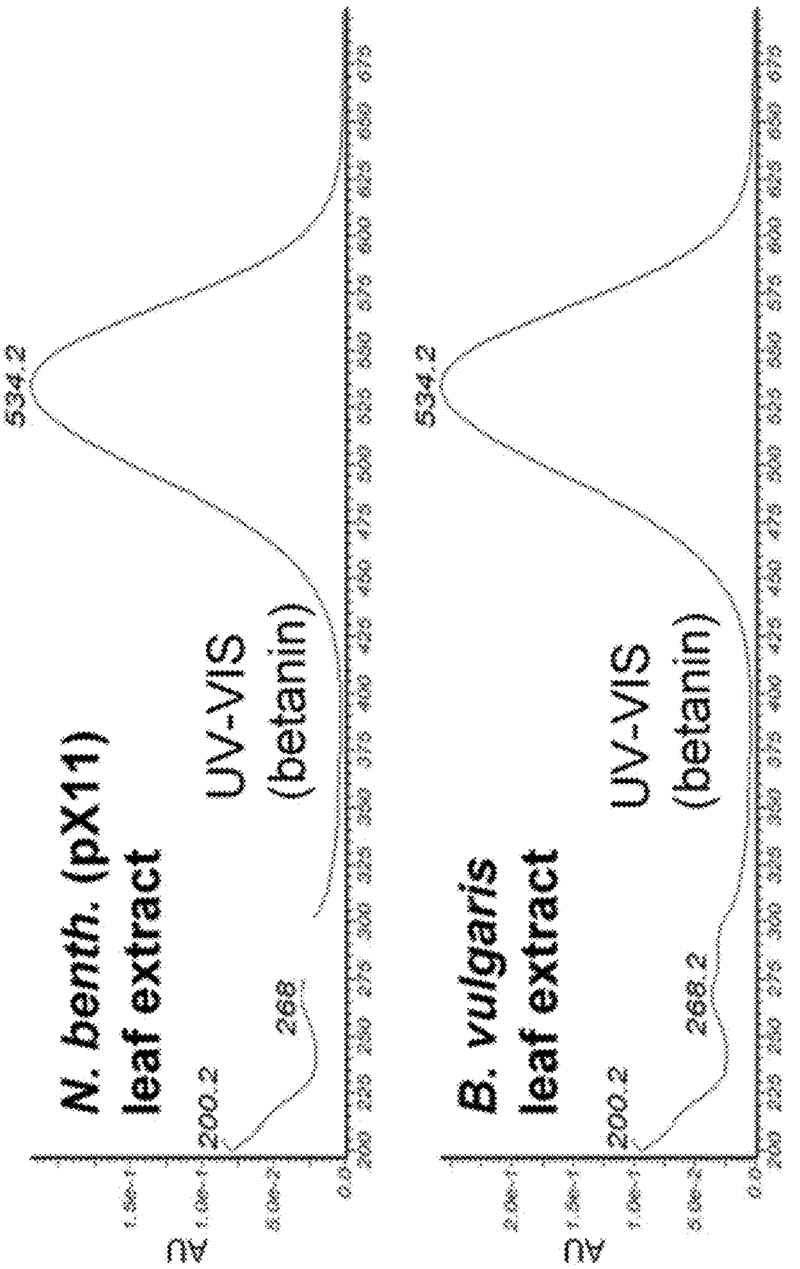
Figure 12A1

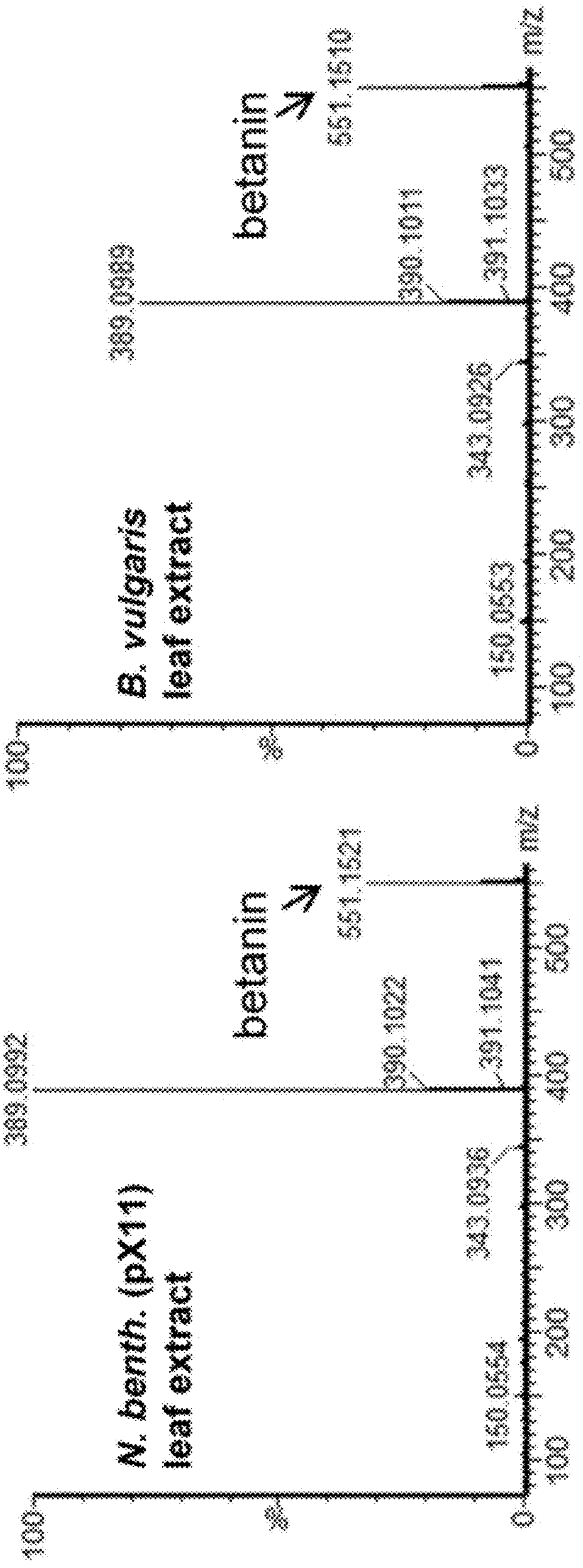
Figure 12A2

Figure 16A
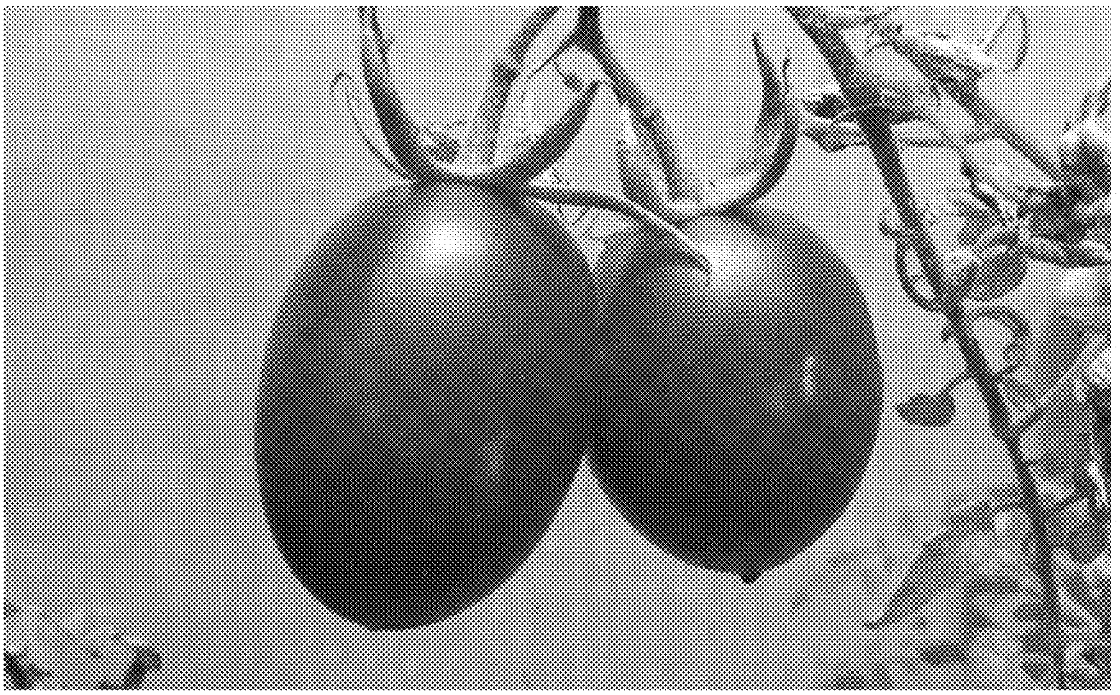
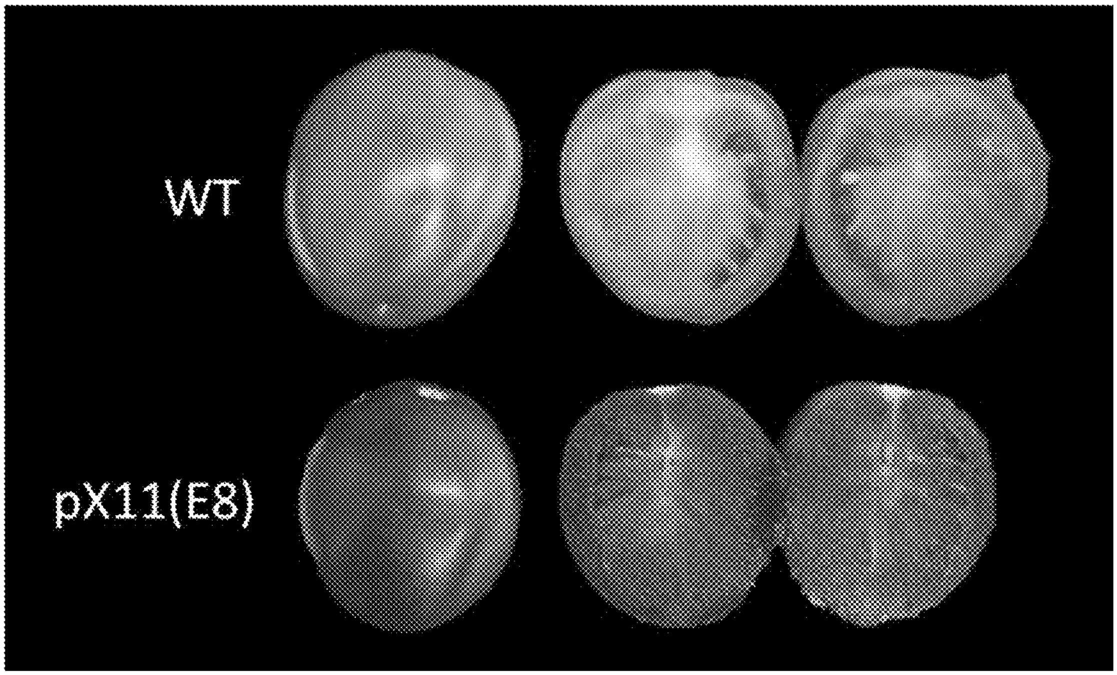
Figure 16B

B

400mM mannitol (day 21)

SEQUENCE LISTING

```
Sequence total quantity: 86
SEQ ID NO: 1          moltype = DNA  length = 1901
FEATURE               Location/Qualifiers
source                1..1901
                      mol_type = other DNA
                      organism = Mirabilis jalapa
SEQUENCE: 1
cttcaaatcc tcccacgtat atatcaacaa aaaccaaaaa catcatctca ttacaataat  60
ggagtatcat cttctcttcc ttctcctcct gccgatcatc cttatcttcg tgttcctcaa  120
tcacaagccc aagcaaacca aactcgaacc accaggacca cgtccatggc ccatcatagg  180
ccacaccaac ctcgtcggct ccaaacctca tcagtccatt gccaaactag ctcatattta  240
cggtcccata atgtcactta agctagggag aatcactact attgtcatat cttcccctga  300
agcagccaaa gacttgttcc tgaaacatga ccttactttc tcaagtaggc aagttcctca  360
cgcttcaacc gctacaaacc atgacaaact atccatggtt tggctccctg tatgtcccaa  420
atggcgctat cttagaaaga tcgcggccat ccaactattc accaaccaac aacttgatgg  480
tggtcaggta ctaaggcgta agaaagtgga cgagttgatc caatttgtga ctcgttgtag  540
taaacaaggg caagtcattg atattggaga ggctgttttt attactactc ttaacttaat  600
gtcaaatacc tttttttcca aggatttgtg tagttatggt ttggccgaat cacgagagtt  660
taaggatcta ttttgggagt tcatgaaagt gctagcgagt cctaatgttt ctgattattt  720
tccatggtta agatggttgg atttgcaagg catcaagaga agaagcgagg gttgttatcg  780
```

```
caagatgttg ggttttttg gggagattat tgatcagaga ttgagagatc caatgtcatg  840
taagaacgat gtattggaca ctctactcaa acttgtcgac caaaaagagt tgagctttga  900
ggatgtcaaa catatgcttg tggatttgtt tgttgcaggg acggatacaa cttcgaacac  960
attggaatgg acaatggtag aacttttacg ccaccctaac atattgacta aagcacaaac  1020
tgaactcagc caagtcatag gcaaggacaa gttagtccaa gaatcatgta tcaccaagtt  1080
gccatatctt caatcaatat tgaaagaaac attcaggttg cacccaccga ctcctttttt  1140
acttccacac aaagcaatcg agaacgttga actatgcaac tatcacatac ctaaaggtgc  1200
tcaagtttgg gtgaatgtgt ggtctattgg ccgcgatccc aacatttggt caagcccgga  1260
cttattttcc ccagagagat ttttaggtac cgacattgat ataaaaggta accatttcga  1320
gctcatacca ttcggagcag gaagaaggat ttgccccggg ttgtcactag cttacaggat  1380
gcttcatttg attttggcca ctctccttca ttcattcaat tggaaccttc ctaatgacgt  1440
atgtccggaa aatatggata ttgaagaaaa atttgggatt acacttcaaa agatcatgcc  1500
actcaaagtc ataccaagct ctaggtgtct ggatcacgac aactaactgg tgttaatctt  1560
ttacaacata ttgaatgata tatatcacgt taaggtacat gcgtctagat gcagaaactt  1620
gcatacgttt ccttttcaat aaagtcttgc atatgtatgg tttatagggt gatgtaattt  1680
cttgtttgtt tttacttaag tttataagac attttttttt tttttttatc gatgctctta  1740
ctcattaaaa tattggaaca tatacaaaat tttatatgtt ttagataaaa ttatacaggt  1800
tttaatttta ggaacttacc acttgttcac actgcgagac ttaaatagtc aaaatagaaa  1860
atacacacta ttaaaaagta ctcactattt atcaaattta t                      1901

SEQ ID NO: 2           moltype = DNA  length = 1663
FEATURE                Location/Qualifiers
source                 1..1663
                       mol_type = other DNA
                       organism = Mirabilis jalapa
SEQUENCE: 2
cctcacctcc ataacaaaga aatgaccgcc attaaaatga acaccaatgg tgaaggtgaa  60
acacaacata tactaatgat acctttcatg gcgcaagggc atttacgtcc tttccttgag  120
cttgctatgt ttctatataa acgaagtcat gttatcatta ctcttcttac taccccgctc  180
aatgcgggtt tcctacgaca tctccttcac caccatagct attctagctc ggggatcaga  240
attgtcgagt tacctttcaa ctcaaccaat catggtcttc cacctggcat tgaaaacact  300
gataaactta cactcccact tgtagtatca ctttttcatt caaccatttc tcttgaccct  360
caccttagag attatatttc ccgccatttc tcccctgcgc gccctcctct gtgtgtcata  420
catgatgtgt tccttggttg ggttgatcaa gttgctaaag acgtgggctc aactggtgtt  480
gtttttacta cgggtggcgc gtatggtaca agcgcatatg tgtccatttg gaatgatctg  540
cctcaccaga attactctga tgatcaagag tttccgcttc ctggtttccc ggagaatcat  600
aaattccgac gttctcaact tcatcggttt ctgaggtatg ccgatggatc agatgattgg  660
tcgaaatatt tccaaccgca attgaggcaa tcaatgaaga gttttggatg gctatgtaat  720
tcagttgagg aaatcgaaac acttgggttt agtatcctca ggaactacac taaactaccc  780
atttggggta ttggaccgtt gatagcttca cctgtacaac attcatcatc tgataataac  840
agtactggtg ccgagtttgt tcaatggttg agcttgaaag aaccagattc tgtattatac  900
atctcatttg gatcacagaa cacaatttca ccaacccaga tgatggaact agcagccggt  960
ttggagtcaa gtgagaagcc gtttttgtgg gtgattcgag caccatttgg gttcgatatc  1020
aatgaggaaa tgagaccaga atggctacca gagggattcg aggagcgaat gaaggtgaaa  1080
aaacaaggaa agttggtgta taagttggga ccacagttgg agatacttaa ccatgagtca  1140
atcggagggt tcttaactca ttgtgggtgg aattcgatcc ttgagtcact tcgagaaggt  1200
gtgcctatgt tagggtggcc attggcagcc gaacaagctt ataatttgaa gtatttggag  1260
gacgaaatgg gggttgcagt cgagttagcg aggggattgg aaggagagat aagtaaagag  1320
aaagtgaaga gaattgtgga gatgatttta gagagaaatg aaggaagtaa aggatgggaa  1380
atgaaaaata gagcagtaga aatggggaag aaacttaaag acgctgtcaa tgaggagaag  1440
gaactgaagg gttcttctgt taaggcaata gatgatttct tagatgcggt catgcaagct  1500
aagttggaac cttctcttca ataataagat cgatagttta tctcgtctca gagactcaaa  1560
caattgacta ctaggatgat cagaaagaga gttatgttca gtgttctgtt attatgcaag  1620
acttcaataa taacagaaaa attcgtgatt agattcataa ctt                    1663

SEQ ID NO: 3           moltype = DNA  length = 1005
FEATURE                Location/Qualifiers
source                 1..1005
                       mol_type = other DNA
                       organism = Mirabilis jalapa
SEQUENCE: 3
atgaaaggaa catactatat aaatcatggt gatccactaa tgtacttaaa aaaacatata  60
aaactaaggc aattcttaga aggatggcaa gaaaatgttg ttattgaaaa accaaagagt  120
atacttatca tttctgctca ttgggatact aatgtaccta ctgtcaactt tgttgaacat  180
tgtgatacta ttcatgattt tgatgactat cctgatcctt tgtaccagat acaatatcga  240
gcaccgggag caccaaattt agcaaaaaag gtggaagagt tactaaaaga gtcaggaatg  300
gaatgtgaga tagatacaaa gagaggactc gatcatgcag catggtttcc actaatgttt  360
atgtatcctg aagctaatat tcctatttgt gagctctcag tccaaccaag caaagatggg  420
atccaccact ataatgttgg gaaagctctt tctcctcttt tgcaacaagg tgttctcatc  480
attggctctg gtggtactgt tcatccttct gatgatactc ctcattgtcc caatggtgtt  540
gctccttggg ctattgagtt tgataactgg cttgaagatg ctcttcttag tggaaggtat  600
gaagatgtga acaacttcaa gaaattggca ccaaattggg agatatctca tccaggacaa  660
gaacatttgt accctttgca tgtggcatta ggggctgctg gcaaaaatcc aaagacacaa  720
cttattcatc gaagctgggc tgccaatggt gtctttggat attccaccta caacttcact  780
cccaccactc aaaaaactga ttaaaacttc ttttatatat ctcctattct tgctttattt  840
cttccttgtt caattgtttt atttatgttg taatattatg taaaatttgc ctaaattggg  900
ctaccggtgt attatactat gactaacatt tgatatagtt gctccgacta ctatgtcaaa  960
gctgtaaggt gtttgatcat tgtgtaatcg aaaaatgttg gattc                  1005
```

```
SEQ ID NO: 4            moltype = DNA  length = 1680
FEATURE                 Location/Qualifiers
source                  1..1680
                        mol_type = other DNA
                        organism = Mirabilis jalapa
SEQUENCE: 4
aaagcataca atgaccacca gcaatcatta aacaagagtt aacactgtca ctcatctaat  60
tttcttcaaa acactatttc ttctctcatc tctttaagta gttatttatt taattttgat  120
catcataata tggatttctt aacccttgtc atgatattat ctattatctt cttcttttac  180
aatctattaa aaatgaaatt cactacccat tcagatgccc aacttcctcc aggacctaaa  240
ccaatgccaa tattcggtaa tatcttcgaa ctaggtgaaa aacctcaccg atcatttgct  300
aacttagcaa aaacacacgg accactaatg tcgttaaggt taggaagtgt caccaccatt  360
gtcgtctcct cggcagaggt tgctaaagaa atgttcctta aaaatgacca gtcccttgca  420
gatagaagtg tccctaattc tgtaacggca ggtgaccatc acaagctaac catgtcatgg  480
ttgcctgtct ctccaaaatg gaaaaatttc cgaaaaatca cagccgttca tttgctttct  540
cctcaaaggc ttgatgcttg ccatgcactt agacatgcca aggtcaaaca actctatgaa  600
tatgttcaag agtgtgccct aaaaggagaa gcagttgata ttggcaaggc cgcatttacc  660
acttcactta atctattatc caatttgttc ttttcggttg agttagctaa tcatacttct  720
aatacttccc aagagtttaa acaacttata tgggatataa tggaagatat tggaaagcct  780
aactatgctg attattttcc tttacttaaa tatgttgatc cctctggcat acgacgtcgt  840
ttagcggcta attttgataa acttattgat gtatttcaaa gctttatctc caaaaggtta  900
tcatctgctt attctagtgc aacaagtctc gatgatgtgc ttgatgttct tctcaaactc  960
ctcaaggaaa aggagcttaa tatgggtgag attaatcatc ttcttgtgga catatttgat  1020
gcaggtacag acacaacatc aaatacattc gaatgggcaa tggcagaact aatgaggaac  1080
ccaataatga tgaaaagagc tcaaaatgag atagcattag tattaggcaa agataatgcc  1140
actattcaag aatctgatat agcaaacatg ccttatctac aagcaattat caaagaaaca  1200
ttacgtttac atcctccaac tgtctttcta ttgccacgaa aagccattac taatgttaag  1260
ctatatggtt atattgtccc aaaaaatgca cagatacttg ttaacttgtg ggccattggt  1320
cgcgaccccca aggtctggaa gaaccctaat gagttcttac ctgataggtt tttgaattct  1380
gatattgatg tcaaaggtcg agattttggg ttgttgcctt ttggtgcagg gagaaggata  1440
tgtcctggta tgaacttggc ttataggatg ttaactttga tgttggcaac tcttcttcaa  1500
tcttttgatt ggaagcttcc tcatcggaat agtcctctgg atttggatat ggatgagaaa  1560
tttggtatcg ctttacaaaa gactaaacca cttgagatta ttcctcttat taaatattga  1620
tgttttatat gttgtattat tattgcaatt gtttaaacat ctttcttatt attttggttg  1680

SEQ ID NO: 5            moltype = DNA  length = 749
FEATURE                 Location/Qualifiers
source                  1..749
                        mol_type = other DNA
                        organism = Mirabilis jalapa
SEQUENCE: 5
tcgatgtcac caatttcccc tatggacgtc caaaccacat tcccaaagca actagactca  60
gtgattcgaa ccaaggtggc aaggccagca aaaaaaagga accaagaaga gaagaagaaa  120
gaagaagaga tacttgtgat agagttagaa gagctaaaac aaaacgagta cgtcaaattt  180
gatgtgtaca taaatgatga ttatgattac gagaataaga atgacggcgt gacgaggcca  240
acggaaaaat atgcagggag tttcgtgagt ttggcatcat cgggacaggg aatggagagc  300
aagaagagtg ggttgagatt ggcgttgacc aagttgatcg atgaaattgg tgctgatggt  360
gatgacttct tagatgtggt gctagtggct aaagctggga aaggtggtgt tgttataaat  420
gacgtcaaga ttgagttcct tgcttgattt agttaagtat tagtatggta gtggttgatg  480
tattgccttt taatttgtgt acaagttaca actttatttg caattcacca cttgttttta  540
tttgtatatg agtttctggt ttatctcaat atttagtcat ggtgttactg ttttatggtg  600
tttcctcacg tatctaagaa aaaataacaa tagatattgg aattatcatg aattgtgcgc  660
ccatcactgg tggtttgaaa aagaaagaca ataaaaataa gaaaaaatta taaaaaaaat  720
tctataatat atttattttt ttaaaaaaa                                  749

SEQ ID NO: 6            moltype = DNA  length = 2176
FEATURE                 Location/Qualifiers
source                  1..2176
                        mol_type = other DNA
                        organism = Mirabilis jalapa
SEQUENCE: 6
catcccactt ccattccgac aaccaactca accaccatca tcaaccctcc tcacaacaac  60
ccccttctct ctcacctttc tccgatcaat cgccgccgtt cattccgcca cctttcaccc  120
aaactctcca tccgaaacaa ccaacaatcc accaacaacg accctctttt cgacccatca  180
aaactcgacc gaagaaacat ccttatcggg agtggtctcg ccggcatcta cggcggagcc  240
accactctcg gaggtaaccc cgccctagct gctcccccgc tccctgacgt caaaacatgc  300
aacctcacgt ccacctccgg tgggggccct gaggggctcg aatgttgccc accctcattc  360
agaaacatcg tagatttcaa ccctcgaaac tacgccggcc cggcactccg ggtcagacgt  420
ccggctcatg aagtcgcgaa tgacccggag tacatggcta aatttaaaga agcaataaga  480
agaatgagag cacttcctag atctgatcca agaaactttg tacaacaagc taatgttcat  540
tgtgcttatt gtgatggctc ataccgtcaa gataaacaca gtgacgtcga ttacacggtt  600
catttttctt ggttattctt cccattccat agagtttacc tctatttctt cgaacgtatc  660
ttggggaaat tgatcgatga tccaactttc gcaatcccat actggaactg ggatcatcca  720
gatggtatga gaatgccaac tatttacacg aacccagatt caccattgtt tgatgctctt  780
agagatccgg ctcatcagcc gcctagagtt gcagatctta actacaatga tgttgatact  840
gatataagtc cagagttgca gattgagtat aacttaagag tgatgaatta tcaaatgaca  900
aggaataata aacctgagtt gtttatgggt gcacctttgt accctggtaa tgctgctgaa  960
gagaagggta ctggtgcact tgaaaatgtt cctcataatt tgcttcatgt ttgggttggt  1020
gatcgtaatg acgatccatt tcacaggaac atgggatcct tcttctcggc tggaagagac  1080
```

```
ccaatattct acggtcacca tgcaaacgta gacagaatgt ggtacatttg gaataccaag  1140
cttagccatc aaaatttcac tacaaaagat tggctagaca cttactttgt tctctacgac  1200
gagaacaaac aagctgtcag gattcgaact tcagactgtc tggatgttga aaaacaactc  1260
ggctacacct attcgaacca agacttaccc tggttagact caacgactgg aggaggagcc  1320
attgaaccaa ccccaccccc accatctggt gtggccgagt tcccacaagt tctagacaag  1380
gttatcagaa ccagggtggc tcgacccaag acctcaaggt cacaacagga aaaggaagtt  1440
gctacagaag tgctgaaagt gtctgtcaac attgataaag aagataatta cattaagttt  1500
gatgttttta tcaatgatgg tcaggatttt gagaccggtg gtcagactga tatcggtaag  1560
tcttatgcag gaagctttac tagcgtccct cataagacta gaaaaggtgc taggatggat  1620
atgaaccgcc gggtttcact tcccttgact gagattttgg agaatttggg tgctgatggt  1680
gatgattata ttgatgttgc tattgttcct aaggctggtt taggtaatgt caccattact  1740
gctgttaagg ttgattatat tatttgatta gtcactaatc aagtaattaa taaattaaaa  1800
ttactaccat atataataat tagttatgat gagtgtgtta atgtagtaag tggtattatt  1860
attaagtgag taaaataaaa agcgaccatg cattatgatt catgattgtg ggagtcgtgt  1920
ttcatgcatg gtagtgatgg gatgttatcg tatcttttgg tgcgctttaa atctgtttcc  1980
actttattat tttttttttt tccaagtatt tccactttat tgttatgact tgtcaaaagt  2040
tggtattata taagtttgtc gttctatatt aaaattattt tttaatgttt tttttttattt  2100
ttacttttag taaagttgtt atcaaggaca tgatattttt gaaggaatga agacaaacat  2160
taatataact gtaagg                                                  2176

SEQ ID NO: 7           moltype = DNA  length = 282
FEATURE                Location/Qualifiers
source                 1..282
                       mol_type = other DNA
                       organism = Mirabilis jalapa
SEQUENCE: 7
caaacaagct gtcaggattc gaacctctga ttgcctcgat gttgaaaacc aactcggcta  60
cacctatgag gaccaagatt tgccatggtt agactcatct gtcggaaaag acgcccctat  120
acccaccaaa ccccaaccat ctgatgtggc cgagttccca caagtcctag acaaagttat  180
ccgtactaga gtggctcgac ccaaggccac aaggtccgag caagaaaagc aggttgctgc  240
agaagccctg aaagtatccg tcaacattga taaagaagat aa                     282

SEQ ID NO: 8           moltype = DNA  length = 1016
FEATURE                Location/Qualifiers
source                 1..1016
                       mol_type = other DNA
                       organism = Mirabilis jalapa
SEQUENCE: 8
acggaggcgc ataaaaaaat ggttgtatta ttttgctatt gatatctgct gggaaaacaa  60
ggagtagtgt attcggattc tcacatcccc gaaatcgatc aacgtcttta tttgggcggt  120
ttaaagcaag gaatatctga ggaattgcta tcagtgactc atttgtgtgt caaagcatat  180
caaccagcta taggaggtgc taccgtgggt aacttgaatt ctttaggccc cttttgaatg  240
tcacgaaaga gatgtgtcct tattggtaaa ctgtttgatt tctattgttg agaagtcaaa  300
acctggacat tagacaacca cttgtattat ttgactgttt ccgattaatc ctactaatga  360
cggtctctct cccttctcct ataacgacca tcaacattcc cgttgccact agaaacacta  420
aaccactccc taagccattg atgctttatc aatcctgcca ccctaccttg aaaatttcat  480
gccaagcctc ccacaacctc aaggtgaatc cacaacgccg agatctccta attgggctag  540
ccaccctatg tgggaccccc accttgtgtg tcccactagt ctcagcagca ccagcagcag  600
caacccccttt tccacagctg ttggactccg tggttcggac cagggtggca aggccagcaa  660
aagaaagaag ccaaagagag aaggatgatg aagaggaggt gcttgtggtt agcttggagc  720
aactaaggga agatgaatat gtcaaatttg atgtgtacat caatgatgat tatgactttg  780
agaataagaa tgatgggctg acaaggccaa caaaagaata tgcggggagt tattctagcc  840
tgccatctcc aaggcgactc atggagagca agaagattgc gttgaagctg gcgttgacac  900
agctgattga tgacattggt gccgatagcg atgactatat tgacgtggtg ctggtgccta  960
aagcaggaaa aggtgctctt gttgtaaaaa atgtcaagat tgagttcctt gcttga      1016

SEQ ID NO: 9           moltype = DNA  length = 1922
FEATURE                Location/Qualifiers
source                 1..1922
                       mol_type = other DNA
                       organism = Beta vulgaris
SEQUENCE: 9
cagtcattta aaatcctgta aattactcac atacataacc aaattaaagt tgccgccgta  60
ctgatttcca aaggtcctac atctatcaat ggagtattac accataacgc tattattcat  120
catcttcaca atatcaatat tcggtacaaa aattttgagc aagtccaaac ttcctccagg  180
accaacacca tggcctatca taggcaacat cctcgagcta ggcaagttac ctcatcaggc  240
agttgacaag ctctcaaaaa cctatggccc tatattatct ctcaaactcg gaagcatcac  300
tacaatagta atatcatccc ctgaaatcgt taaagaaatg ttcctcgagc acgacttagc  360
cctttctagt aggccttccc cggatgcttc gagggtggga aaccataaca aattttccat  420
tgtttggctc ccagtgtccc ccaaatggcg ggaccttaga aaaattgcta ctatccaatt  480
gtttactact caacgcctag attctagcca agaactacgg cagatcaagg tgaacgagct  540
ggttgattat gtacgacagt gttgtgaaaa gggtctacct gttgatgttg gtaaagccgg  600
gtttactacc acgttaaata tgttgtctaa cacgtttttc tccatggatt tggctagcca  660
tgcttcttcg aattcgcaag agttcaagga tcttgtttgg agtcttttgg aagagggtgc  720
aaagcctaat gtgtcggatt ttttcccgat agttagagaa ttggatttgc agggagtatc  780
gaaaaataga agggtgcaca tgaagaagct aatgggaatt ttcgaggaaa tcattgatgg  840
aaggttgaca aagttaaagg atgtgaagga tgatgttcta agtactttac tcaaacttgt  900
taaggatgaa gaattgaacc ttgacgacgt caaacatatg ctcatggatt tatttttagc  960
gggaacagat acaacctcta tcacattgga gtgggcgatg acagaattac ttcgcaatcc  1020
```

```
agaaaagatg gaaaaggttc aaattgagtt ggacaaagta cttggcaagg atagttctct  1080
gcaagagtca atgatctcaa aattaccata tattcaagca atagtgaaag aaacattaag  1140
attacaccca ccaactcctt tcttgattcc tcacaaagca gaaaaagatg tattgttatg  1200
caactattta gtgcccaaaa actcaattat ttgggttaat ttatggtcga tcgctcgtag  1260
tccaagtgtg tggccaaatc cagaatcatt ttctcctgaa aggtttttgg agatggaaat  1320
tgatattaaa ggacgagatt tcaaactcat accctttgga tcaggaagaa gaatgtgtcc  1380
tggaatgcca cttgcttata ggatgacaca tatgttgttg gctactcttc ttcattcatt  1440
taactggaag tatggtgagg caagtccaaa agatatagac atgaaagaaa agtttgggtt  1500
gacgttgcaa aaggctcagc cacttcaagc aattccaatt cccagatgat caatctcttt  1560
tgaggagtta gacgatttct ttgtgtcaac caactagtac ttatcggaac atttattgtt  1620
aaatgtgtct gttagatgta catatgatgt tgttatacta agaaataacg gtgtttaagt  1680
gcaacatggg acaagaggat tatgtaaagt atcctagatt ttattaggtg ctcctacacc  1740
tatgtattgg tgcatttgca ccaagtcgtc tgtagaaaac ttgagacttg ggaggcaaga  1800
actttacctc tgtaaaaaaa acgcgttttt tgcattctcc ttgtatcttt tgcaagagat  1860
tgtacgcatt cacaaaacat caaatacatt tgtgtttaca caataagaat cgccaacact  1920
ga                                                                 1922

SEQ ID NO: 10          moltype = AA  length = 495
FEATURE                Location/Qualifiers
source                 1..495
                       mol_type = protein
                       organism = Beta vulgaris
SEQUENCE: 10
MDNATLAVIL SILFVFYHIF KSFFTNSSSR RLPPGPKPVP IFGNIFDLGE KPHRSFANLS  60
KIHGPLISLK LGSVTTIVVS SASVAEEMFL KNDQALANRT IPDSVRAGDH DKLSMSWLPV  120
SQKWRNMRKI SAVQLLSNQK LDASQPLRQA KVKQLLSYVQ DCSKKMQPVD IGRAAFTTSL  180
LLSNTFFSIE LASHESSASQ EFKQLMWNIM EEIGRPNYAD FFPILGYIDP FGIRRRLAGY  240
FDKLIDVFQD IIRERQKLRS SNSSGAKQTN DILDTLLKLH EDNELSMPEI NHLLVDIFDA  300
GTDTTASTLE WAMAELVKNP EMMTKVQNEI EEALGKDCLD IQESDISKLP YLQAIIKETL  360
RLHPPTVFLL PRKADNDVEL YGYVVPKNAQ VLVNLWAIGR DPKVWKNPEV FSPERFLDCN  420
IDYKGRDFEL LPFGAGRRIC PGLTLAYRML NLMLATLLQN YNWKLEDGIN PKDLDMDEKF  480
GITLQKIKPL QVIPV                                                  495

SEQ ID NO: 11          moltype = AA  length = 499
FEATURE                Location/Qualifiers
source                 1..499
                       mol_type = protein
                       organism = Froelichia latifolia
SEQUENCE: 11
MDNTTLAVVL SVMFVLFHLL KTIFTNSSNN KLPPGPKRMP IFGNIFDLGE KPHRSFANFA  60
KIHGPLISLK LGSVTTIVVS SASVAEEMFL KNDQALANRT IPDSVRAGDH DKLSMSWLPV  120
SAKWRNLRKI SAVQLLSNQR LDASQPLRQA KVKQLLAYVQ NCSEKNQAVD IGRAAFTTSL  180
NLLSNTFFSM ELASHESSAS QEFKQLMWNI MEEIGRPNYA DFFPILGYID PFGIRRRLAG  240
YFDKLIDVFQ DIIRERQKIR ASNANGTKQT SDILDTLLKL YEDNELSMGE INHLLVDIFD  300
AGTDTTASTL EWAMAELVKN PEMMVRAQNE IEEVLGKDCS NIQESDISKL PYLQAIIKES  360
LRLHPPTVFL LPRKADVDVE LYGYVVPKNA QVLVNLWAIG RDPKVWKNPE VFSPERFLEC  420
DIDYKGRDFE LLPFGAGRRI CPGLTLAYRM LNLMLATLLH NYNWKLGDDM DPKDLDMEEK  480
FGITLQKIKP LQVIPVARK                                              499

SEQ ID NO: 12          moltype = AA  length = 495
FEATURE                Location/Qualifiers
source                 1..495
                       mol_type = protein
                       organism = Alternanthera caracasana
SEQUENCE: 12
MDNTTLAVVL SIMFACFHLI KTIFSNSSNS KLPPGPKRLP IFGNIFDLGE KPHRSFANYA  60
KLHGPLISLQ LGSVMTVIVS SASVAEEMFL KNDQALANRT IPDSVRAGDH DKLSMSWLPV  120
SPKWRNLRKI SAVQLLSTQR LDASQPLRQA KVQQLLAYVQ DCSKKGQPVD IGRAAFTTSL  180
NLLSNTFFSM ELASHESSAS QEFKQLMWNI MEEIGRPNYA DFFPILGYID PFGIRRRLAS  240
YFDKLIAVFQ DIIRERQKIR SSNVSGTKQT NDILDTLLKL HEENELSMGE INHLLVDIFD  300
AGTDTTASTL EWAMAELVKN PYMMVKAQNE IEEALGKDCS NIQESDISKL PYLQAIIKES  360
LRLHPPTVFL LPRKADHDVE LYGYVVPKNA QVLVNLWAIG RDPKVWKNPE VFFPERFLGC  420
DIDYKGRDFE LLPFGAGRRI CPGLTLAYRM LNLMLATLLH NYNWKLGDGM NPKDMDMEEK  480
FGITLQKIKP LQVIP                                                  495

SEQ ID NO: 13          moltype = AA  length = 493
FEATURE                Location/Qualifiers
source                 1..493
                       mol_type = protein
                       organism = Alternanthera ficoidea
SEQUENCE: 13
MDNTTLALLL SGLFVFFHLI RSLVSHSSKS SKLPPGPKRM PIFGNIFDLG EKPHRSFANF  60
SKIYGPLISL KLGSVTTVVV SSAEVAKEMF LKNDQALANR TIPDSVRAGD HDKLSMSWLP  120
VSNKWRNLRK ISAVQLLSTQ RLDASQANRQ AKVQQLLAYV QDCSKKGQPV DIGRAAFTTS  180
LNLLSNTFFS IELASHESSA SQEFKQLMWN IMEEIGRPNY ADFFPILGYI DPFGIRRRLA  240
AYFDKLIAVF QDIIQERQKI RSSGTKQTND ILDTLLNLYE ENELSMGEIN HLLVDIFDAG  300
TDTTASTLEW AMAELVKNPE MMIRVQNEIE QAVGKDCPMI QESDISKLPY LQAIIKETLR  360
LHPPTVFLLP RKADVDVELY GYTVPKDAQV LVNLWAIGRD PKVWKNSEVF SPERFLECDI  420
DYKGRDFELL PFGAGRRICP GLTLAYRMLN LMMANFLYSF DWKLEGGMHP KDLDMDEKFG  480
```

```
ITLQKVKPLQ VIP                                                  493

SEQ ID NO: 14          moltype = AA  length = 497
FEATURE                Location/Qualifiers
source                 1..497
                       mol_type = protein
                       organism = Beta vulgaris
SEQUENCE: 14
MDHATLAMIL AIWFISFHFI KLLFSQQTTK LLPPGPKPLP IIGNILEVGK KPHRSFANLA  60
KIHGPLISLR LGSVTTIVVS SADVAKEMFL KKDHPLSNRT IPNSVTAGDH HKLTMSWLPV  120
SPKWRNFRKI TAVHLLSPQR LDACQTFRHA KVQQLYEYVQ ECAQKGQAVD IGKAAFTTSL  180
NLLSKLFFSV ELAHHKSHTS QEFKELIWNI MEDIGKPNYA DYFPILGCVD PSGIRRRLAC  240
SFDKLIAVFQ GIICERLAPD SSTTTTTTTD DVLDVLLQLF KQNELTMGEI NHLLVDIFDA  300
GTDTTSSTFE WVMTELIRNP EMMEKAQEEI KQVLGKDKQI QESDIINLPY LQAIIKETLR  360
LHPPTVFLLP RKADTDVELY GYIVPKDAQI LVNLWAIGRD PNAWQNADIF SPERFIGCEI  420
DVKGRDFGLL PFGAGRRICP GMNLAIRMLT LMLATLLQFF NWKLEGDISP KDLDMDEKFG  480
IALQKTKPLK LIPIPRY                                              497

SEQ ID NO: 15          moltype = AA  length = 496
FEATURE                Location/Qualifiers
source                 1..496
                       mol_type = protein
                       note = subsp. cruentus
                       organism = Amaranthus hybridus
SEQUENCE: 15
MDNATLAMIL TIWFISINFI KMFFYHQNTK LSLPPGPKPL PIIGNILEVG KKPHRSFANL  60
AKIHGPLISL RLGSVTTIVV SSAEVAKEMF LKKDQPLSNR NVPNSVTAGD HHKLTMSWLP  120
VSPKWRNFRK ITAVHLLSPL RLDACQSLRH AKVQQLYQYV QECALKGQSV DIGKAAFTTS  180
LNLLSKLFFS KELACHKSHE SQELKQLIWN IMEDIGKPNY ADYFPILGCI DPLGIRRRLA  240
ANFDKLISVF QTIISERLEN DINSNATTND VLDVLLQLYK QKELSMGEIN HLLVDIFDAG  300
TDTTSSTFEW VMAELIRNPK MMEKAQQEIH EVLGKDRQIQ ESDIIKLPYL QALIKETLRL  360
HPPTVFLLPR KADMDVELYG YVVPKDAQIL VNLWAIGRDS QVWEKPNVFL PERFLGSDVD  420
VKGRDFGLLP FGAGKRICPG MNLAIRMLTL MLATLLQFFN WKLEDGMNPQ DLDMDEKFGI  480
ALQKNKPLEI IPSLRH                                               496

SEQ ID NO: 16          moltype = AA  length = 496
FEATURE                Location/Qualifiers
source                 1..496
                       mol_type = protein
                       organism = Mirabilis jalapa
SEQUENCE: 16
MDFLTLVMIL SIIFFFYNLL KMKFTTHSDA QLPPGPKPMP IFGNIFELGE KPHRSFANLA  60
KTHGPLMSLR LGSVTTIVVS SAEVAKEMFL KNDQSLADRS VPNSVTAGDH HKLTMSWLPV  120
SPKWKNFRKI TAVHLLSPQR LDACHALRHA KVKQLYEYVQ ECALKGEAVD IGKAAFTTSL  180
NLLSNLFFSV ELANHTSNTS QEFKQLIWDI MEDIGKPNYA DYFPLLKYVD PSGIRRRLAA  240
NFDKLIDVFQ SFISKRLSSA YSSATSLDDV LDVLLKLLKE KELNMGEINH LLVDIFDAGT  300
DTTSNTFEWA MAELMRNPIM MKRAQNEIAL VLGKDNATIQ ESDIANMPYL QAIIKETLRL  360
HPPTVFLLPR KAITNVKLYG YIVPKNAQIL VNLWAIGRDP KVWKNPNEFL PDRFLNSDID  420
VKGRDFGLLP FGAGRRICPG MNLAYRMLTL MLATLLQSFD WKLPHRNSPL DLDMDEKFGI  480
ALQKTKPLEI IPLIKY                                               496

SEQ ID NO: 17          moltype = AA  length = 494
FEATURE                Location/Qualifiers
source                 1..494
                       mol_type = protein
                       organism = Celosia cristata
SEQUENCE: 17
MDNATLAMLL AIWFISFHFI KMLFTNQSTK LLPPGPKPLP IIGNILEVGK KPHRSFANLA  60
KIHGPLISLK LGSVTTIVVS SAEVAKEMFL KKDQPLSNRT VPNSVTAGDH HKLTMSWLPV  120
SPKWRNFRKI TAVHLLSPLR LDACQSLRHA KVQQLFQYVQ ECAQKGQAVD IGKAAFTTSL  180
NLLSKLFFSK ELASHKSRES QEFKQLIWNI MEDIGKPNYA DYFPILGCVD PSGIRRRLAS  240
NFDKLIEVFQ CIIRQRLERN PSTPPTNDVL DVLLELYKQN ELSMGEINHL LVDIFDAGTD  300
TTSSTFEWVM AELIRNPEMM AKAQDEIEQV LGKDRQIQES DIIKLPYLQA IIKETLRLHP  360
PTVFLLPRKA DTDVELYGYI VPKDAQILVN LWAIGRDSQA WENPKVFSPD RFLGCEIDVK  420
GRDFGLLPFG AGKRICPGMN LAIRMLTLML ATLLQFFNWK LQDGMSLEDL DMEEKFGIAL  480
QKTKPLRIIP VSRY                                                 494

SEQ ID NO: 18          moltype = AA  length = 499
FEATURE                Location/Qualifiers
source                 1..499
                       mol_type = protein
                       organism = Beta vulgaris
SEQUENCE: 18
MDNATLAVIL SILFVFYHIF KSFFTNSSSR RLPPGPKPVP IFGNIFDLGE KPHRSFANLS  60
KIHGPLISLK LGSVTTIVVS SASVAEEMFL KNDQALANRT IPDSVRAGDH DKLSMSWLPV  120
SQKWRNMRKI SAVQLLSNQK LDASQPLRQA KVKQLLSYVQ VCSEKMQPVD IGRAAFTTSL  180
NLLSNTFFSI ELASHESSAS QEFKQLMWNI MEEIGRPNYA DFFPILGYID PFGIRRRLAG  240
YFDKLIDVFQ DIIRERQKLR SSNSSGAKQT NDILDTLLKL HEDNELSMPE INHLLVDIFD  300
AGTDTTASTL EWAMAELVKN PEMMTKVQIE IEQALGKDCL DIQESDISKL PYLQAIIKET  360
```

```
LRLHPPTVFL LPRKADNDVE LYGYVVPKNA QVLVNLWAIG RDPKVWKNPE VFSPERFLDC  420
NIDYKGRDFE LLPFGAGRRI CPGLTLAYRM LNLMLATLLQ NYNWKLEDGI NPKDLDMDEK  480
FGITLQKVKP LQVIPVPRN                                               499

SEQ ID NO: 19          moltype = DNA  length = 16212
FEATURE                Location/Qualifiers
misc_feature           1..16212
                       note = pX11 overexpression vector
source                 1..16212
                       mol_type = other DNA
                       organism = synthetic construct
SEQUENCE: 19
cgctgtcatg agacgaattc tgacaggata tattggcggg taaacctaag agaaaagagc  60
gtttattaga ataatcggat atttaaaagg gcgtgaaaag gtttatccgt tcgtccattt  120
gtatgtgcat gccaaccaca gggttcccct cgggatcaaa gtactttgat ccaacccctc  180
cgctgctata gtgcagtcgg cttctgacgt tcagtgcagc cgtcatctga aaacgacatg  240
tcgcacaagt cctaagttac gcgacaggct gccgccctgc ccttttcctg gcgttttctt  300
gtcgcgtgtt ttagtcgcat aaagtagaat acttgcgact agaaccggag acattacgcc  360
atgaacaaga gcgccgccgc tggcctgctg ggctatgccc gcgtcagcac cgacgaccag  420
gacttgacca accaacgggc cgaactgcac gcggccggct gcaccaagct gttttccgag  480
aagatcaccg gcaccaggcg cgaccgcccg gagctggcca ggatgcttga ccacctacgc  540
cctggcgacg ttgtgacagt gaccaggcta gaccgcctgg cccgcagcac ccgcgaccta  600
ctggacattg ccgagcgcat ccaggaggcc ggcgcgggcc tgcgtagcct ggcagagccg  660
tgggccgaca ccaccacgcc ggccggccgc atggtgttga ccgtgttcgc cggcattgcc  720
gagttcgagc gttccctaat catcgaccgc acccggagcg ggcgcgaggc cgccaaggcc  780
cgaggcgtga agtttggccc ccgccctacc ctcaccccgg cacagatcgc gcacgcccgc  840
gagctgatcg accaggaagg ccgcaccgtg aaagaggcgg ctgcactgct tggcgtgcat  900
cgctcgaccc tgtaccgcgc acttgagcgc agcgaggaag tgacgcccac cgaggccagg  960
cggcgcggtg ccttccgtga ggacgcattg accgaggccg acgccctggc ggccgccgag  1020
aatgaacgcc aagaggaaca agcatgaaac cgcaccagga cggccaggac gaaccgtttt  1080
tcattaccga agagatcgag gcggagatga tcgcggccgg gtacgtgttc gagccgcccg  1140
cgcacctctc aaccgtgcgg ctgcatgaaa tcctggccgg tttgtctgat gccaagctgg  1200
cggcctggcc ggccagcttg gccgctgaag aaaccgagcg ccgccgtcta aaaaggtgat  1260
gtgtatttga gtaaaacagc ttgcgtcatg cggtcgctgc gtatatgatc cgatgagtaa  1320
ataaacaaat acgcaagggg aacgcatgaa ggttatcgct gtacttaacc agaaaggcgg  1380
gtcaggcaag acgaccatcg gaacccatct agcccgcgcc ctgcaactcg ccggggccga  1440
tgttctgtta gtcgattccg atccccaggg cagtgcccgc gattgggcgg ccgtgcggga  1500
agatcaaccg ctaaccgttg tcggcatcga ccgcccgacg attgaccgcg acgtgaaggc  1560
catcggccgg cgcgacttcg tagtgatcga cggagcgccc caggcggcgg acttggctgt  1620
gtccgcgatc aaggcagccg acttcgtgct gattccggtg cagccaagcc cttacgacat  1680
atgggccacc gccgacctgg tggagctggt taagcagcgc attgaggtca cggatggaag  1740
gctacaagcg gcctttgtcg tgtcgcgggc gatcaaaggc acgcgcatcg gcggtgaggt  1800
tgccgaggcg ctggccgggt acgagctgcc cattcttgag tcccgtatca cgcagcgcgt  1860
gagctaccca ggcactgccg ccgccggcac aaccgttctt gaatcagaac ccgagggcga  1920
cgctgcccgc gaggtccagg cgctggccgc tgaaattaaa tcaaaactca tttgagttaa  1980
tgaggtaaag agaaaatgag caaaagcaca aacacgctaa gtgccggccg tccgagcgca  2040
cgcagcagca aggctgcaac gttggccagc ctggcagaca cgccagccat gaagcgggtc  2100
aactttcagt tgccggcgga ggatcacacc aagctgaaga tgtacgcggt acgccaaggc  2160
aagaccatta ccgagctgct atctgaatag atcgcgcagc taccagagta aatgagcaaa  2220
tgaataaatg agtagatgaa ttttagcggc taaaggaggc ggcatggaaa atcaagaaca  2280
accaggcacc gacgccgtgg aatgccccat gtgtggagga acgggcggtt ggccaggcgt  2340
aagcggctgg gttgtctgcc ggccctgcaa tggcactgga acccccaagc ccgaggaatc  2400
ggcgtgacgg tcgcaaacca tccggcccgg tacaaatcgg cgcggcgctg ggtgatgacc  2460
tggtggagaa gttgaaggcc gcgcaggccg cccagcggca acgcatcgag gcagaagcac  2520
gccccggtga atcgtggcaa gcggccgctg atcgaatccg caaagaatcc cggcaaccgc  2580
cggcagccgg tgcgccgtcg attaggaagc cgcccaaggg cgacgagcaa ccagattttt  2640
tcgttccgat gctctatgac gtgggcaccc gcgatagtcg cagcatcatg gacgtggccg  2700
ttttccgtct gtcgaagcgt gaccgacgag ctggcgaggt gatccgctac gagcttccag  2760
acgggcacgt agaggtttcc gcagggccgg ccggcatggc cagtgtgtgg gattacgacc  2820
tggtactgat ggcggtttcc catctaaccg aatccatgaa ccgataccgg gaagggaagg  2880
gagacaagcc cggccgcgtg ttccgtccac acgttgcgga cgtactcaag ttctgccggc  2940
gagccgatgg cggaaagcag aaagacgacc tggtagaaac ctgcattcgg ttaaacacca  3000
cgcacgttgc catgcagcgt acgaagaagg ccaagaacgg ccgcctggtg acggtatccg  3060
agggtgaagc cttgattagc cgctacaaga tcgtaaagag cgaaaccggg cggccggagt  3120
acatcgagat cgagctagct gattggatgt accgcgagat cacagaaggc aagaacccgg  3180
acgtgctgac ggttcacccc gattactttt tgatcgatcc cggcatcggc cgttttctct  3240
accgcctggc acgccgcgcc gcaggcaagg cagaagccag atggttgttc aagacgatct  3300
acgaacgcag tggcagcgcc ggagagttca agaagttctg tttcaccgtg cgcaagctga  3360
tcgggtcaaa tgacctgccg gagtacgatt tgaaggagga ggcggggcag gctggcccga  3420
tcctagtcat gcgctaccgc aacctgatcg agggcgaagc atccgccggt tcctaatgta  3480
cggagcagat gctagggcaa attgccctag caggggaaaa aggtcgaaaa ggactctttc  3540
ctgtggatag cacgtacatt gggaacccaa agccgtacat tgggaaccgg aacccgtaca  3600
ttgggaaccc aaagccgtac attgggaacc ggtcacacat gtaagtgact gatataaaag  3660
agaaaaaagg cgatttttcc gcctaaaact ctttaaaact tattaaaact cttaaaaccc  3720
gcctggcctg tgcataactg tctggccagc gcacagccga agagctgcaa aaagcgccta  3780
cccttcggtc gctgcgctcc ctacgccccg ccgcttcgcg tcggcctatc gcggccgctg  3840
gccgctcaaa aatggctggc ctacggccag gcaatctacc agggcgcgga caagccgcgc  3900
cgtcgccact cgaccgccgg cgcccacatc aaggcaccct gcctcgcgcg tttcggtgat  3960
gacggtgaaa acctctgaca catgcagctc ccggtgacgg tcacagcttg tctgtaagcg  4020
```

-continued gatgccggga gcagacaagc ccgtcagggc gcgtcagcgg gtgttggcgg gtgtcggggc 4080
gcagccatga cccagtcacg tagcgatagc ggagtgtata ctggcttaac tatgcggcat 4140
cagagcagat tgtactgaga gtgcaccata tgcggtgtga aataccgcac agatgcgtaa 4200
ggagaaaata ccgcatcagg cgctcttccg cttcctcgct cactgactcg ctgcgctcgg 4260
tcgttcggct gcggcgagcg gtatcagctc actcaaaggc ggtaatacgg ttatccacag 4320
aatcagggga taacgcagga aagaacatgt gagcaaaagg ccagcaaaag gccaggaacc 4380
gtaaaaaggc cgcgttgctg gcgtttttcc ataggctccg cccccctgac gagcatcaca 4440
aaaatcgacg ctcaagtcag aggtggcgaa acccgacagg actataaaga taccaggcgt 4500
ttccccctgg aagctccctc gtgcgctctc ctgttccgac cctgccgctt accggatacc 4560
tgtccgcctt tctcccttcg ggaagcgtgg cgctttctca tagctcacgc tgtaggtatc 4620
tcagttcggt gtaggtcgtt cgctccaagc tgggctgtgt gcacgaaccc cccgttcagc 4680
ccgaccgctg cgccttatcc ggtaactatc gtcttgagtc caacccggta agacacgact 4740
tatcgccact ggcagcagcc actggtaaca ggattagcag agcgaggtat gtaggcggtg 4800
ctacagagtt cttgaagtgg tggcctaact acggctacac tagaaggaca gtatttggta 4860
tctgcgctct gctgaagcca gttaccttcg gaaaaagagt tggtagctct tgatccggca 4920
aacaaaccac cgctggtagc ggtggttttt ttgtttgcaa gcagcagatt acgcgcagaa 4980
aaaaaggatc tcaagaagat cctttgatct tttctacggg gtctgacgct cagtggaacg 5040
aaaactcacg ttaagggatt ttggtcatgc attctaggtg attagaaaaa ctcatcgagc 5100
atcaaatgaa actgcaattt attcatatca ggattatcaa taccatattt ttgaaaaagc 5160
cgtttctgta atgaaggaga aaactcaccg aggcagttcc ataggatggc aagatcctgg 5220
tatcggtctg cgattccgac tcgtccaaca tcaatacaac ctattaattt cccctcgtca 5280
aaaataaggt tatcaagtga gaaatcacca tgagtgacga ctgaatccgg tgagaatggc 5340
aaaagtttat gcatttcttt ccagacttgt tcaacaggcc agccattacg ctcgtcatca 5400
aaatcactcg catcaaccaa accgttattc attcgtgatt gcgcctgagc gagtcgaaat 5460
acgcgatcgc tgttaaaagg acaattacaa acaggaatcg aatgcaaccg gcgcaggaac 5520
actgccagcg catcaacaat attttcacct gaatcaggat attcttctaa tacctggaat 5580
gctgttttcc ctgggatcgc agtggtgagt aaccatgcat catcaggagt acggataaaa 5640
tgcttgatgg tcggaagagg cataaattcc gtcagccagt ttagtctgac catctcatct 5700
gtaacatcat tggcaacgct acctttgcca tgtttcagaa acaactctgg cgcatcgggc 5760
ttcccataca atcggtagat tgtcgcacct gattgcccga cattatcgcg agcccattta 5820
tacccatata aatcagcatc catgttggaa tttaatcgcg gccttgagca agacgtttcc 5880
cgttgaatat ggctcataac agaacttatt atttccttcc tcttttctac agtatttaaa 5940
gataccccaa gaagctaatt ataacaagac gaactccaat tcactgttcc ttgcattcta 6000
aaaccttaaa taccagaaaa cagctttttc aaagttgttt tcaaagttgg cgtataacat 6060
agtatcgacg gagccgattt tgaaaccgcg gtgatcacag gcagcaacgc tctgtcatcg 6120
ttacaatcaa catgctaccc tccgcgagat catccgtgtt tcaaacccgg cagcttagtt 6180
gccgttcttc cgaatagcat cggtaacatg agcaaagtct gccgccttac aacggctctc 6240
ccgctgacgc cgtcccggac tgatgggctg cctgtatcga gtggtgattt tgtgccgagc 6300
tgccggtcgg ggagctgttg gctggctggt ggcaggatat attgtggtgt aaacataacg 6360
aattcgtctc aggagagcgt cgatctagta acatagatga caccgcgcgc gataatttat 6420
cctagtttgc gcgctatatt ttgttttcta tcgcgtatta aatgtataat tgcgggactc 6480
taatcataaa aacccatctc ataaataacg tcatgcatta catgttaatt attacatgct 6540
taacgtaatt caacagaaat tatatgataa tcatcgcaag accggcaaca ggattcaatc 6600
ttaagaaact ttattgccaa atgtttgaac gatctgcttc gacgcactcc ttctttactc 6660
caccatctcg tccttattga aaacgtgggt agcaccaaaa cgaatcaagt cgctggaact 6720
gaagttacca atcacgctgg atgatttgcc agttggatta atcttgcctt tccccgcatg 6780
aataatattg atgaatgcat gcgtgagggg tagttcgatg ttggcaatag ctgcaattgc 6840
cgcgacatcc tccaacgagc ataattcttc agaaaaatag cgatgttcca tgttgtcagg 6900
gcatgcatga tgcacgttat gaggtgacgg tgctaggcag tattccctca aagtttcata 6960
gtcagtatca tattcatcat tgcattcctg caagagagaa ttgagacgca atccacacgc 7020
tgcggcaacc ttccggcgtt cgtggtctat ttgctcttgg acgttgcaaa cgtaagtgtt 7080
ggatcggggt gggcgaagaa ctccagcatg agatccccgc gctggaggat catccagccg 7140
gcgtcccgga aaacgattcc gaagcccaac ctttcataga aggcggcggt ggaatcgaaa 7200
tctcgtgatg gcaggttggg cgtcgcttgg tcggtcattt cgaaccccag agtcccgctc 7260
agaagaactc gtcaagaagg cgatagaagg cgatgcgctg cgaatcggga gcggcgatac 7320
cgtaaagcac gaggaagcgg tcagcccatt cgccgccaag ctcttcagca atatcacggg 7380
tagccaacgc tatgtcctga tagcggtccg ccacacccag ccggccacag tcgatgaatc 7440
cagaaaagcg gccattttcc accatgatat tcggcaagca ggcatcgcca tgggtcacga 7500
cgagatcctc gccgtcgggc atgcgcgcct tgagcctggc gaacagttcg gctggcgcga 7560
gcccctgatg ctcttcgtcc agatcatcct gatcgacaag accggcttcc atccgagtac 7620
gtgctcgctc gatgcgatgt ttcgcttggt ggtcgaatgg gcaggtagcc ggatcaagcg 7680
tatgcagccg ccgcattgca tcagccatga tggatacttt ctcggcagga gcaaggtgag 7740
atgacaggag atcctgcccc ggcacttcgc ccaatagcag ccagtccctt cccgcttcag 7800
tgacaacgtc gagcacagct gcgcaaggaa cgcccgtcgt ggccagccac gatagccgcg 7860
ctgcctcgtc ctgcagttca ttcagggcac cggacaggtc ggtcttgaca aaaagaaccg 7920
ggcgcccctg cgctgacagc cggaacacgg cggcatcaga gcagccgatt gtctgttgtg 7980
cccagtcata gccgaatagc ctctccaccc aagcggccgg agaacctgcc cggatccggg 8040
cggaaatagg taaagaagtt gcggataagg taattgccat tgcagattat ttggattgag 8100
agtgaatatg agactctaat tggataccga ggggaattta tggaacgtca gtggagcatt 8160
tttgacaaga aatatttgct agctgatagt gaccttaggc gacttttgaa cgcgcaataa 8220
tggtttctga cgtatgtgct tagctcatta aactccagaa acccctccgt caggagacta 8280
gagccaagct gatctccttt gccccggaga tcaccatgga cgactttctc tatctctacg 8340
atctaggaag aaagttcgac ggagaaggtg acgataccat gttcaccacc gataatgaga 8400
agattagcct cttcaatttc agaaagaatg ctgacccaca gatggttaga gaggcctacg 8460
cggcaggtct gatcaagacg atctacccga gtaataatct ccaggagatc aaataccttc 8520
ccaagaaggt taaagatgca gtcaaaagat tcaggactaa ctgcatcaag aacacagaga 8580
aagatatatt tctcaagatc agaagtacta ttccagtatg gacgattcaa ggcttgcttc 8640
ataaaccaag gcaagtaata gagattggag tctctaagaa agtagttcct actgaatcaa 8700
aggccatgga gtcaaaaatt cagatcgagg atctaacaga actcgccgtg aagactggcg 8760
aacagttcat acagagtctt ttacgactca atgacaagaa gaaaatcttc gtcaacatgg 8820
tggagcacga cactctcgtc tactccaaga atatcaaaga tacagtctca gaagaccaaa 8880
gggctattga gacttttcaa caaagggtaa tatcgggaaa cctcctcgga ttccattgcc 8940
cagctatctg tcacttcatc aaaaggacag tagaaaagga aggtggcacc tacaaatgcc 9000
atcattgcga taaaggaaag gctatcgttc aagatgcctc tgccgacagt ggtcccaaag 9060
atggaccccc acccacgagg agcatcgtgg aaaaagaaga cgttccaacc acgtcttcaa 9120
agcaagtgga ttgatgtgat atctccactg acgtaaggga tgacgcacaa tcccactatc 9180
cttcgcaaga cccttcctct atataaggaa gttcatttca tttggagagg actccggtat 9240
ttttacaaca ataccacaac aaaacaaaca acaaacaaca ttacaattta ctattctagt 9300
cgaaatgaaa atgatgaatg gtgaagatgc taatgatcaa atgatcaaag aaagcttctt 9360
cataacacat ggaaacccaa tattaacagt agaagacaca catccattaa gacctttctt 9420
tgaaacttgg agagagaaaa tcttttctaa gaaacctaag gcaattctta ttatttctgg 9480
tcattgggaa actgttaaac ctactgttaa tgctgtccat atcaatgata ctatccatga 9540
ttttgatgac tatcctgctg ctatgtacca gttcaagtat ccagctcctg gggaaccaga 9600
attggcaaga aaagtagagg aaattctgaa aaaatcgggt ttcgaaacgg cggaaactga 9660
tcaaaaacgt gggcttgatc atggtgcatg ggtacctcta atgctaatgt atcctgaggc 9720
tgatatacca gtatgtcagc tctcagttca gccgcattta gatggaacat accattacaa 9780
cttaggacga gcattggctc ccttgaaaaa cgacggcgta ttaatcattg gttcaggaag 9840
tgcaactcac cctttggatg aaactcctca ttattttgat ggagttgcac cttgggcagc 9900
tgcctttgat tcatggcttc gtaaagctct cattaatgga aggtttgaag aagtgaatat 9960
atatgaaagc aaagcaccaa attggaaatt agcacatcct ttcccagaac atttttatcc 10020
attgcatgtt gttcttggcg ctgctggtga aaaatggaag gcagagctta ttcatagcag 10080
ttgggatcat ggcaccttgt gtcatggctc ctacaagttc acttcagcct aggcttggaa 10140
tggatcttcg atcccgatcg ttcaaacatt tggcaataaa gtttcttaag attgaatcct 10200
gttgccggtc ttgcgacgat tatcatataa tttctgttga attacgttaa gcatgtaata 10260
attaacatgt aatgcatgac gttatttatg agatgggttt ttatgattag agtcccgcaa 10320
ttatacattt aatacgcgat agaaaacaaa atatagcgcg caaactagga taaattatcg 10380
cgcdcggtgt catctatgtt actagatcgg gaattgccaa gctaattctt gaagacgaaa 10440
gggcctcgtg atacgcctat ttttataggt taatgtcatg ataataatgg tttcttagac 10500
gtcaggtggc acttttcggg gaaatgtgcg cggaacccct atttgtttat ttttctaaat 10560
acattcaaat atgtatccgc tcatgagaca ataaccctga taaatgcttc aataatggga 10620
ccgactcgcg ctgtcaggag actagagcca agctgatctc ctttgccccg gagatcacca 10680
tggacgactt tctctatctc tacgatctag gaagaaagtt cgacggagaa ggtgacgata 10740
ccatgttcac caccgataat gagaagatta gcctcttcaa tttcagaaag aatgctgacc 10800
cacagatggt tagagaggcc tacgcggcag gtctgatcaa gacgatctac ccgagtaata 10860
atctccagga gatcaaatac cttcccaaga aggttaaaga tgcagtcaaa agattcagga 10920
ctaactgcat caagaacaca gagaaagata tatttctcaa gatcagaagt actattccag 10980
tatggacgat tcaaggcttg cttcataaac caaggcaagt aatagagatt ggagtctcta 11040
agaaagtagt tcctactgaa tcaaaggcca tggagtcaaa aattcagatc gaggatctaa 11100
cagaactcgc cgtgaagact ggcgaacagt tcatacagag tcttttacga ctcaatgaca 11160
agaagaaaat cttcgtcaac atggtggagc acgacactct cgtctactcc aagaatatca 11220
aagatacagt ctcagaagac caaagggcta ttgagacttt tcaacaaagg gtaatatcgg 11280
gaaacctcct cggattccat tgcccagcta tctgtcactt catcaaaagg acagtagaaa 11340
aggaaggtgg cacctacaaa tgccatcatt gcgataaagg aaaggctatc gttcaagatg 11400
cctctgccga cagtggtccc aaagatggac ccccacccac gaggagcatc gtggaaaaag 11460
aagacgttcc aaccacgtct tcaaagcaag tggattgatg tgatatctcc actgacgtaa 11520
gggatgacgc acaatcccac tatccttcgc aagacccttc ctctatataa ggaagttcat 11580
ttcatttgga gaggactccg gtatttttac aacaatacca caacaaaaca aacaacaaac 11640
aacattacaa tttactattc tagtcgaaat ggatcatgca acattagcaa tgatactagc 11700
catttggttc atttcttttc atttcataaa attacttttt agccaacaaa ctaccaaact 11760
tcttcctcct ggtccaaaac cattgccaat aattggtaac atcttagaag ttggtaaaaa 11820
accccatcgt tcatttgcta atcttgctaa aattcacggc cctttaatat cgttacgtct 11880
aggaagtgta acaactattg ttgtatcatc agcagatgta gctaaagaaa tgttcttaaa 11940
aaaagaccac cctctttcta accgtactat tcctaattct gtcacggccg gtgaccacca 12000
taaactcacc atgtcgtggt tgcccgtttc gccgaaatgg cggaattttc gtaagattac 12060
agccgtccat ttgctttctc ctcaaagact tgatgcttgc caaacctttc gccatgccaa 12120
ggtgcaacag ctttatgaat atgtacaaga atgtgcacaa aaaggccaag ctgttgatat 12180
tggcaaagct gcatttacta cctcccttaa tttgttatct aaactattct tttcagtgga 12240
attagcccac cataaatcac acacttctca agagtttaag gaactaatat ggaacattat 12300
ggaagatatt gggaaaccta attatgctga ttattttcct attttaggct gtgttgatcc 12360
atcaggtatt cgtcgaagat tagcatgtag ttttgacaag ttgattgcag tttttcaggg 12420
tataatatgt gaaaggcttg cgcctgattc ttcaactaca acaacaacga cgactgatga 12480
tgtgctagac gttcttcttc agctcttcaa acaaaatgag ctcactatgg gcgagattaa 12540
ccatttgctc gtcgacattt ttgatgctgg aacagacact acatcaagta cttttgagtg 12600
ggtcatgaca gagttaatta ggaatcctga aatgatggaa aaggctcaag aagaaattaa 12660
gcaagtattg ggcaaagata aacaaattca ggaatcagac attattaacc taccttactt 12720
acaagccatt atcaaagaaa ctttgcgact acatccacca actgtatttc ttttgcctcg 12780
taaagccgac actgatgttg aactatatgg ttatattgtg cctaaagatg cacaaatact 12840
tgttaactta tgggctattg gaagagatcc taatgcatgg caaaatgctg atattttttc 12900
gcccgaaaga tttatagggt gtgaaaytga tgtcaaagga agagattttg gactcttacc 12960
ttttggagcc ggaagaagga tatgtcctgg gatgaatttg gccattagaa tgttaacttt 13020
gatgctagct actttacttc aattcttcaa ttggaagctt gaaggagaca taagtccaaa 13080
agacttagac atggatgaga aatttgggat tgcgttacaa aagacaaagc ctttaaaact 13140
tattccaata cctaggtatt gataataagc ttgctctcaa gatcaaaggc ttaaaaagct 13200
ggggtttat gaatgggatc aaagttctt tttttctttt atatttgctt ctccatttgt 13260
ttgtttcatt tccctttttg ttttcgtttc tatgatgcac ttgtgtgtga caaactctct 13320
gggtttttac ttacgtctgc gtttcaaaaa aaaaaaccgc tttcgttttg cgttttagtc 13380
ccattgtttt gtagctctga gtgatcgaat tgatgcctct ttattccttt tgttccctat 13440
aatttctttc aaaactcaga agaaaaacct tgaaactctt tgcaatgtta atataagtat 13500

```
tgtataagat ttttattgat ttggttatta gtcttacttt tgctacctcc atcttcactt  13560
ggaactgata ttctgaatag ttaaagcgtt acatgtcttc cattcacaaa tgaacttaaa  13620
ctagcacaaa gtcagatatt ttaagatcgc accattttat ataaccccaa tcgtcaattc  13680
tactgtttca agttttacac caaaacaatt acgaggtgta tctattcgtt actcttttcg  13740
cttattaatc cttttacatg atgcaaaata taacaaatta atttcaaatt gtcctgcaca  13800
tttggtttat acatcttgat tccaaaaagt cgctgtcagg aggtcgacga gtcagtaata  13860
aacggcgtca aagtggttgc agccggcaca cacgagtcgt gtttatcaac tcaaagcaca  13920
aatacttttc ctcaacctaa aaataaggca attagccaaa aacaactttg cgtgtaaaca  13980
acgctcaata cacgtgtcat tttattatta gctattgctt caccgcctta gctttctcgt  14040
gacctagtcg tcctcgtctt ttcttcttct tcttctataa aacaataccc aaagagctct  14100
tcttcttcac aattcagatt tcaatttctc aaaatcttaa aaactttctc tcaattctct  14160
ctaccgtgat caaggtaaat ttctgtgttc cttattctct caaaatcttc gattttgttt  14220
tcgttcgatc ccaatttcgt atatgttctt tggtttagat tctgttaatc ttagatcgaa  14280
gacgattttc tgggtttgat cgttagatat catcttaatt ctcgattagg gtttcataga  14340
tatcatccga tttgttcaaa taatttgagt tttgtcgaat aattactctt cgatttgtga  14400
tttctatcta gatctggtgt tagtttctag tttgtgcgat cgaatttgtc gattaatctg  14460
agtttttctg attaacagaa tgaccgccat taaaatgaac accaatggtg aaggtgaaac  14520
acaacatata ctaatgatac ctttcatggc gcaagggcat ttacgtcctt tccttgagct  14580
tgctatgttt ctatataaac gaagtcattt tatcattact cttcttacta ccccgctcaa  14640
tgcgggtttc ctacgacatc tccttcacca ccatagctat tctagctcgg ggatcagaat  14700
tgtcgagtta cctttcaact caaccaatca tggtcttcca cctggcattg aaaacactga  14760
taaacttaca ctcccacttg tagtatcact ttttcattca accatttctc ttgaccctca  14820
ccttagagat tatatttccc gccatttctc ccctgcgcgc cctcctctgt gtgtcataca  14880
tgatgtgttc cttggttggg ttgatcaagt tgctaaagac gtgggctcaa ctggtgttgt  14940
ttttactacg ggtggcgcgt atggtacaag cgcatatgtg tccatttgga atgatctgcc  15000
tcaccagaat tactctgatg atcaagagtt tccgcttcct ggtttcccgg agaatcataa  15060
attccgacgt tctcaacttc atcggtttct gaggtatgcc gatggatcag atgattggtc  15120
gaaatatttc caaccgcaat tgaggcaatc aatgaagagt tttggatggc tatgtaattc  15180
agttgaggaa atcgaaacac ttgggtttag tatcctcagg aactacacta aactacccat  15240
ttggggtatt ggaccgttga tagcttcacc tgtacaacat tcatcatctg ataataacag  15300
tactggtgcc gagtttgttc aatggttgag cttgaaagaa ccagattctg tattatacat  15360
ctcatttgga tcacagaaca caatttcacc aacccagatg atggaactag cagccggttt  15420
ggagtcaagt gagaagccgt ttttgtgggt gattcgagca ccatttgggt tcgatatcaa  15480
tgaggaaatg agrccagaat ggctaccaga gggattcgag gagcgaatga aggtgaaaaa  15540
acaaggaaag ttggtgtata agttgggacc acagttggag atacttaacc atgagtcaat  15600
cggagggttc ttaactcatt gtgggtggaa ttcgatcctt gagtcacttc gagaaggtgt  15660
gcctatgtta gggtggccat tggcagccga acaagcttat aatttgaagt atttggagga  15720
cgaaatgggg gttgcagtcg agttagcgag gggattggaa ggagagataa gtaaagagaa  15780
agtgaagaga attgtggaga tgattttaga gagaaatgaa ggaagtaaag gatgggaaat  15840
gaaaaataga gcagtagaaa tggggaagaa acttaaagac gctgtcaatg aggagaagga  15900
actgaagggt tcttctgtta aggcaataga tgatttctta gatgcggtca tgcaagctaa  15960
gttggaacct tctcttcaat aagcttcggc catgctagag tccgcaaaaa tcaccagtct  16020
ctctctacaa atctatctct ctctattttt ctccagaata atgtgtgagt agttcccaga  16080
taagggaatt agggttctta tagggtttcg ctcatgtgtt gagcatataa gaaaccctta  16140
gtatgtattt gtatttgtaa aatacttcta tcaataaaat ttctaattcc taaaaccaaa  16200
atccagtgac ct                                                     16212

SEQ ID NO: 20           moltype = DNA  length = 16919
FEATURE                 Location/Qualifiers
misc_feature            1..16919
                        note = pX11(E8)
source                  1..16919
                        mol_type = other DNA
                        organism = synthetic construct
SEQUENCE: 20
ggaggggttt ctggagttta atgagctaag cacatacgtc agaaaccatt attgcgcgtt  60
caaaagtcgc ctaaggtcac tatcagctag caaatatttc ttgtcaaaaa tgctccactg  120
acgttccata aattcccctc ggtatccaat tagagtctca tattcactct caatccaaat  180
aatctgcaat ggcaattacc ttatccgcaa cttctttacc tatttccgcc cggatccggg  240
caggttctcc ggccgcttgg gtggagaggc tattcggcta tgactgggca caacagacaa  300
tcggctgctc tgatgccgcc gtgttccggc tgtcagcgca ggggcgcccg gttctttttg  360
tcaagaccga cctgtccggt gccctgaatg aactgcagga cgaggcagcg cggctatcgt  420
ggctggccac gacgggcgtt ccttgcgcag ctgtgctcga cgttgtcact gaagcgggaa  480
gggactggct gctattgggc gaagtgccgg ggcaggatct cctgtcatct caccttgctc  540
ctgccgagaa agtatccatc atggctgatg caatgcggcg gctgcatacg cttgatccgg  600
ctacctgccc attcgaccac caagcgaaac atcgcatcga gcgagcacgt actcggatgg  660
aagccggtct tgtcgatcag gatgatctgg acgaagagca tcaggggctc gcgccagccg  720
aactgttcgc caggctcaag gcgcgcatgc ccgacggcga ggatctcgtc gtgacccatg  780
gcgatgcctg cttgccgaat atcatggtgg aaaatggccg cttttctgga ttcatcgact  840
gtggccggct gggtgtggcg gaccgctatc aggacatagc gttggctacc cgtgatattg  900
ctgaagagct tggcggcgaa tgggctgacc gcttcctcgt gctttacggt atcgccgctc  960
ccgattcgca gcgcatcgcc ttctatcgcc ttcttgacga gttcttctga gcgggactct  1020
ggggttcgaa atgaccgacc aagcgacgcc caacctgcca tcacgagatt tcgattccac  1080
cgccgccttc tatgaaaggt tgggcttcgg aatcgttttc cgggacgccg gctggatgat  1140
cctccagcgc ggggatctca tgctggagtt cttcgcccac cccgatccaa cacttacgtt  1200
tgcaacgtcc aagagcaaat agaccacgaa cgccggaagg ttgccgcagc gtgtggattg  1260
cgtctcaatt ctctcttgca ggaatgcaat gatgaatatg atactgacta tgaaactttg  1320
agggaatact gcctagcacc gtcacctcat aacgtgcatc atgcatgccc tgacaacatg  1380
gaacatcgct atttttctga agaattatgc tcgttggagg atgtcgcggc aattgcagct  1440
```

-continued attgccaaca tcgaactacc cctcacgcat gcattcatca atattattca tgcggggaaa 1500
ggcaagatta atccaactgg caaatcatcc agcgtgattg gtaacttcag ttccagcgac 1560
ttgattcgtt ttggtgctac ccacgttttc aataaggacg agatggtgga gtaaagaagg 1620
agtgcgtcga agcagatcgt tcaaacattt ggcaataaag tttcttaaga ttgaatcctg 1680
ttgccggtct tgcgatgatt atcatataat ttctgttgaa ttacgttaag catgtaataa 1740
ttaacatgta atgcatgacg ttatttatga gatgggtttt tatgattaga gtcccgcaat 1800
tatacattta atacgcgata gaaaacaaaa tatagcgcgc aaactaggat aaattatcgc 1860
gcgcggtgtc atctatgtta ctagatcgac gctgtcagga gactagagcc aagctgatct 1920
cctttgcccc ggagatcacc atggacgact ttctctatct ctacgatcta ggaagaaagt 1980
tcgacggaga aggtgacgat accatgttca ccaccgataa tgagaagatt agcctcttca 2040
atttcagaaa gaatgctgac ccacagatgg ttagagaggc ctacgcggca ggtctgatca 2100
agacgatcta cccgagtaat aatctccagg agatcaaata ccttcccaag aaggttaaag 2160
atgcagtcaa aagattcagg actaactgca tcaagaacac agagaaagat atatttctca 2220
agatcagaag tactattcca gtatggacga ttcaaggctt gcttcataaa ccaaggcaag 2280
taatagagat tggagtctct aagaaagtag ttcctactga atcaaaggcc atggagtcaa 2340
aaattcagat cgaggatcta acagaactcg ccgtgaagac tggcgaacag ttcatacaga 2400
gtcttttacg actcaatgac aagaagaaaa tcttcgtcaa catggtggag cacgacactc 2460
tcgtctactc caagaatatc aaagatacag tctcagaaga ccaaagggct attgagactt 2520
ttcaacaaag ggtaatatcg ggaaacctcc tcggattcca ttgcccagct atctgtcact 2580
tcatcaaaag gacagtagaa aaggaaggtg gcacctacaa atgccatcat tgcgataaag 2640
gaaaggctat cgttcaagat gcctctgccg acagtggtcc caaagatgga cccccaccca 2700
cgaggagcat cgtggaaaaa gaagacgttc caaccacgtc ttcaaagcaa gtggattgat 2760
gtgatatctc cactgacgta agggatgacg cacaatccca ctatccttcg caagaccctt 2820
cctctatata aggaagttca tttcatttgg agaggactcc ggtattttta caacaatacc 2880
acaacaaaac aaacaacaaa caacattaca atttactatt ctagtcgaaa tgaaaatgat 2940
gaatggtgaa gatgctaatg atcaaatgat caaagaaagc ttcttcataa cacatggaaa 3000
cccaatatta acagtagaag acacacatcc attaagacct ttctttgaaa cttggagaga 3060
gaaaatcttt tctaagaaac ctaaggcaat tcttattatt tctggtcatt gggaaactgt 3120
taaacctact gttaatgctg tccatatcaa tgatactatc catgattttg atgactatcc 3180
tgctgctatg taccagttca agtatccagc tcctggggaa ccagaattgg caagaaaagt 3240
agaggaaatt ctgaaaaaat cgggtttcga aacggcggaa actgatcaaa aacgtgggct 3300
tgatcatggt gcatgggtac ctctaatgct aatgtatcct gaggctgata taccagtatg 3360
tcagctctca gttcagccgc atttagatgg aacataccat tacaacttag gacgagcatt 3420
ggctcccttg aaaaacgacg gcgtattaat cattggttca ggaagtgcaa ctcacccttt 3480
ggatgaaact cctcattatt ttgatggagt tgcaccttgg gcagctgcct ttgattcatg 3540
gcttcgtaaa gctctcatta atggaaggtt tgaagaagtg aatatatatg aaagcaaagc 3600
accaaattgg aaattagcac atcctttccc agaacatttt tatccattgc atgttgttct 3660
tggcgctgct ggtgaaaaat ggaaggcaga gcttattcat agcagttggg atcatggcac 3720
cttgtgtcat ggctcctaca agttcacttc agcctaggct tggaatggat cttcgatccc 3780
gatcgttcaa acatttggca ataaagtttc ttaagattga atcctgttgc cggtcttgcg 3840
acgattatca tataatttct gttgaattac gttaagcatg taataattaa catgtaatgc 3900
atgacgttat ttatgagatg ggtttttatg attagagtcc cgcaattata catttaatac 3960
gcgatagaaa acaaaatata gcgcgcaaac taggataaat tatcgcgcdc ggtgtcatct 4020
atgttactag atcgggaatt gccaagctaa ttcttgaaga cgaaagggcc tcgtgatacg 4080
cctattttta taggttaatg tcatgataat aatggtttct tagacgtcag gtggcacttt 4140
tcggggaaat gtgcgcggaa cccctatttg tttatttttc taaatacatt caaatatgta 4200
tccgctcatg agacaataac cctgataaat gcttcaataa tgggaccgac tcgcgctgtc 4260
aggaggaatt catttttgac atccctaatg atattgttca cgtaattaag ttttgtggaa 4320
gtgagagagt ccaatttga taagaaaaga gtcagaaaac gtaatatttt aaaagtctaa 4380
atctttctac aaataagagc aaatttattt atttttaat ccaataaata ttaatggagg 4440
acaaattcaa ttcacttggt tgtaaaataa acttaaacca ataaccaaag aactaataaa 4500
tctgaagtgg aattattaag gataatgtac atagacaatg aagaaataat aggttcgatg 4560
aattaataat aattaaggat gttacaatca tcatgtgcca agtatataca caatattcta 4620
tgggatttat aatttcgtta cttcacttaa cttttgcgta aataaaacga attatctgat 4680
attttataat aaaacagtta attaagaacc atcattttta acaacataga tatattattt 4740
ctaatagttt aatgatactt ttaaatcttt taaattttat gtttctttta gaaaataaaa 4800
attcaaaaaa attaaatata tttacaaaaa ctacaatcaa acacaacttc atatattaaa 4860
agcaaaatat attttgaaaa tttcaagtgt cctaacaaat aagacaagag gaaaatgtac 4920
gatgagagac ataaagagaa ctaataattg aggagtccta taatatataa taaagtttat 4980
tagtaaactt aattattaag gactcctaaa atatatgata ggagaaaatg aatggtgaga 5040
gatattggaa aacttaataa ttaaggatat taaaatatat ggtaaaagat aggcaaagta 5100
tccattatcc ccttttaact tgaagtctac ctaggcgcat gtgaaaggtt gattttttgt 5160
cacgtcatat agctataacg taaaaaaaga aagtaaaatt tttaattttt tttaatatat 5220
gacatatttt aaacgaaata taggacaaaa tgtaaatgaa tagtaaagga aacaaagatt 5280
aatacttact ttgtaagaat ttaagataaa tttaaaattt aatagatcaa ctttacgtct 5340
agaaagaccc atatctagaa ggaatttcac gaaatcggcc cttattcaaa aataactttt 5400
aaataatgaa ttttaaattt taagaaataa tatccaatga ataaatgaca tgtagcattt 5460
tacctaaata tttcaactat tttaatccaa tattaatttg ttttattccc aacaatagaa 5520
agtcttgtgc agacatttaa tctgactttt ccagtactaa atattaattt tctgaagatt 5580
ttcgggttta gtccacaagt tttagtgaga agttttgctc aaaattttag gtgagaaggt 5640
ttgatattta tcttttgtta aattaattta tctaggtgac tattatttat ttaagtagaa 5700
attcatatca ttacttttgc caacttgtag tcataatagg agtaggtgta tatgatgaag 5760
gaataaacaa gttcagtgaa gtgattaaaa taaaatataa tttaggtgta catcaaataa 5820
aaaccttaaa gtttagaaag gcaccgaata attttgcata gaagatatta gtaaatttat 5880
aaaaataaaa gaaatgtagt tgtcaagttg tcttcttttt tttggataaa aatagcagtt 5940
ggcttatgtc attcttttac aacctccatg ccacttgtcc aattgttgac acttaactaa 6000
ttagtttgat tcatgtatga atactaaata attttttagg actgactcaa atatttttat 6060
attatcatag taatatttat ctaattttta ggaccactta ttactaaata ataaattaac 6120
tactactata ttattgttgt gaaacaacaa cgttttggtt gttatgatga acactatatc 6180

-continued

```
agtatgaaaa attcaaaacg attagtataa attatattga aaatttgata tttttctatt  6240
cttaatcaga cgtattgggt ttcatatttt aaaaagggac taaacttaga agagaagttt  6300
gtttgaaact acttttgtct ctttcttgtt cccatttctc tcttagattt caaaaagtga  6360
actactttat ctctttcttt gttcacattt tattttattc tattataaat atggcatcct  6420
catattgaga tttttaatgg atcatgcaac attagcaatg atactagcca tttggttcat  6480
ttcttttcat ttcataaaat tactttttag ccaacaaact accaaacttc ttcctcctgg  6540
tccaaaacca ttgccaataa ttggtaacat cttagaagtt ggtaaaaaac cccatcgttc  6600
atttgctaat cttgctaaaa ttcacggccc tttaatatcg ttacgtctag gaagtgtaac  6660
aactattgtt gtatcatcag cagatgtagc taaagaaatg ttcttaaaaa aagaccaccc  6720
tctttctaac cgtactattc ctaattctgt cacggccggt gaccaccata aactcaccat  6780
gtcgtggttg cccgtttcgc cgaaatggcg gaattttcgt aagattacag ccgtccattt  6840
gctttctcct caaagacttg atgcttgcca aacctttcgc catgccaagg tgcaacagct  6900
ttatgaatat gtacaagaat gtgcacaaaa aggccaagct gttgatattg gcaaagctgc  6960
atttactacc tcccttaatt tgttatctaa actattcttt tcagtggaat tagcccacca  7020
taaatcacac acttctcaag agtttaagga actaatatgg aacattatgg aagatattgg  7080
gaaacctaat tatgctgatt attttcctat tttaggctgt gttgatccat caggtattcg  7140
tcgaagatta gcatgtagtt ttgacaagtt gattgcagtt tttcagggta taatatgtga  7200
aaggcttgcg cctgattctt caactacaac aacaacgacg actgatgatg tgctagacgt  7260
tcttcttcag ctcttcaaac aaaatgagct cactatgggc gagattaacc atttgctcgt  7320
cgacattttt gatgctggaa cagacactac atcaagtact tttgagtggg tcatgacaga  7380
gttaattagg aatcctgaaa tgatggaaaa ggctcaagaa gaaattaagc aagtattggg  7440
caaagataaa caaattcagg aatcagacat tattaaccta ccttacttac aagccattat  7500
caaagaaact ttgcgactac atccaccaac tgtatttctt ttgcctcgta aagccgacac  7560
tgatgttgaa ctatatggtt atattgtgcc taaagatgca caaatacttg ttaacttatg  7620
ggctattgga agagatccta atgcatggca aaatgctgat atttttttcgc ccgaaagatt  7680
tatagggtgt gaaaytgatg tcaaaggaag agattttgga ctcttacctt ttggagccgg  7740
aagaaggata tgtcctggga tgaatttggc cattagaatg ttaactttga tgctagctac  7800
tttacttcaa ttcttcaatt ggaagcttga aggagacata agtccaaaag acttagacat  7860
ggatgagaaa tttgggattg cgttacaaaa gacaaagcct ttaaaactta ttccaatacc  7920
taggtattga taataagctt cggccatgct agagtccgca aaaatcacca gtctctctct  7980
acaaatctat ctctctctat ttttctccag aataatgtgt gagtagttcc cagataaggg  8040
aattagggtt cttatagggt ttcgctcatg tgttgagcat ataagaaacc cttagtatgt  8100
atttgtattt gtaaaatact tctatcaata aaatttctaa ttcctaaaac caaaatccag  8160
tgacctcgct gtcaggaggt cgacgagtca gtaataaacg gcgtcaaagt ggttgcagcc  8220
ggcacacacg agtcgtgttt atcaactcaa agcacaaata cttttcctca acctaaaaat  8280
aaggcaatta gccaaaaaca actttgcgtg taaacaacgc tcaatacacg tgtcatttta  8340
ttattagcta ttgcttcacc gccttagctt tctcgtgacc tagtcgtcct cgtcttttct  8400
tcttcttctt ctataaaaca atacccaaag agctcttctt cttcacaatt cagatttcaa  8460
tttctcaaaa tcttaaaaac tttctctcaa ttctctctac cgtgatcaag gtaaatttct  8520
gtgttcctta ttctctcaaa atcttcgatt ttgttttcgt tcgatcccaa tttcgtatat  8580
gttctttggt ttagattctg ttaatcttag atcgaagacg attttctggg tttgatcgtt  8640
agatatcatc ttaattctcg attagggttt catagatatc atccgatttg ttcaaataat  8700
ttgagttttg tcgaataatt actcttcgat ttgtgatttc tatctagatc tggtgttagt  8760
ttctagtttg tgcgatcgaa tttgtcgatt aatctgagtt tttctgatta acagaatgac  8820
cgccattaaa atgaacacca atggtgaagg tgaaacacaa catatactaa tgataccttt  8880
catggcgcaa gggcatttac gtcctttcct tgagcttgct atgtttctat ataaacgaag  8940
tcattttatc attactcttc ttactacccc gctcaatgcg ggtttcctac gacatctcct  9000
tcaccaccat agctattcta gctcggggat cagaattgtc gagttacctt tcaactcaac  9060
caatcatggt cttccacctg gcattgaaaa cactgataaa cttacactcc cacttgtagt  9120
atcacttttt cattcaacca tttctcttga ccctcacctt agagattata tttcccgcca  9180
tttctcccct gcgcgccctc ctctgtgtgt catacatgat gtgttccttg gttgggttga  9240
tcaagttgct aaagacgtgg gctcaactgg tgttgttttt actacgggtg gcgcgtatgg  9300
tacaagcgca tatgtgtcca tttggaatga tctgcctcac cagaattact ctgatgatca  9360
agagtttccg cttcctggtt tcccggagaa tcataaattc cgacgttctc aacttcatcg  9420
gtttctgagg tatgccgatg gatcagatga ttggtcgaaa tatttccaac cgcaattgag  9480
gcaatcaatg aagagttttg gatggctatg taattcagtt gaggaaatcg aaacacttgg  9540
gtttagtatc ctcaggaact acactaaact acccatttgg ggtattggac cgttgatagc  9600
ttcacctgta caacattcat catctgataa taacagtact ggtgccgagt ttgttcaatg  9660
gttgagcttg aaagaaccag attctgtatt atacatctca tttggatcac agaacacaat  9720
ttcaccaacc cagatgatgg aactagcagc cggtttggag tcaagtgaga agccgttttt  9780
gtgggtgatt cgagcaccat ttgggttcga tatcaatgag gaaatgagrc cagaatggct  9840
accagaggga ttcgaggagc gaatgaaggt gaaaaaacaa ggaaagttgg tgtataagtt  9900
gggaccacag ttggagatac ttaaccatga gtcaatcgga gggttcttaa ctcattgtgg  9960
gtggaattcg atccttgagt cacttcgaga aggtgtgcct atgttagggt ggccattggc  10020
agccgaacaa gcttataatt tgaagtattt ggaggacgaa atgggggttg cagtcgagtt  10080
agcgagggga ttggaaggag agataagtaa agagaaagtg aagagaattg tggagatgat  10140
tttagagaga aatgaaggaa gtaaaggatg ggaaatgaaa aatagagcag tagaaatggg  10200
gaagaaactt aaagacgctg tcaatgagga gaaggaactg aagggttctt ctgttaaggc  10260
aatagatgat ttcttagatg cggtcatgca agctaagttg gaaccttctc ttcaataagc  10320
ttcggccatg ctagagtccg caaaaatcac cagtctctct ctacaaatct atctctctct  10380
atttttctcc agaataatgt gtgagtagtt cccagataag ggaattaggg ttcttatagg  10440
gtttcgctca tgtgttgagc atataagaaa cccttagtat gtatttgtat ttgtaaaata  10500
cttctatcaa taaaatttct aattcctaaa accaaaatcc agtgacctcg ctgtcatgag  10560
acgaattctg acaggatata ttggcgggta aacctaagag aaaagagcgt ttattagaat  10620
aatcggatat ttaaaagggc gtgaaaaggt ttatccgttc gtccatttgt atgtgcatgc  10680
caaccacagg gttcccctcg ggatcaaagt actttgatcc aacccctccg ctgctatagt  10740
gcagtcggct tctgacgttc agtgcagccg tcatctgaaa acgacatgtc gcacaagtcc  10800
taagttacgc gacaggctgc cgccctgccc ttttcctggc gtttcttgt cgcgtgtttt  10860
agtcgcataa agtagaatac ttgcgactag aaccggagac attacgccat gaacaagagc  10920
```

-continued

```
gccgccgctg gcctgctggg ctatgcccgc gtcagcaccg acgaccagga cttgaccaac  10980
caacgggccg aactgcacgc ggccggctgc accaagctgt tttccgagaa gatcaccggc  11040
accaggcgcg accgcccgga gctggccagg atgcttgacc acctacgccc tggcgacgtt  11100
gtgacagtga ccaggctaga ccgcctggcc cgcagcaccc gcgacctact ggacattgcc  11160
gagcgcatcc aggaggccgg cgcgggcctg cgtagcctgg cagagccgtg ggccgacacc  11220
accacgccgg ccggccgcat ggtgttgacc gtgttcgccg gcattgccga gttcgagcgt  11280
tccctaatca tcgaccgcac ccggagcggg cgcgaggccg ccaaggcccg aggcgtgaag  11340
tttggccccc gccctaccct caccccggca cagatcgcgc acgcccgcga gctgatcgac  11400
caggaaggcc gcaccgtgaa agaggcggct gcactgcttg gcgtgcatcg ctcgaccctg  11460
taccgcgcac ttgagcgcag cgaggaagtg acgcccaccg aggccaggcg gcgcggtgcc  11520
ttccgtgagg acgcattgac cgaggccgac gccctggcgg ccgccgagaa tgaacgccaa  11580
gaggaacaag catgaaaccg caccaggacg gccaggacga accgtttttc attaccgaag  11640
agatcgaggc ggagatgatc gcggccgggt acgtgttcga gccgcccgcg cacctctcaa  11700
ccgtgcggct gcatgaaatc ctggccggtt tgtctgatgc caagctggcg gcctggccgg  11760
ccagcttggc cgctgaagaa accgagcgcc gccgtctaaa aaggtgatgt gtatttgagt  11820
aaaacagctt gcgtcatgcg gtcgctgcgt atatgatccg atgagtaaat aaacaaatac  11880
gcaaggggaa cgcatgaagg ttatcgctgt acttaaccag aaaggcgggt caggcaagac  11940
gaccatcgga acccatctag cccgcgccct gcaactcgcc ggggccgatg ttctgttagt  12000
cgattccgat ccccagggca gtgcccgcga ttgggcggcc gtgcgggaag atcaaccgct  12060
aaccgttgtc ggcatcgacc gcccgacgat tgaccgcgac gtgaaggcca tcggccggcg  12120
cgacttcgta gtgatcgacg gagcgcccca ggcggcggac ttggctgtgt ccgcgatcaa  12180
ggcagccgac ttcgtgctga ttccggtgca gccaagccct tacgacatat gggccaccgc  12240
cgacctggtg gagctggtta agcagcgcat tgaggtcacg gatggaaggc tacaagcggc  12300
ctttgtcgtg tcgcgggcga tcaaaggcac gcgcatcggc ggtgaggttg ccgaggcgct  12360
ggccgggtac gagctgccca ttcttgagtc ccgtatcacg cagcgcgtga gctacccagg  12420
cactgccgcc gccggcacaa ccgttcttga atcagaaccc gagggcgacg ctgcccgcga  12480
ggtccaggcg ctggccgctg aaattaaatc aaaactcatt tgagttaatg aggtaaagag  12540
aaaatgagca aaagcacaaa cacgctaagt gccggccgtc cgagcgcacg cagcagcaag  12600
gctgcaacgt tggccagcct ggcagacacg ccagccatga agcgggtcaa ctttcagttg  12660
ccggcggagg atcacaccaa gctgaagatg tacgcggtac gccaaggcaa gaccattacc  12720
gagctgctat ctgaatagat cgcgcagcta ccagagtaaa tgagcaaatg aataaatgag  12780
tagatgaatt ttagcggcta aaggaggcgg catggaaaat caagaacaac caggcaccga  12840
cgccgtggaa tgccccatgt gtggaggaac gggcggttgg ccaggcgtaa gcggctgggt  12900
tgtctgccgg ccctgcaatg gcactggaac ccccaagccc gaggaatcgg cgtgacggtc  12960
gcaaaccatc cggcccggta caaatcggcg cggcgctggg tgatgacctg gtggagaagt  13020
tgaaggccgc gcaggccgcc cagcggcaac gcatcgaggc agaagcacgc cccggtgaat  13080
cgtggcaagc ggccgctgat cgaatccgca aagaatcccg gcaaccgccg gcagccggtg  13140
cgccgtcgat taggaagccg cccaagggcg acgagcaacc agattttttc gttccgatgc  13200
tctatgacgt gggcacccgc gatagtcgca gcatcatgga cgtggccgtt ttccgtctgt  13260
cgaagcgtga ccgacgagct ggcgaggtga tccgctacga gcttccagac gggcacgtag  13320
aggtttccgc agggccggcc ggcatggcca gtgtgtggga ttacgacctg gtactgatgg  13380
cggtttccca tctaaccgaa tccatgaacc gataccggga agggaaggga gacaagcccg  13440
gccgcgtgtt ccgtccacac gttgcggacg tactcaagtt ctgccggcga gccgatggcg  13500
gaaagcagaa agacgacctg gtagaaacct gcattcggtt aaacaccacg cacgttgcca  13560
tgcagcgtac gaagaaggcc aagaacggcc gcctggtgac ggtatccgag ggtgaagcct  13620
tgattagccg ctacaagatc gtaaagagcg aaaccgggcg gccggagtac atcgagatcg  13680
agctagctga ttggatgtac cgcgagatca cagaaggcaa gaacccggac gtgctgacgg  13740
ttcaccccga ttactttttg atcgatcccg gcatcggccg ttttctctac cgcctggcac  13800
gccgcgccgc aggcaaggca gaagccagat ggttgttcaa gacgatctac gaacgcagtg  13860
gcagcgccgg agagttcaag aagttctgtt tcaccgtgcg caagctgatc gggtcaaatg  13920
acctgccgga gtacgatttg aaggaggagg cggggcaggc tggcccgatc ctagtcatgc  13980
gctaccgcaa cctgatcgag ggcgaagcat ccgccggttc ctaatgtacg gagcagatgc  14040
tagggcaaat tgccctagca ggggaaaaag gtcgaaaagg actctttcct gtggatagca  14100
cgtacattgg gaacccaaag ccgtacattg ggaaccggaa cccgtacatt gggaacccaa  14160
agccgtacat tgggaaccgg tcacacatgt aagtgactga tataaaagag aaaaaaggcg  14220
atttttccgc ctaaaactct ttaaaactta ttaaaactct taaaacccgc ctggcctgtg  14280
cataactgtc tggccagcgc acagccgaag agctgcaaaa agcgcctacc cttcggtcgc  14340
tgcgctccct acgccccgcc gcttcgcgtc ggcctatcgc ggccgctggc cgctcaaaaa  14400
tggctggcct acggccaggc aatctaccag ggcgcggaca agccgcgccg tcgccactcg  14460
accgccggcg cccacatcaa ggcaccctgc ctcgcgcgtt tcggtgatga cggtgaaaac  14520
ctctgacaca tgcagctccc ggtgacggtc acagcttgtc tgtaagcgga tgccgggagc  14580
agacaagccc gtcagggcgc gtcagcgggt gttggcgggt gtcggggcgc agccatgacc  14640
cagtcacgta gcgatagcgg agtgtatact ggcttaacta tgcggcatca gagcagattg  14700
tactgagagt gcaccatatg cggtgtgaaa taccgcacag atgcgtaagg agaaaatacc  14760
gcatcaggcg ctcttccgct tcctcgctca ctgactcgct gcgctcggtc gttcggctgc  14820
ggcgagcggt atcagctcac tcaaaggcgg taatacggtt atccacagaa tcaggggata  14880
acgcaggaaa gaacatgtga gcaaaaggcc agcaaaaggc caggaaccgt aaaaaggccg  14940
cgttgctggc gtttttccat aggctccgcc cccctgacga gcatcacaaa aatcgacgct  15000
caagtcagag gtggcgaaac ccgacaggac tataaagata ccaggcgttt ccccctggaa  15060
gctccctcgt gcgctctcct gttccgaccc tgccgcttac cggatacctg tccgcctttc  15120
tcccttcggg aagcgtggcg ctttctcata gctcacgctg taggtatctc agttcggtgt  15180
aggtcgttcg ctccaagctg ggctgtgtgc acgaaccccc cgttcagccc gaccgctgcg  15240
ccttatccgg taactatcgt cttgagtcca acccggtaag acacgactta tcgccactgg  15300
cagcagccac tggtaacagg attagcagag cgaggtatgt aggcggtgct acagagttct  15360
tgaagtggtg gcctaactac ggctacacta gaaggacagt atttggtatc tgcgctctgc  15420
tgaagccagt taccttcgga aaaagagttg gtagctcttg atccggcaaa caaaccaccg  15480
ctggtagcgg tggttttttt gtttgcaagc agcagattac gcgcagaaaa aaaggatctc  15540
aagaagatcc tttgatcttt tctacggggt ctgacgctca gtggaacgaa aactcacgtt  15600
aagggatttt ggtcatgcat tctaggtgat tagaaaaact catcgagcat caaatgaaac  15660
```

```
tgcaatttat tcatatcagg attatcaata ccatattttt gaaaaagccg tttctgtaat  15720
gaaggagaaa actcaccgag gcagttccat aggatggcaa gatcctggta tcggtctgcg  15780
attccgactc gtccaacatc aatacaacct attaatttcc cctcgtcaaa aataaggtta  15840
tcaagtgaga aatcaccatg agtgacgact gaatccggtg agaatggcaa aagtttatgc  15900
atttctttcc agacttgttc aacaggccag ccattacgct cgtcatcaaa atcactcgca  15960
tcaaccaaac cgttattcat tcgtgattgc gcctgagcga gtcgaaatac gcgatcgctg  16020
ttaaaaggac aattacaaac aggaatcgaa tgcaaccggc gcaggaacac tgccagcgca  16080
tcaacaatat tttcacctga atcaggatat tcttctaata cctggaatgc tgttttccct  16140
gggatcgcag tggtgagtaa ccatgcatca tcaggagtac ggataaaatg cttgatggtc  16200
ggaagaggca taaattccgt cagccagttt agtctgacca tctcatctgt aacatcattg  16260
gcaacgctac ctttgccatg tttcagaaac aactctggcg catcgggctt cccatacaat  16320
cggtagattg tcgcacctga ttgcccgaca ttatcgcgag cccatttata cccatataaa  16380
tcagcatcca tgttggaatt taatcgcggc cttgagcaag acgtttcccg ttgaatatgg  16440
ctcataacag aacttattat ttccttcctc ttttctacag tatttaaaga taccccaaga  16500
agctaattat aacaagacga actccaattc actgttcctt gcattctaaa accttaaata  16560
ccagaaaaca gctttttcaa agttgttttc aaagttggcg tataacatag tatcgacgga  16620
gccgattttg aaaccgcggt gatcacaggc agcaacgctc tgtcatcgtt acaatcaaca  16680
tgctaccctc cgcgagatca tccgtgtttc aaacccggca gcttagttgc cgttcttccg  16740
aatagcatcg gtaacatgag caaagtctgc cgccttacaa cggctctccc gctgacgccg  16800
tcccggactg atgggctgcc tgtatcgagt ggtgattttg tgccgagctg ccggtcgggg  16860
agctgttggc tggctggtgg caggatatat tgtggtgtaa acataacgaa ttcgtctca   16919
```

```
SEQ ID NO: 21          moltype = DNA  length = 15191
FEATURE                Location/Qualifiers
misc_feature           1..15191
                       note = pX11(CHS)
source                 1..15191
                       mol_type = other DNA
                       organism = synthetic construct
SEQUENCE: 21
cgctgtcatg agacgaattc tgacaggata tattggcggg taaacctaag agaaaagagc  60
gtttattaga ataatcggat atttaaaagg gcgtgaaaag gtttatccgt tcgtccattt  120
gtatgtgcat gccaaccaca gggttcccct cgggatcaaa gtactttgat ccaacccctc  180
cgctgctata gtgcagtcgg cttctgacgt tcagtgcagc cgtcatctga aaacgacatg  240
tcgcacaagt cctaagttac gcgacaggct gccgccctgc ccttttcctg gcgttttctt  300
gtcgcgtgtt ttagtcgcat aaagtagaat acttgcgact agaaccggag acattacgcc  360
atgaacaaga gcgccgccgc tggcctgctg ggctatgccc gcgtcagcac cgacgaccag  420
gacttgacca accaacgggc cgaactgcac gcggccggct gcaccaagct gttttccgag  480
aagatcaccg gcaccaggcg cgaccgcccg gagctggcca ggatgcttga ccacctacgc  540
cctggcgacg ttgtgacagt gaccaggcta gaccgcctgg cccgcagcac ccgcgaccta  600
ctggacattg ccgagcgcat ccaggaggcc ggcgcgggcc tgcgtagcct ggcagagccg  660
tgggccgaca ccaccacgcc ggccggccgc atggtgttga ccgtgttcgc cggcattgcc  720
gagttcgagc gttccctaat catcgaccgc acccggagcg ggcgcgaggc cgccaaggcc  780
cgaggcgtga agtttggccc ccgccctacc ctcaccccgg cacagatcgc gcacgcccgc  840
gagctgatcg accaggaagg ccgcaccgtg aaagaggcgg ctgcactgct tggcgtgcat  900
cgctcgaccc tgtaccgcgc acttgagcgc agcgaggaag tgacgcccac cgaggccagg  960
cggcgcggtg ccttccgtga ggacgcattg accgaggccg acgccctggc ggccgccgag  1020
aatgaacgcc aagaggaaca agcatgaaac cgcaccagga cggccaggac gaaccgtttt  1080
tcattaccga agagatcgag gcggagatga tcgcggccgg gtacgtgttc gagccgcccg  1140
cgcacctctc aaccgtgcgg ctgcatgaaa tcctggccgg tttgtctgat gccaagctgg  1200
cggcctggcc ggccagcttg gccgctgaag aaaccgagcg ccgccgtcta aaaaggtgat  1260
gtgtatttga gtaaaacagc ttgcgtcatg cggtcgctgc gtatatgatc cgatgagtaa  1320
ataaacaaat acgcaagggg aacgcatgaa ggttatcgct gtacttaacc agaaaggcgg  1380
gtcaggcaag acgaccatcg gaacccatct agcccgcgcc ctgcaactcg ccggggccga  1440
tgttctgtta gtcgattccg atccccaggg cagtgcccgc gattgggcgg ccgtgcggga  1500
agatcaaccg ctaaccgttg tcggcatcga ccgcccgacg attgaccgcg acgtgaaggc  1560
catcggccgg cgcgacttcg tagtgatcga cggagcgccc caggcggcgg acttggctgt  1620
gtccgcgatc aaggcagccg acttcgtgct gattccggtg cagccaagcc cttacgacat  1680
atgggccacc gccgacctgg tggagctggt taagcagcgc attgaggtca cggatggaag  1740
gctacaagcg gcctttgtcg tgtcgcgggc gatcaaaggc acgcgcatcg gcggtgaggt  1800
tgccgaggcg ctggccgggt acgagctgcc cattcttgag tcccgtatca cgcagcgcgt  1860
gagctaccca ggcactgccg ccgccggcac aaccgttctt gaatcagaac ccgagggcga  1920
cgctgcccgc gaggtccagg cgctggccgc tgaaattaaa tcaaaactca tttgagttaa  1980
tgaggtaaag agaaaatgag caaaagcaca aacacgctaa gtgccggccg tccgagcgca  2040
cgcagcagca aggctgcaac gttggccagc ctggcagaca cgccagccat gaagcgggtc  2100
aactttcagt tgccggcgga ggatcacacc aagctgaaga tgtacgcggt acgccaaggc  2160
aagaccatta ccgagctgct atctgaatag atcgcgcagc taccagagta aatgagcaaa  2220
tgaataaatg agtagatgaa ttttagcggc taaaggaggc ggcatggaaa atcaagaaca  2280
accaggcacc gacgccgtgg aatgccccat gtgtggagga acgggcggtt ggccaggcgt  2340
aagcggctgg gttgtctgcc ggccctgcaa tggcactgga acccccaagc ccgaggaatc  2400
ggcgtgacgg tcgcaaacca tccggcccgg tacaaatcgg cgcggcgctg ggtgatgacc  2460
tggtggagaa gttgaaggcc gcgcaggccg cccagcggca acgcatcgag gcagaagcac  2520
gccccggtga atcgtggcaa gcggccgctg atcgaatccg caaagaatcc cggcaaccgc  2580
cggcagccgg tgcgccgtcg attaggaagc cgcccaaggg cgacgagcaa ccagattttt  2640
tcgttccgat gctctatgac gtgggcaccc gcgatagtcg cagcatcatg gacgtggccg  2700
ttttccgtct gtcgaagcgt gaccgacgag ctggcgaggt gatccgctac gagcttccag  2760
acgggcacgt agaggtttcc gcagggccgg ccggcatggc cagtgtgtgg gattacgacc  2820
tggtactgat ggcggtttcc catctaaccg aatccatgaa ccgataccgg gaagggaagg  2880
gagacaagcc cggccgcgtg ttccgtccac acgttgcgga cgtactcaag ttctgccggc  2940
```

```
gagccgatgg cggaaagcag aaagacgacc tggtagaaac ctgcattcgg ttaaacacca  3000
cgcacgttgc catgcagcgt acgaagaagg ccaagaacgg ccgcctggtg acggtatccg  3060
agggtgaagc cttgattagc cgctacaaga tcgtaaagag cgaaaccggg cggccggagt  3120
acatcgagat cgagctagct gattggatgt accgcgagat cacagaaggc aagaacccgg  3180
acgtgctgac ggttcacccc gattactttt tgatcgatcc cggcatcggc cgttttctct  3240
accgcctggc acgccgcgcc gcaggcaagg cagaagccag atggttgttc aagacgatct  3300
acgaacgcag tggcagcgcc ggagagttca agaagttctg tttcaccgtg cgcaagctga  3360
tcgggtcaaa tgacctgccg gagtacgatt tgaaggagga ggcggggcag gctggcccga  3420
tcctagtcat gcgctaccgc aacctgatcg agggcgaagc atccgccggt tcctaatgta  3480
cggagcagat gctagggcaa attgccctag caggggaaaa aggtcgaaaa ggactctttc  3540
ctgtggatag cacgtacatt gggaacccaa agccgtacat tgggaaccgg aacccgtaca  3600
ttgggaaccc aaagccgtac attgggaacc ggtcacacat gtaagtgact gatataaaag  3660
agaaaaaagg cgatttttcc gcctaaaact ctttaaaact tattaaaact cttaaaaccc  3720
gcctggcctg tgcataactg tctggccagc gcacagccga agagctgcaa aaagcgccta  3780
cccttcggtc gctgcgctcc ctacgccccg ccgcttcgcg tcggcctatc gcggccgctg  3840
gccgctcaaa aatggctggc ctacggccag gcaatctacc agggcgcgga caagccgcgc  3900
cgtcgccact cgaccgccgg cgcccacatc aaggcaccct gcctcgcgcg tttcggtgat  3960
gacggtgaaa acctctgaca catgcagctc ccggtgacgg tcacagcttg tctgtaagcg  4020
gatgccggga gcagacaagc ccgtcagggc gcgtcagcgg gtgttggcgg gtgtcggggc  4080
gcagccatga cccagtcacg tagcgatagc ggagtgtata ctggcttaac tatgcggcat  4140
cagagcagat tgtactgaga gtgcaccata tgcggtgtga aataccgcac agatgcgtaa  4200
ggagaaaata ccgcatcagg cgctcttccg cttcctcgct cactgactcg ctgcgctcgg  4260
tcgttcggct gcggcgagcg gtatcagctc actcaaaggc ggtaatacgg ttatccacag  4320
aatcagggga taacgcagga aagaacatgt gagcaaaagg ccagcaaaag gccaggaacc  4380
gtaaaaaggc cgcgttgctg gcgtttttcc ataggctccg cccccctgac gagcatcaca  4440
aaaatcgacg ctcaagtcag aggtggcgaa acccgacagg actataaaga taccaggcgt  4500
ttccccctgg aagctccctc gtgcgctctc ctgttccgac cctgccgctt accggatacc  4560
tgtccgcctt tctcccttcg ggaagcgtgg cgctttctca tagctcacgc tgtaggtatc  4620
tcagttcggt gtaggtcgtt cgctccaagc tgggctgtgt gcacgaaccc cccgttcagc  4680
ccgaccgctg cgccttatcc ggtaactatc gtcttgagtc caacccggta agacacgact  4740
tatcgccact ggcagcagcc actggtaaca ggattagcag agcgaggtat gtaggcggtg  4800
ctacagagtt cttgaagtgg tggcctaact acggctacac tagaaggaca gtatttggta  4860
tctgcgctct gctgaagcca gttaccttcg gaaaaagagt tggtagctct tgatccggca  4920
aacaaaccac cgctggtagc ggtggttttt ttgtttgcaa gcagcagatt acgcgcagaa  4980
aaaaaggatc tcaagaagat cctttgatct tttctacggg gtctgacgct cagtggaacg  5040
aaaactcacg ttaagggatt ttggtcatgc attctaggtg attagaaaaa ctcatcgagc  5100
atcaaatgaa actgcaattt attcatatca ggattatcaa taccatattt ttgaaaaagc  5160
cgtttctgta atgaaggaga aaactcaccg aggcagttcc ataggatggc aagatcctgg  5220
tatcggtctg cgattccgac tcgtccaaca tcaatacaac ctattaattt cccctcgtca  5280
aaaataaggt tatcaagtga gaaatcacca tgagtgacga ctgaatccgg tgagaatggc  5340
aaaagtttat gcatttcttt ccagacttgt tcaacaggcc agccattacg ctcgtcatca  5400
aaatcactcg catcaaccaa accgttattc attcgtgatt gcgcctgagc gagtcgaaat  5460
acgcgatcgc tgttaaaagg acaattacaa acaggaatcg aatgcaaccg gcgcaggaac  5520
actgccagcg catcaacaat attttcacct gaatcaggat attcttctaa tacctggaat  5580
gctgttttcc ctgggatcgc agtggtgagt aaccatgcat catcaggagt acggataaaa  5640
tgcttgatgg tcggaagagg cataaattcc gtcagccagt ttagtctgac catctcatct  5700
gtaacatcat tggcaacgct acctttgcca tgtttcagaa acaactctgg cgcatcgggc  5760
ttcccataca atcggtagat tgtcgcacct gattgcccga cattatcgcg agcccattta  5820
tacccatata aatcagcatc catgttggaa tttaatcgcg gccttgagca agacgtttcc  5880
cgttgaatat ggctcataac agaacttatt atttccttcc tcttttctac agtatttaaa  5940
gataccccaa gaagctaatt ataacaagac gaactccaat tcactgttcc ttgcattcta  6000
aaaccttaaa taccagaaaa cagctttttc aaagttgttt tcaaagttgg cgtataacat  6060
agtatcgacg gagccgattt tgaaaccgcg gtgatcacag gcagcaacgc tctgtcatcg  6120
ttacaatcaa catgctaccc tccgcgagat catccgtgtt tcaaacccgg cagcttagtt  6180
gccgttcttc cgaatagcat cggtaacatg agcaaagtct gccgccttac aacggctctc  6240
ccgctgacgc cgtcccggac tgatgggctg cctgtatcga gtggtgattt tgtgccgagc  6300
tgccggtcgg ggagctgttg gctggctggt ggcaggatat attgtggtgt aaacataacg  6360
aattcgtctc aggaggggtt tctggagttt aatgagctaa gcacatacgt cagaaaccat  6420
tattgcgcgt tcaaaagtcg cctaaggtca ctatcagcta gcaaatattt cttgtcaaaa  6480
atgctccact gacgttccat aaattcccct cggtatccaa ttagagtctc atattcactc  6540
tcaatccaaa taatctgcaa tggcaattac cttatccgca acttctttac ctatttccgc  6600
ccggatccgg gcaggttctc cggccgcttg ggtggagagg ctattcggct atgactgggc  6660
acaacagaca atcggctgct ctgatgccgc cgtgttccgg ctgtcagcgc aggggcgccc  6720
ggttcttttt gtcaagaccg acctgtccgg tgccctgaat gaactgcagg acgaggcagc  6780
gcggctatcg tggctggcca cgacgggcgt tccttgcgca gctgtgctcg acgttgtcac  6840
tgaagcggga agggactggc tgctattggg cgaagtgccg gggcaggatc tcctgtcatc  6900
tcaccttgct cctgccgaga aagtatccat catggctgat gcaatgcggc ggctgcatac  6960
gcttgatccg gctacctgcc cattcgacca ccaagcgaaa catcgcatcg agcgagcacg  7020
tactcggatg gaagccggtc ttgtcgatca ggatgatctg gacgaagagc atcaggggct  7080
cgcgccagcc gaactgttcg ccaggctcaa ggcgcgcatg cccgacggcg aggatctcgt  7140
cgtgacccat ggcgatgcct gcttgccgaa tatcatggtg gaaaatggcc gcttttctgg  7200
attcatcgac tgtggccggc tgggtgtggc ggaccgctat caggacatag cgttggctac  7260
ccgtgatatt gctgaagagc ttggcggcga atgggctgac cgcttcctcg tgctttacgg  7320
tatcgccgct cccgattcgc agcgcatcgc cttctatcgc cttcttgacg agttcttctg  7380
agcgggactc tggggttcga aatgaccgac caagcgacgc ccaacctgcc atcacgagat  7440
ttcgattcca ccgccgcctt ctatgaaagg ttgggcttcg gaatcgtttt ccgggacgcc  7500
ggctggatga tcctccagcg cggggatctc atgctggagt tcttcgccca ccccgatcca  7560
acacttacgt ttgcaacgtc caagagcaaa tagaccacga acgccggaag gttgccgcag  7620
cgtgtggatt gcgtctcaat tctctcttgc aggaatgcaa tgatgaatat gatactgact  7680
```

```
atgaaacttt gagggaatac tgcctagcac cgtcacctca taacgtgcat catgcatgcc  7740
ctgacaacat ggaacatcgc tatttttctg aagaattatg ctcgttggag gatgtcgcgg  7800
caattgcagc tattgccaac atcgaactac ccctcacgca tgcattcatc aatattattc  7860
atgcggggaa aggcaagatt aatccaactg gcaaatcatc cagcgtgatt ggtaacttca  7920
gttccagcga cttgattcgt tttggtgcta cccacgtttt caataaggac gagatggtgg  7980
agtaaagaag gagtgcgtcg aagcagatcg ttcaaacatt tggcaataaa gtttcttaag  8040
attgaatcct gttgccggtc ttgcgatgat tatcatataa tttctgttga attacgttaa  8100
gcatgtaata attaacatgt aatgcatgac gttatttatg agatgggttt ttatgattag  8160
agtcccgcaa ttatacattt aatacgcgat agaaaacaaa atatagcgcg caaactagga  8220
taaattatcg cgcgcggtgt catctatgtt actagatcga cgctgtcagg agactagagc  8280
caagctgatc tcctttgccc cggagatcac catggacgac tttctctatc tctacgatct  8340
aggaagaaag ttcgacggag aaggtgacga taccatgttc accaccgata atgagaagat  8400
tagcctcttc aatttcagaa agaatgctga cccacagatg gttagagagg cctacgcggc  8460
aggtctgatc aagacgatct acccgagtaa taatctccag gagatcaaat accttcccaa  8520
gaaggttaaa gatgcagtca aaagattcag gactaactgc atcaagaaca cagagaaaga  8580
tatatttctc aagatcagaa gtactattcc agtatggacg attcaaggct tgcttcataa  8640
accaaggcaa gtaatagaga ttggagtctc taagaaagta gttcctactg aatcaaaggc  8700
catggagtca aaaattcaga tcgaggatct aacagaactc gccgtgaaga ctggcgaaca  8760
gttcatacag agtcttttac gactcaatga caagaagaaa atcttcgtca acatggtgga  8820
gcacgacact ctcgtctact ccaagaatat caaagataca gtctcagaag accaaagggc  8880
tattgagact tttcaacaaa gggtaatatc gggaaacctc ctcggattcc attgcccagc  8940
tatctgtcac ttcatcaaaa ggacagtaga aaaggaaggt ggcacctaca aatgccatca  9000
ttgcgataaa ggaaaggcta tcgttcaaga tgcctctgcc gacagtggtc ccaaagatgg  9060
acccccaccc acgaggagca tcgtggaaaa agaagacgtt ccaaccacgt cttcaaagca  9120
agtggattga tgtgatatct ccactgacgt aagggatgac gcacaatccc actatccttc  9180
gcaagaccct tcctctatat aaggaagttc atttcatttg gagaggactc cggtattttt  9240
acaacaatac cacaacaaaa caaacaacaa acaacattac aatttactat tctagtcgaa  9300
atgaaaatga tgaatggtga agatgctaat gatcaaatga tcaaagaaag cttcttcata  9360
acacatggaa acccaatatt aacagtagaa gacacacatc cattaagacc tttctttgaa  9420
acttggagag agaaaatctt ttctaagaaa cctaaggcaa ttcttattat ttctggtcat  9480
tgggaaactg ttaaacctac tgttaatgct gtccatatca atgatactat ccatgatttt  9540
gatgactatc ctgctgctat gtaccagttc aagtatccag ctcctgggga accagaattg  9600
gcaagaaaag tagaggaaat tctgaaaaaa tcgggtttcg aaacggcgga aactgatcaa  9660
aaacgtgggc ttgatcatgg tgcatgggta cctctaatgc taatgtatcc tgaggctgat  9720
ataccagtat gtcagctctc agttcagccg catttagatg gaacatacca ttacaactta  9780
ggacgagcat tggctccctt gaaaaacgac ggcgtattaa tcattggttc aggaagtgca  9840
actcaccctt tggatgaaac tcctcattat tttgatggag ttgcaccttg ggcagctgcc  9900
tttgattcat ggcttcgtaa agctctcatt aatggaaggt ttgaagaagt gaatatatat  9960
gaaagcaaag caccaaattg gaaattagca catcctttcc cagaacattt ttatccattg  10020
catgttgttc ttggcgctgc tggtgaaaaa tggaaggcag agcttattca tagcagttgg  10080
gatcatggca ccttgtgtca tggctcctac aagttcactt cagcctaggc ttggaatgga  10140
tcttcgatcc cgatcgttca aacatttggc aataaagttt cttaagattg aatcctgttg  10200
ccggtcttgc gacgattatc atataatttc tgttgaatta cgttaagcat gtaataatta  10260
acatgtaatg catgacgtta tttatgagat gggtttttat gattagagtc ccgcaattat  10320
acatttaata cgcgatagaa aacaaaatat agcgcgcaaa ctaggataaa ttatcgcgcd  10380
cggtgtcatc tatgttacta gatcgggaat tgccaagcta attcttgaag acgaaagggc  10440
ctcgtgatac gcctattttt ataggttaat gtcatgataa taatggtttc ttagacgtca  10500
ggtggcactt ttcggggaaa tgtgcgcgga acccctattt gtttattttt ctaaatacat  10560
tcaaatatgt atccgctcat gagacaataa ccctgataaa tgcttcaata atgggaccga  10620
ctcgcgctgt caggaggtgc actgtcaaat tatgtcataa attctaatga gatgagttta  10680
tatagcattt acaaattcaa atacttaaaa aggatactac aatttggtat tacgtgtcaa  10740
attcctgttc aaagctgatg ctagaggtga cagaaatcat atgcaagaac gtcaaggcca  10800
ttcattttgg ttcaacagat tgatgaaaaa tctaagagcc tttgatcttg agaagtaggt  10860
aaccattaat ttgtgttgaa ggtttgctac gaaaataaaa aggatgtcac gtgccatcaa  10920
gttatagcta cacgtgatta ctatctacca ttctccttta gggttctcgt ataaatactc  10980
tacaatcccc atgcaaacca taacacaata taaaagatac ttacacttgt cacgtactac  11040
ataaaaaaaa aaaaatacca aactttttc aagcaaaaaa tggatcatgc aacattagca  11100
atgatactag ccatttggtt catttctttt catttcataa aattactttt tagccaacaa  11160
actaccaaac ttcttcctcc tggtccaaaa ccattgccaa taattggtaa catcttagaa  11220
gttggtaaaa aaccccatcg ttcatttgct aatcttgcta aaattcacgg ccctttaata  11280
tcgttacgtc taggaagtgt aacaactatt gttgtatcat cagcagatgt agctaaagaa  11340
atgttcttaa aaaaagacca ccctctttct aaccgtacta ttcctaattc tgtcacggcc  11400
ggtgaccacc ataaactcac catgtcgtgg ttgcccgttt cgccgaaatg gcggaatttt  11460
cgtaagatta cagccgtcca tttgctttct cctcaaagac ttgatgcttg ccaaaccttt  11520
cgccatgcca aggtgcaaca gctttatgaa tatgtacaag aatgtgcaca aaaaggccaa  11580
gctgttgata ttggcaaagc tgcatttact acctccctta atttgttatc taaactattc  11640
ttttcagtgg aattagccca ccataaatca cacacttctc aagagtttaa ggaactaata  11700
tggaacatta tggaagatat tgggaaacct aattatgctg attattttcc tattttaggc  11760
tgtgttgatc catcaggtat tcgtcgaaga ttagcatgta gttttgacaa gttgattgca  11820
gtttttcagg gtataatatg tgaaaggctt gcgcctgatt cttcaactac aacaacaacg  11880
acgactgatg atgtgctaga cgttcttctt cagctcttca aacaaaatga gctcactatg  11940
ggcgagatta accatttgct cgtcgacatt tttgatgctg gaacagacac tacatcaagt  12000
acttttgagt gggtcatgac agagttaatt aggaatcctg aaatgatgga aaaggctcaa  12060
gaagaaatta agcaagtatt gggcaaagat aaacaaattc aggaatcaga cattattaac  12120
ctaccttact tacaagccat tatcaaagaa actttgcgac tacatccacc aactgtattt  12180
cttttgcctc gtaaagccga cactgatgtt gaactatatg gttatattgt gcctaaagat  12240
gcacaaatac ttgttaactt atgggctatt ggaagagatc ctaatgcatg gcaaaatgct  12300
gatatttttt cgcccgaaag atttataggg tgtgaaaytg atgtcaaagg aagagatttt  12360
ggactcttac cttttggagc cggaagaagg atatgtcctg ggatgaattt ggccattaga  12420
```

```
atgttaactt tgatgctagc tactttactt caattcttca attggaagct tgaaggagac  12480
ataagtccaa aagacttaga catggatgag aaatttggga ttgcgttaca aaagacaaag  12540
cctttaaaac ttattccaat acctaggtat tgataataag cttcggccat gctagagtcc  12600
gcaaaaatca ccagtctctc tctacaaatc tatctctctc tatttttctc cagaataatg  12660
tgtgagtagt tcccagataa gggaattagg gttcttatag ggtttcgctc atgtgttgag  12720
catataagaa acccttagta tgtatttgta tttgtaaaat acttctatca ataaaatttc  12780
taattcctaa aaccaaaatc cagtgacctc gctgtcagga ggtcgacgag tcagtaataa  12840
acggcgtcaa agtggttgca gccggcacac acgagtcgtg tttatcaact caaagcacaa  12900
atacttttcc tcaacctaaa aataaggcaa ttagccaaaa acaactttgc gtgtaaacaa  12960
cgctcaatac acgtgtcatt ttattattag ctattgcttc accgccttag ctttctcgtg  13020
acctagtcgt cctcgtcttt tcttcttctt cttctataaa acaataccca aagagctctt  13080
cttcttcaca attcagattt caatttctca aaatcttaaa aactttctct caattctctc  13140
taccgtgatc aaggtaaatt tctgtgttcc ttattctctc aaaatcttcg attttgtttt  13200
cgttcgatcc caatttcgta tatgttcttt ggtttagatt ctgttaatct tagatcgaag  13260
acgattttct gggtttgatc gttagatatc atcttaattc tcgattaggg tttcatagat  13320
atcatccgat ttgttcaaat aatttgagtt ttgtcgaata attactcttc gatttgtgat  13380
ttctatctag atctggtgtt agtttctagt ttgtgcgatc gaatttgtcg attaatctga  13440
gtttttctga ttaacagaat gaccgccatt aaaatgaaca ccaatggtga aggtgaaaca  13500
caacatatac taatgatacc tttcatggcg caagggcatt tacgtccttt ccttgagctt  13560
gctatgtttc tatataaacg aagtcatttt atcattactc ttcttactac cccgctcaat  13620
gcgggtttcc tacgacatct ccttcaccac catagctatt ctagctcggg gatcagaatt  13680
gtcgagttac ctttcaactc aaccaatcat ggtcttccac ctggcattga aaacactgat  13740
aaacttacac tcccacttgt agtatcactt tttcattcaa ccatttctct tgaccctcac  13800
cttagagatt atatttcccg ccatttctcc cctgcgcgcc ctcctctgtg tgtcatacat  13860
gatgtgttcc ttggttgggt tgatcaagtt gctaaagacg tgggctcaac tggtgttgtt  13920
tttactacgg gtggcgcgta tggtacaagc gcatatgtgt ccatttggaa tgatctgcct  13980
caccagaatt actctgatga tcaagagttt ccgcttcctg gtttcccgga gaatcataaa  14040
ttccgacgtt ctcaacttca tcggtttctg aggtatgccg atggatcaga tgattggtcg  14100
aaatatttcc aaccgcaatt gaggcaatca atgaagagtt ttggatggct atgtaattca  14160
gttgaggaaa tcgaaacact tgggtttagt atcctcagga actacactaa actacccatt  14220
tggggtattg gaccgttgat agcttcacct gtacaacatt catcatctga taataacagt  14280
actggtgccg agtttgttca atggttgagc ttgaaagaac cagattctgt attatacatc  14340
tcatttggat cacagaacac aatttcacca acccagatga tggaactagc agccggtttg  14400
gagtcaagtg agaagccgtt tttgtgggtg attcgagcac catttgggtt cgatatcaat  14460
gaggaaatga grccagaatg gctaccagag ggattcgagg agcgaatgaa ggtgaaaaaa  14520
caaggaaagt tggtgtataa gttgggacca cagttggaga tacttaacca tgagtcaatc  14580
ggagggttct taactcattg tgggtggaat tcgatccttg agtcacttcg agaaggtgtg  14640
cctatgttag ggtggccatt ggcagccgaa caagcttata atttgaagta tttggaggac  14700
gaaatggggg ttgcagtcga gttagcgagg ggattggaag gagagataag taaagagaaa  14760
gtgaagagaa ttgtggagat gattttagag agaaatgaag gaagtaaagg atgggaaatg  14820
aaaaatagag cagtagaaat ggggaagaaa cttaaagacg ctgtcaatga ggagaaggaa  14880
ctgaagggtt cttctgttaa ggcaatagat gatttcttag atgcggtcat gcaagctaag  14940
ttggaacctt ctcttcaata agcttcggcc atgctagagt ccgcaaaaat caccagtctc  15000
tctctacaaa tctatctctc tctatttttc tccagaataa tgtgtgagta gttcccagat  15060
aagggaatta gggttcttat agggtttcgc tcatgtgttg agcatataag aaacccttag  15120
tatgtatttg tatttgtaaa atacttctat caataaaatt tctaattcct aaaaccaaaa  15180
tccagtgacc t                                                       15191

SEQ ID NO: 22          moltype = DNA  length = 19745
FEATURE                Location/Qualifiers
misc_feature           1..19745
                       note = pX12
source                 1..19745
                       mol_type = other DNA
                       organism = synthetic construct
SEQUENCE: 22
cgctgtcatg agaccggatc ctgacaggat atattggcgg gtaaacctaa gagaaaagag  60
cgtttattag aataatcgga tatttaaaag ggcgtgaaaa ggtttatccg ttcgtccatt  120
tgtatgtgca tgccaaccac agggttcccc tcgggatcaa agtactttga tccaacccct  180
ccgctgctat agtgcagtcg gcttctgacg ttcagtgcag ccgtcatctg aaaacgacat  240
gtcgcacaag tcctaagtta cgcgacaggc tgccgccctg ccctttttcct ggcgttttct  300
tgtcgcgtgt tttagtcgca taaagtagaa tacttgcgac tagaaccgga gacattacgc  360
catgaacaag agcgccgccg ctggcctgct gggctatgcc cgcgtcagca ccgacgacca  420
ggacttgacc aaccaacggg ccgaactgca cgcggccggc tgcaccaagc tgttttccga  480
gaagatcacc ggcaccaggc gcgaccgccc ggagctggcc aggatgcttg accacctacg  540
ccctggcgac gttgtgacag tgaccaggct agaccgcctg gcccgcagca cccgcgacct  600
actggacatt gccgagcgca tccaggaggc cggcgcgggc ctgcgtagcc tggcagagcc  660
gtgggccgac accaccacgc cggccggccg catggtgttg accgtgttcg ccggcattgc  720
cgagttcgag cgttccctaa tcatcgaccg cacccggagc gggcgcgagg ccgccaaggc  780
ccgaggcgtg aagtttggcc cccgccctac cctcaccccg gcacagatcg cgcacgcccg  840
cgagctgatc gaccaggaag gccgcaccgt gaaagaggcg gctgcactgc ttggcgtgca  900
tcgctcgacc ctgtaccgcg cacttgagcg cagcgaggaa gtgacgccca ccgaggccag  960
gcggcgcggt gccttccgtg aggacgcatt gaccgaggcc gacgccctgg cggccgccga  1020
gaatgaacgc caagaggaac aagcatgaaa ccgcaccagg acggccagga cgaaccgttt  1080
ttcattaccg aagagatcga ggcggagatg atcgcggccg ggtacgtgtt cgagccgccc  1140
gcgcacctct caaccgtgcg gctgcatgaa atcctggccg gtttgtctga tgccaagctg  1200
gcggcctggc cggccagctt ggccgctgaa gaaaccgagc gccgccgtct aaaaaggtga  1260
tgtgtatttg agtaaaacag cttgcgtcat gcggtcgctg cgtatatgat ccgatgagta  1320
aataaacaaa tacgcaaggg gaacgcatga aggttatcgc tgtacttaac cagaaaggcg  1380
```

```
ggtcaggcaa gacgaccatc ggaacccatc tagcccgcgc cctgcaactc gccggggccg  1440
atgttctgtt agtcgattcc gatccccagg gcagtgcccg cgattgggcg gccgtgcggg  1500
aagatcaacc gctaaccgtt gtcggcatcg accgcccgac gattgaccgc gacgtgaagg  1560
ccatcggccg gcgcgacttc gtagtgatcg acggagcgcc ccaggcggcg gacttggctg  1620
tgtccgcgat caaggcagcc gacttcgtgc tgattccggt gcagccaagc ccttacgaca  1680
tatgggccac cgccgacctg gtggagctgg ttaagcagcg cattgaggtc acggatggaa  1740
ggctacaagc ggcctttgtc gtgtcgcggg cgatcaaagg cacgcgcatc ggcggtgagg  1800
ttgccgaggc gctggccggg tacgagctgc ccattcttga gtcccgtatc acgcagcgcg  1860
tgagctaccc aggcactgcc gccgccggca caaccgttct tgaatcagaa cccgagggcg  1920
acgctgcccg cgaggtccag gcgctggccg ctgaaattaa atcaaaactc atttgagtta  1980
atgaggtaaa gagaaaatga gcaaaagcac aaacacgcta agtgccggcc gtccgagcgc  2040
acgcagcagc aaggctgcaa cgttggccag cctggcagac acgccagcca tgaagcgggt  2100
caactttcag ttgccggcgg aggatcacac caagctgaag atgtacgcgg tacgccaagg  2160
caagaccatt accgagctgc tatctgaata gatcgcgcag ctaccagagt aaatgagcaa  2220
atgaataaat gagtagatga attttagcgg ctaaaggagg cggcatggaa aatcaagaac  2280
aaccaggcac cgacgccgtg gaatgcccca tgtgtggagg aacgggcggt tggccaggcg  2340
taagcggctg ggttgtctgc cggccctgca atggcactgg aacccccaag cccgaggaat  2400
cggcgtgacg gtcgcaaacc atccggcccg gtacaaatcg gcgcggcgct gggtgatgac  2460
ctggtggaga agttgaaggc cgcgcaggcc gcccagcggc aacgcatcga ggcagaagca  2520
cgccccggtg aatcgtggca agcggccgct gatcgaatcc gcaaagaatc ccggcaaccg  2580
ccggcagccg gtgcgccgtc gattaggaag ccgcccaagg gcgacgagca accagatttt  2640
ttcgttccga tgctctatga cgtgggcacc cgcgatagtc gcagcatcat ggacgtggcc  2700
gttttccgtc tgtcgaagcg tgaccgacga gctggcgagg tgatccgcta cgagcttcca  2760
gacgggcacg tagaggtttc cgcagggccg gccggcatgg ccagtgtgtg ggattacgac  2820
ctggtactga tggcggtttc ccatctaacc gaatccatga accgataccg ggaagggaag  2880
ggagacaagc ccggccgcgt gttccgtcca cacgttgcgg acgtactcaa gttctgccgg  2940
cgagccgatg gcggaaagca gaaagacgac ctggtagaaa cctgcattcg gttaaacacc  3000
acgcacgttg ccatgcagcg tacgaagaag gccaagaacg gccgcctggt gacggtatcc  3060
gagggtgaag ccttgattag ccgctacaag atcgtaaaga gcgaaaccgg gcggccggag  3120
tacatcgaga tcgagctagc tgattggatg taccgcgaga tcacagaagg caagaacccg  3180
gacgtgctga cggttcaccc cgattacttt ttgatcgatc ccggcatcgg ccgttttctc  3240
taccgcctgg cacgccgcgc cgcaggcaag gcagaagcca gatggttgtt caagacgatc  3300
tacgaacgca gtggcagcgc cggagagttc aagaagttct gtttcaccgt gcgcaagctg  3360
atcgggtcaa atgacctgcc ggagtacgat ttgaaggagg aggcggggca ggctggcccg  3420
atcctagtca tgcgctaccg caacctgatc gagggcgaag catccgccgg ttcctaatgt  3480
acggagcaga tgctagggca aattgcccta gcaggggaaa aaggtcgaaa aggactcttt  3540
cctgtggata gcacgtacat tgggaaccca aagccgtaca ttgggaaccg gaacccgtac  3600
attgggaacc caaagccgta cattgggaac cggtcacaca tgtaagtgac tgatataaaa  3660
gagaaaaaag gcgatttttc cgcctaaaac tctttaaaac ttattaaaac tcttaaaacc  3720
cgcctggcct gtgcataact gtctggccag cgcacagccg aagagctgca aaaagcgcct  3780
acccttcggt cgctgcgctc cctacgcccc gccgcttcgc gtcggcctat cgcggccgct  3840
ggccgctcaa aaatggctgg cctacggcca ggcaatctac cagggcgcgg acaagccgcg  3900
ccgtcgccac tcgaccgccg gcgcccacat caaggcaccc tgcctcgcgc gtttcggtga  3960
tgacggtgaa aacctctgac acatgcagct cccggtgacg gtcacagctt gtctgtaagc  4020
ggatgccggg agcagacaag cccgtcaggg cgcgtcagcg ggtgttggcg ggtgtcgggg  4080
cgcagccatg acccagtcac gtagcgatag cggagtgtat actggcttaa ctatgcggca  4140
tcagagcaga ttgtactgag agtgcaccat atgcggtgtg aaataccgca cagatgcgta  4200
aggagaaaat accgcatcag gcgctcttcc gcttcctcgc tcactgactc gctgcgctcg  4260
gtcgttcggc tgcggcgagc ggtatcagct cactcaaagg cggtaatacg gttatccaca  4320
gaatcagggg ataacgcagg aaagaacatg tgagcaaaag gccagcaaaa ggccaggaac  4380
cgtaaaaagg ccgcgttgct ggcgtttttc cataggctcc gcccccctga cgagcatcac  4440
aaaaatcgac gctcaagtca gaggtggcga aacccgacag gactataaag ataccaggcg  4500
tttccccctg gaagctccct cgtgcgctct cctgttccga ccctgccgct taccggatac  4560
ctgtccgcct ttctcccttc gggaagcgtg gcgctttctc atagctcacg ctgtaggtat  4620
ctcagttcgg tgtaggtcgt tcgctccaag ctgggctgtg tgcacgaacc ccccgttcag  4680
cccgaccgct gcgccttatc cggtaactat cgtcttgagt ccaacccggt aagacacgac  4740
ttatcgccac tggcagcagc cactggtaac aggattagca gagcgaggta tgtaggcggt  4800
gctacagagt tcttgaagtg gtggcctaac tacggctaca ctagaaggac agtatttggt  4860
atctgcgctc tgctgaagcc agttaccttc ggaaaaagag ttggtagctc ttgatccggc  4920
aaacaaacca ccgctggtag cggtggtttt tttgtttgca agcagcagat tacgcgcaga  4980
aaaaaaggat ctcaagaaga tcctttgatc ttttctacgg ggtctgacgc tcagtggaac  5040
gaaaactcac gttaagggat tttggtcatg cattctaggt gattatttgc cgactacctt  5100
ggtgatctcg cctttcacgt agtggacaaa ttcttccaac tgatctgcgc gcgaggccaa  5160
gcgatcttct tcttgtccaa gataagcctg tctagcttca agtatgacgg gctgatactg  5220
ggccggcagg cgctccattg cccagtcggc agcgacatcc ttcggcgcga ttttgccggt  5280
tactgcgctg taccaaatgc gggacaacgt aagcactaca tttcgctcat caccagccca  5340
gtcgggcggc gagttccata gcgttaaggt ttcatttagc gcctcaaata gatcctgttc  5400
aggaaccgga tcaaagagtt cctccgccgc tggacctacc aaggcaacgc tatgttctct  5460
tgcttttgtc agcaagatag ccagatcaat gtcgatcgtg gctggctcga agatacctgc  5520
aagaatgtca ttgcgctgcc attctccaaa ttgcagttcg cgcttagctg gataacgcca  5580
cggaatgatg tcgtcgtgca caacaatggt gacttctaca gcgcggagaa tctcgctctc  5640
tccaggggaa gccgaagttt ccaaaaggtc gttgatcaaa gctcgccgcg ttgtttcatc  5700
aagccttacg gtcaccgtaa ccagcaaatc aatatcactg tgtggcttca ggccgccatc  5760
cactgcggag ccgtacaaat gtacggccag caacgtcggt tcgagatggc gctcgatgac  5820
gccaactacc tctgatagtt gagtcgatac ttcggcgatc accgcttccc tcataatgtt  5880
taactttgtt ttagggcgac tgccctgctg cgtaacatcg ttgctgctcc ataacatcaa  5940
acatcgaccc acggcgtaac gcgcttgctg cttggatgcc cgaggcatag actgtacccc  6000
aaaaaaacag tcataacaag ccatgaaaac cgccactgcg ccgttaccac cgctgcgttc  6060
ggtcaaggtt ctggaccagt tgcgtgagcg catacgctac ttgcattaca gcttacgaac  6120
```

-continued

```
cgaacaggct tatgtccact gggttcgtgc cttcatccgt ttccacggtg tgcgtcaccc  6180
ggcaaccttg ggtagcagcg aagtcgaggc atttctgtcc tggctggaac agaacttatt  6240
atttccttcc tcttttctac agtatttaaa gataccccaa gaagctaatt ataacaagac  6300
gaactccaat tcactgttcc ttgcattcta aaaccttaaa taccagaaaa cagctttttc  6360
aaagttgttt tcaaagttgg cgtataacat agtatcgacg gagccgattt tgaaaccgcg  6420
gtgatcacag gcagcaacgc tctgtcatcg ttacaatcaa catgctaccc tccgcgagat  6480
catccgtgtt tcaaacccgg cagcttagtt gccgttcttc cgaatagcat cggtaacatg  6540
agcaaagtct gccgccttac aacggctctc ccgctgacgc cgtcccggac tgatgggctg  6600
cctgtatcga gtggtgattt tgtgccgagc tgccggtcgg ggagctgttg gctggctggt  6660
ggcaggatat attgtggtgt aaacataacg gatccggtct caggagagcg tcgatctagt  6720
aacatagatg acaccgcgcg cgataattta tcctagtttg cgcgctatat tttgttttct  6780
atcgcgtatt aaatgtataa ttgcgggact ctaatcataa aaacccatct cataaataac  6840
gtcatgcatt acatgttaat tattacatgc ttaacgtaat tcaacagaaa ttatatgata  6900
atcatcgcaa gaccggcaac aggattcaat cttaagaaac tttattgcca aatgtttgaa  6960
cgatctgctt cgacgcactc cttctttact ccaccatctc gtccttattg aaaacgtggg  7020
tagcaccaaa acgaatcaag tcgctggaac tgaagttacc aatcacgctg gatgatttgc  7080
cagttggatt aatcttgcct ttccccgcat gaataatatt gatgaatgca tgcgtgaggg  7140
gtagttcgat gttggcaata gctgcaattg ccgcgacatc ctccaacgag cataattctt  7200
cagaaaaata gcgatgttcc atgttgtcag ggcatgcatg atgcacgtta tgaggtgacg  7260
gtgctaggca gtattccctc aaagtttcat agtcagtatc atattcatca ttgcattcct  7320
gcaagagaga attgagacgc aatccacacg ctgcggcaac cttccggcgt tcgtggtcta  7380
tttgctcttg gacgttgcaa acgtaagtgt tggatcgggg tgggcgaaga actccagcat  7440
gagatccccg cgctggagga tcatccagcc ggcgtcccgg aaaacgattc cgaagcccaa  7500
cctttcatag aaggcggcgg tggaatcgaa atctcgtgat ggcaggttgg gcgtcgcttg  7560
gtcggtcatt tcgaacccca gagtcccgct cagaagaact cgtcaagaag gcgatagaag  7620
gcgatgcgct gcgaatcggg agcggcgata ccgtaaagca cgaggaagcg gtcagcccat  7680
tcgccgccaa gctcttcagc aatatcacgg gtagccaacg ctatgtcctg atagcggtcc  7740
gccacaccca gccggccaca gtcgatgaat ccagaaaagc ggccattttc caccatgata  7800
ttcggcaagc aggcatcgcc atgggtcacg acgagatcct cgccgtcggg catgcgcgcc  7860
ttgagcctgg cgaacagttc ggctggcgcg agcccctgat gctcttcgtc cagatcatcc  7920
tgatcgacaa gaccggcttc catccgagta cgtgctcgct cgatgcgatg tttcgcttgg  7980
tggtcgaatg ggcaggtagc cggatcaagc gtatgcagcc gccgcattgc atcagccatg  8040
atggatactt tctcggcagg agcaaggtga gatgacagga gatcctgccc cggcacttcg  8100
cccaatagca gccagtccct tcccgcttca gtgacaacgt cgagcacagc tgcgcaagga  8160
acgcccgtcg tggccagcca cgatagccgc gctgcctcgt cctgcagttc attcagggca  8220
ccggacaggt cggtcttgac aaaaagaacc gggcgcccct gcgctgacag ccggaacacg  8280
gcggcatcag agcagccgat tgtctgttgt gcccagtcat agccgaatag cctctccacc  8340
caagcggccg gagaacctgc ccggatccgg gcggaaatag gtaaagaagt tgcggataag  8400
gtaattgcca ttgcagatta tttggattga gagtgaatat gagactctaa ttggataccg  8460
aggggaattt atggaacgtc agtggagcat ttttgacaag aaatatttgc tagctgatag  8520
tgaccttagg cgacttttga acgcgcaata atggtttctg acgtatgtgc ttagctcatt  8580
aaactccaga aacccctccg tcaggagact agagccaagc tgatctcctt tgccccggag  8640
atcaccatgg acgactttct ctatctctac gatctaggaa gaaagttcga cggagaaggt  8700
gacgatacca tgttcaccac cgataatgag aagattagcc tcttcaattt cagaaagaat  8760
gctgacccac agatggttag agaggcctac gcggcaggtc tgatcaagac gatctacccg  8820
agtaataatc tccaggagat caaatacctt cccaagaagg ttaaagatgc agtcaaaaga  8880
ttcaggacta actgcatcaa gaacacagag aaagatatat ttctcaagat cagaagtact  8940
attccagtat ggacgattca aggcttgctt cataaaccaa ggcaagtaat agagattgga  9000
gtctctaaga aagtagttcc tactgaatca aaggccatgg agtcaaaaat tcagatcgag  9060
gatctaacag aactcgccgt gaagactggc gaacagttca tacagagtct tttacgactc  9120
aatgacaaga agaaaatctt cgtcaacatg gtggagcacg acactctcgt ctactccaag  9180
aatatcaaag atacagtctc agaagaccaa agggctattg agacttttca acaaagggta  9240
atatcgggaa acctcctcgg attccattgc ccagctatct gtcacttcat caaaaggaca  9300
gtagaaaagg aaggtggcac ctacaaatgc catcattgcg ataaaggaaa ggctatcgtt  9360
caagatgcct ctgccgacag tggtcccaaa gatggacccc cacccacgag gagcatcgtg  9420
gaaaaagaag acgttccaac cacgtcttca aagcaagtgg attgatgtga tatctccact  9480
gacgtaaggg atgacgcaca atcccactat ccttcgcaag acccttcctc tatataagga  9540
agttcatttc atttggagag gactccggta tttttacaac aataccacaa caaaacaaac  9600
aacaaacaac attacaattt actattctag tcgaaatgaa aatgatgaat ggtgaagatg  9660
ctaatgatca aatgatcaaa gaaagcttct tcataacaca tggaaaccca atattaacag  9720
tagaagacac acatccatta agacctttct ttgaaacttg gagagagaaa atcttttcta  9780
agaaacctaa ggcaattctt attatttctg gtcattggga aactgttaaa cctactgtta  9840
atgctgtcca tatcaatgat actatccatg attttgatga ctatcctgct gctatgtacc  9900
agttcaagta tccagctcct ggggaaccag aattggcaag aaaagtagag gaaattctga  9960
aaaaatcggg tttcgaaacg gcggaaactg atcaaaaacg tgggcttgat catggtgcat  10020
gggtacctct aatgctaatg tatcctgagg ctgatatacc agtatgtcag ctctcagttc  10080
agccgcattt agatggaaca taccattaca acttaggacg agcattggct cccttgaaaa  10140
acgacggcgt attaatcatt ggttcaggaa gtgcaactca ccctttggat gaaactcctc  10200
attattttga tggagttgca ccttgggcag ctgcctttga ttcatggctt cgtaaagctc  10260
tcattaatgg aaggtttgaa gaagtgaata tatatgaaag caaagcacca aattggaaat  10320
tagcacatcc tttcccagaa catttttatc cattgcatgt tgttcttggc gctgctggtg  10380
aaaaatggaa ggcagagctt attcatagca gttgggatca tggcaccttg tgtcatggct  10440
cctacaagtt cacttcagcc taggcttgga atggatcttc gatcccgatc gttcaaacat  10500
ttggcaataa agtttcttaa gattgaatcc tgttgccggt cttgcgacga ttatcatata  10560
atttctgttg aattacgtta agcatgtaat aattaacatg taatgcatga cgttatttat  10620
gagatgggtt tttatgatta gagtcccgca attatacatt taatacgcga tagaaaacaa  10680
aatatagcgc gcaaactagg ataaattatc gcgcdcggtg tcatctatgt tactagatcg  10740
ggaattgcca agctaattct tgaagacgaa agggcctcgt gatacgccta tttttatagg  10800
ttaatgtcat gataataatg gtttcttaga cgtcaggtgg cacttttcgg ggaaatgtgc  10860
```

```
gcggaacccc tatttgttta tttttctaaa tacattcaaa tatgtatccg ctcatgagac  10920
aataaccctg ataaatgctt caataatggg accgactcgc gctgtcagga gactagagcc  10980
aagctgatct cctttgcccc ggagatcacc atggacgact ttctctatct ctacgatcta  11040
ggaagaaagt tcgacggaga aggtgacgat accatgttca ccaccgataa tgagaagatt  11100
agcctcttca atttcagaaa gaatgctgac ccacagatgg ttagagaggc ctacgcggca  11160
ggtctgatca agacgatcta cccgagtaat aatctccagg agatcaaata ccttcccaag  11220
aaggttaaag atgcagtcaa aagattcagg actaactgca tcaagaacac agagaaagat  11280
atatttctca agatcagaag tactattcca gtatggacga ttcaaggctt gcttcataaa  11340
ccaaggcaag taatagagat tggagtctct aagaaagtag ttcctactga atcaaaggcc  11400
atggagtcaa aaattcagat cgaggatcta acagaactcg ccgtgaagac tggcgaacag  11460
ttcatacaga gtcttttacg actcaatgac aagaagaaaa tcttcgtcaa catggtggag  11520
cacgacactc tcgtctactc caagaatatc aaagatacag tctcagaaga ccaaagggct  11580
attgagactt ttcaacaaag ggtaatatcg ggaaacctcc tcggattcca ttgcccagct  11640
atctgtcact tcatcaaaag gacagtagaa aaggaaggtg gcacctacaa atgccatcat  11700
tgcgataaag gaaaggctat cgttcaagat gcctctgccg acagtggtcc caaagatgga  11760
cccccaccca cgaggagcat cgtggaaaaa gaagacgttc caaccacgtc ttcaaagcaa  11820
gtggattgat gtgatatctc cactgacgta agggatgacg cacaatccca ctatccttcg  11880
caagaccctt cctctatata aggaagttca tttcatttgg agaggactcc ggtattttta  11940
caacaatacc acaacaaaac aaacaacaaa caacattaca atttactatt ctagtcgaaa  12000
tggatcatgc aacattagca atgatactag ccatttggtt catttctttt catttcataa  12060
aattactttt tagccaacaa actaccaaac ttcttcctcc tggtccaaaa ccattgccaa  12120
taattggtaa catcttagaa gttggtaaaa aaccccatcg ttcatttgct aatcttgcta  12180
aaattcacgg ccctttaata tcgttacgtc taggaagtgt aacaactatt gttgtatcat  12240
cagcagatgt agctaaagaa atgttcttaa aaaaagacca ccctctttct aaccgtacta  12300
ttcctaattc tgtcacggcc ggtgaccacc ataaactcac catgtcgtgg ttgcccgttt  12360
cgccgaaatg gcggaatttt cgtaagatta cagccgtcca tttgctttct cctcaaagac  12420
ttgatgcttg ccaaaccttt cgccatgcca aggtgcaaca gctttatgaa tatgtacaag  12480
aatgtgcaca aaaaggccaa gctgttgata ttggcaaagc tgcatttact acctccctta  12540
atttgttatc taaactattc ttttcagtgg aattagccca ccataaatca cacacttctc  12600
aagagtttaa ggaactaata tggaacatta tggaagatat tgggaaacct aattatgctg  12660
attattttcc tattttaggc tgtgttgatc catcaggtat tcgtcgaaga ttagcatgta  12720
gttttgacaa gttgattgca gtttttcagg gtataatatg tgaaaggctt gcgcctgatt  12780
cttcaactac aacaacaacg acgactgatg atgtgctaga cgttcttctt cagctcttca  12840
aacaaaatga gctcactatg ggcgagatta accatttgct cgtcgacatt tttgatgctg  12900
gaacagacac tacatcaagt acttttgagt gggtcatgac agagttaatt aggaatcctg  12960
aaatgatgga aaaggctcaa gaagaaatta agcaagtatt gggcaaagat aaacaaattc  13020
aggaatcaga cattattaac ctaccttact tacaagccat tatcaaagaa actttgcgac  13080
tacatccacc aactgtattt cttttgcctc gtaaagccga cactgatgtt gaactatatg  13140
gttatattgt gcctaaagat gcacaaatac ttgttaactt atgggctatt ggaagagatc  13200
ctaatgcatg gcaaaatgct gatatttttt cgcccgaaag atttataggg tgtgaaaytg  13260
atgtcaaagg aagagatttt ggactcttac cttttggagc cggaagaagg atatgtcctg  13320
ggatgaattt ggccattaga atgttaactt tgatgctagc tactttactt caattcttca  13380
attggaagct tgaaggagac ataagtccaa aagacttaga catggatgag aaatttggga  13440
ttgcgttaca aaagacaaag cctttaaaac ttattccaat acctaggtat tgataataag  13500
cttgctctca agatcaaagg cttaaaaagc tggggtttta tgaatgggat caaagtttct  13560
tttttctttt tatatttgct tctccatttg tttgtttcat ttcccttttt gtttcgtttt  13620
ctatgatgca cttgtgtgtg acaaactctc tgggttttta cttacgtctg cgtttcaaaa  13680
aaaaaaaccg ctttcgtttt gcgttttagt cccattgttt tgtagctctg agtgatcgaa  13740
ttgatgcctc tttattcctt ttgttcccta taatttcttt caaaactcag aagaaaaacc  13800
ttgaaactct ttgcaatgtt aatataagta ttgtataaga tttttattga tttggttatt  13860
agtcttactt ttgctacctc catcttcact tggaactgat attctgaata gttaaagcgt  13920
tacatgtctt ccattcacaa atgaacttaa actagcacaa agtcagatat tttaagatcg  13980
caccatttta tataacccca atcgtcaatt ctactgtttc aagttttaca ccaaaacaat  14040
tacgaggtgt atctattcgt tactcttttc gcttattaat ccttttacat gatgcaaaat  14100
ataacaaatt aatttcaaat tgtcctgcac atttggttta tacatcttga ttccaaaaag  14160
tcgctgtcag gaggtcgacg agtcagtaat aaacggcgtc aaagtggttg cagccggcac  14220
acacgagtcg tgtttatcaa ctcaaagcac aaatactttt cctcaaccta aaaataaggc  14280
aattagccaa aaacaacttt gcgtgtaaac aacgctcaat acacgtgtca ttttattatt  14340
agctattgct tcaccgcctt agctttctcg tgacctagtc gtcctcgtct tttcttcttc  14400
ttcttctata aaacaatacc caaagagctc ttcttcttca caattcagat ttcaatttct  14460
caaaatctta aaaactttct ctcaattctc tctaccgtga tcaaggtaaa tttctgtgtt  14520
ccttattctc tcaaaatctt cgattttgtt ttcgttcgat cccaatttcg tatatgttct  14580
ttggtttaga ttctgttaat cttagatcga agacgatttt ctgggtttga tcgttagata  14640
tcatcttaat tctcgattag ggtttcatag atatcatccg atttgttcaa ataatttgag  14700
ttttgtcgaa taattactct tcgatttgtg atttctatct agatctggtg ttagtttcta  14760
gtttgtgcga tcgaatttgt cgattaatct gagtttttct gattaacaga atgaccgcca  14820
ttaaaatgaa caccaatggt gaaggtgaaa cacaacatat actaatgata cctttcatgg  14880
cgcaagggca tttacgtcct ttccttgagc ttgctatgtt tctatataaa cgaagtcatt  14940
ttatcattac tcttcttact accccgctca atgcgggttt cctacgacat ctccttcacc  15000
accatagcta ttctagctcg gggatcagaa ttgtcgagtt acctttcaac tcaaccaatc  15060
atggtcttcc acctggcatt gaaaacactg ataaacttac actcccactt gtagtatcac  15120
tttttcattc aaccatttct cttgaccctc accttagaga ttatatttcc cgccatttct  15180
cccctgcgcg ccctcctctg tgtgtcatac atgatgtgtt ccttggttgg gttgatcaag  15240
ttgctaaaga cgtgggctca actggtgttg tttttactac gggtggcgcg tatggtacaa  15300
gcgcatatgt gtccatttgg aatgatctgc ctcaccagaa ttactctgat gatcaagagt  15360
ttccgcttcc tggtttcccg gagaatcata aattccgacg ttctcaactt catcggtttc  15420
tgaggtatgc cgatggatca gatgattggt cgaaatattt ccaaccgcaa ttgaggcaat  15480
caatgaagag ttttggatgg ctatgtaatt cagttgagga aatcgaaaca cttgggttta  15540
gtatcctcag gaactacact aaactaccca tttggggtat tggaccgttg atagcttcac  15600
```

```
ctgtacaaca ttcatcatct gataataaca gtactggtgc cgagtttgtt caatggttga  15660
gcttgaaaga accagattct gtattataca tctcatttgg atcacagaac acaatttcac  15720
caacccagat gatggaacta gcagccggtt tggagtcaag tgagaagccg tttttgtggg  15780
tgattcgagc accatttggg ttcgatatca atgaggaaat gagrccagaa tggctaccag  15840
agggattcga ggagcgaatg aaggtgaaaa aacaaggaaa gttggtgtat aagttgggac  15900
cacagttgga gatacttaac catgagtcaa tcggagggtt cttaactcat tgtgggtgga  15960
attcgatcct tgagtcactt cgagaaggtg tgcctatgtt agggtggcca ttggcagccg  16020
aacaagctta taatttgaag tatttggagg acgaaatggg ggttgcagtc gagttagcga  16080
ggggattgga aggagagata agtaaagaga aagtgaagag aattgtggag atgattttag  16140
agagaaatga aggaagtaaa ggatgggaaa tgaaaaatag agcagtagaa atggggaaga  16200
aacttaaaga cgctgtcaat gaggagaagg aactgaaggg ttcttctgtt aaggcaatag  16260
atgatttctt agatgcggtc atgcaagcta agttggaacc ttctcttcaa taagcttcgg  16320
ccatgctaga gtccgcaaaa atcaccagtc tctctctaca aatctatctc tctctatttt  16380
tctccagaat aatgtgtgag tagttcccag ataagggaat tagggttctt atagggtttc  16440
gctcatgtgt tgagcatata agaaaccctt agtatgtatt tgtatttgta aaatacttct  16500
atcaataaaa tttctaattc ctaaaaccaa aatccagtga cctcgctgtc aggagactag  16560
agccaagctg atctcctttg ccccggagat caccatggac gactttctct atctctacga  16620
tctaggaaga aagttcgacg gagaaggtga cgataccatg ttcaccaccg ataatgagaa  16680
gattagcctc ttcaatttca gaaagaatgc tgacccacag atggttagag aggcctacgc  16740
ggcaggtctg atcaagacga tctacccgag taataatctc caggagatca aataccttcc  16800
caagaaggtt aaagatgcag tcaaaagatt caggactaac tgcatcaaga acacagagaa  16860
agatatattt ctcaagatca gaagtactat tccagtatgg acgattcaag gcttgcttca  16920
taaaccaagg caagtaatag agattggagt ctctaagaaa gtagttccta ctgaatcaaa  16980
ggccatggag tcaaaaattc agatcgagga tctaacagaa ctcgccgtga agactggcga  17040
acagttcata cagagtcttt tacgactcaa tgacaagaag aaaatcttcg tcaacatggt  17100
ggagcacgac actctcgtct actccaagaa tatcaaagat acagtctcag aagaccaaag  17160
ggctattgag acttttcaac aaagggtaat atcgggaaac ctcctcggat tccattgccc  17220
agctatctgt cacttcatca aaaggacagt agaaaaggaa ggtggcacct acaaatgcca  17280
tcattgcgat aaaggaaagg ctatcgttca agatgcctct gccgacagtg gtcccaaaga  17340
tggaccccca cccacgagga gcatcgtgga aaaagaagac gttccaacca cgtcttcaaa  17400
gcaagtggat tgatgtgata tctccactga cgtaagggat gacgcacaat cccactatcc  17460
ttcgcaagac ccttcctcta tataaggaag ttcatttcat ttggagagga ctccggtatt  17520
tttacaacaa taccacaaca aaacaaacaa caaacaacat tacaatttac tattctagtc  17580
gaaatggata acgcaacact tgctgtgatc ctttccattt tgtttgtgtt ttaccacatt  17640
ttcaaatcct ttttcaccaa ttcttcatct cgtaggcttc ctcctggtcc caaacccgtg  17700
ccaatttttg gcaacatttt cgatcttggc gaaaagcctc atcgatcttt tgccaatcta  17760
tctaaaattc acggcccttt gattagccta aagttaggaa gtgtaacaac tattgttgtt  17820
tcctcggcct ctgtggccga ggaaatgttc cttaaaaatg accaagcact tgctaaccga  17880
accattcctg actcggttag ggctggtgac cacgacaaat tatccatgtc gtggttgcct  17940
gtttcccaaa aatggagaaa tatgagaaaa atctccgctg tccaattact ctccaaccaa  18000
aaacttgatg ctagtcaacc tcttagacaa gctaaggtga aacaactttt atcatacgta  18060
caagtttgtt ccgaaaaaat gcaacccgtc gatattggac gggccgcatt tacaacgtca  18120
cttaatttat tatcaaacac atttttctca atcgaattag caagtcatga atctagtgct  18180
tcccaagagt ttaaacaact catgtggaat attatggagg aaattggaag gcctaattat  18240
gctgattttt tccctattct tggttacatt gatcccttttg gtataagacg tcgtttggct  18300
ggttactttg ataaactcat tgatgttttc caagacatta ttcgtgaaag acaaaagctt  18360
cgatcttcta attcttccgg cgcaaaacaa acaaatgaca ttcttgatac tcttcttaaa  18420
ctccatgaag ataatgagtt gagtatgcct gaaattaatc accttctcgt ggatatcttt  18480
gacgccggaa cagacacaac agcaagcaca ttagaatggg caatggccga acttgtgaaa  18540
aacccggaaa tgatgactaa agttcaaatt gaaatcgaac aagctcttgg aaaagattgc  18600
ttagacatac aagaatccga catctcaaaa ctaccttatt tacaagccat tataaaagaa  18660
acgttacgtt tacaccctcc tactgtgttt ttgctgcctc gaaaggcaga caatgacgta  18720
gagttatatg gctacgttgt accaaagaat gctcaagtcc ttgtcaatct ttgggcaatt  18780
ggtcgtgatc caaaggtatg gaaaaatccg gaagtatttt ctcctgaaag gtttttagat  18840
tgcaatatcg attataaagg acgagatttc gaacttttac cctttggtgc tggtagaagg  18900
atatgccctg gacttacttt ggcatataga atgttgaact tgatgttggc tactcttctt  18960
caaaactaca attggaaact tgaagatggt atcaatccta aggatttaga catggatgag  19020
aaatttggga ttacattgca aaaggttaaa cctcttcaag ttattccagt tcccagaaac  19080
taggcttgct ctcaagatca aaggcttaaa aagctggggt tttatgaatg ggatcaaagt  19140
ttcttttttt cttttatatt tgcttctcca tttgtttgtt tcatttccct ttttgttttc  19200
gtttctatga tgcacttgtg tgtgacaaac tctctgggtt tttacttacg tctgcgtttc  19260
aaaaaaaaaa accgctttcg ttttgcgttt tagtcccatt gttttgtagc tctgagtgat  19320
cgaattgatg cctctttatt ccttttgttc cctataattt ctttcaaaac tcagaagaaa  19380
aaccttgaaa ctctttgcaa tgttaatata agtattgtat aagattttta ttgatttggt  19440
tattagtctt acttttgcta cctccatctt cacttggaac tgatattctg aatagttaaa  19500
gcgttacatg tcttccattc acaaatgaac ttaaactagc acaaagtcag atattttaag  19560
atcgcaccat tttatataac cccaatcgtc aattctactg tttcaagttt tacaccaaaa  19620
caattacgag gtgtatctat tcgttactct tttcgcttat taatcctttt acatgatgca  19680
aaatataaca aattaatttc aaattgtcct gcacatttgg tttatacatc ttgattccaa  19740
aaagt                                                              19745
```

```
SEQ ID NO: 23           moltype = DNA  length = 13992
FEATURE                 Location/Qualifiers
misc_feature            1..13992
                        note = pX13
source                  1..13992
                        mol_type = other DNA
                        organism = synthetic construct
SEQUENCE: 23
```

-continued

```
cgctgtcatg agacgaattc tgacaggata tattggcggg taaacctaag agaaaagagc  60
gtttattaga ataatcggat atttaaaagg gcgtgaaaag gtttatccgt tcgtccattt  120
gtatgtgcat gccaaccaca gggttcccct cgggatcaaa gtactttgat ccaacccctc  180
cgctgctata gtgcagtcgg cttctgacgt tcagtgcagc cgtcatctga aaacgacatg  240
tcgcacaagt cctaagttac gcgacaggct gccgccctgc ccttttcctg gcgttttctt  300
gtcgcgtgtt ttagtcgcat aaagtagaat acttgcgact agaaccggag acattacgcc  360
atgaacaaga gcgccgccgc tggcctgctg ggctatgccc gcgtcagcac cgacgaccag  420
gacttgacca accaacgggc cgaactgcac gcggccggct gcaccaagct gttttccgag  480
aagatcaccg gcaccaggcg cgaccgcccg gagctggcca ggatgcttga ccacctacgc  540
cctggcgacg ttgtgacagt gaccaggcta gaccgcctgg cccgcagcac ccgcgaccta  600
ctggacattg ccgagcgcat ccaggaggcc ggcgcgggcc tgcgtagcct ggcagagccg  660
tgggccgaca ccaccacgcc ggccggccgc atggtgttga ccgtgttcgc cggcattgcc  720
gagttcgagc gttccctaat catcgaccgc acccggagcg ggcgcgaggc cgccaaggcc  780
cgaggcgtga agtttggccc ccgccctacc ctcaccccgg cacagatcgc gcacgcccgc  840
gagctgatcg accaggaagg ccgcaccgtg aaagaggcgg ctgcactgct tggcgtgcat  900
cgctcgaccc tgtaccgcgc acttgagcgc agcgaggaag tgacgcccac cgaggccagg  960
cggcgcggtg ccttccgtga ggacgcattg accgaggccg acgccctggc ggccgccgag  1020
aatgaacgcc aagaggaaca agcatgaaac cgcaccagga cggccaggac gaaccgtttt  1080
tcattaccga agagatcgag gcggagatga tcgcggccgg gtacgtgttc gagccgcccg  1140
cgcacctctc aaccgtgcgg ctgcatgaaa tcctggccgg tttgtctgat gccaagctgg  1200
cggcctggcc ggccagcttg gccgctgaag aaaccgagcg ccgccgtcta aaaaggtgat  1260
gtgtatttga gtaaaacagc ttgcgtcatg cggtcgctgc gtatatgatc cgatgagtaa  1320
ataaacaaat acgcaagggg aacgcatgaa ggttatcgct gtacttaacc agaaaggcgg  1380
gtcaggcaag acgaccatcg gaacccatct agcccgcgcc ctgcaactcg ccggggccga  1440
tgttctgtta gtcgattccg atccccaggg cagtgcccgc gattgggcgg ccgtgcggga  1500
agatcaaccg ctaaccgttg tcggcatcga ccgcccgacg attgaccgcg acgtgaaggc  1560
catcggccgg cgcgacttcg tagtgatcga cggagcgccc caggcggcgg acttggctgt  1620
gtccgcgatc aaggcagccg acttcgtgct gattccggtg cagccaagcc cttacgacat  1680
atgggccacc gccgacctgg tggagctggt taagcagcgc attgaggtca cggatggaag  1740
gctacaagcg gcctttgtcg tgtcgcgggc gatcaaaggc acgcgcatcg gcggtgaggt  1800
tgccgaggcg ctggccgggt acgagctgcc cattcttgag tcccgtatca cgcagcgcgt  1860
gagctaccca ggcactgccg ccgccggcac aaccgttctt gaatcagaac ccgagggcga  1920
cgctgcccgc gaggtccagg cgctggccgc tgaaattaaa tcaaaactca tttgagttaa  1980
tgaggtaaag agaaaatgag caaaagcaca aacacgctaa gtgccggccg tccgagcgca  2040
cgcagcagca aggctgcaac gttggccagc ctggcagaca cgccagccat gaagcgggtc  2100
aactttcagt tgccggcgga ggatcacacc aagctgaaga tgtacgcggt acgccaaggc  2160
aagaccatta ccgagctgct atctgaatag atcgcgcagc taccagagta aatgagcaaa  2220
tgaataaatg agtagatgaa ttttagcggc taaaggaggc ggcatggaaa atcaagaaca  2280
accaggcacc gacgccgtgg aatgccccat gtgtggagga acgggcggtt ggccaggcgt  2340
aagcggctgg gttgtctgcc ggccctgcaa tggcactgga acccccaagc ccgaggaatc  2400
ggcgtgacgg tcgcaaacca tccggcccgg tacaaatcgg cgcggcgctg ggtgatgacc  2460
tggtggagaa gttgaaggcc gcgcaggccg cccagcggca acgcatcgag gcagaagcac  2520
gccccggtga atcgtggcaa gcggccgctg atcgaatccg caaagaatcc cggcaaccgc  2580
cggcagccgg tgcgccgtcg attaggaagc cgcccaaggg cgacgagcaa ccagattttt  2640
tcgttccgat gctctatgac gtgggcaccc gcgatagtcg cagcatcatg gacgtggccg  2700
ttttccgtct gtcgaagcgt gaccgacgag ctggcgaggt gatccgctac gagcttccag  2760
acgggcacgt agaggtttcc gcagggccgg ccggcatggc cagtgtgtgg gattacgacc  2820
tggtactgat ggcggtttcc catctaaccg aatccatgaa ccgataccgg gaagggaagg  2880
gagacaagcc cggccgcgtg ttccgtccac acgttgcgga cgtactcaag ttctgccggc  2940
gagccgatgg cggaaagcag aaagacgacc tggtagaaac ctgcattcgg ttaaacacca  3000
cgcacgttgc catgcagcgt acgaagaagg ccaagaacgg ccgcctggtg acggtatccg  3060
agggtgaagc cttgattagc cgctacaaga tcgtaaagag cgaaaccggg cggccggagt  3120
acatcgagat cgagctagct gattggatgt accgcgagat cacagaaggc aagaacccgg  3180
acgtgctgac ggttcacccc gattactttt tgatcgatcc cggcatcggc cgttttctct  3240
accgcctggc acgccgcgcc gcaggcaagg cagaagccag atggttgttc aagacgatct  3300
acgaacgcag tggcagcgcc ggagagttca agaagttctg tttcaccgtg cgcaagctga  3360
tcgggtcaaa tgacctgccg gagtacgatt tgaaggagga ggcggggcag gctggcccga  3420
tcctagtcat gcgctaccgc aacctgatcg agggcgaagc atccgccggt tcctaatgta  3480
cggagcagat gctagggcaa attgccctag caggggaaaa aggtcgaaaa ggactctttc  3540
ctgtggatag cacgtacatt gggaacccaa agccgtacat tgggaaccgg aacccgtaca  3600
ttgggaaccc aaagccgtac attgggaacc ggtcacacat gtaagtgact gatataaaag  3660
agaaaaaagg cgatttttcc gcctaaaact ctttaaaact tattaaaact cttaaaaccc  3720
gcctggcctg tgcataactg tctggccagc gcacagccga agagctgcaa aaagcgccta  3780
cccttcggtc gctgcgctcc ctacgccccg ccgcttcgcg tcggcctatc gcggccgctg  3840
gccgctcaaa aatggctggc ctacggccag gcaatctacc agggcgcgga caagccgcgc  3900
cgtcgccact cgaccgccgg cgcccacatc aaggcaccct gcctcgcgcg tttcggtgat  3960
gacggtgaaa acctctgaca catgcagctc ccggtgacgg tcacagcttg tctgtaagcg  4020
gatgccggga gcagacaagc ccgtcagggc gcgtcagcgg gtgttggcgg gtgtcggggc  4080
gcagccatga cccagtcacg tagcgatagc ggagtgtata ctggcttaac tatgcggcat  4140
cagagcagat tgtactgaga gtgcaccata tgcggtgtga aataccgcac agatgcgtaa  4200
ggagaaaata ccgcatcagg cgctcttccg cttcctcgct cactgactcg ctgcgctcgg  4260
tcgttcggct gcggcgagcg gtatcagctc actcaaaggc ggtaatacgg ttatccacag  4320
aatcagggga taacgcagga aagaacatgt gagcaaaagg ccagcaaaag gccaggaacc  4380
gtaaaaaggc cgcgttgctg gcgtttttcc ataggctccg cccccctgac gagcatcaca  4440
aaaatcgacg ctcaagtcag aggtggcgaa acccgacagg actataaaga taccaggcgt  4500
ttccccctgg aagctccctc gtgcgctctc ctgttccgac cctgccgctt accggatacc  4560
tgtccgcctt tctcccttcg ggaagcgtgg cgctttctca tagctcacgc tgtaggtatc  4620
tcagttcggt gtaggtcgtt cgctccaagc tgggctgtgt gcacgaaccc cccgttcagc  4680
ccgaccgctg cgccttatcc ggtaactatc gtcttgagtc caacccggta agacacgact  4740
```

```
tatcgccact ggcagcagcc actggtaaca ggattagcag agcgaggtat gtaggcggtg  4800
ctacagagtt cttgaagtgg tggcctaact acggctacac tagaaggaca gtatttggta  4860
tctgcgctct gctgaagcca gttaccttcg gaaaaagagt tggtagctct tgatccggca  4920
aacaaaccac cgctggtagc ggtggttttt ttgtttgcaa gcagcagatt acgcgcagaa  4980
aaaaaggatc tcaagaagat cctttgatct tttctacggg gtctgacgct cagtggaacg  5040
aaaactcacg ttaagggatt ttggtcatgc attctaggtg attagaaaaa ctcatcgagc  5100
atcaaatgaa actgcaattt attcatatca ggattatcaa taccatattt ttgaaaaagc  5160
cgtttctgta atgaaggaga aaactcaccg aggcagttcc ataggatggc aagatcctgg  5220
tatcggtctg cgattccgac tcgtccaaca tcaatacaac ctattaattt cccctcgtca  5280
aaaataaggt tatcaagtga gaaatcacca tgagtgacga ctgaatccgg tgagaatggc  5340
aaaagtttat gcatttcttt ccagacttgt tcaacaggcc agccattacg ctcgtcatca  5400
aaatcactcg catcaaccaa accgttattc attcgtgatt gcgcctgagc gagtcgaaat  5460
acgcgatcgc tgttaaaagg acaattacaa acaggaatcg aatgcaaccg gcgcaggaac  5520
actgccagcg catcaacaat attttcacct gaatcaggat attcttctaa tacctggaat  5580
gctgttttcc ctgggatcgc agtggtgagt aaccatgcat catcaggagt acggataaaa  5640
tgcttgatgg tcggaagagg cataaattcc gtcagccagt ttagtctgac catctcatct  5700
gtaacatcat tggcaacgct acctttgcca tgtttcagaa acaactctgg cgcatcgggc  5760
ttcccataca atcggtagat tgtcgcacct gattgcccga cattatcgcg agcccattta  5820
tacccatata aatcagcatc catgttggaa tttaatcgcg gccttgagca agacgtttcc  5880
cgttgaatat ggctcataac agaacttatt atttccttcc tcttttctac agtatttaaa  5940
gataccccaa gaagctaatt ataacaagac gaactccaat tcactgttcc ttgcattcta  6000
aaaccttaaa taccagaaaa cagcttttttc aaagttgttt tcaaagttgg cgtataacat  6060
agtatcgacg gagccgattt tgaaaccgcg gtgatcacag gcagcaacgc tctgtcatcg  6120
ttacaatcaa catgctaccc tccgcgagat catccgtgtt tcaaacccgg cagcttagtt  6180
gccgttcttc cgaatagcat cggtaacatg agcaaagtct gccgccttac aacggctctc  6240
ccgctgacgc cgtcccggac tgatgggctg cctgtatcga gtggtgattt tgtgccgagc  6300
tgccggtcgg ggagctgttg gctggctggt ggcaggatat attgtggtgt aaacataacg  6360
aattcgtctc aggagagcgt cgatctagta acatagatga caccgcgcgc gataatttat  6420
cctagtttgc gcgctatatt ttgttttcta tcgcgtatta aatgtataat tgcgggactc  6480
taatcataaa aacccatctc ataaataacg tcatgcatta catgttaatt attacatgct  6540
taacgtaatt caacagaaat tatatgataa tcatcgcaag accggcaaca ggattcaatc  6600
ttaagaaact ttattgccaa atgtttgaac gatctgcttc gacgcactcc ttctttactc  6660
caccatctcg tccttattga aaacgtgggt agcaccaaaa cgaatcaagt cgctggaact  6720
gaagttacca atcacgctgg atgatttgcc agttggatta atcttgcctt tccccgcatg  6780
aataatattg atgaatgcat gcgtgagggg tagttcgatg ttggcaatag ctgcaattgc  6840
cgcgacatcc tccaacgagc ataattcttc agaaaaatag cgatgttcca tgttgtcagg  6900
gcatgcatga tgcacgttat gaggtgacgg tgctaggcag tattccctca aagtttcata  6960
gtcagtatca tattcatcat tgcattcctg caagagagaa ttgagacgca atccacacgc  7020
tgcggcaacc ttccggcgtt cgtggtctat ttgctcttgg acgttgcaaa cgtaagtgtt  7080
ggatcggggt gggcgaagaa ctccagcatg agatccccgc gctggaggat catccagccg  7140
gcgtcccgga aaacgattcc gaagcccaac ctttcataga aggcggcggt ggaatcgaaa  7200
tctcgtgatg gcaggttggg cgtcgcttgg tcggtcattt cgaaccccag agtcccgctc  7260
agaagaactc gtcaagaagg cgatagaagg cgatgcgctg cgaatcggga gcggcgatac  7320
cgtaaagcac gaggaagcgg tcagcccatt cgccgccaag ctcttcagca atatcacggg  7380
tagccaacgc tatgtcctga tagcggtccg ccacacccag ccggccacag tcgatgaatc  7440
cagaaaagcg gccattttcc accatgatat tcggcaagca ggcatcgcca tgggtcacga  7500
cgagatcctc gccgtcgggc atgcgcgcct tgagcctggc gaacagttcg gctggcgcga  7560
gcccctgatg ctcttcgtcc agatcatcct gatcgacaag accggcttcc atccgagtac  7620
gtgctcgctc gatgcgatgt ttcgcttggt ggtcgaatgg gcaggtagcc ggatcaagcg  7680
tatgcagccg ccgcattgca tcagccatga tggatacttt ctcggcagga gcaaggtgag  7740
atgacaggag atcctgcccc ggcacttcgc ccaatagcag ccagtccctt cccgcttcag  7800
tgacaacgtc gagcacagct gcgcaaggaa cgcccgtcgt ggccagccac gatagccgcg  7860
ctgcctcgtc ctgcagttca ttcagggcac cggacaggtc ggtcttgaca aaaagaaccg  7920
ggcgcccctg cgctgacagc cggaacacgg cggcatcaga gcagccgatt gtctgttgtg  7980
cccagtcata gccgaatagc ctctccaccc aagcggccgg agaacctgcc cggatccggg  8040
cggaaatagg taaagaagtt gcggataagg taattgccat tgcagattat ttggattgag  8100
agtgaatatg agactctaat tggataccga ggggaattta tggaacgtca gtggagcatt  8160
tttgacaaga aatatttgct agctgatagt gaccttaggc gacttttgaa cgcgcaataa  8220
tggtttctga cgtatgtgct tagctcatta aactccagaa acccctccgt caggagacta  8280
gagccaagct gatctccttt gccccggaga tcaccatgga cgactttctc tatctctacg  8340
atctaggaag aaagttcgac ggagaaggtg acgataccat gttcaccacc gataatgaga  8400
agattagcct cttcaatttc agaaagaatg ctgacccaca gatggttaga gaggcctacg  8460
cggcaggtct gatcaagacg atctacccga gtaataatct ccaggagatc aaataccttc  8520
ccaagaaggt taaagatgca gtcaaaagat tcaggactaa ctgcatcaag aacacagaga  8580
aagatatatt tctcaagatc agaagtacta ttccagtatg gacgattcaa ggcttgcttc  8640
ataaaccaag gcaagtaata gagattggag tctctaagaa agtagttcct actgaatcaa  8700
aggccatgga gtcaaaaatt cagatcgagg atctaacaga actcgccgtg aagactggcg  8760
aacagttcat acagagtctt ttacgactca atgacaagaa gaaaatcttc gtcaacatgg  8820
tggagcacga cactctcgtc tactccaaga atatcaaaga tacagtctca gaagaccaaa  8880
gggctattga gacttttcaa caaagggtaa tatcgggaaa cctcctcgga ttccattgcc  8940
cagctatctg tcacttcatc aaaaggacag tagaaaagga aggtggcacc tacaaatgcc  9000
atcattgcga taaaggaaag gctatcgttc aagatgcctc tgccgacagt ggtcccaaag  9060
atggaccccc acccacgagg agcatcgtgg aaaaagaaga cgttccaacc acgtcttcaa  9120
agcaagtgga ttgatgtgat atctccactg acgtaaggga tgacgcacaa tcccactatc  9180
cttcgcaaga cccttcctct atataaggaa gttcatttca tttggagagg actccggtat  9240
ttttacaaca ataccacaac aaaacaaaca acaaacaaca ttacaattta ctattctagt  9300
cgaaatgaaa atgatgaatg gtgaagatgc taatgatcaa atgatcaaag aaagcttctt  9360
cataacacat ggaaacccaa tattaacagt agaagacaca catccattaa gacctttctt  9420
tgaaacttgg agagagaaaa tcttttctaa gaaacctaag gcaattctta ttatttctgg  9480
```

```
tcattgggaa actgttaaac ctactgttaa tgctgtccat atcaatgata ctatccatga  9540
ttttgatgac tatcctgctg ctatgtacca gttcaagtat ccagctcctg gggaaccaga  9600
attggcaaga aaagtagagg aaattctgaa aaaatcgggt ttcgaaacgg cggaaactga  9660
tcaaaaacgt gggcttgatc atggtgcatg ggtacctcta atgctaatgt atcctgaggc  9720
tgatatacca gtatgtcagc tctcagttca gccgcattta gatggaacat accattacaa  9780
cttaggacga gcattggctc ccttgaaaaa cgacggcgta ttaatcattg gttcaggaag  9840
tgcaactcac cctttggatg aaactcctca ttattttgat ggagttgcac cttgggcagc  9900
tgcctttgat tcatggcttc gtaaagctct cattaatgga aggtttgaag aagtgaatat  9960
atatgaaagc aaagcaccaa attggaaatt agcacatcct ttcccagaac atttttatcc  10020
attgcatgtt gttcttggcg ctgctggtga aaaatggaag gcagagctta ttcatagcag  10080
ttgggatcat ggcaccttgt gtcatggctc ctacaagttc acttcagcct aggcttggaa  10140
tggatcttcg atcccgatcg ttcaaacatt tggcaataaa gtttcttaag attgaatcct  10200
gttgccggtc ttgcgacgat tatcatataa tttctgttga attacgttaa gcatgtaata  10260
attaacatgt aatgcatgac gttatttatg agatgggttt ttatgattag agtcccgcaa  10320
ttatacattt aatacgcgat agaaaacaaa atatagcgcg caaactagga taaattatcg  10380
cgcdcggtgt catctatgtt actagatcgg gaattgccaa gctaattctt gaagacgaaa  10440
gggcctcgtg atacgcctat ttttataggt taatgtcatg ataataatgg tttcttagac  10500
gtcaggtggc acttttcggg gaaatgtgcg cggaacccct atttgtttat ttttctaaat  10560
acattcaaat atgtatccgc tcatgagaca ataaccctga taaatgcttc aataatggga  10620
ccgactcgcg ctgtcaggag actagagcca agctgatctc ctttgccccg gagatcacca  10680
tggacgactt tctctatctc tacgatctag gaagaaagtt cgacggagaa ggtgacgata  10740
ccatgttcac caccgataat gagaagatta gcctcttcaa tttcagaaag aatgctgacc  10800
cacagatggt tagagaggcc tacgcggcag gtctgatcaa gacgatctac ccgagtaata  10860
atctccagga gatcaaatac cttcccaaga aggttaaaga tgcagtcaaa agattcagga  10920
ctaactgcat caagaacaca gagaaagata tatttctcaa gatcagaagt actattccag  10980
tatggacgat tcaaggcttg cttcataaac caaggcaagt aatagagatt ggagtctcta  11040
agaaagtagt tcctactgaa tcaaaggcca tggagtcaaa aattcagatc gaggatctaa  11100
cagaactcgc cgtgaagact ggcgaacagt tcatacagag tcttttacga ctcaatgaca  11160
agaagaaaat cttcgtcaac atggtggagc acgacactct cgtctactcc aagaatatca  11220
aagatacagt ctcagaagac caaagggcta ttgagacttt tcaacaaagg gtaatatcgg  11280
gaaacctcct cggattccat tgcccagcta tctgtcactt catcaaaagg acagtagaaa  11340
aggaaggtgg cacctacaaa tgccatcatt gcgataaagg aaaggctatc gttcaagatg  11400
cctctgccga cagtggtccc aaagatggac ccccacccac gaggagcatc gtggaaaaag  11460
aagacgttcc aaccacgtct tcaaagcaag tggattgatg tgatatctcc actgacgtaa  11520
gggatgacgc acaatcccac tatccttcgc aagacccttc ctctatataa ggaagttcat  11580
ttcatttgga gaggactccg gtatttttac aacaatacca caacaaaaca aacaacaaac  11640
aacattacaa tttactattc tagtcgaaat ggataacgca acacttgctg tgatcctttc  11700
cattttgttt gtgttttacc acattttcaa atcctttttc accaattctt catctcgtag  11760
gcttcctcct ggtcccaaac ccgtgccaat ttttggcaac atttcgatc ttggcgaaaa  11820
gcctcatcga tcttttgcca atctatctaa aattcacggc cctttgatta gcctaaagtt  11880
aggaagtgta acaactattg ttgtttcctc ggcctctgtg gccgaggaaa tgttccttaa  11940
aaatgaccaa gcacttgcta accgaaccat tcctgactcg gttagggctg gtgaccacga  12000
caaattatcc atgtcgtggt tgcctgtttc ccaaaaatgg agaaatatga gaaaaatctc  12060
cgctgtccaa ttactctcca accaaaaact tgatgctagt caacctctta gacaagctaa  12120
ggtgaaacaa cttttatcat acgtacaagt ttgttccgaa aaaatgcaac ccgtcgatat  12180
tggacgggcc gcatttacaa cgtcacttaa tttattatca aacacatttt tctcaatcga  12240
attagcaagt catgaatcta gtgcttccca agagtttaaa caactcatgt ggaatattat  12300
ggaggaaatt ggaaggccta attatgctga ttttttccct attcttggtt acattgatcc  12360
ctttggtata agacgtcgtt tggctggtta ctttgataaa ctcattgatg ttttccaaga  12420
cattattcgt gaaagacaaa agcttcgatc ttctaattct tccggcgcaa aacaaacaaa  12480
tgacattctt gatactcttc ttaaactcca tgaagataat gagttgagta tgcctgaaat  12540
taatcacctt ctcgtggata tctttgacgc cggaacagac acaacagcaa gcacattaga  12600
atgggcaatg gccgaacttg tgaaaaaccc ggaaatgatg actaaagttc aaattgaaat  12660
cgaacaagct cttggaaaag attgcttaga catacaagaa tccgacatct caaaactacc  12720
ttatttacaa gccattataa aagaaacgtt acgtttacac cctcctactg tgtttttgct  12780
gcctcgaaag gcagacaatg acgtagagtt atatggctac gttgtaccaa agaatgctca  12840
agtccttgtc aatctttggg caattggtcg tgatccaaag gtatggaaaa atccggaagt  12900
attttctcct gaaaggtttt tagattgcaa tatcgattat aaaggacgag atttcgaact  12960
tttacccttt ggtgctggta gaaggatatg ccctggactt actttggcat atagaatgtt  13020
gaacttgatg ttggctactc ttcttcaaaa ctacaattgg aaacttgaag atggtatcaa  13080
tcctaaggat ttagacatgg atgagaaatt tgggattaca ttgcaaaagg ttaaacctct  13140
tcaagttatt ccagttccca gaaactaggc ttgctctcaa gatcaaaggc ttaaaaagct  13200
ggggttttat gaatgggatc aaagtttctt tttttctttt atatttgctt ctccatttgt  13260
ttgtttcatt tccctttttg ttttcgtttc tatgatgcac ttgtgtgtga caaactctct  13320
gggtttttac ttacgtctgc gtttcaaaaa aaaaaaccgc tttcgttttg cgttttagtc  13380
ccattgtttt gtagctctga gtgatcgaat tgatgcctct ttattccttt tgttccctat  13440
aatttctttc aaaactcaga agaaaaacct tgaaactctt tgcaatgtta atataagtat  13500
tgtataagat ttttattgat ttggttatta gtcttacttt tgctacctcc atcttcactt  13560
ggaactgata ttctgaatag ttaaagcgtt acatgtcttc cattcacaaa tgaacttaaa  13620
ctagcacaaa gtcagatatt ttaagatcgc accattttat ataaccccaa tcgtcaattc  13680
tactgtttca agttttacac caaaacaatt acgaggtgta tctattcgtt actcttttcg  13740
cttattaatc cttttacatg atgcaaaata taacaaatta atttcaaatt gtcctgcaca  13800
tttggtttat acatcttgat tccaaaaagt cgctgtcagg agtctcaatg gtaactttac  13860
tctttattta accatacatt tttttttatt tttttcactt tgttcttcat ccactattgt  13920
tctttgttca tcttgaacaa aagctccctc cttctttgtt cttcatccac cattgttctt  13980
catcaatcat tt                                                      13992

SEQ ID NO: 24          moltype = DNA  length = 11797
FEATURE                Location/Qualifiers
```

```
misc_feature           1..11797
                       note = pDOPA1 overexpression vector
source                 1..11797
                       mol_type = other DNA
                       organism = synthetic construct
SEQUENCE: 24
cgctgtcatg agaccggatc ctgacaggat atattggcgg gtaaacctaa gagaaaagag  60
cgtttattag aataatcgga tatttaaaag ggcgtgaaaa ggtttatccg ttcgtccatt  120
tgtatgtgca tgccaaccac agggttcccc tcgggatcaa agtactttga tccaacccct  180
ccgctgctat agtgcagtcg gcttctgacg ttcagtgcag ccgtcatctg aaaacgacat  240
gtcgcacaag tcctaagtta cgcgacaggc tgccgccctg cccttttcct ggcgttttct  300
tgtcgcgtgt tttagtcgca taaagtagaa tacttgcgac tagaaccgga gacattacgc  360
catgaacaag agcgccgccg ctggcctgct gggctatgcc cgcgtcagca ccgacgacca  420
ggacttgacc aaccaacggg ccgaactgca cgcggccggc tgcaccaagc tgttttccga  480
gaagatcacc ggcaccaggc gcgaccgccc ggagctggcc aggatgcttg accacctacg  540
ccctggcgac gttgtgacag tgaccaggct agaccgcctg gcccgcagca cccgcgacct  600
actggacatt gccgagcgca tccaggaggc cggcgcgggc ctgcgtagcc tggcagagcc  660
gtgggccgac accaccacgc cggccggccg catggtgttg accgtgttcg ccggcattgc  720
cgagttcgag cgttccctaa tcatcgaccg cacccggagc gggcgcgagg ccgccaaggc  780
ccgaggcgtg aagtttggcc cccgccctac cctcaccccg gcacagatcg cgcacgcccg  840
cgagctgatc gaccaggaag gccgcaccgt gaaagaggcg gctgcactgc ttggcgtgca  900
tcgctcgacc ctgtaccgcg cacttgagcg cagcgaggaa gtgacgccca ccgaggccag  960
gcggcgcggt gccttccgtg aggacgcatt gaccgaggcc gacgccctgg cggccgccga  1020
gaatgaacgc caagaggaac aagcatgaaa ccgcaccagg acggccagga cgaaccgttt  1080
ttcattaccg aagagatcga ggcggagatg atcgcggccg ggtacgtgtt cgagccgccc  1140
gcgcacctct caaccgtgcg gctgcatgaa atcctggccg gtttgtctga tgccaagctg  1200
gcggcctggc cggccagctt ggccgctgaa gaaaccgagc gccgccgtct aaaaaggtga  1260
tgtgtatttg agtaaaacag cttgcgtcat gcggtcgctg cgtatatgat ccgatgagta  1320
aataaacaaa tacgcaaggg gaacgcatga aggttatcgc tgtacttaac cagaaaggcg  1380
ggtcaggcaa gacgaccatc ggaacccatc tagcccgcgc cctgcaactc gccggggccg  1440
atgttctgtt agtcgattcc gatccccagg gcagtgcccg cgattgggcg gccgtgcggg  1500
aagatcaacc gctaaccgtt gtcggcatcg accgcccgac gattgaccgc gacgtgaagg  1560
ccatcggccg gcgcgacttc gtagtgatcg acggagcgcc ccaggcggcg gacttggctg  1620
tgtccgcgat caaggcagcc gacttcgtgc tgattccggt gcagccaagc ccttacgaca  1680
tatgggccac cgccgacctg gtggagctgg ttaagcagcg cattgaggtc acggatggaa  1740
ggctacaagc ggcctttgtc gtgtcgcggg cgatcaaagg cacgcgcatc ggcggtgagg  1800
ttgccgaggc gctggccggg tacgagctgc ccattcttga gtcccgtatc acgcagcgcg  1860
tgagctaccc aggcactgcc gccgccggca caaccgttct tgaatcagaa cccgagggcg  1920
acgctgcccg cgaggtccag gcgctggccg ctgaaattaa atcaaaactc atttgagtta  1980
atgaggtaaa gagaaaatga gcaaaagcac aaacacgcta agtgccggcc gtccgagcgc  2040
acgcagcagc aaggctgcaa cgttggccag cctggcagac acgccagcca tgaagcgggt  2100
caactttcag ttgccggcgg aggatcacac caagctgaag atgtacgcgg tacgccaagg  2160
caagaccatt accgagctgc tatctgaata gatcgcgcag ctaccagagt aaatgagcaa  2220
atgaataaat gagtagatga attttagcgg ctaaaggagg cggcatggaa aatcaagaac  2280
aaccaggcac cgacgccgtg gaatgcccca tgtgtggagg aacgggcggt tggccaggcg  2340
taagcggctg ggttgtctgc cggccctgca atggcactgg aacccccaag cccgaggaat  2400
cggcgtgacg gtcgcaaacc atccggcccg gtacaaatcg gcgcggcgct gggtgatgac  2460
ctggtggaga agttgaaggc cgcgcaggcc gcccagcggc aacgcatcga ggcagaagca  2520
cgccccggtg aatcgtggca agcggccgct gatcgaatcc gcaaagaatc ccggcaaccg  2580
ccggcagccg gtgcgccgtc gattaggaag ccgcccaagg gcgacgagca accagatttt  2640
ttcgttccga tgctctatga cgtgggcacc cgcgatagtc gcagcatcat ggacgtggcc  2700
gttttccgtc tgtcgaagcg tgaccgacga gctggcgagg tgatccgcta cgagcttcca  2760
gacgggcacg tagaggtttc cgcagggccg gccggcatgg ccagtgtgtg ggattacgac  2820
ctggtactga tggcggtttc ccatctaacc gaatccatga accgataccg ggaagggaag  2880
ggagacaagc ccggccgcgt gttccgtcca cacgttgcgg acgtactcaa gttctgccgg  2940
cgagccgatg gcggaaagca gaaagacgac ctggtagaaa cctgcattcg gttaaacacc  3000
acgcacgttg ccatgcagcg tacgaagaag gccaagaacg gccgcctggt gacggtatcc  3060
gagggtgaag ccttgattag ccgctacaag atcgtaaaga gcgaaaccgg gcggccggag  3120
tacatcgaga tcgagctagc tgattggatg taccgcgaga tcacagaagg caagaacccg  3180
gacgtgctga cggttcaccc cgattacttt ttgatcgatc ccggcatcgg ccgttttctc  3240
taccgcctgg cacgccgcgc cgcaggcaag gcagaagcca gatggttgtt caagacgatc  3300
tacgaacgca gtggcagcgc cggagagttc aagaagttct gtttcaccgt gcgcaagctg  3360
atcgggtcaa atgacctgcc ggagtacgat ttgaaggagg aggcggggca ggctggcccg  3420
atcctagtca tgcgctaccg caacctgatc gagggcgaag catccgccgg ttcctaatgt  3480
acggagcaga tgctagggca aattgcccta gcaggggaaa aaggtcgaaa aggactcttt  3540
cctgtggata gcacgtacat tgggaaccca aagccgtaca ttgggaaccg gaacccgtac  3600
attgggaacc caaagccgta cattgggaac cggtcacaca tgtaagtgac tgatataaaa  3660
gagaaaaaag gcgatttttc cgcctaaaac tctttaaaac ttattaaaac tcttaaaacc  3720
cgcctggcct gtgcataact gtctggccag cgcacagccg aagagctgca aaaagcgcct  3780
acccttcggt cgctgcgctc cctacgcccc gccgcttcgc gtcggcctat cgcggccgct  3840
ggccgctcaa aaatggctgg cctacggcca ggcaatctac cagggcgcgg acaagccgcg  3900
ccgtcgccac tcgaccgccg gcgcccacat caaggcaccc tgcctcgcgc gtttcggtga  3960
tgacggtgaa aacctctgac acatgcagct cccggtgacg gtcacagctt gtctgtaagc  4020
ggatgccggg agcagacaag cccgtcaggg cgcgtcagcg ggtgttggcg ggtgtcgggg  4080
cgcagccatg acccagtcac gtagcgatag cggagtgtat actggcttaa ctatgcggca  4140
tcagagcaga ttgtactgag agtgcaccat atgcggtgtg aaataccgca cagatgcgta  4200
aggagaaaat accgcatcag gcgctcttcc gcttcctcgc tcactgactc gctgcgctcg  4260
gtcgttcggc tgcggcgagc ggtatcagct cactcaaagg cggtaatacg gttatccaca  4320
gaatcagggg ataacgcagg aaagaacatg tgagcaaaag gccagcaaaa ggccaggaac  4380
```

```
cgtaaaaagg ccgcgttgct ggcgtttttc cataggctcc gcccccctga cgagcatcac  4440
aaaaatcgac gctcaagtca gaggtggcga aacccgacag gactataaag ataccaggcg  4500
tttccccctg gaagctccct cgtgcgctct cctgttccga ccctgccgct taccggatac  4560
ctgtccgcct ttctcccttc gggaagcgtg gcgctttctc atagctcacg ctgtaggtat  4620
ctcagttcgg tgtaggtcgt tcgctccaag ctgggctgtg tgcacgaacc ccccgttcag  4680
cccgaccgct gcgccttatc cggtaactat cgtcttgagt ccaacccggt aagacacgac  4740
ttatcgccac tggcagcagc cactggtaac aggattagca gagcgaggta tgtaggcggt  4800
gctacagagt tcttgaagtg gtggcctaac tacggctaca ctagaaggac agtatttggt  4860
atctgcgctc tgctgaagcc agttaccttc ggaaaaagag ttggtagctc ttgatccggc  4920
aaacaaacca ccgctggtag cggtggtttt tttgtttgca agcagcagat tacgcgcaga  4980
aaaaaaggat ctcaagaaga tcctttgatc ttttctacgg ggtctgacgc tcagtggaac  5040
gaaaactcac gttaagggat tttggtcatg cattctaggt gattatttgc cgactacctt  5100
ggtgatctcg cctttcacgt agtggacaaa ttcttccaac tgatctgcgc gcgaggccaa  5160
gcgatcttct tcttgtccaa gataagcctg tctagcttca agtatgacgg gctgatactg  5220
ggccggcagg cgctccattg cccagtcggc agcgacatcc ttcggcgcga ttttgccggt  5280
tactgcgctg taccaaatgc gggacaacgt aagcactaca tttcgctcat caccagccca  5340
gtcgggcggc gagttccata gcgttaaggt ttcatttagc gcctcaaata gatcctgttc  5400
aggaaccgga tcaaagagtt cctccgccgc tggacctacc aaggcaacgc tatgttctct  5460
tgcttttgtc agcaagatag ccagatcaat gtcgatcgtg gctggctcga agatacctgc  5520
aagaatgtca ttgcgctgcc attctccaaa ttgcagttcg cgcttagctg gataacgcca  5580
cggaatgatg tcgtcgtgca caacaatggt gacttctaca gcgcggagaa tctcgctctc  5640
tccaggggaa gccgaagttt ccaaaaggtc gttgatcaaa gctcgccgcg ttgtttcatc  5700
aagccttacg gtcaccgtaa ccagcaaatc aatatcactg tgtggcttca ggccgccatc  5760
cactgcggag ccgtacaaat gtacggccag caacgtcggt tcgagatggc gctcgatgac  5820
gccaactacc tctgatagtt gagtcgatac ttcggcgatc accgcttccc tcataatgtt  5880
taactttgtt ttagggcgac tgccctgctg cgtaacatcg ttgctgctcc ataacatcaa  5940
acatcgaccc acggcgtaac gcgcttgctg cttggatgcc cgaggcatag actgtacccc  6000
aaaaaaacag tcataacaag ccatgaaaac cgccactgcg ccgttaccac cgctgcgttc  6060
ggtcaaggtt ctggaccagt tgcgtgagcg catacgctac ttgcattaca gcttacgaac  6120
cgaacaggct tatgtccact gggttcgtgc cttcatccgt ttccacggtg tgcgtcaccc  6180
ggcaaccttg ggtagcagcg aagtcgaggc atttctgtcc tggctggaac agaacttatt  6240
atttccttcc tcttttctac agtatttaaa gataccccaa gaagctaatt ataacaagac  6300
gaactccaat tcactgttcc ttgcattcta aaaccttaaa taccagaaaa cagctttttc  6360
aaagttgttt tcaaagttgg cgtataacat agtatcgacg gagccgattt tgaaaccgcg  6420
gtgatcacag gcagcaacgc tctgtcatcg ttacaatcaa catgctaccc tccgcgagat  6480
catccgtgtt tcaaacccgg cagcttagtt gccgttcttc cgaatagcat cggtaacatg  6540
agcaaagtct gccgccttac aacggctctc ccgctgacgc cgtcccggac tgatgggctg  6600
cctgtatcga gtggtgattt tgtgccgagc tgccggtcgg ggagctgttg gctggctggt  6660
ggcaggatat attgtggtgt aaacataacg gatccggtct caggagagcg tcgatctagt  6720
aacatagatg acaccgcgcg cgataattta tcctagtttg cgcgctatat tttgttttct  6780
atcgcgtatt aaatgtataa ttgcgggact ctaatcataa aaacccatct cataaataac  6840
gtcatgcatt acatgttaat tattacatgc ttaacgtaat tcaacagaaa ttatatgata  6900
atcatcgcaa gaccggcaac aggattcaat cttaagaaac tttattgcca aatgtttgaa  6960
cgatctgctt cgacgcactc cttctttact ccaccatctc gtccttattg aaaacgtggg  7020
tagcaccaaa acgaatcaag tcgctggaac tgaagttacc aatcacgctg gatgatttgc  7080
cagttggatt aatcttgcct ttccccgcat gaataatatt gatgaatgca tgcgtgaggg  7140
gtagttcgat gttggcaata gctgcaattg ccgcgacatc ctccaacgag cataattctt  7200
cagaaaaata gcgatgttcc atgttgtcag ggcatgcatg atgcacgtta tgaggtgacg  7260
gtgctaggca gtattccctc aaagtttcat agtcagtatc atattcatca ttgcattcct  7320
gcaagagaga attgagacgc aatccacacg ctgcggcaac cttccggcgt tcgtggtcta  7380
tttgctcttg gacgttgcaa acgtaagtgt tggatcgggg tgggcgaaga actccagcat  7440
gagatccccg cgctggagga tcatccagcc ggcgtcccgg aaaacgattc cgaagcccaa  7500
cctttcatag aaggcggcgg tggaatcgaa atctcgtgat ggcaggttgg gcgtcgcttg  7560
gtcggtcatt tcgaacccca gagtcccgct cagaagaact cgtcaagaag gcgatagaag  7620
gcgatgcgct gcgaatcggg agcggcgata ccgtaaagca cgaggaagcg gtcagcccat  7680
tcgccgccaa gctcttcagc aatatcacgg gtagccaacg ctatgtcctg atagcggtcc  7740
gccacaccca gccggccaca gtcgatgaat ccagaaaagc ggccattttc caccatgata  7800
ttcggcaagc aggcatcgcc atgggtcacg acgagatcct cgccgtcggg catgcgcgcc  7860
ttgagcctgg cgaacagttc ggctggcgcg agcccctgat gctcttcgtc cagatcatcc  7920
tgatcgacaa gaccggcttc catccgagta cgtgctcgct cgatgcgatg tttcgcttgg  7980
tggtcgaatg ggcaggtagc cggatcaagc gtatgcagcc gccgcattgc atcagccatg  8040
atggatactt tctcggcagg agcaaggtga gatgacagga gatcctgccc cggcacttcg  8100
cccaatagca gccagtccct tcccgcttca gtgacaacgt cgagcacagc tgcgcaagga  8160
acgcccgtcg tggccagcca cgatagccgc gctgcctcgt cctgcagttc attcagggca  8220
ccggacaggt cggtcttgac aaaaagaacc gggcgcccct gcgctgacag ccggaacacg  8280
gcggcatcag agcagccgat tgtctgttgt gcccagtcat agccgaatag cctctccacc  8340
caagcggccg gagaacctgc ccggatccgg gcggaaatag gtaaagaagt tgcggataag  8400
gtaattgcca ttgcagatta tttggattga gagtgaatat gagactctaa ttggataccg  8460
aggggaattt atggaacgtc agtggagcat ttttgacaag aaatatttgc tagctgatag  8520
tgaccttagg cgacttttga acgcgcaata atggtttctg acgtatgtgc ttagctcatt  8580
aaactccaga aacccctccg tcaggagact agagccaagc tgatctcctt tgccccggag  8640
atcaccatgg acgactttct ctatctctac gatctaggaa gaaagttcga cggagaaggt  8700
gacgatacca tgttcaccac cgataatgag aagattagcc tcttcaattt cagaaagaat  8760
gctgacccac agatggttag agaggcctac gcggcaggtc tgatcaagac gatctacccg  8820
agtaataatc tccaggagat caaatacctt cccaagaagg ttaaagatgc agtcaaaaga  8880
ttcaggacta actgcatcaa gaacacagag aaagatatat ttctcaagat cagaagtact  8940
attccagtat ggacgattca aggcttgctt cataaaccaa ggcaagtaat agagattgga  9000
gtctctaaga aagtagttcc tactgaatca aaggccatgg agtcaaaaat tcagatcgag  9060
gatctaacag aactcgccgt gaagactggc gaacagttca tacagagtct tttacgactc  9120
```

```
aatgacaaga agaaaatctt cgtcaacatg gtggagcacg acactctcgt ctactccaag  9180
aatatcaaag atacagtctc agaagaccaa agggctattg agacttttca acaaagggta  9240
atatcgggaa acctcctcgg attccattgc ccagctatct gtcacttcat caaaaggaca  9300
gtagaaaagg aaggtggcac ctacaaatgc catcattgcg ataaaggaaa ggctatcgtt  9360
caagatgcct ctgccgacag tggtcccaaa gatggacccc cacccacgag gagcatcgtg  9420
gaaaaagaag acgttccaac cacgtcttca aagcaagtgg attgatgtga tatctccact  9480
gacgtaaggg atgacgcaca atcccactat ccttcgcaag acccttcctc tatataagga  9540
agttcatttc atttggagag gactccggta tttttacaac aataccacaa caaaacaaac  9600
aacaaacaac attacaattt actattctag tcgaaatgga taacgcaaca cttgctgtga  9660
tcctttccat tttgtttgtg ttttaccaca ttttcaaatc ctttttcacc aattcttcat  9720
ctcgtaggct tcctcctggt cccaaacccg tgccaatttt tggcaacatt ttcgatcttg  9780
gcgaaaagcc tcatcgatct tttgccaatc tatctaaaat tcacggccct ttgattagcc  9840
taaagttagg aagtgtaaca actattgttg tttcctcggc ctctgtggcc gaggaaatgt  9900
tccttaaaaa tgaccaagca cttgctaacc gaaccattcc tgactcggtt agggctggtg  9960
accacgacaa attatccatg tcgtggttgc ctgtttccca aaaatggaga aatatgagaa  10020
aaatctccgc tgtccaatta ctctccaacc aaaaacttga tgctagtcaa cctcttagac  10080
aagctaaggt gaaacaactt ttatcatacg tacaagtttg ttccgaaaaa atgcaacccg  10140
tcgatattgg acgggccgca tttacaacgt cacttaattt attatcaaac acatttttct  10200
caatcgaatt agcaagtcat gaatctagtg cttcccaaga gtttaaacaa ctcatgtgga  10260
atattatgga ggaaattgga aggcctaatt atgctgattt tttccctatt cttggttaca  10320
ttgatccctt tggtataaga cgtcgtttgg ctggttactt tgataaactc attgatgttt  10380
tccaagacat tattcgtgaa agacaaaagc ttcgatcttc taattcttcc ggcgcaaaac  10440
aaacaaatga cattcttgat actcttctta aactccatga agataatgag ttgagtatgc  10500
ctgaaattaa tcaccttctc gtggatatct ttgacgccgg aacagacaca acagcaagca  10560
cattagaatg ggcaatggcc gaacttgtga aaaacccgga aatgatgact aaagttcaaa  10620
ttgaaatcga acaagctctt ggaaaagatt gcttagacat acaagaatcc gacatctcaa  10680
aactacctta tttacaagcc attataaaag aaacgttacg tttacaccct cctactgtgt  10740
ttttgctgcc tcgaaaggca gacaatgacg tagagttata tggctacgtt gtaccaaaga  10800
atgctcaagt ccttgtcaat ctttgggcaa ttggtcgtga tccaaaggta tggaaaaatc  10860
cggaagtatt ttctcctgaa aggtttttag attgcaatat cgattataaa ggacgagatt  10920
tcgaactttt accctttggt gctggtagaa ggatatgccc tggacttact ttggcatata  10980
gaatgttgaa cttgatgttg gctactcttc ttcaaaacta caattggaaa cttgaagatg  11040
gtatcaatcc taaggattta gacatggatg agaaatttgg gattacattg caaaaggtta  11100
aacctcttca agttattcca gttcccagaa actaggcttg ctctcaagat caaaggctta  11160
aaaagctggg gttttatgaa tgggatcaaa gtttcttttt ttcttttata tttgcttctc  11220
catttgtttg tttcatttcc ctttttgttt tcgtttctat gatgcacttg tgtgtgacaa  11280
actctctggg tttttactta cgtctgcgtt tcaaaaaaaa aaaccgcttt cgttttgcgt  11340
tttagtccca ttgttttgta gctctgagtg atcgaattga tgcctcttta ttccttttgt  11400
tccctataat ttctttcaaa actcagaaga aaaaccttga aactctttgc aatgttaata  11460
taagtattgt ataagatttt tattgatttg gttattagtc ttacttttgc tacctccatc  11520
ttcacttgga actgatattc tgaatagtta aagcgttaca tgtcttccat tcacaaatga  11580
acttaaacta gcacaaagtc agatatttta agatcgcacc attttatata accccaatcg  11640
tcaattctac tgtttcaagt tttacaccaa aacaattacg aggtgtatct attcgttact  11700
cttttcgctt attaatcctt ttacatgatg caaaatataa caaattaatt tcaaattgtc  11760
ctgcacattt ggtttataca tcttgattcc aaaaagt                          11797
```

```
SEQ ID NO: 25          moltype = DNA  length = 13626
FEATURE                Location/Qualifiers
misc_feature           1..13626
                       note = pDOPA2 overexpression vector
source                 1..13626
                       mol_type = other DNA
                       organism = synthetic construct
SEQUENCE: 25
cgctgtcatg agaccggatc ctgacaggat atattggcgg gtaaacctaa gagaaaagag  60
cgtttattag aataatcgga tatttaaaag ggcgtgaaaa ggtttatccg ttcgtccatt  120
tgtatgtgca tgccaaccac aggcttcccc tcgggatcaa agtactttga tccaacccct  180
ccgctgctat agtgcagtcg gcttctgacg ttcagtgcag ccgtcatctg aaaacgacat  240
gtcgcacaag tcctaagtta cgcgacaggc tgccgccctg ccctttcct ggcgttttct  300
tgtcgcgtgt tttagtcgca taaagtagaa tacttgcgac tagaaccgga gacattacgc  360
catgaacaag agcgccgccg ctggcctgct gggctatgcc cgcgtcagca ccgacgacca  420
ggacttgacc aaccaacggg ccgaactgca cgcggccggc tgcaccaagc tgttttccga  480
gaagatcacc ggcaccaggc gcgaccgccc ggagctggcc aggatgcttg accacctacg  540
ccctggcgac gttgtgacag tgaccaggct agaccgcctg gcccgcagca cccgcgacct  600
actggacatt gccgagcgca tccaggaggc cggcgcgggc ctgcgtagcc tggcagagcc  660
gtgggccgac accaccacgc cggccggccg catggtgttg accgtgttcg ccggcattgc  720
cgagttcgag cgttccctaa tcatcgaccg cacccggagc gggcgcgagg ccgccaaggc  780
ccgaggcgtg aagtttggcc cccgccctac cctcaccccg gcacagatcg cgcacgcccg  840
cgagctgatc gaccaggaag gccgcaccgt gaaagaggcg gctgcactgc ttggcgtgca  900
tcgctcgacc ctgtaccgcg cacttgagcg cagcgaggaa gtgacgccca ccgaggccag  960
gcggcgcggt gccttccgtg aggacgcatt gaccgaggcc gacgccctgg cggccgccga  1020
gaatgaacgc caagaggaac aagcatgaaa ccgcaccagg acggccagga cgaaccgttt  1080
ttcattaccg aagagatcga ggcggagatg atcgcggccg ggtacgtgtt cgagccgccc  1140
gcgcacctct caaccgtgcg gctgcatgaa atcctggccg gtttgtctga tgccaagctg  1200
gcggcctggc cggccagctt ggccgctgaa gaaaccgagc gccgccgtct aaaaaggtga  1260
tgtgtatttg agtaaaacag cttgcgtcat gcggtcgctg cgtatatgat ccgatgagta  1320
aataaacaaa tacgcaaggg gaacgcatga aggttatcgc tgtacttaac cagaaaggcg  1380
ggtcaggcaa gacgaccatc ggaacccatc tagcccgcgc cctgcaactc gccggggccg  1440
atgttctgtt agtcgattcc gatccccagg gcagtgcccg cgattgggcg gccgtgcggg  1500
```

-continued

```
aagatcaacc gctaaccgtt gtcggcatcg accgcccgac gattgaccgc gacgtgaagg  1560
ccatcggccg gcgcgacttc gtagtgatcg acggagcgcc ccaggcggcg gacttggctg  1620
tgtccgcgat caaggcagcc gacttcgtgc tgattccggt gcagccaagc ccttacgaca  1680
tatgggccac cgccgacctg gtggagctgg ttaagcagcg cattgaggtc acggatggaa  1740
ggctacaagc ggcctttgtc gtgtcgcggg cgatcaaagg cacgcgcatc ggcggtgagg  1800
ttgccgaggc gctggccggg tacgagctgc ccattcttga gtcccgtatc acgcagcgcg  1860
tgagctaccc aggcactgcc gccgccggca caaccgttct tgaatcagaa cccgagggcg  1920
acgctgcccg cgaggtccag gcgctggccg ctgaaattaa atcaaaactc atttgagtta  1980
atgaggtaaa gagaaaatga gcaaaagcac aaacacgcta agtgccggcc gtccgagcgc  2040
acgcagcagc aaggctgcaa cgttggccag cctggcagac acgccagcca tgaagcgggt  2100
caactttcag ttgccggcgg aggatcacac caagctgaag atgtacgcgg tacgccaagg  2160
caagaccatt accgagctgc tatctgaata gatcgcgcag ctaccagagt aaatgagcaa  2220
atgaataaat gagtagatga attttagcgg ctaaaggagg cggcatggaa aatcaagaac  2280
aaccaggcac cgacgccgtg gaatgcccca tgtgtggagg aacgggcggt tggccaggcg  2340
taagcggctg ggttgtctgc cggccctgca atggcactgg aacccccaag cccgaggaat  2400
cggcgtgacg gtcgcaaacc atccggcccg gtacaaatcg gcgcggcgct gggtgatgac  2460
ctggtggaga agttgaaggc cgcgcaggcc gcccagcggc aacgcatcga ggcagaagca  2520
cgccccggtg aatcgtggca agcggccgct gatcgaatcc gcaaagaatc ccggcaaccg  2580
ccggcagccg gtgcgccgtc gattaggaag ccgcccaagg gcgacgagca accagatttt  2640
ttcgttccga tgctctatga cgtgggcacc cgcgatagtc gcagcatcat ggacgtggcc  2700
gttttccgtc tgtcgaagcg tgaccgacga gctggcgagg tgatccgcta cgagcttcca  2760
gacgggcacg tagaggtttc cgcagggccg gccggcatgg ccagtgtgtg ggattacgac  2820
ctggtactga tggcggtttc ccatctaacc gaatccatga accgataccg ggaagggaag  2880
ggagacaagc ccggccgcgt gttccgtcca cacgttgcgg acgtactcaa gttctgccgg  2940
cgagccgatg gcggaaagca gaaagacgac ctggtagaaa cctgcattcg gttaaacacc  3000
acgcacgttg ccatgcagcg tacgaagaag gccaagaacg gccgcctggt gacggtatcc  3060
gagggtgaag ccttgattag ccgctacaag atcgtaaaga gcgaaaccgg gcggccggag  3120
tacatcgaga tcgagctagc tgattggatg taccgcgaga tcacagaagg caagaacccg  3180
gacgtgctga cggttcaccc cgattacttt ttgatcgatc ccggcatcgg ccgttttctc  3240
taccgcctgg cacgccgcgc cgcaggcaag gcagaagcca gatggttgtt caagacgatc  3300
tacgaacgca gtggcagcgc cggagagttc aagaagttct gtttcaccgt gcgcaagctg  3360
atcgggtcaa atgacctgcc ggagtacgat ttgaaggagg aggcggggca ggctggcccg  3420
atcctagtca tgcgctaccg caacctgatc gagggcgaag catccgccgg ttcctaatgt  3480
acggagcaga tgctagggca aattgcccta gcaggggaaa aaggtcgaaa aggactcttt  3540
cctgtggata gcacgtacat tgggaaccca aagccgtaca ttgggaaccg gaacccgtac  3600
attgggaacc caaagccgta cattgggaac cggtcacaca tgtaagtgac tgatataaaa  3660
gagaaaaaag gcgatttttc cgcctaaaac tctttaaaac ttattaaaac tcttaaaacc  3720
cgcctggcct gtgcataact gtctggccag cgcacagccg aagagctgca aaaagcgcct  3780
acccttcggt cgctgcgctc cctacgcccc gccgcttcgc gtcggcctat cgcggccgct  3840
ggccgctcaa aaatggctgg cctacggcca ggcaatctac cagggcgcgg acaagccgcg  3900
ccgtcgccac tcgaccgccg gcgcccacat caaggcaccc tgcctcgcgc gtttcggtga  3960
tgacggtgaa aacctctgac acatgcagct cccggtgacg gtcacagctt gtctgtaagc  4020
ggatgccggg agcagacaag cccgtcaggg cgcgtcagcg ggtgttggcg ggtgtcgggg  4080
cgcagccatg acccagtcac gtagcgatag cggagtgtat actggcttaa ctatgcggca  4140
tcagagcaga ttgtactgag agtgcaccat atgcggtgtg aaataccgca cagatgcgta  4200
aggagaaaat accgcatcag gcgctcttcc gcttcctcgc tcactgactc gctgcgctcg  4260
gtcgttcggc tgcggcgagc ggtatcagct cactcaaagg cggtaatacg gttatccaca  4320
gaatcagggg ataacgcagg aaagaacatg tgagcaaaag gccagcaaaa ggccaggaac  4380
cgtaaaaagg ccgcgttgct ggcgtttttc cataggctcc gcccccctga cgagcatcac  4440
aaaaatcgac gctcaagtca gaggtggcga aacccgacag gactataaag ataccaggcg  4500
tttccccctg gaagctccct cgtgcgctct cctgttccga ccctgccgct taccggatac  4560
ctgtccgcct ttctcccttc gggaagcgtg gcgctttctc atagctcacg ctgtaggtat  4620
ctcagttcgg tgtaggtcgt tcgctccaag ctgggctgtg tgcacgaacc ccccgttcag  4680
cccgaccgct gcgccttatc cggtaactat cgtcttgagt ccaacccggt aagacacgac  4740
ttatcgccac tggcagcagc cactggtaac aggattagca gagcgaggta tgtaggcggt  4800
gctacagagt tcttgaagtg gtggcctaac tacggctaca ctagaaggac agtatttggt  4860
atctgcgctc tgctgaagcc agttaccttc ggaaaaagag ttggtagctc ttgatccggc  4920
aaacaaacca ccgctggtag cggtggtttt tttgtttgca agcagcagat tacgcgcaga  4980
aaaaaaggat ctcaagaaga tcctttgatc ttttctacgg ggtctgacgc tcagtggaac  5040
gaaaactcac gttaagggat tttggtcatg cattctaggt gattatttgc cgactacctt  5100
ggtgatctcg cctttcacgt agtggacaaa ttcttccaac tgatctgcgc gcgaggccaa  5160
gcgatcttct tcttgtccaa gataagcctg tctagcttca agtatgacgg gctgatactg  5220
ggccggcagg cgctccattg cccagtcggc agcgacatcc ttcggcgcga ttttgccggt  5280
tactgcgctg taccaaatgc gggacaacgt aagcactaca tttcgctcat caccagccca  5340
gtcgggcggc gagttccata gcgttaaggt ttcatttagc gcctcaaata gatcctgttc  5400
aggaaccgga tcaaagagtt cctccgccgc tggacctacc aaggcaacgc tatgttctct  5460
tgcttttgtc agcaagatag ccagatcaat gtcgatcgtg gctggctcga agatacctgc  5520
aagaatgtca ttgcgctgcc attctccaaa ttgcagttcg cgcttagctg gataacgcca  5580
cggaatgatg tcgtcgtgca caacaatggt gacttctaca gcgcggagaa tctcgctctc  5640
tccaggggaa gccgaagttt ccaaaaggtc gttgatcaaa gctcgccgcg ttgtttcatc  5700
aagccttacg gtcaccgtaa ccagcaaatc aatatcactg tgtggcttca ggccgccatc  5760
cactgcggag ccgtacaaat gtacggccag caacgtcggt tcgagatggc gctcgatgac  5820
gccaactacc tctgatagtt gagtcgatac ttcggcgatc accgcttccc tcataatgtt  5880
taactttgtt ttagggcgac tgccctgctg cgtaacatcg ttgctgctcc ataacatcaa  5940
acatcgaccc acggcgtaac gcgcttgctg cttggatgcc cgaggcatag actgtacccc  6000
aaaaaaacag tcataacaag ccatgaaaac cgccactgcg ccgttaccac cgctgcgttc  6060
ggtcaaggtt ctggaccagt tgcgtgagcg catacgctac ttgcattaca gcttacgaac  6120
cgaacaggct tatgtccact gggttcgtgc cttcatccgt ttccacggtg tgcgtcaccc  6180
ggcaaccttg ggtagcagcg aagtcgaggc atttctgtcc tggctggaac agaacttatt  6240
```

```
atttccttcc tcttttctac agtatttaaa gataccccaa gaagctaatt ataacaagac  6300
gaactccaat tcactgttcc ttgcattcta aaaccttaaa taccagaaaa cagctttttc  6360
aaagttgttt tcaaagttgg cgtataacat agtatcgacg gagccgattt tgaaaccgcg  6420
gtgatcacag gcagcaacgc tctgtcatcg ttacaatcaa catgctaccc tccgcgagat  6480
catccgtgtt tcaaacccgg cagcttagtt gccgttcttc cgaatagcat cggtaacatg  6540
agcaaagtct gccgccttac aacggctctc ccgctgacgc cgtcccggac tgatgggctg  6600
cctgtatcga gtggtgattt tgtgccgagc tgccggtcgg ggagctgttg gctggctggt  6660
ggcaggatat attgtggtgt aaacataacg gatccggtct caggagagcg tcgatctagt  6720
aacatagatg acaccgcgcg cgataattta tcctagtttg cgcgctatat tttgttttct  6780
atcgcgtatt aaatgtataa ttgcgggact ctaatcataa aaacccatct cataaataac  6840
gtcatgcatt acatgttaat tattacatgc ttaacgtaat tcaacagaaa ttatatgata  6900
atcatcgcaa gaccggcaac aggattcaat cttaagaaac tttattgcca aatgtttgaa  6960
cgatctgctt cgacgcactc cttctttact ccaccatctc gtccttattg aaaacgtggg  7020
tagcaccaaa acgaatcaag tcgctggaac tgaagttacc aatcacgctg gatgatttgc  7080
cagttggatt aatcttgcct ttccccgcat gaataatatt gatgaatgca tgcgtgaggg  7140
gtagttcgat gttggcaata gctgcaattg ccgcgacatc ctccaacgag cataattctt  7200
cagaaaaata gcgatgttcc atgttgtcag ggcatgcatg atgcacgtta tgaggtgacg  7260
gtgctaggca gtattccctc aaagtttcat agtcagtatc atattcatca ttgcattcct  7320
gcaagagaga attgagacgc aatccacacg ctgcggcaac cttccggcgt tcgtggtcta  7380
tttgctcttg gacgttgcaa acgtaagtgt tggatcgggg tgggcgaaga actccagcat  7440
gagatccccg cgctggagga tcatccagcc ggcgtcccgg aaaacgattc cgaagcccaa  7500
cctttcatag aaggcggcgg tggaatcgaa atctcgtgat ggcaggttgg gcgtcgcttg  7560
gtcggtcatt tcgaacccca gagtcccgct cagaagaact cgtcaagaag gcgatagaag  7620
gcgatgcgct gcgaatcggg agcggcgata ccgtaaagca cgaggaagcg gtcagcccat  7680
tcgccgccaa gctcttcagc aatatcacgg gtagccaacg ctatgtcctg atagcggtcc  7740
gccacaccca gccggccaca gtcgatgaat ccagaaaagc ggccattttc caccatgata  7800
ttcggcaagc aggcatcgcc atgggtcacg acgagatcct cgccgtcggg catgcgcgcc  7860
ttgagcctgg cgaacagttc ggctggcgcg agcccctgat gctcttcgtc cagatcatcc  7920
tgatcgacaa gaccggcttc catccgagta cgtgctcgct cgatgcgatg tttcgcttgg  7980
tggtcgaatg ggcaggtagc cggatcaagc gtatgcagcc gccgcattgc atcagccatg  8040
atggatactt tctcggcagg agcaaggtga gatgacagga gatcctgccc cggcacttcg  8100
cccaatagca gccagtccct tcccgcttca gtgacaacgt cgagcacagc tgcgcaagga  8160
acgcccgtcg tggccagcca cgatagccgc gctgcctcgt cctgcagttc attcagggca  8220
ccggacaggt cggtcttgac aaaaagaacc gggcgcccct gcgctgacag ccggaacacg  8280
gcggcatcag agcagccgat tgtctgttgt gcccagtcat agccgaatag cctctccacc  8340
caagcggccg gagaacctgc ccggatccgg gcggaaatag gtaaagaagt tgcggataag  8400
gtaattgcca ttgcagatta tttggattga gagtgaatat gagactctaa ttggataccg  8460
aggggaattt atggaacgtc agtggagcat ttttgacaag aaatatttgc tagctgatag  8520
tgaccttagg cgacttttga acgcgcaata atggtttctg acgtatgtgc ttagctcatt  8580
aaactccaga aacccctccg tcaggaggtc aactacccca atttaaattt tatttgatta  8640
agatattttt atggacctac tttataatta aaaatatttt ctatttgaaa aggaaggaca  8700
aaaatcatac aattttggtc caactactcc tctctttttt tttttggctt tataaaaaag  8760
gaaagtgatt agtaataaat aattaaataa tgaaaaaagg aggaaataaa attttcgaat  8820
taaaatgtaa aagagaaaaa ggagagggag taatcattgt ttaactttat ctaaagtacc  8880
ccaattcgat tttacatgta tatcaaatta tacaaatatt ttattaaaat atagatattg  8940
aataatttta ttattcttga acatgtaaat aaaaattatc tattatttca atttttatat  9000
aaactattat ttgaaatctc aattatgatt ttttaatatc actttctatc catgataatt  9060
tcagcttaaa aagttttgtc aataattaca ttaattttgt tgatgaggat gacaagattt  9120
cggtcatcaa ttacatatac acaaattgaa atagtaagca acttgatttt ttttctcata  9180
atgataatga caaagacacg aaaagacaat tcaatattca cattgattta tttttatatg  9240
ataataatta caataataat attcttataa agaaagagat caattttgac tgatccaaaa  9300
atttatttat ttttactata ccaacgtcac taattatatc taataatgta aaacaattca  9360
atcttactta aatattaatt tgaaataaac tatttttata acgaaattac taaatttatc  9420
caataacaaa aaggtcttaa gaagacataa attctttttt tgtaatgctc aaataaattt  9480
gagtaaaaaa gaatgaaatt gagtgatttt tttttaatca taagaaaata aataattaat  9540
ttcaatataa taaaacagta atataatttc ataaatggaa ttcaatactt acctcttaga  9600
tataaaaaat aaatataaaa ataaagtgtt tctaataaac ccgcaattta aataaaatat  9660
ttaatatttt caatcaaatt taaataatta tattaaaata tcgtagaaaa agagcaatat  9720
ataatacaag aaagaagatt taagtacaat tatcaactat tattatactc taattttgtt  9780
atatttaatt tcttacggtt aaggtcatgt tcacgataaa ctcaaaatac gctgtatgag  9840
gacatatttt aaattttaac caataataaa actaagttat ttttagtata ttttttttgtt  9900
taacgtgact taatttttct tttctagagg agcgtgtaag tgtcaacctc attctcctaa  9960
ttttcccaac cacataaaaa aaaaataaag gtagcttttg cgtgttgatt tggtacacta  10020
cacgtcatta ttacacgtgt tttcgtatga ttggttaatc catgaggcgg tttcctctag  10080
agtcggccat accatctata aaataaagct ttctgcagct catttttttca tcttctatct  10140
gatttctatt ataatttctc tgaattgcct tcaaatttct ctttcaaggt tagaattttt  10200
ctctattttt tggtttttgt ttgtttagat tctgagttta gttaatcagg tgctgttaaa  10260
gccctaaatt ttgagttttt ttcggttgtt ttgatggaaa atacctaaca attgagtttt  10320
ttcatgttgt tttgtcggag aatgcctaca attggagttc ctttcgttgt tttgatgaga  10380
aagcccctaa tttgagtgtt tttccgtcga tttgatttta aaggtttata ttcgagtttt  10440
tttcgtcggt ttaatgagaa ggcctaaaat aggagttttt ctggttgatt tgactaaaaa  10500
agccatggaa ttttgtgttt ttgatgtcgc tttggttctc aaggcctaag atctgagttt  10560
ctccggttgt tttgatgaaa aagccctaaa attggagttt ttatcttgtg ttttaggttg  10620
ttttaatcct tataatttga gttttttcgt tgttctgatt gttgttttta tgaattttgc  10680
agaatggata acgcaacact tgctgtgatc ctttccattt tgtttgtgtt ttaccacatt  10740
ttcaaatcct ttttcaccaa ttcttcatct cgtaggcttc ctcctggtcc caaacccgtg  10800
ccaatttttg gcaacatttt cgatcttggc gaaaagcctc atcgatcttt tgccaatcta  10860
tctaaaattc acggcccttt gattagccta aagttaggaa gtgtaacaac tattgttgtt  10920
tcctcggcct ctgtggccga ggaaatgttc cttaaaaatg accaagcact tgctaaccga  10980
```

```
accattcctg actcggttag ggctggtgac cacgacaaat tatccatgtc gtggttgcct  11040
gtttcccaaa aatggagaaa tatgagaaaa atctccgctg tccaattact ctccaaccaa  11100
aaacttgatg ctagtcaacc tcttagacaa gctaaggtga aacaactttt atcatacgta  11160
caagtttgtt ccgaaaaaat gcaacccgtc gatattggac gggccgcatt tacaacgtca  11220
cttaatttat tatcaaacac atttttctca atcgaattag caagtcatga atctagtgct  11280
tcccaagagt ttaaacaact catgtggaat attatggagg aaattggaag gcctaattat  11340
gctgattttt tccctattct tggttacatt gatccctttg gtataagacg tcgtttggct  11400
ggttactttg ataaactcat tgatgttttc caagacatta ttcgtgaaag acaaaagctt  11460
cgatcttcta attcttccgg cgcaaaacaa acaaatgaca ttcttgatac tcttcttaaa  11520
ctccatgaag ataatgagtt gagtatgcct gaaattaatc accttctcgt ggatatcttt  11580
gacgccggaa cagacacaac agcaagcaca ttagaatggg caatggccga acttgtgaaa  11640
aacccggaaa tgatgactaa agttcaaatt gaaatcgaac aagctcttgg aaaagattgc  11700
ttagacatac aagaatccga catctcaaaa ctaccttatt tacaagccat tataaaagaa  11760
acgttacgtt tacaccctcc tactgtgttt ttgctgcctc gaaaggcaga caatgacgta  11820
gagttatatg gctacgttgt accaaagaat gctcaagtcc ttgtcaatct ttgggcaatt  11880
ggtcgtgatc caaaggtatg gaaaaatccg gaagtatttt ctcctgaaag gtttttagat  11940
tgcaatatcg attataaagg acgagatttc gaacttttac cctttggtgc tggtagaagg  12000
atatgccctg gacttacttt ggcatataga atgttgaact tgatgttggc tactcttctt  12060
caaaactaca attggaaact tgaagatggt atcaatccta aggatttaga catggatgag  12120
aaatttggga ttacattgca aaaggttaaa cctcttcaag ttattccagt tcccagaaac  12180
taggcttgtt gtggttgtct ggttgcgtct gttgcccgtt gtctgttgcc cattgtggtg  12240
gttgtgtttg tatgatggtc gttaaggatc atcaatgtgt tttcgctttt tgttccattc  12300
tgtttctcat ttgtgaataa taatggtatc tttatgaata tgcagtttgt ggtttctttt  12360
ctgattgcag ttctgagcat tttgtttttg cttccgttta ctataccact tacagtttgc  12420
actaatttag ttgatatgcg agccatctga tgtttgatga ttcaaatggc gtttatgtaa  12480
ctcgtacccg agtggatgga gaagagctcc attgccggtt tgtttcatgg gtggcggagg  12540
gcaactcctg ggaaggaaca aaagaaaaac cgtgatacga gttcatgggt gagagctcca  12600
gcttgatccc ttctctgtcg atcaaatttg aatttttgga tcacggcagg ctcacaagat  12660
aatccaaagt aaaacataat gaatagtact tctcaatgat cacttatttt tagcaaatca  12720
gcaattgtgc atgtcaaatg atttcggtgt aagagaaaga gttgatgaat caaaatatct  12780
gtagctggat caagaatctg aggcagttgt atgtatcaat gatctttccg ctacaatgat  12840
gttagctatc cgagtcaaat tgttgtagaa ttgcatactt cggcatcaca ttctggatga  12900
cataataaat aggaagtctt cagatcccta aaaaattgag agctaataac attagtccta  12960
gatgtaactg ggtgacaacc aagaaagaga catgcaaata ctacttttgt ttgaaggagc  13020
atccctggtt tgacatattt tttctgaata tcaaactttg aaactctacc tagtctaatg  13080
tctaacgaca gatcttactg gtttaactgc agtgatatct actatctttt ggaatgtttt  13140
ctccttcagt tatacatcaa gttccaagat gcaggtgtgc ttgattgatg tacatggctg  13200
tgagaagtgc atcctgatgt tcagatgatg gttcattcta atgtcttttc cttcaatcag  13260
ttttctcagt ctgacttagc ttgtttcatc tgcatgtttg aatgttcgtt tactcatagt  13320
aattgcattt ttgtagcaga acatatcatt ggtcatggtt tcaactgtgc gcgagtctta  13380
tgcttattca aactaggaaa gcctccgtct agagggtaca cgagttgttg ctctgtgtgc  13440
gtcagtccat agtattaatc ttgctagttg tagtatattg tttatgtgga ctcggaattc  13500
atcatatgct ccttctttgc atcaagtaag gcaaggtaat gtatagaagc tttttaactc  13560
tttcatggaa gctggccttt gccagcatac catccagaag atatcaaccc tgcatcttgg  13620
ctgccg                                                             13626
```

```
SEQ ID NO: 26          moltype = DNA  length = 16818
FEATURE                Location/Qualifiers
misc_feature           1..16818
                       note = pDOPA3 overexpression vector
source                 1..16818
                       mol_type = other DNA
                       organism = synthetic construct
SEQUENCE: 26
cgctgtcatg agacgaattc tgacaggata tattggcggg taaacctaag agaaaagagc  60
gtttattaga ataatcggat atttaaaagg gcgtgaaaag gtttatccgt tcgtccattt  120
gtatgtgcat gccaaccaca gggttcccct cgggatcaaa gtactttgat ccaacccctc  180
cgctgctata gtgcagtcgg cttctgacgt tcagtgcagc cgtcatctga aaacgacatg  240
tcgcacaagt cctaagttac gcgacaggct gccgccctgc ccttttcctg gcgttttctt  300
gtcgcgtgtt ttagtcgcat aaagtagaat acttgcgact agaaccggag acattacgcc  360
atgaacaaga gcgccgccgc tggcctgctg ggctatgccc gcgtcagcac cgacgaccag  420
gacttgacca accaacgggc cgaactgcac gcggccggct gcaccaagct gttttccgag  480
aagatcaccg gcaccaggcg cgaccgcccg gagctggcca ggatgcttga ccacctacgc  540
cctggcgacg ttgtgacagt gaccaggcta gaccgcctgg cccgcagcac ccgcgaccta  600
ctggacattg ccgagcgcat ccaggaggcc ggcgcgggcc tgcgtagcct ggcagagccg  660
tgggccgaca ccaccacgcc ggccggccgc atggtgttga ccgtgttcgc cggcattgcc  720
gagttcgagc gttccctaat catcgaccgc acccggagcg ggcgcgaggc cgccaaggcc  780
cgaggcgtga agtttggccc ccgccctacc ctcaccccgg cacagatcgc gcacgcccgc  840
gagctgatcg accaggaagg ccgcaccgtg aaagaggcgg ctgcactgct tggcgtgcat  900
cgctcgaccc tgtaccgcgc acttgagcgc agcgaggaag tgacgcccac cgaggccagg  960
cggcgcggtg ccttccgtga ggacgcattg accgaggccg acgccctggc ggccgccgag  1020
aatgaacgcc aagaggaaca agcatgaaac cgcaccagga cggccaggac gaaccgtttt  1080
tcattaccga agagatcgag gcggagatga tcgcggccgg gtacgtgttc gagccgcccg  1140
cgcacctctc aaccgtgcgg ctgcatgaaa tcctggccgg tttgtctgat gccaagctgg  1200
cggcctggcc ggccagcttg gccgctgaag aaaccgagcg ccgccgtcta aaaaggtgat  1260
gtgtatttga gtaaaacagc ttgcgtcatg cggtcgctgc gtatatgatc cgatgagtaa  1320
ataaacaaat acgcaagggg aacgcatgaa ggttatcgct gtacttaacc agaaaggcgg  1380
gtcaggcaag acgaccatcg gaacccatct agcccgcgcc ctgcaactcg ccggggccga  1440
tgttctgtta gtcgattccg atccccaggg cagtgcccgc gattgggcgg ccgtgcggga  1500
```

```
agatcaaccg ctaaccgttg tcggcatcga ccgcccgacg attgaccgcg acgtgaaggc  1560
catcggccgg cgcgacttcg tagtgatcga cggagcgccc caggcggcgg acttggctgt  1620
gtccgcgatc aaggcagccg acttcgtgct gattccggtg cagccaagcc cttacgacat  1680
atgggccacc gccgacctgg tggagctggt taagcagcgc attgaggtca cggatggaag  1740
gctacaagcg gcctttgtcg tgtcgcgggc gatcaaaggc acgcgcatcg gcggtgaggt  1800
tgccgaggcg ctggccgggt acgagctgcc cattcttgag tcccgtatca cgcagcgcgt  1860
gagctaccca ggcactgccg ccgccggcac aaccgttctt gaatcagaac ccgagggcga  1920
cgctgcccgc gaggtccagg cgctggccgc tgaaattaaa tcaaaactca tttgagttaa  1980
tgaggtaaag agaaaatgag caaaagcaca aacacgctaa gtgccggccg tccgagcgca  2040
cgcagcagca aggctgcaac gttggccagc ctggcagaca cgccagccat gaagcgggtc  2100
aactttcagt tgccggcgga ggatcacacc aagctgaaga tgtacgcggt acgccaaggc  2160
aagaccatta ccgagctgct atctgaatag atcgcgcagc taccagagta aatgagcaaa  2220
tgaataaatg agtagatgaa ttttagcggc taaaggaggc ggcatggaaa atcaagaaca  2280
accaggcacc gacgccgtgg aatgccccat gtgtggagga acgggcggtt ggccaggcgt  2340
aagcggctgg gttgtctgcc ggccctgcaa tggcactgga acccccaagc ccgaggaatc  2400
ggcgtgacgg tcgcaaacca tccggcccgg tacaaatcgg cgcggcgctg ggtgatgacc  2460
tggtggagaa gttgaaggcc gcgcaggccg cccagcggca acgcatcgag gcagaagcac  2520
gccccggtga atcgtggcaa gcggccgctg atcgaatccg caaagaatcc cggcaaccgc  2580
cggcagccgg tgcgccgtcg attaggaagc cgcccaaggg cgacgagcaa ccagattttt  2640
tcgttccgat gctctatgac gtgggcaccc gcgatagtcg cagcatcatg gacgtggccg  2700
ttttccgtct gtcgaagcgt gaccgacgag ctggcgaggt gatccgctac gagcttccag  2760
acgggcacgt agaggtttcc gcagggccgg ccggcatggc cagtgtgtgg gattacgacc  2820
tggtactgat ggcggtttcc catctaaccg aatccatgaa ccgataccgg gaagggaagg  2880
gagacaagcc cggccgcgtg ttccgtccac acgttgcgga cgtactcaag ttctgccggc  2940
gagccgatgg cggaaagcag aaagacgacc tggtagaaac ctgcattcgg ttaaacacca  3000
cgcacgttgc catgcagcgt acgaagaagg ccaagaacgg ccgcctggtg acggtatccg  3060
agggtgaagc cttgattagc cgctacaaga tcgtaaagag cgaaaccggg cggccggagt  3120
acatcgagat cgagctagct gattggatgt accgcgagat cacagaaggc aagaacccgg  3180
acgtgctgac ggttcacccc gattactttt tgatcgatcc cggcatcggc cgttttctct  3240
accgcctggc acgccgcgcc gcaggcaagg cagaagccag atggttgttc aagacgatct  3300
acgaacgcag tggcagcgcc ggagagttca agaagttctg tttcaccgtg cgcaagctga  3360
tcgggtcaaa tgacctgccg gagtacgatt tgaaggagga ggcggggcag gctggcccga  3420
tcctagtcat gcgctaccgc aacctgatcg agggcgaagc atccgccggt tcctaatgta  3480
cggagcagat gctagggcaa attgccctag caggggaaaa aggtcgaaaa ggactctttc  3540
ctgtggatag cacgtacatt gggaacccaa agccgtacat tgggaaccgg aacccgtaca  3600
ttgggaaccc aaagccgtac attgggaacc ggtcacacat gtaagtgact gatataaaag  3660
agaaaaaagg cgatttttcc gcctaaaact ctttaaaact tattaaaact cttaaaaccc  3720
gcctggcctg tgcataactg tctggccagc gcacagccga agagctgcaa aaagcgccta  3780
cccttcggtc gctgcgctcc ctacgccccg ccgcttcgcg tcggcctatc gcggccgctg  3840
gccgctcaaa aatggctggc ctacggccag gcaatctacc agggcgcgga caagccgcgc  3900
cgtcgccact cgaccgccgg cgcccacatc aaggcaccct gcctcgcgcg tttcggtgat  3960
gacggtgaaa acctctgaca catgcagctc ccggtgacgg tcacagcttg tctgtaagcg  4020
gatgccggga gcagacaagc ccgtcagggc gcgtcagcgg gtgttggcgg gtgtcggggc  4080
gcagccatga cccagtcacg tagcgatagc ggagtgtata ctggcttaac tatgcggcat  4140
cagagcagat tgtactgaga gtgcaccata tgcggtgtga aataccgcac agatgcgtaa  4200
ggagaaaata ccgcatcagg cgctcttccg cttcctcgct cactgactcg ctgcgctcgg  4260
tcgttcggct gcggcgagcg gtatcagctc actcaaaggc ggtaatacgg ttatccacag  4320
aatcagggga taacgcagga aagaacatgt gagcaaaagg ccagcaaaag gccaggaacc  4380
gtaaaaaggc cgcgttgctg gcgtttttcc ataggctccg cccccctgac gagcatcaca  4440
aaaatcgacg ctcaagtcag aggtggcgaa acccgacagg actataaaga taccaggcgt  4500
ttccccctgg aagctccctc gtgcgctctc ctgttccgac cctgccgctt accggatacc  4560
tgtccgcctt tctcccttcg ggaagcgtgg cgctttctca tagctcacgc tgtaggtatc  4620
tcagttcggt gtaggtcgtt cgctccaagc tgggctgtgt gcacgaaccc cccgttcagc  4680
ccgaccgctg cgccttatcc ggtaactatc gtcttgagtc caacccggta agacacgact  4740
tatcgccact ggcagcagcc actggtaaca ggattagcag agcgaggtat gtaggcggtg  4800
ctacagagtt cttgaagtgg tggcctaact acggctacac tagaaggaca gtatttggta  4860
tctgcgctct gctgaagcca gttaccttcg gaaaaagagt tggtagctct tgatccggca  4920
aacaaaccac cgctggtagc ggtggttttt ttgtttgcaa gcagcagatt acgcgcagaa  4980
aaaaaggatc tcaagaagat cctttgatct tttctacggg gtctgacgct cagtggaacg  5040
aaaactcacg ttaagggatt ttggtcatgc attctaggtg attagaaaaa ctcatcgagc  5100
atcaaatgaa actgcaattt attcatatca ggattatcaa taccatattt ttgaaaaagc  5160
cgtttctgta atgaaggaga aaactcaccg aggcagttcc ataggatggc aagatcctgg  5220
tatcggtctg cgattccgac tcgtccaaca tcaatacaac ctattaattt cccctcgtca  5280
aaaataaggt tatcaagtga gaaatcacca tgagtgacga ctgaatccgg tgagaatggc  5340
aaaagtttat gcatttcttt ccagacttgt tcaacaggcc agccattacg ctcgtcatca  5400
aaatcactcg catcaaccaa accgttattc attcgtgatt gcgcctgagc gagtcgaaat  5460
acgcgatcgc tgttaaaagg acaattacaa acaggaatcg aatgcaaccg gcgcaggaac  5520
actgccagcg catcaacaat attttcacct gaatcaggat attcttctaa tacctggaat  5580
gctgttttcc ctgggatcgc agtggtgagt aaccatgcat catcaggagt acggataaaa  5640
tgcttgatgg tcggaagagg cataaattcc gtcagccagt ttagtctgac catctcatct  5700
gtaacatcat tggcaacgct acctttgcca tgtttcagaa acaactctgg cgcatcgggc  5760
ttcccataca atcggtagat tgtcgcacct gattgcccga cattatcgcg agcccattta  5820
tacccatata aatcagcatc catgttggaa tttaatcgcg gccttgagca agacgtttcc  5880
cgttgaatat ggctcataac agaacttatt atttccttcc tcttttctac agtatttaaa  5940
gataccccaa gaagctaatt ataacaagac gaactccaat tcactgttcc ttgcattcta  6000
aaaccttaaa taccagaaaa cagctttttc aaagttgttt tcaaagttgg cgtataacat  6060
agtatcgacg gagccgattt tgaaaccgcg gtgatcacag gcagcaacgc tctgtcatcg  6120
ttacaatcaa catgctaccc tccgcgagat catccgtgtt tcaaacccgg cagcttagtt  6180
gccgttcttc cgaatagcat cggtaacatg agcaaagtct gccgccttac aacggctctc  6240
```

-continued ccgctgacgc cgtcccggac tgatgggctg cctgtatcga gtggtgattt tgtgccgagc 6300
tgccggtcgg ggagctgttg gctggctggt ggcaggatat attgtggtgt aaacataacg 6360
aattcgtctc aggagagcgt cgatctagta acatagatga caccgcgcgc gataatttat 6420
cctagtttgc gcgctatatt ttgttttcta tcgcgtatta aatgtataat tgcgggactc 6480
taatcataaa aacccatctc ataaataacg tcatgcatta catgttaatt attacatgct 6540
taacgtaatt caacagaaat tatatgataa tcatcgcaag accggcaaca ggattcaatc 6600
ttaagaaact ttattgccaa atgtttgaac gatctgcttc gacgcactcc ttctttactc 6660
caccatctcg tccttattga aaacgtgggt agcaccaaaa cgaatcaagt cgctggaact 6720
gaagttacca atcacgctgg atgatttgcc agttggatta atcttgcctt tccccgcatg 6780
aataatattg atgaatgcat gcgtgagggg tagttcgatg ttggcaatag ctgcaattgc 6840
cgcgacatcc tccaacgagc ataattcttc agaaaaatag cgatgttcca tgttgtcagg 6900
gcatgcatga tgcacgttat gaggtgacgg tgctaggcag tattccctca aagtttcata 6960
gtcagtatca tattcatcat tgcattcctg caagagagaa ttgagacgca atccacacgc 7020
tgcggcaacc ttccggcgtt cgtggtctat ttgctcttgg acgttgcaaa cgtaagtgtt 7080
ggatcggggt gggcgaagaa ctccagcatg agatccccgc gctggaggat catccagccg 7140
gcgtcccgga aaacgattcc gaagcccaac ctttcataga aggcggcggt ggaatcgaaa 7200
tctcgtgatg gcaggttggg cgtcgcttgg tcggtcattt cgaaccccag agtcccgctc 7260
agaagaactc gtcaagaagg cgatagaagg cgatgcgctg cgaatcggga gcggcgatac 7320
cgtaaagcac gaggaagcgg tcagcccatt cgccgccaag ctcttcagca atatcacggg 7380
tagccaacgc tatgtcctga tagcggtccg ccacacccag ccggccacag tcgatgaatc 7440
cagaaaagcg gccattttcc accatgatat tcggcaagca ggcatcgcca tgggtcacga 7500
cgagatcctc gccgtcgggc atgcgcgcct tgagcctggc gaacagttcg gctggcgcga 7560
gcccctgatg ctcttcgtcc agatcatcct gatcgacaag accggcttcc atccgagtac 7620
gtgctcgctc gatgcgatgt ttcgcttggt ggtcgaatgg gcaggtagcc ggatcaagcg 7680
tatgcagccg ccgcattgca tcagccatga tggatacttt ctcggcagga gcaaggtgag 7740
atgacaggag atcctgcccc ggcacttcgc ccaatagcag ccagtccctt cccgcttcag 7800
tgacaacgtc gagcacagct gcgcaaggaa cgcccgtcgt ggccagccac gatagccgcg 7860
ctgcctcgtc ctgcagttca ttcagggcac cggacaggtc ggtcttgaca aaaagaaccg 7920
ggcgcccctg cgctgacagc cggaacacgg cggcatcaga gcagccgatt gtctgttgtg 7980
cccagtcata gccgaatagc ctctccaccc aagcggccgg agaacctgcc cggatccggg 8040
cggaaatagg taaagaagtt gcggataagg taattgccat tgcagattat ttggattgag 8100
agtgaatatg agactctaat tggataccga ggggaattta tggaacgtca gtggagcatt 8160
tttgacaaga aatatttgct agctgatagt gaccttaggc gacttttgaa cgcgcaataa 8220
tggtttctga cgtatgtgct tagctcatta aactccagaa acccctccgt caggagacta 8280
gagccaagct gatctccttt gccccggaga tcaccatgga cgactttctc tatctctacg 8340
atctaggaag aaagttcgac ggagaaggtg acgataccat gttcaccacc gataatgaga 8400
agattagcct cttcaatttc agaaagaatg ctgacccaca gatggttaga gaggcctacg 8460
cggcaggtct gatcaagacg atctacccga gtaataatct ccaggagatc aaataccttc 8520
ccaagaaggt taaagatgca gtcaaaagat tcaggactaa ctgcatcaag aacacagaga 8580
aagatatatt tctcaagatc agaagtacta ttccagtatg gacgattcaa ggcttgcttc 8640
ataaaccaag gcaagtaata gagattggag tctctaagaa agtagttcct actgaatcaa 8700
aggccatgga gtcaaaaatt cagatcgagg atctaacaga actcgccgtg aagactggcg 8760
aacagttcat acagagtctt ttacgactca atgacaagaa gaaaatcttc gtcaacatgg 8820
tggagcacga cactctcgtc tactccaaga atatcaaaga tacagtctca gaagaccaaa 8880
gggctattga gacttttcaa caaagggtaa tatcgggaaa cctcctcgga ttccattgcc 8940
cagctatctg tcacttcatc aaaaggacag tagaaaagga aggtggcacc tacaaatgcc 9000
atcattgcga taaaggaaag gctatcgttc aagatgcctc tgccgacagt ggtcccaaag 9060
atggaccccc acccacgagg agcatcgtgg aaaaagaaga cgttccaacc acgtcttcaa 9120
agcaagtgga ttgatgtgat atctccactg acgtaaggga tgacgcacaa tcccactatc 9180
cttcgcaaga cccttcctct atataaggaa gttcatttca tttggagagg actccggtat 9240
ttttacaaca ataccacaac aaaacaaaca acaaacaaca ttacaattta ctattctagt 9300
cgaaatggat aacgcaacac ttgctgtgat cctttccatt ttgtttgtgt tttaccacat 9360
tttcaaatcc tttttcacca attcttcatc tcgtaggctt cctcctggtc ccaaacccgt 9420
gccaattttt ggcaacattt tcgatcttgg cgaaaagcct catcgatctt ttgccaatct 9480
atctaaaatt cacggccctt tgattagcct aaagttagga agtgtaacaa ctattgttgt 9540
ttcctcggcc tctgtggccg aggaaatgtt ccttaaaaat gaccaagcac ttgctaaccg 9600
aaccattcct gactcggtta gggctggtga ccacgacaaa ttatccatgt cgtggttgcc 9660
tgtttcccaa aaatggagaa atatgagaaa aatctccgct gtccaattac tctccaacca 9720
aaaacttgat gctagtcaac ctcttagaca agctaaggtg aaacaacttt tatcatacgt 9780
acaagtttgt tccgaaaaaa tgcaacccgt cgatattgga cgggccgcat ttacaacgtc 9840
acttaattta ttatcaaaca catttttctc aatcgaatta gcaagtcatg aatctagtgc 9900
ttcccaagag tttaaacaac tcatgtggaa tattatggag gaaattggaa ggcctaatta 9960
tgctgatttt ttccctattc ttggttacat tgatcccttt ggtataagac gtcgtttggc 10020
tggttacttt gataaactca ttgatgtttt ccaagacatt attcgtgaaa gacaaaagct 10080
tcgatcttct aattcttccg gcgcaaaaca aacaaatgac attcttgata ctcttcttaa 10140
actccatgaa gataatgagt tgagtatgcc tgaaattaat caccttctcg tggatatctt 10200
tgacgccgga acagacacaa cagcaagcac attagaatgg gcaatggccg aacttgtgaa 10260
aaacccggaa atgatgacta aagttcaaat tgaaatcgaa caagctcttg gaaaagattg 10320
cttagacata caagaatccg acatctcaaa actaccttat ttacaagcca ttataaaaga 10380
aacgttacgt ttacaccctc ctactgtgtt tttgctgcct cgaaaggcag acaatgacgt 10440
agagttatat ggctacgttg taccaaagaa tgctcaagtc cttgtcaatc tttgggcaat 10500
tggtcgtgat ccaaaggtat ggaaaaatcc ggaagtattt tctcctgaaa ggtttttaga 10560
ttgcaatatc gattataaag gacgagattt cgaactttta ccctttggtg ctggtagaag 10620
gatatgccct ggacttactt tggcatatag aatgttgaac ttgatgttgg ctactcttct 10680
tcaaaactac aattggaaac ttgaagatgg tatcaatcct aaggatttag acatggatga 10740
gaaatttggg attacattgc aaaaggttaa acctcttcaa gttattccag ttcccagaaa 10800
ctaggcttgc tctcaagatc aaaggcttaa aaagctgggg ttttatgaat gggatcaaag 10860
tttctttttt tcttttatat ttgcttctcc atttgtttgt ttcatttccc tttttgtttt 10920
cgtttctatg atgcacttgt gtgtgacaaa ctctctgggt ttttacttac gtctgcgttt 10980

```
caaaaaaaaa aaccgctttc gttttgcgtt ttagtcccat tgttttgtag ctctgagtga  11040
tcgaattgat gcctctttat tccttttgtt ccctataatt tctttcaaaa ctcagaagaa  11100
aaaccttgaa actctttgca atgttaatat aagtattgta taagattttt attgatttgg  11160
ttattagtct tacttttgct acctccatct tcacttggaa ctgatattct gaatagttaa  11220
agcgttacat gtcttccatt cacaaatgaa cttaaactag cacaaagtca gatattttaa  11280
gatcgcacca ttttatataa ccccaatcgt caattctact gtttcaagtt ttacaccaaa  11340
acaattacga ggtgtatcta ttcgttactc ttttcgctta ttaatccttt tacatgatgc  11400
aaaatataac aaattaattt caaattgtcc tgcacatttg gtttatacat cttgattcca  11460
aaaagtcgct gtcaggagat acatgagaat taagggagtc acggtatgac ccccgccgat  11520
gacgcgggac aagccgtttt acgtttggaa ctgacagaac cgcaacgttg aaggagccac  11580
tgagccgcgg gtttctggag tttaatgagc taagcacata cgtcagaaac cattattgcg  11640
cgttcaaaag tcgcctaagg tcactatcag ctagcaaata tttcttgtca aaaatgctcc  11700
actgacgttc cataaattcc cctcggtatc caattagagt ctcatattca ctctcaactc  11760
gatcgaggca atgatggcta tggaagtggg ttatcttcgg cactcgacaa cgatcaccaa  11820
cggactgtgt tgtaactgtg atccgaagcc ccgaggagca cgtcgtgtac agactaggct  11880
gcctggcacc ctgtgtctcg tcaaggatac ctttacctct agcaaagcta aactaaaaaa  11940
gccgtcgcag agagaaatct ttctaacaag taggaagagg ctgaatcaga tacaagctgt  12000
ttcaacggct gaaaaggaga gagaggcaga caaaacatcc actccaccta ttcccagtag  12060
catccacgat atttcaaatg gagatcacat tcttggcttc ggagccgatt tgaccgaaga  12120
tcatcctggc taccatgatc ttgaatataa gaggaggcgt agtcgtattg ctgaccttgc  12180
gaagatacat aaaataggtg aacccattcc ttgcgtggac tacacatcgg aagagattcg  12240
tgtgtggggt catgtgttag atactctagt ggacctctac ccaactcatg cttgtaagga  12300
atacctgaat tgctacgagc tgtttaactt caagccaaac tatattccac agctgcaaga  12360
actttcggag gtcctggaac ggagcacagg atggcacatc cgcccagtag ctggactcct  12420
ccaccctcgt gacttcctaa acggtctagc cttccgcact ttccattcaa cccagtatgt  12480
tcggcatggc agcaatccca tgtacacccc cgagccagac atttgtcacg aggttttagg  12540
ccacgtcccc attctggctg atccggagtt tgctgactta gcttgggcca ttggccaagc  12600
ttctctgggt gcttcagaga aggatatctg gcaccttacg aagctctact ggtacactgt  12660
ggagtttggc acagtaaagg aaggtaacga gattaaagcg ttcggtgcag gccttctgtc  12720
tagttttggg gagctgaagc acatgcgggt ggggacggat ggattcatgc ctgagttcgt  12780
ggagcttgac ccgtttaaga agatgcccaa gatgagctac aaagacgggt accagaagag  12840
gtattttcta tgcgagagct ttgcagatgc agcggcaaag cttagggcgt attccagaag  12900
cattctgaag cctgaggtgc agtccatcaa gtttggagat acgccaatcc ggctctaagc  12960
ttatatgaag atgaagatga aatatttggt gtgtcaaata aaaagcttgt gtgcttaagt  13020
ttgtgttttt ttcttggctt gttgtgttat gaatttgtgg ctttttctaa tattaaatga  13080
atgtaagatc tcattataat gaataaacaa atgtttctat aatccattgt gaatgttttg  13140
ttggatctct tctgcagcat ataactactg tatgtgctat ggtatggact atggaatatg  13200
attaaagata agcgctgtca ggagccgtac aaaattgatt attgatgtca caaatcaatc  13260
agagctaaat tccaaaaaaa atatgatctt tgaaacttgc atcaataact aacgattcta  13320
ggaagagccc atttcgattt caacaaaaag atgagagctt gattacatat aaaatcaaga  13380
gaaattaacg acattgaaga gaattcgatc tcgaaaccgg aaacaaagac ttataagtcg  13440
attagtctaa ttcaatgcag aagaaagaat accaggtttg gccttcacga tggaaagctt  13500
cggatttgga gccaagtctc ataaacgcca ttgtggaaga aagtcttgag ttggtggtaa  13560
tgtaacagag tagtaagaac agagaagaga gagagtgtga gatacatgaa ttgtcgggca  13620
acaaaaatcc tgaacatctt attttagcaa agagaaagag ttccgagtct gtagcagaag  13680
agtgaggaga aatttaagct cttggacttg tgaattgttc cgcctcttga atacttcttc  13740
aatcctcata tattcttctt ctatgttacc tgaaaaccgg catttaatct cgcgggttta  13800
ttccggttca acattttttt tgttttgagt tattatctgg gcttaataac gcaggcctga  13860
aataaattca aggcccaact gttttttttt ttaagaagtt gctgttaaaa aaaaaaaaag  13920
ggaattaaca acaacaacaa aaaaagataa agaaaataat aacaattact ttaattgtag  13980
actaaaaaaa catagatttt atcatgaaaa aaagagaaaa gaaataaaaa cttggatcaa  14040
aaaaaaaaac atacagatct tctaattatt aacttttctt aaaaattagg tccttttttcc  14100
caacaattag gtttagagtt ttggaattaa accaaaaaga ttgttctaaa aaatactcaa  14160
atttggtaga taagtttcct tattttaatt agtcaatggt agatactttt ttttcttttc  14220
tttattagag tagattagaa tcttttatgc caagtattga taaattaaat caagaagata  14280
aactatcata atcaacatga aattaaaaga aaaatctcat atatagtatt agtattctct  14340
atatatatta tgattgctta ttcttaatgg gttgggttaa ccaagacata gtcttaatgg  14400
aaagaatctt ttttgaactt tttccttatt gattaaattc ttctatagaa aagaaagaaa  14460
ttatttgagg aaaagtatat acaaaaagaa aaatagaaaa atgtcagtga agcagatgta  14520
atggatgacc taatccaacc accaccatag gatgtttcta cttgagtcgg tcttttaaaa  14580
acgcacggtg gaaaatatga cacgtatcat atgattcctt cctttagttt cgtgataata  14640
atcctcaact gatatcttcc ttttttttgtt ttggctaaag atattttatt ctcattaata  14700
gaaaagacgg ttttgggctt ttggtttgcg atataaagaa gaccttcgtg tggaagataa  14760
taattcatcc tttcgtcttt ttctgactct tcaatctctc ccaaagccta aagcgatctc  14820
tgcaaatctc tcgcgactct ctctttcaag gtatatttc tgattctttt tgtttttgat  14880
tcgtatctga tctccaattt ttgttatgtg gattattgaa tcttttgtat aaattgcttt  14940
tgacaatatt gttcgtttcg tcaatccagc ttctaaattt tgtcctgatt actaagatat  15000
cgattcgtag tgtttacatc tgtgtaattt cttgcttgat tgtgaaatta ggattttcaa  15060
ggacgatcta ttcaattttt gtgtttttctt tgttcgattc tctctgtttt aggtttctta  15120
tgtttagatc cgtttctctt tggtgttgtt ttgatttctc ttacggcttt tgatttggta  15180
tatgttcgct gattggtttc tacttgttct attgttttat ttcagaatgg cttctatgat  15240
atcctcttca gctgtgacta cagtcagccg tgcttctacg gtgcaatcgg ccgcggtggc  15300
tccattcggc ggcctcaaat ccatgactgg attcccagtt aagaaggtca acactgacat  15360
tacttccatt acaagcaatg gtggaagagt aaagtgcatg ctgatgaatt atcagaacga  15420
cgatttacgc atcaaagaaa tcaaagagtt acttcctcct gtcgcattgc tggaaaaatt  15480
ccccgctact gaaaatgccg cgaatacggt tgcccatgcc cgaaaagcga tccataagat  15540
cctgaaaggt aatgatgatc gcctgttggt tgtgattggc ccatgctcaa ttcatgatcc  15600
tgtcgcggca aaagagtatg ccactcgctt gctggcgctg cgtgaagagc tgaaagatga  15660
gctggaaatc gtaatgcgcg tctattttga aaagccgcgt accacggtgg gctggaaagg  15720
```

```
gctgattaac gatccgcata tggataatag cttccagatc aacgacggtc tgcgtatagc  15780
ccgtaaattg ctgcttgata ttaacgacag cggtctgcca gcggcaggtg agtttctcga  15840
tatgatcacc ccacaatatc tcgctgacct gatgagctgg ggcgcaattg gcgcacgtac  15900
caccgaatcg caggtgcacc gcgaacaggc atcagggctt tcttgtccgg tcggcttcaa  15960
aaatggcacc gacggtacga ttaaagtggc tatcgatgcc attaatgccg ccggtgcgcc  16020
gcactgcttc ctgtccgtaa cgaaatgggg gcattcggcg attgtgaata ccagcggtaa  16080
cggcgattgc catatcattc tgcgcggcgg taaagagcct aactacagcg cgaagcacgt  16140
tgctgaagtg aaagaagggc tgaacaaagc aggcctgcca gcacaggtga tgatcgattt  16200
cagccatgct aactcgtcca aacaattcaa aaagcagatg gatgtttgtg ctgacgtttg  16260
ccagcagatt gccggtggcg aaaaggccat tattggcgtg atggtggaaa gccatctggt  16320
ggaaggcaat cagagcctcg agagcgggga gccgctggcc tacggtaaga gcatcaccga  16380
tgcctgcatc ggctgggaag ataccgatgc tctgttacgt caactggcga atgcagtaaa  16440
agcgcgtcgc ggggaattca tcttttaccc atacgatgtt cctgactatg cgggctatcc  16500
ctatgacgtc ccggactatg caggatccta tccatatgac gttccagatt acgctgctca  16560
gtaggcttat atgaagatga agatgaaata tttggtgtgt caaataaaaa gcttgtgtgc  16620
ttaagtttgt gttttttttct tggcttgttg tgttatgaat ttgtggcttt ttctaatatt  16680
aaatgaatgt aagatctcat tataatgaat aaacaaatgt ttctataatc cattgtgaat  16740
gttttgttgg atctcttctg cagcatataa ctactgtatg tgctatggta tggactatgg  16800
aatatgatta aagataag                                                16818

SEQ ID NO: 27          moltype = DNA  length = 18647
FEATURE                Location/Qualifiers
misc_feature           1..18647
                       note = pDOPA4 overexpression vector
source                 1..18647
                       mol_type = other DNA
                       organism = synthetic construct
SEQUENCE: 27
cgctgtcatg agacgaattc tgacaggata tattggcggg taaacctaag agaaaagagc  60
gtttattaga ataatcggat atttaaaagg gcgtgaaaag gtttatccgt tcgtccattt  120
gtatgtgcat gccaaccaca gggttcccct cgggatcaaa gtactttgat ccaacccctc  180
cgctgctata gtgcagtcgg cttctgacgt tcagtgcagc cgtcatctga aaacgacatg  240
tcgcacaagt cctaagttac gcgacaggct gccgccctgc ccttttcctg gcgttttctt  300
gtcgcgtgtt ttagtcgcat aaagtagaat acttgcgact agaaccggag acattacgcc  360
atgaacaaga gcgccgccgc tggcctgctg ggctatgccc gcgtcagcac cgacgaccag  420
gacttgacca accaacgggc cgaactgcac gcggccggct gcaccaagct gttttccgag  480
aagatcaccg gcaccaggcg cgaccgcccg gagctggcca ggatgcttga ccacctacgc  540
cctggcgacg ttgtgacagt gaccaggcta gaccgcctgg cccgcagcac ccgcgaccta  600
ctggacattg ccgagcgcat ccaggaggcc ggcgcgggcc tgcgtagcct ggcagagccg  660
tgggccgaca ccaccacgcc ggccggccgc atggtgttga ccgtgttcgc cggcattgcc  720
gagttcgagc gttccctaat catcgaccgc acccggagcg ggcgcgaggc cgccaaggcc  780
cgaggcgtga agtttggccc ccgccctacc ctcaccccgg cacagatcgc gcacgcccgc  840
gagctgatcg accaggaagg ccgcaccgtg aaagaggcgg ctgcactgct tggcgtgcat  900
cgctcgaccc tgtaccgcgc acttgagcgc agcgaggaag tgacgcccac cgaggccagg  960
cggcgcggtg ccttccgtga ggacgcattg accgaggccg acgccctggc ggccgccgag  1020
aatgaacgcc aagaggaaca agcatgaaac cgcaccagga cggccaggac gaaccgtttt  1080
tcattaccga agagatcgag gcggagatga tcgcggccgg gtacgtgttc gagccgcccg  1140
cgcacctctc aaccgtgcgg ctgcatgaaa tcctggccgg tttgtctgat gccaagctgg  1200
cggcctggcc ggccagcttg gccgctgaag aaaccgagcg ccgccgtcta aaaaggtgat  1260
gtgtatttga gtaaaacagc ttgcgtcatg cggtcgctgc gtatatgatc cgatgagtaa  1320
ataaacaaat acgcaagggg aacgcatgaa ggttatcgct gtacttaacc agaaaggcgg  1380
gtcaggcaag acgaccatcg gaacccatct agcccgcgcc ctgcaactcg ccggggccga  1440
tgttctgtta gtcgattccg atccccaggg cagtgcccgc gattgggcgg ccgtgcggga  1500
agatcaaccg ctaaccgttg tcggcatcga ccgcccgacg attgaccgcg acgtgaaggc  1560
catcggccgg cgcgacttcg tagtgatcga cggagcgccc caggcggcgg acttggctgt  1620
gtccgcgatc aaggcagccg acttcgtgct gattccggtg cagccaagcc cttacgacat  1680
atgggccacc gccgacctgg tggagctggt taagcagcgc attgaggtca cggatggaag  1740
gctacaagcg gcctttgtcg tgtcgcgggc gatcaaaggc acgcgcatcg gcggtgaggt  1800
tgccgaggcg ctggccgggt acgagctgcc cattcttgag tcccgtatca cgcagcgcgt  1860
gagctaccca ggcactgccg ccgccggcac aaccgttctt gaatcagaac ccgagggcga  1920
cgctgcccgc gaggtccagg cgctggccgc tgaaattaaa tcaaaactca tttgagttaa  1980
tgaggtaaag agaaaatgag caaaagcaca aacacgctaa gtgccggccg tccgagcgca  2040
cgcagcagca aggctgcaac gttggccagc ctggcagaca cgccagccat gaagcgggtc  2100
aactttcagt tgccggcgga ggatcacacc aagctgaaga tgtacgcggt acgccaaggc  2160
aagaccatta ccgagctgct atctgaatag atcgcgcagc taccagagta aatgagcaaa  2220
tgaataaatg agtagatgaa ttttagcggc taaaggaggc ggcatggaaa atcaagaaca  2280
accaggcacc gacgccgtgg aatgccccat gtgtggagga acgggcggtt ggccaggcgt  2340
aagcggctgg gttgtctgcc ggccctgcaa tggcactgga acccccaagc ccgaggaatc  2400
ggcgtgacgg tcgcaaacca tccggcccgg tacaaatcgg cgcggcgctg ggtgatgacc  2460
tggtggagaa gttgaaggcc gcgcaggccg cccagcggca acgcatcgag gcagaagcac  2520
gccccggtga atcgtggcaa gcggccgctg atcgaatccg caaagaatcc cggcaaccgc  2580
cggcagccgg tgcgccgtcg attaggaagc cgcccaaggg cgacgagcaa ccagattttt  2640
tcgttccgat gctctatgac gtgggcaccc gcgatagtcg cagcatcatg gacgtggccg  2700
ttttccgtct gtcgaagcgt gaccgacgag ctggcgaggt gatccgctac gagcttccag  2760
acgggcacgt agaggtttcc gcagggccgg ccggcatggc cagtgtgtgg gattacgacc  2820
tggtactgat ggcggtttcc catctaaccg aatccatgaa ccgataccgg gaagggaagg  2880
gagacaagcc cggccgcgtg ttccgtccac acgttgcgga cgtactcaag ttctgccggc  2940
gagccgatgg cggaaagcag aaagacgacc tggtagaaac ctgcattcgg ttaaacacca  3000
cgcacgttgc catgcagcgt acgaagaagg ccaagaacgg ccgcctggtg acggtatccg  3060
```

```
agggtgaagc cttgattagc cgctacaaga tcgtaaagag cgaaaccggg cggccggagt  3120
acatcgagat cgagctagct gattggatgt accgcgagat cacagaaggc aagaacccgg  3180
acgtgctgac ggttcacccc gattactttt tgatcgatcc cggcatcggc cgttttctct  3240
accgcctggc acgccgcgcc gcaggcaagg cagaagccag atggttgttc aagacgatct  3300
acgaacgcag tggcagcgcc ggagagttca agaagttctg tttcaccgtg cgcaagctga  3360
tcgggtcaaa tgacctgccg gagtacgatt tgaaggagga ggcggggcag gctggcccga  3420
tcctagtcat gcgctaccgc aacctgatcg agggcgaagc atccgccggt tcctaatgta  3480
cggagcagat gctagggcaa attgccctag caggggaaaa aggtcgaaaa ggactctttc  3540
ctgtggatag cacgtacatt gggaacccaa agccgtacat tgggaaccgg aacccgtaca  3600
ttgggaaccc aaagccgtac attgggaacc ggtcacacat gtaagtgact gatataaaag  3660
agaaaaaagg cgatttttcc gcctaaaact ctttaaaact tattaaaact cttaaaaccc  3720
gcctggcctg tgcataactg tctggccagc gcacagccga agagctgcaa aaagcgccta  3780
cccttcggtc gctgcgctcc ctacgccccg ccgcttcgcg tcggcctatc gcggccgctg  3840
gccgctcaaa aatggctggc ctacggccag gcaatctacc agggcgcgga caagccgcgc  3900
cgtcgccact cgaccgccgg cgcccacatc aaggcaccct gcctcgcgcg tttcggtgat  3960
gacggtgaaa acctctgaca catgcagctc ccggtgacgg tcacagcttg tctgtaagcg  4020
gatgccggga gcagacaagc ccgtcagggc gcgtcagcgg gtgttggcgg gtgtcggggc  4080
gcagccatga cccagtcacg tagcgatagc ggagtgtata ctggcttaac tatgcggcat  4140
cagagcagat tgtactgaga gtgcaccata tgcggtgtga aataccgcac agatgcgtaa  4200
ggagaaaata ccgcatcagg cgctcttccg cttcctcgct cactgactcg ctgcgctcgg  4260
tcgttcggct gcggcgagcg gtatcagctc actcaaaggc ggtaatacgg ttatccacag  4320
aatcagggga taacgcagga aagaacatgt gagcaaaagg ccagcaaaag gccaggaacc  4380
gtaaaaaggc cgcgttgctg gcgtttttcc ataggctccg cccccctgac gagcatcaca  4440
aaaatcgacg ctcaagtcag aggtggcgaa acccgacagg actataaaga taccaggcgt  4500
ttccccctgg aagctccctc gtgcgctctc ctgttccgac cctgccgctt accggatacc  4560
tgtccgcctt tctcccttcg ggaagcgtgg cgctttctca tagctcacgc tgtaggtatc  4620
tcagttcggt gtaggtcgtt cgctccaagc tgggctgtgt gcacgaaccc cccgttcagc  4680
ccgaccgctg cgccttatcc ggtaactatc gtcttgagtc caacccggta agacacgact  4740
tatcgccact ggcagcagcc actggtaaca ggattagcag agcgaggtat gtaggcggtg  4800
ctacagagtt cttgaagtgg tggcctaact acggctacac tagaaggaca gtatttggta  4860
tctgcgctct gctgaagcca gttaccttcg gaaaaagagt tggtagctct tgatccggca  4920
aacaaaccac cgctggtagc ggtggttttt ttgtttgcaa gcagcagatt acgcgcagaa  4980
aaaaaggatc tcaagaagat cctttgatct tttctacggg gtctgacgct cagtggaacg  5040
aaaactcacg ttaagggatt ttggtcatgc attctaggtg attagaaaaa ctcatcgagc  5100
atcaaatgaa actgcaattt attcatatca ggattatcaa taccatattt ttgaaaaagc  5160
cgtttctgta atgaaggaga aaactcaccg aggcagttcc ataggatggc aagatcctgg  5220
tatcggtctg cgattccgac tcgtccaaca tcaatacaac ctattaattt cccctcgtca  5280
aaaataaggt tatcaagtga gaaatcacca tgagtgacga ctgaatccgg tgagaatggc  5340
aaaagtttat gcatttcttt ccagacttgt tcaacaggcc agccattacg ctcgtcatca  5400
aaatcactcg catcaaccaa accgttattc attcgtgatt gcgcctgagc gagtcgaaat  5460
acgcgatcgc tgttaaaagg acaattacaa acaggaatcg aatgcaaccg gcgcaggaac  5520
actgccagcg catcaacaat attttcacct gaatcaggat attcttctaa tacctggaat  5580
gctgttttcc ctgggatcgc agtggtgagt aaccatgcat catcaggagt acggataaaa  5640
tgcttgatgg tcggaagagg cataaattcc gtcagccagt ttagtctgac catctcatct  5700
gtaacatcat tggcaacgct acctttgcca tgtttcagaa acaactctgg cgcatcgggc  5760
ttcccataca atcggtagat tgtcgcacct gattgcccga cattatcgcg agcccattta  5820
tacccatata aatcagcatc catgttggaa tttaatcgcg gccttgagca agacgtttcc  5880
cgttgaatat ggctcataac agaacttatt atttccttcc tcttttctac agtatttaaa  5940
gataccccaa gaagctaatt ataacaagac gaactccaat tcactgttcc ttgcattcta  6000
aaaccttaaa taccagaaaa cagctttttc aaagttgttt tcaaagttgg cgtataacat  6060
agtatcgacg gagccgattt tgaaaccgcg gtgatcacag gcagcaacgc tctgtcatcg  6120
ttacaatcaa catgctaccc tccgcgagat catccgtgtt tcaaacccgg cagcttagtt  6180
gccgttcttc cgaatagcat cggtaacatg agcaaagtct gccgccttac aacggctctc  6240
ccgctgacgc cgtcccggac tgatgggctg cctgtatcga gtggtgattt tgtgccgagc  6300
tgccggtcgg ggagctgttg gctggctggt ggcaggatat attgtggtgt aaacataacg  6360
aattcgtctc aggagagcgt cgatctagta acatagatga caccgcgcgc gataatttat  6420
cctagtttgc gcgctatatt ttgttttcta tcgcgtatta aatgtataat tgcgggactc  6480
taatcataaa aacccatctc ataaataacg tcatgcatta catgttaatt attacatgct  6540
taacgtaatt caacagaaat tatatgataa tcatcgcaag accggcaaca ggattcaatc  6600
ttaagaaact ttattgccaa atgtttgaac gatctgcttc gacgcactcc ttctttactc  6660
caccatctcg tccttattga aaacgtgggt agcaccaaaa cgaatcaagt cgctggaact  6720
gaagttacca atcacgctgg atgatttgcc agttggatta atcttgcctt tccccgcatg  6780
aataatattg atgaatgcat gcgtgagggg tagttcgatg ttggcaatag ctgcaattgc  6840
cgcgacatcc tccaacgagc ataattcttc agaaaaatag cgatgttcca tgttgtcagg  6900
gcatgcatga tgcacgttat gaggtgacgg tgctaggcag tattccctca aagtttcata  6960
gtcagtatca tattcatcat tgcattcctg caagagagaa ttgagacgca atccacacgc  7020
tgcggcaacc ttccggcgtt cgtggtctat ttgctcttgg acgttgcaaa cgtaagtgtt  7080
ggatcggggt gggcgaagaa ctccagcatg agatccccgc gctggaggat catccagccg  7140
gcgtcccgga aaacgattcc gaagcccaac ctttcataga aggcggcggt ggaatcgaaa  7200
tctcgtgatg gcaggttggg cgtcgcttgg tcggtcattt cgaaccccag agtcccgctc  7260
agaagaactc gtcaagaagg cgatagaagg cgatgcgctg cgaatcggga gcggcgatac  7320
cgtaaagcac gaggaagcgg tcagcccatt cgccgccaag ctcttcagca atatcacggg  7380
tagccaacgc tatgtcctga tagcggtccg ccacacccag ccggccacag tcgatgaatc  7440
cagaaaagcg gccattttcc accatgatat tcggcaagca ggcatcgcca tgggtcacga  7500
cgagatcctc gccgtcgggc atgcgcgcct tgagcctggc gaacagttcg gctggcgcga  7560
gcccctgatg ctcttcgtcc agatcatcct gatcgacaag accggcttcc atccgagtac  7620
gtgctcgctc gatgcgatgt ttcgcttggt ggtcgaatgg gcaggtagcc ggatcaagcg  7680
tatgcagccg ccgcattgca tcagccatga tggatacttt ctcggcagga gcaaggtgag  7740
atgacaggag atcctgcccc ggcacttcgc ccaatagcag ccagtccctt cccgcttcag  7800
```

```
tgacaacgtc gagcacagct gcgcaaggaa cgcccgtcgt ggccagccac gatagccgcg  7860
ctgcctcgtc ctgcagttca ttcagggcac cggacaggtc ggtcttgaca aaaagaaccg  7920
ggcgcccctg cgctgacagc cggaacacgg cggcatcaga gcagccgatt gtctgttgtg  7980
cccagtcata gccgaatagc ctctccaccc aagcggccgg agaacctgcc cggatccggg  8040
cggaaatagg taaagaagtt gcggataagg taattgccat tgcagattat ttggattgag  8100
agtgaatatg agactctaat tggataccga ggggaattta tggaacgtca gtggagcatt  8160
tttgacaaga aatatttgct agctgatagt gaccttaggc gacttttgaa cgcgcaataa  8220
tggtttctga cgtatgtgct tagctcatta aactccagaa acccctccgt caggaggtca  8280
actaccccaa tttaaatttt atttgattaa gatattttta tggacctact ttataattaa  8340
aaatatttc tatttgaaaa ggaaggacaa aaatcataca attttggtcc aactactcct  8400
ctctttttt ttttggcttt ataaaaaagg aaagtgatta gtaataaata attaaataat  8460
gaaaaaagga ggaaataaaa ttttcgaatt aaaatgtaaa agagaaaaag gagagggagt  8520
aatcattgtt taactttatc taaagtaccc caattcgatt ttacatgtat atcaaattat  8580
acaaatattt tattaaaata tagatattga ataattttat tattcttgaa catgtaaata  8640
aaaattatct attatttcaa tttttatata aactattatt tgaaatctca attatgattt  8700
tttaatatca ctttctatcc atgataattt cagcttaaaa agttttgtca ataattacat  8760
taattttgtt gatgaggatg acaagatttc ggtcatcaat tacatataca caaattgaaa  8820
tagtaagcaa cttgattttt tttctcataa tgataatgac aaagacacga aaagacaatt  8880
caatattcac attgatttat ttttatatga taataattac aataataata ttcttataaa  8940
gaaagagatc aattttgact gatccaaaaa tttatttatt tttactatac caacgtcact  9000
aattatatct aataatgtaa aacaattcaa tcttacttaa atattaattt gaaataaact  9060
atttttataa cgaaattact aaatttatcc aataacaaaa aggtcttaag aagacataaa  9120
ttcttttttt gtaatgctca aataaatttg agtaaaaaag aatgaaattg agtgattttt  9180
ttttaatcat aagaaaataa ataattaatt tcaatataat aaaacagtaa tataatttca  9240
taaatggaat tcaatactta cctcttagat ataaaaaata aatataaaaa taaagtgttt  9300
ctaataaacc cgcaatttaa ataaaatatt taatatttc aatcaaattt aaataattat  9360
attaaaatat cgtagaaaaa gagcaatata taatacaaga aagaagattt aagtacaatt  9420
atcaactatt attatactct aattttgtta tatttaattt cttacggtta aggtcatgtt  9480
cacgataaac tcaaaatacg ctgtatgagg acatattttta aattttaacc aataataaaa  9540
ctaagttatt tttagtatat ttttttgttt aacgtgactt aatttttctt ttctagagga  9600
gcgtgtaagt gtcaacctca ttctcctaat tttcccaacc acataaaaaa aaaataaagg  9660
tagcttttgc gtgttgattt ggtacactac acgtcattat tacacgtgtt ttcgtatgat  9720
tggttaatcc atgaggcggt ttcctctaga gtcggccata ccatctataa aataaagctt  9780
tctgcagctc atttttttcat cttctatctg atttctatta taatttctct gaattgcctt  9840
caaatttctc tttcaaggtt agaattttc tctattttt ggtttttgtt tgtttagatt  9900
ctgagtttag ttaatcaggt gctgttaaag ccctaaattt tgagtttttt tcggttgttt  9960
tgatggaaaa tacctaacaa ttgagttttt tcatgttgtt ttgtcggaga atgcctacaa  10020
ttggagttcc tttcgttgtt ttgatgagaa agcccctaat ttgagtgttt ttccgtcgat  10080
ttgattttaa aggtttatat tcgagttttt ttcgtcggtt taatgagaag gcctaaaata  10140
ggagtttttc tggttgattt gactaaaaaa gccatggaat tttgtgtttt tgatgtcgct  10200
ttggttctca aggcctaaga tctgagtttc tccggttgtt ttgatgaaaa agccctaaaa  10260
ttggagtttt tatcttgtgt tttaggttgt tttaatcctt ataatttgag ttttttcgtt  10320
gttctgattg ttgtttttat gaattttgca gaatggataa cgcaacactt gctgtgatcc  10380
tttccatttt gtttgtgttt taccacattt tcaaatcctt tttcaccaat tcttcatctc  10440
gtaggcttcc tcctggtccc aaacccgtgc caatttttgg caacattttc gatcttggcg  10500
aaaagcctca tcgatctttt gccaatctat ctaaaattca cggccctttg attagcctaa  10560
agttaggaag tgtaacaact attgttgttt cctcggcctc tgtggccgag gaaatgttcc  10620
ttaaaaatga ccaagcactt gctaaccgaa ccattcctga ctcggttagg gctggtgacc  10680
acgacaaatt atccatgtcg tggttgcctg tttcccaaaa atggagaaat atgagaaaaa  10740
tctccgctgt ccaattactc tccaaccaaa aacttgatgc tagtcaacct cttagacaag  10800
ctaaggtgaa acaactttta tcatacgtac aagtttgttc cgaaaaaatg caacccgtcg  10860
atattggacg ggccgcattt acaacgtcac ttaatttatt atcaaacaca tttttctcaa  10920
tcgaattagc aagtcatgaa tctagtgctt cccaagagtt taaacaactc atgtggaata  10980
ttatggagga aattggaagg cctaattatg ctgatttttt ccctattctt ggttacattg  11040
atcccctttgg tataagacgt cgtttggctg gttactttga taaactcatt gatgttttcc  11100
aagacattat tcgtgaaaga caaaagcttc gatcttctaa ttcttccggc gcaaaacaaa  11160
caaatgacat tcttgatact cttcttaaac tccatgaaga taatgagttg agtatgcctg  11220
aaattaatca ccttctcgtg gatatctttg acgccggaac agacacaaca gcaagcacat  11280
tagaatgggc aatggccgaa cttgtgaaaa acccggaaat gatgactaaa gttcaaattg  11340
aaatcgaaca agctcttgga aaagattgct tagacataca agaatccgac atctcaaaac  11400
taccttattt acaagccatt ataaaagaaa cgttacgttt acaccctcct actgtgtttt  11460
tgctgcctcg aaaggcagac aatgacgtag agttatatgg ctacgttgta ccaaagaatg  11520
ctcaagtcct tgtcaatctt tgggcaattg gtcgtgatcc aaaggtatgg aaaaatccgg  11580
aagtattttc tcctgaaagg tttttagatt gcaatatcga ttataaagga cgagatttcg  11640
aacttttacc ctttggtgct ggtagaagga tatgccctgg acttactttg gcatatagaa  11700
tgttgaactt gatgttggct actcttcttc aaaactacaa ttggaaactt gaagatggta  11760
tcaatcctaa ggatttagac atggatgaga aatttgggat tacattgcaa aaggttaaac  11820
ctcttcaagt tattccagtt cccagaaact aggcttgttg tggttgtctg gttgcgtctg  11880
ttgcccgttg tctgttgccc attgtggtgg ttgtgtttgt atgatggtcg ttaaggatca  11940
tcaatgtgtt ttcgcttttt gttccattct gtttctcatt tgtgaataat aatggtatct  12000
ttatgaatat gcagtttgtg gtttcttttc tgattgcagt tctgagcatt ttgtttttgc  12060
ttccgtttac tataccactt acagtttgca ctaatttagt tgatatgcga gccatctgat  12120
gtttgatgat tcaaatggcg tttatgtaac tcgtacccga gtggatggag aagagctcca  12180
ttgccggttt gtttcatggg tggcggaggg caactcctgg gaaggaacaa aagaaaaacc  12240
gtgatacgag ttcatgggtg agagctccag cttgatccct tctctgtcga tcaaatttga  12300
atttttggat cacggcaggc tcacaagata atccaaagta aaacataatg aatagtactt  12360
ctcaatgatc acttattttt agcaaatcag caattgtgca tgtcaaatga tttcggtgta  12420
agagaaagag ttgatgaatc aaaatatctg tagctggatc aagaatctga ggcagttgta  12480
tgtatcaatg atctttccgc tacaatgatg ttagctatcc gagtcaaatt gttgtagaat  12540
```

```
tgcatacttc ggcatcacat tctggatgac ataataaata ggaagtcttc agatccctaa  12600
aaaattgaga gctaataaca ttagtcctag atgtaactgg gtgacaacca agaaagagac  12660
atgcaaatac tacttttgtt tgaaggagca tccctggttt gacatatttt ttctgaatat  12720
caaactttga aactctacct agtctaatgt ctaacgacag atcttactgg tttaactgca  12780
gtgatatcta ctatctttg gaatgtttc tccttcagtt atacatcaag ttccaagatg  12840
caggtgtgct tgattgatgt acatggctgt gagaagtgca tcctgatgtt cagatgatgg  12900
ttcattctaa tgtcttttcc ttcaatcagt tttctcagtc tgacttagct tgtttcatct  12960
gcatgtttga atgttcgttt actcatagta attgcatttt tgtagcagaa catatcattg  13020
gtcatggttt caactgtgcg cgagtcttat gcttattcaa actaggaaag cctccgtcta  13080
gagggtacac gagttgttgc tctgtgtgcg tcagtccata gtattaatct tgctagttgt  13140
agtatattgt ttatgtggac tcggaattca tcatatgctc cttctttgca tcaagtaagg  13200
caaggtaatg tatagaagct ttttaactct ttcatggaag ctggcctttg ccagcatacc  13260
atccagaaga tatcaaccct gcatcttggc tgccgcgctg tcaggagata catgagaatt  13320
aagggagtca cggtatgacc cccgccgatg acgcgggaca agccgtttta cgtttggaac  13380
tgacagaacc gcaacgttga aggagccact gagccgcggg tttctggagt ttaatgagct  13440
aagcacatac gtcagaaacc attattgcgc gttcaaaagt cgcctaaggt cactatcagc  13500
tagcaaatat ttcttgtcaa aaatgctcca ctgacgttcc ataaattccc ctcggtatcc  13560
aattagagtc tcatattcac tctcaactcg atcgaggcaa tgatggctat ggaagtgggt  13620
tatcttcggc actcgacaac gatcaccaac ggactgtgtt gtaactgtga tccgaagccc  13680
cgaggagcac gtcgtgtaca gactaggctg cctggcaccc tgtgtctcgt caaggatacc  13740
tttacctcta gcaaagctaa actaaaaaag ccgtcgcaga gagaaatctt tctaacaagt  13800
aggaagaggc tgaatcagat acaagctgtt tcaacggctg aaaaggagag agaggcagac  13860
aaaacatcca ctccacctat tcccagtagc atccacgata tttcaaatgg agatcacatt  13920
cttggcttcg gagccgattt gaccgaagat catcctggct accatgatct tgaatataag  13980
aggaggcgta gtcgtattgc tgaccttgcg aagatacata aaataggtga acccattcct  14040
tgcgtggact acacatcgga agagattcgt gtgtggggtc atgtgttaga tactctagtg  14100
gacctctacc caactcatgc ttgtaaggaa tacctgaatt gctacgagct gtttaacttc  14160
aagccaaact atattccaca gctgcaagaa ctttcggagg tcctggaacg gagcacagga  14220
tggcacatcc gcccagtagc tggactcctc caccctcgtg acttcctaaa cggtctagcc  14280
ttccgcactt tccattcaac ccagtatgtt cggcatggca gcaatcccat gtacaccccc  14340
gagccagaca tttgtcacga ggttttaggc cacgtcccca ttctggctga tccggagttt  14400
gctgacttag cttgggccat tggccaagct tctctgggtg cttcagagaa ggatatctgg  14460
caccttacga agctctactg gtacactgtg gagtttggca cagtaaagga aggtaacgag  14520
attaaagcgt tcggtgcagg ccttctgtct agttttgggg agctgaagca catgcgggtg  14580
gggacggatg gattcatgcc tgagttcgtg gagcttgacc cgtttaagaa gatgcccaag  14640
atgagctaca aagacgggta ccagaagagg tattttctat gcgagagctt tgcagatgca  14700
gcggcaaagc ttagggcgta ttccagaagc attctgaagc ctgaggtgca gtccatcaag  14760
tttggagata cgccaatccg gctctaagct tatatgaaga tgaagatgaa atatttggtg  14820
tgtcaaataa aaagcttgtg tgcttaagtt tgtgtttttt tcttggcttg ttgtgttatg  14880
aatttgtggc tttttctaat attaaatgaa tgtaagatct cattataatg aataaacaaa  14940
tgtttctata atccattgtg aatgttttgt tggatctctt ctgcagcata taactactgt  15000
atgtgctatg gtatggacta tggaatatga ttaaagataa gcgctgtcag gagccgtaca  15060
aaattgatta ttgatgtcac aaatcaatca gagctaaatt ccaaaaaaaa tatgatcttt  15120
gaaacttgca tcaataacta acgattctag gaagagccca tttcgatttc aacaaaaaga  15180
tgagagcttg attacatata aaatcaagag aaattaacga cattgaagag aattcgatct  15240
cgaaaccgga aacaaagact tataagtcga ttagtctaat tcaatgcaga agaaagaata  15300
ccaggtttgg ccttcacgat ggaaagcttc ggatttggag ccaagtctca taaacgccat  15360
tgtggaagaa agtcttgagt tggtggtaat gtaacagagt agtaagaaca gagaagagag  15420
agagtgtgag atacatgaat tgtcgggcaa caaaaatcct gaacatctta ttttagcaaa  15480
gagaaagagt tccgagtctg tagcagaaga gtgaggagaa atttaagctc ttggacttgt  15540
gaattgttcc gcctcttgaa tacttcttca atcctcatat attcttcttc tatgttacct  15600
gaaaaccggc atttaatctc gcgggtttat tccggttcaa cattttttt gttttgagtt  15660
attatctggg cttaataacg caggcctgaa ataaattcaa ggcccaactg ttttttttt  15720
taagaagttg ctgttaaaaa aaaaaaaagg gaattaacaa caacaacaaa aaaagataaa  15780
gaaaataata acaattactt taattgtaga ctaaaaaaac atagatttta tcatgaaaaa  15840
aagagaaaag aaataaaaac ttggatcaaa aaaaaaaaca tacagatctt ctaattatta  15900
acttttctta aaaattaggt ccttttttccc aacaattagg tttagagttt tggaattaaa  15960
ccaaaaagat tgttctaaaa aatactcaaa tttggtagat aagtttcctt attttaatta  16020
gtcaatggta gatacttttt tttcttttct ttattagagt agattagaat cttttatgcc  16080
aagtattgat aaattaaatc aagaagataa actatcataa tcaacatgaa attaaaagaa  16140
aaatctcata tatagtatta gtattctcta tatatattat gattgcttat tcttaatggg  16200
ttgggttaac caagacatag tcttaatgga aagaatcttt tttgaacttt ttccttattg  16260
attaaattct tctatagaaa agaaagaaat tatttgagga aaagtatata caaaaagaaa  16320
aatagaaaaa tgtcagtgaa gcagatgtaa tggatgacct aatccaacca ccaccatagg  16380
atgtttctac ttgagtcggt cttttaaaaa cgcacggtgg aaaatatgac acgtatcata  16440
tgattccttc ctttagtttc gtgataataa tcctcaactg atatcttcct tttttgttt  16500
tggctaaaga tattttattc tcattaatag aaaagacggt tttgggcttt tggtttgcga  16560
tataaagaag accttcgtgt ggaagataat aattcatcct ttcgtctttt tctgactctt  16620
caatctctcc caaagcctaa agcgatctct gcaaatctct cgcgactctc tctttcaagg  16680
tatattttct gattcttttt gtttttgatt cgtatctgat ctccaatttt tgttatgtgg  16740
attattgaat cttttgtata aattgctttt gacaatattg ttcgtttcgt caatccagct  16800
tctaaatttt gtcctgatta ctaagatatc gattcgtagt gtttacatct gtgtaatttc  16860
ttgcttgatt gtgaaattag gattttcaag gacgatctat tcaatttttg tgttttcttt  16920
gttcgattct ctctgtttta ggtttcttat gtttagatcc gtttctcttt ggtgttgttt  16980
tgatttctct tacggctttt gatttggtat atgttcgctg attggtttct acttgttcta  17040
ttgttttatt tcagaatggc ttctatgata tcctcttcag ctgtgactac agtcagccgt  17100
gcttctacgg tgcaatcggc cgcggtggct ccattcggcg gcctcaaatc catgactgga  17160
ttcccagtta agaaggtcaa cactgacatt acttccatta caagcaatgg tggaagagta  17220
aagtgcatgc tgatgaatta tcagaacgac gatttacgca tcaaagaaat caaagagtta  17280
```

```
cttcctcctg tcgcattgct ggaaaaattc cccgctactg aaaatgccgc gaatacggtt  17340
gcccatgccc gaaaagcgat ccataagatc ctgaaaggta atgatgatcg cctgttggtt  17400
gtgattggcc catgctcaat tcatgatcct gtcgcggcaa aagagtatgc cactcgcttg  17460
ctggcgctgc gtgaagagct gaaagatgag ctggaaatcg taatgcgcgt ctattttgaa  17520
aagccgcgta ccacggtggg ctggaaaggg ctgattaacg atccgcatat ggataatagc  17580
ttccagatca acgacggtct gcgtatagcc cgtaaattgc tgcttgatat taacgacagc  17640
ggtctgccag cggcaggtga gtttctcgat atgatcaccc cacaatatct cgctgacctg  17700
atgagctggg gcgcaattgg cgcacgtacc accgaatcgc aggtgcaccg cgaacaggca  17760
tcagggcttt cttgtccggt cggcttcaaa aatggcaccg acggtacgat taaagtggct  17820
atcgatgcca ttaatgccgc cggtgcgccg cactgcttcc tgtccgtaac gaaatggggg  17880
cattcggcga ttgtgaatac cagcggtaac ggcgattgcc atatcattct gcgcggcggt  17940
aaagagccta actacagcgc gaagcacgtt gctgaagtga aagaagggct gaacaaagca  18000
ggcctgccag cacaggtgat gatcgatttc agccatgcta actcgtccaa acaattcaaa  18060
aagcagatgg atgtttgtgc tgacgtttgc cagcagattg ccggtggcga aaaggccatt  18120
attggcgtga tggtggaaag ccatctggtg gaaggcaatc agagcctcga gagcggggag  18180
ccgctggcct acggtaagag catcaccgat gcctgcatcg gctgggaaga taccgatgct  18240
ctgttacgtc aactggcgaa tgcagtaaaa gcgcgtcgcg gggaattcat cttttaccca  18300
tacgatgttc ctgactatgc gggctatccc tatgacgtcc cggactatgc aggatcctat  18360
ccatatgacg ttccagatta cgctgctcag taggcttata tgaagatgaa gatgaaatat  18420
ttggtgtgtc aaataaaaag cttgtgtgct taagtttgtg ttttttttctt ggcttgttgt  18480
gttatgaatt tgtggctttt tctaatatta aatgaatgta agatctcatt ataatgaata  18540
aacaaatgtt tctataatcc attgtgaatg ttttgttgga tctcttctgc agcatataac  18600
tactgtatgt gctatggtat ggactatgga atatgattaa agataag                18647
```

```
SEQ ID NO: 28          moltype = DNA  length = 1050
FEATURE                Location/Qualifiers
misc_feature           1..1050
                       note = Polynucleotide encoding E Coli AroG175 mutant
source                 1..1050
                       mol_type = other DNA
                       organism = synthetic construct
SEQUENCE: 28
atgaattatc agaacgacga tttacgcatc aaagaaatca aagagttact tcctcctgtc  60
gcattgctgg aaaaattccc cgctactgaa aatgccgcga atacggttgc ccatgcccga  120
aaagcgatcc ataagatcct gaaaggtaat gatgatcgcc tgttggttgt gattggccca  180
tgctcaattc atgatcctgt cgcggcaaaa gagtatgcca ctcgcttgct ggcgctgcgt  240
gaagagctga aagatgagct ggaaatcgta atgcgcgtct attttgaaaa gccgcgtacc  300
acggtgggct ggaaagggct gattaacgat ccgcatatgg ataatagctt ccagatcaac  360
gacggtctgc gtatagcccg taaattgctg cttgatatta acgacagcgg tctgccagcg  420
gcaggtgagt ttctcgatat gatcacccca caatatctcg ctgacctgat gagctggggc  480
gcaattggcg cacgtaccac cgaatcgcag gtgcaccgcg aacaggcatc agggctttct  540
tgtccggtcg gcttcaaaaa tggcaccgac ggtacgatta aagtggctat cgatgccatt  600
aatgccgccg gtgcgccgca ctgcttcctg tccgtaacga aatgggggca ttcggcgatt  660
gtgaatacca gcggtaacgg cgattgccat atcattctgc gcggcggtaa agagcctaac  720
tacagcgcga agcacgttgc tgaagtgaaa gaagggctga acaaagcagg cctgccagca  780
caggtgatga tcgatttcag ccatgctaac tcgtccaaac aattcaaaaa gcagatggat  840
gtttgtgctg acgtttgcca gcagattgcc ggtggcgaaa aggccattat tggcgtgatg  900
gtggaaagcc atctggtgga aggcaatcag agcctcgaga gcggggagcc gctggcctac  960
ggtaagagca tcaccgatgc ctgcatcggc tgggaagata ccgatgctct gttacgtcaa  1020
ctggcgaatg cagtaaaagc gcgtcgcggg                                   1050
```

```
SEQ ID NO: 29          moltype = DNA  length = 1185
FEATURE                Location/Qualifiers
source                 1..1185
                       mol_type = other DNA
                       organism = Physcomitrella patens
SEQUENCE: 29
atggctatgg aagtgggtta tcttcggcac tcgacaacga tcaccaacgg actgtgttgt  60
aactgtgatc cgaagccccg aggagcacgt cgtgtacaga ctaggctgcc tggcaccctg  120
tgtctcgtca aggatacctt tacctctagc aaagctaaac taaaaaagcc gtctcagaga  180
gaaatctttc taacaagtag gaagaggctg aatcagatac aagctgtttc aacggctgaa  240
aaggagagag aggcagacaa aacatccact ccacctattc ccagtagcat ccacgatatt  300
tcaaatggag accacattct tggcttcgga gccgatttga ccgaagatca tcctggctac  360
catgatcttg aatataagag gaggcgtagt cgtattgctg accttgcgaa gatacataaa  420
ataggtgaac ccattccttg cgtggactac acatcggaag agattcgtgt gtggggtcat  480
gtgttagata ctctagtgga cctctaccca actcatgctt gtaaggaata cctgaattgc  540
tacgagctgt ttaacttcaa gccaaactat attccacagc tgcaagaact ttcggaggtc  600
ctggaacgga gcacaggatg gcacatccgc ccagtagctg gactcctcca ccctcgtgac  660
ttcctaaacg gtctagcctt ccgcactttc cattcaaccc agtatgttcg gcatggcagc  720
aatcccatgt acacccccga gccagacatt tgtcacgagg ttttaggcca cgtccccatt  780
ctggctgatc cggagtttgc tgacttagct tgggccattg gccaagcttc tctgggtgct  840
tcagagaagg atatctggca ccttacgaag ctctactggt acactgtgga gtttggcaca  900
gtaaaggaag gtaacgagat taaagcgttc ggtgcaggcc ttctgtctag ttttggggag  960
ctgaagcaca tgcgggtggg gacggatgga ttcatgcctg agttcgtgga gcttgacccg  1020
tttaagaaga tgcccaagat gagctacaaa gacgggtacc agaagaggta ttttctatgc  1080
gagagctttg cagatgcagc ggcaaagctt agggcgtatt ccagaagcat tctgaagcct  1140
gaggtgcagt ccatcaagtt tggagatacg ccaatccggc tctaa                  1185
```

```
SEQ ID NO: 30          moltype = DNA  length = 1988
```

```
FEATURE                Location/Qualifiers
source                 1..1988
                       mol_type = other DNA
                       organism = Beta vulgaris
SEQUENCE: 30
tcgatgtgtt ttcaagaaga gcttgagcct acattctaca acaatatatt gttcctctct  60
tgcgcaatta agcccttaaa cctgcaatta tcttagaatt tttgggtttc taatttattc  120
tctcctttaa ttagctagct tcttagatta ttcatatttt tccagcattt tcaaacaatg  180
gataacgcaa cacttgctgt gatcctttcc attttgtttg tgttttacca cattttcaaa  240
tcctttttca ccaattcttc atctcgtagg cttcctcctg gtcccaaacc cgtgccaatt  300
tttggcaaca ttttcgatct tggcgaaaag cctcatcgat cttttgccaa tctatctaaa  360
attcacggcc ctttgattag cctaaagtta ggaagtgtaa caactattgt tgtttcctcg  420
gcctctgtgg ccgaggaaat gttccttaaa aatgaccaag cacttgctaa ccgaaccatt  480
cctgactcgg ttagggctgg tgaccacgac aaattatcca tgtcgtggtt gcctgtttcc  540
caaaaatgga gaaatatgag aaaaatctcc gctgtccaat tactctccaa ccaaaaactt  600
gatgctagtc aacctcttag acaagctaag gtgaaacaac ttttatcata cgtacaagtt  660
tgttccgaaa aaatgcaacc cgtcgatatt ggacgggccg catttacaac gtcacttaat  720
ttattatcaa acacattttt ctcaatcgaa ttagcaagtc atgaatctag tgcttcccaa  780
gagtttaaac aactcatgtg gaatattatg gaggaaattg gaaggcctaa ttatgctgat  840
tttttcccta ttcttggtta cattgatccc tttggtataa gacgtcgttt ggctggttac  900
tttgataaac tcattgatgt tttccaagac attattcgtg aaagacaaaa gcttcgatct  960
tctaattctt ccggcgcaaa acaaacaaat gacattcttg atactcttct taaactccat  1020
gaagataatg agttgagtat gcctgaaatt aatcaccttc tcgtggatat ctttgacgcc  1080
ggaacagaca caacagcaag cacattagaa tgggcgatgg ccgaacttgt gaaaaacccg  1140
gaaatgatga ctaaagttca aattgaaatc gaacaagctc ttggaaaaga ttgcttagac  1200
atacaagaat ccgacatctc aaaactacct tatttacaag ccattataaa agaaacgtta  1260
cgtttacacc ctcctactgt gtttttgctg cctcgaaagg cagacaatga cgtagagtta  1320
tatggctacg ttgtaccaaa gaatgctcaa gtccttgtca atctttgggc aattggtcgt  1380
gatccaaagg tatggaaaaa tccggaagta ttttctcctg aaaggttttt agattgcaat  1440
atcgattata aaggacgaga tttcgaactt ttaccctttg gtgctggtag aaggatatgc  1500
cctggactta ctttggcata tagaatgttg aacttgatgt tggctactct tcttcaaaac  1560
tacaattgga aacttgaaga tggtatcaat cctaaggatt tagacatgga tgagaaattt  1620
gggattacat tgcaaaaggt taaacctctt caagttattc cagttcccag aaactagcta  1680
gtgggttgtg ccgttgtggg ctgtgggctg attgtgcact tttgtttcct ctaattgttg  1740
ttgcaaactt ctctagaagg gtattatctt ttgtataaat aaagcgaaag ctacatgtcc  1800
tattattaaa ttagtgtata ctatattaag taagtatgag catatagtat ccattattgt  1860
ttttggttga atcgtattaa actgataaat caagtaaatg tctccaacct aagcattcaa  1920
ttattctgtt agtcataaca tatgtagagg gtaagtatga agaattaata acggcgtgat  1980
catcctta                                                           1988

SEQ ID NO: 31          moltype = DNA  length = 1500
FEATURE                Location/Qualifiers
source                 1..1500
                       mol_type = other DNA
                       organism = Beta vulgaris
SEQUENCE: 31
atggataacg caacacttgc tgtgatcctt tccattttgt ttgtgtttta ccacattttc  60
aaatcctttt tcaccaattc ttcatctcgt aggcttcctc ctggtcccaa acccgtgcca  120
atttttggca acattttcga tcttggcgaa aagcctcatc gatcttttgc caatctatct  180
aaaattcacg gccctttgat tagcctaaag ttaggaagtg taacaactat tgttgtttcc  240
tcggcctctg tggccgagga aatgttcctt aaaaatgacc aagcacttgc taaccgaacc  300
attcctgact cggttagggc tggtgaccac gacaaattat ccatgtcgtg gttgcctgtt  360
tcccaaaaat ggagaaatat gagaaaaatc tccgctgtcc aattactctc caaccaaaaa  420
cttgatgcta gtcaacctct tagacaagct aaggtgaaac aacttttatc atacgtacaa  480
gtttgttccg aaaaaatgca acccgtcgat attggacggg ccgcatttac aacgtcactt  540
aatttattat caaacacatt tttctcaatc gaattagcaa gtcatgaatc tagtgcttcc  600
caagagttta aacaactcat gtggaatatt atggaggaaa ttggaaggcc taattatgct  660
gattttttcc ctattcttgg ttacattgat ccctttggta taagacgtcg tttggctggt  720
tactttgata aactcattga tgttttccaa gacattattc gtgaaagaca aaagcttcga  780
tcttctaatt cttccggcgc aaaacaaaca aatgacattc ttgatactct tcttaaactc  840
catgaagata atgagttgag tatgcctgaa attaatcacc ttctcgtgga tatctttgac  900
gccggaacag acacaacagc aagcacatta gaatgggcaa tggccgaact tgtgaaaaac  960
ccggaaatga tgactaaagt tcaaattgaa atcgaacaag ctcttggaaa agattgctta  1020
gacatacaag aatccgacat ctcaaaacta ccttatttac aagccattat aaaagaaacg  1080
ttacgtttac accctcctac tgtgtttttg ctgcctcgaa aggcagacaa tgacgtagag  1140
ttatatggct acgttgtacc aaagaatgct caagtccttg tcaatctttg ggcaattggt  1200
cgtgatccaa aggtatggaa aaatccggaa gtattttctc ctgaaaggtt tttagattgc  1260
aatatcgatt ataaaggacg agatttcgaa cttttaccct ttggtgctgg tagaaggata  1320
tgccctggac ttactttggc atatagaatg ttgaacttga tgttggctac tcttcttcaa  1380
aactacaatt ggaaacttga agatggtatc aatcctaagg atttagacat ggatgagaaa  1440
tttgggatta cattgcaaaa ggttaaacct cttcaagtta ttccagttcc cagaaactag  1500

SEQ ID NO: 32          moltype = DNA  length = 2200
FEATURE                Location/Qualifiers
source                 1..2200
                       mol_type = other DNA
                       organism = Beta vulgaris
SEQUENCE: 32
tactaatgtg caaatgcata aatttaattt cagatactct tttttataaa tattattata  60
```

-continued ctgtgcattc ttttaaccca aaaaaaaaac tgtcttaata caccatttaa ttcctttctc 120
taggatccac tatcacatgt agtatataaa tataatccta tacagttcac gttatcaaac 180
accaaagcat caaaagcctt ccacacttgt attattttgg ggtagttgat ttgttagcgt 240
gttatttgtg agatcatcat ggatcatgca acattagcaa tgatactagc catttggttc 300
atttcttttc atttcataaa attacttttt agccaacaaa ctaccaaact tcttcctcct 360
ggtccaaaac cattgccaat aattggtaac atcttagaag ttggtaaaaa accccatcgt 420
tcatttgcta atcttgctaa aattcacggc cctttaatat cgttacgtct aggaagtgta 480
acaactattg ttgtatcatc agcagatgta gctaaagaaa tgttcttaaa aaaagaccac 540
cctctttcta accgtactat tcctaattct gtcacggccg gtgaccacca taaactcacc 600
atgtcgtggt tgcccgtttc gccgaaatgg cggaattttc gtaagattac agccgtccat 660
ttgctttctc ctcaaagact tgatgcttgc caaacctttc gccatgccaa ggtgcaacag 720
ctttatgaat atgtacaaga atgtgcacaa aaaggccaag ctgttgatat tggcaaagct 780
gcatttacta cctcccttaa tttgttatct aaactattct tttcagtgga attagcccac 840
cataaatcac acacttctca agagtttaag gaactaatat ggaacattat ggaagatatt 900
gggaaaccta attatgctga ttattttcct attttaggct gtgttgatcc atcaggtatt 960
cgtcgaagat tagcatgtag ttttgacaag ttgattgcag tttttcaggg tataatatgt 1020
gaaaggcttg cgcctgattc ttcaactaca acaacaacga cgactgatga tgtgctagac 1080
gttcttcttc agctcttcaa acaaaatgag ctcactatgg gcgagattaa ccatttgctc 1140
gtcgacattt ttgatgctgg aacagacact acatcaagta cttttgagtg ggtcatgaca 1200
gagttaatta ggaatcctga aatgatggaa aaggctcaag aagaaattaa gcaagtattg 1260
ggcaaagata aacaaattca ggaatcagac attattaacc taccttactt acaagccatt 1320
atcaaagaaa ctttgcgact acatccacca actgtatttc ttttgcctcg taaagccgac 1380
actgatgttg aactatatgg ttatattgtg cctaaagatg cacaaatact tgttaactta 1440
tgggctattg gaagagatcc taatgcatgg caaaatgctg atattttttc gcccgaaaga 1500
tttatagggt gtgaaattga tgtcaaagga agagattttg gactcttacc ttttggagcc 1560
ggaagaagga tatgtcctgg gatgaatttg gccattagaa tgttaacttt gatgctagct 1620
actttacttc aattcttcaa ttggaagctt gaaggagaca taagtccaaa agacttagac 1680
atggatgaga aatttgggat tgcgttacaa aagacaaagc ctttaaaact tattccaata 1740
cctaggtatt gaaatttgtt agacttacgt acaacaatta ttattgtttg tggttggttt 1800
tgggttagct tcctgttcat gtttgtttga tgtgctcgat tgaatttact acaaatcaac 1860
gaactccaat tatatcttgt caacttggag taatggcttg ggtttctcat ctgtcatctc 1920
ttttggttgg ctgtgcaagg gagtgagctt gcagcttagc atccttcaag aagatttaat 1980
taataatatg tgtatgtgta tgtgtatgtg tggattgtat ctcgtcattc attttgcttg 2040
ttgtaatgat tttagttaat tattgtaatt ataaaggatt tgatcctcct ttgtgttgaa 2100
attatatata taatgtgtag cacgacaata aagtgacaga taacttatat aatcttattt 2160
tctatgaaat gttacagact tgctttgtgt tttaaaaaaa 2200

SEQ ID NO: 33 moltype = DNA length = 1161
FEATURE Location/Qualifiers
source 1..1161
mol_type = other DNA
organism = Beta vulgaris
SEQUENCE: 33
aaaacaagaa gaaaacaaaa caacctttta tataactaga aagcaacaaa aaaaaaagaa 60
tgaaaatgat gaatggtgaa gatgctaatg atcaaatgat caaagaaagc ttcttcataa 120
cacatggaaa cccaatatta acagtagaag acacacatcc attaagacct ttctttgaaa 180
cttggagaga gaaaatcttt tctaagaaac ctaaggcaat tcttattatt tctggtcatt 240
gggaaactgt taaacctact gttaatgctg tccatatcaa tgatactatc catgattttg 300
atgactatcc tgctgctatg taccagttca agtatccagc tcctggggaa ccagaattgg 360
caagaaaagt agaggaaatt ctgaaaaaat cgggtttcga aacggcggaa actgatcaaa 420
aacgtgggct tgatcatggt gcatgggtac ctctaatgct aatgtatcct gaggctgata 480
taccagtatg tcagctctca gttcagccgc atttagatgg aacataccat tacaacttag 540
gacgagcatt ggctcccttg aaaaacgacg gcgtattaat cattggttca ggaagtgcaa 600
ctcacccttt ggatgaaact cctcattatt ttgatggagt tgcaccttgg gcagctgcct 660
ttgattcatg gcttcgtaaa gctctcatta atggaaggtt tgaagaagtg aatatatatg 720
aaagcaaagc accaaattgg aaattagcac atcctttccc agaacatttt tatccattgc 780
atgttgttct tggcgctgct ggtgaaaaat ggaaggcaga gcttattcat agcagttggg 840
atcatggcac cttgtgtcat ggctcctaca agttcacttc agcctagttt tacttttaaa 900
cactatgtct acagtctatg ttattgtatt tggtaatttg gtatgtggtg ttgtttttgt 960
tttattcttt tgagttattg tacttggtat ttggtgttgt tttcatttgg tgcataattc 1020
ttttagtcta tatattgcta ttcttttgaa tgaggaataa atcgcgagct cgatgtaata 1080
gtttgtttta ttgtttcaaa tctatcatta tatatatata tatattatta aaaaaaaatt 1140
attgtgttac tcgcaaaaaa a 1161

SEQ ID NO: 34 moltype = AA length = 499
FEATURE Location/Qualifiers
source 1..499
mol_type = protein
organism = Beta vulgaris
SEQUENCE: 34
MDNATLAVIL SILFVFYHIF KSFFTNSSSR RLPPGPKPVP IFGNIFDLGE KPHRSFANLS 60
KIHGPLISLK LGSVTTIVVS SASVAEEMFL KNDQALANRT IPDSVRAGDH DKLSMSWLPV 120
SQKWRNMRKI SAVQLLSNQK LDASQPLRQT KVKQLLSYVQ DCSKKMQPVD IGRAAFTTSL 180
NLLSNTFFSI ELASHESSAS QEFKQLMWNI MEEIGRPNYA DFFPILGYID PFGIRRRLAG 240
YFDKLIDVFQ DIIRERQKLR SSNSSGAKQT NDILDTLLKL HEDNELSMPE INHLLVDIFD 300
AGTDTTASTL EWAMAELVKN PEMMTKVQIE IEQALGKDCL DIQESDISKL PYLQGIIKET 360
LRLHPPTVFL LPRKADNDVE LYGYVVPKNA QVLVNLWAIG RDPKVWKNPE VFSPERFLDC 420
NIDYKGRDFE LLPFGAGRRI CPGLTLAYRM LNLMLATLLQ NYNWKLEDGI NPKDLDMDEK 480
FGITLQKVKP LQVIPVPRN 499

```
SEQ ID NO: 35          moltype = DNA  length = 1799
FEATURE                Location/Qualifiers
source                 1..1799
                       mol_type = other DNA
                       organism = Mirabilis jalapa
SEQUENCE: 35
tttgtctatt attggctcaa aatccctctc tctatctttt tgtaaaagaa aatagttgtt  60
caacttaggg aattattgat atttcattat ggaaaacaca atgttaggtg ttatcctagc  120
aaccattttc ctcacttttc acataatgaa gatgttattt agtccttcca aggttaaact  180
acccccgggt ccgagaccat tgccaattat tggtaatatt ctcgagcttg ggataaaccc  240
acatcgttct tttgcaaacc ttgcgaaaat tcacggtcct ttagttactt tgaaactcgg  300
gagtgtaacc actattgtgg tttcctcttc tgaagttgct aaagaaatgt ttttgaaaaa  360
tgaccaacct ttggcaaatc gtaccatacc tgactcagta agagcaggta accatgacaa  420
actatcaatg tcgtggttgc ctgtatcacc caaatggcga aatcttagaa agatttcagc  480
cgtccaattg ctctcaactc aacgacttga tgcaagtcaa gctcatagac aagctaaaat  540
caaacaactt attgagtacg taaaaaaatg cagtaaaatc ggccaatacg tcgatattgg  600
ccaagttgca ttcactacat cacttaattt actatcaaac acattctttt caaaagaact  660
agcatcattt gattcagata atgcacaaga gttcaaacaa ctaatgtggt gcattatgga  720
agaaattggt aggcctaatt atgccgatta ttttcctatc ttgggttatg tcgatccatt  780
cggtgctaga cgtcgacttt ctcgttactt cgatcaacta attgaagtat ttcaagtgat  840
tattcgtgag agacttacac atgataataa tattgtgggt aataacaatg atgttttagc  900
tacgttgctc gatctttata aacaaaacga gttaactatg gatgaaatca accatttact  960
agtggacatt tttgatgctg gtacggatac aacagcaagt acactagaat gggcaatgtc  1020
agagctcata aaaaatccac acataatggc caaagctcaa gaggaggtcc ggcgagccac  1080
catgtctcac ggcggagcta cggtggcgga aatacaagaa tcggatatca ataatcttcc  1140
atacatacaa tctattatta aagaaacact tcgtttacac ccaccaactg tgtttttact  1200
tcctagaaaa gctgacgtgg atgtccaatt attcggctat gtggtcccca aaaatgctca  1260
agtcctagtc aatttatggg ccattggtcg tgacccaaat gtgtggcccg acccggaagt  1320
ttttagtccc gaaagattta tggattgtga gattgatgtc aagggtcgtg attttgagct  1380
attgcctttc ggggcgggtc gtcggatttg tccgggattg tctttggctt atcggatgct  1440
taatttgatg ttggctaata tggtacattc ttttgattgg aaattacccg gtgttgaaaa  1500
tggatccggg tcggaaatgg atagtttgga tatggatgag aaatttggta tcactttgca  1560
aaaggttcaa ccccttaagg ttattcctgt ctcaaggaaa tagatttttg gaagatcgat  1620
ggttgggaga taatcatatt gtttttaatt attgttggtg tattttattg ttattattgg  1680
ggacaatttt ataataaaag atataaataa gttcctaatt gtgatttata ttgtgaattt  1740
tctagttaat ataaatacat atgaatattt atgatgaaaa aaaaaaaaaa aaaaaaagg   1799

SEQ ID NO: 36          moltype = DNA  length = 2130
FEATURE                Location/Qualifiers
source                 1..2130
                       mol_type = other DNA
                       organism = Mirabilis jalapa
SEQUENCE: 36
tacgtctatt cttgcctccc atttcctccc tgcaaaaagg aagaaaatgg aaatacccctt  60
taatttgcaa cctatttttc taattattgt actatctacc ttcattctaa cccacctaat  120
aacaaaaaac acaagaaagt tcaaccaatg caaatcaaaa accaagccaa taccaaaacc  180
acctggctca ctacccataa taggtcactt gcacctccta agaggtcatg gaaccacccct  240
aggtcgcacc ctcggagcca tggccgacaa gtccggaccc attttcggcc tcaagctagg  300
ccaacacaag gctatagtca ttagtaactg ggagatagtc aaggattgtt tcaccaataa  360
tgacatgaac cttgcaacta gacctagcat ggctattagc aaatatattg gttatgactt  420
tgcctctttc tctatctcac cttatggccg atattggcgt gagattcgta agatctctac  480
tgttgagctc ttgtcaaaca aacgccttga gaaaatgaag catgttcgaa cttttgaggt  540
gaactcttgc cttcaaatct tctatgaaaa atgtgtcaaa tcagaggata atgaaagtaa  600
taaagtagca aaaatttgtc ttaaaaaagtg gttagaatat attggtttta atatcgcact  660
atctatgata gttggcaaga gattctccta cgaccagtat tataaaaaaa atactgttgc  720
atcgagattt atgaaggcaa tagaaagagc aacccactta gcaggacttc ctataccctc  780
ggattttta ccatgggttg aatggatgga tttggtgggt tacattggtg ctatgaagga  840
aactcataag gaaattgatg tgattattgg acattggctt gatgagcata ttcaaaagag  900
gaaagagacg ttagaaaggc gaggtacaag cattgatgat agtgacttca tggatgtaat  960
gttatctaac attactgaac aatttgccaa gtcaacctac tctaaaaaca ccatcattaa  1020
agcaacagct ttgacactac ttctaacagg ttcagaaagc acctcaatca cactaacatg  1080
ggccatatca ctacttctaa acaaccctac ggcccaaaat ttggcccaac aagaaatgga  1140
caaacaagtt ggtaaacaaa gatgggttga agaatctgac atcaccaatc taccatacct  1200
ccaagccatc ataaaggaaa ctttacgttt gtatccacca agcccattag caggcccaag  1260
agtggcccaa gaagactgcc aaatcaatgg acattgtatc acaaaaggaa cccgggtgat  1320
tgttaacata tggaagttgc atcgtgatcc gatggtttgg tccgacccag ataagttccg  1380
acccgaaagg tttattgggg agcataagga tattgatttt aagggtcaat actttgggta  1440
tataccttttt agcttgggta ggaggggttg tcctgggatg aattttgggc tacaagtggt  1500
ccatttgatg ttagctcgtt tggtccaagg gttcgatatt tgggctcaaa atggtggcct  1560
aattgatttg aaggaagggt tgggcttggc tttgcccaag gctggtccat tggatgtcat  1620
tcttgcacca cgtttgtcca gtgagcttta tggagcttta tcaaaggtga atgttactta  1680
tggtcgggca atgaatgaac tagctttgta tttataattt tacaaataat ttgtaagata  1740
tgaactgttt atctagtcac ttttccgcgt cttagaatat caataagcaa aaagttttat  1800
gtaataatat gtattagtgt gttattgtat catgattcgt cggtatactg aaaatatttt  1860
acgtctagga gaatgtgcac acatttaatc ttatttgctt ataagtatta tatacataaa  1920
attttctact ttataattta ggtatattga gctttcgacc aaaacccaaa aactaaagaa  1980
gtttttttta aaacatacaa gttggtattg tttagatttt tatttatttt tattatctct  2040
tttatttgta cttagtgggt gtgttaataa tgtaaagaag tattaaatat ttatagagtt  2100
```

```
ggaaaaaccc aatattttac attggaaaaa                              2130

SEQ ID NO: 37          moltype = DNA  length = 1903
FEATURE                Location/Qualifiers
source                 1..1903
                       mol_type = other DNA
                       organism = Mirabilis jalapa
SEQUENCE: 37
tacgtctcta acctccttct cctcaccatc atcatcttat ttctctctct aacttcctat  60
ttctctctct agaatggtct caactagtga ctcactctgg cttttcacct acttagcttc  120
aaaatatgat cattttacga cccctaactt tatttattct ttgttttgtt tcgtaatatt  180
ttttattttg attcatctac tgtactggtc ccacccaggt ggtccggcat gggggaagta  240
ttcatggact catctctcgg gatgggccgg gaagcccatc ccgggcccaa gaagttggcc  300
cattataggt ggtttggacc tgaagatggg actggctcat cggaagttag ccacaatggc  360
tgagaaatac gggaccatgg ctaagaggct catggctttt agcctaggag aaacacgcgt  420
gattgtcacg tgcaatcccg acgtggcgaa agaaatacta aatagcccgg ttttcttgga  480
ccgacccgac caggagtcgg cttatgggtt gatgtttaac cggtctatag ggttcgcacc  540
ctatgggacc tactggcgaa ccctaaggaa aataacatca acccatttat taagccctaa  600
acacgtaaaa gaatatgaga acctacgtag ggaaataatg gaacaaatgg ttgactcgat  660
atcgaaccaa gccggaccgg ttcgggtccg ggaaatacta aggagggctt cattggataa  720
tatgatgggg tcagtgtttg gtgggcccca caaggaggtc gttgaacagt tgatagaaat  780
ggttggtgaa gggtatgact tattgggtgt ccttaatttg ggggaccatc tatcttggct  840
agccgagttt gactttcaaa aggttcggtt caggtgctct caacttgttc caaaagtcaa  900
ccggttcgtt ggtgaaatta tcgatgaaca tcggtctagt tcgggtcaaa ttatgaaccg  960
ggactttgtt gatgttttgt tgactctacc acaacatgaa caactttctc attctgacat  1020
ggtcgctgtt ctttgggaga tgatatttag aggaacagat gcaacagcag tattaataga  1080
atggacatta gcacgattag taattcataa agatattcaa tcaaaggtcc aaaatgagtt  1140
agaccaagta gttggaacat cacgagccgt tgaagagtct gacctatcat cactgatata  1200
tctaacggct gtgattaaag aagtattgcg ggtccaccca cctgggcccc tcctatcgtg  1260
gtctcgcctt tcaattcaag atactactat agatggttgt catgtgccaa aaggtactac  1320
tgctatggtt aacatgtggg ctattgctag agatcctaat gtgtgggcca acccagatga  1380
atttgacccg gatagatttt taatcggtgg gtccgagttt gagttctctg ttcttgggtc  1440
ggatcttaga cttgcccctt tcgggtcggg tcgtaggtca tgtcctggga aggtcttagg  1500
tttgaccaca gtcagttttt gggttgcttc actcttgcat gagtttgagt gggtgacatc  1560
acctaacgct gacgtggatt tgagtgaagt gcttaagctt tcgtgtgaga tggctcatcc  1620
tcttaccgtg gaagctaggc cgcgacgtca ttaattttac aaaagacgat attctcatac  1680
acagattatt gtcaacttta tcaatatata cgggtgatag tttgacattg ttatagtatt  1740
cggaaaaata ttttctagag ataagtaaat ttataataat ctaaaaaact gaatgtataa  1800
ttatattaat taatgtacta atgttattat aatgtttata aatgattgtg aaatatatat  1860
ggttaacatt atatgtaatg agaaatggtt tgcttggcaa aaa                   1903

SEQ ID NO: 38          moltype = DNA  length = 1915
FEATURE                Location/Qualifiers
source                 1..1915
                       mol_type = other DNA
                       organism = Mirabilis jalapa
SEQUENCE: 38
gctagctgcc ttgttcattt caagaacaat atacactagt caatccattt caaatggcct  60
acttagaaat tgtcatattc ttcatttttc tcatcgtaat ttgtttttct tttcgtgaca  120
aaaatggtct cccaacaaat tggccgattg ttgggatgct accagctgtt ctaatcaatc  180
ttcatagaat taatgactat tttgctgaac ttgttgctaa atcaaattta acattctcat  240
ttaagggtcc ttggtttagc aacatgcgaa ttttagcgac agttgatcca gcaaatgtgc  300
accatataat gagtaagaat tttaacaatt atcctaaggg tgctaagttt tacgacatct  360
ttgatatact tggagatggt atttttaaca ccgactttaa tatatggcaa taccatcgga  420
aaatggctca gtcatatatt ggtgactcaa gatttcaaca atttttgttg aagaaagttg  480
gggaaaagat tgaaggtgga ttaattccta tccttgatca tgttgccatg caagggttac  540
aagttgattt acaagattta tttgaaaggt ttacttttga tactatttgt tcacttatta  600
tgaactatga tcctatgtct ttgtccattg attttcctga tgttccatca tctaaggctc  660
tagatgttgc tgaagaagtc atacttcttc gtcatttagt acctacaagt gtttggaagt  720
ttcaaagatg gttaggtgta gggatggaaa agaagcataa gatagcttgg caagtacttg  780
atgatttcat ttatgagtgc atatcaagga aaagagaaga gatgagagat agtttgtcct  840
atgagaataa ggacaatgag atgggtgttg atttaatgac attgtatatg aatgaaatca  900
aaagtaatga acttgtcaag gatgatccta acaagttttt gagggatact attcttaact  960
tttttattgc aggtcgagat acaactagta ctgctttatc gtggtttttc tatctactat  1020
ccaagaatcc acaagtggta gaaaagatta gacaagagtt atcttggatc gtttcacaag  1080
aaaaaactaa aaattatgct aatttgattg ataaacttgt ttatcttcat gccgcattat  1140
gtgaagcttt aagattatat cctccggtgg tatttgaagc aaagtctccg attgaatcgg  1200
acactttacc aagtggtcat aagattgatc ctgacacaca aataatctta aatatgtacg  1260
caatggcgag gatgaaaaca atatggggcg atgattgcga tcaatttaaa cctgagaggt  1320
ggatatcatc aacaacagga aagattaagc atgaaccttc gtacaagttc ttggctttta  1380
atgcaggacc aagaacttgt gtaggaaaaa atatggcttt tactcaaatg aaagcaatag  1440
caatagctat attacaaaac tatcatatac atggtattga tggacaagtt attgaacctg  1500
atctatccat aattctccat atgaagaatg gattcagagt aactgtttca ccgtgtaacg  1560
tttctatata accatcgaga gaaccaagtt tcctcgatct cttttaaaca ttgtaatgtt  1620
taattatcaa ctaaaaaatc gtatattctc ttcgtttcat ttttttcttt ttctttttat  1680
caaagatcaa ggtaacgtcg gaaataacca tattgttttc tttggttaaa tgaaaagaca  1740
atgtaagttg taaaagtatg taagtgtaaa aataaattta aaaaattgtg tgaaaataag  1800
ttgtaataaa taaagaataa tgttggtatt ttattgttta ctattttgat aaacagaaaa  1860
aataaaataa aactgtttaa aaataaaagt gagaagaaaa aaaataaaag aaaat       1915
```

```
SEQ ID NO: 39          moltype = DNA  length = 817
FEATURE                Location/Qualifiers
source                 1..817
                       mol_type = other DNA
                       organism = Portulaca grandiflora
SEQUENCE: 39
atgggtgttg ggaaggaagt gtcgtttaag gagagtttct tcttgtctca tgggaatcca  60
gccatgttgg cggatgaatc ctttatagcg aggaacttcc ttttgggatg gaaaaagaat  120
gtgtttcctg tgaaacccaa gtccatttta gtagtctctg ctcactggga gactgatgtc  180
ccttgtgtat ctgctggtca gtaccctaat gttatctacg atttcactga agtccctgct  240
tccatgtttc agatgaagta cccagctcca gggtgcccaa agctggcaaa aagagtgcag  300
gaactgctga tagcgggagg tttcaagagc gcgaagctag atgaggagcg gggtttcgac  360
cacagctcat gggtgccact gagcatgatg tgcccggagg cggacatccc ggtgtgccag  420
ctttcggtgc agcctgggct tgacgcgacc caccacttca acgtggggcg agcgttggcc  480
ccactcaaag gggaaggtgt cctcttcatt ggctccggtg gggctgtcca cccttctgat  540
gacacccctc attggttcga tggtgttgct ccctgggctg ctgagtttga tcaatggctt  600
gaggatgctc tcctagaagg aaggtacgaa gatgtgaata actatcaaac aaaagcacca  660
gaagggtgga agctagcaca tccaattcca gaacattttc taccattgca tgtagccatg  720
ggtgcaggtg gtgagaaatc aaaggcagag cttatttatc gtacttggga tcatggtact  780
cttggctacg cctcttacaa gttcacttcc atatgat                           817

SEQ ID NO: 40          moltype = DNA  length = 1078
FEATURE                Location/Qualifiers
source                 1..1078
                       mol_type = other DNA
                       organism = Bougainvillea glabra
SEQUENCE: 40
atgggtgggg agaaaaaaat gaagggaaca tactatatag cacatggtga tccaattatg  60
tacatcaata aatcaataaa acttaggcac tttttagaag agtggaaaga gaatgtggtt  120
atggagaaac ctatatgtat tcttgtgatt tcagctcatt gggatactga tgttcccact  180
gttaaccttg ttgaacattg tgataccatc catgattttg atgactatcc tgatcccttg  240
taccagataa agtatccagc tcctggggct ccaaaattgg caatgaaagt gcaagagtta  300
ttgaaaggtg gaggattcaa atgtgaagtg gatacaaagc gtggacttga ccatgctgca  360
tggtttccac tcatgttgat gtatcctgaa gctgatattc caatttgtga gctctcagtt  420
caaaccaaca aggatgggac ccaccactac aaccttggaa aagcactttc tcctctcttg  480
aatgatgatg ttctcatcat tggctctggt ggagctgttc atccctcaga tgatactcct  540
cattgtccta atggtgttgc tccttgggct ttgcagtttg acaattggct tgaagatgct  600
cttctcagtg gaaggtatga agatgtgaaa gaattcaaaa aaatggcacc aaattgggag  660
atatcacatc cagggcaaga gcacttgtac cctttgcatg tggctcttgg ggctgcaggc  720
aacaacgtaa agacagagct tattcatcaa acttgggctg ccaatggcgt ctttggatat  780
tcctcctaca agttcacatc cacttgaaca ataaattaaa tattcatctt tacacatttc  840
aataattccc ttcttgtgtt tgctttttct ggtattaaat ttgtttgtca ttttttttta  900
gagtcgacag ttgagggtct ttttaaaaca atttttttta tctttatggc gagagtgaca  960
tccttgtaaa attcatttat tatggtgtat ttggatacta gtatttcatt tgagatgcat  1020
gaattatgtt aaattcactg tttgaataac aataaattta taaatttgaa tttgactc    1078

SEQ ID NO: 41          moltype = AA  length = 228
FEATURE                Location/Qualifiers
source                 1..228
                       mol_type = protein
                       organism = Amanita muscaria
SEQUENCE: 41
MVPSFVVYSS WVNGRQRYIR QAFASILFYI IRDTTLSFPS HTTMSTKPET DLQTVLDSEI  60
KEWHFHIYFH QNNAAEHQAA LELRDAVLRL RQDGAFVAVP LFRVNMDPMG PHPVGSYEIW  120
VPSETFASVF SYLCMNRGRL SILVHPLTRE ELRDHEIRNA WIGPSFPLNL ANLPIKSDEI  180
PLQYPSLKLG YSSTAHKMSL EERRKLGDDI EAVLRGEKEA ARAPHRDA               228

SEQ ID NO: 42          moltype = AA  length = 275
FEATURE                Location/Qualifiers
source                 1..275
                       mol_type = protein
                       organism = Beta vulgaris
SEQUENCE: 42
MKMMNGEDAN DQMIKESFFI THGNPILTVE DTHPLRPFFE TWREKIFSKK PKAILIISGH  60
WETVKPTVNA VHINDTIHDF DDYPAAMYQF KYPAPGEPEL ARKVEEILKK SGFETAETDQ  120
KRGLDHGAWV PLMLMYPEAD IPVCQLSVQP HLDGTYHYNL GRALAPLKND GVLIIGSGSA  180
THPLDETPHY FDGVAPWAAA FDSWLRKALI NGRFEEVNIY ESKAPNWKLA HPFPEHFYPL  240
HVVLGAAGEK WKAELIHSSW DHGTLCHGSY KFTSA                             275

SEQ ID NO: 43          moltype = AA  length = 500
FEATURE                Location/Qualifiers
source                 1..500
                       mol_type = protein
                       organism = Mirabilis jalapa
SEQUENCE: 43
MTAIKMNTNG EGETQHILMI PFMAQGHLRP FLELAMFLYK RSHVIITLLT TPLNAGFLRH  60
LLHHHSYSSS GIRIVELPFN STNHGLPPGI ENTDKLTLPL VVSLFHSTIS LDPHLRDYIS  120
RHFSPARPPL CVIHDVFLGW VDQVAKDVGS TGVVFTTGGA YGTSAYVSIW NDLPHQNYSD  180
```

-continued

```
DQEFPLPGFP ENHKFRRSQL HRFLRYADGS DDWSKYFQPQ LRQSMKSFGW LCNSVEEIET  240
LGFSILRNYT KLPIWGIGPL IASPVQHSSS DNNSTGAEFV QWLSLKEPDS VLYISFGSQN  300
TISPTQMMEL AAGLESSEKP FLWVIRAPFG FDINEEMRPE WLPEGFEERM KVKKQGKLVY  360
KLGPQLEILN HESIGGFLTH CGWNSILESL REGVPMLGWP LAAEQAYNLK YLEDEMGVAV  420
ELARGLEGEI SKEKVKRIVE MILERNEGSK GWEMKNRAVE MGKKLKDAVN EEKELKGSSV  480
KAIDDFLDAV MQAKLEPSLQ                                              500

SEQ ID NO: 44          moltype = AA  length = 504
FEATURE                Location/Qualifiers
source                 1..504
                       mol_type = protein
                       organism = Mirabilis jalapa
SEQUENCE: 44
MENTMLGVIL ATIFLTFHIM KMLFSPSKVK LPPGPRPLPI IGNILELGDK PHRSFANLAK  60
IHGPLVTLKL GSVTTIVVSS SEVAKEMFLK NDQPLANRTI PDSVRAGNHD KLSMSWLPVS  120
PKWRNLRKIS AVQLLSTQRL DASQAHRQAK IKQLIEYVKK CSKIGQYVDI GQVAFTTSLN  180
LLSNTFFSKE LASFDSDNAQ EFKQLMWCIM EEIGRPNYAD YFPILGYVDP FGARRRLSRY  240
FDQLIEVFQV IIRERLTHDN NIVGNNNDVL ATLLDLYKQN ELTMDEINHL LVDIFDAGTD  300
TTASTLEWAM SELIKNPHIM AKAQEEVRRA TMSHGGATVA EIQESDINNL PYIQSIIKET  360
LRLHPPTVFL LPRKADVDVQ LFGYVVPKNA QVLVNLWAIG RDPNVWPDPE VFSPERFMDC  420
EIDVKGRDFE LLPFGAGRRI CPGLSLAYRM LNLMLANMVH SFDWKLPGVE NGSGSEMDSL  480
DMDEKFGITL QKVQPLKVIP VSRK                                         504

SEQ ID NO: 45          moltype = DNA  length = 24
FEATURE                Location/Qualifiers
misc_feature           1..24
                       note = BvDODA1 Fwd + XhoI
source                 1..24
                       mol_type = other DNA
                       organism = synthetic construct
SEQUENCE: 45
tgtgctagac gttcttcttc agct                                         24

SEQ ID NO: 46          moltype = DNA  length = 20
FEATURE                Location/Qualifiers
misc_feature           1..20
                       note = BvDODA1 Rev + SacI
source                 1..20
                       mol_type = other DNA
                       organism = synthetic construct
SEQUENCE: 46
aaaatgtcga cgagcaaatg                                              20

SEQ ID NO: 47          moltype = DNA  length = 22
FEATURE                Location/Qualifiers
misc_feature           1..22
                       note = CYP76AD1 Fwd + XhoI
source                 1..22
                       mol_type = other DNA
                       organism = synthetic construct
SEQUENCE: 47
cttcatctcg taggcttcct cc                                           22

SEQ ID NO: 48          moltype = DNA  length = 20
FEATURE                Location/Qualifiers
misc_feature           1..20
                       note = CYP76AD1 Rev + SacI
source                 1..20
                       mol_type = other DNA
                       organism = synthetic construct
SEQUENCE: 48
gatgaggctt ttcgccaaga                                              20

SEQ ID NO: 49          moltype = DNA  length = 20
FEATURE                Location/Qualifiers
misc_feature           1..20
                       note = CYP76AD1 Fwd + BamHI
source                 1..20
                       mol_type = other DNA
                       organism = synthetic construct
SEQUENCE: 49
cctgtatcgg ctaaatggcg                                              20

SEQ ID NO: 50          moltype = DNA  length = 21
FEATURE                Location/Qualifiers
misc_feature           1..21
                       note = CYP76AD1 Rev + EcoRI
source                 1..21
                       mol_type = other DNA
```

```
                          organism = synthetic construct
SEQUENCE: 50
caattgcaca gcggagattt t                                              21

SEQ ID NO: 51             moltype = DNA  length = 20
FEATURE                   Location/Qualifiers
misc_feature              1..20
                          note = BvCYP76new Fwd + XhoI
source                    1..20
                          mol_type = other DNA
                          organism = synthetic construct
SEQUENCE: 51
ttgatgctgt ttgcgcagtc                                                20

SEQ ID NO: 52             moltype = DNA  length = 20
FEATURE                   Location/Qualifiers
misc_feature              1..20
                          note = BvCYP76new Rev + SacI
source                    1..20
                          mol_type = other DNA
                          organism = synthetic construct
SEQUENCE: 52
tgcgaagatt tcgccatttt                                                20

SEQ ID NO: 53             moltype = DNA  length = 23
FEATURE                   Location/Qualifiers
misc_feature              1..23
                          note = CYP76AD6 Fwd + XhoI
source                    1..23
                          mol_type = other DNA
                          organism = synthetic construct
SEQUENCE: 53
tggtgctgat tttcgtcgta gag                                            23

SEQ ID NO: 54             moltype = DNA  length = 19
FEATURE                   Location/Qualifiers
misc_feature              1..19
                          note = CYP76AD6 Rev + SacI
source                    1..19
                          mol_type = other DNA
                          organism = synthetic construct
SEQUENCE: 54
tggcaccacc cttcaagtg                                                 19

SEQ ID NO: 55             moltype = DNA  length = 20
FEATURE                   Location/Qualifiers
misc_feature              1..20
                          note = BvDODA1 Fwd
source                    1..20
                          mol_type = other DNA
                          organism = synthetic construct
SEQUENCE: 55
taaagctccc tcctggtcca                                                20

SEQ ID NO: 56             moltype = DNA  length = 20
FEATURE                   Location/Qualifiers
misc_feature              1..20
                          note = BvDODA1 Rev
source                    1..20
                          mol_type = other DNA
                          organism = synthetic construct
SEQUENCE: 56
ccgcagaacg atgaggtttg                                                20

SEQ ID NO: 57             moltype = DNA  length = 23
FEATURE                   Location/Qualifiers
misc_feature              1..23
                          note = CYP76AD1 Fwd
source                    1..23
                          mol_type = other DNA
                          organism = synthetic construct
SEQUENCE: 57
tcaaactcgg aagcatcact aca                                            23

SEQ ID NO: 58             moltype = DNA  length = 20
FEATURE                   Location/Qualifiers
misc_feature              1..20
                          note = CYP76AD1 Rev
source                    1..20
```

```
                        mol_type = other DNA
                        organism = synthetic construct
SEQUENCE: 58
gggctaagtc gtgctcgagg                                            20

SEQ ID NO: 59           moltype = DNA  length = 35
FEATURE                 Location/Qualifiers
misc_feature            1..35
                        note = CYP76AD6 Fwd1
source                  1..35
                        mol_type = other DNA
                        organism = synthetic construct
SEQUENCE: 59
aaaaactcga ggttaaacct actgttaatg ctgtc                           35

SEQ ID NO: 60           moltype = DNA  length = 31
FEATURE                 Location/Qualifiers
misc_feature            1..31
                        note = CYP76AD6 Rev1
source                  1..31
                        mol_type = other DNA
                        organism = synthetic construct
SEQUENCE: 60
aaaaagagct cgctgcccaa ggtgcaactc c                               31

SEQ ID NO: 61           moltype = DNA  length = 34
FEATURE                 Location/Qualifiers
misc_feature            1..34
                        note = CYP76AD6 Fwd2
source                  1..34
                        mol_type = other DNA
                        organism = synthetic construct
SEQUENCE: 61
aaaaactcga ggctaatctt gctaaaattc acgg                            34

SEQ ID NO: 62           moltype = DNA  length = 33
FEATURE                 Location/Qualifiers
misc_feature            1..33
                        note = CYP76AD6 Rev2
source                  1..33
                        mol_type = other DNA
                        organism = synthetic construct
SEQUENCE: 62
aaaaagagct cttatggtgg gctaattcca ctg                             33

SEQ ID NO: 63           moltype = DNA  length = 34
FEATURE                 Location/Qualifiers
misc_feature            1..34
                        note = cDOPA5GT Fwd1
source                  1..34
                        mol_type = other DNA
                        organism = synthetic construct
SEQUENCE: 63
aaaaaggatc cgctaatctt gctaaaattc acgg                            34

SEQ ID NO: 64           moltype = DNA  length = 33
FEATURE                 Location/Qualifiers
misc_feature            1..33
                        note = cDOPA5GT Rev1
source                  1..33
                        mol_type = other DNA
                        organism = synthetic construct
SEQUENCE: 64
aaaaagaatt cttatggtgg gctaattcca ctg                             33

SEQ ID NO: 65           moltype = DNA  length = 32
FEATURE                 Location/Qualifiers
misc_feature            1..32
                        note = cDOPA5GT Fwd2
source                  1..32
                        mol_type = other DNA
                        organism = synthetic construct
SEQUENCE: 65
aaaaactcga gctgcaagag tcaatgatct ca                              32

SEQ ID NO: 66           moltype = DNA  length = 33
FEATURE                 Location/Qualifiers
misc_feature            1..33
                        note = cDOPA5GT Rev2
```

```
source                  1..33
                        mol_type = other DNA
                        organism = synthetic construct
SEQUENCE: 66
aaaaagagct ctcatctggg aattggaatt gct                          33

SEQ ID NO: 67           moltype = DNA  length = 32
FEATURE                 Location/Qualifiers
misc_feature            1..32
                        note = BvDODA1 Fwd
source                  1..32
                        mol_type = other DNA
                        organism = synthetic construct
SEQUENCE: 67
aaaaactcga gcacaacagc aagcacatta ga                           32

SEQ ID NO: 68           moltype = DNA  length = 33
FEATURE                 Location/Qualifiers
misc_feature            1..33
                        note = BvDODA1 Rev
source                  1..33
                        mol_type = other DNA
                        organism = synthetic construct
SEQUENCE: 68
aaaaagagct cagtccaggg catatccttc tac                          33

SEQ ID NO: 69           moltype = DNA  length = 41
FEATURE                 Location/Qualifiers
misc_feature            1..41
                        note = CYP76AD1 Fwd
source                  1..41
                        mol_type = other DNA
                        organism = synthetic construct
SEQUENCE: 69
gcgccgtctc gctcgaatga aaatgatgaa tggtgaagat g                 41

SEQ ID NO: 70           moltype = DNA  length = 40
FEATURE                 Location/Qualifiers
misc_feature            1..40
                        note = CYP76AD1 Rev
source                  1..40
                        mol_type = other DNA
                        organism = synthetic construct
SEQUENCE: 70
gcgccgtctc gctcgaagcc taggctgaag tgaacttgta                   40

SEQ ID NO: 71           moltype = DNA  length = 40
FEATURE                 Location/Qualifiers
misc_feature            1..40
                        note = CYP76AD6 Fwd
source                  1..40
                        mol_type = other DNA
                        organism = synthetic construct
SEQUENCE: 71
gcgccgtctc gctcgaatgg atcatgcaac attagcaatg                   40

SEQ ID NO: 72           moltype = DNA  length = 43
FEATURE                 Location/Qualifiers
misc_feature            1..43
                        note = CYP76AD6 Rev
source                  1..43
                        mol_type = other DNA
                        organism = synthetic construct
SEQUENCE: 72
gcgccgtctc gctcgaagct caatacctag gtattggaat aag               43

SEQ ID NO: 73           moltype = DNA  length = 37
FEATURE                 Location/Qualifiers
misc_feature            1..37
                        note = Synthetic
source                  1..37
                        mol_type = other DNA
                        organism = synthetic construct
SEQUENCE: 73
gcgccgtctc gctcgaatgg ataacgcaac acttgct                      37

SEQ ID NO: 74           moltype = DNA  length = 32
FEATURE                 Location/Qualifiers
misc_feature            1..32
```

```
                         note = Synthetic
source                   1..32
                         mol_type = other DNA
                         organism = synthetic construct
SEQUENCE: 74
gcgccgtctc gttgcccatt ctaatgtgct tg                               32

SEQ ID NO: 75            moltype = DNA  length = 31
FEATURE                  Location/Qualifiers
misc_feature             1..31
                         note = Synthetic
source                   1..31
                         mol_type = other DNA
                         organism = synthetic construct
SEQUENCE: 75
gcgccgtctc ggcaatggcc gaacttgtga a                                31

SEQ ID NO: 76            moltype = DNA  length = 40
FEATURE                  Location/Qualifiers
misc_feature             1..40
                         note = Synthetic
source                   1..40
                         mol_type = other DNA
                         organism = synthetic construct
SEQUENCE: 76
gcgccgtctc gctcgaagcc tagtttctgg gaactggaat                       40

SEQ ID NO: 77            moltype = DNA  length = 39
FEATURE                  Location/Qualifiers
misc_feature             1..39
                         note = Synthetic
source                   1..39
                         mol_type = other DNA
                         organism = synthetic construct
SEQUENCE: 77
gcgccgtctc gctcgaatga ccgccattaa aatgaacac                        39

SEQ ID NO: 78            moltype = DNA  length = 33
FEATURE                  Location/Qualifiers
misc_feature             1..33
                         note = Synthetic
source                   1..33
                         mol_type = other DNA
                         organism = synthetic construct
SEQUENCE: 78
gcgccgtctc ggcctcattt cctcattgat atc                              33

SEQ ID NO: 79            moltype = DNA  length = 31
FEATURE                  Location/Qualifiers
misc_feature             1..31
                         note = Synthetic
source                   1..31
                         mol_type = other DNA
                         organism = synthetic construct
SEQUENCE: 79
gcgccgtctc gaggccagaa tggctaccag a                                31

SEQ ID NO: 80            moltype = DNA  length = 43
FEATURE                  Location/Qualifiers
misc_feature             1..43
                         note = Synthetic
source                   1..43
                         mol_type = other DNA
                         organism = synthetic construct
SEQUENCE: 80
gcgccgtctc gctcgaagct tattgaagag aaggttccaa ctt                   43

SEQ ID NO: 81            moltype = DNA  length = 55
FEATURE                  Location/Qualifiers
misc_feature             1..55
                         note = Synthetic
source                   1..55
                         mol_type = other DNA
                         organism = synthetic construct
SEQUENCE: 81
ggggacaagt ttgtacaaaa aagcaggctt catgaaaatg atgaatggtg aagat       55

SEQ ID NO: 82            moltype = DNA  length = 55
FEATURE                  Location/Qualifiers
```

```
misc_feature          1..55
                      note = Synthetic
source                1..55
                      mol_type = other DNA
                      organism = synthetic construct
SEQUENCE: 82
ggggaccact ttgtacaaga aagctgggtc ctaggctgaa gtgaacttgt aggag       55

SEQ ID NO: 83         moltype = DNA  length = 53
FEATURE               Location/Qualifiers
misc_feature          1..53
                      note = Synthetic
source                1..53
                      mol_type = other DNA
                      organism = synthetic construct
SEQUENCE: 83
ggggacaagt ttgtacaaaa aagcaggctt catggatcat gcaacattag caa         53

SEQ ID NO: 84         moltype = DNA  length = 57
FEATURE               Location/Qualifiers
misc_feature          1..57
                      note = Synthetic
source                1..57
                      mol_type = other DNA
                      organism = synthetic construct
SEQUENCE: 84
ggggaccact ttgtacaaga aagctgggtc tcaataccta ggtattggaa taagttt     57

SEQ ID NO: 85         moltype = DNA  length = 59
FEATURE               Location/Qualifiers
misc_feature          1..59
                      note = Synthetic
source                1..59
                      mol_type = other DNA
                      organism = synthetic construct
SEQUENCE: 85
ggggacaagt ttgtacaaaa aagcaggctt catggataac gcaacacttg ctgtgatcc   59

SEQ ID NO: 86         moltype = DNA  length = 62
FEATURE               Location/Qualifiers
misc_feature          1..62
                      note = Synthetic
source                1..62
                      mol_type = other DNA
                      organism = synthetic construct
SEQUENCE: 86
ggggaccact ttgtacaaga aagctgggtc ctagtttctg ggaactggaa taacttgaag  60
ag                                                                 62
```

CYP76AD1-BETA CLADE POLYNUCLEOTIDES, POLYPEPTIDES, AND METHODS FOR PRODUCING BETALAINS

CROSS REFERENCE TO RELATED APPLICATIONS

This application is a continuation of U.S. patent application Ser. No. 16/940,666 filed on Jul. 28, 2020 (now issued as U.S. Pat. No. 11,932,887 on Mar. 19, 2024), which is a continuation of U.S. patent application Ser. No. 15/758,372 filed on Mar. 8, 2018, now U.S. Pat. No. 10,767,201, issued on Sep. 8, 2020, which is a National Phase of PCT Patent Application No. PCT/IL2016/051010 having an International filing date of Sep. 11, 2016, which claims the benefit of priority under 35 U.S.C. § 119(e) of Israel Patent Application No. 241462, filed on Sep. 10, 2015. The contents of the above applications are all incorporated by reference as if fully set forth herein in their entirety.

REFERENCE TO AN ELECTRONIC SEQUENCE LISTING

The contents of the electronic sequence listing (PHYT-P-001-US2 corrected.xml; Size: 276,696 bytes; and Date of Creation: Apr. 1, 2024) is herein incorporated by reference in its entirety.

FIELD OF THE INVENTION

The invention provides recombinant polynucleotides comprising a nucleic acid encoding a CYP76AD6 or related gene and their use for producing L-DOPA from tyrosine and treating dopamine-responsive disorders, such as Parkinson's Disease. The invention also provides recombinant polynucleotides comprising a nucleic acid encoding a CYP76AD1 and/or CYP76AD6, a nucleic acid encoding a DOPA 4,5-dioxygenase (DOD) enzyme, such as *Beta vulgaris* DODA1, and, in some cases, a nucleic acid encoding betalain related glucosyltransferase, such as *M. jalapa* gene cyclo-DOPA 5-O-glucosyltransferase (cDOPA5GT), and their use for producing betalains. Finally, the invention provides chimeric polypeptides, expression vectors, cells, compositions, and organisms, including plants, and their uses in various methods of the invention.

BACKGROUND OF THE INVENTION

Betalains are tyrosine-derived, red-violet and yellow plant pigments found in only one group of angiosperms, the Caryophyllales order, in which they occur in a mutually exclusive fashion with the chemically distinct and widespread anthocyanin pigments. The betalain class contains a wide array of compounds, which are generally classified into two groups; the red-violet betacyanins, and the yellow betaxanthins.

A key enzyme in betalain biosynthesis, DOPA 4,5-dioxygenase (DOD) converts L-DOPA to betalamic acid, which constitutes the basic backbone of all betalains (FIG. 1). Spontaneous conjugation of betalamic acid with amines or with L-DOPA derivatives, results in the formation of yellow betaxanthins or red-violet betacyanins, respectively. Betalain related glucosyltransferase have also been characterized in several Caryophyllales plant species, catalyzing 5-0 glucosylation of cyclo-DOPA or alternatively 5-0 or 6-0 glucosylation of betanidin. The enzyme catalyzing the formation of L-DOPA from tyrosine is unknown.

Due to their high stability, pH independence and antioxidative properties, betalains may be used as natural food colorants and dietary supplements.

While potential edible plant sources of anthocyanins are numerous, betalains are found in very few edible plants, with red beet being the only major source for betalain extraction in commercial use today. Despite its high betacyanin content, red beet extract has several drawbacks as a source of food colorants; it mainly produces betanin and thus has limited color variability, it carries adverse earthy flavors due to the occurrence of geosmin and various pyrazines, and it holds the risk of carry-over of soil-borne microbes. There are currently no natural sources in large-scale use for betaxanthins as food dyes. Yellow beet, for example, is not used likely due to co-occurring phenolics that are easily oxidized and mask the yellow hue of betaxanthins. Evidently, it is of interest to develop alternative sources for betalains, particularly betaxanthins, as there are currently no natural yellow, water-soluble pigments available for commercial use in the food industry. Heterologous production of betalains may provide numerous new viable sources for these pigments, such as plants, plant cell cultures, algae and yeast.

A betalain pathway intermediate, L-3,4-dihydroxyphenylalanine (L-DOPA), is also a commercially valuable metabolite that is widely used for treatment of Parkinson's disease.

Parkinson's disease is a progressive disorder of the nervous system primarily affecting the motor system of the body. It is the second most common neurodegenerative disorder and the most common movement disorder, affecting an estimate of 5 million people worldwide. A major feature of Parkinson's disease is the reduced levels of dopamine, an important signaling molecule in the nervous system. The most effective therapy for Parkinson's disease is the administration L-DOPA (3,4-dihydroxyphenylalanine), which is converted to dopamine in the brain. L-DOPA is the most effective drug for the treatment of Parkinson's disease, since dopamine fails to pass through the blood brain barrier.

L-DOPA is also widely marketed as a dietary supplement and is a precursor of additional high-value metabolites, which include among others catecholeamines (e.g. dopamine, epinephrine), benzilisoquinoline alkaloids (e.g. morphine and other opiates), betalain pigments and melanin.

Although L-DOPA is produced in many plants and animal species, it rarely accumulates in substantial quantities. This is partially due to the fact that L-DOPA is universally formed by the enzyme tyrosinase, which catalyzes the hydroxylation of tyrosine to L-DOPA but also immediately converts it to its oxidized form, dopaquinone.

L-DOPA for the pharma industry is currently produced using one of several methods, all of which have severe limitations, as chemical synthesis can only be achieved in a costly process that involves many chemical reactions and requires the use of expensive substrates and harsh production conditions. Biotechnological production of L-DOPA via the use of tyrosinase enzymes (also called polyphenol oxidase—PPO) has also been explored. The dual reaction of tyrosinase described above is highly problematic for the commercial production of L-DOPA, as the product of interest is directly metabolized to the commercially useless dopaquinone, and is therefore a major bottleneck for its use in enzymatic biosynthesis for large-scale production of L-DOPA from tyrosine. Thus, there is an unmet need for a more efficient and less expensive method for preparing L-DOPA.

Betalain biosynthesis has remained poorly understood in comparison to the other major classes of plant pigments, namely anthocyanins and carotenoids, especially in regard to the enzyme that catalyzes the conversion of tyrosine to L-DOPA in the betalain synthetic pathway in Caryophyllales.

SUMMARY OF THE INVENTION

In one embodiment, the present invention provides a recombinant polynucleotide comprising a nucleic acid encoding a CYP76AD6 gene, a nucleic acid encoding CYP76AD15 gene, or a nucleic acid encoding a combination thereof under the control of a promoter. In one embodiment, the polynucleotide further comprises a nucleic acid encoding a DOPA 4,5-dioxygenase (DOD) enzyme.

In another embodiment, the present invention provides a recombinant polynucleotide comprising a nucleic acid encoding CYP76AD1, a nucleic acid encoding a DOPA 4,5-dioxygenase (DOD) enzyme, and a nucleic acid encoding betalain related glucosyltransferase, wherein said nucleic acids are inserted into the polynucleotide in frame. In one embodiment, the polynucleotide further comprises a nucleic acid encoding CYP76AD6.

In another embodiment, the present invention provides a composition comprising a recombinant polynucleotide as described hereinabove.

In another embodiment, the present invention provides an expression vector comprising a recombinant polynucleotide as described hereinabove.

In another embodiment, the present invention provides a cell comprising the expression vector as described hereinabove.

In another embodiment, the present invention provides a chimeric polypeptide encoded by a recombinant polynucleotide as described hereinabove.

In another embodiment, the present invention provides a method of producing L-DOPA in a cell comprising the step of contacting said cell with a recombinant polynucleotide comprising a nucleic acid encoding a CYP76AD6 gene, a nucleic acid encoding CYP76AD15 gene, or a nucleic acid encoding a combination thereof under the control of a promoter, under conditions sufficient to produce L-DOPA, thereby producing L-DOPA.

In another embodiment, the present invention provides a method of producing L-DOPA from tyrosine comprising the step of combining CYP76AD6, CYP76AD15, or a combination thereof, and tyrosine under conditions sufficient to produce L-DOPA, thereby producing L-DOPA.

In another embodiment, the present invention provides a use of a CYP76AD1-β clade gene or one or more cells from an organism comprising high levels of said CYP76AD1-β clade gene in the preparation of a composition for treating or suppressing a dopamine-responsive disorder in a subject.

In another embodiment, the present invention provides a method of betalain production comprising the step of contacting a recombinant polynucleotide comprising a nucleic acid encoding a CYP76AD6 gene, a nucleic acid encoding CYP76AD15 gene, or a nucleic acid encoding a combination thereof under the control of a promoter; a nucleic acid encoding a DOPA 4,5-dioxygenase (DOD) enzyme; and a nucleic acid encoding CYP76AD1, wherein said nucleic acids are inserted into the polynucleotide in frame, with one or more cells, under conditions sufficient to produce betalains, thereby producing betalains.

In another embodiment, the present invention provides a method of producing betaxanthins comprising the step of contacting a recombinant polynucleotide comprising a nucleic acid encoding a CYP76AD6 gene, a nucleic acid encoding CYP76AD15 gene, or a nucleic acid encoding a combination thereof under the control of a promoter; and a nucleic acid encoding a DOPA 4,5-dioxygenase (DOD) enzyme, wherein said nucleic acids are inserted into the polynucleotide in frame, with one or more cells, under conditions sufficient to produce betaxanthins, thereby producing betaxanthins.

In another embodiment, the present invention provides a method of increasing the resistance of a plant or plant part to one or more biotic or abiotic stress factors comprising the step of contacting one or more cells of said plant or plant part with a nucleic acid encoding CYP76AD6, a nucleic acid encoding CYP76AD15, a nucleic acid encoding CYP76AD1, or a combination thereof, a nucleic acid encoding a DOPA 4,5-dioxygenase (DOD) enzyme; and, optionally a nucleic acid encoding a betalain related glucosyltransferase, under conditions sufficient to produce betalains, thereby producing betalains and increasing the resistance of said plant or plant part to said one or more stress factors.

In another embodiment, the present invention provides a method of increasing the resistance of a plant or plant part to one or more fungal diseases comprising the step of contacting one or more cells of a plant or plant part with a nucleic acid encoding CYP76AD6, a nucleic acid encoding CYP76AD15, a nucleic acid encoding CYP76AD1, or a combination thereof, a nucleic acid encoding a DOPA 4,5-dioxygenase (DOD) enzyme; and, optionally a nucleic acid encoding a betalain related glucosyltransferase, under conditions sufficient to produce betalains, thereby producing betalains and increasing the resistance of said plant or plant part to said one or more fungal diseases.

In another embodiment, the present invention provides a method of increasing the levels of one or more betalains in an organism or in a part of an organism comprising causing or allowing within at least one part of the organism the expression of a DOPA 4,5-dioxygenase (DOD) enzyme and CYP76AD6, CYP76AD1, or a combination thereof, wherein if said organism expresses CYP76AD1 and DOD and not CYP76AD6 or CYP76AD15, said organism also expresses a betalain related glucosyltransferase, thereby increasing the levels of one or more betalains in said organism or in said part of an organism.

In another embodiment, the present invention provides an organism or part thereof comprising a recombinant nucleic acid sequence encoding a CYP76AD1-α clade gene, a nucleic acid sequence encoding a CYP76AD1-β clade gene, or a nucleic acid sequence encoding a combination thereof, and a nucleic acid sequence encoding a DOPA 4,5-dioxygenase (DOD) enzyme.

In another embodiment, the present invention provides a method of betalain production from tyrosine comprising the step of contacting a composition comprising CYP76AD1, a DOPA 4,5-dioxygenase (DOD) enzyme with tyrosine, and CYP76AD6, CYP76AD15, or a combination thereof, under conditions sufficient to produce betalains, thereby producing betalains.

In another embodiment, the present invention provides a method of producing betaxanthins from tyrosine comprising the step of contacting a composition comprising CYP76AD6, CYP76AD15, or a combination thereof, and a DOPA 4,5-dioxygenase (DOD) enzyme with tyrosine, under conditions sufficient to produce betaxanthins, thereby producing betaxanthins.

BRIEF DESCRIPTION OF THE DRAWINGS

The subject matter regarded as the invention is particularly pointed out and distinctly claimed in the concluding portion of the specification. The invention, however, both as to organization and method of operation, together with objects, features, and advantages thereof, may best be understood by reference to the following detailed description when read with the accompanying drawings in which:

FIG. 2A: Petals. FIG. 2B: Stamen filaments. FIG. 2C: Stem epidermis from node or internode. FIG. 2D: Stigmas. FIG. 2E: Anthers. FIG. 2F: Red-young or mature-green leaf FIG. 2G: Betalain-related genes cyclo-dopa-5-O-glucosyltransferase (cDOPA5GT; SEQ ID NO: 2), DOPA 4,5-dioxygenase (MjDOD; SEQ ID NO: 3) and the cytochrome P450 CYP76AD3 (Genbank Accession No. HQ656026.1; SEQ ID NO: 4) exhibit expression patterns which parallel pigment accumulation. The cytochrome P450 gene MjCYP76 (SEQ ID NO: 1) is highly co-expressed with cDOPA5GT (Pearson correlation r value=0.90) and to a lesser extent with MjDOD (r value=0.67).

In FIG. 5A, whole-plant images, 3.5 weeks post infiltration are presented; in FIG. 5B, single-leaf images, bright field and in FIG. 5C, single-leaf images, blue light are shown.

FIG. 7A: Co-infiltration of agrobacteria harboring plasmids for expression of CYP76AD1 with cDOPA5GT (pAD1-GT) and BvDODA1 (pDODA) in *Nicotiana benthamiana* leaves causes red pigmentation. FIG. 7B: LC-MS analysis of red-pigmented tissue shows occurrence of betanin and iso-betanin. FIG. 7C: Co-infiltration of the CYP76AD6 expression vector (pAD6) and pDODA in *N. benthamiana* leaves causes yellow pigmentation. FIG. 7D: Infiltration of pAD1-GT in *N. benthamiana* leaves enables production of L-DOPA. L-DOPA was not detected in control experiment, where YFP is expressed (pYFP). FIG. 7E: Analysis of yellow-pigmented tissue allows the identification of several betaxanthin compounds, including indicaxanthin. FIG. 7F: Infiltration of pAD6 in *N. benthamiana* leaves enables production of L-DOPA. L-DOPA was not detected in control experiment (pDODA+pYFP). XIC, extracted ion chromatogram.

FIG. 8A: Recombinant expression of CYP76AD1, CYP76AD6 and BvDODA1 in yeast cells. The image presented is of media in which yeast were grown following overnight galactose induction. Each yeast clone was transformed with three vectors, for expression of CYP76AD1, CYP76AD6, BvDODA1 and beta-glucoronidase (GUS) in different combinations, and grown in standard SD media without L-DOPA supplementation. Combined expression of BvDODA1 and CYP76AD1 resulted in red-violet pigmentation of the culture media, whereas expression of BvDODA1 together with CYP76AD6 led to formation of yellow pigmentation, indicative of the distinction in catalytic activity between CYP76AD1 and CYP76AD6. Expression of BvDODA1 with both cytochrome P450S resulted in orange-red pigmentation of the media. No pigmentation was observed when each of the cytochrome P450s or BvDODA1 was expressed alone.

FIG. 8B: Multiple sequence alignment of CYP76AD1-like protein sequences from betalain-producing Caryophyllales plants was processed into a maximum-likelihood phylogenetic tree, resulting in the formation of two separate clades, previously named alpha and beta clades (Brockington et al., 2015). CYP76AD6 falls in the R clade, while CYP76AD1 is positioned in the α clade. In the CYP76AD1-β clade: *B. vulgaris, Beta vulgaris* (CYP76AD6; GenBank accession KT962274; SEQ ID NO: 30); *Bv. maritima, Beta vulgaris* ssp. *maritima* (accession AKI33834.1; SEQ ID NO: 10); *F. latifolia, Froelichia latifolia* (accession AKI33838.1; SEQ ID NO: 11); *A. caracasana, Alternanthera caracasana* (accession AKI33835.1; SEQ ID NO: 12); *A. ficoidea, Alternanthera ficoidea* (accession AKI33831.1; SEQ ID NO: 13). In the CYP76AD1-a clade: *B. vulgaris, Beta vulgaris* (CYP76AD1; accession AET43289.1; SEQ ID NO: 14); *A. cruentus, Amaranthus cruentus* (CYP76AD2; accession AET43291.1; SEQ ID NO: 15); *M. jalapa, Mirabilis jalapa* (CYP76AD3; accession AET43292.1; SEQ ID NO: 16); *C. cristata, Celosia cristata* (CYP76AD4; accession AGI78466.1; SEQ ID NO: 17).

FIG. 8C: Liquid chromatography-mass spectrometry (LC-MS) analysis of pigmented yeast media revealed the occurrence of the betalamic acid chromophore when either CYP76AD1, CYP76AD6 or both were expressed with BvDODA1, in addition to several betaxanthins, including glutamine-betaxanthin and valinebetaxanthin (Table 2; not shown in chromatogram). Occurrence of the betacyanins betanidin and iso-betanidin was observed only where CYP76AD1 was expressed. No peaks corresponding to betalain compounds were found where BvDODA1 was not expressed. The y-axes (peak intensity) of all six chromatograms are linked. XIC, extracted ion chromatograms of masses corresponding to betalamic acid [M+H=212.05] and betanidin isomers [M+H=389.10]. Time, retention time (min).

FIGS. 11A-11B. Production of betalains in multiple naturally-non-producing plant species.

FIG. 11A: Agrobacteria-mediated transformation of the pX11 vector, overexpressing cytochrome P450 CYP76AD1, DOPA 4,5-dioxygenase (BvDODA1) and cyclo-dopa 5-O-glucosyltransferase (cDOPA5GT), causes development of red-violet calli or shoots in a variety of Solanaceous plant species, typically observed within 1-2 wk of cultivation in tissue culture: *Solanum lycopersicum* (tomato), *Solanum tuberosum* (potato), *Solanum melongena* (eggplant), *Nicotiana tabacum* (tobacco), *Nicotiana glauca* (tree tobacco), *Solanum nigrum* (European black nightshade), *Petunia* x *hybrida* (*Petunia*), *Nicotiana benthamiana.*

FIGS. 11B1-11B2: *Nicotiana glauca* (FIG. 11B1) and *Nicotiana benthamiana* (FIG. 11B2) calli were sampled and analyzed with liquid chromatography-mass spectrometry (LC-MS), allowing the identification of the betacyanins betanin and isobetaninin in both species, in addition to a novel unidentified betacyanin compound, found only in the *N. glauca* tissue (betacyanin III; Table 2). XIC, extracted ion chromatograms of masses corresponding to the novel betacyanin [M+H=593.10] and betanin isomers [M+H=551.10]. Time, retention time (min).

FIGS. 12A-12C. Betacyanin identification and quantification in engineered and naturally-producing species.

FIG. 12A1-12A2: LC-MS analysis of *Nicotiana benthamiana* leaves agroinfiltrated with the pX11 vector enabled the identification of betanin, which exhibits the same accurate mass, retention time, fragmentation patterns and UV-VIS absorption spectra as betanin from red beet (*Beta vulgaris*) leaf extract.

FIG. 12B: Agroinfiltration of agrobacteria harbouring the pX11 vector into *N. benthamiana* leaves leads to intense red pigmentation in infiltrated area, typically observed within 2-3 days.

FIG. 12C: Betacyanin content of pX11-agroinfiltrated *N. benthamiana* and pX11-transformed *Nicotiana tabacum* was assessed in comparison to several betalain-producing species. Betacyanin content was assessed spectrophotometrically by light absorption measurements at 535 nm and 600 nm. Values indicate the mean±SE of the mean of four biological replicates, each consisting of 100 mg tissue (fresh weight).

FIG. 13A: Left, wild-type tobacco; right, pX11-transformed tobacco. FIG. 13B: Top row, wild-type tobacco flower; bottom row, pX11 flower. Pigment accumulation was also evident in pX11 roots (FIG. 13C), stem epidermis section, ×20 magnified (FIG. 13D) and leaf glandular trichomes, ×20 magnified (FIG. 13E).

FIG. 14A: Transformation of the pX11 vector results in formation of red-pigmented plants in potato (*Solanum tuberosum* var. Desiree—top left panels), eggplant (*Solanum melongena* line DR2—bottom left panels) and tomato (*Solanum lycopersicum* var. MicroTom—right panels).

FIG. 14B: Betanin and isobetanin were identified as the major betacyanins in potato tuber, tomato fruit and eggplant fruit by LC-MS analysis. Extracted ion chromatogram (XIC) of betanin/isobetanin-corresponding mass [M+H=551.1] and UV-VIS absorption of betanin peak is shown for all three tissues.

FIGS. 16A-16B. Fruit-specific accumulation of betalains in tomato.

FIG. 16A: Introduction of the pX11(E8) vector into tomato (*Solanum lycopersicum* var. M-82) results in betalain pigmentation that is restricted to ripening and ripe fruit.

FIG. 16B: Whole fruit and cross-section of wildtype and pX11(E8) tomato fruit.

FIG. 17A: Introduction of pX11, pX12 or pX13 vectors into tobacco results in formation of different colored flowers. Viewed from top (top row) or magnified and viewed under bright-field (middle row) or blue light (bottom row), in which betaxanthins are typically fluorescent.

FIG. 17B: LC-MS analysis of pX11, pX12 and pX13 tobacco petals. Extracted ion chromatograms (XIC) of masses [M+H=309.1, 331.1, 340.1, 551.1], respectively corresponding to proline-betaxanthin, tyramine-betaxanthin, glutamine-betaxanthin, and betanin/isobetanin. Vertical axes are linked.

FIG. 18A: Introduction of pX11 or pX13 into cells of tobacco BY2 line results in red-violet or yellow-orange pigmentation, respectively.

FIG. 18B: LC-MS analysis of pX11 and pX13 BY2 cells. Extracted ion chromatograms (XIC) of masses [M+H=283.1, 340.1, 551.1], respectively corresponding to alanine-betaxanthin, glutamine-betaxanthin, and betanin/isobetanin. Vertical axes are linked.

FIG. 20A: Identification of L-DOPA in leaf extracts of pDOPA1 and pDOPA3-expressing tobacco plants by LC-MS analysis. FIG. 20B: pDOPA2 and pDOPA4 expression in BY2 cells causes blackening of calli in varying degrees, after several weeks of cultivation. FIG. 20C: L-DOPA relative quantification in pDOPA2, pDOPA4 and wildtype BY2 cells by LC-MS analysis.

FIG. 21A: Wildtype and pX11 tobacco seedlings grown under high salinity stress conditions (150 mM NaCl) and control conditions (MS) were photographed and scored for seed germination rates. FIG. 21B: Wildtype and pX11 tobacco seedlings grown under osmotic stress conditions (400 mM mannitol) and control conditions (MS) were photographed and scored for seed germination rates.

FIG. 22A: Leaves of wildtype and pX11 tobacco plants were infected with droplets of *B. cinerea* suspension and photographed 5 days post infection. FIG. 22B: Wildtype and pX11 plants infected with a total of approximately 500 *B. cinerea* spores per plant were scored for lesion size. Average lesion areas are shown of approximately 30 plants per genotype. FIG. 22C: Infected leaves of wildtype tobacco plants showed increased signs of necrosis versus leaves of pX11 plants.

FIG. 23A: Co-infiltration of agrobacteria harboring plasmids for expression of CYP76AD15 and BvDODA1 in *Nicotiana benthamiana* leaves causes yellow pigmentation in infiltrated area. FIG. 23B: LC-MS analysis of yellow-pigmented tissue shows occurrence of several betaxanthins, including dopamine-betaxanthin [M+H=347.1] and valine-betaxanthin [M+H=311.1]. XIC, extracted ion chromatogram. FIG. 23C: UV-VIS absorption of peaks representing dopamine-betaxanthin and valine-betaxanthin in analyzed tissue. FIG. 23D: Mass-spectra of L-DOPA peak identified in leaf tissue of *N. benthamiana* expressing CYP76AD15 shows typical L-DOPA fragments [M+H=181.05, 152.07] and molecular ion [M+H=198.07].

DETAILED DESCRIPTION OF THE PRESENT INVENTION

Figure 1:
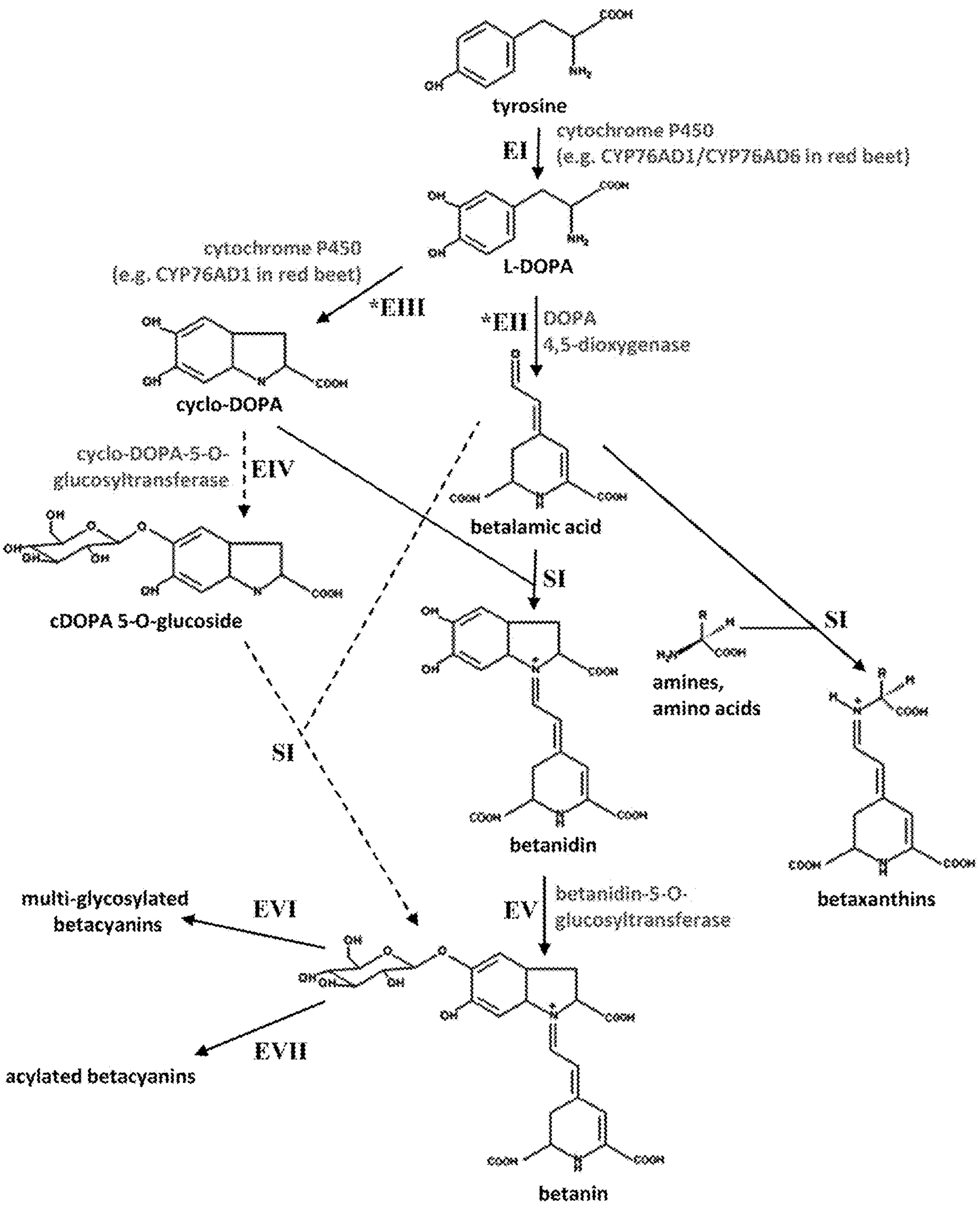
FIG. 1. The betalain biosynthetic pathway. Genes taking part in the pathway are shown in magenta. Enzymatic reactions: EI, hydroxylation of tyrosine; EII, DOPA-4,5 dioxygenase; EIII, oxidation of DOPA; EIV, glucosylation of cyclo-DOPA; EV, glucosylation of betanidin; EVI, additional glucosylation of betacyanins; EVII, acylation of betacyanins. Predicted spontaneous reactions: SI, condensation (aldimine formation). Enzymatic reactions EII and EIII are followed by a spontaneous cyclization reaction and are therefore marked with an asterisk. EV can alternatively be catalyzed by a betanidin-6-O-glucosyltransferase, leading to formation of gomphrenin instead of betanin. Dashed lines designate reactions of an alternative pathway, which was shown to occur in *Mirabilis jalapa*, in which cyclo-DOPA is first glycosylated and then condensates with betalamic acid to form betanin.

In the following detailed description, numerous specific details are set forth in order to provide a thorough understanding of the invention. However, it will be understood by those skilled in the art that the present invention may be practiced without these specific details. In other instances, well-known methods, procedures, and components have not been described in detail so as not to obscure the present invention.

In one embodiment, the present invention provides compositions comprising an enzyme that catalyzes the first step in betalain synthesis in Caryophyllales and uses of the enzyme in genetic engineering of plants and for the production of L-DOPA from tyrosine. In general, tyrosinases are substrate promiscuous oxygenases that exhibit unwanted catechol oxidase activity. A prior study demonstrated that the plant cytochrome P450 CYP76AD1 exhibited this characteristic promiscuity and despite a screening strategy to identify mutations that increased the enzyme's substrate specificity and activity, still produced undesired side products (DeLoache et al., 2015; Nat Chem Biol. 2015 July; 11(7):465-71, incorporated herein by reference in its entirety). It was therefore not expected that a different plant cytochrome P450 would be specific to tyrosine and would catalyze only the reaction to L-DOPA, thereby avoiding the accumulation of undesired end products.

CYP76AD6

The present invention provides a novel gene (belonging to the Cytochrome P450 gene family) which catalyzes tyrosine hydroxylation, to form L-DOPA. This enzyme potentially holds a significant advantage over the tyrosinase enzyme which is being used today for production of L-DOPA; while tyrosinase catalyzes the formation of L-DOPA from tyrosine, and immediately oxidizes it to the unusable metobolite dopaquinone, the novel P450 enzyme only catalyzes the formation of L-DOPA without its oxidation. This P450 enzyme can therefore be used for a more efficient method for L-DOPA production than the use of a tyrosinase enzyme.

Thus, in one embodiment, the present invention provides a novel enzyme which can be used for the biosynthetic production of L-DOPA, a pharmaceutical used for treatment of Parkinson's disease, and a precursor for the economically important drugs benzylisoquinoline alkaloids (e.g. morphine). This enzyme can potentially be used for the commercial production of L-DOPA in several ways; its encoding gene can be expressed in plants or microorganisms to induce production of L-DOPA in vivo, or alternatively it can be recombinantly expressed and used for in vitro enzymatic catalysis.

Methods for L-DOPA and Betalain Production

Production from Proteins

In one embodiment, the methods of the present invention are performed in vitro, such that the tyrosine and enzymes required to produce L-DOPA or betalains are provided in vitro.

In one embodiment, the present invention provides a method of producing L-DOPA from tyrosine comprising the step of combining a CYP76AD1-β clade protein and tyrosine under conditions sufficient to produce L-DOPA, thereby producing L-DOPA.

In one embodiment, the present invention provides a method of producing L-DOPA from tyrosine comprising the step of combining CYP76AD6, CYP76AD15, or a combination thereof, and tyrosine under conditions sufficient to produce L-DOPA, thereby producing L-DOPA.

In another embodiment, the present invention provides a method of producing L-DOPA from tyrosine in vitro comprising the step of combining CYP76AD6, CYP76AD15, or a combination thereof, and tyrosine under conditions sufficient to produce L-DOPA, thereby producing L-DOPA.

In another embodiment, the present invention provides a method of betalain production from tyrosine comprising the step of contacting tyrosine with CYP76AD6, CYP76AD1, or a combination thereof, under conditions sufficient to produce betalains, thereby producing betalains. In one embodiment, the method further comprises the step of contacting the tyrosine and CYP76AD6, CYP76AD15, or a combination thereof, CYP76AD1, or a combination thereof with a DOPA 4,5-dioxygenase (DOD) enzyme.

In another embodiment, the present invention provides a method of betalain production from tyrosine comprising the step of contacting tyrosine with a CYP76AD1-β clade protein and a DOPA 4,5-dioxygenase (DOD) enzyme and, optionally, CYP76AD1, under conditions sufficient to produce betalains, thereby producing betalains.

In another embodiment, the present invention provides a method of betalain production from tyrosine comprising the step of contacting tyrosine with CYP76AD6, CYP76AD15, or a combination thereof, and a DOPA 4,5-dioxygenase (DOD) enzyme and, optionally, CYP76AD1, under conditions sufficient to produce betalains, thereby producing betalains.

In another embodiment, the present invention provides a method of producing a mixture of betalains comprising the step of contacting tyrosine with CYP76AD6, CYP76AD15, or a combination thereof, CYP76AD1, a DOPA 4,5-dioxygenase (DOD) enzyme and a betalain related glucosyltransferase, under conditions sufficient to produce a combination of betacyanin and betaxanthin, thereby producing a mixture of betalains.

In one embodiment, the betalain production described in the present invention is performed without provision of L-DOPA, which had never before been accomplished. In one embodiment, betalains comprise betacyanin and betaxanthin. In one embodiment, betalains, betacyanin, and betaxanthin may be used as food coloring or other dyes.

In one embodiment, betacyanins produce a red-violet color. In one embodiment, betaxanthins produce a yellow color. In one embodiment, a combination of betacyanin and betaxanthin produce an orange color. In one embodiment, a combination of betacyanin and betaxanthin produce an orange-pink color.

In another embodiment, the present invention provides a method of producing an orange dye comprising the step of contacting tyrosine with CYP76AD6, CYP76AD15, or a combination thereof, CYP76AD1, a DOPA 4,5-dioxygenase (DOD) enzyme and a betalain related glucosyltransferase, under conditions sufficient to produce a combination of betacyanin and betaxanthin, thereby producing an orange dye.

In another embodiment, the present invention provides a method of producing betaxanthins from tyrosine comprising the step of contacting tyrosine with CYP76AD6, CYP76AD15, or a combination thereof, and a DOPA 4,5-dioxygenase (DOD) enzyme, under conditions sufficient to produce betaxanthins, thereby producing betaxanthins.

In another embodiment, the present invention provides a method of producing a yellow dye comprising the step of contacting tyrosine with CYP76AD6, CYP76AD15, or a combination thereof and a DOPA 4,5-dioxygenase (DOD) enzyme under conditions sufficient to produce betaxanthins, thereby producing a yellow dye. In one embodiment, said yellow dye is a food coloring.

In one embodiment, the methods of the present invention produce one or more betaxanthins. In one embodiment, the betaxanthin comprises Vulgaxanthin I (glutamine-betaxanthin). In another embodiment, the betaxanthin comprises Indicaxanthin (proline-betaxanthin). In another embodiment, the betaxanthin comprises Dopaxanthin-hexoside. In another embodiment, the betaxanthin comprises Betaxanthin I (unknown), as described in Table 2 herein below. In another embodiment, the betaxanthin comprises histamine-betaxanthin. In another embodiment, the betaxanthin comprises alanine-betaxanthin. In another embodiment, the betaxanthin comprises dopamine-betaxanthin. In another embodiment, the betaxanthin comprises valine-betaxanthin.

In another embodiment, the present invention provides a method of producing betacyanins from tyrosine comprising the step of contacting tyrosine with CYP76AD1, a DOPA 4,5-dioxygenase (DOD) enzyme, and a betalain related glucosyltransferase under conditions sufficient to produce betacyanins, thereby producing betacyanins.

In another embodiment, the present invention provides a method of producing red-violet dye comprising the step of contacting tyrosine with CYP76AD1, a DOPA 4,5-dioxygenase (DOD) enzyme, and a betalain related glucosyltransferase under conditions sufficient to produce betacyanins, thereby producing a red-violet dye. In one embodiment, said red-violet dye is a food coloring.

In one embodiment, the method as described herein provides a glycosylated betalain (betanin) rather than an aglycone (betanidin). In one embodiment, there is a substantial advantage in that betanin is more stable than betanidin. Betanidin is a highly labile compound and ascorbic acid must be added to prevent its degradation. Betanidin is much more susceptible to both enzymatic and non-enzymatic oxidative degradation. The betalain extract used for food coloration comprises betanin. Betanidin would not be usable for food coloration, because of its instability.

In another embodiment, the methods of the present invention produce one or more betacyanins. In one embodiment, the betacyanins comprise betanin. In another embodiment, the betacyanins comprise iso-betanin. In another embodiment, the betacyanins comprise betacyanin I (unknown) or betacyanin II (unknown), as described in Table 2 herein below. In another embodiment, the methods of the present invention produce one or more betacyanin fragments, where, in one embodiment, the betacyanin fragment is betanidin.

In another embodiment, the present invention provides a method of producing a pigment or dye comprising the step of contacting tyrosine with CYP76AD6, CYP76AD15, or a combination thereof, and a DOPA 4,5-dioxygenase (DOD) enzyme and, optionally, CYP76AD1, under conditions sufficient to produce betalains, thereby producing betalains, thereby producing a pigment or dye.

In another embodiment, the present invention provides a method of increasing the levels of one or more betalains in an organism, plant or in a plant part comprising causing or allowing the expression of a DOPA 4,5-dioxygenase (DOD) enzyme, a betalain related glucosyltransferase, and CYP76AD6, CYP76AD15, or a combination thereof, CYP76AD1, or a combination thereof, within said organism, plant or plant part, thereby increasing the levels of one or more betalains in said organism, plant or plant part. In one embodiment, said plant is an ornamental plant. In another embodiment, said plant is a food crop. In one embodiment, the organism or plant does not naturally produce detectable levels of betalains.

Production from Nucleic Acids

In another embodiment, the methods of the present invention are performed in vivo. In one embodiment, the tyrosine is endogenous to the cell. In another embodiment, the tyrosine is provided to the cell. In another embodiment, the cell is transformed with a gene that enhances tyrosine availability. In one embodiment, the gene is AroG175 (Tzin et al., 2012 New Phytologist 194: 430-439; Genbank Accession No. JC233128.1, SEQ ID NO: 28), aromatic amino acid hydroxylase (AAH) (Pribat et al., 2010 Plant Cell 22: 3410-3422; Genbank Accession No. HQ003815.1, SEQ ID NO: 29), or a combination thereof. In one embodiment, the enzymes required to produce betalains are provided to a cell via transfer of a polynucleotide encoding the enzymes.

In one embodiment, the present invention provides a method of L-DOPA production comprising the step of contacting an organism with a nucleic acid encoding a CYP76AD1-β clade gene under conditions sufficient to produce L-DOPA, thereby producing L-DOPA.

In another embodiment, the present invention provides a method of L-DOPA production comprising the step of contacting an organism with a nucleic acid encoding CYP76AD6, CYP76AD15, or a combination thereof, under conditions sufficient to produce L-DOPA, thereby producing L-DOPA.

In another embodiment, the present invention provides a method of L-DOPA production comprising the step of contacting an organism with a nucleic acid encoding CYP76AD6, CYP76AD15, or a combination thereof, under conditions sufficient to produce L-DOPA, thereby producing L-DOPA.

In one embodiment, the organism is a plant. In one embodiment, the plant is a tobacco plant.

In another embodiment, the present invention provides a method of betalain production comprising the step of contacting an organism with a nucleic acid encoding a CYP76AD1-β clade gene, a nucleic acid encoding a CYP76AD1-α clade gene, or a combination thereof, under conditions sufficient to produce betalains, thereby producing betalains.

In another embodiment, the present invention provides a method of betalain production comprising the step of contacting an organism with a nucleic acid encoding CYP76AD6, CYP76AD15, or a combination thereof, a nucleic acid encoding CYP76AD1, or a combination thereof, under conditions sufficient to produce betalains, thereby producing betalains.

In one embodiment, the method further comprises the step of contacting the organism comprising tyrosine with a nucleic acid encoding a DOPA 4,5-dioxygenase (DOD) enzyme.

In one embodiment, the nucleic acid encoding genes disclosed in the present invention, including, inter alia, CYP76AD6, CYP76AD15, or a combination thereof, CYP76AD1, and DOD are present together on a single recombinant polynucleotide, as described in more detail herein below.

In another embodiment, the present invention provides a method of betalain production comprising the step of contacting an organism with a nucleic acid encoding CYP76AD6, CYP76AD15, or a combination thereof, a nucleic acid encoding CYP76AD1, a nucleic acid encoding a DOPA 4,5-dioxygenase (DOD) enzyme, and a nucleic acid encoding a betalain related glucosyltransferase under conditions sufficient to produce betalains, thereby producing betalains.

In another embodiment, the present invention provides a method of producing orange dye comprising the step of contacting an organism comprising tyrosine with a nucleic acid encoding CYP76AD6, CYP76AD15, or a combination thereof, a nucleic acid encoding CYP76AD1, a nucleic acid encoding a DOPA 4,5-dioxygenase (DOD) enzyme, and a nucleic acid encoding a betalain related glucosyltransferase, under conditions sufficient to produce betalains, thereby producing orange dye.

In another embodiment, the betalain production described in the present invention is performed without substrate feeding.

In another embodiment, the present invention provides a method of producing betaxanthins comprising the step of contacting an organism comprising tyrosine with a nucleic acid encoding CYP76AD6, CYP76AD15, or a combination thereof, a nucleic acid encoding a DOPA 4,5-dioxygenase (DOD) enzyme, and a nucleic acid encoding a betalain related glucosyltransferase under conditions sufficient to produce betaxanthins, thereby producing betaxanthins.

In another embodiment, the present invention provides a method of producing yellow dye comprising the step of contacting an organism comprising tyrosine with a nucleic acid encoding CYP76AD6, CYP76AD15, or a combination thereof, a nucleic acid encoding a DOPA 4,5-dioxygenase (DOD) enzyme under conditions sufficient to produce betaxanthins, thereby producing yellow dye.

In another embodiment, the present invention provides a method of producing betacyanins comprising the step of contacting an organism comprising tyrosine with a nucleic acid encoding CYP76AD1, a nucleic acid encoding a DOPA 4,5-dioxygenase (DOD) enzyme, and a nucleic acid encoding a betalain related glucosyltransferase under conditions sufficient to produce betacyanins, thereby producing betacyanins. In one embodiment, the method of producing betacyanins is a method of producing predominantly betacyanins.

In another embodiment, the present invention provides a method of producing red-violet dye comprising the step of contacting an organism comprising tyrosine with a nucleic acid encoding CYP76AD1, a nucleic acid encoding a DOPA 4,5-dioxygenase (DOD) enzyme, and a nucleic acid encoding a betalain related glucosyltransferase under conditions sufficient to produce betacyanins, thereby producing red-violet dye.

In one embodiment, the methods described hereinabove provide methods of producing a natural red-violet dye. In another embodiment, the methods described hereinabove provide methods of producing a natural yellow dye. In another embodiment, the methods described hereinabove provide methods of producing a natural orange dye. In one embodiment, the dyes may be used for textiles.

In one embodiment, the organism is a plant. In another embodiment, the organism is yeast. In another embodiment, the organism is a bacterium. In another embodiment, the organism is an alga.

In one embodiment, the methods of the present invention are conducted in planta. In one embodiment, the color of the pigment in the plant is dependent upon other natural or engineered pigments expressed in the plant. Thus, in one embodiment, the method of the present invention produce a red pigment, a yellow pigment, an orange pigment, a brown pigment, and the like, or any of the pigment colors that are known in the art.

It is also to be understood that by varying the ratio of CYP76AD6, CYP76AD15, or a combination thereof, and/or CYP76AD1 expression, it is possible to change the pigment color as well.

In another embodiment, the present invention provides a method of betalain production from tyrosine comprising the step of contacting tyrosine with a nucleic acid encoding CYP76AD6, CYP76AD15, or a combination thereof, a nucleic acid encoding a DOPA 4,5-dioxygenase (DOD) enzyme, and, optionally, a nucleic acid encoding CYP76AD1, under conditions sufficient to produce betalains, thereby producing betalains.

In another embodiment, the present invention provides a method of producing orange dye comprising the step of contacting tyrosine with a nucleic acid encoding CYP76AD1, a nucleic acid encoding CYP76AD6, CYP76AD15, or a combination thereof, and a nucleic acid encoding a DOPA 4,5-dioxygenase (DOD) enzyme, under conditions sufficient to produce betalains, thereby producing orange dye.

In another embodiment, the present invention provides a method of producing betaxanthins from tyrosine comprising the step of contacting tyrosine with a nucleic acid encoding CYP76AD6, CYP76AD15, or a combination thereof, and a nucleic acid encoding a DOPA 4,5-dioxygenase (DOD) enzyme, under conditions sufficient to produce betaxanthins, thereby producing betaxanthins.

In another embodiment, the present invention provides a method of producing yellow dye comprising the step of contacting tyrosine with a nucleic acid encoding CYP76AD6, CYP76AD15, or a combination thereof, and a nucleic acid encoding a DOPA 4,5-dioxygenase (DOD) enzyme under conditions sufficient to produce betaxanthins, thereby producing yellow dye.

In another embodiment, the present invention provides a method of producing betacyanins from tyrosine comprising the step of contacting tyrosine with a nucleic acid encoding CYP76AD1 and a nucleic acid encoding a DOPA 4,5-dioxygenase (DOD) enzyme, under conditions sufficient to produce betacyanins, thereby producing betacyanins.

In another embodiment, the present invention provides a method of producing red-violet dye comprising the step of contacting tyrosine with a nucleic acid encoding CYP76AD1, a nucleic acid encoding a DOPA 4,5-dioxygenase (DOD) enzyme, and a nucleic acid encoding a betalain related glucosyltransferase, under conditions sufficient to produce betacyanins, thereby producing red-violet dye.

In one embodiment, a dye of the present invention is food coloring. In one embodiment, methods of the present invention for producing dyes may be applied to producing pigments, and the like.

In one embodiment, the present invention provides a food coloring, dye, or pigment produced by the methods of the present invention or comprising the compositions of the present invention.

In another embodiment, the present invention provides a method of producing L-DOPA in a cell comprising the step of contacting said cell with a polynucleotide comprising a nucleic acid encoding CYP76AD6, CYP76AD15, or a combination thereof, under conditions sufficient to produce L-DOPA, thereby producing L-DOPA.

In another embodiment, the present invention provides a method of producing betalains, orange dye, or a combination thereof in a cell comprising the step of contacting said cell with a nucleic acid encoding CYP76AD6, CYP76AD15, or a combination thereof, a nucleic acid encoding CYP76AD1, or a combination thereof, under conditions sufficient to produce betalains, thereby producing betalains, orange dye, or a combination thereof.

In another embodiment, the present invention provides a method of producing betaxanthins, yellow dye, or a combination thereof in a cell comprising the step of contacting said cell with a nucleic acid encoding CYP76AD6, CYP76AD15, or a combination thereof, and a nucleic acid encoding a DOPA 4,5-dioxygenase (DOD) enzyme, under conditions sufficient to produce betaxanthins, thereby producing betaxanthins, yellow dye, or a combination thereof.

In another embodiment, the present invention provides a method of producing betacyanins, red-violet dye, or a combination thereof in a cell comprising the step of contacting said cell with a nucleic acid encoding CYP76AD1, a nucleic acid encoding a DOPA 4,5-dioxygenase (DOD) enzyme, and a nucleic acid encoding a betalain related glucosyltransferase, under conditions sufficient to produce betacyanins, thereby producing betacyanins, red-violet dye, or a combination thereof.

In one embodiment, the cell described hereinabove is part of a cell line.

In one embodiment, betalains obtained by the methods of the present invention, including betaxanthins, betacyanins, or a combination thereof, are produced in a cell line. In one embodiment, the cell line is a plant cell line. In one embodiment, the plant cell line is tobacco BY2 or *Arabidopsis* T87.

In another embodiment, L-DOPA obtained by the methods of the present invention is produced in a cell line. In one embodiment, the cell line is a tobacco cell line. In one embodiment, the tobacco cell line is BY2.

In another embodiment, the present invention provides a method of producing a metabolite of L-DOPA comprising the step of producing L-DOPA by contacting a cell with a nucleic acid encoding CYP76AD6, CYP76AD15, or a combination thereof, under conditions sufficient to produce L-DOPA, and either allowing formation of the L-DOPA metabolite or further contacting said cell with a nucleic acid encoding an enzyme that metabolizes L-DOPA, thereby producing a metabolite of L-DOPA. In one embodiment, the L-DOPA metabolite is a catecholeamine, benzilisoquinoline alkaloid, betalain, melanin, or a combination thereof. In one embodiment, the catecholeamine is dopamine, norepinephrine, or a combination thereof. In one embodiment, the benzilisoquinoline alkaloid is an opiate, which in one embodiment is morphine.

In one embodiment, the enzyme that metabolizes L-DOPA is a DOPA 4,5-dioxygenase (DOD). In another embodiment, the enzyme is CYP76AD1. In another embodiment, the enzyme is a glucosyltransferase. In one embodiment, the glucosyltransferase is cyclo-DOPA 5-O-glucosyltransferase or betanidin-5-O-glucosyltransferase. In one embodiment, the cyclo-DOPA 5-O-glucosyltransferase is *M. jalapa* gene cyclo-DOPA 5-O-glucosyltransferase (cDOPA5GT).

In another embodiment, the enzyme that metabolizes L-DOPA is DOPA decarboxylase. In another embodiment, the enzyme that metabolizes L-DOPA is dopamine beta-hydroxylase. In another embodiment, the enzyme that metabolizes L-DOPA is aromatic L-amino acid decarboxylase. In another embodiment, the enzyme that metabolizes L-DOPA is catechol-O-methyl transferase. In another embodiment, the enzyme that metabolizes L-DOPA is phenylethanolamine N-methyltransferase.

In another embodiment, the enzyme that metabolizes L-DOPA is norcoclaurine synthetase (NCS). In another embodiment, the enzyme that metabolizes L-DOPA is norcoclaurine 6-O-methyltransferase (6OMT). In another embodiment, the enzyme that metabolizes L-DOPA is coclaurine-N-methyltransferase (CNMT). In another embodiment, the enzyme that metabolizes L-DOPA is 3'-hydroxy-N-methylcoclaurine 4'-O-methyltransferase (4'OMT).

Methods of Genetic Transformation

In one embodiment, the present invention provides methods comprising the step of "contacting" a cell with a polynucleotide or expression vector as described herein.

In one embodiment, contacting comprises transforming a cell with the nucleic acid molecule or construct of the invention. Methods for transforming a plant cell with nucleic acids sequences are well known in the art. As used herein the term "transformation" or "transforming" may refer to a process by which a foreign DNA, such as a DNA construct, including expression vector, enters and changes a recipient cell into a transformed, genetically modified or transgenic cell. Transformation may be stable, wherein the nucleic acid sequence is integrated into the plant genome and as such represents a stable and inherited trait, or transient, wherein the nucleic acid sequence is expressed by the cell transformed but is not integrated into the genome, and as such represents a transient trait.

In one embodiment, the present invention provides a transgenic plant. In one embodiment, a transgenic plant of the present invention is genetically modified with foreign or heterologous genes. In one embodiment, transgenic plants of the present invention are used for biofuel. In another embodiment, transgenic plants of the present invention are food crop plants.

In another embodiment, the present invention provides a cisgenic plant. In one embodiment, a cisgenic plant of the present invention is genetically modified, but contains no foreign or heterologous genes. According to this aspect and in one embodiment, betalain enzymes may be overexpressed in plants already comprising betalain enzymes, thereby changing the ratio between betacyanins and betaxanthins. In one embodiment, food crops of the present invention are cisgenic.

Any method or delivery system may be used for the delivery and/or transformation (plant cells)/transfection (algae cells) of the nucleic acid vectors encoding CYP76AD6 and homologs, paralogs, etc. in the host cell, e.g., plant protoplast. The vectors may be delivered to the host cell either alone, or in combination with other agents. Transient expression systems may also be used. Homologous recombination may also be used.

In one embodiment, polynucleotides as described herein are provided to a cell of the present invention via transformation. Transformation may be accomplished by a wide variety of means, as is known to those of ordinary skill in the art. Such methods include, but are not limited to, particle bombardment mediated transformation (e.g., Finer et al., 1999, Curr. Top. Microbiol. Immunol., 240:59), protoplast electroporation (e.g., Bates, 1999, Methods Mol. Biol., 111:359), viral infection (e.g., Porta and Lomonossoff, 1996, Mol. Biotechnol. 5:209), microinjection, and liposome injection. Other exemplary delivery systems that can be used to facilitate uptake by a cell of the nucleic acid include calcium phosphate and other chemical mediators of intracellular transport, microinjection compositions, and homologous recombination compositions (e.g., for integrating a gene into a preselected location within the chromosome of the cell). Alternative methods may involve, for example, the use of liposomes, electroporation, or chemicals that increase free (or "naked") DNA uptake, transformation using viruses or pollen and the use of microprojection. Standard molecular biology techniques are common in the art (e.g., Sambrook et al., 1989, Molecular Cloning: A Laboratory Manual, 2nd ed., Cold Spring Harbor Laboratory Press, New York).

Plant Transformation

There are various methods of introducing foreign genes into both monocotyledonous and dicotyledonous plants (See Potrykus I 1991. *Annu Rev Plant Physiol Plant Mol Biol* 42, 205-225; Shimamoto K. et al., 1989. *Nature* 338, 274-276). Transformation methods may include, for example, but are not limited to, the use of liposomes, electroporation, chemicals that increase free DNA uptake, injection of the DNA directly into the plant, particle gun bombardment, transformation using viruses and microprojection.

In one embodiment, polynucleotides as described herein are provided to a cell via agroinfiltration, in one embodiment, via *Agrobacterium*-mediated transformation (e.g., Komari et al., 1998, Curr. Opin. Plant Biol., 1:161), including floral dip transformation. In one embodiment agroinfiltration induces transient expression of genes in a plant to produce a desired protein, by injected a suspension of *Agrobacterium tumefaciens* containing the desired gene or genes into a plant leaf. In one embodiment, the transformation can be performed by an *Agrobacterium*-mediated gene transfer. The *Agrobacterium*-mediated system includes the use of plasmid vectors that contain defined DNA segments which integrate into the plant genomic DNA. Methods of inoculation of the plant tissue vary depending upon the plant species and the *Agrobacterium* delivery system. The transformation can be performed with any suitable tissue explant that provides a good source for initiation of whole-plant differentiation (See Horsch et al., 1988. Plant Molecular Biology Manual A5, 1-9, Kluwer Academic Publishers, Dordrecht).

Plant transformation methods are fully described in U.S. Patent Application Publications US 20110209247; US 20110113514; US 20100199371; US 20070079396; US 20080307541; US 20030028913; and US20030196219; and U.S. Pat. Nos. 5,015,580; 5,550,318; 5,538,880; 6,160,208; 6,399,861; 6,403,865; 5,635,055; 5,824,877; 5,591,616; 5,981,840 and 6,384,301, which are incorporated by reference herein in their entirety.

For the *Agrobacterium tumefaciens*-based plant transformation system, additional elements present on transformation constructs will, in one embodiment, include T-DNA left and right border sequences to facilitate incorporation of the recombinant polynucleotide into the plant genome.

In one embodiment, the transformation can be performed by a direct DNA uptake. There are various methods of direct DNA transfer into plant cells. In electroporation, the protoplasts are briefly exposed to a strong electric field, opening up mini-pores to allow DNA to enter. In microinjection, the DNA is mechanically injected directly into the cells using micropipettes. In microparticle bombardment, the DNA is adsorbed on microprojectiles such as magnesium sulfate crystals or tungsten particles, and the microprojectiles are physically accelerated into cells or plant tissues.

In another embodiment, polynucleotides as described herein are provided to a cell via viral transformation (transduction) using a suitable plant virus, using gene gun techniques or electroporation.

In one embodiment, the heterologous genes of the polynucleotide of the present invention are integrated into the plant chromosome. In another embodiment, the heterologous genes of the polynucleotide of the present invention remain extrachromosomal. In one embodiment, the heterologous genes are in a plasmid within the cell. Plasmids useful for either application are known to one skilled in the art.

In one embodiment, DNA is inserted randomly, i.e. at a non-specific location, in the genome of a target plant line. In another embodiment, DNA insertion is targeted in order to achieve site-specific integration, e.g. to replace an existing gene in the genome, to use an existing promoter in the plant genome, or to insert a recombinant polynucleotide at a predetermined site known to be active for gene expression. Several site specific recombination systems exist which are known to function in plants including cre-lox and FLP-FRT.

In one embodiment, transformation methods of this invention are practiced in tissue culture on media and in a controlled environment. "Media" refers to the numerous nutrient mixtures that are used to grow cells in vitro, that is, outside of the intact living organism. Recipient cell targets include, but are not limited to, meristem cells, callus, immature embryos and gametic cells such as microspores, pollen, sperm and egg cells. It is contemplated that any cell from which a fertile plant may be regenerated is useful as a recipient cell. Callus may be initiated from tissue sources including, but not limited to, immature embryos, seedling apical meristems, microspores and the like. Cells capable of proliferating as callus are also recipient cells for genetic transformation. Practical transformation methods and materials for making genetically modified plants of this invention, e.g. various media and recipient target cells, transformation of immature embryos and subsequent regeneration of fertile genetically modified plants are known in the art.

In another embodiment in which polynucleotides are introduced into plant cells, the betalains may be expressed or detected in any plant organ, including leaves, stems, roots, flowers, seeds, tuber, or fruit, or a combination thereof.

In another embodiment, the methods of the present invention may be performed in a whole plant, such that the whole plant expresses the betalains as described herein. In addition and in one embodiment, the compositions of the present invention may describe a whole plant that has been genetically modified to express a polynucleotide or polypeptide of the present invention.

Algae Transformation

In one embodiment, the method of transformation of algae comprises any of the methods as described hereinabove. In one embodiment, transformation of algae is accomplished using glass bead-assisted transformation, particle gun-mediated (biolistic) transformation, treatment with cellulolytic enzymes to weaken their cell walls, or homologous recombination.

In another aspect, the nucleic acids of the present invention can be transformed into algae. In one embodiment, the alga is a single cell alga. In another embodiment, the alga is a multi-cellular alga. In one embodiment, the alga is a cyanobacterium, diatom, *chlamydomonas, Dunaliella*, or hematococus. The genes can be over expressed in algae. Betalain, DOPA, or a combination thereof can be produced through such transgenic algae. Method for algae transformation are well known in the art and fully described in U.S. Patent Application Publications US 20150011008; US 20150004704; US 20130130389; US 20120094385; US 20120034698; US 20110300633; and US 20040133937, which are incorporated by reference herein in their entirety.

In one embodiment, the genetically modified algae of the present invention may be used in biofuel production.

Yeast Transformation

In another aspect, the nucleic acids of the present invention can be transformed into yeast. The genes can be over expressed in yeast. Betalain, DOPA, or a combination thereof can be produced through such transgenic yeast. Method for yeast transformation are described herein below and are well known in the art and fully described in U.S. Patent Application Publications US 20090264320; US 20010031724; US 20030049785; US 20050158861; US 20070264716; US 20090325247; and US 20100190223, which are incorporated by reference herein in their entirety.

Viral Transformation

In another embodiment, the nucleic acids of the present invention can be transformed into a virus. In another embodiment, the nucleic acids may be over-expressed in a virus. Betalain, dyes, pigments, DOPA, or a combination thereof can be produced through such viral over expression.

Markers of Genetic Transformation

In one embodiment, DNA is introduced into only a small percentage of target cells in any one experiment.

In one embodiment, cells comprising the transferred exogenous DNA may be identified by color, as described in Example 6 for yeast. In one embodiment, cells expressing CYP76AD1 and DODA are red-violet. In one embodiment, cells expressing CYP76AD6, CYP76AD15, or a combination thereof, and DODA are yellow. In one embodiment, cells expressing CYP76AD1, CYP76AD6, CYP76AD15, or a combination thereof, and DODA are orange or orange-red.

In another embodiment, marker genes are used to provide an efficient system for identification of those cells that are stably transformed by receiving and integrating a genetically modified DNA construct into their genomes.

In another embodiment, selection genes provide selective markers that confer resistance to a selective agent, such as an antibiotic or herbicide. Potentially transformed cells are exposed to the selective agent. In the population of surviving cells will be those cells where, generally, the resistance-conferring gene has been integrated and expressed at sufficient levels to permit cell survival. Cells may be tested further to confirm stable integration of the exogenous DNA.

Useful selective marker genes include those conferring resistance to antibiotics such as kanamycin (nptII), hygromycin B (aph IV), nptII, hpt, aad4 and gentamycin (aac3 and aacC4) or resistance to herbicides such as glufosinate (bar or pat) and glyphosate (EPSPS). In another embodiment, the selection gene is an antimetabolite. In one embodiment, the antimetabolite is dhf.

Screenable markers which provide an ability to visually identify transformants can also be employed, e.g., a gene expressing a colored or fluorescent protein such as a cat, h Z, uidA, luciferase or green fluorescent protein (GFP) or a gene expressing a beta-glucuronidase or uidA gene (GUS) for which various chromogenic substrates are known. It is also contemplated that combinations of screenable and selectable markers will be useful for identification of transformed cells.

In one embodiment, the selection gene is a positive selectable marker gene that is conditional on non-toxic agents that may be substrates for growth or that induce growth and differentiation of the transformed tissues.

In one embodiment, cells that survive exposure to the selective agent, or cells that have been scored positive in a screening assay, may be cultured in regeneration media and allowed to mature into plants. Developing plantlets can be transferred to soil less plant growth mix, and hardened off, e.g., in an environmentally controlled chamber at about 85% relative humidity, 600 ppm $CO_2$, and 25-250 microeinsteins $m^{-2}$ $s^{-1}$ of light, prior to transfer to a greenhouse or growth chamber for maturation. Plants are preferably matured either in a growth chamber or greenhouse. Plants are regenerated from about 6 weeks to 10 months after a transformant is identified, depending on the initial tissue. During regeneration, cells are grown to plants on solid media at about 19 to 28° C. After regenerating plants have reached the stage of shoot and root development, they may be transferred to a greenhouse for further growth and testing. Plants may be pollinated using conventional plant breeding methods known to those of skill in the art and seed produced.

Progeny may be recovered from transformed plants and tested for expression of the exogenous recombinant polynucleotide. Useful assays include, for example, "molecular biological" assays, such as Southern and Northern blotting and PCR; "biochemical" assays, such as detecting the presence of RNA, e.g. double stranded RNA, or a protein product, e.g., by immunological means (ELISAs and Western blots) or by enzymatic function; plant part assays, such as leaf or root assays; and also, by analyzing the phenotype of the whole regenerated plant.

One of skill in the art will be able to select an appropriate vector for introducing the encoding nucleic acid sequence in a relatively intact state. Thus, any vector which will produce a host cell, e.g., plant protoplast, carrying the introduced encoding nucleic acid should be sufficient. The selection of the vector, or whether to use a vector, is typically guided by the method of transformation selected.

Promoters

In another aspect, cell, tissue, or organ specific promoters can be used to transform the genes of the invention and make them express in a specific cell, tissue, or organ. For example, fruit specific promoter can be used to transform the genes of the invention into a plant (e.g., tomato) or plant cell in order to produce betalains in fruits (e.g., tomato fruits).

In one embodiment, a recombinant polynucleotide of the present invention comprises at least one promoter. In one embodiment, a recombinant polynucleotide of the present invention comprises a single promoter controlling the expression of the tandem nucleic acids that are in the same reading frame. In another embodiment, each nucleic acid in the recombinant polynucleotide of the present invention is under the control of a separate promoter.

In one embodiment, the promoter is a constitutive promoter. In one embodiment, the constitutive promoter is the CaMV 35S promoter. In another embodiment, the constitutive promoter is an opine promoter. In another embodiment, the constitutive promoter is a monocot promoter. In another embodiment, the constitutive promoter is a Plant ubiquitin promoter (Ubi). In another embodiment, the constitutive promoter is the *Arabidopsis* ubiquitin-10 promoter. In another embodiment, the constitutive promoter is the *Solanum lycopersicum* ubiquitin 10 promoter (SlUb10). In another embodiment, the constitutive promoter is Rice actin 1 promoter (Act-1). In another embodiment, the constitutive promoter is Maize alcohol dehydrogenase 1 promoter (Adh-1).

In another embodiment, the promoter is an inducible promoter. In one embodiment, the inducible promoter is a galactose-inducible promoter. In another embodiment, the inducible promoter is selected from AlcR/AlcA (ethanol inducible); GR fusions, GVG, and pOp/LhGR (dexamethasone inducible); XVE/OlexA (beta-estradiol inducible); and heat shock induction. In another embodiment, the inducible promoter is selected from tetracycline, dexamethasone, copper, salicyclic acid and herbicide inducible promoters. In another embodiment, mGal4:VP16/UAS or pOp/LhG4 may be used for transactivation, and the alc-switch, GVE/VGE, and XVE systems may be used for chemical induction. These methods are known in the art.

In another embodiment, the promoter is a tissue-specific or a development-stage-specific promoter. In another embodiment, the promoter is a synthetic promoter, which is produced by bringing together the primary elements of a promoter region from diverse origins.

In some embodiments, a fruit specific promoter can be used to transform the genes of the invention in combination with one or more other genes (e.g. anthocyanin genes) into a plant (e.g., tomato) or plant cell in order to produce betalains in fruits (e.g., tomato fruits). In one embodiment, the genes of the invention can be transformed into a transgenic plant (e.g., transgenic tomato plant already transformed with recombinant anthocyanin genes) or plant cell in order to produce betalains in fruits (e.g., tomato fruits).

Thus, in one embodiment, a promoter for any of the polynucleotides described herein, may be a fruit-specific promoter. In one embodiment, the fruit-specific promoter is the E8 promoter. In another embodiment, the promoter may be a flower-specific promoter. In one embodiment, the flower-specific promoter is a chalcone synthase (CHS) promoter. In one embodiment, the CHS promoter is a *Petunia* x *hybrida* CHS promoter. In another embodiment, the promoter may be a root-specific promoter. In another embodiment, the promoter may be a stem-specific promoter. In another embodiment, the promoter may be a leaf-specific promoter. In another embodiment, the promoter may be a seed-specific promoter. In another embodiment, the promoter may be a tuber-specific promoter.

In one embodiment, the promoter may be specific to a part of the tissue. For example and in one embodiment, a promoter may be specific to the petal, stamen, anther, stigma, or a combination thereof.

In another embodiment, the same nucleic acid may be expressed under different non-constitutive promoter sequences to engineer an organism that exhibits two colors of pigmentation and/or expresses both betacyanins and betaxanthins in different organs or in different parts of the same organ. For example, in one embodiment, CYP76AD6 or CYP76AD15 or a homolog thereof may be expressed under a flower-specific promoter and CYP76AD1 may be expressed under a fruit-specific promoter so that the fruit is red-purple due to the presence of both betacyanins and betaxanthins, and the flower is yellow due to the presence of betaxanthins only. In addition, inducible promoters may be used to engineer an organism that exhibits two colors of pigmentation and/or expresses both betacyanins and betaxanthins in different organs or in different parts of the same organ.

In another embodiment, the promoter may be specific to a developmental stage. For example and in one embodiment, a promoter may be specific to Stage 1, which, in one embodiment, is when the flower length is approximately 1 cm. In another embodiment, the developmental stage is Stage 2, which, in one embodiment, is when the flower length is approximately 2 cm. In another embodiment, the developmental stage is Stage 3, which, in one embodiment, is when the flower length is approximately 3 cm. In another embodiment, the developmental stage is Stage 4, which, in one embodiment, is when the flower length is approximately 4 cm. In another embodiment, the developmental stage is Stage 5, which, in one embodiment, is when the flower length is approximately 5-6 cm.

In one embodiment, the promoter may be specific to a tissue and a developmental stage. In one embodiment, the fruit specific E8 promoter is expressed in ripening and ripe fruit. In another embodiment, the flower-specific CHS promoter is expressed in petals during flower maturation.

Gene Silencing Applications

In one embodiment, the present invention provides a method of treating or suppressing a dopamine-responsive disorder in a subject comprising the step of administering a food crop, cell, or cell line comprising high levels of a CYP76AD1-β clade polypeptide, thereby providing said subject with L-DOPA, thereby treating or inhibiting said dopamine-responsive disorder in said subject. In one embodiment, said food crop, cell, or cell line endogenously produces betalains. In one embodiment, the expression of DOPA 4,5-dioxygenase, cyclo-DOPA 5-O-glucosyltransferase, and a CYP76AD1-alpha clade gene in said food crop, cell, or cell line has been suppressed.

In one embodiment, the present invention provides a method of producing yellow plant parts in a plant comprising betalains, comprising silencing CYP76AD1 gene expression.

In one embodiment, the present invention provides a method of producing green plant parts in a plant comprising betalains, comprising silencing CYP76AD1 and CYP76AD6, CYP76AD15, or a combination thereof, gene expression.

In one embodiment, the plant parts comprise leaves, stems, roots, flowers, tuber, fruit, seeds, or a combination thereof.

In one embodiment, gene silencing is gene knockdown, which in one embodiment, is a reduced expression of the gene. In one embodiment, virus induced gene silencing is used to silence the genes encoding CYP76AD1 and/or CYP76AD6. In one embodiment, virus-induced gene silencing (VIGS) is a technology that exploits an RNA-mediated antiviral defense mechanism. In plants infected with unmodified viruses the mechanism is specifically targeted against the viral genome. However, with virus vectors carrying inserts derived from host genes the process can be additionally targeted against the corresponding mRNAs. Such methods are exemplified herein below in Examples 1 and 3.

Other methods of gene silencing that may be used in the present invention include gene silencing with antisense oligonucleotides, ribozymes, RNA interference, three prime untranslated regions/microRNAs. Such methods are well known in the art as well as being described in Example 1 herein below.

In another embodiment, the genes encoding CYP76AD1 and/or CYP76AD6, CYP76AD15, or a combination thereof, are knocked out using methods known in the art.

In one embodiment, the plant comprises betalains, which in one embodiment, is a betacyanin, and in another embodiment, is a betaxanthin.

In one embodiment, methods of gene silencing are performed in plants comprising betalains. In one embodiment, plants comprising betalains are from the Caryophyllales plant order.

In one embodiment, methods of gene silencing are performed in Caryophyllales which comprises cacti, carnations, amaranths, ice plants, beets, and many carnivorous plants. In another embodiment, the plant is from the Caryophyllineae suborder. In another embodiment, the plant is from the Polygonineae suborder. In another embodiment, the plant is from a family selected from one of the following families of the Caryophyllales plant order: Achatocarpaceae; Aizoaceae; Amaranthaceae; Anacampserotaceae; Ancistrocladaceae; Asteropeiaceae; Barbeuiaceae; Basellaceae; Cactaceae; Caryophyllaceae; Didiereaceae; Dioncophyllaceae; Droseraceae; Drosophyllaceae; Frankeniaceae; Gisekiaceae; Halophytaceae; Kewaceae; Limeaceae; Lophiocarpaceae; Macarthuriaceae; Microteaceae; Molluginaceae; Montiaceae; Nepenthaceae; Nyctaginaceae; Physenaceae; Phytolaccaceae; Plumbaginaceae; Polygonaceae; Portulacaceae; Rhabdodendraceae; Sarcobataceae; Simmondsiaceae; Stegnospermataceae; Talinaceae; and Tamaricaceae.

In some embodiments, polynucleotides of the present invention are prepared using PCR techniques using procedures and methods known to one skilled in the art. In some embodiments, the procedure involves the legation of two different DNA sequences (See, for example, "Current Protocols in Molecular Biology", eds. Ausubel et al., John Wiley & Sons, 1992).

Polynucleotides

In one embodiment, the present invention provides a recombinant polynucleotide comprising a nucleic acid encoding CYP76AD6. In one embodiment, the nucleic acid sequence encoding CYP76AD6 comprises:

(SEQ ID NO: 30)

```
tcgatgtgttttcaagaagagcttgagcctacattctacaacaatatatt
gttcctctcttgcgcaattaagcccttaaacctgcaattatcttagaatt
tttgggtttctaatttattactcctttaattagctagatatagattattc
atatttttccagcattttcaaacaatggataacgcaacacttgctgtgat
cattccattttgtttgtgttttaccacattttcaaatcctattcaccaat
tatcatacgtaggatcctcctggtcccaaacccgtgccaattttggcaa
cattttcgatcttggcgaaaagcctcatcgatctgccaatctatctaaaa
ttcacggccattgattagcctaaagttaggaagtgtaacaactattgttg
tttcctcggcctagtggccgaggaaatgttccttaaaaatgaccaagcac
ttgctaaccgaaccattcctgactcggttagggctggtgaccacgacaaa
ttatccatgtcgtggttgcctgtttcccaaaaatggagaaatatgagaaa
aataccgctgtccaattactaccaaccaaaaacttgatgctagtcaacct
cttagacaagctaaggtgaaacaacttttatcatacgtacaagtttgttc
cgaaaaaatgcaacccgtcgatattggacgggccgcatttacaacgtcac
ttaatttattatcaaacacatttttctcaatcgaattagcaagtcatgaa
tctagtgatcccaagagtttaaacaactcatgtggaatattatggaggaa
attggaaggcctaattatgctgatttttccctattcttggttacattga
tccattggtataagacgtcgtttggctggttactttgataaactcattga
tgattccaagacattattcgtgaaagacaaaagatcgatcttctaattct
tccggcgcaaaacaaacaaatgacattcttgatactatcttaaactccat
gaagataatgagttgagtatgcctgaaattaatcaccttctcgtggatat
ctttgacgccggaacagacacaacagcaagcacattagaatgggcgatgg
ccgaacttgtgaaaaacccggaaatgatgactaaagttcaaattgaaatc
gaacaagctcttggaaaagattgcttagacatacaagaatccgacatctc
aaaactaccttatttacaagccattataaaagaaacgttacgtttacacc
ctcctactgtgtttttgctgcctcgaaaggcagacaatgacgtagagtta
tatggctacgttgtaccaaagaatgctcaagtccttgtcaatctttgggc
```

-continued

```
aattggtcgtgatccaaaggtatggaaaaatccggaagtattttacctga
aaggtttttagattgcaatatcgattataaaggacgagatttcgaacttt
taccattggtgctggtagaaggatatgccaggacttactttggcatatag
aatgttgaacttgatgttggctactatcttcaaaactacaattggaaact
tgaagatggtatcaatcctaaggatttagacatggatgagaaatttggga
ttacattgcaaaaggttaaacctcttcaagttattccagttcccagaaac
tagctagtgggttgtgccgttgtgggctgtgggctgattgtgcactgttt
cctctaattgttgttgcaaacttctctagaagggtattatcttttgtata
aataaagcgaaagctacatgtcctattattaaattagtgtatactatatt
aagtaagtatgagcatatagtatccattattgatttggttgaatcgtatt
aaactgataaatcaagtaaatgtctccaacctaagcattcaattattctg
ttagtcataacatatgtagagggtaagtatgaagaattaataacggcgtg
atcatcctta.
```

In another embodiment, the coding sequence of CYP76AD6 comprises the following sequence:

```
                                       (SEQ ID NO: 31)
atggataacgcaacacttgctgtgatcattccattttgtttgtgttttac
cacattttcaaatcctttttcaccaattcttcatctcgtaggcttcctcc
tggtcccaaacccgtgccaatttttggcaacattttcgatatggcgaaaa
gcctcatcgatatttgccaatctatctaaaattcacggccctttgattag
cctaaagttaggaagtgtaacaactattgttgtttcctcggcctagtggc
cgaggaaatgttccttaaaaatgaccaagcacttgctaaccgaaccattc
ctgactcggttagggctggtgaccacgacaaattatccatgtcgtggttg
cctgtttcccaaaaatggagaaatatgagaaaaatctccgctgtccaatt
actaccaaccaaaaacttgatgctagtcaacctatagacaagctaaggtg
aaacaacttttatcatacgtacaagtttgttccgaaaaaatgcaacccgt
cgatattggacgggccgcatttacaacgtcacttaatttattatcaaaca
catttttctcaatcgaattagcaagtcatgaatctagtgatcccaagagt
ttaaacaactcatgtggaatattatggaggaaattggaaggcctaattat
gctgatttttccctattatggttacattgatccattggtataagacgtc
gtttggctggttactttgataaactcattgatgttttccaagacattatt
cgtgaaagacaaaagatcgatcttctaattcttccggcgcaaaacaaaca
aatgacattcttgatactcttcttaaactccatgaagataatgagttgag
tatgcctgaaattaatcaccttctcgtggatatctttgacgccggaacag
acacaacagcaagcacattagaatgggcaatggccgaacttgtgaaaaac
ccggaaatgatgactaaagttcaaattgaaatcgaacaagctatggaaaa
gattgatagacatacaagaatccgacatacaaaactaccttatttacaag
ccattataaaagaaacgttacgtttacaccctcctactgtgtttttgctg
cctcgaaaggcagacaatgacgtagagttatatggctacgttgtaccaaa
gaatgctcaagtccttgtcaatattgggcaattggtcgtgatccaaaggt
atggaaaaatccggaagtattttacctgaaaggtttttagattgcaatat
```

-continued

```
cgattataaaggacgagatttcgaacttttaccattggtgctggtagaag
gatatgccaggacttactttggcatatagaatgttgaacttgatgttggc
tactatcttcaaaactacaattggaaacttgaagatggtatcaatcctaa
ggatttagacatggatgagaaatttgggattacattgcaaaaggttaaac
ctatcaagttattccagttcccagaaactag.
```

Figure 19:
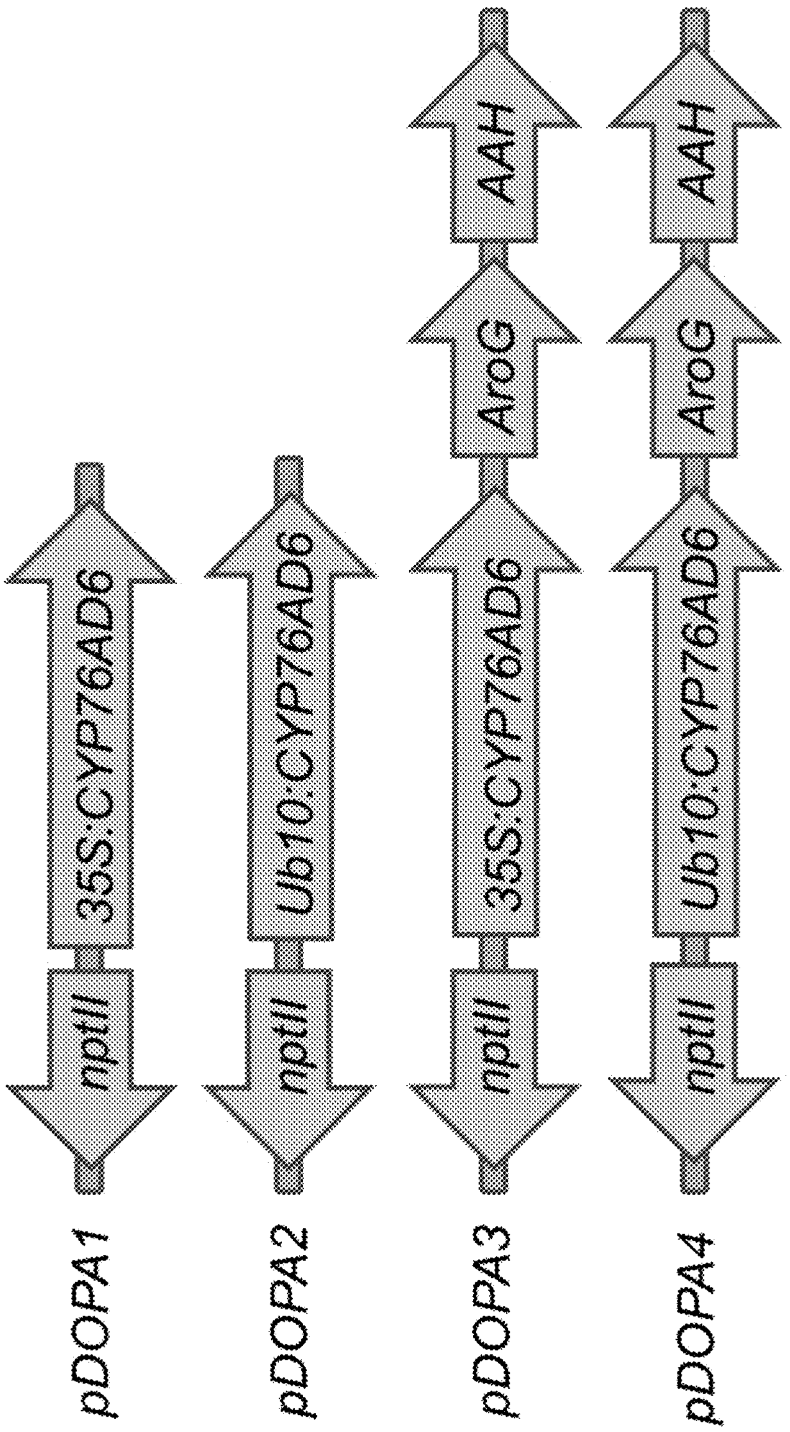
FIG. 19. Schematic of the pDOPA1-pDOPA4 (SEQ ID NOs: 24-27) overexpression vectors. nptII, kanamycin resistance-conferring gene neomycin phosphotransferase II; CYP76AD6, *B. vulgaris* cytochrome P450; AroG, *E. coli* AroG175 (DAHPS) mutant; AAH, *Physcomitrella patens* aromatic amino acid hydroxylase; 35S, CaMV 35S promoter/terminator; Ub10, *Solanum lycopersicum* ubiquitin 10 promoter.

In one embodiment, the nucleic acid encoding CYP76AD6 is driven by the CaMV 35S promoter (pDOPA1; FIG. 19). In another embodiment, the nucleic acid encoding CYP76AD6 is driven by the *Solanum lycopersicum* ubiquitin 10 promoter (SlUb10) (pDOPA2; FIG. 19).

In one embodiment, the nucleic acid encoding CYP76AD6, CYP76AD15, or a combination thereof, is expressed together with AroG175 and aromatic amino acid hydroxylase (AAH).

In one embodiment, the polynucleotide comprising the nucleic acid encoding CYP76AD6, CYP76AD15, or a combination thereof, also comprises the neomycin phosphotransferase II (nptII) gene, which in one embodiment, confers kanamycin resistance.

In another embodiment, the present invention provides a recombinant polynucleotide comprising a nucleic acid encoding a CYP76AD1-α clade gene. In one embodiment, the CYP76AD1-α clade gene comprises CYP76AD1. In one embodiment, the nucleic acid sequence encoding CYP76AD1 comprises:

```
                                       (SEQ ID NO: 32)
tactaatgtgcaaatgcataaatttaatttcagatactcttattataaat
attattatactgtgcattatttaacccaaaaaaaaaactgtcttaataca
ccatttaattcctttctctaggatccactatcacatgtagtatataaata
taatcctatacagttcacgttatcaaacaccaaagcatcaaaagccttcc
acacttgtattattttggggtagttgatttgttagcgtgttatttgtgag
atcatcatggatcatgcaacattagcaatgatactagccatttggttcat
ttcttttcatttcataaaattactttttagccaacaaactaccaaacttc
ttcctcctggtccaaaaccattgccaataattggtaacatcttagaagtt
ggtaaaaaaccccatcgttcatttgctaatcttgctaaaattcacggccc
tttaatatcgttacgtctaggaagtgtaacaactattgttgtatcatcag
cagatgtagctaaagaaatgttcttaaaaaaagaccaccctattctaacc
gtactattcctaattctgtcacggccggtgaccaccataaactcaccatg
tcgtggttgcccgtttcgccgaaatggcggaattttcgtaagattacagc
cgtccatttgattctcctcaaagacttgatgatgccaaacctttcgccat
gccaaggtgcaacagctttatgaatatgtacaagaatgtgcacaaaaagg
ccaagctgttgatattggcaaagctgcatttactacctcccttaatttgt
tatctaaactattcttttcagtggaattagcccaccataaatcacacact
tacaagagtttaaggaactaatatggaacattatggaagatattgggaaa
cctaattatgctgattattttcctattttaggctgtgttgatccatcagg
tattcgtcgaagattagcatgtagttttgacaagttgattgcagtttttc
```

-continued

```
agggtataatatgtgaaaggcttgcgcctgattatcaactacaacaacaa
cgacgactgatgatgtgctagacgttatcttcagacttcaaacaaaatga
gacactatgggcgagattaaccatttgacgtcgacatttttgatgctgga
acagacactacatcaagtacttttgagtgggtcatgacagagttaattag
gaatcctgaaatgatggaaaaggctcaagaagaaattaagcaagtattgg
gcaaagataaacaaattcaggaatcagacattattaacctaccttactta
caagccattatcaaagaaactttgcgactacatccaccaactgtatttct
tttgcctcgtaaagccgacactgatgttgaactatatggttatattgtgc
ctaaagatgcacaaatacttgttaacttatgggctattggaagagatcct
aatgcatggcaaaatgctgatatttttcgcccgaaagatttatagggtg
tgaaattgatgtcaaaggaagagattttggactcttacctttggagccg
gaagaaggatatgtcctgggatgaatttggccattagaatgttaactttg
atgctagctactttacttcaattcttcaattggaagcttgaaggagacat
aagtccaaaagacttagacatggatgagaaatttgggattgcgttacaaa
agacaaagcctttaaaacttattccaatacctaggtattgaaatttgtta
gacttacgtacaacaattattattgtttgtggttggttttgggttagctt
cctgttcatgtttgtttgatgtgacgattgaatttactacaaatcaacga
actccaattatatcttgtcaacttggagtaatggcttgggtttctcatct
gtcatctcttttggttggctgtgcaagggagtgagcttgcagcttagcat
ccttcaagaagatttaattaataatatgtgtatgtgtatgtgtatgtgtg
gattgtatacgtcattcattttgcttgttgtaatgattttagttaattat
tgtaattataaaggatttgatcctcattgtgttgaaattatatatataat
gtgtagcacgacaataaagtgacagataacttatataatcttattttcta
tgaaatgttacagacttgattgtgttttaaaaaaa.
```

In another embodiment, the CYP76AD1-α clade gene comprises *A. cruentus, Amaranthus cruentus* (CYP76AD2, accession AET43291.1; SEQ ID NO: 15); *M. jalapa, Mirabilis jalapa* (CYP76AD3, accession AET43292.1; SEQ ID NO: 16); *C. cristata, Celosia cristata* (CYP76AD4, accession AGI78466.1; SEQ ID NO: 17); or a combination thereof.

In one embodiment, the present invention provides a recombinant polynucleotide comprising a nucleic acid encoding a DOPA 4,5-dioxygenase (DOD) enzyme. In one embodiment, the DOD is *Beta vulgaris* DODA1 (BvDODA1). In one embodiment, the nucleic acid sequence encoding BvDODA1 comprises:

```
                                        (SEQ ID NO: 33)
aaaacaagaagaaaacaaaacaaccttttatataactagaaagcaacaaa
aaaaaaagaatgaaaatgatgaatggtgaagatgctaatgatcaaatgat
caaagaaagcttcttcataacacatggaaacccaatattaacagtagaag
acacacatccattaagacctttctttgaaacttggagagagaaaatcttt
tctaagaaacctaaggcaattcttattatttctggtcattgggaaactgt
taaacctactgttaatgctgtccatatcaatgatactatccatgattttg
atgactatcctgctgctatgtaccagttcaagtatccagctcctgggga
```

-continued

```
ccagaattggcaagaaaagtagaggaaattctgaaaaaatcgggtttcga
aacggcggaaactgatcaaaaacgtgggcttgatcatggtgcatgggtac
ctctaatgctaatgtatcctgaggctgatataccagtatgtcagctctca
gttcagccgcatttagatggaacataccattacaacttaggacgagcatt
ggctcccttgaaaaacgacggcgtattaatcattggttcaggaagtgcaa
ctcacccttttggatgaaactcctcattattttgatggagttgcaccttgg
gcagctgcctttgattcatggcttcgtaaagctctcattaatggaaggtt
tgaagaagtgaatatatatgaaagcaaagcaccaaattggaaattagcac
atcctttcccagaacatttttatccattgcatgttgttcttggcgctgct
ggtgaaaaatggaaggcagagcttattcatagcagttgggatcatggcac
cttgtgtcatggctcctacaagttcacttcagcctagttttacttttaaa
cactatgtctacagtctatgttattgtatttggtaatttggtatgtggtg
ttgtttttgttttattcttttgagttattgtacttggtatttggtgttgt
tttcatttggtgcataattcttttagtctatatattgctattcttttgaa
tgaggaataaatcgcgagctcgatgtaatagtttgttttattgtttcaaa
tctatcattatatatatatatatattattaaaaaaaaattattgtgttac
tcgcaaaaaaa.
```

In one embodiment, the DOD is not *Mirabilis jalapa* DOD.

In one embodiment, the present invention provides a recombinant polynucleotide comprising a nucleic acid encoding a betalain related glucosyltransferase. In one embodiment, the nucleic acid sequence encoding the betalain related glucosyltransferase is the nucleic acid sequence encoding cyclo-DOPA 5-O-glucosyltransferase (cDOPA5GT). In one embodiment, cDOPA5GT is from *Mirabilis Jalapa*. In one embodiment, the nucleic acid sequence encoding cDOPA5GT comprises:

```
                                        (SEQ ID NO: 2)
cctcacctccataacaaagaaatgaccgccattaaaatgaacaccaatgg
tgaaggtgaaacacaacatatactaatgataccttttcatggcgcaagggc
atttacgtcctttccttgagcttgctatgtttctatataaacgaagtcat
gttatcattactcttcttactaccccgctcaatgcgggtttcctacgaca
tctccttcaccaccatagctattctagctcggggatcagaattgtcgagt
tacctttcaactcaaccaatcatggtcttccacctggcattgaaaacact
gataaacttacactcccacttgtagtatcactattcattcaaccatttct
cttgaccctcaccttagagattatatttcccgccatttctcccctgcgcg
ccctcctctgtgtgtcatacatgatgtgttccttggttgggttgatcaag
ttgctaaagacgtgggctcaactggtgttgtttttactacgggtggcgcg
tatggtacaagcgcatatgtgtccatttggaatgatctgcctcaccagaa
ttactctgatgatcaagagtttccgcttcctggtttcccggagaatcata
aattccgacgttctcaacttcatcggtttctgaggtatgccgatggatca
gatgattggtcgaaatatttccaaccgcaattgaggcaatcaatgaagag
ttttggatggctatgtaattcagttgaggaaatcgaaacacttgggttta
```

-continued

```
gtatcctcaggaactacactaaactacccatttggggtattggaccgttg

atagcttcacctgtacaacattcatcatctgataataacagtactggtgc

cgagtttgttcaatggttgagcttgaaagaaccagattctgtattataca

tctcatttggatcacagaacacaatttcaccaacccagatgatggaacta

gcagccggtttggagtcaagtgagaagccgtattgtgggtgattcgagca

ccatttgggttcgatatcaatgaggaaatgagaccagaatggctaccaga

gggattcgaggagcgaatgaaggtgaaaaaacaaggaaagttggtgtata

agttgggaccacagttggagatacttaaccatgagtcaatcggagggttc

ttaactcattgtgggtggaattcgatccttgagtcacttcgagaaggtgt

gcctatgttagggtggccattggcagccgaacaagcttataatttgaagt

atttggaggacgaaatgggggttgcagtcgagttagcgaggggattggaa

ggagagataagtaaagagaaagtgaagagaattgtggagatgattttaga

gagaaatgaaggaagtaaaggatgggaaatgaaaaatagagcagtagaaa

tggggaagaaacttaaagacgctgtcaatgaggagaaggaactgaagggt

tcttctgttaaggcaatagatgatttcttagatgcggtcatgcaagctaa

gttggaaccttctcttcaataataagatcgatagtttatctcgtctcaga

gactcaaacaattgactactaggatgatcagaaagagagttatgttcagt

gttctgttattatgcaagacttcaataataacagaaaaattcgtgattag

attcataactt.
```

In one embodiment, several nucleic acids are combined into a single recombinant polynucleotide as described herein. In one embodiment, the present invention provides a recombinant polynucleotide comprising a nucleic acid encoding CYP76AD6, CYP76AD15, or a combination thereof, and a nucleic acid encoding DOD. In another embodiment, the present invention provides a recombinant polynucleotide comprising a nucleic acid encoding CYP76AD1 and a nucleic acid encoding DOD. In another embodiment, the present invention provides a recombinant polynucleotide comprising a nucleic acid encoding CYP76AD1 and a nucleic acid encoding CYP76AD6. In another embodiment, the present invention provides a recombinant polynucleotide comprising a nucleic acid encoding CYP76AD1, a nucleic acid encoding CYP76AD6, CYP76AD15, or a combination thereof, and a nucleic acid encoding DOD.

In another embodiment, several nucleic acids are incorporated into a cell, but each nucleic acid is a separate polynucleotide as described herein.

In one embodiment, a polynucleotide of the present invention comprises a nucleic acid sequence encoding CYP76AD6, CYP76AD15, or a combination thereof, and a nucleic acid sequence encoding CYP76AD1. In another embodiment, a polynucleotide of the present invention comprises a nucleic acid sequence encoding CYP76AD6, CYP76AD15, or a combination thereof, and a nucleic acid sequence encoding a DOD enzyme. In another embodiment, a polynucleotide of the present invention comprises a nucleic acid sequence encoding CYP76AD1 and a nucleic acid sequence encoding a DOD enzyme. In another embodiment, a polynucleotide of the present invention comprises a nucleic acid sequence encoding CYP76AD6, CYP76AD15, or a combination thereof, a nucleic acid sequence encoding CYP76AD1, and a nucleic acid sequence encoding a DOD enzyme. In another embodiment, a polynucleotide of the present invention comprises a nucleic acid sequence encoding CYP76AD6, CYP76AD15, or a combination thereof, a nucleic acid sequence encoding CYP76AD1, and a nucleic acid sequence encoding a betalain related glucosyltransferase. In another embodiment, a polynucleotide of the present invention comprises a nucleic acid sequence encoding CYP76AD6, CYP76AD15, or a combination thereof, a nucleic acid sequence encoding a DOD enzyme and a nucleic acid sequence encoding a betalain related glucosyltransferase. In another embodiment, a polynucleotide of the present invention comprises a nucleic acid sequence encoding CYP76AD1, a nucleic acid sequence encoding a DOD enzyme and a nucleic acid sequence encoding a betalain related glucosyltransferase. In another embodiment, a polynucleotide of the present invention comprises a nucleic acid sequence encoding CYP76AD6, CYP76AD15, or a combination thereof, a nucleic acid sequence encoding CYP76AD1, a nucleic acid sequence encoding a DOD enzyme and a nucleic acid sequence encoding a betalain related glucosyltransferase.

In another embodiment, any of the recombinant polynucleotides described hereinabove further comprises a betalain related glucosyltransferase. In one embodiment, the betalain related glucosyltransferase is cyclo-DOPA 5-O-glucosyltransferase or betanidin-5-O-glucosyltransferase. In one embodiment, the cyclo-DOPA 5-O-glucosyltransferase is *M. jalapa* gene cyclo-DOPA 5-O-glucosyltransferase (cDOPA5GT) (SEQ ID NO: 2).

In another embodiment, the present invention provides a recombinant polynucleotide comprising a nucleic acid encoding CYP76AD1, a nucleic acid encoding CYP76AD6, CYP76AD15, or a combination thereof, a nucleic acid encoding a DOPA 4,5-dioxygenase (DOD) enzyme, and a nucleic acid sequence encoding a betalain related glucosyltransferase, wherein said nucleic acids are in the same reading frame.

In another embodiment, the present invention provides a recombinant polynucleotide comprising a nucleic acid encoding CYP76AD1, a nucleic acid encoding a DOPA 4,5-dioxygenase (DOD) enzyme, and a nucleic acid sequence encoding a betalain related glucosyltransferase, wherein said nucleic acids are in the same reading frame.

In another embodiment, the present invention provides a recombinant polynucleotide comprising a nucleic acid encoding CYP76AD6, CYP76AD15, or a combination thereof and a nucleic acid encoding a DOPA 4,5-dioxygenase (DOD) enzyme expressed in tandem.

In another embodiment, the present invention provides a recombinant polynucleotide comprising a nucleic acid encoding CYP76AD1, CYP76AD6, CYP76AD15, or a combination thereof, or a combination thereof, a nucleic acid encoding a DOPA 4,5-dioxygenase (DOD) enzyme, and a nucleic acid sequence encoding a betalain related glucosyltransferase, expressed in tandem.

In one embodiment, the polynucleotides as described herein comprise multiple nucleic acid sequences that are in the same reading frame. In one embodiment, the polynucleotides as described herein comprise multiple nucleic acid sequences that are expressed in tandem.

In one embodiment, a polynucleotide of the present invention comprises a nucleic acid encoding CYP76AD1, a nucleic acid encoding a DOPA 4,5-dioxygenase (DOD) enzyme, and a nucleic acid sequence encoding a betalain related glucosyltransferase, wherein said nucleic acids are in the same reading frame. In one embodiment, the DOD gene is under a CaMV 35S promoter. In one embodiment, the CYP76AD1 gene is under a CaMV 35S promoter. In one embodiment, the betalain related glucosyltransferase gene is under an *Arabidopsis* Ubiquitin-10 promoter. In one embodiment, the polynucleotide further comprises a kanamycin resistance gene. In one embodiment, the polynucleotide is the pX11 vector, as described in Example 8, hereinbelow. In one embodiment, the nucleic acid sequence of the pX11 vector comprises (SEQ ID NO: 19).

Figure 15:
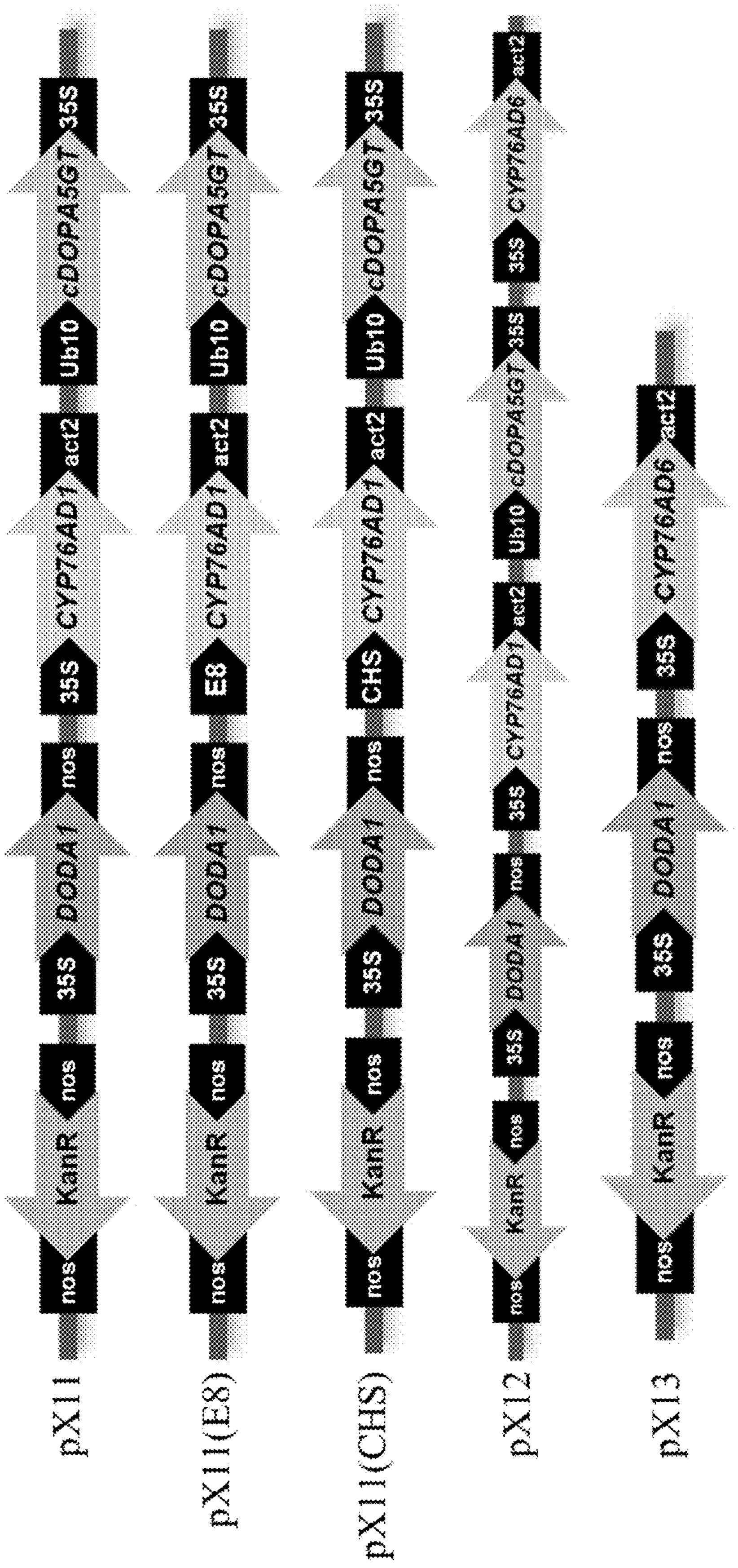
FIG. 15. Schematic of the pX11 (SEQ ID NO: 19), pX11(E8)(SEQ ID NO: 20), pX11(CHS) (SEQ ID NO: 21), pX12 (SEQ ID NO: 22), and pX13 (SEQ ID NO: 23) overexpression vectors. KanR, kanamycin resistance-conferring gene nptII; DODA1, *B. vulgaris* DOPA 4,5-dioxygenase; CYP76AD1/CYP76AD6, *B. vulgaris* cytochrome P450; cDOPA5GT, *M. jalapa* cyclo-DOPA-5-O-glucosyltransferase; nos, nopaline synthase promoter/terminator; 35S, CaMV 35S promoter/terminator; Act2, *Arabidopsis* actin 2 terminator; Ub10, *Arabidopsis* ubiquitin 10 promoter; E8, *S. lycopersicum* E8 promoter; CHS, *Petunia* x *hybrida* chalcone synthase promoter.

In another embodiment, the CYP76AD1 gene is under an E8 promoter (pX11(E8), SEQ ID NO: 20; FIG. 15). In another embodiment, the CYP76AD1 gene is under a CHS promoter (pX11(CHS) SEQ ID NO: 21; FIG. 15).

In another embodiment, a polynucleotide of the present invention comprises a nucleic acid encoding CYP76AD6, CYP76AD15, or a combination thereof, a nucleic acid encoding a DOPA 4,5-dioxygenase (DOD) enzyme, and a nucleic acid sequence encoding a betalain related glucosyltransferase, wherein said nucleic acids are in the same reading frame. In one embodiment, the DOD gene is under a CaMV 35S promoter. In one embodiment, the CYP76AD6, CYP76AD15, or a combination thereof, gene is under a CaMV 35S promoter. In one embodiment, the betalain related glucosyltransferase gene is under an *Arabidopsis* Ubiquitin-10 promoter. In one embodiment, the polynucleotide further comprises a kanamycin resistance gene. In one embodiment, the polynucleotide is the pX13 vector, as described in Example 14, hereinbelow.

In another embodiment, the CYP76AD6, CYP76AD15, or a combination thereof, gene is under an E8 promoter. In another embodiment, the CYP76AD6, CYP76AD15, or a combination thereof, gene is under a CHS promoter.

In another embodiment, a polynucleotide of the present invention comprises a nucleic acid encoding CYP76AD6, CYP76AD15, or a combination thereof, a nucleic acid encoding CYP76AD1, a nucleic acid encoding a DOPA 4,5-dioxygenase (DOD) enzyme, and a nucleic acid sequence encoding a betalain related glucosyltransferase, wherein said nucleic acids are in the same reading frame. In one embodiment, the DOD gene is under a CaMV 35S promoter. In one embodiment, the CYP76AD6, CYP76AD15, or a combination thereof, gene is under a CaMV 35S promoter. In one embodiment, the CYP76AD1 gene is under a CaMV 35S promoter. In one embodiment, the betalain related glucosyltransferase gene is under an *Arabidopsis* Ubiquitin-10 promoter. In one embodiment, the polynucleotide further comprises a kanamycin resistance gene. In one embodiment, the polynucleotide is the pX12 vector, as described in Example 14, hereinbelow.

In another embodiment, the CYP76AD6, CYP76AD15, or a combination thereof, gene is under an E8 promoter. In another embodiment, the CYP76AD6, CYP76AD15, or a combination thereof, gene is under a CHS promoter. In another embodiment, the CYP76AD1 gene is under an E8 promoter. In another embodiment, the CYP76AD1 gene is under a CHS promoter.

In one embodiment, the present invention provides a comprising a nucleic acid encoding a CYP76AD1-β clade gene under the control of a promoter. In one embodiment, the CYP76AD1-β clade gene is CYP76AD6. In another embodiment, the CYP76AD1-β clade gene is CYP76AD15.

In one embodiment, the present invention provides a recombinant nucleic acid comprising a CYP76AD1-β clade gene from red beet. In one embodiment, the present invention provides a recombinant nucleic acid comprising a CYP76AD1-β clade gene that is not from sugar beet. In one embodiment, the present invention provides a recombinant nucleic acid comprising a CYP76AD1-β clade gene but excluding the nucleic acid sequence of the CYP76AD1 paralogs from sugar beet (DeLoache et al., 2015), which do not produce betaxanthin when transformed into yeast with DOD. In one embodiment, the present invention provides a recombinant nucleic acid comprising a CYP76AD1-β clade gene but excluding the nucleic acid encoding SEQ ID NO: 34.

In another embodiment, the CYP76AD1-β clade gene is a CYP76AD1-β clade gene as set forth in Brockington et al. 2015 (New Phytol. 2015 September; 207(4):1170-80), which is incorporated herein by reference in its entirety). In one embodiment, the CYP76AD1-β clade gene is a CYP76AD1-β clade gene as set forth in Supplemental FIG. 2 of Brockington et al. 2015.

In one embodiment, the present invention provides a recombinant polynucleotide comprising a nucleic acid encoding a CYP76AD6 gene, a CYP76AD15 gene, or a combination thereof under the control of a promoter.

In one embodiment, the present invention provides a recombinant polynucleotide comprising a nucleic acid encoding a CYP76AD1-β clade gene and a nucleic acid encoding a DOPA 4,5-dioxygenase (DOD) enzyme, wherein said nucleic acids are inserted into the polynucleotide in frame. In one embodiment, the polynucleotide further comprises a nucleic acid encoding betalain related glucosyltransferase.

In one embodiment, the nucleic acid encoding a CYP76AD1-β clade gene is *Bv. maritima, Beta vulgaris* ssp. *maritima* (GenBank accession AKI33834.1; SEQ ID NO: 10); *F. latifolia, Froelichia latifolia* (accession AKI33838.1; SEQ ID NO: 11); *A. caracasana, Alternanthera caracasana* (accession AKI33835.1; SEQ ID NO: 12); *A. ficoidea, Alternanthera ficoidea* (accession AKI33831.1; SEQ ID NO: 13), or a combination thereof.

In one embodiment, the present invention provides a recombinant polynucleotide comprising a nucleic acid encoding a CYP76AD6 gene, a CYP76AD15 gene, or a combination thereof and a nucleic acid encoding a DOPA 4,5-dioxygenase (DOD) enzyme, wherein said nucleic acids are inserted into the polynucleotide in frame. In one embodiment, the polynucleotide further comprises a nucleic acid encoding betalain related glucosyltransferase.

In another embodiment, the present invention comprises additional nucleic acids encoding polypeptides that modify betalain structure. In one embodiment, the polypeptide is a glycosylating enzyme. In another embodiment, the polypeptide is an acylating enzyme. In another embodiment, additional nucleic acids encode polypeptides involved in subcellular transport. In another embodiment, additional nucleic acids encode polypeptides involved in detoxification.

Homologs and Variants

In another embodiment, a recombinant polynucleotide or polypeptide of the present invention is homologous to a sequence set forth herein, either expressly or by reference to a GenBank entry. The terms "homology," "homologous," etc, when in reference to any amino acid or nucleic acid sequence, refer, in one embodiment, to a percentage of amino acids or nucleotides, respectively, in the candidate sequence that are identical with the residues of a corresponding native polypeptide or polynucleotide, after aligning the sequences and introducing gaps, if necessary, to achieve the maximum percent homology, and not considering any conservative substitutions as part of the sequence identity. Methods and computer programs for the alignment are well known in the art such as, for example, the BLAST, DOMAIN, BEAUTY (BLAST Enhanced Alignment Utility), GENPEPT and TREMBL packages.

In one embodiment, a homolog of CYP76AD1 may be used instead of CYP76AD1 in accordance with the compositions and methods of the present invention.

In another embodiment, a homolog of CYP76AD6 may be used instead of CYP76AD6, in accordance with the compositions and methods of the present invention.

In another embodiment, a homolog of DOPA 4,5-dioxygenase (DOD) enzyme may be used instead of DOPA 4,5-dioxygenase (DOD) enzyme, in accordance with the compositions and methods of the present invention.

Homology may be at the nucleotide sequence and/or encoded amino acid sequence level. In one embodiment, the nucleic acid and/or amino acid sequence shares at least about 50%, or 60%, or 70%, or 80% homology. In another embodiment, the nucleic acid and/or amino acid sequence shares at least about 90%, 95%, 96%, 97%, 98% or 99% homology with a sequence of the present invention. Homology may be at the nucleotide sequence and/or encoded amino acid sequence level. In one embodiment, the nucleic acid and/or amino acid sequence shares at least about 72% homology. In one embodiment, the nucleic acid and/or amino acid sequence shares at least about 75% homology.

In another embodiment, homology is determined via determination of candidate sequence hybridization, methods of which are well described in the art (See, for example, "Nucleic Acid Hybridization" Hames, B. D., and Higgins S. J., Eds. (1985); Sambrook et al., 2001, Molecular Cloning, A Laboratory Manual, Cold Spring Harbor Press, N.Y.; and Ausubel et al., 1989, Current Protocols in Molecular Biology, Green Publishing Associates and Wiley Interscience, N.Y).

In one embodiment, the homolog is isolated from another Caryophyllales plant. In one embodiment, the homolog is isolated from a cactus, a carnation, an amaranth, an ice plant, a beet, a carnivorous plant, or a combination thereof. In one embodiment, the carnivorous plant is a Dionocophyllaceae such as *Triphyophyllum*, a Droseraceae, such as *Aldrovanda* (Waterwheel Plant), *Dionaea* (Venus Flytrap), *Drosera* (Sundew), a Drosophyllaceae such as a *Drosophyllum* (Dewy Pine or Portugese Sundew), or a Nepenthaceae such as Tropical Pitcher Plant or Monkey Cup.

In one embodiment, the homolog is isolated based on temporal expression. In one embodiment, the homolog is isolated based on developmental stage. In one embodiment, the developmental stage is Stage 1, which, in one embodiment, is when the flower length is approximately 1 cm. In another embodiment, the developmental stage is Stage 2, which, in one embodiment, is when the flower length is approximately 2 cm. In another embodiment, the developmental stage is Stage 3, which, in one embodiment, is when the flower length is approximately 3 cm. In another embodiment, the developmental stage is Stage 4, which, in one embodiment, is when the flower length is approximately 4 cm. In another embodiment, the developmental stage is Stage 5, which, in one embodiment, is when the flower length is approximately 5-6 cm.

In another embodiment, the homolog is isolated based on tissue expression. In one embodiment, the tissue expression of a CYP76AD1, CYP76AD6, CYP76AD15, or a combination thereof, or DOD homolog is in a floral tissue. In one embodiment, the floral tissue is a petal. In another embodiment, the floral tissue is a stamen. In another embodiment, the floral tissue is an anther. In another embodiment, the floral tissue is a stigma.

In another embodiment, a recombinant polynucleotide or polypeptide of the present invention is a variant of a sequence set forth herein. In another embodiment, a recombinant polynucleotide or polypeptide of the present invention is an isoform of a sequence set forth herein. In another embodiment, a recombinant polynucleotide or polypeptide of the present invention is a fragment of a sequence set forth herein. In one embodiment, a recombinant polynucleotide or polypeptide of the present invention is a functional variant of a sequence set forth herein. In another embodiment, a recombinant polynucleotide or polypeptide of the present invention is a functional isoform of a sequence set forth herein. In another embodiment, a recombinant polynucleotide or polypeptide of the present invention is a functional fragment of a sequence set forth herein. In another embodiment, a recombinant polynucleotide or polypeptide of the present invention is a functional homologue of a sequence set forth herein.

In another embodiment, the present invention provides a recombinant polynucleotide comprising a nucleic acid encoding a polypeptide as described herein.

In one embodiment, the nucleic acid sequence encoding CYP76AD6 is as set forth in SEQ ID NO: 30. In another embodiment a polynucleotide of the present invention optionally comprises a nucleic acid sequence encoding CYP76AD6. In one embodiment, the nucleic acid sequence of CYP76AD6 is as set forth in SEQ ID NO: 30. In another embodiment, the CYP76AD6 utilized in methods and compositions of the present invention is a homologue of SEQ ID NO: 30. In another embodiment, the CYP76AD6 utilized in methods and compositions of the present invention is a variant of SEQ ID NO: 30. In another embodiment, the CYP76AD6 utilized in methods and compositions of the present invention is a fragment of SEQ ID NO: 30. In another embodiment, the CYP76AD6 utilized in methods and compositions of the present invention is an isoform of SEQ ID NO: 30. In another embodiment, the CYP76AD6 utilized in methods and compositions of the present invention is a functional homologue, functional variant, functional fragment, or functional isoform of SEQ ID NO: 30.

As demonstrated in Example 19, CYP76AD15, an ortholog of CYP76AD6 in *Mirabilis jalapa*, had the same activity as CYP76AD6 during transient expression in *Nicotiana benthamiana*. In another embodiment, CYP76AD15 or a homologue, isoform, or variant thereof, may be used in place of CYP76AD6 in the compositions and methods of the present invention. In one embodiment, the CYP76AD15 gene product from *Mirabilis jalapa* has a similar function as the CYP76AD6 gene product from *Beta vulgaris*. In one embodiment, CYP76AD15 from *Mirabilis jalapa* is the gene encoding an enzyme involved in converting tyrosine to L-DOPA.

In one embodiment, the present invention provides a recombinant polynucleotide comprising a nucleic acid encoding CYP76AD15. In one embodiment, the nucleic acid sequence encoding CYP76AD15 comprises:

```
                                          (SEQ ID NO: 35)
tttgtctattattggctcaaaatccactactatctttttgtaaaagaaaa

tagttgttcaacttagggaattattgatatttcattatggaaaacacaat

gttaggtgttatcctagcaaccattttcctcacttttcacataatgaaga

tgttatttagtccttccaaggttaaactacccccgggtccgagaccattg

ccaattattggtaatattctcgagcttggggataaaccacatcgttattt

gcaaaccttgcgaaaattcacggtcctttagttactttgaaactcgggag
```

-continued

```
tgtaaccactattgtggtttcctcttctgaagttgctaaagaaatgtttt
tgaaaaatgaccaacctttggcaaatcgtaccatacctgactcagtaaga
gcaggtaaccatgacaaactatcaatgtcgtggttgcctgtatcacccaa
atggcgaaatcttagaaagatttcagccgtccaattgactcaactcaacg
acttgatgcaagtcaagctcatagacaagctaaaatcaaacaacttattg
agtacgtaaaaaaatgcagtaaaatcggccaatacgtcgatattggccaa
gttgcattcactacatcacttaatttactatcaaacacattcttttcaaa
agaactagcatcatttgattcagataatgcacaagagttcaaacaactaa
tgtggtgcattatggaagaaattggtaggcctaattatgccgattatttt
cctatcttgggttatgtcgatccattcggtgctagacgtcgactttacgt
tacttcgatcaactaattgaagtatttcaagtgattattcgtgagagact
tacacatgataataatattgtgggtaataacaatgatgttttagctacgt
tgctcgatattataaacaaaacgagttaactatggatgaaatcaaccatt
tactagtggacatttttgatgctggtacggatacaacagcaagtacacta
gaatgggcaatgtcagagctcataaaaaatccacacataatggccaaagc
tcaagaggaggtccggcgagccaccatgtctcacggcggagctacggtgg
cggaaatacaagaatcggatatcaataatcttccatacatacaatctatt
attaaagaaacacttcgtttacacccaccaactgtgtttttacttcctag
aaaagctgacgtggatgtccaattattcggctatgtggtccccaaaaatg
ctcaagtcctagtcaatttatgggccattggtcgtgacccaaatgtgtgg
cccgacccggaagtttttagtcccgaaagatttatggattgtgagattga
tgtcaagggtcgtgattttgagctattgcctttcggggcgggtcgtcgga
tttgtccgggattgtattggcttatcggatgcttaatttgatgttggcta
atatggtacattatttgattggaaattacccggtgttgaaaatggatccg
ggtcggaaatggatagtttggatatggatgagaaatttggtatcactttg
caaaaggttcaaccccttaaggttattcctgtctcaaggaaatagatgga
agatcgatggttgggagataatcatattgtttttaattattgttggtgta
ttttattgttattattggggacaattttataataaaagatataaataagt
tcctaattgtgatttatattgtgaattttctagttaatataaatacatat
gaatatttatgatgaaaaaaaaaaaaaaaaaaaaagg.
```

In another embodiment, a polynucleotide of the present invention comprises a nucleic acid sequence encoding BvCYP76new, as described in Example 3. In another embodiment, a polynucleotide of the present invention comprises a nucleic acid sequence encoding MjCYP76 from *M. jalapa* (SEQ ID NO: 1). In one embodiment, CYP76AD15, BvCYP76new or MjCYP76 may be used in the compositions and methods of the present invention. In another embodiment, other cytochrome P450-encoding genes co-expressed with one or more of the known betalain related genes used as baits may be used in the compositions and methods of the present invention. In one embodiment, CYP82G1-like (SEQ ID NO: 36), CYP78A9-like (SEQ ID NO: 37), CYP86B1-like (SEQ ID NO: 38), or a combination thereof may be used in the compositions and methods of the present invention. In one embodiment, may be used in place of CYP76AD6.

In one embodiment a polynucleotide of the present invention comprises a nucleic acid sequence encoding CYP76AD1. In one embodiment a polynucleotide of the present invention optionally comprises a nucleic acid sequence encoding CYP76AD1. In one embodiment, the nucleic acid sequence of CYP76AD1 is as set forth in SEQ ID NO: 32. In another embodiment, the CYP76AD1 utilized in methods and compositions of the present invention is a homologue of SEQ ID NO: 32. In another embodiment, the CYP76AD1 utilized in methods and compositions of the present invention is a variant of SEQ ID NO: 32. In another embodiment, the CYP76AD1 utilized in methods and compositions of the present invention is a fragment of SEQ ID NO: 32. In another embodiment, the CYP76AD1 utilized in methods and compositions of the present invention is an isoform of SEQ ID NO: 32. In another embodiment, the CYP76AD1 utilized in methods and compositions of the present invention is a functional homologue, functional variant, functional fragment, or functional isoform of SEQ ID NO: 32.

In another embodiment, a polynucleotide of the present invention comprises a nucleic acid sequence encoding CYP76AD3 (SEQ ID NO: 4), as described in Example 9. In one embodiment, CYP76AD3 may be used instead of CYP76AD1 in the compositions and methods of the present invention.

In one embodiment a polynucleotide of the present invention comprises a nucleic acid sequence encoding *Beta vulgaris* DODA1 (BvDODA1). In one embodiment a polynucleotide of the present invention optionally comprises a nucleic acid sequence encoding BvDODA1. In one embodiment, the nucleic acid sequence of BvDODA1 is as set forth in SEQ ID NO: 33. In another embodiment, the BVDODA1 utilized in methods and compositions of the present invention is a homologue of SEQ ID NO: 33. In another embodiment, the BVDODA1 utilized in methods and compositions of the present invention is a variant of SEQ ID NO: 33. In another embodiment, the BVDODA1 utilized in methods and compositions of the present invention is a fragment of SEQ ID NO: 33. In another embodiment, the BVDODA1 utilized in methods and compositions of the present invention is an isoform of SEQ ID NO: 33. In another embodiment, the BVDODA1 utilized in methods and compositions of the present invention is a functional homologue, functional variant, functional fragment, or functional isoform of SEQ ID NO: 33.

In another embodiment, the DOD enzyme is PgDOD from *Portulaca grandiflora* (Accession No. AJ580598; encoded by SEQ ID NO: 39), MjDOD from *Mirabilis jalapa* (Accession No. AB435372; encoded by SEQ ID NO: 3), BgDOD from *Bougainvillea glabra* (Accession No. AB435373; encoded by SEQ ID NO: 40), or AmDOD from *Amanita muscaria* (Accession No. P87064; encoded by SEQ ID NO: 41).

In one embodiment, a polynucleotide of the present invention comprises a nucleic acid sequence encoding cyclo-DOPA 5-O-glucosyltransferase (cDOPA5GT). In one embodiment, a polynucleotide of the present invention optionally comprises a nucleic acid sequence encoding cDOPA5GT. In one embodiment, the nucleic acid sequence of cDOPA5GT is as set forth in SEQ ID NO: 2. In another embodiment, the cDOPA5GT utilized in methods and compositions of the present invention is a homologue of SEQ ID NO: 2. In another embodiment, the cDOPA5GT utilized in methods and compositions of the present invention is a variant of SEQ ID NO: 2. In another embodiment, the cDOPA5GT utilized in methods and compositions of the present invention is a fragment of SEQ ID NO: 2. In another embodiment, the cDOPA5GT utilized in methods and compositions of the present invention is an isoform of SEQ ID NO: 2. In another embodiment, the cDOPA5GT utilized in methods and compositions of the present invention is a functional homologue, functional variant, functional fragment, or functional isoform of SEQ ID NO: 2.

In one embodiment, "variant" refers to an amino acid or nucleic acid sequence (or in other embodiments, an organism or tissue) that is different from the majority of the population but is still sufficiently similar to the common mode to be considered to be one of them, for example splice variants. In one embodiment, the variant may a sequence conservative variant, while in another embodiment, the variant may be a functional conservative variant. In one embodiment, a variant may comprise an addition, deletion or substitution of 1 amino acid. In one embodiment, a variant may comprise an addition, deletion, substitution, or combination thereof of 2 amino acids. In one embodiment, a variant may comprise an addition, deletion or substitution, or combination thereof of 3 amino acids. In one embodiment, a variant may comprise an addition, deletion or substitution, or combination thereof of 4 amino acids. In one embodiment, a variant may comprise an addition, deletion or substitution, or combination thereof of 5 amino acids. In one embodiment, a variant may comprise an addition, deletion or substitution, or combination thereof of 7 amino acids. In one embodiment, a variant may comprise an addition, deletion or substitution, or combination thereof of 10 amino acids. In one embodiment, a variant may comprise an addition, deletion or substitution, or combination thereof of 2-15 amino acids. In one embodiment, a variant may comprise an addition, deletion or substitution, or combination thereof of 3-20 amino acids. In one embodiment, a variant may comprise an addition, deletion or substitution, or combination thereof of 4-25 amino acids.

In one embodiment, the term "fragment" is used herein to refer to a protein or polypeptide that is shorter or comprises fewer amino acids than the full length protein or polypeptide. In another embodiment, fragment refers to a nucleic acid that is shorter or comprises fewer nucleotides than the full length nucleic acid. In another embodiment, the fragment is an N-terminal fragment. In another embodiment, the fragment is a C-terminal fragment. In one embodiment, the fragment is an intrasequential section of the protein, peptide, or nucleic acid. In another embodiment, the fragment is a functional section within the protein, peptide or nucleic acid.

In one embodiment, "isoform" refers to a protein isoform or a gene isoform. In one embodiment, a protein isoform is a different form of a protein coded from the same gene, or a protein from a different gene with amino acid sequence and functional similarities. In one embodiment, a gene isoform is an mRNA that is produced from the same locus but has different transcription start sites (TSSs), protein coding DNA sequences (CDSs) and/or untranslated regions (UTRs). In one embodiment, the gene isoform has altered activity, while in another embodiment, the gene isoform does not have altered activity. Thus, in one embodiment, an isoform is an alternate version of a molecule, for example, a protein, that has the same function as the first molecule but which may have small differences in its structure or sequence. In one embodiment, isoforms may be produced from different but related genes, or in another embodiment, may arise from the same gene by alternative splicing. In another embodiment, isoforms are caused by single nucleotide polymorphisms.

In one embodiment, "functional" within the meaning of the invention, is used herein to refer to the innate ability of a protein, peptide, nucleic acid, fragment or a variant thereof to exhibit a biological activity or function. In one embodiment, such a biological function is its binding property to an interaction partner, e.g., a membrane-associated receptor, and in another embodiment, its trimerization property. In the case of functional fragments and the functional variants of the invention, these biological functions may in fact be changed, e.g., with respect to their specificity or selectivity, but with retention of the basic biological function.

Numerous methods for measuring the biological activity of a protein, polypeptide, or molecule are known from the related art, for example, protein assays, which use labeled substrates, substrate analyses by chromatographic methods, such as HPLC or thin-layer chromatography, spectrophotometric methods, etc. (see, e.g., Maniatis et al. (2001) Molecular Cloning: A Laboratory Manual, Cold Spring Harbor Laboratory Press, Cold Spring Harbor, N.Y.).

Expression Vectors

In another embodiment, the present invention provides an expression vector comprising any of the polynucleotides of the present invention as described herein.

In another embodiment, the present invention provides an expression vector comprising a recombinant polynucleotide comprising a nucleic acid encoding CYP76AD1, a nucleic acid encoding a DOPA 4,5-dioxygenase (DOD) enzyme, and, optionally, a nucleic acid sequence encoding a betalain related glucosyltransferase, wherein said nucleic acids are in the same reading frame.

In another embodiment, the present invention provides an expression vector comprising a recombinant polynucleotide comprising a nucleic acid encoding CYP76AD6, CYP76AD15, or a combination thereof, and a nucleic acid encoding a DOPA 4,5-dioxygenase (DOD) enzyme expressed in tandem.

In another embodiment, the present invention provides an expression vector comprising a recombinant polynucleotide comprising a nucleic acid encoding CYP76AD1, CYP76AD6, CYP76AD15, or a combination thereof, a nucleic acid encoding a DOPA 4,5-dioxygenase (DOD) enzyme, and, optionally, a nucleic acid sequence encoding a betalain related glucosyltransferase, expressed in tandem.

In one embodiment, polynucleotides of the present invention are inserted into expression vectors (i.e., a nucleic acid construct) to enable expression of the recombinant polypeptide. In one embodiment, the expression vector of the present invention includes additional sequences which render this vector suitable for replication and integration in prokaryotes. In one embodiment, the expression vector of the present invention includes additional sequences which render this vector suitable for replication and integration in eukaryotes. In one embodiment, the expression vector of the present invention includes a shuttle vector which renders this vector suitable for replication and integration in both prokaryotes and eukaryotes. In some embodiments, cloning vectors comprise transcription and translation initiation sequences (e.g., promoters, enhancer) and transcription and translation terminators (e.g., polyadenylation signals).

In one embodiment, a variety of prokaryotic or eukaryotic cells can be used as host-expression systems to express the polypeptides of the present invention. In some embodiments, these include, but are not limited to, microorganisms, such as bacteria transformed with a recombinant bacteriophage DNA, plasmid DNA or cosmid DNA expression vector containing the polypeptide coding sequence; yeast transformed with recombinant yeast expression vectors containing the polypeptide coding sequence; plant cell systems infected with recombinant virus expression vectors (e.g., cauliflower mosaic virus, CaMV; tobacco mosaic virus, TMV) or transformed with recombinant plasmid expression vectors, such as Ti plasmid, containing the polypeptide coding sequence.

In one embodiment, viral vectors of the present invention overexpress the pathway genes described herein. In another embodiment, viral infection of cells expressing the pathway genes described herein induces the cells to overexpress the pathway genes.

In some embodiments, non-bacterial expression systems are used (e.g. mammalian expression systems such as CHO cells) to express the polypeptide of the present invention. In one embodiment, the expression vector used to express polynucleotides of the present invention in mammalian cells is pCI-DHFR vector comprising a CMV promoter and a neomycin resistance gene.

In some embodiments, in bacterial systems of the present invention, a number of expression vectors can be advantageously selected depending upon the use intended for the polypeptide expressed. In one embodiment, large quantities of polypeptide are desired. In one embodiment, vectors that direct the expression of high levels of the protein product, possibly as a fusion with a hydrophobic signal sequence, which directs the expressed product into the periplasm of the bacteria or the culture medium where the protein product is readily purified are desired. In one embodiment, certain fusion protein engineered with a specific cleavage site to aid in recovery of the polypeptide. In one embodiment, vectors adaptable to such manipulation include, but are not limited to, the pET series of *E. coli* expression vectors (Studier et al., Methods in Enzymol. 185:60-89 1990).

In one embodiment, yeast expression systems are used. In one embodiment, a number of vectors containing constitutive or inducible promoters can be used in yeast as disclosed in U.S. Pat. No. 5,932,447. In another embodiment, vectors which promote integration of foreign DNA sequences into the yeast chromosome are used.

In one embodiment, the expression vector of the present invention can further include additional polynucleotide sequences that allow, for example, the translation of several proteins from a single mRNA such as an internal ribosome entry site (IRES) and sequences for genomic integration of the promoter-chimeric polypeptide.

In some embodiments, mammalian expression vectors include, but are not limited to, pcDNA3, pcDNA3.1(+/−), pGL3, pZeoSV2(+/−), pSecTag2, pDisplay, pEF/myc/cyto, pCMV/myc/cyto, pCR3.1, pSinRep5, DH26S, DHBB, pNMT1, pNMT41, pNMT81, which are available from Invitrogen, pCI which is available from Promega, pMbac, pPbac, pBK-RSV and pBK-CMV which are available from Strategene, pTRES which is available from Clontech, and their derivatives.

In some embodiments, expression vectors containing regulatory elements from eukaryotic viruses such as retroviruses are used by the present invention. SV40 vectors include pSVT7 and pMT2. In some embodiments, vectors derived from bovine papilloma virus include pBV-1MTHA, and vectors derived from Epstein Bar virus include pHEBO, and p2O5. Other exemplary vectors include pMSG, pAV009/A+, pMTO10/A+, pMAMneo-5, baculovirus pDSVE, and any other vector allowing expression of proteins under the direction of the SV-40 early promoter, SV-40 later promoter, metallothionein promoter, murine mammary tumor virus promoter, Rous sarcoma virus promoter, polyhedrin promoter, or other promoters shown effective for expression in eukaryotic cells.

In some embodiments, recombinant viral vectors are useful for in vivo expression of the polypeptides of the present invention since they offer advantages such as lateral infection and targeting specificity. In one embodiment, lateral infection is inherent in the life cycle of, for example, retrovirus and is the process by which a single infected cell produces many progeny virions that bud off and infect neighboring cells. In one embodiment, the result is that a large area becomes rapidly infected, most of which was not initially infected by the original viral particles. In one embodiment, viral vectors are produced that are unable to spread laterally. In one embodiment, this characteristic can be useful if the desired purpose is to introduce a specified gene into only a localized number of targeted cells.

In one embodiment, various methods can be used to introduce the expression vector of the present invention into cells. Such methods include, for example, stable or transient transfection, lipofection, electroporation and infection with recombinant viral vectors.

In some embodiments, introduction of nucleic acid by viral infection offers several advantages over other methods such as lipofection and electroporation, since higher transfection efficiency can be obtained due to the infectious nature of viruses.

In one embodiment, it will be appreciated that the polypeptides of the present invention can also be expressed from a nucleic acid construct administered to the individual employing any suitable mode of administration, described hereinabove (i.e., in-vivo gene therapy). In one embodiment, the nucleic acid construct is introduced into a suitable cell via an appropriate gene delivery vehicle/method (transfection, transduction, homologous recombination, etc.) and an expression system as needed and then the modified cells are expanded in culture and returned to the individual (i.e., ex-vivo gene therapy).

In one embodiment, plant expression vectors are used. In one embodiment, the expression of a polypeptide coding sequence is driven by a number of promoters. In some embodiments, viral promoters such as the 35S RNA and 19S RNA promoters of CaMV [Brisson et al., Nature 310:511-514 (1984)], or the coat protein promoter to TMV [Takamatsu et al., EMBO J. 6:307-311 (1987)] are used. In another embodiment, plant promoters are used such as, for example, the small subunit of RUBISCO [Coruzzi et al., EMBO J. 3:1671-1680 (1984); and Brogli et al., Science 224:838-843 (1984)] or heat shock promoters, e.g., soybean hsp17.5-E or hsp17.3-B [Gurley et al., Mol. Cell. Biol. 6:559-565 (1986)]. In one embodiment, constructs are introduced into plant cells using Ti plasmid, Ri plasmid, plant viral vectors, direct DNA transformation, microinjection, electroporation and other techniques well known to the skilled artisan. See, for example, Weissbach & Weissbach [Methods for Plant Molecular Biology, Academic Press, NY, Section VIII, pp 421-463 (1988)]. Other expression systems such as insects and mammalian host cell systems, which are well known in the art, can also be used by the present invention.

It will be appreciated that other than containing the necessary elements for the transcription and translation of the inserted coding sequence (encoding the polypeptide), the expression construct of the present invention can also include sequences engineered to optimize stability, production, purification, yield or activity of the expressed polypeptide.

Various methods, in some embodiments, can be used to introduce the expression vector of the present invention into the host cell system. In some embodiments, such methods are generally described in Sambrook et al., Molecular Cloning: A Laboratory Manual, Cold Springs Harbor Laboratory, New York (1989, 1992), in Ausubel et al., Current Protocols in Molecular Biology, John Wiley and Sons, Baltimore, Md. (1989), Chang et al., Somatic Gene Therapy, CRC Press, Ann Arbor, Mich. (1995), Vega et al., Gene Targeting, CRC Press, Ann Arbor Mich. (1995), Vectors: A Survey of Molecular Cloning Vectors and Their Uses, Butterworths, Boston Mass. (1988) and Gilboa et at. [Biotechniques 4 (6): 504-512, 1986] and include, for example, stable or transient transfection, lipofection, electroporation and infection with recombinant viral vectors. In addition, see U.S. Pat. Nos. 5,464,764 and 5,487,992 for positive-negative selection methods.

In some embodiments, transformed cells are cultured under effective conditions, which allow for the expression of high amounts of recombinant polypeptide. In some embodiments, effective culture conditions include, but are not limited to, effective media, bioreactor, temperature, pH and oxygen conditions that permit protein production. In one embodiment, an effective medium refers to any medium in which a cell is cultured to produce the recombinant polypeptide of the present invention. In some embodiments, a medium typically includes an aqueous solution having assimilable carbon, nitrogen and phosphate sources, and appropriate salts, minerals, metals and other nutrients, such as vitamins. In some embodiments, cells of the present invention can be cultured in conventional fermentation bioreactors, shake flasks, test tubes, microtiter dishes and petri plates. In some embodiments, culturing is carried out at a temperature, pH and oxygen content appropriate for a recombinant cell. In some embodiments, culturing conditions are within the expertise of one of ordinary skill in the art.

In some embodiments, depending on the vector and host system used for production, resultant polypeptides of the present invention either remain within the recombinant cell, secreted into the fermentation medium, secreted into a space between two cellular membranes, such as the periplasmic space in *E. coli*; or retained on the outer surface of a cell or viral membrane.

Compositions

In another embodiment, the present invention provides a composition comprising one or more recombinant polynucleotides as described herein. In another embodiment, the present invention provides a composition comprising recombinant nucleic acids as described herein.

In one embodiment, the present invention provides a recombinant polynucleotide comprising a nucleic acid encoding CYP76AD1, a nucleic acid encoding a DOPA 4,5-dioxygenase (DOD) enzyme, and, optionally, a nucleic acid sequence encoding a betalain related glucosyltransferase, wherein said nucleic acids are in the same reading frame, wherein said nucleic acids are in the same reading frame.

In another embodiment, the present invention provides a composition comprising a recombinant polynucleotide comprising a nucleic acid encoding CYP76AD6, CYP76AD15, or a combination thereof, and a nucleic acid encoding a DOPA 4,5-dioxygenase (DOD) enzyme expressed in tandem.

In another embodiment, the present invention provides an expression vector comprising a recombinant polynucleotide as described herein.

In another embodiment, the present invention provides a composition comprising an expression vector comprising a recombinant polynucleotide comprising a nucleic acid encoding CYP76AD1, a nucleic acid encoding a DOPA 4,5-dioxygenase (DOD) enzyme, and, optionally, a nucleic acid sequence encoding a betalain related glucosyltransferase, wherein said nucleic acids are in the same reading frame, wherein said nucleic acids are in the same reading frame.

In another embodiment, the present invention provides a composition comprising an expression vector comprising a recombinant polynucleotide comprising a nucleic acid encoding CYP76AD6, CYP76AD15, or a combination thereof, and a nucleic acid encoding a DOPA 4,5-dioxygenase (DOD) enzyme expressed in tandem.

In one embodiment, provides a composition comprising a recombinant polynucleotide or a chimeric polypeptide of the present invention. In one embodiment, the polypeptides and polynucleotides of the present invention can be provided to the individual per se.

In another embodiment, the present invention provides a cell comprising an expression vector or a recombinant polynucleotide as described herein. In another embodiment, the present invention provides a composition comprising a cell as described herein.

Cells

In another embodiment, the present invention provides a cell comprising a recombinant polynucleotide as described herein. In another embodiment, the present invention provides a cell comprising an expression vector as described herein.

In another embodiment, the present invention provides a cell comprising a recombinant polynucleotide comprising a nucleic acid encoding CYP76AD1, a nucleic acid encoding a DOPA 4,5-dioxygenase (DOD) enzyme, and, optionally, a nucleic acid sequence encoding a betalain related glucosyltransferase, wherein said nucleic acids are in the same reading frame.

In another embodiment, the present invention provides a cell comprising a recombinant polynucleotide comprising a nucleic acid encoding CYP76AD6, CYP76AD15, or a combination thereof, and a nucleic acid encoding a DOPA 4,5-dioxygenase (DOD) enzyme expressed in tandem.

In another embodiment, the present invention provides a cell comprising a recombinant polynucleotide comprising a nucleic acid encoding CYP76AD1, CYP76AD6, CYP76AD15, or a combination thereof, a nucleic acid encoding a DOPA 4,5-dioxygenase (DOD) enzyme, and, optionally, a nucleic acid sequence encoding a betalain related glucosyltransferase, expressed in tandem.

In another embodiment, the present invention provides a cell comprising an expression vector comprising a recombinant polynucleotide comprising a nucleic acid encoding CYP76AD1, a nucleic acid encoding a DOPA 4,5-dioxygenase (DOD) enzyme, and, optionally, a nucleic acid sequence encoding a betalain related glucosyltransferase, wherein said nucleic acids are in the same reading frame.

In another embodiment, the present invention provides a cell comprising an expression vector comprising a recombinant polynucleotide comprising a nucleic acid encoding CYP76AD6, CYP76AD15, or a combination thereof, and a nucleic acid encoding a DOPA 4,5-dioxygenase (DOD) enzyme expressed in tandem.

In another embodiment, the present invention provides a cell comprising an expression vector comprising a recombinant polynucleotide comprising a nucleic acid encoding CYP76AD1, CYP76AD6, CYP76AD15, or a combination thereof, a nucleic acid encoding a DOPA 4,5-dioxygenase (DOD) enzyme, and, optionally, a nucleic acid sequence encoding a betalain related glucosyltransferase, expressed in tandem.

In one embodiment, when the genes of the invention can be transformed into a plant cell, a plant cell suspension culture may be produced. In one embodiment, the plant cell is a plant stem cell. Betalain, L-DOPA, or a combination thereof can be isolated from plant suspension culture. Method for making plant cell suspension culture are well known in the art and fully described in U.S. Patent Application Publications US 2014/0051135; US 2011/0251408; US 2010/0159545; and US 2007/0026506, which are incorporated by reference herein in their entirety.

In one embodiment, the plant cells are selected from tobacco (*Nicotiana tabacum*), tomato (*Solanum lycopersicum*), potato (*Solanum tuberosum*), eggplant (*Solanum melongena*), tree tobacco (*Nicotiana glauca*), European black nightshade (*Solanum nigrum*), *Petunia* (*Petunia* x *hybrida*) and *Nicotiana benthamiana* cells. In another embodiment, the plant cells are from any of the plants described hereinbelow.

In one embodiment in which polynucleotides are introduced into plant cells, the plant cells may be derived from any plant organ of interest, as described hereinbelow. In one embodiment, the polynucleotide is introduced into a portion of a plant organ. In one embodiment, the polynucleotide is introduced into a portion of a flower. In one embodiment, the portion of the flower is the petal, stamen, anther, stigma, or a combination thereof.

This invention also provides methods for manufacturing transgenic seed that can be used to produce a crop of transgenic plants with an enhanced trait resulting from expression of a stably-integrated recombinant DNA construct.

In another embodiment, cells of the present invention are cells from a micro-organism. In another embodiment, the cell is a yeast cell. In one embodiment, the yeast cell is a *Saccharomyces cerevisiae* cell. In another embodiment, the cell of the present invention is a bacterial cell. In one embodiment, the bacterial cell is an *Escherichia coli* cell. In another embodiment, the cell is an *Acremonium rutihun, Aspergillus oryzae, Yarrowia lipolytica, Bacillus* sp. JPJ, *Brevundimonas* sp. SGJ, *E. herbicola, Citrobacter freundii, Symbiobacterium*, or *Pseudomonas aeruginosa* cell. In another embodiment, the bacterial cell is from a bacterium involved in fermentation of dairy products. In one embodiment, the bacterium is *Streptococcus lactis*. In another embodiment, the bacterium is a *Lactobacillus*. In one embodiment, the *Lactobacillus* is *Lactobacillus bulgaricus*. In another embodiment, the bacterium is a *Lactococcus* or a *Leuconostoc*.

Plants and Plant Parts

In another embodiment, the present invention provides a plant or part thereof produced by a method of increasing the levels of one or more betalains or L-DOPA in a plant or in a plant part comprising causing or allowing the expression of a DOPA 4,5-dioxygenase (DOD) enzyme, CYP76AD6, CYP76AD15, or a combination thereof, CYP76AD1, or a combination thereof, within said plant or plant part. In one embodiment, a plant expressing DOD and CYP76AD1 and not CYP76AD6 or CYP76AD15, also expresses a betalain related glucosyltransferase.

In one embodiment, the plant does not naturally produce betalains. In another embodiment, the plant produces low levels of betalains. In another embodiment, the plant does not naturally produce detectable levels of betalains.

In another embodiment, plants or plant parts as described herein naturally produce betalains; however, the genetically modified plant or plant parts have an altered level of betalains or of a particular betalain, thereby altering the color and/or properties of the genetically modified plant. In one embodiment, altered levels of betalains are increased levels. In another embodiment, altered levels of betalains are decreased levels.

In another embodiment, the present invention provides a plant or part thereof comprising a nucleic acid sequence encoding CYP76AD1, a nucleic acid sequence encoding CYP76AD6, CYP76AD15, or a combination thereof, a nucleic acid sequence encoding DOPA 4,5-dioxygenase (DOD) enzyme, or a combination thereof.

In another embodiment, betalains or L-DOPA are produced as described herein in a whole plant. In one embodiment, a seed is genetically modified such that betalains or L-DOPA are produced in a whole plant. In another embodiment, betalains or L-DOPA are produced in a particular organ of a plant. In another embodiment, betalains or L-DOPA are produced in a section of an organ of a plant. For example, betalains or L-DOPA may be produced in some plant cells in the leaf or other organ of a plant.

In another embodiment, the present invention provides an ornamental plant produced by a method of increasing the levels of one or more betalains in a plant or in a plant part thereof comprising causing or allowing the expression of a DOPA 4,5-dioxygenase (DOD) enzyme and CYP76AD6, CYP76AD15, or a combination thereof, CYP76AD1, or a combination thereof, within said plant or plant part. In one embodiment, if the ornamental plant expresses CYP76AD1 and DOD and not CYP76AD6 or CYP76AD15, it further expresses a betalain related glucosyltransferase.

In another embodiment, the present invention provides an ornamental plant comprising a nucleic acid sequence encoding CYP76AD1, CYP76AD6, CYP76AD15, or a combination thereof, and a nucleic acid sequence encoding DOPA 4,5-dioxygenase (DOD) enzyme.

In one embodiment, different parts or organs of an organism of the present invention comprise different pigmentation due to the expression of multiple cytochrome P450s (e.g., CYP76AD6, CYP76AD1) under different, non-constitutive promoter sequences (e.g. fruit-specific, flower-specific or inducible promoters). In one embodiment, the organism is a plant and the different pigmentation are in different parts of the plant. In one embodiment, the plant is an ornamental plant.

In another embodiment, the present invention provides a food crop produced by a method of increasing the levels of one or more betalains in a plant or part thereof that serves as a food crop comprising causing or allowing the expression of a DOPA 4,5-dioxygenase (DOD) enzyme and CYP76AD6, CYP76AD15, or a combination thereof, CYP76AD1, or a combination thereof, within said plant or part thereof. In one embodiment, if the food crop expresses CYP76AD1 and DOD and not CYP76AD6 or CYP76AD15, it further expresses a betalain related glucosyltransferase.

In another embodiment, the present invention provides plant or part thereof that serves as a food crop comprising a nucleic acid sequence encoding CYP76AD1, CYP76AD6, CYP76AD15, or a combination thereof, and a nucleic acid sequence encoding DOPA 4,5-dioxygenase (DOD) enzyme.

In one embodiment, the compositions and method of the present invention comprise one or more plant parts. In one embodiment, a plant part as described herein is a plant organ. In one embodiment, the plant part is a leaf, stem, root, flower, seed, tuber, or fruit. In one embodiment, the plant part is the edible portion of the plant. In one embodiment, the compositions and method of the present invention comprise one or more portions of one or more plant parts. In one embodiment, the portion of the plant part is a portion of a flower. In one embodiment, the portion of the flower is the petal, stamen, anther, or stigma.

In one embodiment, CYP76AD6, CYP76AD15, or a combination thereof, and other genes of the invention described herein can be transformed into a plant or a plant cell. The term "plant," as used herein may relate to any monocot or dicot plant. Examples of monocot plants include, but are not limited to, corn, wheat, rice, sugar cane, and banana. Examples of dicot plants include, but are not limited to, soybean, beans, peas, lentils, peanuts, tomatoes, potatoes, cotton, and perennial fruit trees including grapes, apple, and orange.

In one embodiment, the plant is tobacco (*Nicotiana tabacum*), tomato (*Solanum lycopersicum*), potato (*Solanum tuberosum*), eggplant (*Solanum melongena*), tree tobacco (*Nicotiana glauca*), European black nightshade (*Solanum nigrum*), *Petunia* (*Petunia* x *hybrida*) or *Nicotiana benthamiana*. In another embodiment, the plant is *B. vulgaris*. In another embodiment, the plant is *Mirabilis jalapa*.

In one embodiment, a plant of the present invention is a crop plant. In one embodiment, the crop plant is *Solanum tuberosum* (Potato). In another embodiment, the crop plant is *Zea mays* (Maize). In another embodiment, the crop plant is *Oryza sativa* (Rice). In another embodiment, the crop plant is *Manihot esculenta* (Cassava). In another embodiment, the crop plant is *Hordeum vulgare* (Barley). In another embodiment, the crop plant is *Triticum aestivum* (Wheat). In another embodiment, the crop plant is *Sorghum bicolor*. In another embodiment, the crop plant is *Brassica napus* (Rapeseed). In another embodiment, the crop plant is *Ricinus communis* (Castor). In another embodiment, the crop plant is *Phaseolus vulgaris* (Bean). In another embodiment, the crop plant is *Gossypium histrum* (Cotton). In another embodiment, the crop plant is *Glycine max* (Soybean). In another embodiment, the crop plant is *Beta vulgaris* (Beet). In another embodiment, the crop plant is Musa acuminate (Banana). In another embodiment, the crop plant is *Capsicum annuum* (Sweet and Chili Peppers). In another embodiment, the crop plant is *Cicer arietinum* (Chick pea). In another embodiment, the crop plant is *Solanum lycopersicum* (Tomato). In another embodiment, the crop plant is *Elaeis guineensis* (African oilpalm). In another embodiment, the crop plant is *Setaria* italic (Foxtail millet).

In another embodiment, a plant of the present invention is a bamboo, which in one embodiment is river cane (*Arundinaria gigantea*) and switch cane (*Arundinaria tecta*). In another embodiment, the plant is a *Lemna*.

In another embodiment, a plant of the present invention is a moss. In one embodiment, the moss is a *Sphagnum*. In one embodiment, the *Sphagnum* species is *cristatum* or *subnitens*. In one embodiment, the moss is used for peat. In one embodiment, peat is used for fuel, as a horticultural soil additive, and in smoking malt in the production of Scotch whisky. In another embodiment, the moss is used for decorative purposes, such as in gardens and in the florist trade. In another embodiment, the moss is used as insulation. In another embodiment, the moss is used as an absorber of liquids. In another embodiment, moss is used for first-aid dressings, for diapers or napkins. In another embodiment, the moss is a *Physcomitrella patens*. In another embodiment, the moss is a *Fontinalis antipyretica* which, in one embodiment, is used to subdue fires.

Plants included in the invention are any plants amenable to transformation techniques, including gymnosperms and angiosperms, both monocotyledons and dicotyledons.

Examples of monocotyledonous angiosperms include, but are not limited to, asparagus, field and sweet corn, barley, wheat, rice, sorghum, onion, pearl millet, rye and oats and other cereal grains.

Examples of dicotyledonous angiosperms include, but are not limited to tomato, tobacco, cotton, rapeseed, field beans, soybeans, peppers, lettuce, peas, alfalfa, clover, cole crops or *Brassica oleracea* (e.g., cabbage, broccoli, cauliflower, brussel sprouts), radish, carrot, beets, eggplant, spinach, cucumber, squash, melons, cantaloupe, sunflowers and various ornamentals.

In another embodiment, any species of woody, ornamental or decorative, crop or cereal, fruit or vegetable plant, and algae (e.g., *Chlamydomonas reinhardtii*) may be used in the compositions and methods provided herein. Non-limiting examples of plants include plants from the genus *Arabidopsis* or the genus *Oryza*. Other examples include plants from the genuses Acorus, *Aegilops, Allium, Amborella, Antirrhinum, Apium, Arachis, Beta, Betula, Brassica, Capsicum, Ceratopteris, Citrus, Cryptomeria, Cycas, Descurainia, Eschscholzia, Eucalyptus, Glycine, Gossypium, Hedyotis, Helianthus, Hordeum, Ipomoea, Lactuca, Linum, Liriodendron, Lotus, Lupinus, Lycopersicon, Medicago, Mesembryanthemum, Nicotiana, Nuphar, Pennisetum, Peryea, Phaseolus, Physcomitrella, Picea, Pinus, Poncirus, Populus, Prunus, Robinia, Rosa, Saccharum, Schedonorus, Secale, Sesamum, Solanum, Sorghum, Stevia, Thellungiella, Theobroma, Triphysaria, Triticum, Vitis, Zea*, or *Zinnia*.

Examples of woody species include poplar, pine, *sequoia*, cedar, oak, etc.

In certain embodiments, plants of the present invention are crop plants (for example, cereals and pulses, maize, wheat, potatoes, tapioca, rice, sorghum, millet, cassaya, barley, pea, and other root, tuber, or seed crops). Exemplary cereal crops used in the compositions and methods of the invention include, but are not limited to, any species of grass, or grain plant (e.g., barley, corn, oats, rice, wild rice, rye, wheat, millet, sorghum, triticale, etc.), non-grass plants (e.g., buckwheat flax, legumes or soybeans, etc.). Grain plants that provide seeds of interest include oil-seed plants and leguminous plants. Other seeds of interest include grain seeds, such as corn, wheat, barley, rice, sorghum, rye, etc. Oil seed plants include cotton, soybean, safflower, sunflower, *Brassica*, maize, alfalfa, palm, coconut, etc. Other important seed crops are oil-seed rape, sugar beet, maize, sunflower, soybean, and sorghum. Leguminous plants include beans and peas. Beans include guar, locust bean, fenugreek, soybean, garden beans, cowpea, mungbean, lima bean, fava bean, lentils, chickpea, etc.

Horticultural plants to which the present invention may be applied may include lettuce, endive, and vegetable brassicas including cabbage, broccoli, and cauliflower, and carnations and geraniums. The present invention may also be applied to tobacco, cucurbits, carrot, strawberry, sunflower, tomato, pepper, chrysanthemum, poplar, eucalyptus, and pine.

The present invention may be used for transformation of other plant species, including, but not limited to, canola (*Brassica napus, Brassica rapa* ssp.), alfalfa (*Medicago sativa*), rye (*Secale cereale*), sorghum (*Sorghum bicolor, Sorghum vulgare*), sunflower (*Helianthus annuus*), wheat (*Triticum aestivum*), soybean (*Glycine max*), tobacco (*Nicotiana tabacum, Nicotiana benthamiana*), tree tobacco (*Nicotiana glauca*), peanuts (*Arachis hypogaea*), cotton (*Gossypium hirsutum*), sweet potato (*Ipomoea batatus*), cassaya (*Manihot esculenta*), coffee (*Coffea* spp.), coconut (*Cocos nucifera*), pineapple (*Ananas comosus*), citrus trees (Citrus spp.), cocoa (*Theobroma cacao*), tea (*Camellia sinensis*), banana (Musa spp.), avocado (*Persea americana*), fig (*Ficus casica*), guava (*Psidium guajava*), mango (*Mangifera indica*), olive (*Olea europaea*), *papaya* (*Carica papaya*), cashew (*Anacardium occidentale*), macadamia (*Macadamia integrifolia*), almond (*Prunus amygdalus*), sugar beets (*Beta vulgaris*), tomato (*Solanum lycopersicum*), eggplant (*Solanum melongena*), European black nightshade (*Solanum nigrum*), *Petunia* (*Petunia* x *hybrida*), oats, barley, millet, fruit, vegetables, ornamentals, turfgrass, and conifers.

In addition to a plant, the present invention provides any clone of such a plant, seed, selfed or hybrid progeny and descendants, and any part of any of these, such as cuttings, seed. The invention provides any plant propagule, that is any part which may be used in reproduction or propagation, sexual or asexual, including cuttings, seed and so on. Also encompassed by the invention is a plant which is a sexually or asexually propagated off-spring, clone or descendant of such a plant, or any part or propagule of said plant, off-spring, clone or descendant. Plant extracts and derivatives are also provided.

Throughout this application a plant, plant part, seed or plant cell transformed with—or interchangeably transformed by—a construct or transformed with or by a nucleic acid is to be understood as meaning a plant, plant part, seed or plant cell that carries said construct or said nucleic acid as a transgene due the result of an introduction of said construct or said nucleic acid by biotechnological means. The plant, plant part, seed or plant cell therefore comprises said recombinant construct or said recombinant nucleic acid. Any plant, plant part, seed or plant cell that no longer contains said recombinant construct or said recombinant nucleic acid after introduction in the past, is termed null-segregant, nullizygote or null control, but is not considered a plant, plant part, seed or plant cell transformed with said construct or with said nucleic acid within the meaning of this application.

In one embodiment, tyrosine is endogenous to an organism or part of an organism of the present invention. In another embodiment, an organism or part of an organism of the present invention synthesizes tyrosine. In another embodiment, an organism or part of an organism of the present invention is genetically modified to produce tyrosine. In another embodiment, an organism or part of an organism of the present invention is provided or fed with tyrosine. In another embodiment, an organism or part of an organism that comprises endogenous tyrosine is genetically modified as described herein in order to produce larger amounts of tyrosine, thereby increasing L-DOPA or betalain production. In another embodiment, an organism or part of an organism that comprises endogenous tyrosine is fed tyrosine in order to have larger amounts of available tyrosine, thereby increasing L-DOPA or betalain production.

Methods of Extracting L-DOPA and Betalains

In one embodiment, methods of the present invention further provide methods of extracting L-DOPA or betalains as described hereinbelow in Example 1 as well as using other L-DOPA or betalain extraction methods known in the art, such as, for example, Misra and Wagner (Indian J Biochem Biophys. 2007 February; 44(1):56-60), which is incorporated by reference herein in its entirety.

In another embodiment, L-DOPA or betalains are extracted from algae, yeast or bacterial culture using methods known in the art.

In another embodiment, the present invention provides a method of harvesting L-DOPA or betalains comprising the steps of producing L-DOPA or betalains as described herein and further comprising the step of extracting said L-DOPA or said betalain from the plant, plant part, colony, organ, tissue or cells that produce said L-DOPA or said betalain. In one embodiment, the plant part is a leaf, stem, root, flower, seed, tuber, or fruit.

In one embodiment, the L-DOPA or betalain is extracted from the root of a plant. In one embodiment, L-DOPA or betalain is secreted through the roots of a plant to a liquid or other medium and then harvested from the liquid or other medium. In another embodiment, the L-DOPA or betalain is extracted from the medium of a plant cell suspension, such as BY2 tobacco.

In another embodiment, L-DOPA or betalain is extracted from a water plant. In one embodiment, the water plant is a *Lemna*. In one embodiment, the *Lemna* is *Lemna aequinoctialis; Lemna perpusilla; Lemna; Lemna gibba; Lemna minor; Lemna trisulca* Uninerves; *Lemna minuta; Lemna valdiviana; Lemna japonica; Lemna obscura; Lemna tenera; Lemna turionifera; Lemna yungensis*, or a combination thereof.

Polypeptides

In one embodiment, the present invention provides a chimeric polypeptide encoded by a recombinant polynucleotide comprising a nucleic acid encoding CYP76AD6. In one embodiment, the amino acid sequence of CYP76AD6 comprises: the amino acid sequence encoding CYP76AD6 comprises:

(SEQ ID NO: 18)
MDNATLAVILSILFVFYHIFKSFFTNSSSRRLPPGPKPVPIFGNIFDLGE

KPHRSFANLSKIHGPLISLKLGSVTTIVVSSASVAEEMFLKNDQALANRT

IPDSVRAGDHDKLSMSWLPVSQKWRNMRKISAVQLLSNQKLDASQPLRQA

KVKQLLSYVQVCSEKMQPVDIGRAAFTTSLNLLSNTFFSIELASHESSAS

QEFKQLMWNIMEEIGRPNYADFFPILGYIDPFGIRRRLAGYFDKLIDVFQ

DIIRERQKLRSSNSSGAKQTNDILDTLLKLHEDNELSMPEINHLLVDIFD

AGTDTTASTLEWAMAELVKNPEMMTKVQIEIEQALGKDCLDIQESDISKL

PYLQAIIKETLRLHPPTVFLLPRKADNDVELYGYVVPKNAQVLVNLWAIG

RDPKVWKNPEVFSPERFLDCNIDYKGRDFELLPFGAGRRICPGLTLAYRM

LNLMLATLLQNYNWKLEDGINPKDLDMDEKFGITLQKVKPLQVIPVPRN.

In another embodiment, the present invention provides a chimeric polypeptide encoded by a recombinant polynucleotide comprising a nucleic acid encoding CYP76AD1. In one embodiment, the amino acid sequence of CYP76AD1 comprises:

(SEQ ID NO: 14)
MDHATLAMILAIWFISFHFIKLLFSQQTTKLLPPGPKPLPIIGNILEVGK

KPHRSFANLAKIHGPLISLRLGSVTTIVVSSADVAKEMFLKKDHPLSNRT

IPNSVTAGDHHKLTMSWLPVSPKWRNFRKITAVHLLSPQRLDACQTFRHA

KVQQLYEYVQECAQKGQAVDIGKAAFTTSLNLLSKLFFSVELAHHKSHTS

QEFKELIWNEVIEDIGKPNYADYFPILGCVDPSGIRRRLACSFDKLIAVF

QGIICERLAPDSSTTTTTTDDVLDVLLQLFKQNELTMGEINHLLVDIFD

AGTDTTSSTFEWVMTELIRNPEMMEKAQEEIKQVLGKDKQIQESDIINLP

YLQAIIKETLRLHPPTVFLLPRKADTDVELYGYIVPKDAQILVNLWAIGR

-continued

DPNAWQNADIFSPERFIGCEIDVKGRDFGLLPFGAGRRICPGMNLAIRML

TLMLATLLQFFNWKLEGDISPKDLDMDEKFGIALQKTKPLKLIPIPRY.

In another embodiment, the present invention provides a chimeric polypeptide encoded by a recombinant polynucleotide comprising a nucleic acid encoding a DOPA 4,5-dioxygenase (DOD) enzyme. In one embodiment, the DOD enzyme is *Beta vulgaris* DODA1 (BvDODA1). In one embodiment, the amino acid sequence encoding of BvDODA1 comprises:

(SEQ ID NO: 42)

MKMMNGEDANDQMIKESFFITHGNPILTVEDTHPLRPFFETWREKIFSKK

PKAILIISGHWETVKPTVNAVHINDTIHDFDDYPAAMYQFKYPAPGEPEL

ARKVEEILKKSGFETAETDQKRGLDHGAWVPLMLMYPEADIPVCQLSVQP

HLDGTYHYNLGRALAPLKNDGVLIIGSGSATHPLDETPHYFDGVAPWAAA

FDSWLRKALINGRFEEVNIYESKAPNWKLAHPFPEHFYPLHVVLGAAGEK

WKAELIHSSWDHGTLCHGSYKFTSA.

In one embodiment, the present invention provides a chimeric polypeptide encoded by a recombinant polynucleotide comprising a nucleic acid encoding cyclo-DOPA 5-O-glucosyltransferase (cDOPA5GT). In one embodiment, the amino acid sequence of cDOPA5GT comprises:

(SEQ ID NO: 43)

MTAIKMNTNGEGETQHILMIPFMAQGHLRPFLELAMFLYKRSHVIITLLT

TPLNAGFLRHLLHHHSYSSSGIRIVELPFNSTNHGLPPGIENTDKLTLPL

VVSLFHSTISLDPHLRDYISRHFSPARPPLCVIHDVFLGWVDQVAKDVGS

TGVVFTTGGAYGTSAYVSIWNDLPHQNYSDDQEFPLPGFPENHKFRRSQL

HRFLRYADGSDDWSKYFQPQLRQSMKSFGWLCNSVEEIETLGFSILRNYT

KLPIWGIGPLIASPVQHSSSDNNSTGAEFVQWLSLKEPDSVLYISFGSQN

TISPTQMMELAAGLESSEKPFLWVIRAPFGFDINEEMRPEWLPEGFEERM

KVKKQGKLVYKLGPQLEILNHESIGGFLTHCGWNSILESLREGVPMLGWP

LAAEQAYNLKYLEDEMGVAVELARGLEGEISKEKVKRIVEMILERNEGSK

GWEMKNRAVEMGKKLKDAVNEEKELKGSSVKAIDDFLDAVMQAKLEPSL

Q.

In one embodiment, a polypeptide of the present invention comprises an amino acid sequence of CYP76AD6, CYP76AD15, or a combination thereof, and an amino acid sequence of CYP76AD1. In another embodiment, a polypeptide of the present invention comprises an amino acid sequence of CYP76AD6, CYP76AD15, or a combination thereof, and an amino acid sequence of a DOD enzyme. In another embodiment, a polypeptide of the present invention comprises an amino acid sequence of CYP76AD1 and an amino acid sequence of a DOD enzyme. In another embodiment, a polypeptide of the present invention comprises an amino acid sequence of CYP76AD6, CYP76AD15, or a combination thereof, an amino acid sequence of CYP76AD1, and an amino acid sequence of a DOD enzyme. In another embodiment, a polypeptide of the present invention comprises an amino acid sequence of CYP76AD6, CYP76AD15, or a combination thereof, an amino acid sequence of CYP76AD1, and an amino acid sequence of a betalain related glucosyltransferase. In another embodiment, a polypeptide of the present invention comprises an amino acid sequence encoding of CYP76AD6, CYP76AD15, or a combination thereof, an amino acid sequence of a DOD enzyme and an amino acid sequence encoding a betalain related glucosyltransferase. In another embodiment, a polypeptide of the present invention comprises an amino acid sequence of CYP76AD1, an amino acid sequence of a DOD enzyme and an amino acid sequence of a betalain related glucosyltransferase. In another embodiment, a polypeptide of the present invention comprises an amino acid sequence of CYP76AD6, CYP76AD15, or a combination thereof, an amino acid sequence of CYP76AD1, an amino acid sequence of a DOD enzyme and an amino acid sequence of a betalain related glucosyltransferase.

In another embodiment, any of the polypeptides described hereinabove further comprises a betalain related glucosyltransferase. In one embodiment, the betalain related glucosyltransferase is cyclo-DOPA 5-O-glucosyltransferase or betanidin-5-O-glucosyltransferase. In one embodiment, the cyclo-DOPA 5-O-glucosyltransferase is *M. jalapa* gene cyclo-DOPA 5-O-glucosyltransferase (cDOPA5GT) (SEQ ID NO: 43).

In one embodiment, the present invention provides a chimeric polypeptide encoded by a recombinant polynucleotide as described herein.

In another embodiment, the present invention provides a chimeric polypeptide comprising CYP76AD6, CYP76AD15, or a combination thereof, CYP76AD1, a DOPA 4,5-dioxygenase (DOD) enzyme, a betalain related glucosyltransferase, or a combination thereof, wherein said proteins are expressed in tandem.

In another embodiment, the present invention provides a chimeric polypeptide comprising CYP76AD1, a DOPA 4,5-dioxygenase (DOD) enzyme, and, optionally, a betalain related glucosyltransferase, wherein said proteins are expressed in tandem.

In another embodiment, the present invention provides a chimeric polypeptide comprising CYP76AD6, CYP76AD15, or a combination thereof, and a DOPA 4,5-dioxygenase (DOD) enzyme, wherein said proteins are expressed in tandem.

In another embodiment, the present invention provides a chimeric polypeptide comprising CYP76AD6, CYP76AD15, or a combination thereof, CYP76AD1, or a combination thereof, a DOPA 4,5-dioxygenase (DOD) enzyme, and, optionally a betalain related glucosyltransferase, wherein said proteins are expressed in tandem.

In one embodiment, a "chimeric" or "fusion" polypeptide or protein is a polypeptide or protein created through the joining of two or more genes that originally coded for separate proteins.

It is to be understood that according to the present invention, CYP76AD6 and CYP76AD6-like polypeptides from plants other than *Beta vulgaris* can be used in place of CYP76AD6 from *Beta vulgaris* in the compositions and methods described herein. In one embodiment, the CYP76AD6-like polypeptide is from Caryophyllales. In one embodiment, the CYP76AD6-like polypeptide is a homologue within the CYP76AD1-beta clade, as described in Brockington et al. (2015) (New Phytol. 2015 September; 207(4):1170-80), which is incorporated herein by reference in its entirety.

In one embodiment, CYP76AD15 or a homologue, isoform, or variant thereof, may be used in place of CYP76AD6 in the compositions and methods of the present invention.

CYP76AD15 from *Mirabilis jalapa* has a similar function as CYP76AD6 from *Beta vulgaris*. In one embodiment, CYP76AD15 is an enzyme involved in converting tyrosine to L-DOPA. In one embodiment the amino acid sequence of CYP76AD15 comprises:

```
                                          (SEQ ID NO: 44)
MENTMLGVILATIFLTFHIMKMLFSPSKVKLPPGPRPLPIIGNILELG

DKPHRSFANLAKIHGPLVTLKLGSVTTIVVSSSEVAKEMFLKNDQPLA

NRTIPDSVRAGNHDKLSMSWLPVSPKWRNLRKISAVQLLSTQRLDASQ

AHRQAKIKQLIEYVKKCSKIGQYVDIGQVAFTTSLNLLSNTFFSKELA

SFDSDNAQEFKQLMWCIIVIEEIGRPNYADYFPILGYVDPFGARRRLS

RYFDQLIEVFQVIIRERLTHDNNIVGNNNDVLATLLDLYKQNELTMDE

INHLLVDIFDAGTDTTASTLEWAMSELIKNPHIMAKAQEEVRRATMSH

GGATVAEIQESDINNLPYIQSIIKETLRLHPPTVFLLPRKADVDVQLF

GYVVPKNAQVLVNLWAIGRDPNVWPDPEVFSPERFMDCEIDVKGRDFE

LLPFGAGRRICPGLSLAYRMLNLMLANMVHSFDWKLPGVENGSGSEMD

SLDMDEKFGITLQKVQPLKVIPVSRK.
```

In one embodiment, the present invention provides an isolated polypeptide comprising an amino acid sequence of CYP76AD6, CYP76AD15, or a combination thereof, or another polypeptide described herein. In another embodiment, the present invention provides a non-naturally occurring polypeptide comprising an amino acid sequence of CYP76AD6, CYP76AD15, or a combination thereof, or another polypeptide described herein. In one embodiment, the CYP76AD6, CYP76AD15, or a combination thereof, sequence is a modified sequence. In one embodiment, it is an enhanced sequence. In one embodiment, it is an optimized sequence.

In one embodiment a polypeptide of the present invention optionally comprises CYP76AD6. In one embodiment, the amino acid sequence of CYP76AD6 is as set forth in SEQ ID NO: 18. In another embodiment, the CYP76AD6 utilized in methods and compositions of the present invention is a homologue of SEQ ID NO: 18. In another embodiment, the CYP76AD6 utilized in methods and compositions of the present invention is a variant of SEQ ID NO: 18. In another embodiment, the CYP76AD6 utilized in methods and compositions of the present invention is a fragment of SEQ ID NO: 18. In another embodiment, the CYP76AD6 utilized in methods and compositions of the present invention is an isoform of SEQ ID NO: 18. In another embodiment, the CYP76AD6 utilized in methods and compositions of the present invention is a functional homologue, functional variant, functional fragment, or functional isoform of SEQ ID NO: 18.

In one embodiment a polypeptide of the present invention optionally comprises CYP76AD15. In one embodiment, the amino acid sequence of CYP76AD15 is as set forth in SEQ ID NO: 44. In another embodiment, the CYP76AD15 utilized in methods and compositions of the present invention is a homologue of SEQ ID NO: 44. In another embodiment, the CYP76AD15 utilized in methods and compositions of the present invention is a variant of SEQ ID NO: 44. In another embodiment, the CYP76AD15 utilized in methods and compositions of the present invention is a fragment of SEQ ID NO: 44. In another embodiment, the CYP76AD15 utilized in methods and compositions of the present invention is an isoform of SEQ ID NO: 44.

In another embodiment, the CYP76AD15 utilized in methods and compositions of the present invention is a functional homologue, functional variant, functional fragment, or functional isoform SEQ ID NO: 44.

In one embodiment a polypeptide of the present invention optionally comprises CYP76AD1. In one embodiment, the amino acid sequence of CYP76AD1 is as set forth in SEQ ID NO: 14. In another embodiment, the CYP76AD1 utilized in methods and compositions of the present invention is a homologue of SEQ ID NO: 14. In another embodiment, the CYP76AD1 utilized in methods and compositions of the present invention is a variant of SEQ ID NO: 14. In another embodiment, the CYP76AD1 utilized in methods and compositions of the present invention is a fragment of SEQ ID NO: 14. In another embodiment, the CYP76AD1 utilized in methods and compositions of the present invention is an isoform of SEQ ID NO: 14.

In another embodiment, the CYP76AD1 utilized in methods and compositions of the present invention is a functional homologue, functional variant, functional fragment, or functional isoform of SEQ ID NO: 14.

In one embodiment a polypeptide of the present invention optionally comprises BvDODA1. In one embodiment, the amino acid sequence of BvDODA1 is as set forth in SEQ ID NO: 42. In another embodiment, the BVDODA1 utilized in methods and compositions of the present invention is a homologue of SEQ ID NO: 42. In another embodiment, the BVDODA1 utilized in methods and compositions of the present invention is a variant of SEQ ID NO: 42. In another embodiment, the BVDODA1 utilized in methods and compositions of the present invention is a fragment of SEQ ID NO: 42. In another embodiment, the BVDODA1 utilized in methods and compositions of the present invention is an isoform of SEQ ID NO: 42.

In another embodiment, the BVDODA1 utilized in methods and compositions of the present invention is a functional homologue, functional variant, functional fragment, or functional isoform of SEQ ID NO: 42.

In one embodiment, a polypeptide of the present invention optionally comprises cDOPA5GT. In one embodiment, the amino acid sequence of cDOPA5GT is as set forth in SEQ ID NO: 43. In another embodiment, the cDOPA5GT utilized in methods and compositions of the present invention is a homologue of SEQ ID NO: 43. In another embodiment, the cDOPA5GT utilized in methods and compositions of the present invention is a variant of SEQ ID NO: 43. In another embodiment, the cDOPA5GT utilized in methods and compositions of the present invention is a fragment of SEQ ID NO: 43. In another embodiment, the cDOPA5GT utilized in methods and compositions of the present invention is an isoform of SEQ ID NO: 43.

In another embodiment, the cDOPA5GT utilized in methods and compositions of the present invention is a functional homologue, functional variant, functional fragment, or functional isoform of SEQ ID NO: 43.

In some embodiments, “polypeptide”, “engineered polypeptide”, or “protein” as used herein encompasses native polypeptides (either degradation products, synthetically synthesized polypeptides or recombinant polypeptides) and peptidomimetics (typically, synthetically synthesized polypeptides), as well as peptoids and semipeptoids which are polypeptide analogs, which have, in some embodiments, modifications rendering the polypeptides even more stable while in a body or more capable of penetrating into cells.

In some embodiments, modifications include, but are limited to C terminus modification, polypeptide bond modification, including, but not limited to, CH2-NH, CH2-S, CH2-S═O, O═C—NH, CH2-O, CH2-CH2, S═C—NH, CH═CH or CF═CH, backbone modifications, and residue modification. Methods for preparing peptidomimetic compounds are well known in the art and are specified, for example, in Quantitative Drug Design, C. A. Ramsden Gd., Chapter 17.2, F. Choplin Pergamon Press (1992), which is incorporated by reference as if fully set forth herein. Further details in this respect are provided hereinunder.

In some embodiments, polypeptide bonds (—CO—NH—) within the polypeptide are substituted. In some embodiments, the polypeptide bonds are substituted by N-methylated bonds (—N(CH3)—CO—). In some embodiments, the polypeptide bonds are substituted by ester bonds (—C(R)H—C—O—O—C(R)—N—). In some embodiments, the polypeptide bonds are substituted by ketomethylen bonds (—CO—CH2-). In some embodiments, the polypeptide bonds are substituted by α-aza bonds (—NH—N(R)—CO—), wherein R is any alkyl, e.g., methyl, carba bonds (~CH2-NH—). In some embodiments, the polypeptide bonds are substituted by hydroxyethylene bonds (—CH(OH)—CH2-). In some embodiments, the polypeptide bonds are substituted by thioamide bonds (—CS—NH—). In some embodiments, the polypeptide bonds are substituted by olefinic double bonds (—CH═CH—). In some embodiments, the polypeptide bonds are substituted by retro amide bonds (—NH—CO—). In some embodiments, the polypeptide bonds are substituted by polypeptide derivatives (—N(R)—CH2-CO—), wherein R is the "normal" side chain, naturally presented on the carbon atom. In some embodiments, these modifications occur at any of the bonds along the polypeptide chain and in one embodiment at several (2-3 bonds) at the same time.

In some embodiments, natural aromatic amino acids of the polypeptide such as Trp, Tyr and Phe, are substituted for synthetic non-natural acid such as Phenylglycine, TIC, naphthylelanine (Nol), ring-methylated derivatives of Phe, halogenated derivatives of Phe or o-methyl-Tyr. In some embodiments, the polypeptides of the present invention include one or more modified amino acid or one or more non-amino acid monomers (e.g. fatty acid, complex carbohydrates etc).

In one embodiment, "amino acid" or "amino acid sequence" is understood to include the 20 naturally occurring amino acid; those amino acid often modified post-translationally in vivo, including, for example, hydroxyproline, phosphoserine and phosphothreonine; and other unusual amino acid including, but not limited to, 2-aminoadipic acid, hydroxylysine, isodesmosine, nor-valine, nor-leucine and ornithine. In one embodiment, "amino acid" includes both D- and L-amino acids.

In some embodiments, the polypeptides of the present invention are utilized in therapeutics which requires the polypeptides to be in a soluble form. In some embodiments, the polypeptides of the present invention include one or more non-natural or natural polar amino acid, including but not limited to serine and threonine which are capable of increasing polypeptide solubility due to their hydroxyl-containing side chain.

In some embodiments, the engineered polypeptide of the present invention is utilized in a linear form, although it will be appreciated by one skilled in the art that in cases where cyclicization does not severely interfere with engineered polypeptides characteristics, cyclic forms of the engineered polypeptides can also be utilized.

In some embodiments, the engineered polypeptides of the present invention are biochemically synthesized such as by using standard solid phase techniques. In some embodiments, these biochemical methods include exclusive solid phase synthesis, partial solid phase synthesis, fragment condensation, or classical solution synthesis.

In some embodiments, recombinant protein techniques are used to generate the engineered polypeptides of the present invention. In some embodiments, recombinant protein techniques are used for the generation of relatively long polypeptides (e.g., longer than 18-25 amino acids). In some embodiments, recombinant protein techniques are used for the generation of large amounts of the engineered polypeptides of the present invention. In some embodiments, recombinant techniques are described by Bitter et al., (1987) Methods in Enzymol. 153:516-544, Studier et al. (1990) Methods in Enzymol. 185:60-89, Brisson et al. (1984) Nature 310:511-514, Takamatsu et al. (1987) EMBO J. 6:307-311, Coruzzi et al. (1984) EMBO J. 3:1671-1680 and Brogli et al., (1984) Science 224:838-843, Gurley et al. (1986) Mol. Cell. Biol. 6:559-565 and Weissbach & Weissbach, 1988, Methods for Plant Molecular Biology, Academic Press, NY, Section VIII, pp 421-463, which are incorporated herein by reference in their entirety.

In one embodiment, the present invention provides a chimeric polypeptide comprising a CYP76AD1-β clade polypeptide. In one embodiment, the CYP76AD1-β clade polypeptide is CYP76AD6. In another embodiment, the CYP76AD1-β clade polypeptide is CYP76AD15. In one embodiment, the present invention provides a chimeric polypeptide comprising a CYP76AD1-β clade polypeptide but excluding the amino acid sequence of the CYP76AD1 paralogs from sugar beet known as Bv9_228610_yqeq or Bv9_228860 ickx, which do not produce betaxanthin when transformed into yeast with DOD. In one embodiment, the present invention provides a chimeric polypeptide comprising a CYP76AD1-β clade polypeptide but excluding the following amino acid sequence:

(SEQ ID NO: 34)
```
MDNATLAVILSILFVFYHIFKSFFTNSSSRRLPPGPKPVPIFGNIFDL
GEKPHRSFANLSKIHGPLISLKLGSVTTIVVSSASVAEEMFLKNDQAL
ANRTIPDSVRAGDHDKLSMSWLPVSQKWRNMRKISAVQLLSNQKLDAS
QPLRQTKVKQLLSYVQDCSKKMQPVDIGRAAFTTSLNLLSNTFFSIEL
ASHESSASQEFKQLMWNIMEEIGRPNYADFFPILGYIDPFGIRRRLAG
YFDKLIDVFQDIIRERQKLRSSNSSGAKQTNDILDTLLKLHEDNELSM
PEINHLLVDIFDAGTDTTASTLEWAMAELVKNPEMMTKVQIEIEQALG
KDCLDIQESDISKLPYLQGIIKETLRLHPPTVFLLPRKADNDVELYGY
VVPKNAQVLVNLWAIGRDPKVWKNPEVFSPERFLDCNIDYKGRDFELL
PFGAGRRICPGLTLAYRMLNLMLATLLQNYNWKLEDGINPKDLDMDEK
FGITLQKVKPLQVIPVPRN.
```

In one embodiment, the present invention provides methods comprising the step of "contacting" tyrosine with one or more polypeptides as described herein. In one embodiment, said contacting step conducted in vitro under conditions which allow the production of L-DOPA or betalains, as described herein.

Polypeptide Recovery

In one embodiment, methods of the present invention further provide methods of extracting betalains or L-DOPA from plants as described hereinbelow in Example 1 as well as using other betalain extraction methods known in the art. In another embodiment, betalains are extracted from algae, yeast or bacterial culture using methods known in the art. In one embodiment, the algae, yeast or bacterial culture are genetically modified to express betalains or L-DOPA.

In one embodiment, following a predetermined time in culture, recovery of a polypeptide is affected.

In one embodiment, the phrase "recovering the polypeptide" used herein refers to collecting the whole fermentation medium containing the polypeptide and need not imply additional steps of separation or purification.

In one embodiment, polypeptides of the present invention are purified using a variety of standard protein purification techniques, such as, but not limited to, affinity chromatography, ion exchange chromatography, filtration, electrophoresis, hydrophobic interaction chromatography, gel filtration chromatography, reverse phase chromatography, concanavalin A chromatography, chromatofocusing and differential solubilization.

In one embodiment, to facilitate recovery, the expressed coding sequence can be engineered to encode the polypeptide of the present invention and fused cleavable moiety. In one embodiment, a fusion protein can be designed so that the polypeptide can be readily isolated by affinity chromatography; e.g., by immobilization on a column specific for the cleavable moiety. In one embodiment, a cleavage site is engineered between the polypeptide and the cleavable moiety and the polypeptide can be released from the chromatographic column by treatment with an appropriate enzyme or agent that specifically cleaves the fusion protein at this site [e.g., see Booth et al., Immunol. Lett. 19:65-70 (1988); and Gardella et al., J. Biol. Chem. 265:15854-15859 (1990)].

In one embodiment, the polypeptide of the present invention is retrieved in "substantially pure" form.

In one embodiment, the phrase "substantially pure" refers to a purity that allows for the effective use of the protein in the applications described herein.

In one embodiment, the polypeptide of the present invention can also be synthesized using in vitro expression systems. In one embodiment, in vitro synthesis methods are well known in the art and the components of the system are commercially available.

Methods of producing betaxanthins in vitro using a DOD enzyme with its substrate L-DOPA and adding amino acids was described in Sekiguchi et al. (2010) (Journal of Agricultural and Food Chemistry 58, 12504-12509), which is incorporated herein by reference in its entirety. In one embodiment, the present method of in vitro synthesis of betalains is as described in Sekiguchi et al. but with the added step of synthesizing L-DOPA from tyrosine rather than providing L-DOPA as described in Sekiguchi et al.

In one embodiment, in vitro production of red-violet betalains (betacyanins) is performed using the same or similar conditions as for the production of betaxanthins, except that the CYP76AD1 enzyme is provided together with the DOD enzyme, and the substrate could be either tyrosine or L-DOPA. In one embodiment, the co-factor NADPH may be added to activate the CYP76AD1 enzyme.

In some embodiments, the recombinant polypeptides are synthesized and purified; their therapeutic efficacy can be assayed in vivo or in vitro.

Pharmaceutical Compositions

In another embodiment, provides a pharmaceutical composition comprising a recombinant polynucleotide or a chimeric polypeptide of the present invention. In one embodiment, the polypeptides and polynucleotides of the present invention can be provided to the individual as part of a pharmaceutical composition where it is mixed with a pharmaceutically acceptable carrier.

In one embodiment, a "pharmaceutical composition" refers to a preparation of one or more of the active ingredients described herein with other chemical components such as physiologically suitable carriers and excipients. The purpose of a pharmaceutical composition is to facilitate administration of a compound to an organism.

In one embodiment, "active ingredient" refers to the recombinant polynucleotide or the chimeric polypeptide, which is accountable for the biological or biochemical effect.

In other embodiments, the composition comprises additional components. In one embodiment, such additional components may comprise carriers or diluents including, but not limited to, a gum, a starch (e.g. corn starch, pregeletanized starch), a sugar (e.g. lactose, mannitol, sucrose, dextrose), a cellulosic material (e.g. microcrystalline cellulose), an acrylate (e.g. polymethylacrylate), calcium carbonate, magnesium oxide, talc, or mixtures thereof.

In other embodiments, pharmaceutically acceptable carriers for liquid formulations are aqueous or non-aqueous solutions, suspensions, emulsions or oils. Examples of non-aqueous solvents are propylene glycol, polyethylene glycol, and injectable organic esters such as ethyl oleate. Aqueous carriers include water, alcoholic/aqueous solutions, emulsions or suspensions, including saline and buffered media. Examples of oils are those of animal, vegetable, or synthetic origin, for example, peanut oil, soybean oil, olive oil, sunflower oil, fish-liver oil, another marine oil, or a lipid from milk or eggs.

In another embodiment, parenteral vehicles (for subcutaneous, intravenous, intraarterial, or intramuscular injection) include sodium chloride solution, Ringer's dextrose, dextrose and sodium chloride, lactated Ringer's and fixed oils. Intravenous vehicles include fluid and nutrient replenishers, electrolyte replenishers such as those based on Ringer's dextrose, and the like. Examples are sterile liquids such as water and oils, with or without the addition of a surfactant and other pharmaceutically acceptable adjuvants. In general, water, saline, aqueous dextrose and related sugar solutions, and glycols such as propylene glycols or polyethylene glycol are preferred liquid carriers, particularly for injectable solutions. Examples of oils are those of animal, vegetable, or synthetic origin, for example, peanut oil, soybean oil, olive oil, sunflower oil, fish-liver oil, another marine oil, or a lipid from milk or eggs.

In other embodiments, the compositions further comprise binders (e.g. acacia, cornstarch, gelatin, carbomer, ethyl cellulose, guar gum, hydroxypropyl cellulose, hydroxypropyl methyl cellulose, povidone), disintegrating agents (e.g. cornstarch, potato starch, alginic acid, silicon dioxide, croscarmelose sodium, crospovidone, guar gum, sodium starch glycolate), buffers (e.g. Tris-HCl, acetate, phosphate) of various pH and ionic strength, additives such as albumin or gelatin to prevent absorption to surfaces, detergents (e.g. Tween 20, Tween 80, Pluronic F68, bile acid salts), protease inhibitors, surfactants (e.g. sodium lauryl sulfate), permeation enhancers, solubilizing agents (e.g. glycerol, polyethylene glycerol), anti-oxidants (e.g. ascorbic acid, sodium metabisulfite, butylated hydroxyanisole), stabilizers (e.g.

hydroxypropyl cellulose, hyroxypropylmethyl cellulose), viscosity increasing agents (e.g. carbomer, colloidal silicon dioxide, ethyl cellulose, guar gum), sweeteners (e.g. aspartame, citric acid), preservatives (e.g. Thimerosal, benzyl alcohol, parabens), lubricants (e.g. stearic acid, magnesium stearate, polyethylene glycol, sodium lauryl sulfate), flow-aids (e.g. colloidal silicon dioxide), plasticizers (e.g. diethyl phthalate, triethyl citrate), emulsifiers (e.g. carbomer, hydroxypropyl cellulose, sodium lauryl sulfate), polymer coatings (e.g. poloxamers or poloxamines), coating and film forming agents (e.g. ethyl cellulose, acrylates, polymethacrylates) and/or adjuvants. Each of the above excipients represents a separate embodiment of the present invention.

In another embodiment, the pharmaceutical compositions provided herein are controlled-release compositions, i.e., compositions in which the antigen is released over a period of time after administration. Controlled- or sustained-release compositions include formulation in lipophilic depots (e.g. fatty acids, waxes, oils). In another embodiment, the composition is an immediate-release composition, i.e., a composition in which all the antigen is released immediately after administration.

In another embodiment, the pharmaceutical composition is delivered in a controlled release system. In another embodiment, the agent is administered using intravenous infusion, an implantable osmotic pump, a transdermal patch, liposomes, or other modes of administration. In another embodiment, a pump is used (see Langer, supra; Sefton, CRC Crit. Ref Biomed. Eng. 14:201 (1987); Buchwald et al., Surgery 88:507 (1980); Saudek et al., N. Engl. J. Med. 321:574 (1989). In another embodiment, polymeric materials are used; e.g. in microspheres in or an implant.

The compositions also include, in another embodiment, incorporation of the active material into or onto particulate preparations of polymeric compounds such as polylactic acid, polglycolic acid, hydrogels, etc, or onto liposomes, microemulsions, micelles, unilamellar or multilamellar vesicles, erythrocyte ghosts, or spheroplasts.) Such compositions will influence the physical state, solubility, stability, rate of in vivo release, and rate of in vivo clearance.

Also included in the present invention are particulate compositions coated with polymers (e.g. poloxamers or poloxamines) and the compound coupled to antibodies directed against tissue-specific receptors, ligands or antigens or coupled to ligands of tissue-specific receptors.

Also comprehended by the invention are compounds modified by the covalent attachment of water-soluble polymers such as polyethylene glycol, copolymers of polyethylene glycol and polypropylene glycol, carboxymethyl cellulose, dextran, polyvinyl alcohol, polyvinylpyrrolidone or polyproline. The modified compounds are known to exhibit substantially longer half-lives in blood following intravenous injection than do the corresponding unmodified compounds (Abuchowski et al., 1981; Newmark et al., 1982; and Katre et al., 1987). Such modifications also increase, in another embodiment, the compound's solubility in aqueous solution, eliminate aggregation, enhance the physical and chemical stability of the compound, and greatly reduce the immunogenicity and reactivity of the compound. In another embodiment, the desired in vivo biological activity is achieved by the administration of such polymer-compound abducts less frequently or in lower doses than with the unmodified compound.

The preparation of pharmaceutical compositions that contain an active component, for example by mixing, granulating, or tablet-forming processes, is well understood in the art. An active component is, in another embodiment, formulated into the composition as neutralized pharmaceutically acceptable salt forms. Pharmaceutically acceptable salts include the acid addition salts (formed with the free amino groups of the polypeptide or antibody molecule), which are formed with inorganic acids such as, for example, hydrochloric or phosphoric acids, or such organic acids as acetic, oxalic, tartaric, mandelic, and the like. Salts formed from the free carboxyl groups can also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

Each of the above additives, excipients, formulations and methods of administration represents a separate embodiment of the present invention.

In one embodiment, methods of the present invention comprise administering a polynucleotide or polypeptide of the present invention in a pharmaceutically acceptable carrier.

The pharmaceutical compositions containing the polypeptide can be, in another embodiment, administered to a subject by any method known to a person skilled in the art, such as parenterally, transmucosally, transdermally, intramuscularly, intravenously, intra-dermally, intra-nasally, subcutaneously, intra-peritonealy, intra-ventricularly, intra-cranially, or intra-vaginally. In another embodiment, compositions of the instant invention are administered via epidermal injection, in another embodiment, intramuscular injection, in another embodiment, subcutaneous injection, and in another embodiment, intra-respiratory mucosal injection.

In another embodiment, of methods and compositions of the present invention, the pharmaceutical compositions are administered orally, and are thus formulated in a form suitable for oral administration, i.e., as a solid or a liquid preparation. Suitable solid oral formulations include tablets, capsules, pills, granules, pellets and the like. Suitable liquid oral formulations include solutions, suspensions, dispersions, emulsions, oils and the like. In another embodiment, of the present invention, the composition is formulated in a capsule. In another embodiment, compositions of the present invention comprise a hard gelating capsule.

In another embodiment, the pharmaceutical compositions are administered by intravenous, intra-arterial, or intramuscular injection of a liquid preparation. Suitable liquid formulations include solutions, suspensions, dispersions, emulsions, oils and the like. In another embodiment, the pharmaceutical compositions are administered intravenously and are thus formulated in a form suitable for intravenous administration. In another embodiment, the pharmaceutical compositions are administered intra-arterially and are thus formulated in a form suitable for intra-arterial administration. In another embodiment, the pharmaceutical compositions are administered intra-muscularly and are thus formulated in a form suitable for intra-muscular administration.

In another embodiment, the pharmaceutical compositions are administered topically to body surfaces and are thus formulated in a form suitable for topical administration. Suitable topical formulations include gels, ointments, creams, lotions, drops and the like.

In another embodiment, the pharmaceutical composition is administered as a suppository, for example a rectal suppository or a urethral suppository. In another embodiment, the pharmaceutical composition is administered by subcutaneous implantation of a pellet. In another embodiment, the pellet provides for controlled release of antigen agent over a period of time.

In another embodiment, the pharmaceutical composition is delivered in a vesicle, e.g. a liposome.

Plant Regeneration

In one embodiment, a transgenic plant of the present invention is grown under conditions suitable for the expression of the recombinant DNA construct or constructs. The regeneration, development and cultivation of plants from single plant protoplast transformants or from various transformed explants is well known in the art (See Weissbach and Weissbach, In: Methods for Plant Molecular Biology, (Eds.), 1988 Academic Press, Inc., San Diego, Calif). This regeneration and growth process typically includes the steps of selection of transformed cells, culturing those individualized cells through the usual stages of embryonic development through the rooted plantlet stage. Transgenic embryos and seeds are similarly regenerated. The resulting transgenic rooted shoots are thereafter planted in an appropriate plant growth medium such as soil.

Following transformation, plant cells transformed with a plant expression vector may be regenerated, e.g., from single cells, callus tissue or leaf discs according to standard plant tissue culture techniques. Almost any plant can be entirely regenerated from cells, tissues, and organs of the plant using methods that are known in the art.

The transformed plants may then be grown, and either pollinated with the same transformed strain or different strains, and the resulting hybrid having expression of the desired phenotypic characteristic identified. Two or more generations may be grown to ensure that expression of the desired phenotypic characteristic is stably maintained and inherited and then seeds harvested to ensure expression of the desired phenotypic characteristic has been achieved.

In one embodiment, a plant cell is regenerated to obtain a whole plant from the transformation process. The term "growing" or "regeneration" as used herein means growing a whole plant from a plant cell, a group of plant cells, a plant part (including seeds), or a plant piece (e.g., from a protoplast, callus, or tissue part).

Regeneration from protoplasts varies from species to species of plants, but generally a suspension of protoplasts is first made. In certain species, embryo formation can then be induced from the protoplast suspension. In one embodiment, the culture media will contain various amino acids and hormones, necessary for growth and regeneration. Examples of hormones utilized include auxins and cytokinins. Efficient regeneration will depend on the medium, on the genotype, and on the history of the culture. If these variables are controlled, regeneration is reproducible. Regeneration also occurs from plant callus, explants, organs or parts.

In vegetatively propagated crops, the mature genetically modified plants are propagated by utilizing cuttings or tissue culture techniques to produce multiple identical plants. Selection of desirable genetically modified plants is made and new varieties are obtained and propagated vegetatively for commercial use.

In seed propagated crops, mature genetically modified plants can be self-crossed to produce a homozygous inbred plant. The resulting inbred plant produces seed containing the genetic mutation. These seeds can be grown to produce plants that would produce the selected phenotype, e.g., increased lateral root growth, uptake of nutrients, overall plant growth and/or vegetative or reproductive yields.

Parts obtained from the regenerated plant, such as flowers, seeds, leaves, branches, fruit, and the like are included in the invention, provided that these parts comprise cells comprising the isolated nucleic acid of the present invention. Progeny and variants, and mutants of the regenerated plants are also included within the scope of the invention, provided that these parts comprise the introduced nucleic acid sequences. In one embodiment, genetically modified plants expressing a selectable marker can be screened for transmission of the nucleic acid of the present invention by, for example, standard immunoblot and DNA detection techniques. In another embodiment, genetically modified plant cells may be evaluated on levels of expression of the genetically modified nucleic acid. Expression at the RNA level can be determined initially to identify and quantitate expression-positive plants. Standard techniques for RNA analysis can be employed and include PCR amplification assays using oligonucleotide primers designed to amplify only the genetically modified RNA templates and solution hybridization assays using genetically modified nucleic acid-specific probes. The RNA-positive plants can then be analyzed for protein expression by Western immunoblot analysis using the specifically reactive antibodies of the present invention. In addition, in situ hybridization and immunocytochemistry according to standard protocols can be performed using genetically modified nucleic acid specific polynucleotide probes and antibodies, respectively, to localize sites of expression within genetically modified tissue. In one embodiment, a number of genetically modified lines are screened for the incorporated nucleic acid to identify and select plants with the most appropriate expression profiles.

In one embodiment, the present invention provides a genetically modified plant that is homozygous for the introduced nucleic acid; i.e., a genetically modified plant that contains two added nucleic acid sequences, one gene at the same locus on each chromosome of a chromosome pair. A homozygous genetically modified plant can be obtained by sexually mating (selfing) a heterozygous genetically modified plant that contains a single added genetically modified nucleic acid, germinating some of the seed produced and analyzing the resulting plants produced for altered expression of a polynucleotide of the present invention relative to a control plant (i.e., native, non-genetically modified). Backcrossing to a parental plant and out-crossing with a non-genetically modified plant are also contemplated.

Transformed plant cells which are derived by any of the above transformation techniques can be cultured to regenerate a whole plant which possesses the transformed genotype. In one embodiment, such regeneration techniques rely on manipulation of certain phytohormones in a tissue culture growth medium.

The regenerated plants containing the foreign, exogenous gene that encodes a protein of interest can then be further propagated as is well known in the art. The particular method of propagation will depend on the starting plant tissue and the particular plant species to be propagated.

In one embodiment, the generated transformed plants are clonally propagated. In another embodiment, the generated transformed plants are propagated by classical breeding techniques. In a particular embodiment, the regenerated plants are self-pollinated to provide homozygous transgenic plants. Otherwise, pollen obtained from the regenerated plants is crossed to seed-grown plants of agronomically important lines, or pollen from plants of these important lines is used to pollinate regenerated plants. A transgenic plant of the present invention containing a desired polypeptide is cultivated using methods well known to one of skill in the art.

Products of Genetically Modified Plants

In one embodiment, the present invention provides a food crop comprising betalains. In one embodiment, the food crop does not endogenously comprise betalains. In another embodiment, the food crop does endogenously comprise betalains and the methods of the present invention serve to increase or enhance the amount of betalains present in the food crop.

In one embodiment, a food crop comprising betalains or enhanced amounts of betalains is nutritionally enhanced. In one embodiment, a food crop comprising betalains or enhanced amounts of betalains comprises anti-oxidative properties. In one embodiment, consumption of a food crop comprising betalains or enhanced amounts of betalains protects a subject from degenerative diseases or conditions. In one embodiment, consumption of betalains or food crops containing betalains may protect a subject from cancer (e.g. skin, lung, cervical, ovarian and bladder), cardiopathy, or neurodegenerative diseases. Betalains may also inhibit lipid peroxidation and heme decomposition; prevent oxidative hemolysis of red blood cells; and bind to human low-density lipoproteins increasing their resistance to oxidation.

In one embodiment, the present invention provides fruit comprising betalains of the present invention. In another embodiment, the present invention provides vegetables comprising betalains of the present invention. In another embodiment, the present invention provides underground organs, such as potatoes, comprising betalains of the present invention. In another embodiment, the present invention provides juices derived from fruits or vegetables comprising betalains of the present invention.

In one embodiment, the plant organs or derivatives thereof (such as juice) comprise, in addition to betalains of the present invention, natural or engineered anthocyanins, carotenes, or a combination thereof.

In another embodiment, the present invention provides a dietary supplement comprising a betalain produced by the methods as described herein or a plant or plant part as described herein.

In another embodiment, the present invention provides an allelochemical comprising L-DOPA produced by the methods as described herein or a plant or plant part as described herein.

Additional Uses

The heterologous production of betalains enables the biofortification and enhancement of nutritional qualities of essential foods, as well as the development of new varieties of ornamental plants. The simple biosynthetic pathway of these pigments, which starts from the ubiquitous precursor tyrosine and requires expression of two to three genes, allows for the production of these pigments in numerous plant species or other species.

In another embodiment, the present invention provides a method of producing an ornamental plant, comprising the step of: contacting a plant cell with a nucleic acid sequence encoding CYP76AD1, CYP76AD6, CYP76AD15, or a combination thereof, and a nucleic acid sequence encoding DOPA 4,5-dioxygenase (DOD) enzyme and under conditions sufficient to produce betalains, wherein if said cell is contacted with a nucleic acid sequence encoding CYP76AD1 and DOD and not a nucleic acid sequence encoding CYP76AD6 or CYP76AD15, then said cell is contacted with a nucleic acid sequence encoding a betalain related glucosyltransferase, thereby producing an ornamental plant. In one embodiment, the plant is not a naturally betalain-expressing plant. In one embodiment, the plant is not a Caryophyllales plant. In one embodiment, the species of plant is: *Syngonium podophyllum, Nephrolepis exaltata* 'Bostoniensis', *Phoenix canariensis, Aglaonema, Asplenium nidus, Rhapis excelsa, Aspidistra elatior, Nertera granadensis, Pteris cretica, Dieffenbachia amoena, Chamaerops humilis, Epipremnum aureum, Codiaeum variegatum, Alocasia amazonica*, Fiddle Leaf Fig—*Ficus lyrata, Alocasia micholitziana, Philodendron scandens, Dracaena braunii, Adiantum raddianum, Chamaedorea elegans, Howea forsteriana, Dracaena marginata, Pachira aquatica, Calathea makoyana, Davallia fejeensis, Calathea roseopicta, Cycas revoluta, Dracaena reflexa, Calathea lancifolia, Ficus elastica, Howea belmoreana*, Spider Plant—*Chlorophytum comosum, Dionaea muscipula, Peperomia argyela, Aphelandra squarrosa, Zamioculcas zamiifolia, Tradescantia, Ficus benjamina, Calathea zebrina*, or a Cactus.

In one embodiment, changing the color of a plant, and in particular the color of a flower of a plant, will affect the pollination of the plant. In one embodiment, methods of the present invention will increase or enhance the pollination of a plant. In another embodiment, methods of the present invention will decrease the pollination of a plant. In another embodiment, methods of the present invention will change the organisms that are attracted to the plant, thereby changing the pollination of a plant. In one embodiment, the present invention provides a method of increasing the pollination of a plant comprising the step of inserting a recombinant polynucleotide or one or more nucleic acids of the present invention into at least one cell of said plant.

In another embodiment, the present invention provides a method of increasing the pollination of a plant, comprising the step of: contacting a plant with a nucleic acid sequence encoding CYP76AD1, CYP76AD6, CYP76AD15, or a combination thereof, and, optionally, a nucleic acid sequence encoding DOPA 4,5-dioxygenase (DOD) enzyme and under conditions sufficient to produce betalains, thereby changing the color of the plant, thereby increasing the pollination of a plant. In one embodiment, the plant is not a naturally betalain-expressing plant. In one embodiment, the plant is not a Caryophyllales plant.

In another embodiment, the methods of the present invention provide methods of changing the color of an organism. In one embodiment, the organism is a fish.

In another embodiment, the methods of the present invention provide a method of producing an organism in which one or more parts of said organism is red-violet comprising the step of contacting one or more cells of said organism with a recombinant polynucleotide comprising a nucleic acid encoding a CYP76AD1, a nucleic acid encoding a DOPA 4,5-dioxygenase (DOD) enzyme, and a nucleic acid encoding betalain related glucosyltransferase, wherein said nucleic acids are inserted into the polynucleotide in frame.

In another embodiment, the methods of the present invention provide a method of producing an organism in which one or more parts of said organism is yellow comprising the step of contacting one or more cells of said organism with a recombinant polynucleotide comprising a nucleic acid encoding a CYP76AD6 and a nucleic acid encoding a DOPA 4,5-dioxygenase (DOD) enzyme, wherein said nucleic acids are inserted into the polynucleotide in frame.

In another embodiment, the methods of the present invention provide a method of producing an organism in which one or more parts of said organism is orange, comprising the step of contacting one or more cells of said organism with a recombinant polynucleotide comprising a nucleic acid encoding a CYP76AD6, a nucleic acid encoding CYP76AD1, a nucleic acid encoding a DOPA 4,5-dioxygenase (DOD) enzyme, and a nucleic acid encoding betalain related glucosyltransferase, wherein said nucleic acids are inserted into the polynucleotide in frame.

In one embodiment, the organism is a fish. In one embodiment, the fish is an ornamental fish.

In one embodiment, the present invention provides a method of producing an ornamental fish comprising contacting a cell of a fish with a polynucleotide encoding a nucleic acid encoding a DOPA 4,5-dioxygenase (DOD) enzyme and a nucleic acid encoding CYP76AD6, a nucleic acid encoding CYP76AD15, a nucleic acid encoding CYP76AD1, or a combination thereof, wherein if said cell is contacted with a nucleic acid encoding CYP76AD1 and a nucleic acid encoding DOD and not a nucleic acid encoding CYP76AD6 or a nucleic acid encoding CYP76AD15, said cell is also contacted with a nucleic acid encoding a betalain related glucosyltransferase.

In another embodiment, the present invention provides a method of producing a plant expressing a betalain, comprising the step of: contacting one or more cells of said plant with a nucleic acid sequence encoding CYP76AD1, CYP76AD6, CYP76AD15, or a combination thereof, and a nucleic acid sequence encoding DOPA 4,5-dioxygenase (DOD) enzyme, screening said one or more cells to identify cells comprising said nucleic acid sequences, and regenerating plants or plant parts from said cells, thereby producing a plant expressing a betalain.

In one embodiment, the plant does not naturally express a betalain. In another embodiment, the plant expresses a betalain and the methods of the present invention are used to increase the amount of one or more betalains that are expressed by the plant.

In another embodiment, the present invention provides a method of producing a food crop expressing a betalain, comprising the step of: contacting one or more cells of a food crop plant with a nucleic acid sequence encoding CYP76AD1, CYP76AD6, CYP76AD15, or a combination thereof, and a nucleic acid sequence encoding DOPA 4,5-dioxygenase (DOD) enzyme, screening said one or more cells to identify cells comprising said nucleic acid sequences, and regenerating plants or plant parts from said cells, thereby producing a food crop expressing a betalain.

In one embodiment, a "food crop" or an "agricultural crop" is a plant intentionally grown with the primary purpose of being eaten by humans or animals. In one embodiment, the food crop is plantains, yams, sorghum, sweet potatos, soybeans, cassava, rice, wheat, or corn. In another embodiment, the food crop is aubergines, peppers, broccoli, calabrese, buckwheat, maize, barley, grapes, berries, tomatoes, cucumbers, artichoke, onion, rhubarb, blackberries, blueberries, zucchini, radishes, carrots, brussel sprouts, lettuce, melons, beans, peas, grains, peanuts, sugarcane, watermelon, papaya, apple, pear, peach, cherry, strawberry or squash.

In one embodiment, the strong antioxidant activity of betalains is beneficial for human health.

They have been extensively studied for their potential health-promoting properties, including anti-cancer, hypolipidemic, anti-inflammatory, hepatoprotective and anti-diabetic activities. Thus, in one embodiment, the present invention provides a method of treating or suppressing cancer, hyperlipidemia, inflammation, liver disease, and diabetes comprising the step of feeding to a subject in need a plant or plant part of the present invention, which expresses betalains, betacyanins, and/or betaxanthins, thereby treating or suppressing cancer, hyperlipidemia, inflammation, liver disease, or diabetes in said subject.

In one embodiment, ingestion by a subject of a food crop of the present invention comprising betalains or enhanced amounts of betalains protect subjects against Inflammatory-Immune Injury (including, but not limited to glomerulonephritis, vasculitis, autoimmune disease, adult respiratory distress syndrome, rheumatoid arthritis, inflammatory bowel disease, pancreatitis); cancer (including, but not limited to radiation induced cancer, cervical carcinoma, hepatocellular carcinoma, promotors of carcinogenesis, cancer in inflammatory bowel disease); ischemia/reoxygenation (including, but not limited to stroke, myocardial infraction, organ transplantation (heart, lung, skin, cornea, kidney), organ preservation, reattachment of severed limbs, frostbite, Dupuytren's contracture, hemorrhagic shock, endotoxic shock, crush injury); metal overload (including, but not limited to hemochromatosis, thalassemia, kwashlorkor, chemotherapy for leukemias, fulminant hepatic failure, Wilson's disease, alcohol induced iron overload, nickel induced carcinogenesis, lead poisoning); toxins (including, but not limited to hemolytic drugs, lead, halogenated hydrocarbons, ozone, oxides of nitrogen, asbestos, other mineral dusts, sulfur dioxid, paraquat, aluminum, cigarette smoke, diabetogenic drugs, fava beans (hemolytic agents), anthracyclines (cardiotoxicity), heavy metals (nephrotoxicity), photosensitizing drugs, contact dermatitis); eye disorders (including, but not limited to cataract development, deterioration after ocular hemorrhage, photochemical retinal damage, retinopathy of prematurity (retrolental fibroplasia)); inborn disease (including, but not limited to porphyrias, sickle cell anemia, Fanconi's anemia, neuronal ceroid lipofuscinoses, thalassemia); insufficient antioxidant protection (including, but not limited to Keshan disease (severe selenuim deficiency), hemolytic disease of prematurity, retinopathy of prematurity, bronchopulmonary dysplasia, intracranial hemorrhage, neurological degeneration due to severe vitamin E deficiency (in inborn errors affecting intestinal fat absorption), acquired immunodeficiency syndrome); brain and central nervous system disorders (including, but not limited to stroke, trauma, neurotoxicities (e.g., of aluminum), effects of hyperbaric oxygen, Parkinson's disease, potentiation of traumatic injury, cerebral malaria).

In another embodiment, the present invention provides new ways of producing betalains in non-naturally betalain-expressing species, in which betalains may be used as a natural food colorant. Therefore, the present invention also provides a natural food colorant comprising betalains produced as described herein. In one embodiment, betalains are extracted from plants expressing betalain as described herein. In another embodiment, betalains are produced in vitro in a cell line. The heterologous production of betalains enables the biofortification and enhancement of nutritional qualities of essential foods.

In another embodiment, the methods of present invention may be used to enhance the aesthetic quality of a food crop or produce by changing its color by genetically engineering a plant to express one or more betalains.

Thus, in one embodiment, the present invention provides methods of treating or suppressing the diseases, disorders, and conditions mentioned hereinabove comprising the step of providing a subject with a food crop that has been genetically modified to express betalains, as described herein. In another embodiment, the present invention provides uses of polynucleotides, nucleic acids and other compositions described herein in the preparation of a composition for treating or suppressing the diseases, disorders, and conditions mentioned hereinabove. In one embodiment, the composition is a pharmaceutical composition. In another embodiment, the present invention provides polynucleotides, nucleic acids and other compositions described herein for use in treating or suppressing the diseases, disorders, and conditions mentioned hereinabove.

In another embodiment, a food crop comprising betalains or enhanced amounts of betalains has an increased shelf life compared to the same food crop lacking betalains or having lower level of betalains. In another embodiment, a food crop comprising betalains or enhanced amounts of betalains has increased resistance to fungal diseases compared to the same food crop lacking betalains or having lower level of betalains.

In another embodiment, betalains produced by the methods described herein may be used for food preservation.

Therefore, in one embodiment, the present invention provides methods of increasing the shelf life of a food crop comprising the step of contacting one or more cells of a food crop plant comprising tyrosine with a nucleic acid encoding CYP76AD6, CYP76AD15, or a combination thereof, a nucleic acid encoding CYP76AD1, or a combination thereof, under conditions sufficient to produce betalains, thereby producing betalains and increasing the shelf life of said food crop.

Within the plant kingdom, betalains are found in only one group of angiosperms, the Caryophyllales. In this order, betalains and anthocyanins occur in a mutually exclusive fashion, i.e. no plant species produces both types of pigments. One of the most prominent features of the Caryophyllales order is its dominance in arid and semi-arid regions, and habitation of saline and alkaline soils. While some families within the Caryophyllales are distributed worldwide in a variety of habitats, members of several families are particularly adapted to arid or saline regions, including the Aizoaceae (ice-plant family), Portulacaceae (purslane family) and most notably, the Cactaceae (cactus family; www.britannica.com/plant/Caryophyllales). Heterologous betalain production in plants was used hereinbelow for studying the roles for these pigments in conferring tolerance to different a-biotic stress cues that are associated with arid regions such as drought, high UV radiation, excess light and high salinity and as plant defense compounds, acting against pathogenic fungi.

In another embodiment, the present invention provides methods of increasing the resistance of an organism or part of an organism to one or more stress factors comprising the step of contacting one or more cells of said organism with a nucleic acid encoding CYP76AD6, CYP76AD15, or a combination thereof, a nucleic acid encoding CYP76AD1, or a combination thereof, under conditions sufficient to produce betalains, thereby producing betalains and increasing the resistance of said organism or said part of an organism to said one or more stress factors. In one embodiment, the organism is a plant. In one embodiment, the organism comprises tyrosine. In one embodiment, the stress factor is an abiotic stress factor. In another embodiment, the stress factor is high osmotic pressure, high salinity condition, or a combination thereof. In another embodiment, the stress factor is drought. In another embodiment, the stress factor is excess light. In one embodiment, the plant part is a seed. In one embodiment, the plant is a food crop.

In one embodiment, the method comprises the step of contacting one or more cells of a plant or plant part with a nucleic acid encoding CYP76AD1, a nucleic acid encoding a DOPA 4,5-dioxygenase (DOD) enzyme, and a nucleic acid encoding a betalain related glucosyltransferase.

In another embodiment, the present invention provides methods of increasing the resistance of a plant or plant part to high osmotic pressure comprising the step of contacting one or more cells of a plant or plant part comprising tyrosine with a nucleic acid encoding CYP76AD6, CYP76AD15, or a combination thereof, a nucleic acid encoding CYP76AD1, or a combination thereof, under conditions sufficient to produce betalains, thereby producing betalains and increasing the resistance of said plant or plant part to high osmotic pressure.

In another embodiment, the present invention provides methods of increasing the resistance of a plant or plant part to high salinity conditions comprising the step of contacting one or more cells of a plant or plant part comprising tyrosine with a nucleic acid encoding CYP76AD6, CYP76AD15, or a combination thereof, a nucleic acid encoding CYP76AD1, or a combination thereof, under conditions sufficient to produce betalains, thereby producing betalains and increasing the resistance of said plant or plant part to high salinity conditions.

In another embodiment, the present invention provides a method of increasing seed germination rates in a plant comprising the step of contacting one or more cells of a plant or plant part with a polynucleotide comprising a nucleic acid encoding CYP76AD1, a nucleic acid encoding DODA1 and a nucleic acid encoding cDOPA5GT, under conditions sufficient to produce betalains, thereby increasing seed germination rates in said plant.

In another embodiment, the present invention provides methods of increasing the resistance of an organism or part of an organism to one or more fungal diseases comprising the step of contacting one or more cells of said organism with a nucleic acid encoding CYP76AD6, CYP76AD15, or a combination thereof, a nucleic acid encoding CYP76AD1, or a combination thereof, under conditions sufficient to produce betalains, thereby producing betalains and increasing the resistance of said organism or said part of an organism to said one or more fungal diseases. In one embodiment, the organism comprises tyrosine. In one embodiment, the organism is a plant. In one embodiment, the plant is a food crop.

In one embodiment, the fungus causing said fungal disease is a phytopathogenic fungus. In one embodiment, the fungus causing said fungal disease is *Botrytis cinerea*. In one embodiment, the plant is a tobacco plant. In one embodiment, the plant part is the leaf.

In another embodiment, the present invention provides methods of increasing the resistance of a plant or plant part to one or more fungal diseases comprising the step of contacting one or more cells of a plant or plant part with a nucleic acid encoding CYP76AD1, a nucleic acid encoding a DOPA 4,5-dioxygenase (DOD) enzyme, and a nucleic acid encoding a betalain related glucosyltransferase, under conditions sufficient to produce betalains, thereby producing betalains and increasing the resistance of said plant or plant part to one or more fungal diseases. In one embodiment, the plant is a food crop.

In another embodiment, the present invention provides methods of decreasing the lesion area due to a fungal disease in a plant or plant part comprising the step of contacting one or more cells of said plant or plant part with a nucleic acid encoding CYP76AD1, a nucleic acid encoding a DOPA 4,5-dioxygenase (DOD) enzyme, and a nucleic acid encoding a betalain related glucosyltransferase, under conditions sufficient to produce betalains, thereby producing betalains and thereby decreasing said lesion area due to a fungal disease in said plant or plant part.

In another embodiment, the present invention provides methods of decreasing necrosis due to a fungal disease in a plant or plant part comprising the step of contacting one or more cells of said plant or plant part with a nucleic acid encoding CYP76AD1, a nucleic acid encoding a DOPA 4,5-dioxygenase (DOD) enzyme, and a nucleic acid encoding a betalain related glucosyltransferase, under conditions sufficient to produce betalains, thereby producing betalains and thereby decreasing necrosis due to a fungal disease in said plant or plant part.

In another embodiment, the present invention provides methods of inhibiting growth of plant species near to a first plant or plant part comprising the step of contacting one or more cells of said first plant or plant part with a nucleic acid encoding a CYP76AD1-β clade gene, under conditions sufficient to produce and secrete L-DOPA, thereby inhibiting growth of plants species near to said first plant or plant part. In one embodiment, the plant species is a heterologous plant species to the first plant.

In another embodiment, the present invention provides methods of allelopathic growth of an organism comprising the step of contacting one or more cells of an organism or part thereof with a nucleic acid encoding a CYP76AD1-β clade gene, under conditions sufficient for said organism or part thereof to produce and secrete L-DOPA, thereby allowing allelopathic growth of said organism.

In one embodiment, allelopathy is a biological phenomenon by which an organism produces one or more biochemicals that influence the germination, growth, survival, and reproduction of other organisms.

In another embodiment, the present invention provides methods of weed control comprising the step of contacting one or more cells of a plant or plant part with a nucleic acid encoding a CYP76AD1-β clade gene, under conditions sufficient for said plant or plant part to produce and secrete L-DOPA, thereby inhibiting the growth of weeds near to said plant or plant part.

In one embodiment, the step of contacting one or more cells of a plant or plant part with a nucleic acid encoding CYP76AD6, CYP76AD15, or a combination thereof, a nucleic acid encoding CYP76AD1, or a combination thereof, under conditions sufficient to produce betalains comprises contacting said one or more cells with a nucleic acid encoding CYP76AD1, a nucleic acid encoding a a DOPA 4,5-dioxygenase (DOD) enzyme, and a nucleic acid encoding a betalain related glucosyltransferase. In one embodiment, the DOD is *Beta vulgaris* DODA1. In one embodiment, the betalain related glucosyltransferase is cyclo-DOPA 5-O-glucosyltransferase or betanidin-5-O-glucosyltransferase. In one embodiment, the cyclo-DOPA 5-O-glucosyltransferase is *M. jalapa* gene cyclo-DOPA 5-O-glucosyltransferase (cDOPA5GT).

In one embodiment, a polynucleotide comprises the nucleic acids. In one embodiment, the polynucleotide is pX11. In another embodiment, the polynucleotide is pX12. In another embodiment, the polynucleotide is pX13.

In one embodiment, pX11-expressing species exhibited a predominantly red-violet color due to the production of higher amounts of betacyanins than betaxanthins.

The invention described herein has numerous applications in various diverse industries, including, for example, but not limited to, agriculture, food and beverages, pharmaceuticals, cosmetics, textiles, and consumer products.

In one embodiment, applications of the present invention include production of betalains and/or L-DOPA for fish feed. In another embodiment, production of betalains and/or L-DOPA is for inclusion in a food supplement. In one embodiment, the food supplement is for humans. In another embodiment, the food supplement is for non-human animals. In another embodiment, the food supplement is for veterinary use. In another embodiment, the food supplement is for aquaculture. In another embodiment, the food supplement is in the form of a vitamin. In another embodiment, the food supplement is added to milk or other dairy products.

In another embodiment, the present invention provides a method of increasing one or more betalains in a dairy product comprising the steps of a) contacting a bacterial cell with a polynucleotide encoding a nucleic acid encoding a DOPA 4,5-dioxygenase (DOD) enzyme and a nucleic acid encoding CYP76AD6, a nucleic acid encoding CYP76AD15, a nucleic acid encoding CYP76AD1, or a combination thereof, wherein if said cell is contacted with a nucleic acid encoding CYP76AD1 and a nucleic acid encoding DOD and not a nucleic acid encoding CYP76AD6 or a nucleic acid encoding CYP76AD15, said cell is also contacted with a nucleic acid encoding a betalain related glucosyltransferase, and b) fermenting a dairy product with bacteria grown from said cell, thereby increasing one or more betalains in said dairy product. In one embodiment, the bacteria is a bacteria used in fermentation for preparation of dairy products. In one embodiment, the bacteria is a *Lactobacillus.*

In another aspect, the genes of the invention can be transformed into a plant or a plant cell in order to protect against one or more biotic stresses such as, for example, but not limited to, fungi, bacteria, and virus and/or one or more abiotic stresses such as, for example, but not limited to, heat, cold, salt, drought, and ultraviolet exposure.

In one embodiment, a plant organ expressing a polynucleotide or polypeptide of the present invention may serve as a food coloring, dye, or pigment. In another embodiment, a derivative product of a plant organ expressing a polynucleotide or polypeptide of the present invention may serve as a food coloring, dye, or pigment.

In another embodiment, juice from transformed fruit can be extracted from such fruit for making beverages. In another embodiment, the juice or other extract from a plant organ expressing a polynucleotide or polypeptide of the present invention may serve as a food coloring, dye, or pigment. In one embodiment, such juice may be used to dye yogurt, sweet, chewing gum, ice cream and the like. Such dye or coloring agent can also be used in textile industry to dye clothes.

In another embodiment, an extract of a transgenic plant or plant cell as described herein may be sprayed on vulnerable plants to protect them from biotic and abiotic stresses, as described hereinabove. Thus, the present invention includes both an extract of a plant or food crop as described herein as well as a method of protecting a plant from biotic stress, abiotic stress, or a combination thereof comprising contacting said plant with a plant or plant extract produced by the methods of the present invention as described herein.

In another embodiment, production of betalains and/or L-DOPA is for cosmetic uses. In one embodiment, production of betalains and/or L-DOPA is for inclusion in sunscreens. In another embodiment, betalains and/or L-DOPA for use in sunscreens is produced in yeast.

In another embodiment, the present invention provides a method of treating, inhibiting, suppressing, or preventing a dopamine-responsive disorder in a subject comprising the step of administering a food crop, cell, or cell line comprising high levels of a CYP76AD1-β clade polypeptide, thereby providing said subject with L-DOPA, thereby treating, inhibiting, suppressing, or preventing dopamine-responsive disorder in said subject.

In another embodiment, the present invention provides a use of a CYP76AD1-β clade gene or a food crop, cell, or cell line comprising high levels of said CYP76AD1-β clade gene in the preparation of a composition for treating or inhibiting a dopamine-responsive disorder in a subject.

In another embodiment, the present invention provides a CYP76AD1-β clade gene or a food crop, cell, or cell line comprising high levels of said CYP76AD1-β clade gene for treating or inhibiting a dopamine-responsive disorder in a subject.

In one embodiment, the CYP76AD1-β clade polypeptide is CYP76AD6, CYP76AD15, or a combination thereof. In one embodiment, said dopamine-responsive disorder is Parkinson's Disease, Dopamine-responsive Dystonia, or a combination thereof.

In another embodiment, the present invention provides a method of treating, inhibiting, suppressing, or preventing Parkinson's Disease or Dopamine-responsive Dystonia in a subject, comprising providing said subject with a tyrosine-expressing plant or plant part genetically modified to express CYP76AD6, CYP76AD15, or a combination thereof, thereby providing said subject with L-DOPA, thereby treating, inhibiting, suppressing, or preventing Parkinson's Disease or Dopamine-responsive Dystonia in said subject.

In another embodiment, the present invention provides a method of treating, inhibiting, suppressing, or preventing Parkinson's Disease or Dopamine-responsive Dystonia in a subject, comprising administering a CYP76AD6, CYP76AD15, or a combination thereof, enzyme to said subject, optionally with phenylalanine or tyrosine, thereby producing L-DOPA from tyrosine, thereby treating, inhibiting, suppressing, or preventing Parkinson's Disease or Dopamine-responsive Dystonia in said subject.

In another embodiment, the present invention provides a method of suppressing the symptoms, stabilizing symptoms, delaying the onset, and/or slowing the progression, Parkinson's Disease or Dopamine-responsive Dystonia in a subject, comprising providing said subject with a tyrosine-expressing plant or plant part genetically modified to express CYP76AD6, CYP76AD15, or a combination thereof, thereby providing said subject with L-DOPA, thereby suppressing the symptoms, stabilizing symptoms, delaying the onset, and/or slowing the progression, Parkinson's Disease or Dopamine-responsive Dystonia in said subject.

In another embodiment, the present invention provides a method of suppressing the symptoms, stabilizing symptoms, delaying the onset, and/or slowing the progression, Parkinson's Disease or Dopamine-responsive Dystonia in a subject, comprising administering a CYP76AD6, CYP76AD15, or a combination thereof, enzyme to said subject, optionally with phenylalanine or tyrosine, thereby producing L-DOPA from tyrosine, thereby suppressing the symptoms, stabilizing symptoms, delaying the onset, and/or slowing the progression, Parkinson's Disease or Dopamine-responsive Dystonia in said subject.

In one embodiment, the Parkinson's Disease is idiopathic Parkinson's disease, postencephalitic parkinsonism, or symptomatic parkinsonism.

In one embodiment, the subject is additionally administered a peripheral DOPA decarboxylase inhibitor (DDCI). In one embodiment, the DDCI is carbidopa, a benserazide, or a combination thereof.

In another embodiment, the subject is additionally administered pyridoxine.

In one embodiment, administration of CYP76AD6, CYP76AD15, or a combination thereof, enzyme and/or the L-DOPA produced by the CYP76AD6, CYP76AD15, or a combination thereof, enzyme as described herein is via oral administration. In another embodiment, administration is via a catheter. In another embodiment, the enzyme is administered epidurally, intracerebrally, or intracerebroventricularly. Other suitable methods of administration are described hereinbelow.

According to any of the methods of the present invention and in one embodiment, the subject is human. In another embodiment, the subject is murine, which in one embodiment, is a mouse, and, in another embodiment, is a rat. In another embodiment, the subject is canine, feline, bovine, ovine, or porcine. In another embodiment, the subject is mammalian. In another embodiment, the subject is any organism susceptible to Parkinson's Disease.

In one embodiment, the methods of the present invention are employed in veterinary medicine. In one embodiment, the present invention provides treatment of domesticated mammals which are maintained as human companions (e.g., dogs, cats, horses), which have significant commercial value (e.g., dairy cows, beef cattle, sporting animals), which have significant scientific value (e.g., captive or free specimens of endangered species), or which otherwise have value.

In one embodiment, methods of the present invention include use of the compositions for treating and/or preventing a disease, disorder, or condition. In one embodiment, methods of the present invention include both therapeutic treatment or prophylactic or preventative measures, wherein the object is to prevent or lessen the targeted pathologic condition or disorder as described hereinabove. Thus, in one embodiment, methods of the present invention may include directly affecting or curing, suppressing, inhibiting, preventing, reducing the severity of, delaying the onset of, reducing symptoms associated with the disease, disorder or condition, or a combination thereof. Thus, in one embodiment, "treating" refers inter alia to delaying progression, expediting remission, inducing remission, augmenting remission, speeding recovery, increasing efficacy of or decreasing resistance to alternative therapeutics, or a combination thereof. In one embodiment, "preventing" refers, inter alia, to delaying the onset of symptoms, preventing relapse to a disease, decreasing the number or frequency of relapse episodes, increasing latency between symptomatic episodes, or a combination thereof. In one embodiment, "suppressing" or "inhibiting", refers inter alia to reducing the severity of symptoms, reducing the severity of an acute episode, reducing the number of symptoms, reducing the incidence of disease-related symptoms, reducing the latency of symptoms, ameliorating symptoms, reducing secondary symptoms, reducing secondary infections, prolonging patient survival, or a combination thereof.

In one embodiment, symptoms are primary, while in another embodiment, symptoms are secondary. In one embodiment, "primary" refers to a symptom that is a direct result of the disease, disorder, or condition, while in one embodiment, "secondary" refers to a symptom that is derived from or consequent to a primary cause. In one embodiment, the polynucleotides, polypeptides, compositions, cells and their use in the present invention treat or inhibit primary or secondary symptoms or secondary complications related to Parkinson's Disease.

In another embodiment, "symptoms" may be any manifestation of Parkinson's Disease, comprising tremors, bradykinesia, rigid muscles, impaired posture and balance, loss of automatic movements, speech changes, writing changes, or a combination thereof.

In another embodiment, the present invention provides a method of marking a genetic transformation comprising the step of contacting a cell with a polynucleotide comprising a nucleic acid sequence encoding a) CYP76AD1, CYP76AD6, CYP76AD15, or a combination thereof, b) a nucleic acid sequence encoding DOPA 4,5-dioxygenase (DOD) enzyme; and c) an additional nucleic acid sequence of interest, under conditions sufficient to produce betalains in said cell, wherein the color produced by betalain production in said cell thereby marks said genetic transformation in said cell. In one embodiment, the contacting step further comprises contacting a betalain related glucosyltransferase.

In one embodiment, the method further comprises contacting a growth medium with ascorbic acid as a reducing agent to prevent spontaneous betanidin oxidation, which causes the pigment to polymerize and lose its violet color.

In another embodiment, the present invention provides a method of identifying betalain related genes in an organism comprising the step of searching a plant genome database for genes with expression patterns that highly correlate to those of the betalain related genes described herein. In one embodiment, the gene is MjDOD, cDOPA5GT CYP76AD3, or a combination thereof. In another embodiment, the gene is CYP76AD1, CYP76AD6, CYP76AD15, or a combination thereof.

Combinations

In one embodiment, betalains produced using the compositions and methods of the present invention may be administered or provided by themselves. In another embodiment, betalains produced using the compositions and methods of the present invention may be administered or provided together with an additional dietary supplement. In another embodiment, betalains produced using the compositions and methods of the present invention may be administered or provided together with a terpene, which in one embodiment, is an astaxanthin. In another embodiment, betalains produced using the compositions and methods of the present invention may be administered or provided together with anthocyanins, carotenoids, or a combination thereof.

In another embodiment, betalains produced using the compositions and methods of the present invention may be produced together with an additional component, which in one embodiment, may serve as a dietary supplement. In another embodiment, betalains produced using the compositions and methods of the present invention may be produced together with a terpene, which in one embodiment, is an astaxanthin. In another embodiment, betalains produced using the compositions and methods of the present invention may be produced together with anthocyanins, carotenoids, or a combination thereof.

In another embodiment, the present invention provides a food crop comprising a polynucleotide of the present invention. In one embodiment, the food crop comprising a polynucleotide of the present invention further comprises anthocyanin, carotene, or a combination thereof. In one embodiment, the food crop comprising a polynucleotide of the present invention is genetically modified to comprise anthocyanin, carotene, or a combination thereof. In one embodiment, the food crop is purple anthocyanin tomatoes.

Any reference including patents, patent applications, or scientific publications, cited herein, are incorporated by reference in their entirety.

The following examples are presented in order to more fully illustrate the preferred embodiments of the invention. They should in no way be construed, however, as limiting the broad scope of the invention.

EXAMPLES

Example 1

Materials and Methods (1)

Plant Material and Growth Conditions

*Mirabilis jalapa* plants were soil-grown in a greenhouse with long-day light conditions (25° C.). *Beta vulgaris* and *Nicotiana benthamiana* plants were soil-grown in climate rooms (22° C.; 70% humidity; 18/6 hours of light/dark). Plant material for *M. jalapa* RNA-sequencing was collected from red flowers in five developmental stages (stage 1—flower length approx. 1 cm; stage 2—2 cm; stage 3—3 cm; stage 4—4 cm; stage 5—5-6 cm), red-young or green-mature leaves, and epidermis from stem node (red) or internode (green) areas. Plant material for *B. vulgaris* RNA-sequencing was collected from hypocotyls of 10 day old seedlings of three varieties (Red beet, Burpees Golden beet and Chioggia 'striped' beet). Collected tissue was immediately frozen in liquid nitrogen and maintained at −80° C. until processing.

Transcriptome Sequencing, Assembly and Analysis

*M. jalapa* and *B. vulgaris* libraries for Illumina high-throughput strand-specific RNA-Seq were prepared as follows: total RNA was extracted from sampled tissues with the TRIzol method based on the TRI reagent user manual (Sigma-Aldrich). Five μg of total RNA from each sample was used for preparation of RNA-seq libraries using methods known in the art with minor modifications. Briefly: poly (A) RNA was isolated from total RNA using Dynabeads Oligo (dT) 25 (Invitrogen), fragmented at 94° C. for 5 minutes and eluted. First-strand cDNA was synthesized using reverse transcriptase SuperScript III (Invitrogen) with random primers and dNTPs, and second-strand cDNA was generated using DNA polymerase I (Enzymatics) and dUTPs. After end-repair (Enzymatics), dA-tailing with Klenow 3'-5' (Enzymatics) and adapter ligation (Quick T4 DNA Ligase, NEB), the dUTP-containing second-strand was digested by uracil DNA glycosylase (Enzymatics). The resulting first-strand adaptor-ligated cDNA was used for 13-15 cycles of PCR enrichment with NEBNext High-Fidelity PCR Master Mix (NEB). Indexed libraries were pooled and sequenced with an Illumina HiSeq2000 instrument. De-novo assembly and calculation of normalized count values for the *M. jalapa* dataset were done with Trinity software version Trinityrnaseq_r2013-02-25, following standard procedure. Contig annotations were assigned using Blast2GO. De-novo, genome-guided assembly of the *B. vulgaris* dataset was done with Trinity version Trinityrnaseq_r2014-07-17, using the *B. vulgaris* (sugar beet) genome resource as reference (bvseq.molgen.mpg.de). Gene annotation was obtained with the inclusive Trinotate module.

Generation of DNA Constructs

Gene sequences used in this study; cDOPA5GT (GenBank accession AB182643.1; SEQ ID NO: 2), DODA1 (accession HQ656027.1; SEQ ID NO: 33), CYP76AD1 (accession HQ656023.1; SEQ ID NO: 32). Other sequences are provided in Materials and Methods. CYP76AD6 was named by Dr. David R. Nelson, University of Tennessee, Memphis USA, to maintain consistency in nomenclature. *M. jalapa* cDOPA5GT and *B. vulgaris* CYP76AD1, BvDODA1, BvCYP76new and CYP76AD6 transcripts were amplified from *M. jalapa* red petal and *B. vulgaris* red hypocotyl cDNA libraries, which were prepared using a High-Capacity cDNA Reverse Transcription Kit (Life technologies). PCR amplification was done using 'Phusion' DNA polymerase (Finnzyme) and oligonucleotides specified in Table 1. For VIGS assay, all gene fragments were cloned into a pTRV2 vector using XhoI and SacI restriction. Vectors for co-silencing were constructed by cloning a CYP76AD1 fragment into pTRV2: BvCYP76new and pTRV2: CYP76AD6 using EcoRI and BamHI restriction. DNA constructs used for *N. benthamiana* agroinfiltration and for agrobacteria-mediated plant transformation were constructed with Goldenbraid cloning. CYP76AD1, BvDODA1, CYP76AD6 and cDOPA5GT were cloned into a pUPD vector using oligonucleotides specified in Table 1. pDODA, pAD1-GT, pYFP, pAD6 and pX11 are respectively 2α2, 2Ω2, 2α1, 2α1 and 3α1 vectors, all of which are based on a pCAMBIA backbone.

TABLE 1

Oligonucleotides used in this study

| SEQ ID NO: | Oligonucleotide name | Sequence (5' to 3') |
|---|---|---|
| | **Quantitative real-time PCR** | |
| 45 | CYP76AD1 qPCR Fwd | TGTGCTAGACGTTCTTCTTCAGCT |
| 46 | CYP76AD1 qPCR Rev | AAAATGTCGACGAGCAAATG |
| 47 | CYP76AD6 qPCR Fwd | CTTCATCTCGTAGGCTTCCTCC |
| 48 | CYP76AD6 qPCR Rev | GATGAGGCTTTTCGCCAAGA |
| 49 | Bv15885 qPCR Fwd | CCTGTATCGGCTAAATGGCG |
| 50 | Bv15885 qPCR Rev | CAATTGCACAGCGGAGATTTT |
| 51 | Bv20048 qPCR Fwd | TTGATGCTGTTTGCGCAGTC |
| 52 | Bv20048 qPCR Rev | TGCGAAGATTTCGCCATTTT |
| 53 | BvGAPDH qPCR Fwd | TGGTGCTGATTTTCGTCGTAGAG |
| 54 | BvGAPDH qPCR Rev | TGGCACCACCCTTCAAGTG |
| 55 | Bv10427 qPCR Fwd | TAAAGCTCCCTCCTGGTCCA |
| 56 | Bv10427 qPCR Rev | CCGCAGAACGATGAGGTTTG |
| 57 | BvCYP76new qPCR Fwd | TCAAACTCGGAAGCATCACTACA |
| 58 | BvCYP76new qPCR Rev | GGGCTAAGTCGTGCTCGAGG |
| | **pTRV2 cloning** | |
| 59 | BvDODA1 Fwd + XhoI | AAAAA**CTCGAG**GTTAAACCTACTGTTAATGCTGTC |
| 60 | BvDODA1 Rev + SacI | AAAAA**GAGCTC**GCTGCCCAAGGTGCAACTCC |
| 61 | CYP76AD1 Fwd + XhoI | AAAAA**CTCGAG**GCTAATCTTGCTAAAATTCACGG |
| 62 | CYP76AD1 Rev + SacI | AAAAA**GAGCTC**TTATGGTGGGCTAATTCCACTG |
| 63 | CYP76AD1 Fwd + BamHI | AAAAA**GGATCC**GCTAATCTTGCTAAAATTCACGG |
| 64 | CYP76AD1 Rev + EcoRI | AAAAA**GAATTC**TTATGGTGGGCTAATTCCACTG |
| 65 | BvCYP76new Fwd + XhoI | AAAAA**CTCGAG**CTGCAAGAGTCAATGATCTCA |
| 66 | BvCYP76new Rev + SacI | AAAAA**GAGCTC**TCATCTGGGAATTGGAATTGCT |
| 67 | CYP76AD6 Fwd + XhoI | AAAAA**CTCGAG**CACAACAGCAAGCACATTAGA |
| 68 | CYP76AD6 Rev + SacI | AAAAA**GAGCTC**AGTCCAGGGCATATCCTTCTAC |

TABLE 1-continued

| Oligonucleotides used in this study | | |
|---|---|---|
| SEQ ID NO: | Oligonucleotide name | Sequence (5' to 3') |
| Goldenbraid cloning | | |
| 69 | BvDODA1 Fwd | GCGCCGTCTCGCTCGAATGAAAATGATG AATGGTGAAGATG |
| 70 | BvDODA1 Rev | GCGCCGTCTCGCTCGAAGCCTAGGCTGA AGTGAACTTGTA |
| 71 | CYP76AD1 Fwd | GCGCCGTCTCGCTCGAATGGATCATGCA ACATTAGCAATG |
| 72 | CYP76AD1 Rev | GCGCCGTCTCGCTCGAAGCTCAATACCT AGGTATTGGAATAAG |
| 73 | CYP76AD6 Fwd1 | GCGCCGTCTCGCTCGAATGGATAACGCA ACACTTGCT |
| 74 | CYP76AD6 Rev1 | GCGCCGTCTCGTTGCCCATTCTAATGTG CTTG |
| 75 | CYP76AD6 Fwd2 | GCGCCGTCTCGGCAATGGCCGAACTTGT GAA |
| 76 | CYP76AD6 Rev2 | GCGCCGTCTCGCTCGAAGCCTAGTTTCT GGGAACTGGAAT |
| 77 | cDOPA5GT Fwd1 | GCGCCGTCTCGCTCGAATGACCGCCATT AAAATGAACAC |
| 78 | cDOPA5GT Rev1 | GCGCCGTCTCGGCCTCATTTCCTCATTG ATATC |
| 79 | cDOPA5GT Fwd2 | GCGCCGTCTCGAGGCCAGAATGGCTACC AGA |
| 80 | cDOPA5GT Rev2 | GCGCCGTCTCGCTCGAAGCTTATTGAAG AGAAGGTTCCAACTT |
| Gateway cloning for yeast expression | | |
| 81 | BvDODA1 Fwd | ggggacaagtttgtacaaaaaagcaggatcATGAAAAT GATGAATGGTGAAGAT |
| 82 | BvDODA1 Rev | ggggaccactttgtacaagaaagctgggtcCTAGGCTGA AGTGAACTTGTAGGAG |
| 83 | CYP76AD1 Fwd | ggggacaagtttgtacaaaaaagcaggatcATGGATCA TGCAACATTAGCAA |
| 84 | CYP76AD1 Rev | ggggaccactttgtacaagaaagctgggtcTCAATACCT AGGTATTGGAATAAGTTT |
| 85 | CYP76AD6 Fwd | ggggacaagtttgtacaaaaaagcaggatcATGGATAA CGCAACACTTGCTGTGATCC |
| 86 | CYP76AD6 Rev | ggggaccactttgtacaagaaagagggtcCTAGTTTCT GGGAACTGGAATAACTTGAAGAG |

Virus-Induced Gene Silencing in *Beta vulgaris*

Fragments of BvDODA1 (407 bp), CYP76AD1 (418 bp), BvCYP76new (471 bp), and CYP76AD6 (420 bp) were cloned into a pTRV2 vector, transformed to agrobacteria strain GV3101 and introduced to *B. vulgaris* 'Bull's Blood' variety 10 day old seedlings using the previously described vacuum infiltration method. Agrobacteria were brought to O.D.600 2.0 in VIGS infiltration buffer (10 mM MES, 10 mM MgCl2, 200 μM acetosyringone), incubated at room temperature for 3 hours and mixed in a 1:1 ratio with pTRV1-carrying agrobacteria before infiltration. For each experiment, 48 seedlings were infected. In experiments resulting in visible phenotypes, depigmentation patches were typically observed in over half of the infected seedlings within 2-3 weeks. Tissues for spectrophotometric analysis were sampled 3.5 weeks post infection.

Quantitative Real-Time PCR (qRT-PCR) Analysis qRT-PCR analysis was carried out on VIGS-infected red beet plants. Three biological replicates from each experiment were analyzed, each replicate consisting of leaf tissue from two to three plants, sampled 3.5 wk post infection. RNA was extracted with the TRIzol method (according to the Sigma-Aldrich user manual for the TRI reagent), DNase-treated and reverse-transcribed to cDNA with a High Capacity cDNA Reverse Transcription kit (Applied Biosystems, Foster City, CA, USA), according to the manufacturer's instructions. All oligonucleotides were designed using PRIMEREXPRESS software (Applied Biosystems) (Table 1). qRT-PCR was performed with Fast SYBR Green reagent and a StepOnePlus instrument (Applied Biosystems) in the following conditions: initial step in the thermal cycler for 20 s at 95° C., followed by PCR amplification for 40 cycles of 3 s at 95° C. and 30 s at 59° C., and finally dissociation analysis to confirm the specificity of PCR products. Each reaction consisted of 10 µl total volume, containing 2.5 µM of each primer. Relative transcript levels were calculated according to the ΔΔCt method (Livak & Schmittgen, 2001), using the 'housekeeping' gene GAPDH for reference.

Transient Expression in *Nicotiana benthamiana*

Transient gene expression assays in *N. benthamiana* with the pDODA, pAD1-GT, pYFP, pAD6 and pX11 vectors were based on a previously described agroinfiltration method. All constructs were transformed to *Agrobacterium tumefaciens* GV3101 strain, excluding pX11 which was transformed to *A. tumefaciens* EHA105 strain. In all cases, agrobacteria were grown overnight in LB media and brought to a final O.D.600 0.2 in infiltration buffer. When co-infiltrated, agrobacteria carrying separate constructs were each brought to O.D.600 0.2 and mixed in a 1:1 ratio before infiltration. Tissues used for subsequent LC-MS analysis were sampled from leaves 7 days post infiltration. For LC-MS analysis of L-DOPA and betalains, 3-4 biological replicates for each experiment were sampled, each consisting of infiltrated tissues from 2-3 different leaves.

Metabolite Extraction and Analysis

For betalain analysis, extraction solution (80% ethanol and 0.1% formic acid in DDW) was added to frozen, ground plant tissue (0.1-0.25 g) in a ratio of 200 µL 0.1 g-1 tissue. Samples were incubated at room temperature for 30 min. followed by 5 min. sonication, 5 min. centrifugation and filtration through 0.22 µm PVDF filters (Millipore). Samples diluted 3 fold in DDW were analyzed using a high resolution UPLC/PDA-qTOF system comprised of a UPLC (Waters Acquity) connected on-line to an Acquity PDA detector (200-700 nm) and a qTOF detector (tandem quadrupole/time-of-flight mass spectrometer, XEVO, Waters) equipped with an electrospray ionization (ESI) source. ESI was used in positive ionization mode at the m/z range from 50 to 1600 Da. The following settings were used: capillary—1 kV, cone—27V, collision energy—6 eV. For MS/MS or MSE runs, collision energy ramp from 15 to 40 eV was used. Separation of compounds was performed on a UPLC HSS T3 column (Waters Acquity, 1.8 µm, 2.1×100 mm) using eluents A (1% acetonitrile, 0.1% formic acid) and B (100% acetonitrile, 0.1% formic acid) as follows: the first 3 min.—isocratic elution at 100% A; 3.0-22.0 min—a linear gradient to 75% A, 22.0-22.5 min—a linear gradient to 100% B, 22.5-25.5 min—washing at 100% B, 25.5-26.0 min—return to 100% A and 26.0-28.0 min—equilibration at 100% A. Column temperature was set to 35° C., flow—0.3 ml/min. Betanin and iso-betanin were assigned using red beet leaf extract as reference. Other betalain compounds were putatively identified based on accurate mass, UV-VIS spectra, and MS/MS or MSE fragmentation (detailed in Table 2).

TABLE 2

Betalain compounds identified by LC-MS analysis.

| No. | Name | Elemental composition | [M + H]+, Da | Mass error, ppm | Rt, min | MS fragments | UV/VIS, nm |
|---|---|---|---|---|---|---|---|
| | | | Betacyanins | | | | |
| 1 | Betanin[a, c, d, e, f] | C24H26N2O13 | 551.1513 | 0 | 8.31 | 389.10 [M + H—Hex]<br>345.11<br>[M + H—Hex—COO]-<br>343.0 [M + H—Hex—H2COO]<br>297.09 [M + H—Hex—2H2COO]<br>194.05<br>150.1 [M + H—Hex—H2COO—C9H7NO4] | 534 |
| 2 | Iso-betanin[a, c, d, e, f] | C24H26N2O13 | 551.1502 | 2 | 9.06 | 389.10 [M + H—Hex]<br>343.0 [M + H—Hex—H2COO]<br>150.1 [M + H—Hex—H2COO—C9H7NO4] | 534 |
| 3 | Betacyanin I[c] (unknown) | C31H31N3O14 | 670.189 | 0.9 | 12.67 | 626.20 [M + H—COO]<br>582.21 [M + H—2×COO]<br>538.22 [M + H—3×COO]<br>389.10 [M + H-281.0902 (C13H15NO6)]<br>345.11 [M + H-281-COO]<br>301.11 [M + H-281-2×COO]<br>282.09 [M + H-389.10 (Betanidin)]<br>264.09 [M + H-389.1 (Betanidin)-H2O]<br>257.13 [M + H-281-3×COO]<br>247.08<br>180.10<br>138.06 | 532 |
| 4 | Betacyanin II[c] (unknown) | C31H30N2O14 | 655.1771 | 0.8<br><br><br><br><br>ppm | 15.68 | 389.10 [M + H-266.0790 (C13H14O6)]<br>345.10 [M + H-266-COO]<br>343.10 [M + H-266-H2COO]<br>301.12 [M + H-266-2×COO]<br>299.10 [M + H-266-H2COO—COO]<br>196.06 [M + H—C9H7NO4]<br>194.04 [M + H—C9H9NO4]<br>150.05 [M + H-266.0790-H2COO—C9H7NO4] | 533 |

TABLE 2-continued

Betalain compounds identified by LC-MS analysis.

| No. | Name | Elemental composition | [M + H]+, Da | Mass error, ppm | Rt, min | MS fragments | UV/VIS, nm |
|---|---|---|---|---|---|---|---|
| 5 | Betanidin[g, i] | C18H16N2O8 | 389.0991 | 1.5 | 9.89 | 343.09 [M + H—H2CO2]<br>297.09 [M + H—2H2CO2]<br>255.1 [M + H—2H2CO2—CO2]<br>253.08 [M + H—3H2CO2]<br>150.05 [M + H—Hex—H2CO2—C9H7NO4] | 539 |
| 6 | Iso-betanidin[g, i] | C18H16N2O8 | 389.0988 | 0.8 | 10.83 | 343.09 [M + H—H2CO2]<br>297.09 [M + H—2H2CO2]<br>255.1 [M + H—2H2CO2—CO2]<br>253.08 [M + H—3H2CO2]<br>150.05 [M + H—Hex—H2CO2—C9H7NO4] | 539 |
| 7 | Betacyanin III[e] (unknown) | C26H28N2O14 | 593.1618 | 0.2 | 10.72 | 547.11 [M + H—H2COO]<br>511.17 [M + H—2×H2O]<br>389.09 [M + H—C8H12O6]<br>345.11 [M + H—C8H12O6—COO]<br>325.07 [M + H—C8H12O6—H2COO—H2O]<br>301.11 [M + H—C8H12O6—2—COO]<br>299.10 [M + H—C8H12O6—H2COO—COO]<br>297.08 [M + H—C8H12O6—2×H2COO]<br>194.04 [M + H—C8H12O6—C9H9NO4]<br>178.05 [M + H—C8H12O6—C9H7NO4—H2O]<br>176.03 [M + H—C8H12O6—C9H9NO4—H2O]<br>150.05 [M + H—C8H12O6—H2CO2—C9H7NO4] | 534 |
| | | | | | | Betaxanthins | |
| 1 | Vulgaxanthin I[f, g, h, i] (glutamine-betaxanthin) | C14H17N3O7 | 340.1147 | 0.6 | 2.21 | 323.08 [M + H—NH3]<br>277.08 [M + H—NH3—H2CO2]<br>231.07 [M + H—NH3—2×H2CO2]<br>194.04<br>185.07 [M + H—3H2CO2—NH3]<br>157.06 [M + H—3H2CO2—NH3—CO]<br>150.05 [M + H—COO—C5H10N2O3]<br>148.05 [M + H—H2CO2—C5H10N2O3]<br>132.10<br>86.1 | 476 |
| 2 | Indicaxanthin[b, c] (proline-betaxanthin) | C14H16N2O6 | 309.1090 | 1.0 | 7.69 | 263.10 [M + H—H2COO]<br>217.10 [M + H—2×H2COO]<br>219.11 [M + H—COO—H2COO]<br>189.10<br>175.12 [M + H—H2COO—2COO]<br>173.11 [M + H—2×H2COO—COO]<br>150.05 [M + H—COO—C5H9NO2]<br>145.07<br>106.07 [M + H—2COO—C5H9NO2] | 478 |
| 3 | Dopaxanthin-hexoside[b] | C24H28N2O13 | 553.1667 | 0.5 | 7.97 | 391.11<br>(C18H19N2O8) [M + H—Hex]<br>357.13 [M + H—Hex—2×OH]<br>347.13 [M + H—Hex—COO]<br>345.11 [M + H—Hex—H2COO]<br>303.13 [M + H—Hex—2×COO]<br>299.10 [M + H—Hex—2×H2COO]<br>255.11 [M + H—Hex—COO—2×H2COO]<br>211.07 [M + H—Hex—C9H8O4]<br>208.05<br>194.04<br>181.05 [M + H—C9H10N2O4]<br>165.05 [M + H—Hex—C9H8O4—H2COO]<br>150.05 [M + H—Hex—H2COO—C9H9NO4]<br>106.06 [M + H—Hex—H2COO—COO—C9H9NO4] | 478 |
| 4 | Betaxanthin I[b] (unknown) | C18H19N3O4 | 342.1445 | 2.6 | 6.67 | 298.15 [M + H—COO]<br>254.16 [M + H—2×COO]<br>252.15 [M + H—H2COO—COO]<br>237.14 [M + H—2×COO—NH3]<br>225.14<br>196.10<br>159.09<br>132.08<br>117.05<br>106.06 | 476 |
| 5 | Valine-betaxanthin[g, h, i] | C14H18N2O6 | 311.1245 | 0.6 | 10.69 | 267.11 [M + H—COO]<br>265.11 [M + H—H2COO]<br>221.13 [M + H—COO—H2COO]<br>219.13 [M + H—2×H2COO]<br>193.13 | 469 |

TABLE 2-continued

Betalain compounds identified by LC-MS analysis.

| No. | Name | Elemental composition | [M + H]+, Da | Mass error, ppm | Rt, min | MS fragments | UV/VIS, nm |
|---|---|---|---|---|---|---|---|
| | | | | | | 175.12 [M + H—COO—2×H2COO]<br>166.05<br>150.05 [M + H—H2CO2—C5H9NO2]<br>132.05 [M + H—H2CO2—C5H9NO2—H2O]<br>119.06<br>104.05 [M + H—2×H2CO2—C5H9NO2]<br>94.05 | |
| 6 | Betalamic acid[g, h, i] | C9H9NO5 | 212.0558 | 0.5 | 8.79 | 166.05 [M + H—H2COO]<br>148.04 [M + H—H2COO—H2O]<br>138.05 [M + H—H2COO—CO]<br>120.05 [M + H—2×(H2COO)]<br>92.05 [M + H—2×(H2COO)—CO]<br>65.04 | 408 |

Betalain compounds identified by LC-MS analysis in *N. benthamiana* agroinfiltration experiments of [a]pAD1-GT+pDODA1, [b]pAD6+pDODA1 and [c]pX11, [d]*N. benthamiana* callus, [e]*N. glauca* callus, [f]pX11-transformed *N. tabacum*, yeast expression experiments of [g]CYP76AD1+DODA1, [h]CYP76AD6+DODA1 and [i]CYP76AD1/AD6+DODA1. All fragments were obtained in the MS/MS mode excluding betanidin and iso-betanidin, for which fragments were determined in the $MS^{(E)}$ mode. Rt, retention time; MS fragments, masses of fragments obtained in positive ionization mode; UV/VIS, absorption maxima at UV/visible range; Hex, Hexose.

For L-DOPA analysis, samples were extracted as described above and analyzed using a UPLC/PDA-MSMS instrument, where a UPLC separation module (Waters Acquity) was connected to a photodiode array detector (Waters Acquity 2996, 190-800 nm), and (on-line) to a triple quadrupole MS detector (Waters Xevo TQ MS), equipped with an ESI source. Compounds were separated with a Phenomenex Luna column (2×150 mm, 3 μm) using a following gradient: the first 1 min.—linear gradient from 100 until 90% A, 1-4 min.—90-75% A, 4-5 min.—75-0% A, 5-9.5 min.—washing at 100% B, 9.5-10 min.—return to 100% A, and 10-12 min.—equilibration at 100% A, where A is 0.1% formic acid in water, and B is 0.1% formic acid in acetonitrile. Column temperature was set to 35° C., flow—0.25 ml/min. Samples were analyzed in positive ionization mode, using the following settings: capillary—2 kV, cone—26 eV, with two transitions 198.1>152.1 (collision—15 eV) and 198.1>181.1 (collision—10 eV) used for compound assignment. L-DOPA was identified by comparison with an L-DOPA commercial standard (Sigma-Aldrich), dissolved in DDW (5 μM) and injected with the same LC-MS conditions.

For relative quantification of betaxanthins in VIGS-silenced beet leaves by spectrophotometry, samples were extracted using the same procedure as detailed above, except 80% methanol was used instead of 80% ethanol. Extracts were diluted 4 fold in extraction solution, placed on a 96 well plate and analyzed with a Biotek Synergy HT Microplate Reader. Relative betaxanthin content of each sample was assessed by measuring absorption at 475 nm and subtracting the value of absorption at 600 nm.

For estimation of betacyanin content by spectrophotometry, the same extraction method was used as above. Samples were diluted in DDW to obtain solutions of O.D.535<2.0. Betacyanin quantification was based on absorption measurements at 535 nm and 600 nm, and calculated using a previously described method.

Recombinant Expression in Yeast

Figure 8A:
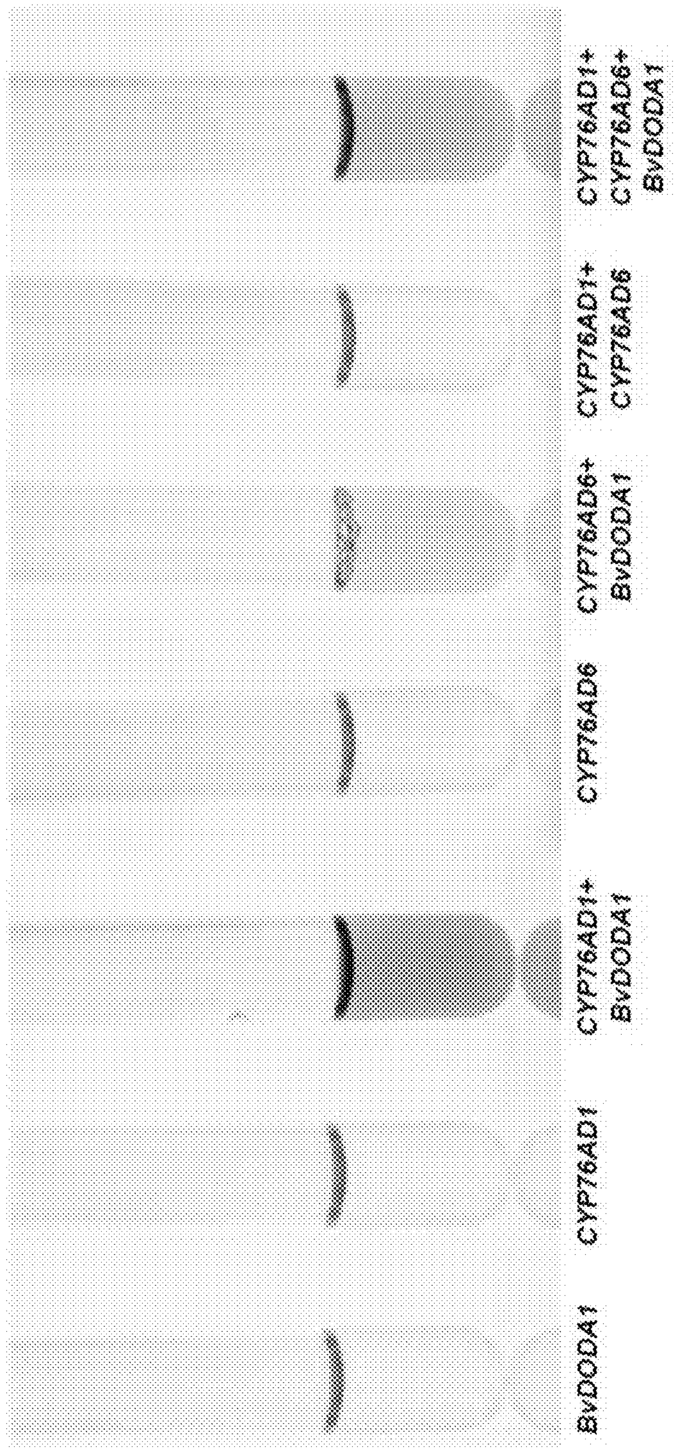
FIGS. 8A-8C. Cytochrome P450s CYP76AD1 and CYP76AD6 differ in activity and phylogeny.
Figure 8B:
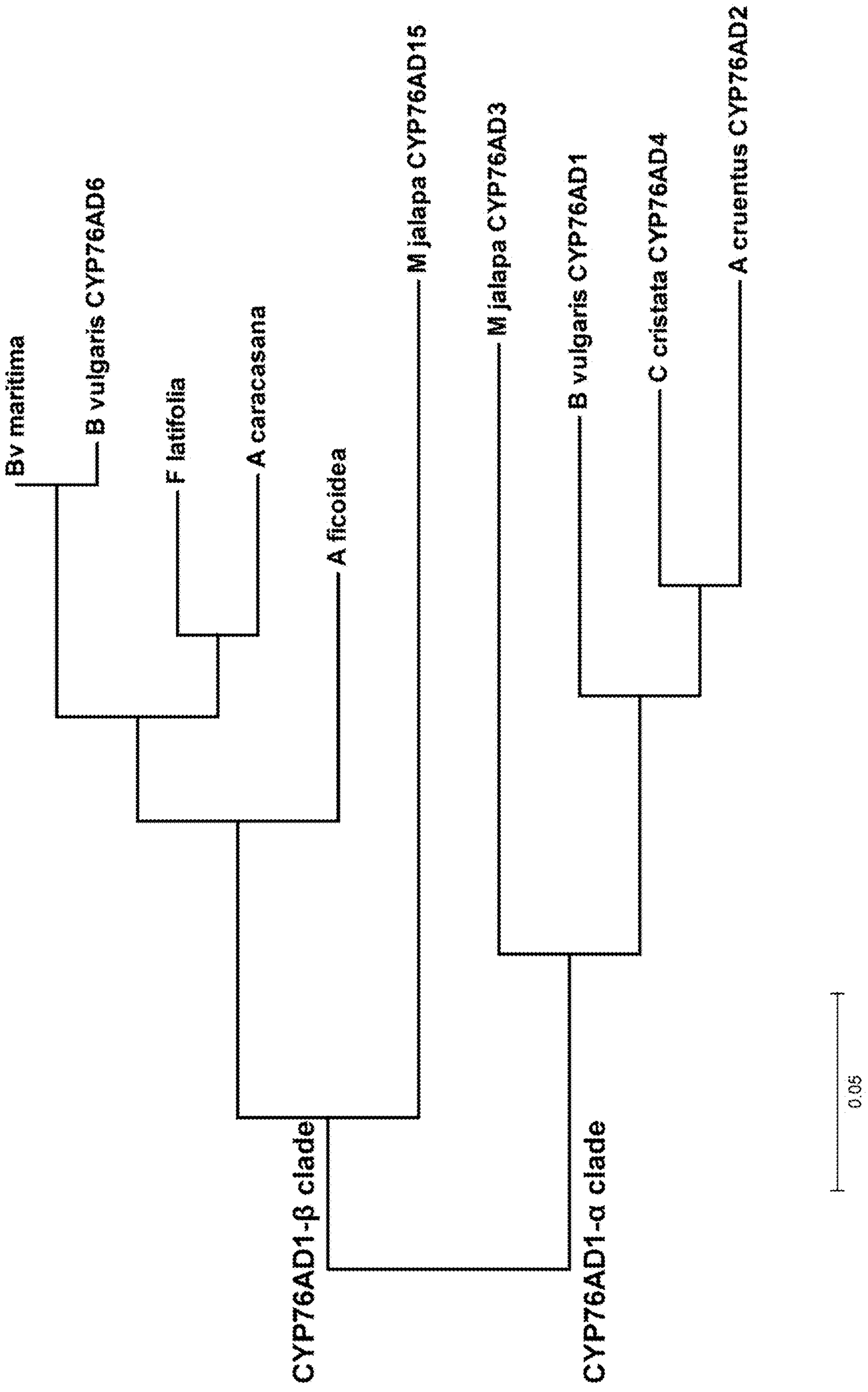
Figure 8C:
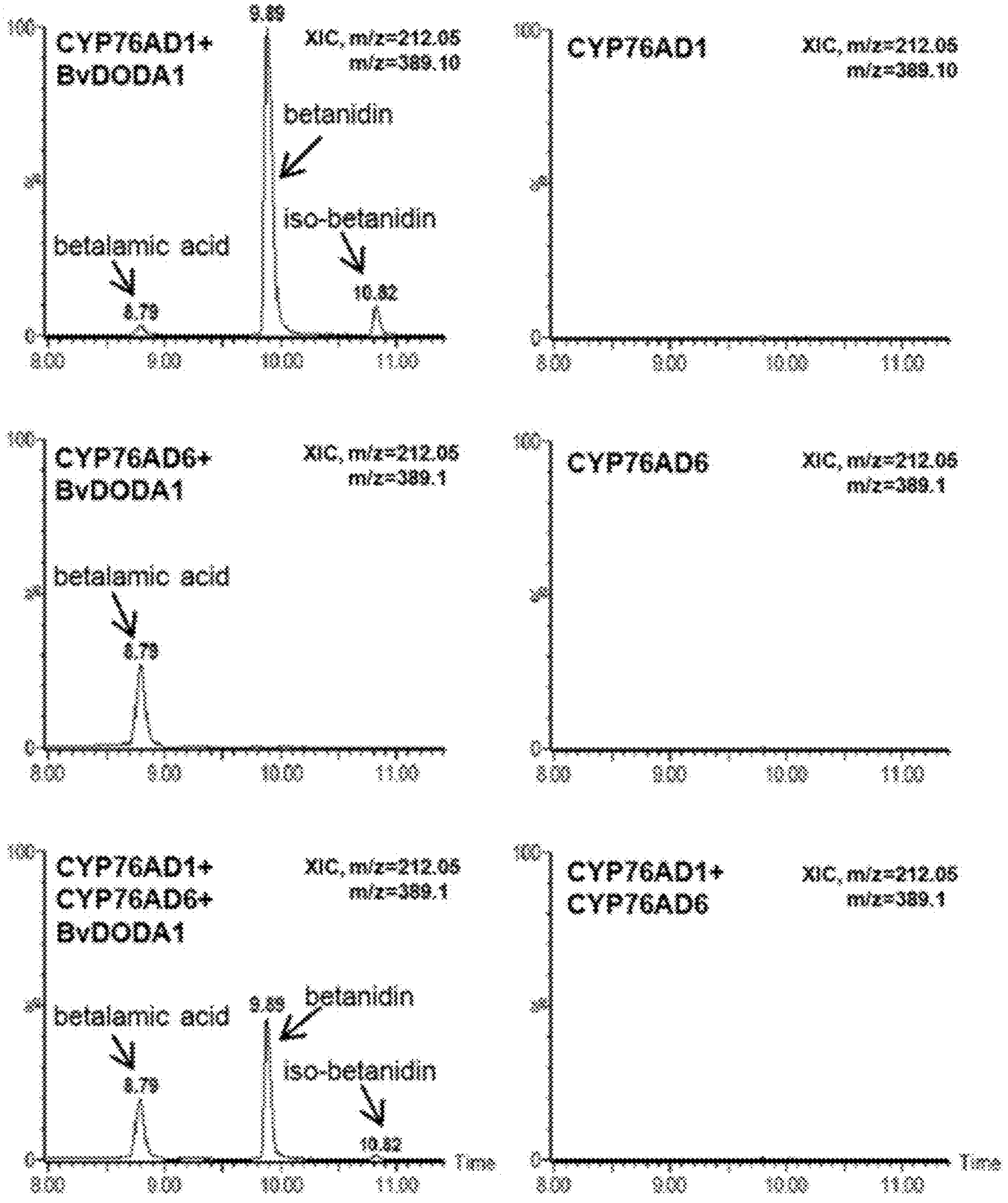

CYP76AD1, CYP76AD6 and BvDODA1 coding sequences were PCR-amplified and cloned to BP sites of a pDONR207 vector using Gateway cloning (Life technologies, Invitrogen) according to manufacturer's manual, and were next recombined to the LR sites of pAG423GAL-ccdB (for CYP76AD6), pAG425GAL (for BvDODA1), and pYES-DEST52 (for CYP76AD1, Invitrogen) vectors. In addition, the beta-glucoronidase (GUS) coding sequence was introduced to these vectors for control assays. The destination vectors were transformed using the PEG/LiAc method to *S. cerevisiae* strain BY4742, in sequential transformation. Each yeast clone was eventually transformed with the three destination vectors, expressing different combinations of CYP76AD1, CYP76AD6, BvDODA1 and GUS. Yeast strains were grown in standard SD medium overnight, containing 2% glucose and lacking histidine, leucine and uracil. The yeast were pelleted, re-suspended to O.D.600 1.0 in 2 ml SD media with 2 mM ascorbate, 1% raffinose and 2% galactose, lacking histidine, leucine and uracil, and grown overnight. Images in FIG. 8 are of media in which yeast were grown, following overnight galactose induction. For LC-MS analysis, 1 ml of liquid medium was dried in an evaporator and re-suspended in 100 μl of DDW.

Bioinformatic Analyses

For co-expression analysis, contigs corresponding to DOPA 4,5-dioxygenase (MjDOD), cyclo-DOPA-5-O-glucosyltransferase (cDOPA5GT) and CYP76AD3 were separately used as 'baits'. Genes co-expressing with either of the 'baits' were identified by using an R script to calculate Pearson correlation values, based on normalized count values of each gene across all 24 libraries.

For generation of the phylogenetic tree of CYP76AD1-like proteins, CYP76AD6 protein sequence was first used for a BLASTp query of the NCBI nr database. BLASTp top four hits with highest sequence identity and full protein sequence were selected for multiple sequence alignment, together with the CYP76AD1 protein and its previously described orthologs CYP76AD2, CYP76AD3 and CYP76AD4. Multiple sequence alignment was performed with Clustal Omega and processed into a neighbor-joining phylogenetic tree with MEGA software version 6.06. Bootstrapping of 100 iterations was used for validation. CYP76AD6 and CYP76AD1 pairwise alignment was done with Clustal Omega using default parameters and edited with GeneDoc software.

Plant Transformation and Regeneration

Agrobacteria-mediated plant transformation and regeneration was done in tobacco leaf discs, eggplant, *N. benthamiana*, tomato, potato, *Petunia, Nicotiana glauca* according to methods known in the art. A protocol used for *Solanum nigrum* transformation is provided in hereinbelow. All plant species were transformed using agrobacteria GV3101 strain. Plant tissue culture was carried out in a climate rooms (22° C.; 70% humidity; 16/8 hours of light/dark, 2500 Lux light intensity).

Sequences of Genes Used in this Study

Sequences provided are contig sequences obtained from de-novo assembly of *Beta vulgaris* and *Mirabilis jalapa* transcriptome (RNA-seq) data. All sequences are presented in the 5'→-3' direction.

>MjCYP76 from *M. jalapa*

(SEQ ID NO: 1)

CTTCAAATCCTCCCACGTATATATCAACAAAAACCAAAAACATCATCT
CATTACAATAATGGAGTATCATCTTCTCTTCCTTCTCCTCCTGCCGAT
CATCCTTATCTTCGTGTTCCTCAATCACAAGCCCAAGCAAACCAAACT
CGAACCACCAGGACCACGTCCATGGCCCATCATAGGCCACACCAACCT
CGTCGGCTCCAAACCTCATCAGTCCATTGCCAAACTAGCTCATATTTA
CGGTCCCATAATGTCACTTAAGCTAGGGAGAATCACTACTATTGTCAT
ATCTTCCCCTGAAGCAGCCAAAGACTTGTTCCTGAAACATGACCTTAC
TTTCTCAAGTAGGCAAGTTCCTCACGCTTCAACCGCTACAAACCATGA
CAAACTATCCATGGTTTGGCTCCCTGTATGTCCCAAATGGCGCTATCT
TAGAAAGATCGCGGCCATCCAACTATTCACCAACCAACAACTTGATGG
TGGTCAGGTACTAAGGCGTAAGAAAGTGGACGAGTTGATCCAATTTGT
GACTCGTTGTAGTAAACAAGGGCAAGTCATTGATATTGGAGAGGCTGT
TTTTATTACTACTCTTAACTTAATGTCAAATACCTTTTTTTCCAAGGA
TTTGTGTAGTTATGGTTTGGCCGAATCACGAGAGTTTAAGGATCTATT
TTGGGAGTTCATGAAAGTGCTAGCGAGTCCTAATGTTTCTGATTATTT
TCCATGGTTAAGATGGTTGGATTTGCAAGGCATCAAGAGAAGAAGCGA
GGGTTGTTATCGCAAGATGTTGGGTTTTTTTGGGGAGATTATTGATCA
GAGATTGAGAGATCCAATGTCATGTAAGAACGATGTATTGGACACTCT
ACTCAAACTTGTCGACCAAAAAGAGTTGAGCTTTGAGGATGTCAAACA
TATGCTTGTGGATTTGTTTGTTGCAGGGACGGATACAACTTCGAACAC
ATTGGAATGGACAATGGTAGAACTTTTACGCCACCCTAACATATTGAC
TAAAGCACAAACTGAACTCAGCCAAGTCATAGGCAAGGACAAGTTAGT
CCAAGAATCATGTATCACCAAGTTGCCATATCTTCAATCAATATTGAA
AGAAACATTCAGGTTGCACCCACCGACTCCTTTTTTACTTCCACACAA
AGCAATCGAGAACGTTGAACTATGCAACTATCACATACCTAAAGGTGC
TCAAGTTTGGGTGAATGTGTGGTCTATTGGCCGCGATCCCAACATTTG
GTCAAGCCCGGACTTATTTTCCCCAGAGAGATTTTTAGGTACCGACAT
TGATATAAAAGGTAACCATTTCGAGCTCATACCATTCGGAGCAGGAAG
AAGGATTTGCCCCGGGTTGTCACTAGCTTACAGGATGCTTCATTTGAT
TTTGGCCACTCTCCTTCATTCATTCAATTGGAACCTTCCTAATGACGT

-continued

ATGTCCGGAAAATATGGATATTGAAGAAAAATTTGGGATTACACTTCA
AAAGATCATGCCACTCAAAGTCATACCAAGCTCTAGGTGTCTGGATCA
CGACAACTAACTGGTGTTAATCTTTTACAACATATTGAATGATATATA
TCACGTTAAGGTACATGCGTCTAGATGCAGAAACTTGCATACGTTTCC
TTTTCAATAAAGTCTTGCATATGTATGGTTTATAGGGTGATGTAATTT
CTTGTTTGTTTTTACTTAAGTTTATAAGACATTTTTTTTTTTTTTTA
TCGATGCTCTTACTCATTAAAATATTGGAACATATACAAAATTTTATA
TGTTTTAGATAAAATTATACAGGTTTTAATTTTAGGAACTTACCACTT
GTTCACACTGCGAGACTTAAATAGTCAAAATAGAAAATACACACTATT
AAAAAGTACTCACTATTTATCAAATTTAT.

>BvCYP76new from *Beta vulgaris*

(SEQ ID NO: 9)

CAGTCATTTAAAATCCTGTAAATTACTCACATACATAACCAAATTAAA
GTTGCCGCCGTACTGATTTCCAAAGGTCCTACATCTATCAATGGAGTA
TTACACCATAACGCTATTATTCATCATCTTCACAATATCAATATTCGG
TACAAAAATTTTGAGCAAGTCCAAACTTCCTCCAGGACCAACACCATG
GCCTATCATAGGCAACATCCTCGAGCTAGGCAAGTTACCTCATCAGGC
AGTTGACAAGCTCTCAAAAACCTATGGCCCTATATTATCTCTCAAACT
CGGAAGCATCACTACAATAGTAATATCATCCCCTGAAATCGTTAAAGA
AATGTTCCTCGAGCACGACTTAGCCCTTTCTAGTAGGCCTTCCCCGGA
TGCTTCGAGGGTGGGAAACCATAACAAATTTTCCATTGTTTGGCTCCC
AGTGTCCCCCAAATGGCGGGACCTTAGAAAAATTGCTACTATCCAATT
GTTTACTACTCAACGCCTAGATTCTAGCCAAGAACTACGGCAGATCAA
GGTGAACGAGCTGGTTGATTATGTACGACAGTGTTGTGAAAAGGGTCT
ACCTGTTGATGTTGGTAAAGCCGGGTTTACTACCACGTTAAATATGTT
GTCTAACACGTTTTTCTCCATGGATTTGGCTAGCCATGCTTCTTCGAA
TTCGCAAGAGTTCAAGGATCTTGTTTGGAGTCTTTTGGAAGAGGGTGC
AAAGCCTAATGTGTCGGATTTTTTCCCGATAGTTAGAGAATTGGATTT
GCAGGGAGTATCGAAAAATAGAAGGGTGCACATGAAGAAGCTAATGGG
AATTTTCGAGGAAATCATTGATGGAAGGTTGACAAAGTTAAAGGATGT
GAAGGATGATGTTCTAAGTACTTTACTCAAACTTGTTAAGGATGAAGA
ATTGAACCTTGACGACGTCAAACATATGCTCATGGATTTATTTTTAGC
GGGAACAGATACAACCTCTATCACATTGGAGTGGGCGATGACAGAATT
ACTTCGCAATCCAGAAAAGATGGAAAAGGTTCAAATTGAGTTGGACAA
AGTACTTGGCAAGGATAGTTCTCTGCAAGAGTCAATGATCTCAAAATT
ACCATATATTCAAGCAATAGTGAAAGAAACATTAAGATTACACCCACC
AACTCCTTTCTTGATTCCTCACAAAGCAGAAAAAGATGTATTGTTATG
CAACTATTTAGTGCCCAAAAACTCAATTATTTGGGTTAATTTATGGTC
GATCGCTCGTAGTCCAAGTGTGTGGCCAAATCCAGAATCATTTTCTCC
TGAAAGGTTTTTGGAGATGGAAATTGATATTAAAGGACGAGATTTCAA
ACTCATACCCTTTGGATCAGGAAGAAGAATGTGTCCTGGAATGCCACT

-continued

TGCTTATAGGATGACACATATGTTGTTGGCTACTCTTCTTCATTCATT
TAACTGGAAGTATGGTGAGGCAAGTCCAAAAGATATAGACATGAAAGA
AAAGTTTGGGTTGACGTTGCAAAAGGCTCAGCCACTTCAAGCAATTCC
AATTCCCAGATGATCAATCTCTTTTGAGGAGTTAGACGATTTCTTTGT
GTCAACCAACTAGTACTTATCGGAACATTTATTGTTAAATGTGTCTGT
TAGATGTACATATGATGTTGTTATACTAAGAAATAACGGTGTTTAAGT
GCAACATGGGACAAGAGGATTATGTAAAGTATCCTAGATTTTATTAGG
TGCTCCTACACCTATGTATTGGTGCATTTGCACCAAGTCGTCTGTAGA
AAACTTGAGACTTGGGAGGCAAGAACTTTACCTCTGTAAAAAAAACGC
GTTTTTTGCATTCTCCTTGTATCTTTTGCAAGAGATTGTACGCATTCA
CAAAACATCAAATACATTTGTGTTTACACAATAAGAATCGCCAACACT
GA.

>CYP82G1-like from *M. jalapa*
(SEQ ID NO: 36)

TACGTCTATTCTTGCCTCCCATTTCCTCCCTGCAAAAAGGAAGAAAAT
GGAAATACCCTTTAATTTGCAACCTATTTTTCTAATTATTGTACTATC
TACCTTCATTCTAACCCACCTAATAACAAAAAACACAAGAAAGTTCAA
CCAATGCAAATCAAAAACCAAGCCAATACCAAAACCACCTGGCTCACT
ACCCATAATAGGTCACTTGCACCTCCTAAGAGGTCATGGAACCACCCT
AGGTCGCACCCTCGGAGCCATGGCCGACAAGTCCGGACCCATTTTCGG
CCTCAAGCTAGGCCAACACAAGGCTATAGTCATTAGTAACTGGGAGAT
AGTCAAGGATTGTTTCACCAATAATGACATGAACCTTGCAACTAGACC
TAGCATGGCTATTAGCAAATATATTGGTTATGACTTTGCCTCTTTCTC
TATCTCACCTTATGGCCGATATTGGCGTGAGATTCGTAAGATCTCTAC
TGTTGAGCTCTTGTCAAACAAACGCCTTGAGAAAATGAAGCATGTTCG
AACTTTTGAGGTGAACTCTTGCCTTCAAATCTTCTATGAAAAATGTGT
CAAATCAGAGGATAATGAAAGTAATAAAGTAGCAAAAATTTGTCTTAA
AAAGTGGTTAGAATATATTGGTTTTAATATCGCACTATCTATGATAGT
TGGCAAGAGATTCTCCTACGACCAGTATTATAAAAAAAATACTGTTGC
ATCGAGATTTATGAAGGCAATAGAAAGAGCAACCCACTTAGCAGGACT
TCCTATACCCTCGGATTTTTTACCATGGGTTGAATGGATGGATTTGGT
GGGTTACATTGGTGCTATGAAGGAAACTCATAAGGAAATTGATGTGAT
TATTGGACATTGGCTTGATGAGCATATTCAAAAGAGGAAAGAGACGTT
AGAAAGGCGAGGTACAAGCATTGATGATAGTGACTTCATGGATGTAAT
GTTATCTAACATTACTGAACAATTTGCCAAGTCAACCTACTCTAAAAA
CACCATCATTAAAGCAACAGCTTTGACACTACTTCTAACAGGTTCAGA
AAGCACCTCAATCACACTAACATGGGCCATATCACTACTTCTAAACAA
CCCTACGGCCCAAAATTTGGCCCAACAAGAAATGGACAAACAAGTTGG
TAAACAAAGATGGGTTGAAGAATCTGACATCACCAATCTACCATACCT
CCAAGCCATCATAAAGGAAACTTTACGTTTGTATCCACCAAGCCCATT
AGCAGGCCCAAGAGTGGCCCAAGAAGACTGCCAAATCAATGGACATTG
TATCACAAAAGGAACCCGGGTGATTGTTAACATATGGAAGTTGCATCG
TGATCCGATGGTTTGGTCCGACCCAGATAAGTTCCGACCCGAAAGGTT
TATTGGGGAGCATAAGGATATTGATTTTAAGGGTCAATACTTTGGGTA
TATACCTTTTAGCTTGGGTAGGAGGGGTTGTCCTGGGATGAATTTTGG
GCTACAAGTGGTCCATTTGATGTTAGCTCGTTTGGTCCAAGGGTTCGA
TATTTGGGCTCAAAATGGTGGCCTAATTGATTTGAAGGAAGGGTTGGG
CTTGGCTTTGCCCAAGGCTGGTCCATTGGATGTCATTCTTGCACCACG
TTTGTCCAGTGAGCTTTATGGAGCTTTATCAAAGGTGAATGTTACTTA
TGGTCGGGCAATGAATGAACTAGCTTTGTATTTATAATTTTACAAATA
ATTTGTAAGATATGAACTGTTTATCTAGTCACTTTTCCGCGTCTTAGA
ATATCAATAAGCAAAAAGTTTTATGTAATAATATGTATTAGTGTGTTA
TTGTATCATGATTCGTCGGTATACTGAAAATATTTTACGTCTAGGAGA
ATGTGCACACATTTAATCTTATTTGCTTATAAGTATTATATACATAAA
ATTTTCTACTTTATAATTTAGGTATATTGAGCTTTCGACCAAAACCCA
AAAACTAAAGAAGTTTTTTTAAAACATACAAGTTGGTATTGTTTAGA
TTTTTATTTATTTTTATTATCTCTTTTATTTGTACTTAGTGGGTGTGT
TAATAATGTAAAGAAGTATTAAATATTTATAGAGTTGGAAAAACCCAA
TATTTTACATTGGAAAAA.

>CYP78A9-like from *M. jalapa*
(SEQ ID NO: 37)

TACGTCTCTAACCTCCTTCTCCTCACCATCATCATCTTATTTCTCTCT
CTAACTTCCTATTTCTCTCTCTAGAATGGTCTCAACTAGTGACTCACT
CTGGCTTTTCACCTACTTAGCTTCAAAATATGATCATTTTACGACCCC
TAACTTTATTTATTCTTTGTTTTGTTTCGTAATATTTTTTATTTTGAT
TCATCTACTGTACTGGTCCCACCCAGGTGGTCCGGCATGGGGGAAGTA
TTCATGGACTCATCTCTCGGGATGGGCCGGGAAGCCCATCCCGGGCCC
AAGAAGTTGGCCCATTATAGGTGGTTTGGACCTGAAGATGGGACTGGC
TCATCGGAAGTTAGCCACAATGGCTGAGAAATACGGGACCATGGCTAA
GAGGCTCATGGCTTTTAGCCTAGGAGAAACACGCGTGATTGTCACGTG
CAATCCCGACGTGGCGAAAGAAATACTAAATAGCCCGGTTTTCTTGGA
CCGACCCGACCAGGAGTCGGCTTATGGGTTGATGTTTAACCGGTCTAT
AGGGTTCGCACCCTATGGGACCTACTGGCGAACCCTAAGGAAAATAAC
ATCAACCCATTTATTAAGCCCTAAACACGTAAAAGAATATGAGAACCT
ACGTAGGGAAATAATGGAACAAATGGTTGACTCGATATCGAACCAAGC
CGGACCGGTTCGGGTCCGGGAAATACTAAGGAGGGCTTCATTGGATAA
TATGATGGGGTCAGTGTTTGGTGGGCCCCACAAGGAGGTCGTTGAACA
GTTGATAGAAATGGTTGGTGAAGGGTATGACTTATTGGGTGTCCTTAA
TTTGGGGGACCATCTATCTTGGCTAGCCGAGTTTGACTTTCAAAAGGT
TCGGTTCAGGTGCTCTCAACTTGTTCCAAAAGTCAACCGGTTCGTTGG
TGAAATTATCGATGAACATCGGTCTAGTTCGGGTCAAATTATGAACCG
GGACTTTGTTGATGTTTTGTTGACTCTACCACAACATGAACAACTTTC
TCATTCTGACATGGTCGCTGTTCTTTGGGAGATGATATTTAGAGGAAC

-continued

AGATGCAACAGCAGTATTAATAGAATGGACATTAGCACGATTAGTAAT

TCATAAAGATATTCAATCAAAGGTCCAAAATGAGTTAGACCAAGTAGT

TGGAACATCACGAGCCGTTGAAGAGTCTGACCTATCATCACTGATATA

TCTAACGGCTGTGATTAAAGAAGTATTGCGGGTCCACCCACCTGGGCC

CCTCCTATCGTGGTCTCGCCTTTCAATTCAAGATACTACTATAGATGG

TTGTCATGTGCCAAAAGGTACTACTGCTATGGTTAACATGTGGGCTAT

TGCTAGAGATCCTAATGTGTGGGCCAACCCAGATGAATTTGACCCGGA

TAGATTTTTAATCGGTGGGTCCGAGTTTGAGTTCTCTGTTCTTGGGTC

GGATCTTAGACTTGCCCCTTTCGGGTCGGGTCGTAGGTCATGTCCTGG

GAAGGTCTTAGGTTTGACCACAGTCAGTTTTTGGGTTGCTTCACTCTT

GCATGAGTTTGAGTGGGTGACATCACCTAACGCTGACGTGGATTTGAG

TGAAGTGCTTAAGCTTTCGTGTGAGATGGCTCATCCTCTTACCGTGGA

AGCTAGGCCGCGACGTCATTAATTTTACAAAAGACGATATTCTCATAC

ACAGATTATTGTCAACTTTATCAATATATACGGGTGATAGTTTGACAT

TGTTATAGTATTCGGAAAAATATTTTCTAGAGATAAGTAAATTTATAA

TAATCTAAAAAACTGAATGTATAATTATATTAATTAATGTACTAATGT

TATTATAATGTTTATAAATGATTGTGAAATATATATGGTTAACATTAT

ATGTAATGAGAAATGGTTTGCTTGGCAAAAA.

>CYP86B1-like from *M. jalapa*

(SEQ ID NO: 38)

GCTAGCTGCCTTGTTCATTTCAAGAACAATATACACTAGTCAATCCAT

TTCAAATGGCCTACTTAGAAATTGTCATATTCTTCATTTTTCTCATCG

TAATTTGTTTTTCTTTTCGTGACAAAAATGGTCTCCCAACAAATTGGC

CGATTGTTGGGATGCTACCAGCTGTTCTAATCAATCTTCATAGAATTA

ATGACTATTTTGCTGAACTTGTTGCTAAATCAAATTTAACATTCTCAT

TTAAGGGTCCTTGGTTTAGCAACATGCGAATTTTAGCGACAGTTGATC

CAGCAAATGTGCACCATATAATGAGTAAGAATTTTAACAATTATCCTA

AGGGTGCTAAGTTTTACGACATCTTTGATATACTTGGAGATGGTATTT

TTAACACCGACTTTAATATATGGCAATACCATCGGAAAATGGCTCAGT

CATATATTGGTGACTCAAGATTTCAACAATTTTTGTTGAAGAAAGTTG

GGGAAAAGATTGAAGGTGGATTAATTCCTATCCTTGATCATGTTGCCA

TGCAAGGGTTACAAGTTGATTTACAAGATTTATTTGAAAGGTTTACTT

TTGATACTATTTGTTCACTTATTATGAACTATGATCCTATGTCTTTGT

CCATTGATTTTCCTGATGTTCCATCATCTAAGGCTCTAGATGTTGCTG

AAGAAGTCATACTTCTTCGTCATTTAGTACCTACAAGTGTTTGGAAGT

TTCAAAGATGGTTAGGTGTAGGGATGGAAAAGAAGCATAAGATAGCTT

GGCAAGTACTTGATGATTTCATTTATGAGTGCATATCAAGGAAAAGAG

AAGAGATGAGAGATAGTTTGTCCTATGAGAATAAGGACAATGAGATGG

GTGTTGATTTAATGACATTGTATATGAATGAAATCAAAAGTAATGAAC

TTGTCAAGGATGATCCTAACAAGTTTTTGAGGGATACTATTCTTAACT

TTTTTATTGCAGGTCGAGATACAACTAGTACTGCTTTATCGTGGTTTT

TCTATCTACTATCCAAGAATCCACAAGTGGTAGAAAAGATTAGACAAG

-continued

AGTTATCTTGGATCGTTTCACAAGAAAAAACTAAAAATTATGCTAATT

TGATTGATAAACTTGTTTATCTTCATGCCGCATTATGTGAAGCTTTAA

GATTATATCCTCCGGTGGTATTTGAAGCAAAGTCTCCGATTGAATCGG

ACACTTTACCAAGTGGTCATAAGATTGATCCTGACACACAAATAATCT

TAAATATGTACGCAATGGCGAGGATGAAAACAATATGGGGCGATGATT

GCGATCAATTTAAACCTGAGAGGTGGATATCATCAACAACAGGAAAGA

TTAAGCATGAACCTTCGTACAAGTTCTTGGCTTTTAATGCAGGACCAA

GAACTTGTGTAGGAAAAAATATGGCTTTTACTCAAATGAAAGCAATAG

CAATAGCTATATTACAAAACTATCATATACATGGTATTGATGGACAAG

TTATTGAACCTGATCTATCCATAATTCTCCATATGAAGAATGGATTCA

GAGTAACTGTTTCACCGTGTAACGTTTCTATATAACCATCGAGAGAAC

CAAGTTTCCTCGATCTCTTTTAAACATTGTAATGTTTAATTATCAACT

AAAAAATCGTATATTCTCTTCGTTTCATTTTTTTCTTTTTCTTTTTAT

CAAAGATCAAGGTAACGTCGGAAATAACCATATTGTTTTCTTTGGTTA

AATGAAAAGACAATGTAAGTTGTAAAAGTATGTAAGTGTAAAAATAAA

TTTAAAAAATTGTGTGAAAATAAGTTGTAATAAATAAAGAATAATGTT

GGTATTTTATTGTTTACTATTTTGATAAACAGAAAAAATAAAATAAAA

CTGTTTAAAAATAAAAGTGAGAAGAAAAAAAATAAAAGAAAAT.

Hypocotyl Transformation of *Solanum nigrum*

Media

- Liquid Jones (pH5.2)
- Basal media (pH to 5.8 with NaOH before adding the agar)
- MS with vitamins (cat M0222)=4.41 g/L
- Sucrose 31=30 g/L
- Agarose (plant agar) 0.6%=6 g/L

TABLE 3

IND1 (first callus induction medium)

| | Stock solution | Final conc. in medium | Amt. to add to 1 L of basal media | Amt. to add to 800 ml of basal media |
|---|---|---|---|---|
| IAA | 0.2 mg/ml | 0.02 mg/L | 100 µl | 80 µl |
| BAP | 1 g/L | 1 mg/L | 1000 µl | 800 µl |

TABLE 4

IND2 (second callus induction medium)

| | Stock solution | Final conc. in medium | Amt. to add to 1 L of basal media | Amt. to add to 800 ml of basal media |
|---|---|---|---|---|
| IAA | 0.2 mg/ml | 0.02 mg/L | 100 µl | 80 µl |
| BAP | 1 g/L | 1 mg/L | 1000 µl | 800 µl |
| Kan* | 100 mg/ml | 75 mg/L | 750 µl | 600 µl |
| Tic | 100 mg/ml | 100 mg/L | 1000 µl | 800 µl |

*Make media without Kan for controls

TABLE 5

| SHOOT (shoot induction medium) | | | | |
|---|---|---|---|---|
| | Stock solution | Final conc. in medium | Amt. to add to 1 L of basal media | Amt. to add to 800 ml of basal media |
| BAP | 1 g/L | 0.5 mg/L | 500 µl | 400 µl |
| Kan* | 100 mg/ml | 25 mg/L | 250 µl | 200 µl |
| Tic | 100 mg/ml | 100 mg/L | 1000 µl | 800 µl |

*Make media without Kan for controls

TABLE 6

| MAT (maturation medium) | | | | |
|---|---|---|---|---|
| | Stock solution | Final conc. in medium | Amt. to add to 1 L of basal media | Amt. to add to 800 ml of basal media |
| Kan* | 100 mg/ml | 25 mg/L | 250 µl | 200 µl |
| Tic | 100 mg/ml | 100 mg/L | 1000 µl | 800 µl |

*Make media without Kan for controls

TABLE 7

| ROOT (rooting medium in magenta) | | | | |
|---|---|---|---|---|
| | Stock solution | Final conc. in medium | Amt. to add to 1 L of basal media | Amt. to add to 800 ml of basal media |
| Kan* | 100 mg/ml | | | |
| Tic | 100 mg/ml | | | |
| IBA | 2 mg/ml | | | |

*Make media without Kan for controls

Procedure

Always work in a flow hood, close to a flame

Use forceps & scalpel sterilised with EtOH & flamed

Seal plates with parafilm before removing from the flow hood

Prepare the *Agrobacterium:*

Pick a colony from a fresh transformation into *Agrobacterium* GV3101 & inoculate 7.5 ml LB buffer in a 50 ml falcon tube Grow, shaking at 28° C. o/n Add liquid Jones (pH5.2) up to a total volume of 25 ml Handling of the Explant:

Using seedlings that have expanded cotyledons, but no true leaves—remove individual seedlings using sterilised forceps & place onto a sterile Petri dish (approx. 30 hypocotyls per plate).

Cut the hypocotyl using a sterile scalpel, dipping the scalpel into the *Agrobacterium* mix before each incision.

For the control, dip the scalpel into liquid Jones before each incision.

Place all of the explants onto IND1 plates & place in the growth room in the dark for 3 days (wrap in foil).

Subsequent Sub-Culturing:

Move the explants onto IND2 plates (spacing them out more ~20 per plate) & place in the growth room with light/dark cycling Check the plates every couple of days for contamination & transfer healthy explants to fresh media sooner if contamination is visible.

After 2-3 weeks, calli will form at the ends of the explants (where they were cut). Cut the calli away from the rest of the tissue & transfer to SHOOT media.

If calli have not formed—move to fresh IND2 media.

After 1-2 weeks, green shoots will start to develop from the calli. Transfer these calli to MAT media.

If shoots have not formed—move to fresh SHOOT media.

After 1-2 weeks, the shoots should be big enough to be cut away from the callus and transferred to ROOT media (in magentas).

If shoots are still small—move to fresh MAT media.

Move the plantlets to fresh ROOT media every 2-3 weeks until they have enough roots to move to soil.

Example 2

Figures 2A, 2B, 2C, 2D, 2E, 2F:
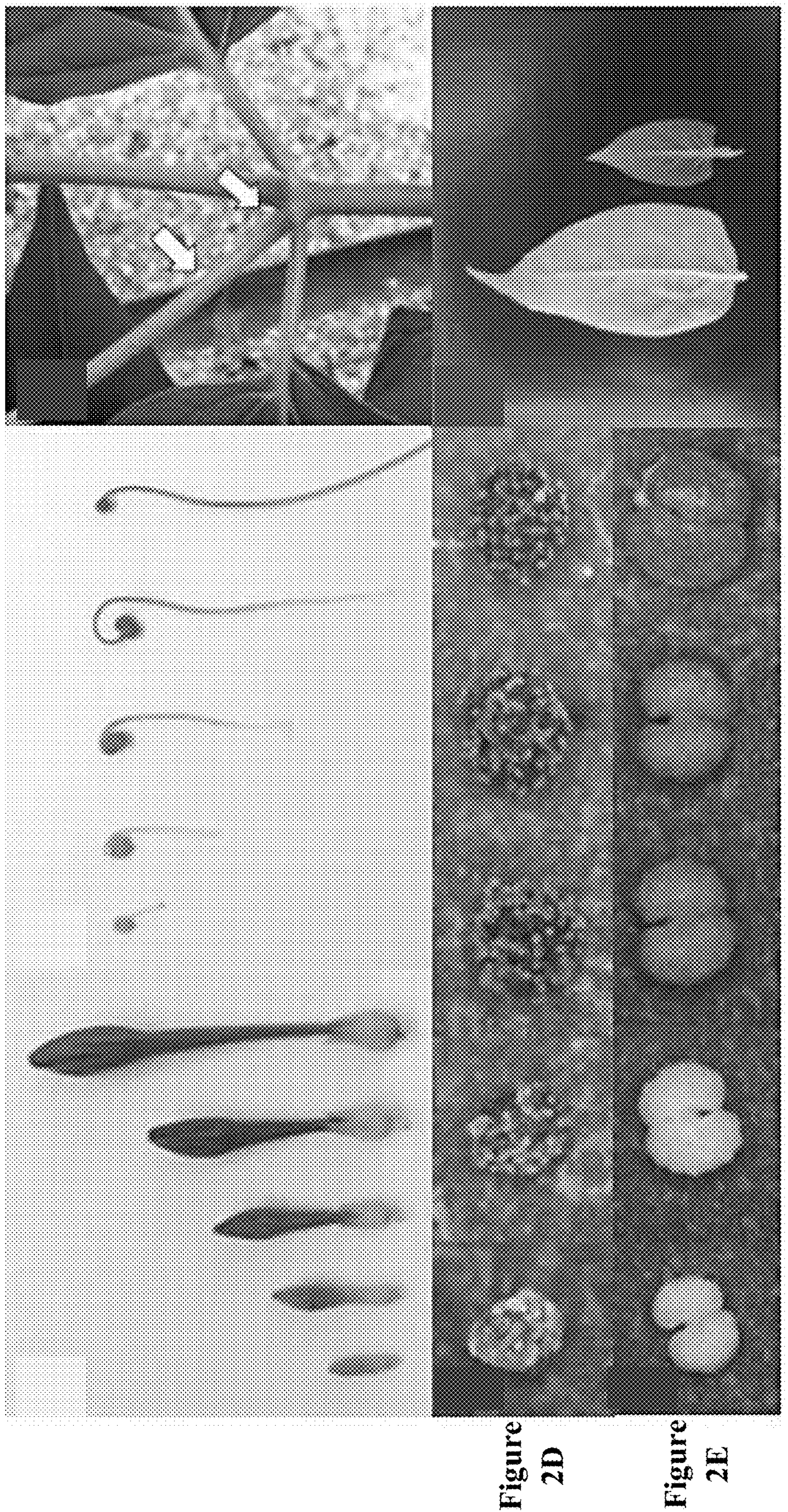
FIGS. 2A-2G. Identification of MjCYP76 (SEQ ID NO: 1) as a betalain-related candidate gene. Gene expression in *Mirabilis jalapa* was analyzed in a transcriptome dataset derived from 24 tissues, including four floral organ types in five developmental stages, red or green stem epidermis, and red or green leaves.

Transcriptome Profiling and Co-Expression Analysis in *Mirabilis jalapa* Suggests the Involvement of a CYP76AD1 Subfamily Member in Betalain Biosynthesis The primary goal of this study was to elucidate the first committed step in biosynthesis of betalains in plants, which commences with the aromatic amino acid tyrosine. Achieving this would close the gap in our current knowledge with respect to the plant enzymes and genes acting in the core betalain pathway (FIG. 1). Since genome and transcriptome sequence data from betalain-producing plants is currently very limited, we generated a comprehensive transcriptome dataset from the betalain pigmented *Mirabilis jalapa* (i.e. four o'clocks) plant. Libraries of 24 *M. jalapa* tissues were sequenced, including both betalain producing and non-producing ones. The selected set of tissues provided a temporal and spatial representation of betalain synthesis, as four different floral parts (i.e. petals, stamen, anthers and stigmas) were sampled in five developmental stages, each exhibiting increasing pigmentation during development (FIG. 2 A to F).

Figure 2G:
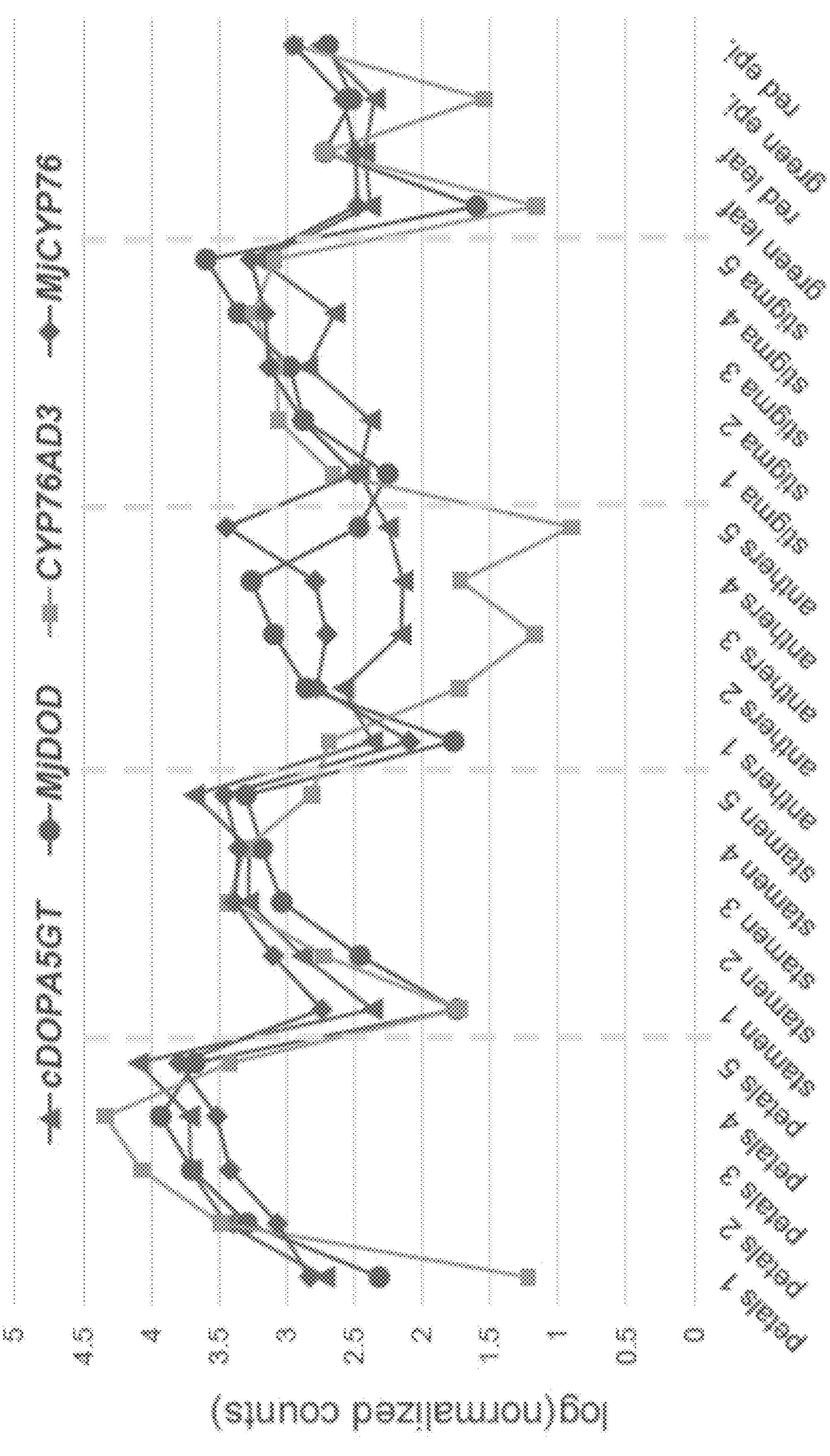

The transcriptome data was first analyzed by examination of gene expression patterns of the previously identified betalain-related genes in *M. jalapa*, namely DOPA 4,5-dioxygenase (MjDOD), cyclo-DOPA-5-O-glucosyltransferase (cDOPA5GT) and the cytochrome P450 CYP76AD3. These three genes were found to exhibit expression patterns which parallel pigment accumulation (i.e. increasing expression during flower development, and higher expression in red vs. green tissues) (FIG. 2G). Additional betalain related genes could thus potentially be found by co-expression analysis, searching for genes with expression patterns which highly correlate to those of MjDOD, cDOPA5GT or CYP76AD3.

Figure 3:
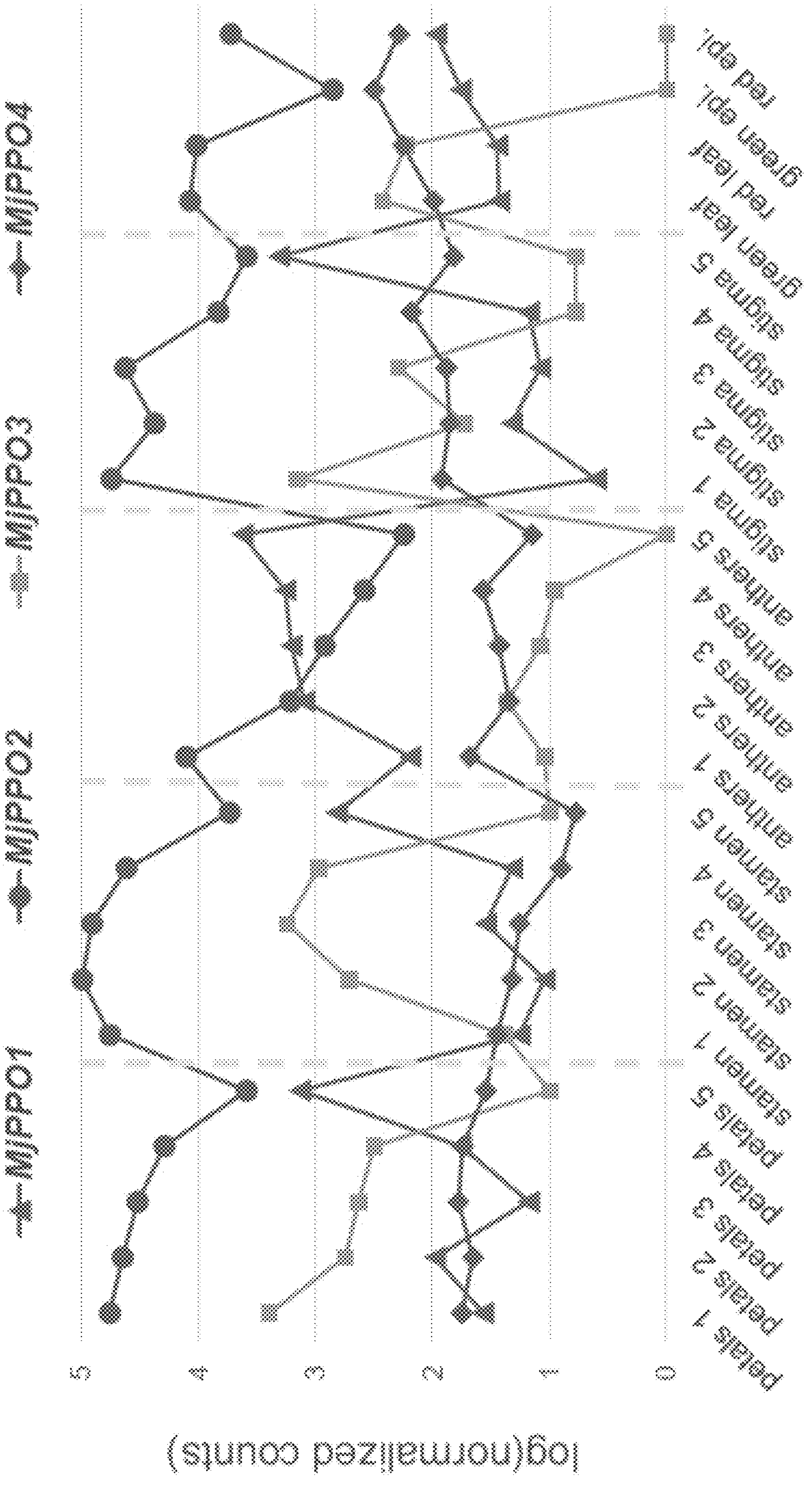
FIG. 3. Gene expression patterns of putative polyphenol oxidase-encoding genes MjPPO1 (SEQ ID NO: 5); MjPPO2 (SEQ ID NO: 6); MjPPO3 (SEQ ID NO: 7); and MjPPO4 (SEQ ID NO: 8) in the *Mirabilis jalapa* RNA-seq dataset.

Tyrosine hydroxylation in betalain-producing plants is commonly thought to be catalyzed by a tyrosinase (polyphenol oxidase) enzyme. We therefore initially searched for a tyrosinase-encoding gene that is co-expressed with either MjDOD, cDOPA5GT or CYP76AD3, however none was found. A polyphenol oxidase expressed in a pattern which parallels betalain accumulation could neither be detected by manual examination of genes annotated as polyphenol oxidases in the *M. jalapa* dataset (FIG. 3). Alternatively, L-DOPA formation could in theory be catalyzed in *M. jalapa* by a cytochrome P450-type enzyme. Four cytochrome P450-encoding genes were found to be co-expressed with one or more of the known betalain related genes used as baits, namely CYP82G1-like (SEQ ID NO: 36), CYP78A9-like (SEQ ID NO: 37), CYP86B1-like (SEQ ID NO: 38) and CYP76AD1-like (SEQ ID NO: 1). The latter, hereinafter named MjCYP76, stood out as a promising candidate, exhibiting high expression values throughout the dataset, in a pattern which highly correlated with betalain accumulation (FIG. 2G).

Example 3

CYP76AD1 and CYP76AD6 Co-Silencing Inhibits Betalain Production in *Beta vulgaris*

In order to examine whether MjCYP76 is indeed involved in betalain biosynthesis, a gene silencing assay was required. Since a robust and stable transformation procedure is not available for any betalain-producing plant we decided to apply Virus Induced Gene Silencing (VIGS), a widely used method for transient gene silencing in plants that is highly suitable for tracking pigmentation phenotypes. However, gene silencing with the VIGS method was previously shown to be particularly challenging in *M. jalapa*, most likely due to the inhibitory activity of the *Mirabilis* Antiviral Protein (MAP), and could only be achieved when the MAP gene is co-silenced with the gene of interest. Attempts for gene silencing in *M. jalapa* using VIGS were unsuccessful in our hands, including the attempted silencing of cDOPA5GT, which should result in partial loss of betalain pigmentation in the plant. We therefore proceeded to try and identify an MjCYP76 ortholog in a different betalain-producing plant species, in which gene silencing assays may be effectively implemented. An efficient VIGS method using vacuum infiltration was previously described in red beet, which was successfully used for silencing betalain related genes. Identification of an MjCYP76 ortholog in red beet could thus aid in assessment of the relevance of this gene to betalain biosynthesis.

Figure 4A:
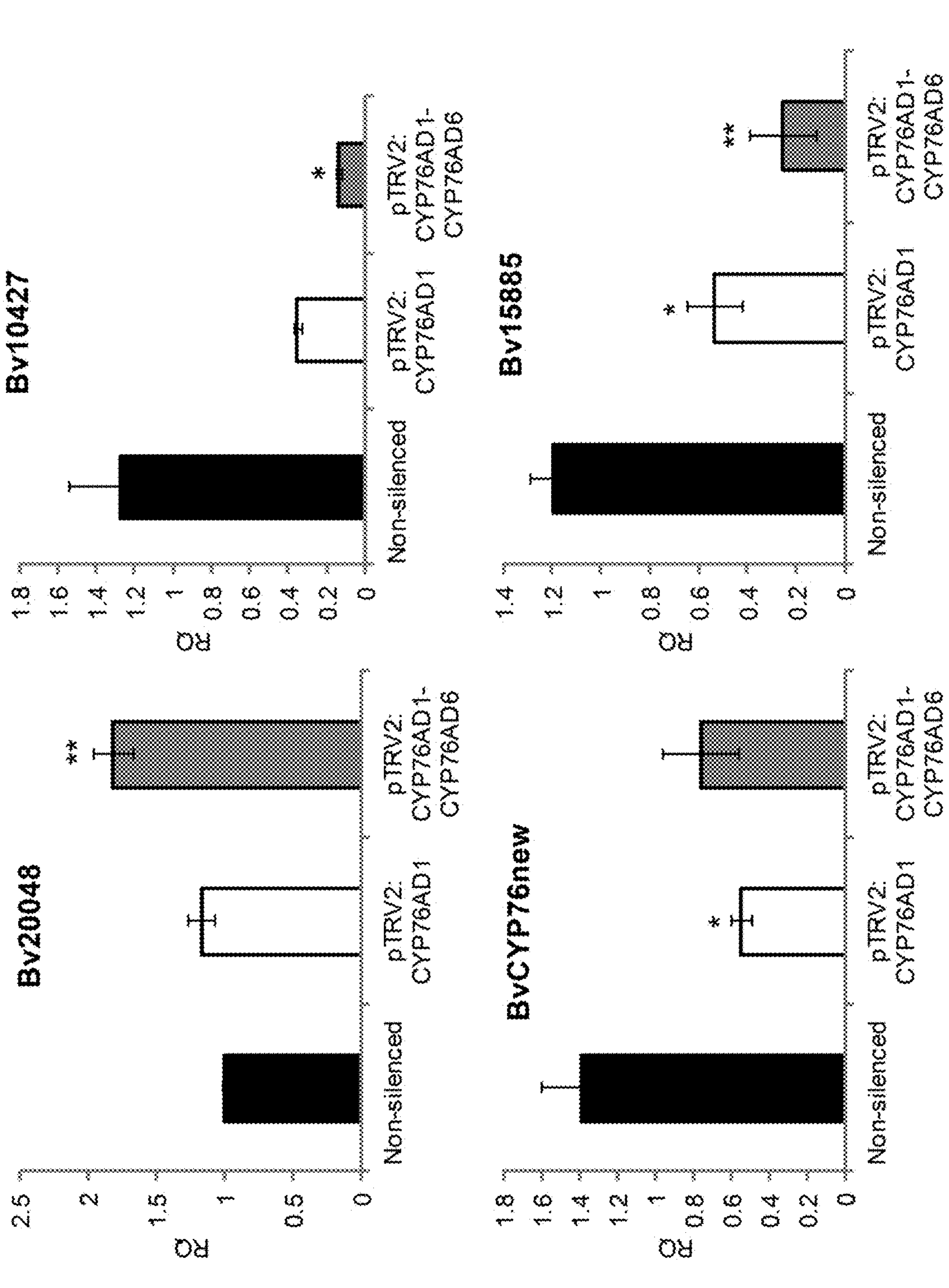
FIG. 4A. qRT-PCR analysis of four CYP76AD paralogs shows partial downregulation following infection with pTRV2:CYP76AD1 or pTRV2:CYP76AD1-CYP76AD6 vectors, suggesting off-target silencing. Upregulation of Bv20048 was observed in tissues infected with pTRV2: CYP76AD1-CYP76AD6. Relative quantification (RQ) values indicate means of three biological replicates ±SE. Asterisks denote statistical significance of differential expression in comparison with non-silenced tissue. *, P<0.05; **, P<0.01.
Figure 4B:
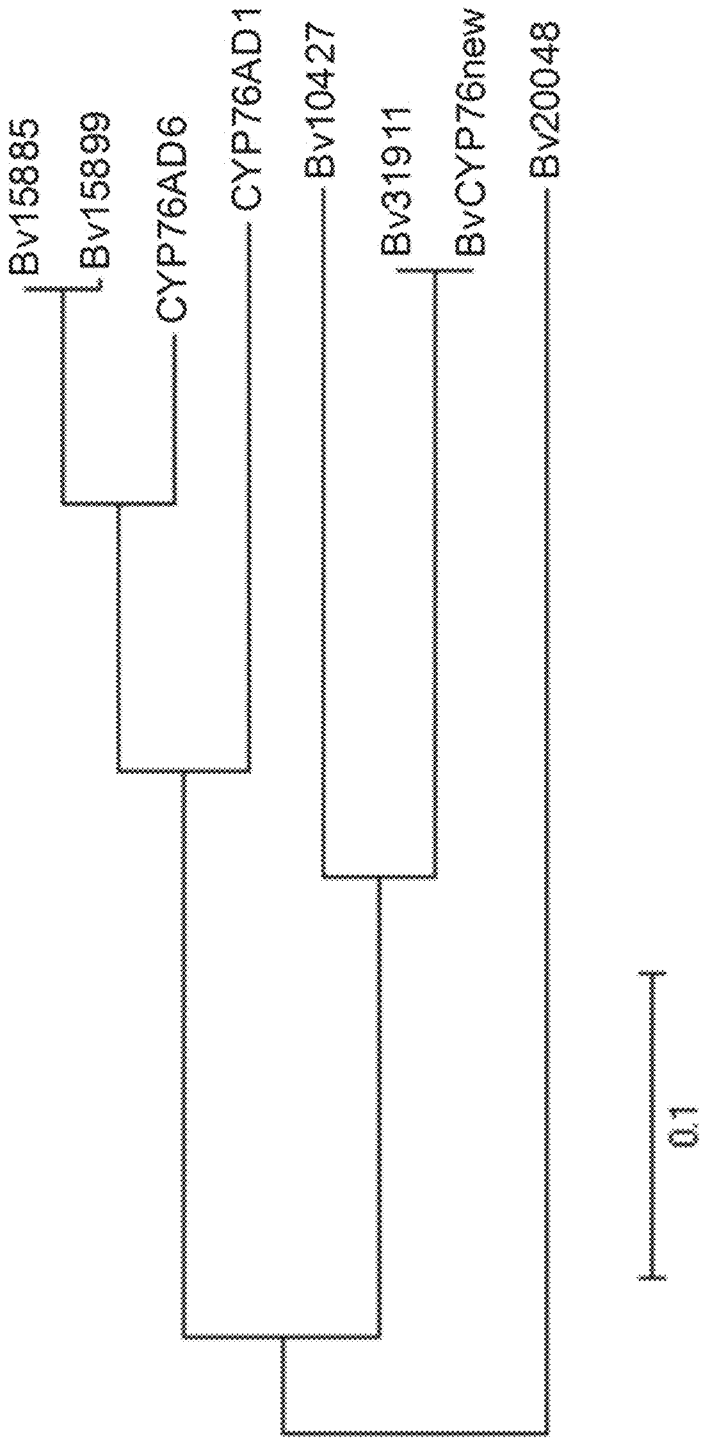
FIG. 4B. Maximum-likelihood phylogenetic tree of CYP76AD paralogs in *B. vulgaris*. CYP76AD6 (GenBank accession KT962274; SEQ ID NO: 30); CYP76AD1 (accession AET43289.1; SEQ ID NO: 14); BvCYP76new (accession KU041699; SEQ ID NO: 9); Bv20048 (accession KU041700); Bv10427 (accession KU041701); Bv31911 (accession KU041702); Bv15899 (accession KU041703); Bv15885 (accession KU041704).

To this end, we sequenced the transcriptomes of hypocotyl tissues of three varieties of beet; a 'golden beet' variety which produces solely yellow betaxanthins, as well as a red beet and a 'striped beet' variety, both of which have red-pigmented hypocotyls. An MjCYP76 ortholog in beet, which would putatively play a key role in betalain biosynthesis, was expected to be highly expressed in all three tissues. Homologs were identified by tBLASTx querying of the beet trasncriptome dataset with the MjCYP76 coding sequence. Contigs representing eight different cytochrome P450 genes with high sequence homology to MjCYP76 (over 50% identity on the protein level) were found, including the previously characterized CYP76AD1 (FIG. 4A). The highest scoring gene, BvCYP76new, was selected as a potential candidate to be a functional ortholog of MjCYP76 in beet. An additional gene within this group, hereinafter named CYP76AD6, which holds a 60% identity with MjCYP76 on the nucleotide level and 53% on the amino acid level, exhibited markedly higher expression values compared to the other paralogs and was therefore also selected for subsequent analysis.

Fragments from BvCYP76new and CYP76AD6 were cloned into the VIGS vector pTRV2 and introduced into seedlings of the 'Bull's Blood' red beet variety, which produces plants with highly pigmented dark red leaves and is therefore particularly compatible for gene silencing assays for betalain related genes. Since the tyrosine hydroxylase reaction to form L-DOPA is essential for formation of all betalain compounds, including both red betacyanins and yellow betaxanthins, silencing of either BvCYP76new or CYP76AD6 was expected to produce plants exhibiting green patches, due to lack of betalain pigmentation. pTRV2:BvDODA1 and pTRV2:CYP76AD1 were also introduced to beet seedlings and served as positive controls for the assay. Silencing of BvCYP76new or CYP76AD6 did not result in any visible phenotype (data not shown), while the silencing of BvDODA1 and CYP76AD1 produced patches of green or yellow color, respectively, as was previously reported. One possible explanation for a lack of visible phenotype when silencing a gene putatively encoding the enzyme responsible for L-DOPA production, was that this enzyme may be redundant with another enzyme or enzymes that also catalyze the same reaction. One such candidate is CYP76AD1, which could possibly catalyze the tyrosine hydroxylation step in addition to its experimentally demonstrated activity of conversion of L-DOPA to cyclo-DOPA. CYP76AD1 would have to be acting redundantly with another enzyme, since the silencing of CYP76AD1 does not prevent the formation of betaxanthins, for which L-DOPA is an essential precursor (FIG. 1). This hypothesis could be examined by co-silencing of BvCYP76new or CYP76AD6 together with CYP76AD1.

Figures 5A, 5B, 5C:
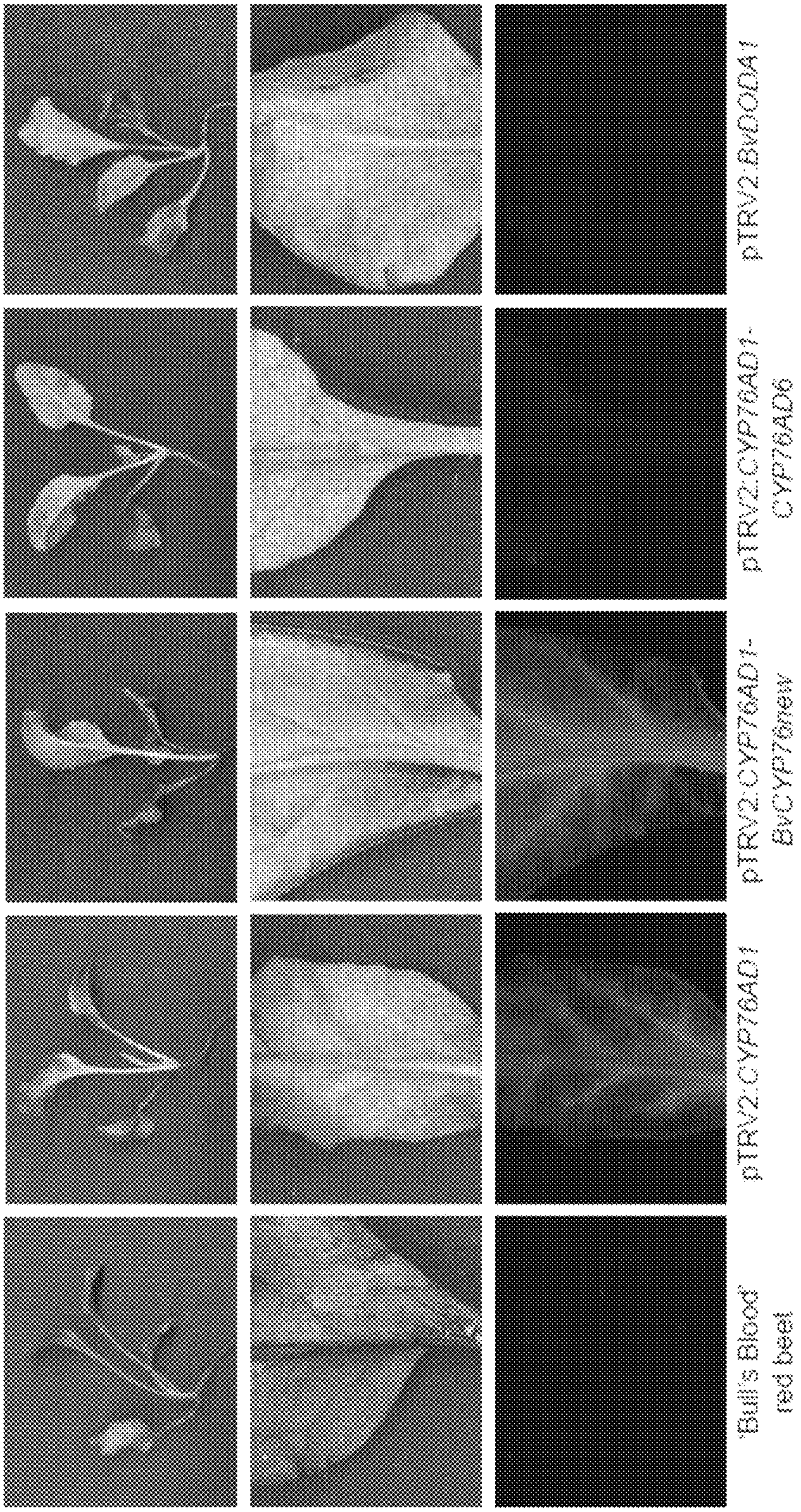
FIGS. 5A-5C. Co-silencing of CYP76AD1 and CYP76AD6 inhibits betalain production. Virus Induced Gene Silencing (VIGS) assays in red beet were used for silencing of BvDODA1 or CYP76AD1. CYP76AD1 was additionally co-silenced with each of the two new candidates BvCYP76new (SEQ ID NO: 9) and CYP76AD6. While silencing of CYP76AD1 alone or co-silencing with BvCYP76new blocks formation of betacyanins but not of betaxanthins, co-silencing of CYP76AD1 and CYP76AD6 prevents production of both types of pigments, resulting in a phenotype similar to the one obtained by silencing of BvDODA1. Reduction of betaxanthin levels is observed by a visible decrease in yellow color and lack of fluorescence under blue light, typical for betaxanthins.
Figure 6A:
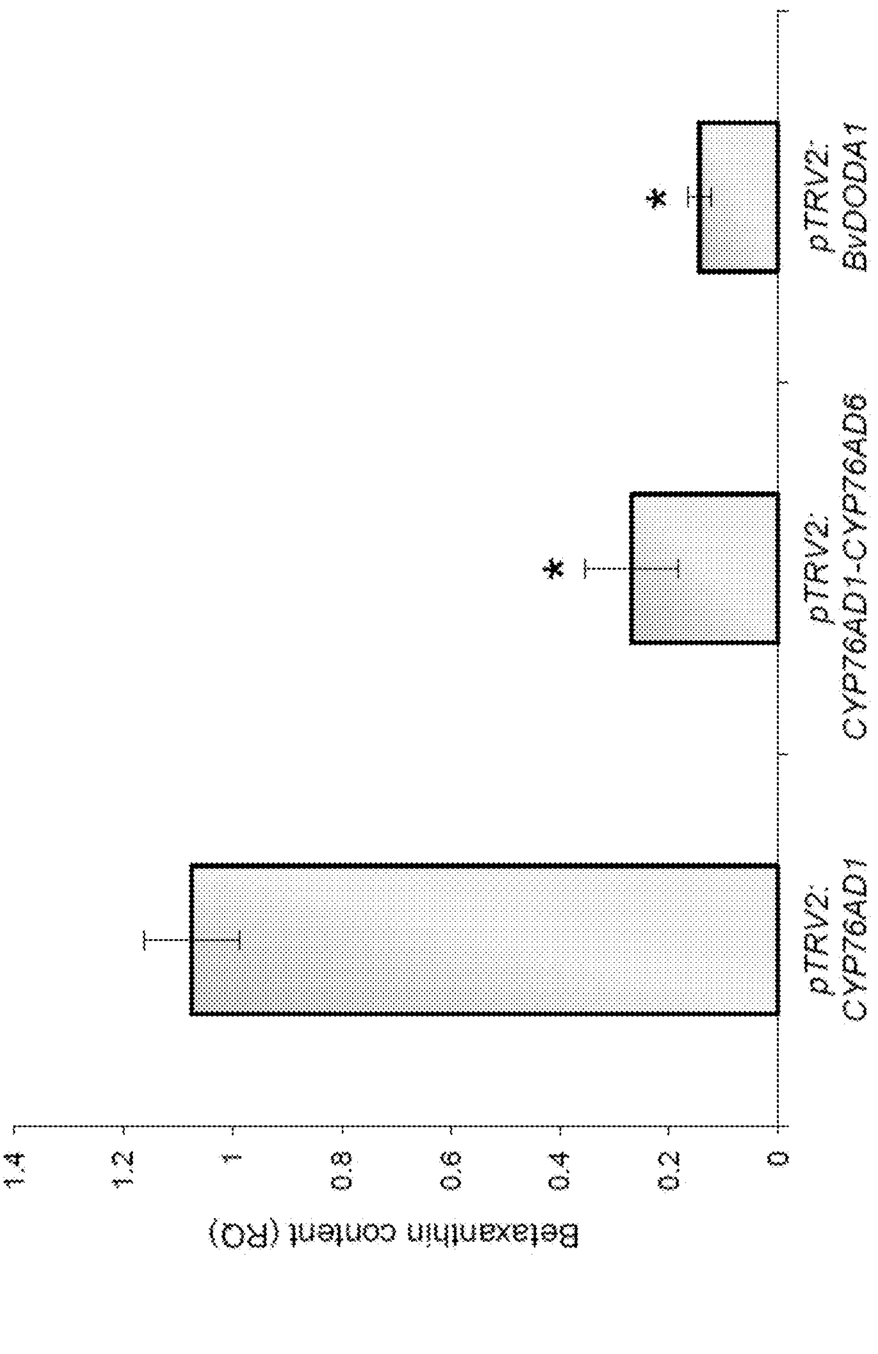
FIG. 6A. Relative quantification of betaxanthin in VIGS-silenced beet leaves. Relative betaxanthin content was assessed spectrophotometrically by light absorption measurements at 475 nm and 600 nm. Values indicate the mean±SEM of four biological replicates, each consisting of gene-silenced tissue from two to three plants. Asterisks denote statistically significant difference from pTRV2: CYP76AD1. **, P value <0.01. RQ, relative quantification.
Figure 6B:
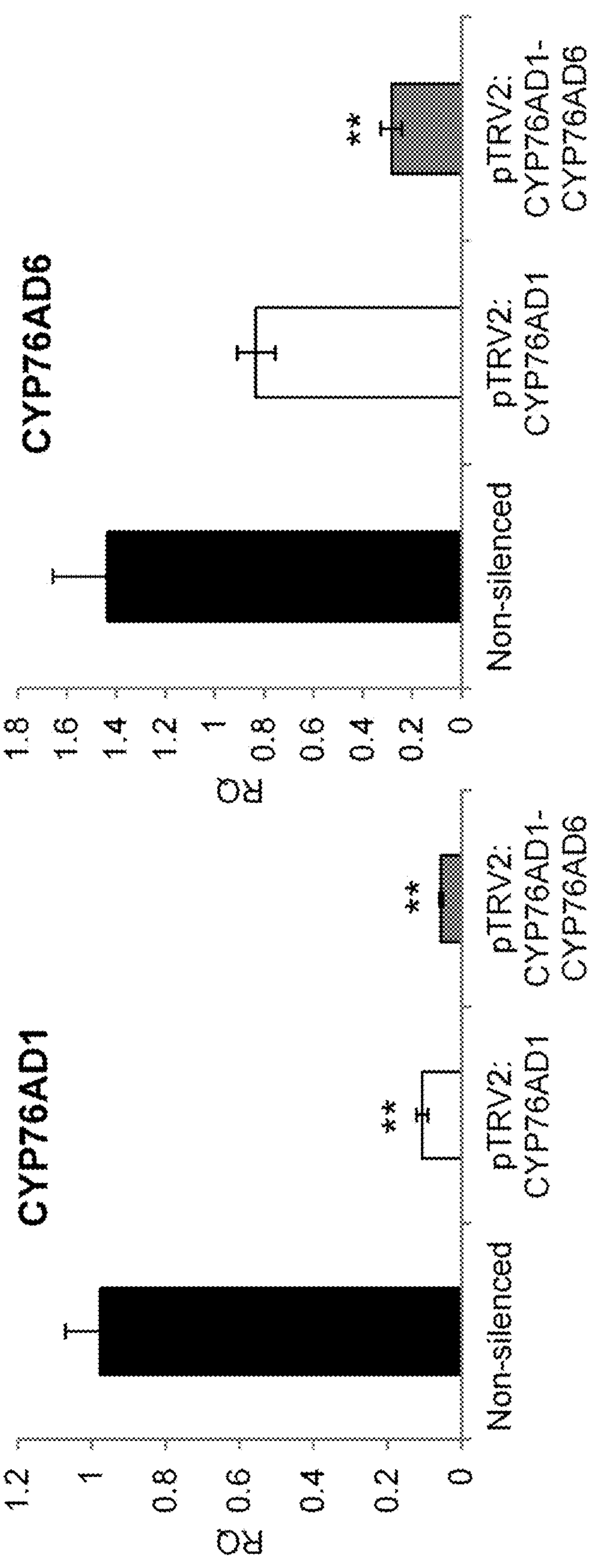
FIG. 6B. Quantitative real-time PCR (qRT-PCR) analysis of CYP76AD1 and CYP76AD6. CYP76AD1 is down-regulated in tissues infected with pTRV2:CYP76AD1 or pTRV2:CYP76AD1-CYP76AD6. CYP76AD6 is significantly down-regulated following infection with pTRV2: CYP76AD1-CYP76AD6. Relative quantification (RQ) values indicate means of three biological replicates ±SE. Asterisks denote statistical significance of differential expression in comparison with noninfected plants. **, P-value <0.01.

We therefore constructed pTRV2 vectors which harbor fragments of CYP76AD1 with either of the BvCYP76new or CYP76AD6 candidates, in tandem. A subsequent experiment was carried out for silencing of BvDODA1, CYP76AD1, BvCYP76new or CYP76AD6, as was done in the aforementioned VIGS experiment, in addition to co-silencing of CYP76AD1 with each of the CYP76 candidates. Plants in which CYP76AD1 and BvCYP76new were co-silenced produced yellow patches in leaves, similarly to plants in which only CYP76AD1 was silenced. However, co-silencing of CYP76AD1 and CYP76AD6 caused a clearly evident phenotype of green patches, which lack both betacyanins and betaxanthins, similarly to the phenotype obtained by BvDODA1 silencing (FIG. 5A, B). Differences in betaxanthin accumulation levels could also be observed by blue light imaging (FIG. 5C), under which betaxanthins typically exhibit strong fluorescence. Reduced betaxanthin accumulation in CYP76AD1-CYP76AD6 co-silenced tissue versus CYP76AD1 silenced tissue was further demonstrated by spectrophotometric analysis (FIG. 6A). These findings supported the notion of redundancy in the tyrosine hydroxylation step of betalain biosynthesis in red beet, by which this step may be catalyzed by either CYP76AD1 or CYP76AD6. Additionally, the fact that silencing of CYP76AD1 alone blocks production of betacyanins but not of betaxanthins, suggested that CYP76AD6 does not catalyze the conversion of L-DOPA to cyclo-DOPA, but only the formation of L-DOPA from tyrosine.

qRT-PCR analysis was performed in order to examine expression of CYP76AD1 and CYP76AD6 in plants infected with the pTRV2:CYP76AD1 or pTRV2:CYP76AD1-CYP76AD6 vectors. CYP76AD1 was found to be down-regulated upon infection with both vectors, while CYP76AD6 only showed down-regulation following infection with pTRV2:CYP76AD1-CYP76AD6 (FIG. 6B). Expression of four CYP76AD1 and CYP76AD6 paralogs was also examined. Three of the four paralogs examined showed down-regulation in tissues infected with at least one of the pTRV2:CYP76AD1 or pTRV2:CYP76AD1-CYP76AD6 vectors (FIG. 4A). Thus, the possible involvement of one or more of these paralogs in betalain biosynthesis cannot be ruled out at present. However, irrelevance of one of the three paralogs, BvCYP76new, to betalain biosynthesis may be inferred from results of the silencing experiments, as silencing of BvCYP76new alone caused no visible change in phenotype, and silencing of this gene together with CYP76AD1 produced the same phenotype as observed when CYP76AD1 was silenced alone.

Example 4

Figure 7A:
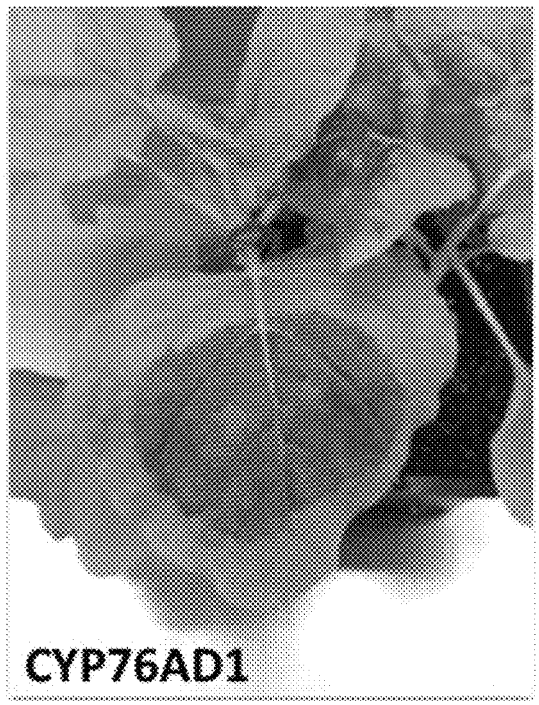
FIGS. 7A-7F. Recombinant expression of CYP76AD1 or CYP76AD6 in *Nicotiana benthamiana* leaves enables L-DOPA and betalain production.
Figure 7B:
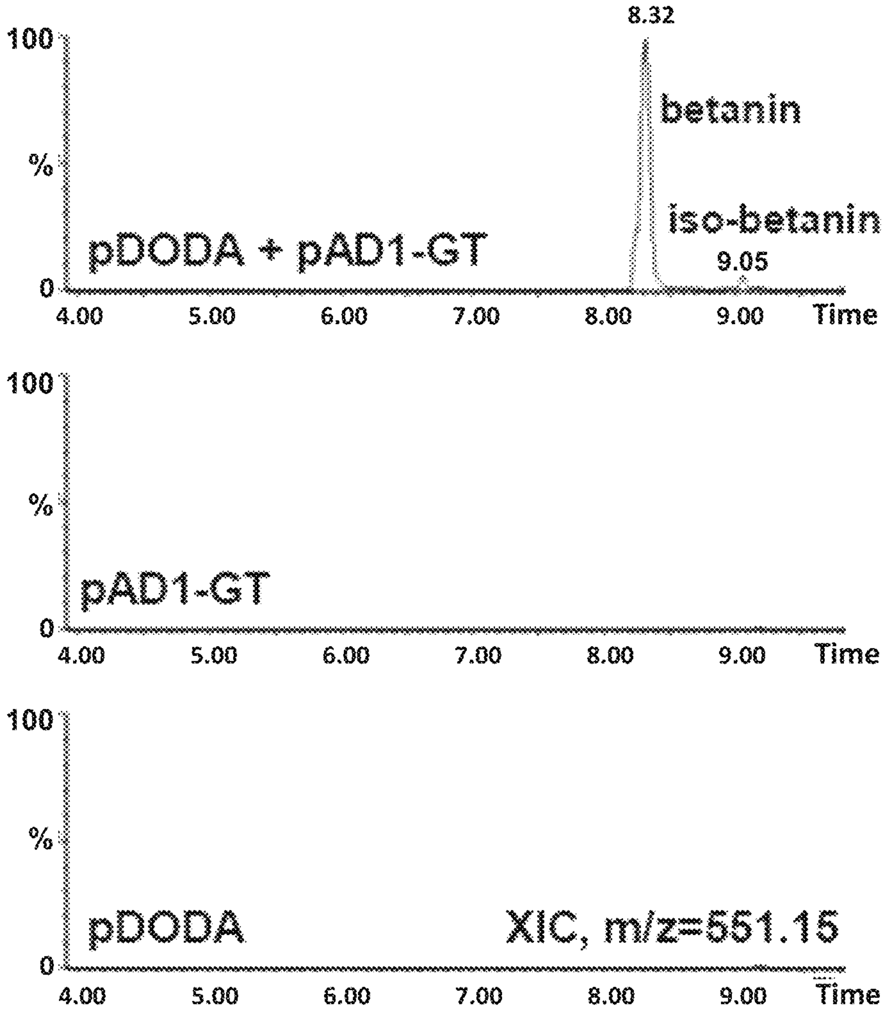

Transient Expression of CYP76AD1 in *N. benthamiana* Enables Production of L-Dopa and Betacyanins If CYP76AD1 indeed catalyzes both the formation of L-DOPA and its conversion to cyclo-DOPA, then heterologous expression of CYP76AD1 together with a DOD enzyme and a betalain related glucosyltransferase (e.g. cyclo-DOPA 5-O-glucosyltransferase or betanidin-5-O-glucosyltransferase) should be sufficient for biosynthesis of the widely common glucosylated betacyanin, betanin. To test this, we generated overexpression constructs for the beet BvDODA1 and CYP76AD1 genes and the *M. jalapa* gene cyclo-DOPA 5-O-glucosyltransferase (cDOPA5GT), to be used for transient, agroinfiltration-mediated overexpression in *Nicotiana benthamiana* leaves. Two vectors were made for this purpose; one for overexpression of BvDODA1 under the CaMV 35S promoter (pDODA) and another vector for the tandem expression of CYP76AD1 and cDOPA5GT, driven by the CaMV 35S and *Arabidopsis* ubiquitin-10 promoters, respectively (pAD1-GT). Co-infiltration of agrobacteria (*Agrobacterium tumefaciens*) harboring the pDODA and pAD1-GT vectors into *N. benthamiana* leaves caused the appearance of dark red pigmentation in infiltrated areas within 2-3 days post infiltration (FIG. 7A). Liquid chromatography-mass spectrometry (LC-MS) analysis revealed that the pigmented leaf tissue contained high levels of betanin, as well as the betanin isomer iso-betanin (FIG. 7B; Table 2). This result provided a first proof of concept for the possibility of engineering betalain production in-planta without substrate feeding. Additionally, the formation of betacyanins without the need for L-DOPA feeding or overexpression of a tyrosine hydroxylating enzyme (e.g. tyrosinase) indicated that CYP76AD1 catalyzes the formation of L-DOPA in addition to its previously known activity of converting L-DOPA to cyclo-DOPA.

Figure 7C:
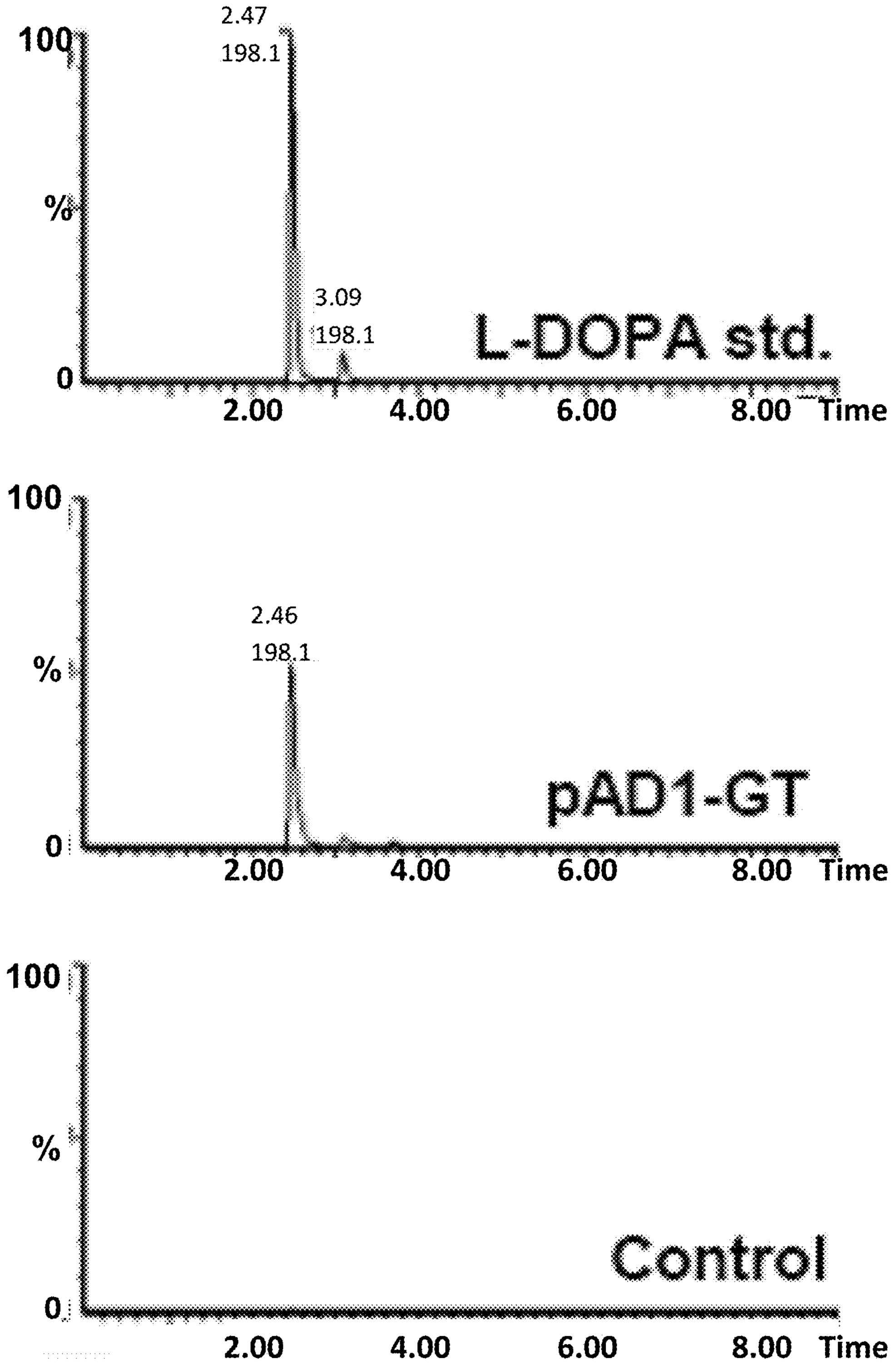

However, the production of betalains may have alternatively been possible due to occurrence of L-DOPA in *N. benthamiana* leaves as a result of tyrosine hydroxylase activity by an endogenous enzyme. To examine whether L-DOPA production was enabled due to the expression of CYP76AD1, pAD1-GT was infiltrated into *N. benthamiana* leaves without pDODA. Introduction of a vector overexpressing YFP protein (pYFP) was used as a control for this experiment. LC-MS analysis confirmed the presence of L-DOPA in pAD1-GT infiltrated tissues but not in pYFP infiltrated tissues (FIG. 7C).

Example 5

Figure 7D:
Figure 7E:
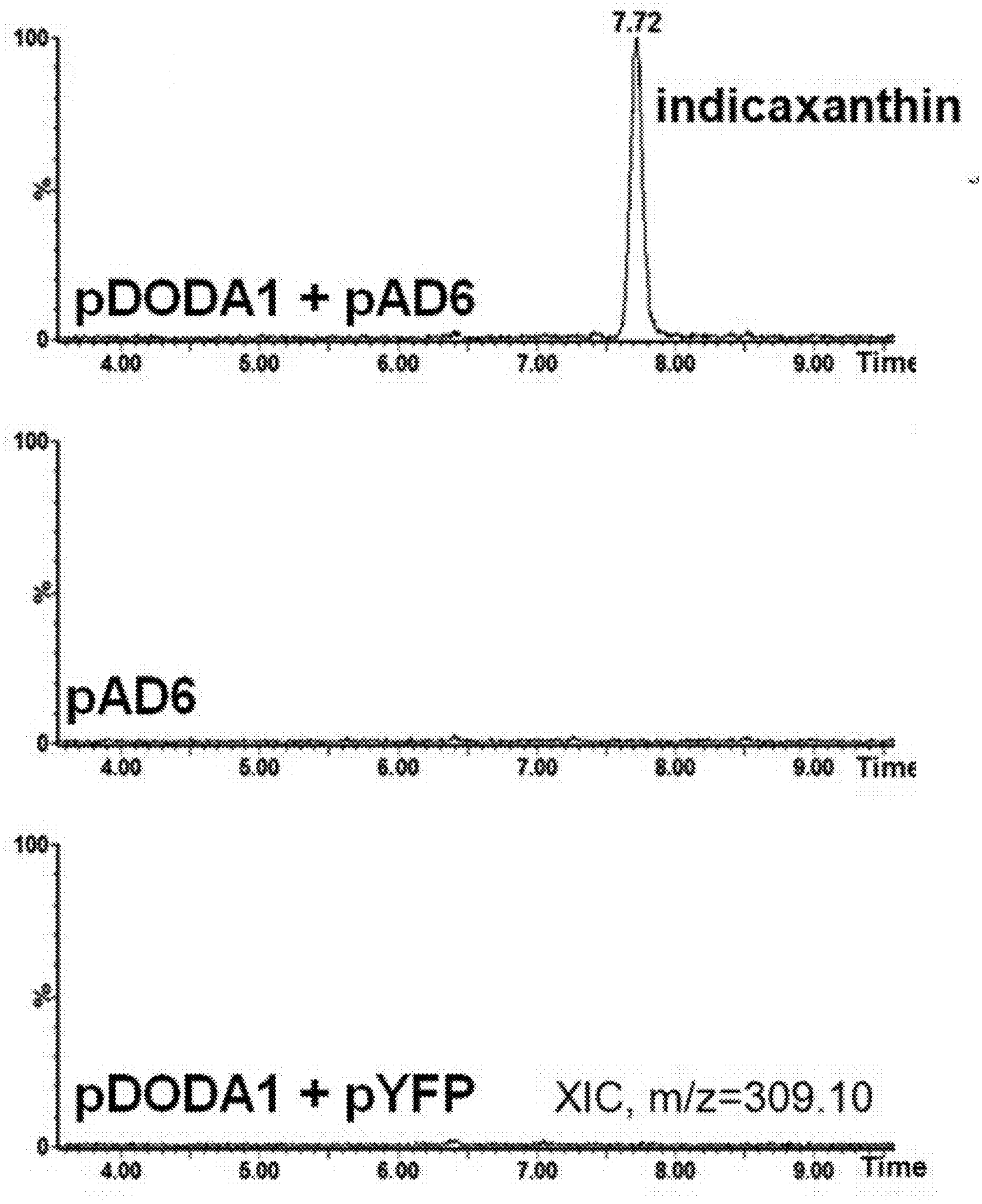
Figure 7F:
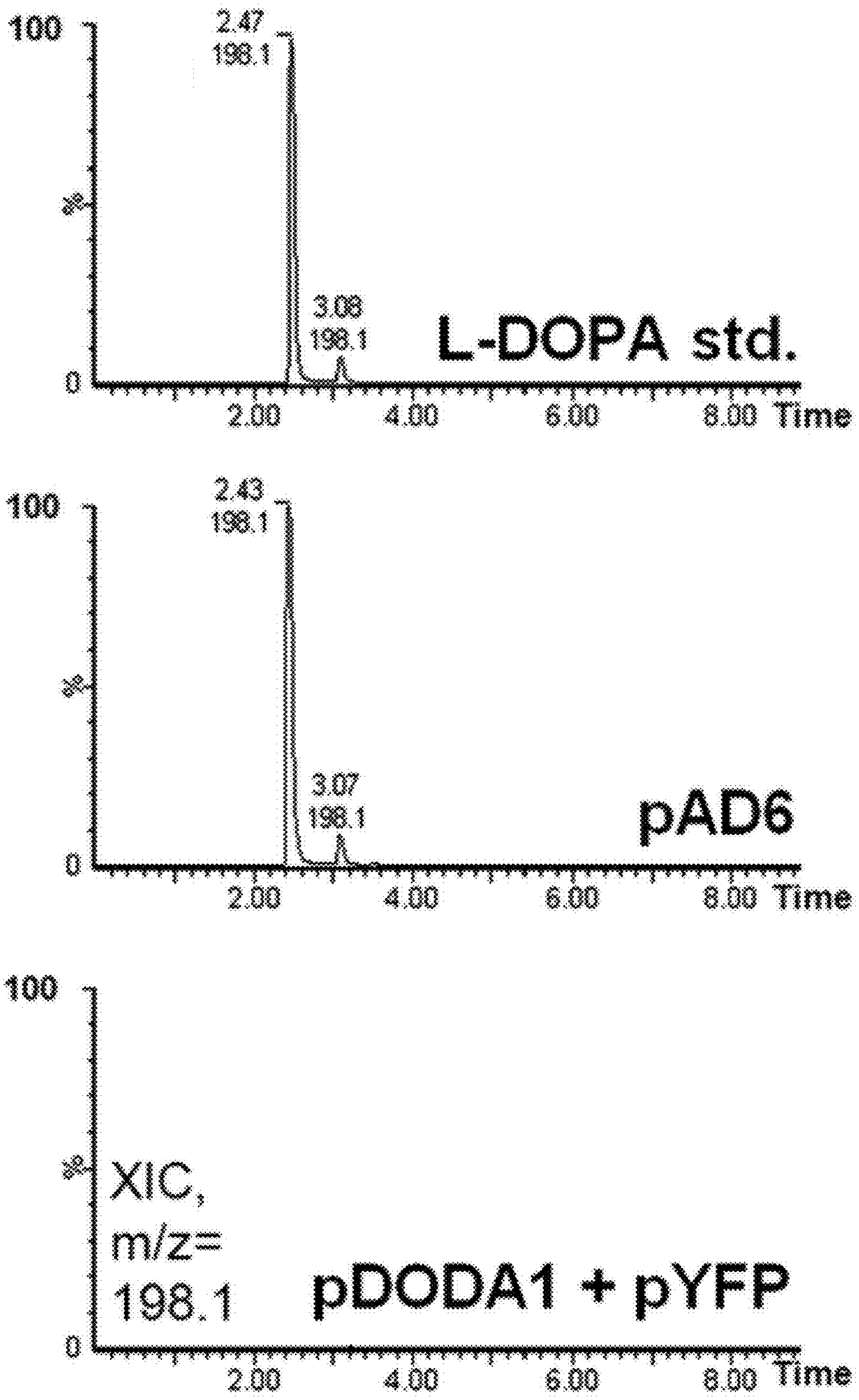

Transient Expression of CYP76AD6 in *N. benthamiana* Enables Production of L-DOPA and Betaxanthins Tyrosine hydroxylase activity of CYP76AD6 was also assessed by transient overexpression in *N. benthamiana* leaves. An overexpression vector for CYP76AD6 under the CaMV 35S promoter (pAD6) was constructed and inserted to agrobacteria. Co-infiltration of pAD6 and pDODA resulted in the appearance of yellow pigmentation in infiltrated areas, visible within several days post infiltration. (FIG. 7D). LC-MS analysis of the yellow-pigmented tissue revealed the occurrence of one major betaxanthin compound, identified as indicaxanthin (proline-betaxanthin) (FIG. 7E). Two additional compounds were found to exhibit typical betaxanthin light absorption spectra, one of which was putatively identified as a dopaxanthin-hexoside, based on accurate mass and fragmentation (Table 2). Notably, glycosylated-betaxanthins do not occur, to the best of our knowledge, in natural betalain-producing species. The fact that co-infiltration of CYP76AD6 and BvDODA1 induced the production of betaxanthins but not of betacyanins coincides with the data obtained in the aforementioned gene silencing assays, confirming that CYP76AD6 catalyzes only the single step of L-DOPA formation and not its subsequent conversion to cyclo-DOPA. Agroinfiltration of the pAD6 vector alone resulted in production of L-DOPA in *N. benthamiana* leaves, verified by LC-MS (FIG. 7F).

Example 6

Recombinant Expression of CYP76AD1 and CYP76AD6 Allows Betalain Synthesis in Yeast CYP76AD1 and CYP76AD6 activity was further evaluated by recombinant expression of each of the two enzymes in yeast, together with BvDODA1. To this end, full coding sequences of BvDODA1, CYP76AD1 and CYP76AD6 were cloned into galactose-inducible yeast overexpression vectors and transformed into *Saccharomyces cerevisiae* cells. Yeast were subsequently grown in standard SD media, with no L-DOPA supplementation. Similarly to the *N. benthamiana* transient expression assays discussed above, red-violet pigmentation was observed in media of yeast expressing CYP76AD1 and BvDODA1, while yellow pigmentation was evident in media of yeast expressing CYP76AD6 and BvDODA1. Expression of each of the cytochrome P450 enzymes without BvDODA1 or expression of BvDODA1 alone did not result in formation of red or yellow pigments. Additionally, expression of CYP76AD1, CYP76AD6, and BvDODA1 together, resulted in formation of orange pigmentation in the media (FIG. 8A). LC-MS analysis was used to verify the occurrence of betalains in the yellow, red-violet and orange-pigmented media (FIG. 7C; Table 2).

Example 7

Figure 9:
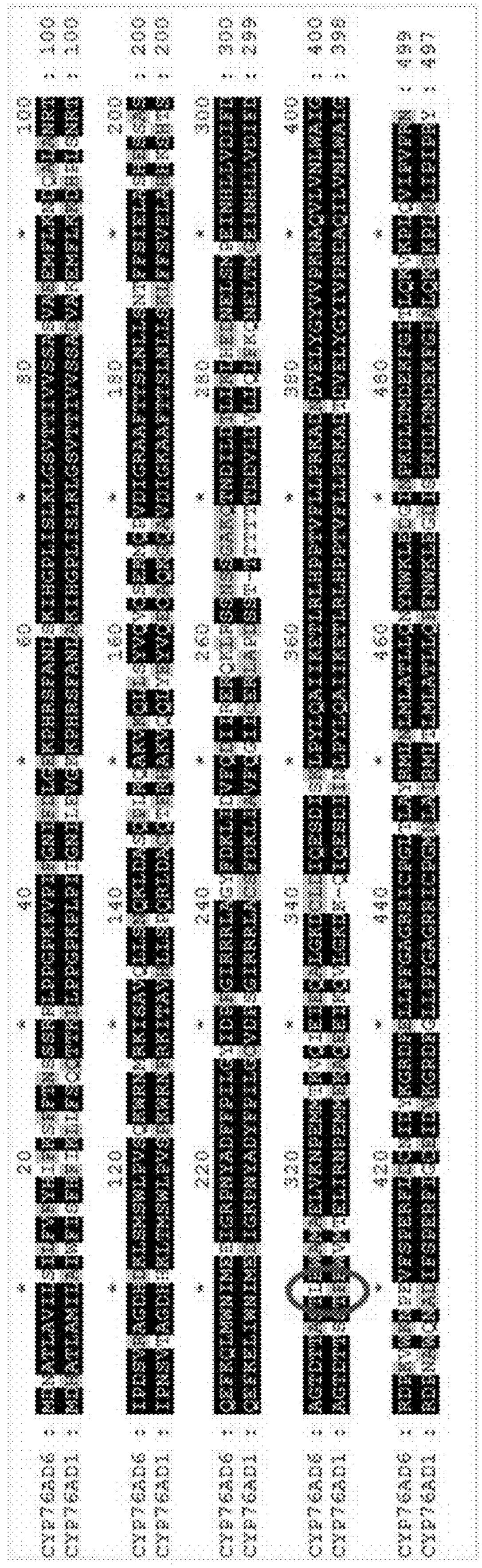
FIG. 9. Alignment of the CYP76AD1 (SEQ ID NO: 14) and CYP76AD6 (SEQ ID NO: 18) protein sequences shows a 72 percent identity between them.

CYP76AD6 Belongs to a Phylogenetic Clade that was not Previously Associated with Betalain Biosynthesis In a recently published study, large-scale phylogenetic analyses of Caryophyllales plants suggested the occurrence of several gene duplication events of the CYP76AD1 locus early in Caryophyllales evolutionary history. These events were suggested to give rise to three clades within the CYP76AD1 lineage, named CYP76AD1-α, CYP76AD1-β and CYP76AD1-γ. The inventors deduced that the CYP76AD1-α clade is directly associated with betalain biosynthesis as it includes, among others, the functionally characterized *B. vulgaris* CYP76AD1 gene and its *M. jalapa* ortholog CYP76AD3, which has also been implicated to play a similar role in betalain biosynthesis. However, nothing is currently known with respect to the function of genes belonging to the CYP76AD1-β and CYP76AD1-γ clades. Interestingly, the CYP76AD6 gene reported here [accession 'Bv9_228610_ygeq.t1' in the *B. vulgaris* genome] is positioned in the CYP76AD1-β clade, as demonstrated in the phylogenetic analyses presented by Brockington and coworkers, and further presented here in a maximum-likelihood phylogenetic tree (FIG. 8B). Pairwise alignment of the CYP76AD6 and CYP76AD1 protein sequences showed a 72% percent identity (FIG. 9). Their corresponding genes exhibit 70% sequence identity at the nucleotide level.

Example 8

Figure 10:
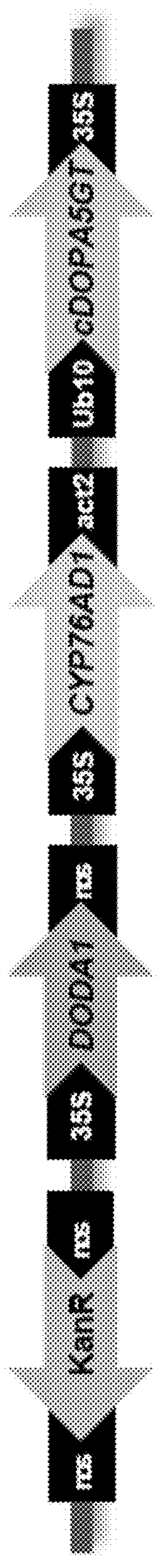
FIG. 10. Schematic of the pX11 overexpression vector (SEQ ID NO: 19). KanR, kanamycin resistance-conferring gene nptII; DODA1, *B. vulgaris* DOPA 4,5-dioxygenase; CYP76AD1, *B. vulgaris* cytochrome P450; cDOPA5GT, *M. jalapa* cyclo-DOPA-5-O-glucosyltransferase; nos, nopaline synthase promoter/terminator; 35S, CaMV 35S promoter/terminator; Act2, *Arabidopsis* actin 2 terminator; Ub10, *Arabidopsis* ubiquitin 10 promoter.
Figure 11A:
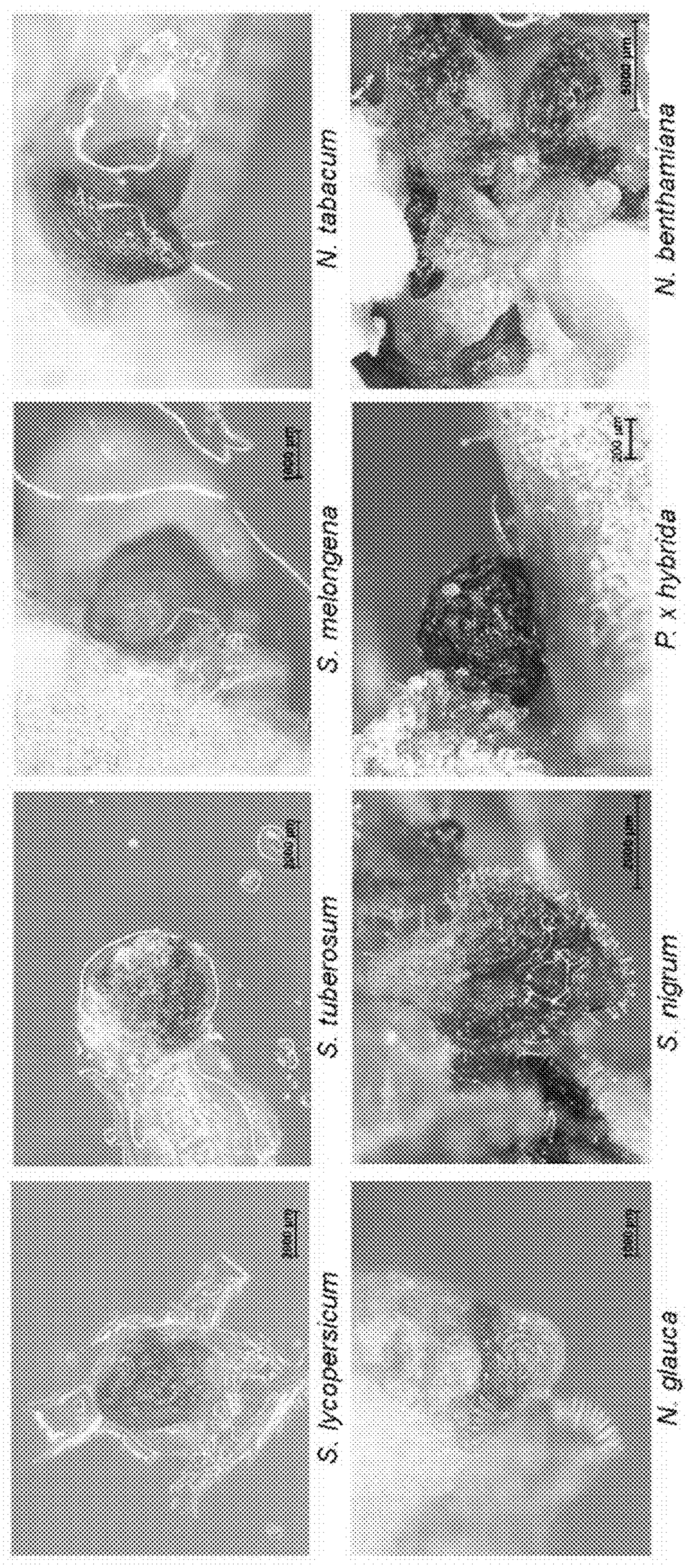
Figure 12C:
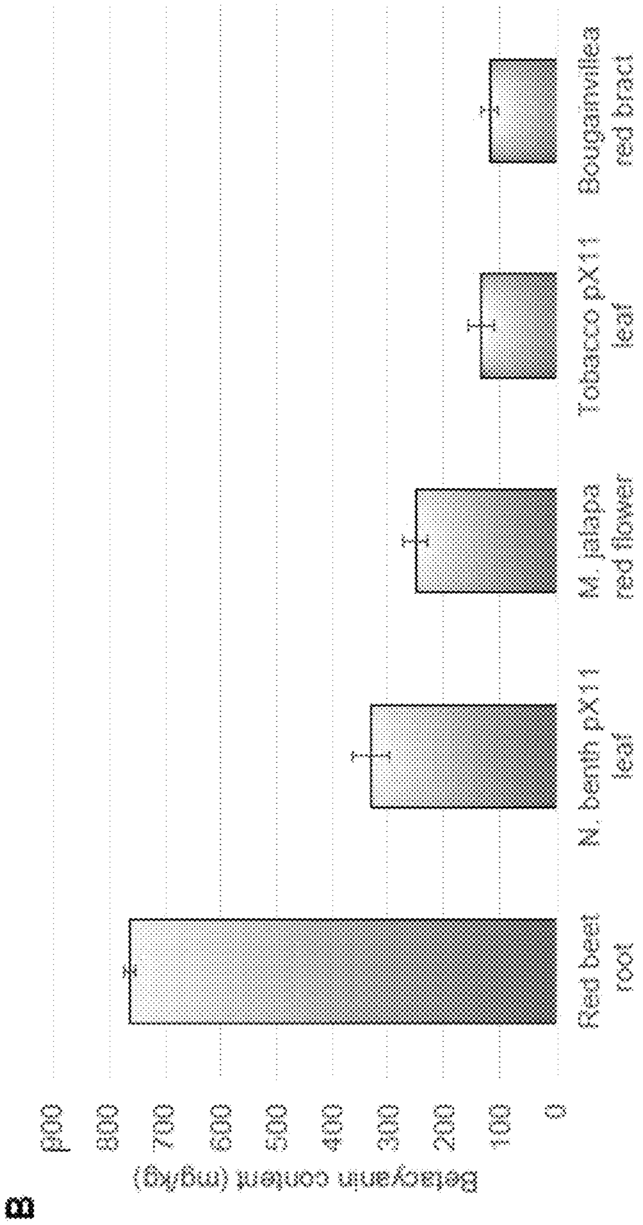
Figure 12B:
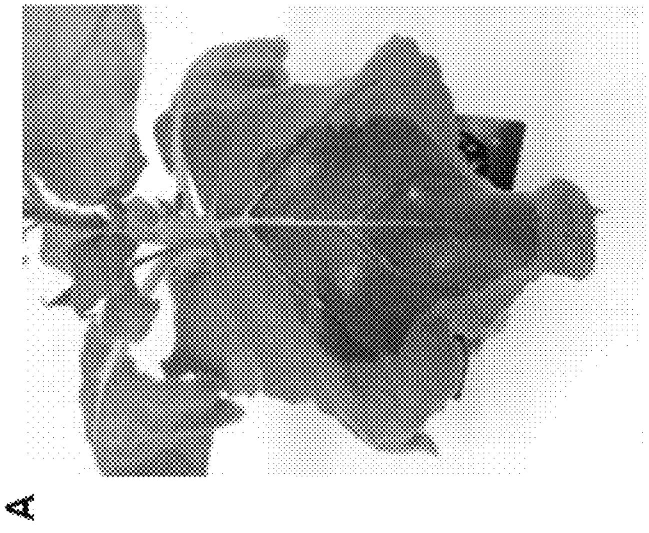
Figure 13A:
FIGS. 13A-13E. Pigmentation phenotypes observed in transgenic tobacco plants engineered for betalain production. Three betalain pathway genes, namely, CYP76AD1, BvDODA1 and cDOPA5GT (in the pX11 binary vector) were heterologously expressed in *Nicotiana tabacum*, resulting in red pigmentation in different plant organs, including leaves, stems, roots and flowers.
Figure 13B:
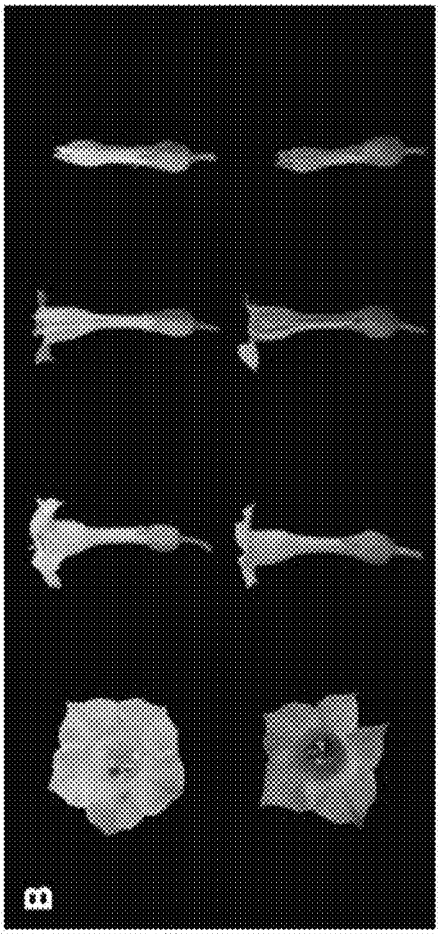
Figure 13C:
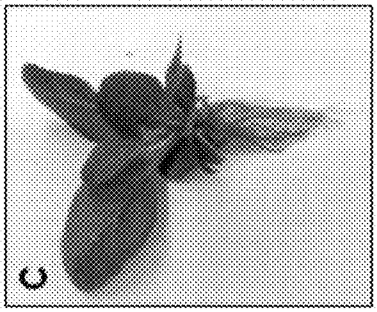
Figure 13D:
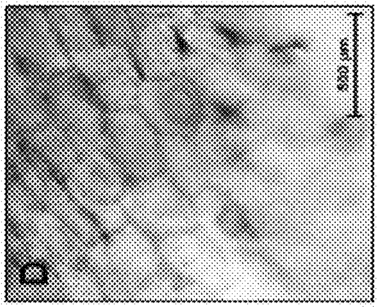
Figure 13E:
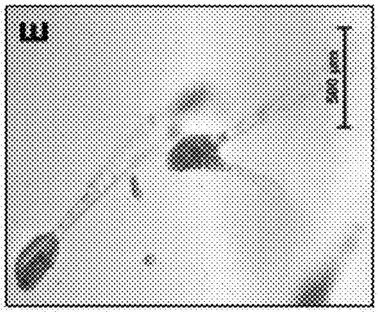

Metabolic Engineering of Red Betalain Pigments in Transgenic Plants Requires Heterologous Expression of Three Biosynthetic Genes As discussed above, we were able to generate both red betacyanins and yellow betaxanthins through transient gene overexpression in *N. benthamiana* leaves. We subsequently attempted to engineer betalain production in naturally non-producing plant species through stable transformation. To this end, Goldenbraid cloning was used to generate a four-gene construct (termed hereafter pX11), in which CYP76AD1, BvDODA1 and cDOPA5GT are expressed in tandem and driven by constitutive promoters, in addition to a kanamycin resistance gene for transgene selection (FIG. 10). The pX11 vector was initially tested by agroinfiltration into *N. benthamiana*. Similarly to the co-infiltration of pDODA and pAD1-GT, introduction of pX11 resulted in red pigmentation of the infiltrated tissue (FIG. 12B). LC-MS analysis of pX11-infiltrated tissue was conducted in order to determine betalain composition. Peaks corresponding to betanin and iso-betanin were found, as previously observed by the co-infiltration of pDODA and pAD1-GT overexpression vectors (FIG. 11A). Also identified was the betaxanthin compound indicaxanthin (proline-betaxanthin), indicating some level of flux towards betaxanthin formation. Two additional metabolites were recognized as betacyanins, based on light absorption spectra and fragmentation, which included the nearly ubiquitous betacyanin fragment, betanidin (m/z=389; Table 2). The pX11-infiltrated leaf tissue appeared intensely red-pigmented, seemingly producing betacyanins in high quantities (FIG. 12B). Infiltrated tissue was therefore assessed for total betacyanin content by spectrophotometric analysis, and was found to contain an estimate of 330 mg kg-1, higher than red bracts of *Bougainvillea glabra* and red petals of *M. jalapa*, containing 120 mg kg-1 and 250 mg kg-1 betacyanins, respectively, and 2.3 fold lower than red beet root, which was estimated to contain 760 mg kg-1 (FIG. 12C).

The pX11 vector was next used for stable transformation of several plant species, including tobacco (*Nicotiana tabacum*), tomato (*Solanum lycopersicum*), potato (*Solanum tuberosum*), eggplant (*Solanum melongena*), tree tobacco (*Nicotiana glauca*), European black nightshade (*Solanum nigrum*), *Petunia* (*Petunia* x *hybrida*) and *Nicotiana benthamiana*. Explants of the different species were co-cultivated with agrobacteria and placed on selective media. In *N. benthamiana, N. glauca, Petunia* and tomato, small patches of red-violet pigmentation were visible on the explant surface within two days of co-cultivation with agrobacteria. In all species transformed, introduction of pX11 caused the formation of red-violet calli, which generally appeared within 1-2 weeks of culture (FIG. 11A). Pigmented *N. benthamiana* and *N. glauca* callus tissues were found to contain betanin and iso-betanin with LC-MS. Additionally, a novel unidentified betacyanin compound was found in the *N. glauca* callus (FIG. 10B, Table 2).

Tissue culture of pX11-transformed tobacco (*Nicotiana tabacum* L. cv. Samsun-NN) eventually led to the generation of mature, intensely red-pigmented plants that displayed betalain accumulation in all major plant organs including stems, leaves, roots, and flowers (FIG. 13). LC-MS analysis of transgenic pX11-tobacco leaves validated the occurrence of the betacyanins, betanin, and iso-betanin as well as the betaxanthin compound vulgaxanthin I (glutamine-betaxanthin) (Table 2). Betacyanin content of pX11-tobacco leaves was additionally measured spectrophotometrically to be 135 mg kg-1 (FIG. 12C).

Example 9

Discussion

CYP76AD1 and CYP76AD6 Redundantly Catalyze Tyrosine Hydroxylation, the First Committed Step in Betalain Biosynthesis in Plants In this study we have demonstrated the involvement of CYP76AD1 in tyrosine hydroxylation to L-DOPA in red beet, apart from its previously reported role in catalyzing the subsequent reaction leading to cyclo-DOPA formation. Furthermore, we identified an additional beet cytochrome P450 enzyme, CYP76AD6, which catalyzes the first hydroxylation step in redundancy with CYP76AD1 (FIG. 1). A CYP76AD6 ortholog, MjCYP76, was primarily identified in *Mirabilis jalapa*, exhibiting an expression pattern which parallels betalain accumulation. It is likely that MjCYP76 and the previously identified CYP76AD3, respectively, serve the same functions in *M. jalapa* as CYP76AD6 and CYP76AD1 do in red beet, although this remains to be conclusively verified by functional analyses, mostly gene silencing assays in *M. jalapa.*

CYP76AD6 involvement in the formation of L-DOPA was initially demonstrated by gene silencing assays; while silencing CYP76AD1 by itself inhibits formation of betacyanins but not betaxanthins, silencing CYP76AD1 and CYP76AD6 in parallel blocks the formation of both betalain groups. Silencing of CYP76AD6 alone produces no visible phenotype, since both L-DOPA and cyclo-DOPA formation continue to be catalyzed by CYP76AD1. This lack of visible phenotype may partially explain why CYP76AD6 and the tyrosine hydroxylation step remained last to be discovered within the core betalain biosynthesis pathway. While DOD and CYP76AD1-like genes could be identified in betalain-producing species by naturally occurring or artificially induced mutations that cause clearly visible phenotypes, CYP76AD6 could not, due do its functional redundancy with CYP76AD1. The suggested roles of CYP76AD1 and CYP76AD6 in betalain biosynthesis were further corroborated by recombinant expression in *N. benthamiana* and yeast cells, which led to the formation of betacyanins or betaxanthins, respectively, when coupled to BvDODA1 expression. Additionally, formation of L-DOPA in *N. benthamiana* was detected when either CYP76AD1 or CYP76AD6 were overexpressed without BvDODA1.

CYP76AD1 and CYP76AD6 belong to two separate clades within the CYP76AD1 subfamily, named CYP76AD1-α and CYP76AD1-β clades. It is conceivable that the two cytochrome P450 enzymes would share some degree of structural relatedness, as they redundantly catalyze an identical enzymatic reaction. Moreover, it was reported previously that cytochrome P450s belonging to a single subfamily catalyze subsequent steps in the same biosynthetic pathway. It is plausible that while the CYP76AD1-α clade may be comprised of enzymes which possess dual activity of L-DOPA and cyclo-DOPA formation, the CYP76AD1-β may include enzymes which catalyze only L-DOPA formation. However, functional analyses of corresponding genes from additional betalain-producing species will be needed to support this hypothesis.

Tyrosinase enzymes catalyze both the ortho-hydroxylation of monophenols and the oxidation of o-diphenols to o-quinones, thus directly converting tyrosine to the oxidized form of L-DOPA, dopaquinone. CYP76AD1, in a currently unknown reaction mechanism, also catalyzes both tyrosine hydroxylation and L-DOPA conversion to cyclo-DOPA. Our experimental results suggest that CYP76AD6 is unique in that it catalyzes the ortho-hydroxylation of tyrosine but not the conversion of L-DOPA to dopaquinone or cyclo-DOPA. The unique activity of the CYP76AD6 enzyme can be harnessed for high-scale production of L-DOPA that is highly advantageous and unexpected compared to current production methods. CYP76AD6 directly forms L-DOPA from the substrate tyrosine. The ubiquitous nature of tyrosine enables the possibility of expression of CYP76D6 in a variety of biological platforms including plants and microbes.

The discovery of a new class of tyrosine hydroxylating enzymes might also facilitate the identification of additional cytochrome P450 genes that may catalyze L-DOPA formation in biosynthesis of other L-DOPA derived metabolites. For example, the gene responsible for tyrosine hydroxylation in the biosynthesis of benzylisoquinoline alkaloids (BIAs) remains unknown to date, in an otherwise well-characterized pathway. It is possible that in BIA producing plants, L-DOPA is also catalyzed by a cytochrome P450 similar to CYP76AD1 and CYP76AD6.

Uncovering of the roles of CYP76AD1 and CYP76AD6 in L-DOPA formation advances our understanding of betalain biosynthesis in plants and essentially completes the identification of genes and enzymes that make the core betalain structures. Yet, the betalain pathway remains relatively poorly understood with regards to betalain structure modification through 'decorating' enzymes (e.g. glycosylating and acylating enzymes), subcellular transport and detoxification. Further characterization of the genes and regulatory factors involved in the biosynthesis of these pigments will hopefully be facilitated by the elucidation of the core pathway and through increasing availability of sequence data from betalain producing plants.

Metabolic Engineering of Betalain Production in Plants

While anthocyanins and carotenoids are prevalent throughout the plant kingdom, betalains are pigments specific to the Caryophyllales plant order, in which they are produced in a phylogenetically ordered, mutually exclusive fashion with anthocyanins. Their enigmatic evolutionary history, as well as their nutritionally beneficial qualities and economical value as natural food colorants, have led to increasing interest in these pigments in recent years, including the prospect of synthesizing them in microorganisms and plants.

In this study, we have demonstrated for the first time the engineering of betalain production in plants, without substrate feeding, by both transient gene expression and stable transformation. This was made possible by identification of the additional tyrosine hydroxylase activity of CYP76AD1. Expression of CYP76AD1, in combination with BvDODA1 and cDOPA5GT, was therefore found to be sufficient for biosynthesis of betanin, without the need for an exogenous supply of L-DOPA. The use of the pX11 vector that includes the CYP76AD1, BvDODA1 and cDOPA5GT genes was first demonstrated by transient, agroinfiltrated-mediated expression in *N. benthamiana*, which resulted in the production of betalains in high quantity, visible within two days post infiltration. Attempts for the stable transformation of pX11 into plants and their subsequent cultivation in tissue culture, resulted in pigmentation of explants and the formation of red-violet calli and shoots in a variety of plant species within several days, demonstrating the potential use of betalains as visible genetic transformation markers. Stable transformation of tobacco plants with pX11 ultimately led to the generation of fully pigmented mature plants. LC-MS analysis of the betalain producing tobacco plants confirmed the occurrence of betanin as the major betalain produced.

The findings in this study therefore open the way for heterologous production of betalains in additional plant species, potentially resulting in the development of nutritionally enhanced food crops as well as new varieties of ornamentals. Apart from engineering red-pigmented betacyanin-producing plants, betalain production could principally be modified to be limited to betaxanthins by expressing CYP76AD6 instead of CYP76AD1, as exemplified by the transient expression experiments in *N. benthamiana*. Engineering of plants which exhibit both red and yellow pigmentation might also hypothetically be achieved by expressing both cytochrome P450s under different, non-constitutive promoter sequences (e.g. fruit-specific, flower-specific or inducible promoters). The engineered betalain producing plants will also serve as an exceptional genetic resource to examine the pigment-based attraction of pollinators to flowers and frugivores to fruit, as well as the role of pigments in assisting plant organs to resist abiotic and biotic cues.

Example 10

Materials and Methods (2)

Generation of DNA Constructs

Gene sequences used in this study; cDOPA5GT (GenBank accession AB182643.1), BvDODA1 (accession HQ656027.1), CYP76AD1 (HQ656023.1). CYP76AD6 (KT962274), AroG175 (JC233128.1), AAH (HQ003815.1). CYP76AD15 sequence is provided herein. *M. jalapa* cDOPA5GT, CYP76AD15 and *B. vulgaris* CYP76AD1, BvDODA1, and CYP76AD6 transcripts were amplified from *M. jalapa* red petal and *B. vulgaris* red hypocotyl cDNA libraries. DNA constructs used for *N. benthamiana* agroinfiltration and for agrobacteria-mediated plant transformation were constructed with Goldenbraid cloning (Sarrion-Perdigones et al., 2013; GoldenBraid 2.0: A Comprehensive DNA Assembly Framework for Plant Synthetic Biology. Plant Physiology 162: 1618-1631). BvDODA1, CYP76AD1, CYP76AD6, CYP76AD15, cDOPA5GL AroG175 and AAH were initially cloned into a pUPD vector. pX11, pX11(E8), pX11(CHS), pX13, pDOPA3 and pDOPA4 are 3αα1 vectors. pX12, pDOPA1 and pDOPA2 are 3Ω1 vectors. All vectors are based on a pCAMBIA backbone (Roberts et al., 1997; A Comprehensive Set of Modular Vectors for Advanced Manipulations and Efficient Transformation of Plants. In pCAMBIA Vector Release Manual Rockefeller Foundation Meeting of the International Program on Rice Biotechnology, September 15-19, Malacca, Malaysia).

Plant Transformation and Regeneration

Agrobacteria-mediated plant transformation and regeneration was done according to the following methods; tobacco leaf discs (Horsch et al., 1985; Science 227: 1229-1231), eggplant (Van Eck and Snyder, 2006; Eggplant (*Solanum melongena* L.). In K Wang, ed, *Agrobacterium* Protocols. Springer, pp 439-448), tomato (McCormick, 1997; Transformation of tomato with *Agrobacterium tumefaciens*. In K Lindsey, ed, Plant tissue culture manual.

Springer, pp 311-319), potato (Perl et al., 1992; Plant Molecular Biology 19: 815-823), and Petunia (Conner et al., 2009; Transformation and regeneration of Petunia. In T Gerats, J Strommer, eds, Petunia. Springer, pp 395-409). Transformation and cultivation of BY2 was done according to An, 1985 (Plant Physiology 79: 568-570). All plant species were transformed using agrobacteria GV3101 strain. Plant tissue culture was carried out in a climate rooms (22° C.; 70% humidity; 16/8 hours of light/dark, 2500 Lux light intensity).

Transient Expression in *Nicotiana benthamiana*

Transient gene expression assays in *N. benthamiana* for the BvDODA1 and CYP76AD15 genes and subsequent sampling for LC-MS analysis were performed as described hereinabove.

Metabolite Extraction and Analysis

For LC-MS analyses, extraction of plant tissue from tomato fruit (flesh and peel), eggplant fruit (flesh), potato tuber (flesh), *N. tabacum* petals and *N. benthamiana* leaf was performed as previously described (Polturak et al., 2016). For extraction of BY2 cells, calli sampled from petri dishes (approx. 500 mg) were lysed by two freeze-thaw cycles with liquid nitrogen followed by disruption with metal beads. Cell-extract was centrifuged to remove cell debris and supernatant collected and filtered through 0.22 μm PVDF filters (Millipore) before analysis. LC-MS Analysis of L-DOPA and betalains was performed as previously described (Polturak et al., 2016). Relative quantification of L-DOPA in BY2 cells was determined by peak area, based on transition 198->152.

Seed Germination Assays

Seeds of pX11 and wildtype (WT) tobacco plants were sown on petri dishes containing full Murashige-Skoog (MS) media (4.4 gr/liter) and 1% agar. For stress condition assays, the MS media additionally contained either 150 mM NaCl or 400 mM mannitol. Seeds were sown in three petri dishes, each containing 50 seeds per genotype. Sealed plates were kept in dark for 1 week and then moved to climate rooms (22° C.; 70% humidity; 16/8 hours of light/dark, 2500 Lux light intensity). Seed germination rates were examined for a period of 26 days.

Plant Material and Growth Conditions

*Mirabilis jalapa, N. tabacum, S. tuberosum, S. melongena* and *S. lycopersicum* plants were soil-grown in a greenhouse with long-day light conditions (25° C.). *Beta vulgaris* and *Nicotiana benthamiana* plants were soil-grown in climate rooms (22° C.; 70% humidity; 18/6 hours of light/dark).

Example 11 pX11 Expression in Tomato, Potato and Eggplant Results in Red-Pigmented Plants

Figure 14A:
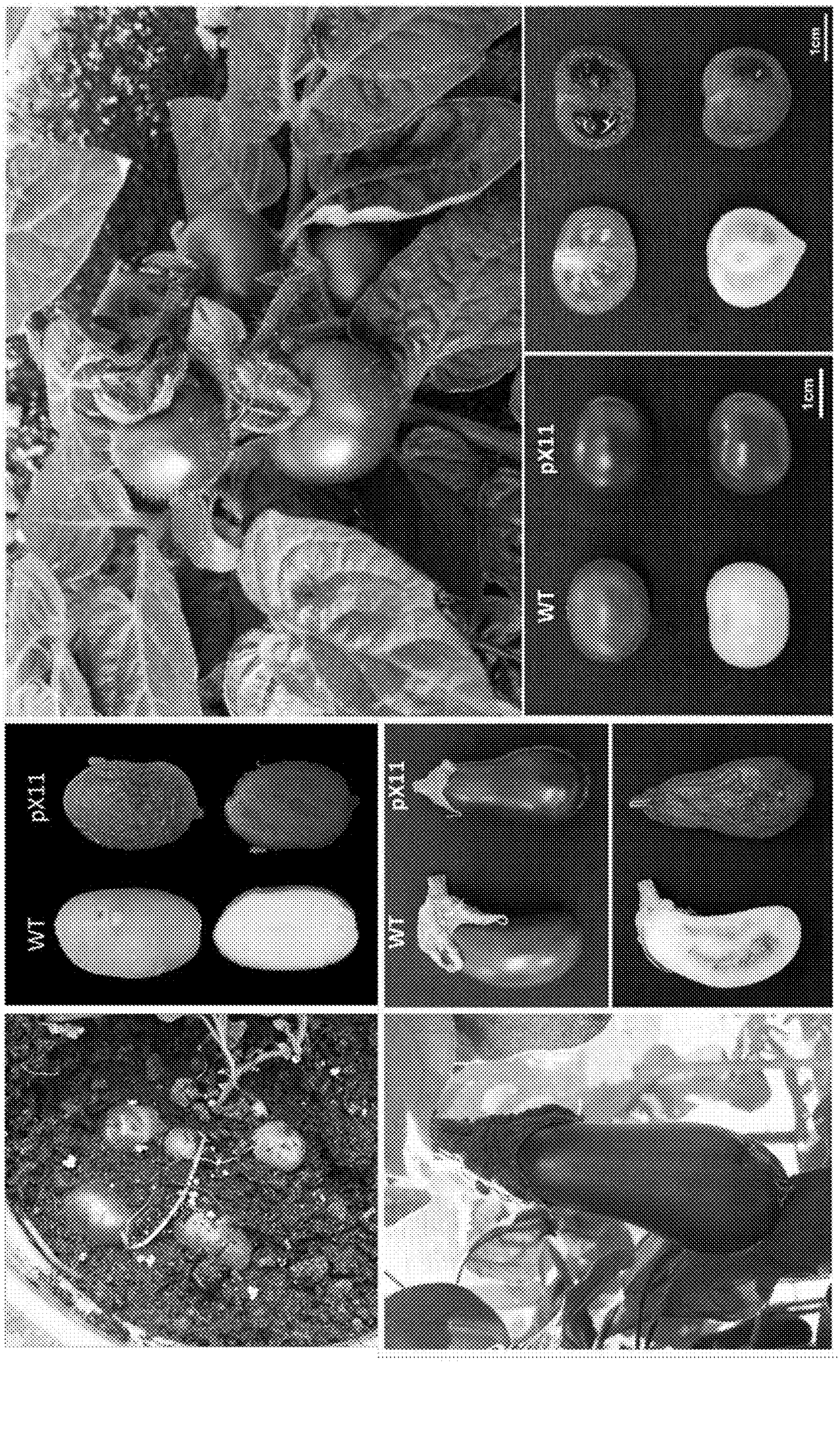
FIGS. 14A-14B. Betalain production in food crops tomato, potato and eggplant.
Figure 14B:
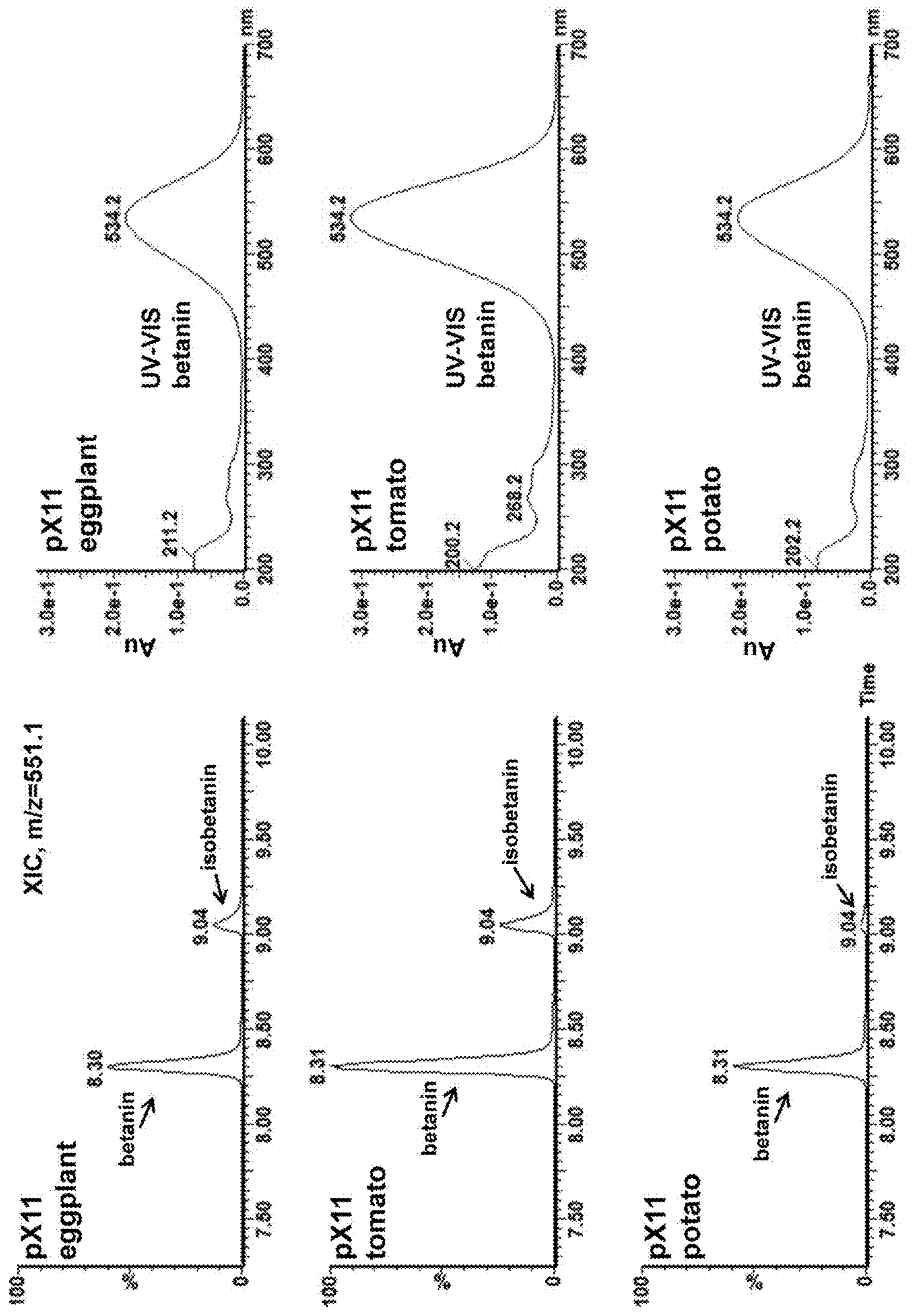

To inspect the feasibility of heterologous betalain production in food crops, the pX11 vector was introduced into tomato (*Solanum lycopersicum* var. MicroTom), potato (*Solanum tuberosum* var. Desiree) and eggplant (*Solanum melongena* line DR2) via agrobacteria-mediated stable transformation. Signs of red-violet pigmentation in transformed explants of all three species were observed within several days after co-cultivation with agrobacteria. As previously observed with pX11-expressing tobacco plants, transformed explants eventually evolved into entirely red-pigmented plants. Tomato and eggplant fruits, as well as potato tubers exhibited strong red-violet coloration (FIG. 14). LC-MS analysis of tomato fruit, eggplant fruit and potato tubers verified the occurrence of betalains, with betanin and isobetanin identified as the major occurring betacyanins (FIG. 14).

Example 12

Fruit-Specific Accumulation of Betalains in Tomato Plants

In all pX11-expressing plant species, betalain accumulation was visible in virtually all plant tissues and organs, owing to the constitutively-expressing promoter sequences used for gene expression, namely CaMV 35S for the BvDODA1 and CYP76AD1 genes, and the *Arabidopsis* Ubiquitin-10 promoter for cDOPA5GT. We initially hypothesized that constitutive production of nitrogen-containing compounds may lead to a significant metabolic burden on the transgenic plants. We therefore constructed a binary vector to be expressed in tomato, which would result in the restriction of pigment accumulation to ripening and ripe fruit. To this end, pX11 was modified to have CYP76AD1 driven by the fruit specific E8 promoter instead of CaMV 35S (FIG. 15). Transformation of the pX11(E8) vector to tomato var. M-82 indeed resulted in generation of plants which have betalain-pigmentation limited to ripe fruit (FIG. 16) albeit with lower betalain concentration than fruit of the pX11-expressing MicroTom tomatoes. Notably, pX11-expressing tomato, potato and eggplant plants did not eventually exhibit any apparent developmental phenotype or growth retardation.

Example 13

Flower-Specific Accumulation of Betalains in Petunias

In a similar approach, an additional version of the pX11 vector was constructed, in which CYP76AD1 is driven by the flower-specific *Petunia* x *hybrida* CHALCONE SYNTHASE (CHS) promoter instead of CaMV 35S (FIG. 15). Transformation of pX11(CHS) into *Petunia* x *hybrida* plants is expected to result in generation of plants that accumulate betalains only in petals, during flower maturation.

Example 14

Figure 17A:
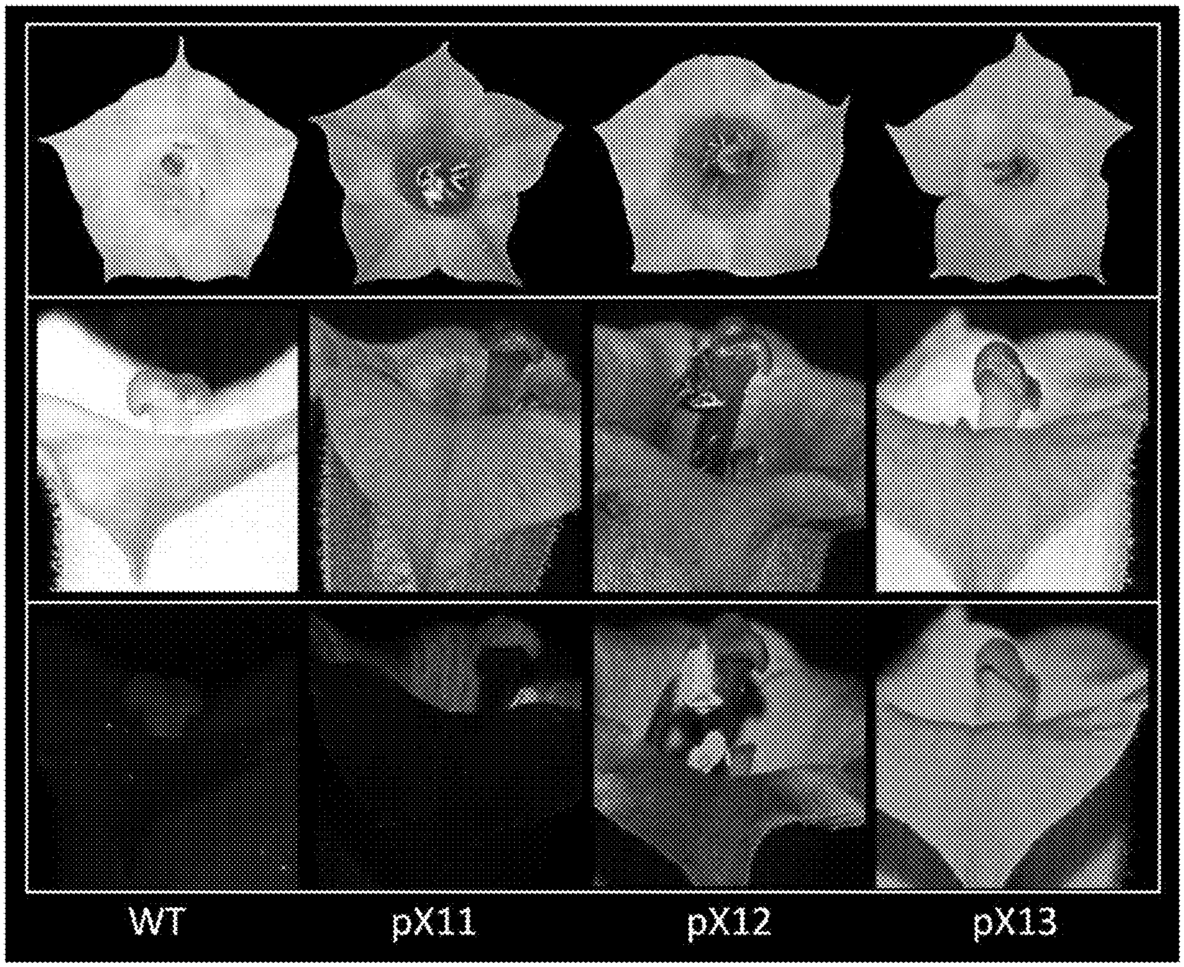
FIGS. 17A-17B. Color variation in flowers of transgenic betalain-producing tobacco is determined by varying betacyanin/betaxanthin ratios.
Figure 17B:
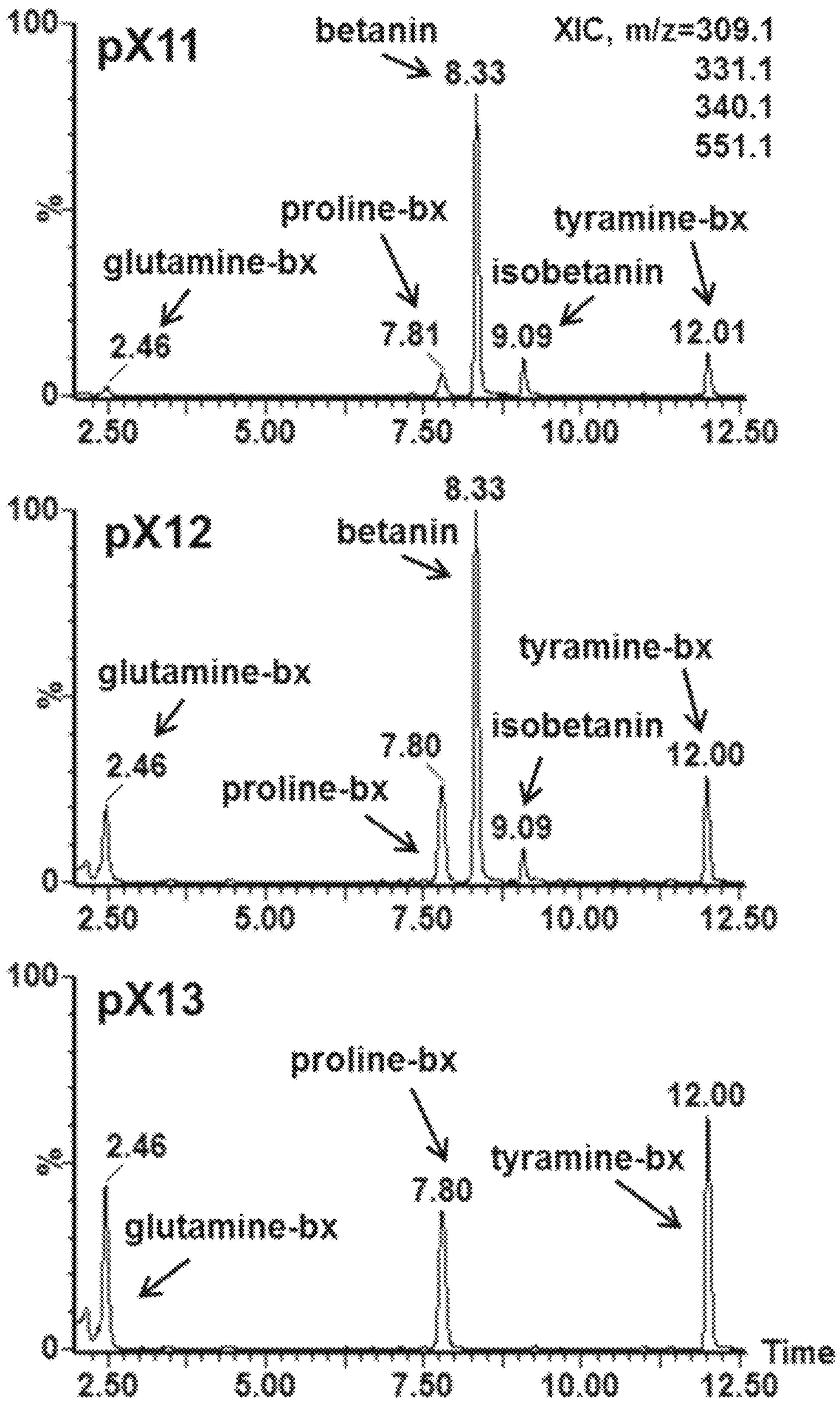

Expression of pX11, pX12 and pX13 in Tobacco Results in Differently-Colored Flowers pX11-expressing plants displayed a predominantly red-violet color due to the accumulation of high amounts of betacyanins versus betaxanthins. pX11 incorporates the expression of CYP76AD1 that encodes an enzyme with dual-activity in betalain biosynthesis, catalyzing both hydroxylation of tyrosine to L-DOPA and conversion of L-DOPA to cyclo-DOPA. As described hereinabove and in Polturak et al. 2016 (New Phytol. 2016 April; 210(1):269-83, which is incorporated herein by reference in its entirety), a related enzyme in red beet, CYP76AD6, uniquely exhibits tyrosine 3-hydroxylation activity, to form L-DOPA. Since cyclo-DOPA derivatives are required for the formation of betacyanins, in-planta expression of CYP76AD6 instead of CYP76AD1 results in the formation of betaxanthins but not betacyanins, as was previously observed by transient expression in *Nicotiana benthamiana*. To explore the possibility of generating transgenic plants that accumulate only betaxanthin-type betalains, a binary vector was constructed for expression of BvDODA1 and CYP76AD6, hereinafter named pX13. An additional vector, pX12, was designed for expression of both cytochrome P450 genes CYP76AD1 and CYP76AD6, alongside BvDODA1 and cDOPA5GT (FIG. 15). pX12 and pX13 were next introduced into tobacco by stable transformation. While pX13-expressing tobacco plants produced only betaxanthins, resulting in formation of yellow-pigmented flowers, expression of pX12 in tobacco plants generated plants with flowers of an orange-pink hue (FIG. 17). LC-MS analysis of petals from pX11, pX12 and pX13 plants verified that the different colors observed in flowers of the three lines are the result of varying betacyanin/betaxanthin ratios; pX11 flower extracts predominantly contained betacyanins, pX13 extracts contained betaxanthins only, while pX12 extracts contained both groups of betalains, with a lower betacyanin/betaxanthin ratio than pX11 (FIG. 17). Differences in betaxanthin versus betacyanin accumulation could also be observed by blue light imaging, under which betaxanthins have a typical strong fluorescence (Gandia-Herrero et al., 2005). Thus, the flux towards biosynthesis of red-violet betacyanins or yellow betaxanthins can be manipulated via expression of CYP76AD1, CYP76AD6 or a combination of both.

Example 15 pX11 and pX13 Expression in BY2 Cells

Biotechnological production of betalain pigments may provide new viable sources for their use as natural colorants for food, pharma and cosmetics industries. To date, most research has mainly been focused on development of *Beta vulgaris* hairy root culture or cell culture for betalain production.

Genetic engineering for heterologous betalain production enables the development of numerous new sources for these pigments. One viable source may be the culture of well-studied plant cell lines such as the tobacco BY2 or *Arabidopsis* T87 lines. A previously reported attempt to use these lines for betalain production involved the expression of the *Mirabilis jalapa* DOD gene MjDOD together with a Shiitake mushroom tyrosinase gene. Production of betaxanthins in BY2 and T87 cells was demonstrated. However, within several weeks the cultured cells turned brown and stunted, most likely due to the toxic accumulation of dopaquinone and its derivatives, as a result of activity of the exogenous tyrosinase (Nakatsuka et al., 2013).

Figure 18A:
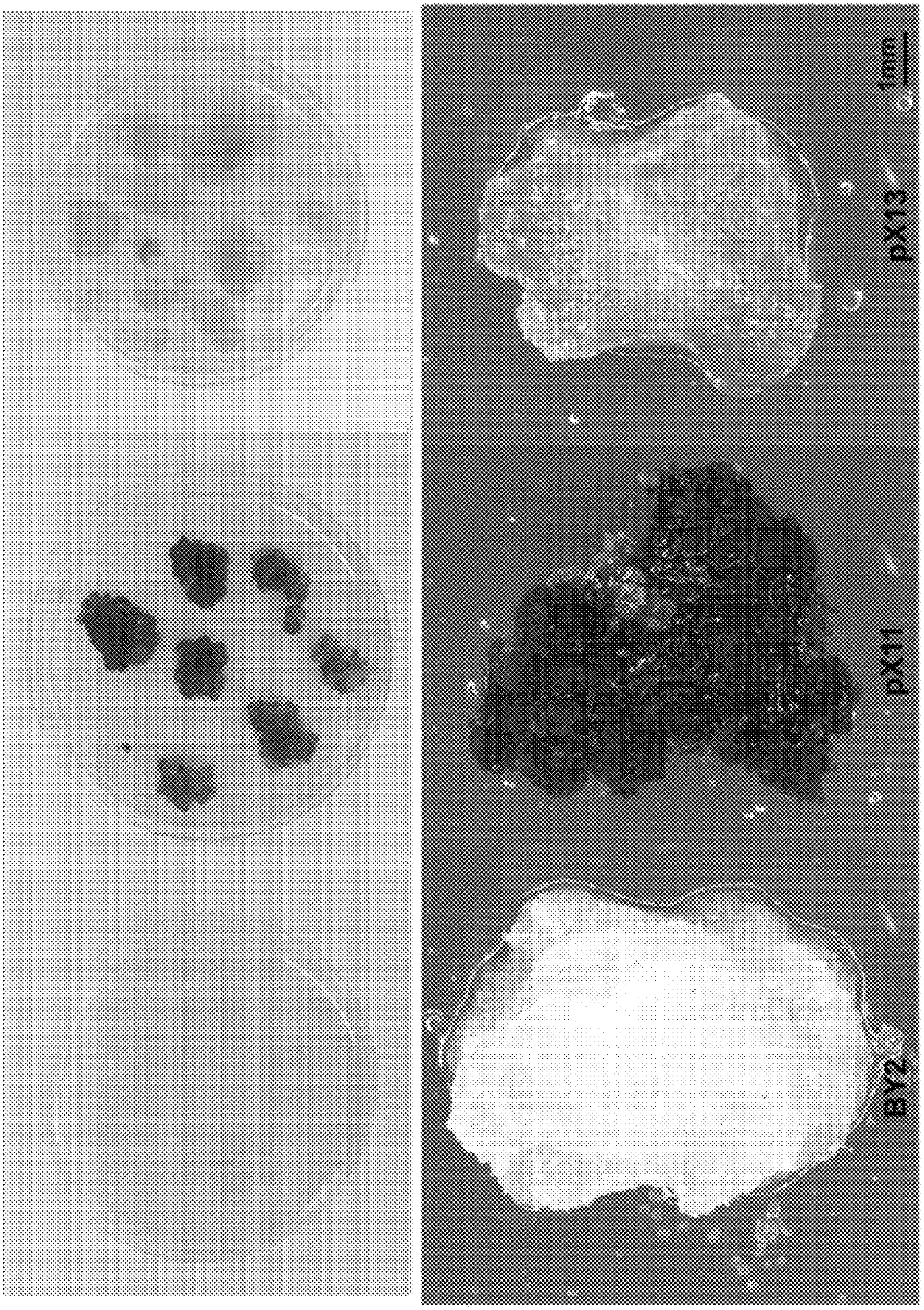
FIGS. 18A-18B. Production of betalains in tobacco BY2 cells.
Figure 18B:
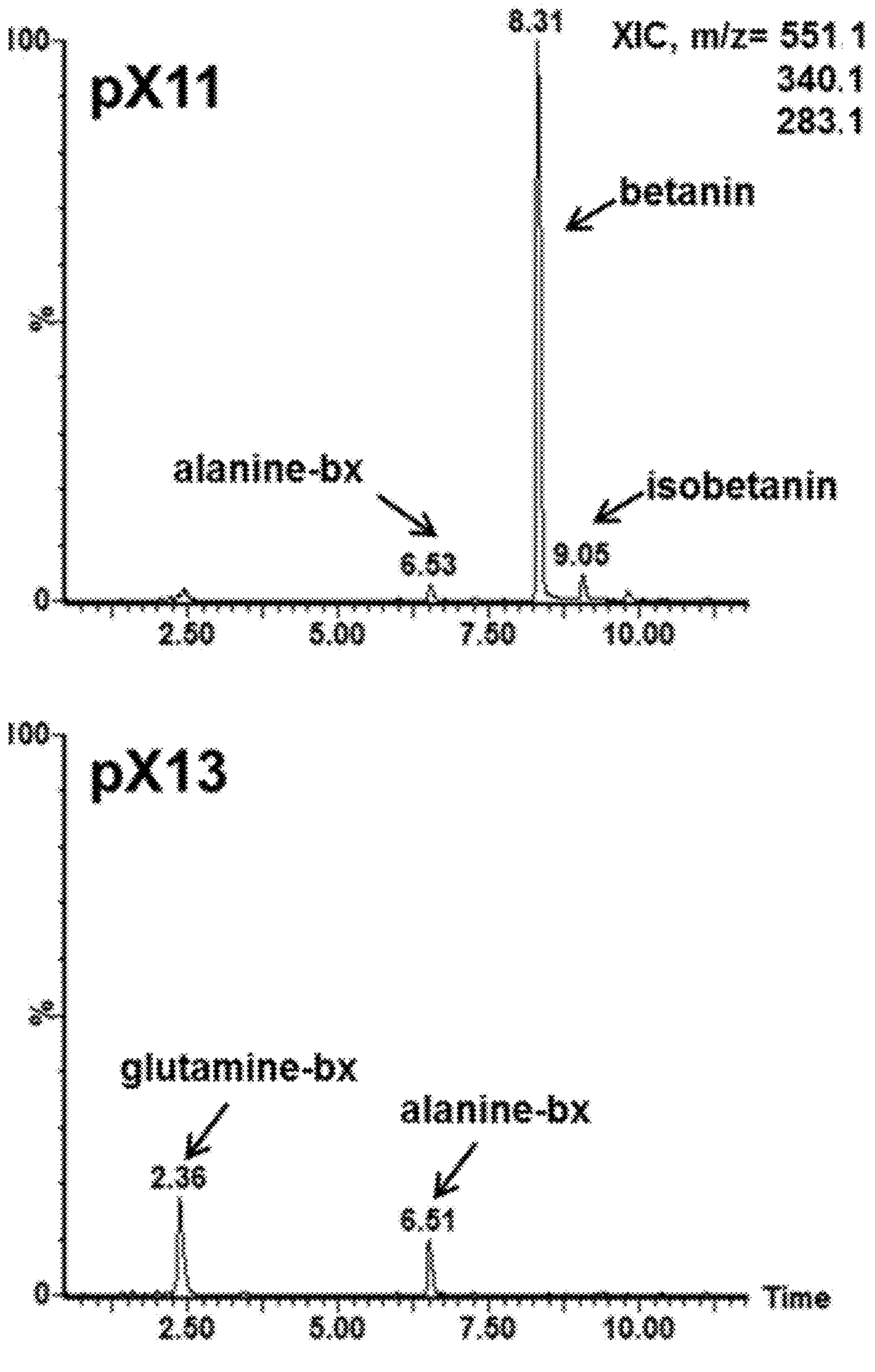

To explore the potential use of plant cell culture for betalain production through expression of betalain-related genes only, we expressed the pX11 and pX13 vectors in tobacco cell line BY2, resulting in generation of red-violet or yellow cells, respectively (FIG. 18). LC-MS analysis of cell extract of the pX11-expressing cells showed betanin and iso-betanin as the major betacyanins. Several betaxanthins were identified in both pX11 and pX13 cell lines, including glutamine-betaxanthin and alanine-betaxanthin (FIG. 18). Notably, pX11 and pX13 cell lines did not exhibit signs of browning or stunted growth as was previously reported for tyrosinase expressing calli (Nakatsuka et al., 2013).

Example 16

L-DOPA Production in Tobacco and BY2 Cells by Expression of CYP76AD6

Figure 20A:
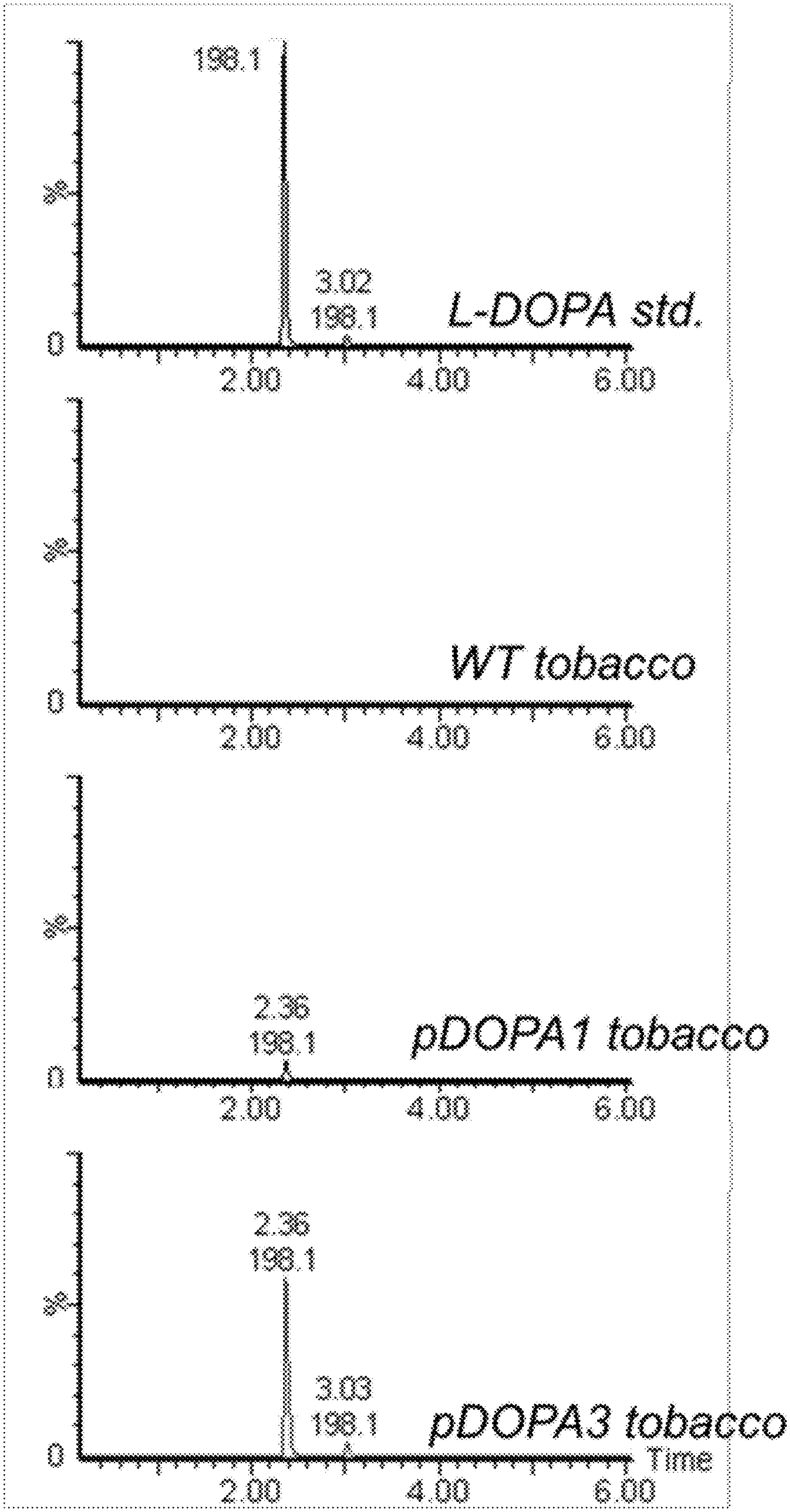
FIGS. 20A-20C. Production of L-DOPA in tobacco plants and BY2 cells.
Figure 20B:
Figure 20C:
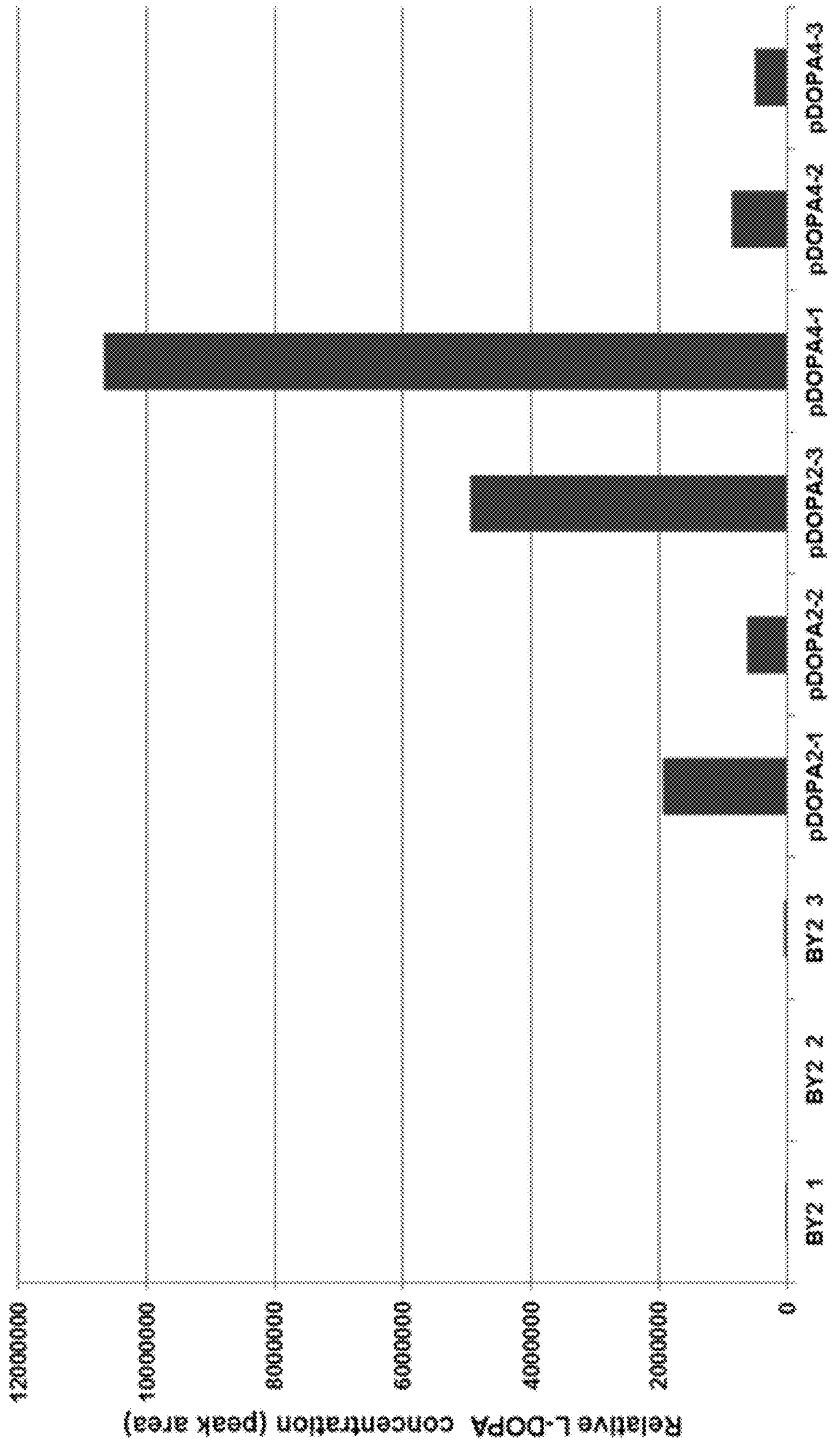
Figure 21A:
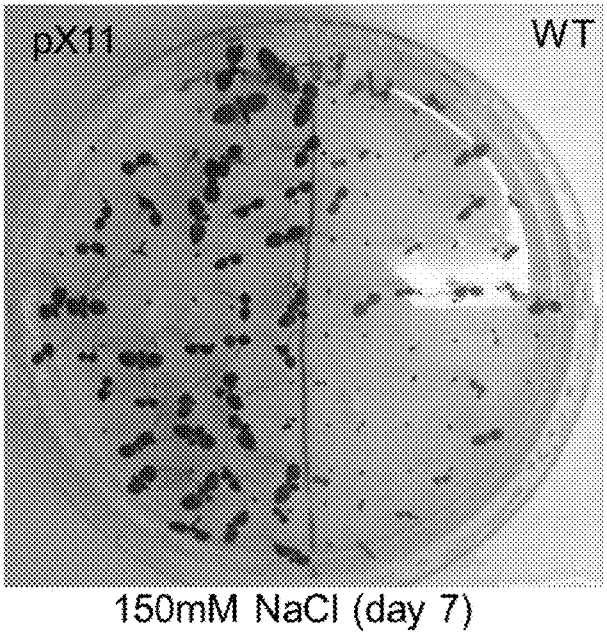
FIGS. 21A-21B. Seed germination assays of betalain-producing tobacco under osmotic and salinity stress conditions.
Figure 21A:
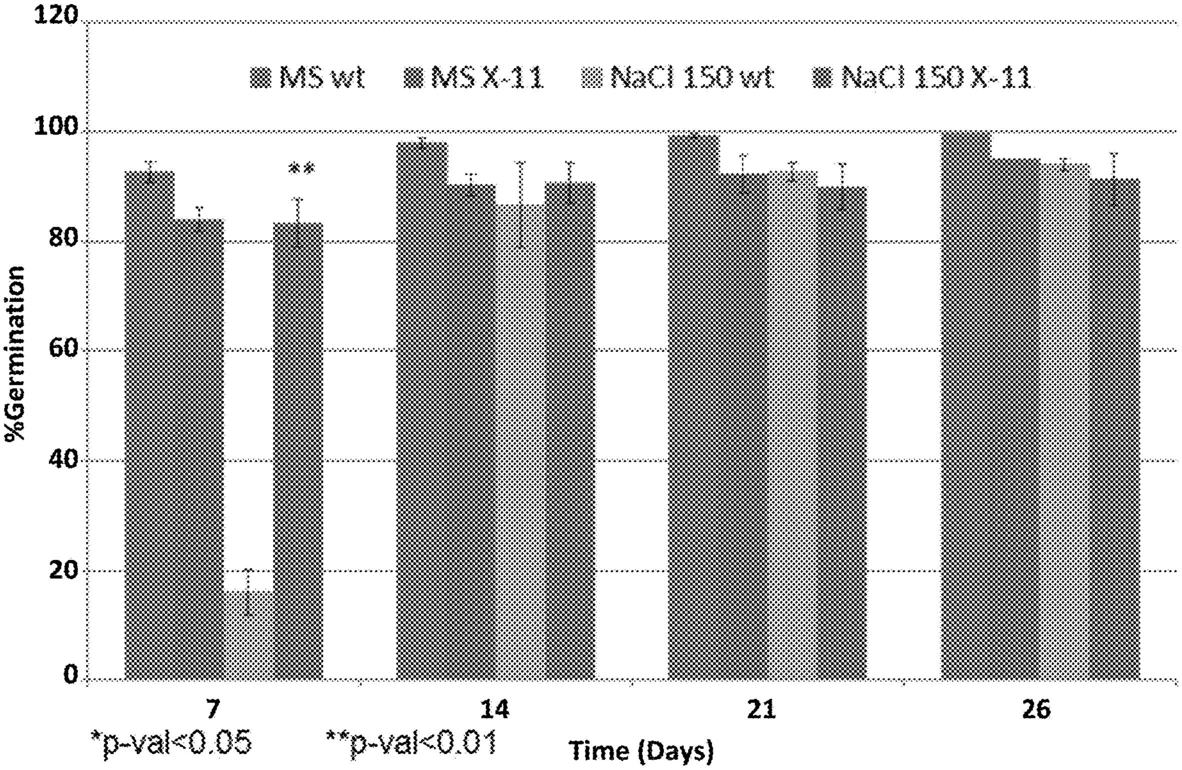
Figure 21B:
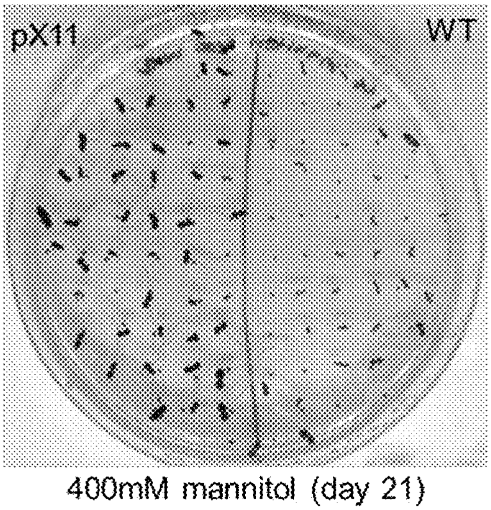
Figure 21B:
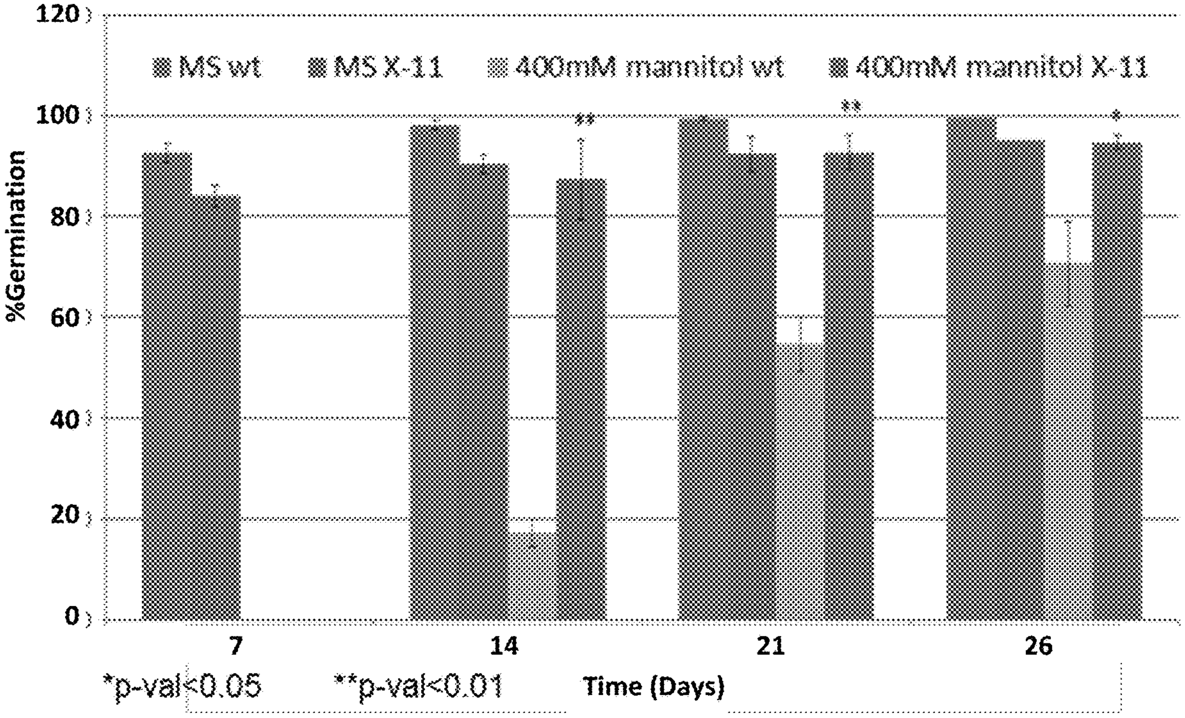

L-DOPA is an economically important compound that has been used for treatment of Parkinson's disease and is a precursor of high-value metabolites, including among others catecholeamines, benzilisoquinoline alkaloids and betalains. Current methods for industrial-scale production of L-DOPA show critical limitations. The tyrosine 3-hydroxylase activity of the CYP76AD6 enzyme may be implemented for production of L-DOPA that is advantageous compared to current production methods, by which L-DOPA would be directly formed from tyrosine. We explored the implementation of CYP76AD6 for L-DOPA production via expression in tobacco plants and in tobacco cell line BY2. To this end, four different vectors for expression of CYP76AD6 were constructed (FIG. 19); in one vector, CYP76AD6 is driven by the CaMV 35S promoter (hereinafter named pDOPA1). In another vector, pDOPA2, CYP76AD6 is driven by the *Solanum lycopersicum* ubiquitin 10 promoter (SlUb10). In vector pDOPA3, CYP76AD6 under 35S promoter is expressed together with two additional genes, AroG175 (Tzin et al., 2012) and aromatic amino acid hydroxylase (AAH) (Pribat et al., 2010), both of which are used in means of increasing tyrosine availability. In vector pDOPA4, CYP76AD6 under SlUb10 promoter is expressed together with AroG175 and AAH. All four vectors additionally express the neomycin phosphotransferase II (nptII) gene to confer kanamycin resistance for transformant selection. pDOPA1, pDOPA2, pDOPA3 and pDOPA4 were introduced into tobacco plants by agrobacteria-mediated stable transformation. LC-MS analysis of first generation (t0) plants confirmed that L-DOPA is produced in lines expressing the four different vectors. Analysis of pDOPA1 and pDOPA3 tobacco plants is presented in FIG. 20. The four pDOPA vectors were also introduced into BY2 cells lines. BY2 cells expressing pDOPA2 or pDOPA4 vectors exhibited varying degrees of gray to black pigmentation after several weeks of cultivation, likely due to formation of L-DOPA derivatives, possibly resulting from enzymatic or non-enzymatic oxidation of L-DOPA. LC-MS analysis of extracts obtained from pDOPA2 and pDOPA4-expressing calli showed occurrence of L-DOPA in varying concentrations (FIG. 20).

Example 17

Betalains Confer Plant Resistance to High Osmotic and High Salinity Stress Conditions Considering the suggested roles of betalains in conferring resistance in plants to various abiotic stress factors such as drought, high salinity and excess light, enabling production of betalains in naturally non-producing plants may serve to increase their tolerance to abiotic stress factors. We therefore proceeded to examine this assumption via seed germination assays of betalain-producing tobacco plants. Seeds of pX11 and wildtype (WT) tobacco were placed on petri dishes containing Murashige-Skoog (MS) media supplemented with 400 mM mannitol or 150 mM NaCl, to mimic conditions of high osmotic stress or high salinity stress, respectively. Petri dishes containing MS media without additional supplementation were used as control. Germination rates of seeds sown on all plates were determined over a period of 26 days. While pX11 and WT tobacco seeds exhibited similar germination rates in the control MS media, pX11 seeds exhibited significantly higher germination versus WT seeds in plates containing 400 mM mannitol throughout the experiment time period. In plates containing 150 mM NaCl, pX11 seeds showed significantly higher germination rates after one week of incubation, but WT seeds obtained similar germination rates within two weeks and onwards (FIG. 21). Betalain-producing tobacco plants therefore exhibit increased tolerance to high osmotic and high salinity conditions compared with wildtype plants, having a higher germination rate in high osmotic stress conditions and faster germination in high salinity conditions.

Example 18

Figure 22A:
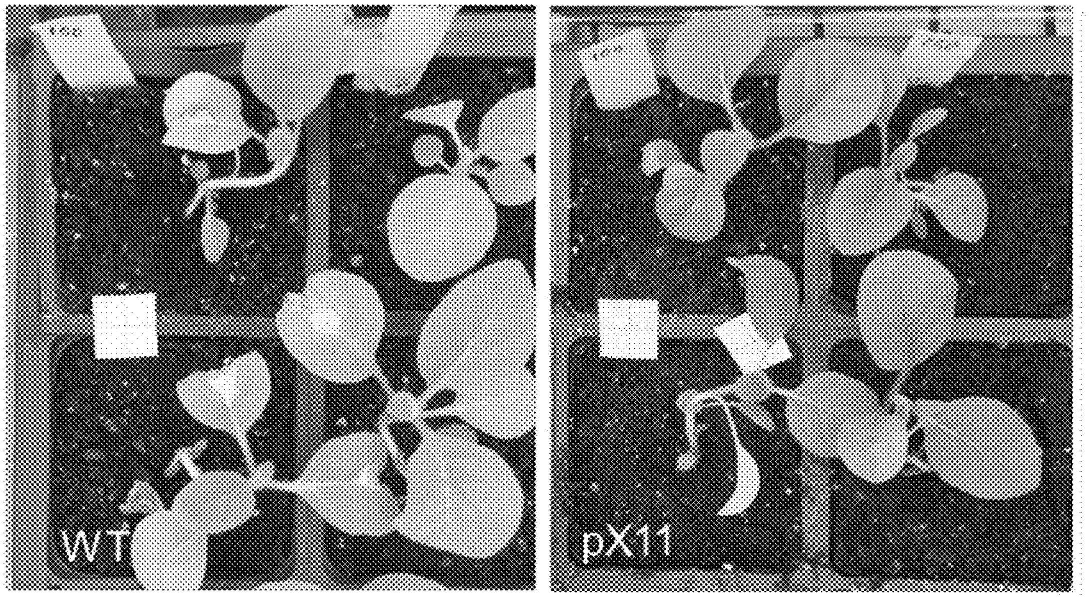
FIGS. 22A-22C. *Botrytis cinerea* resistance assays of betalain-producing tobacco plants.
Figure 22B:
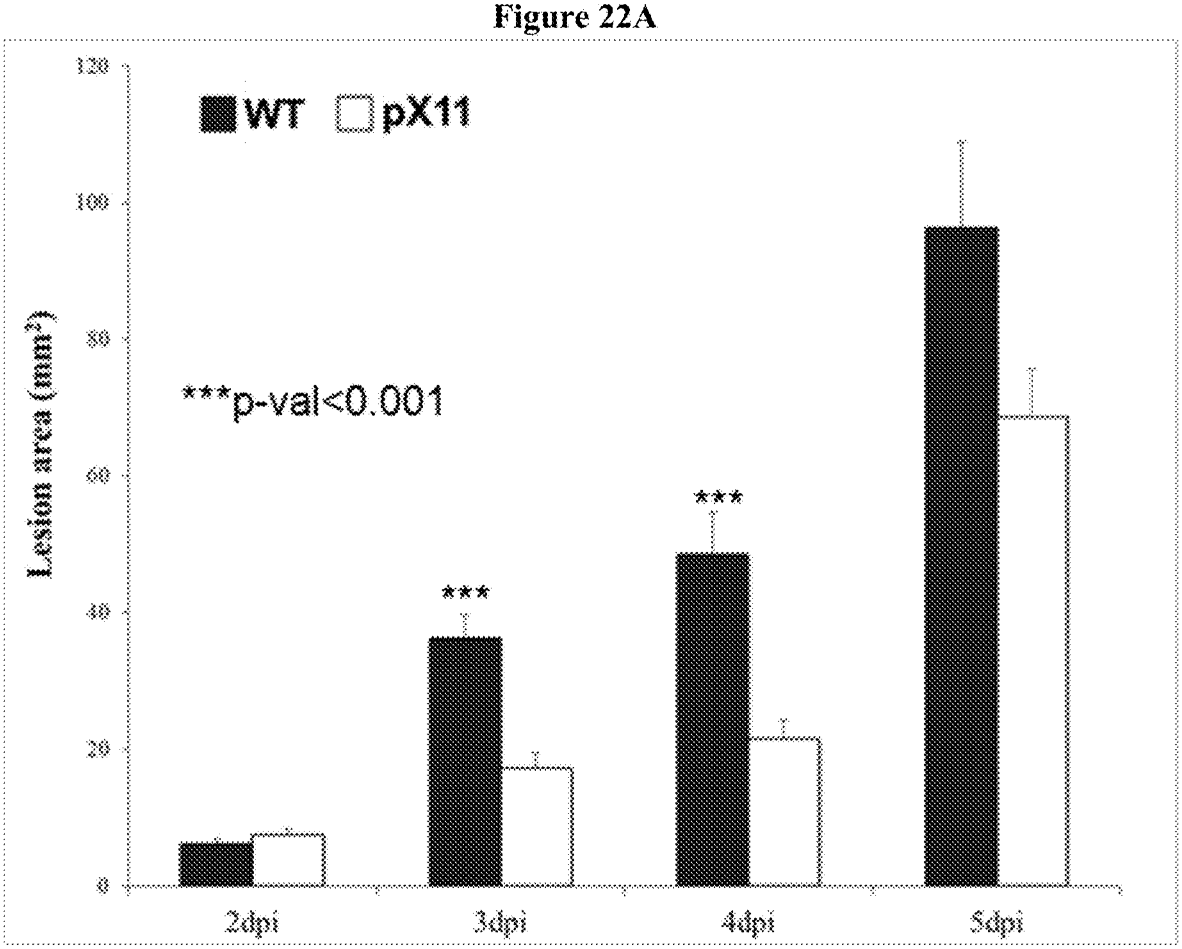
Figure 22C:
Figure 23A:
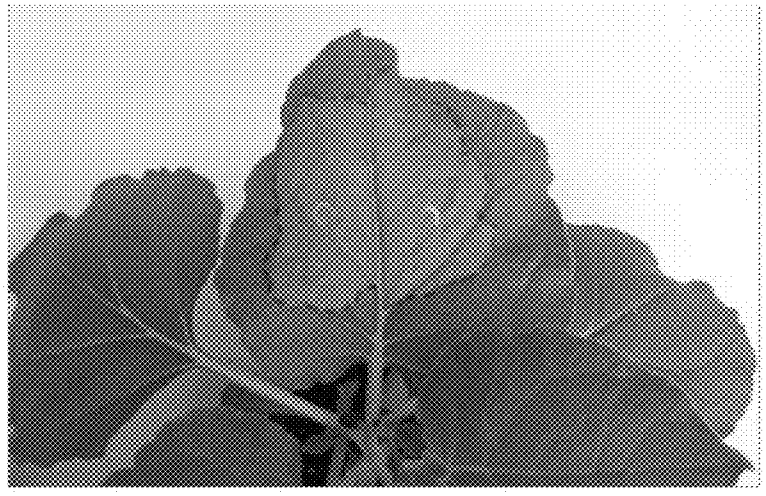
FIGS. 23A-23D. Recombinant expression of CYP76AD15 in *Nicotiana benthamiana* enables betaxanthin and L-DOPA production.
Figure 23B:
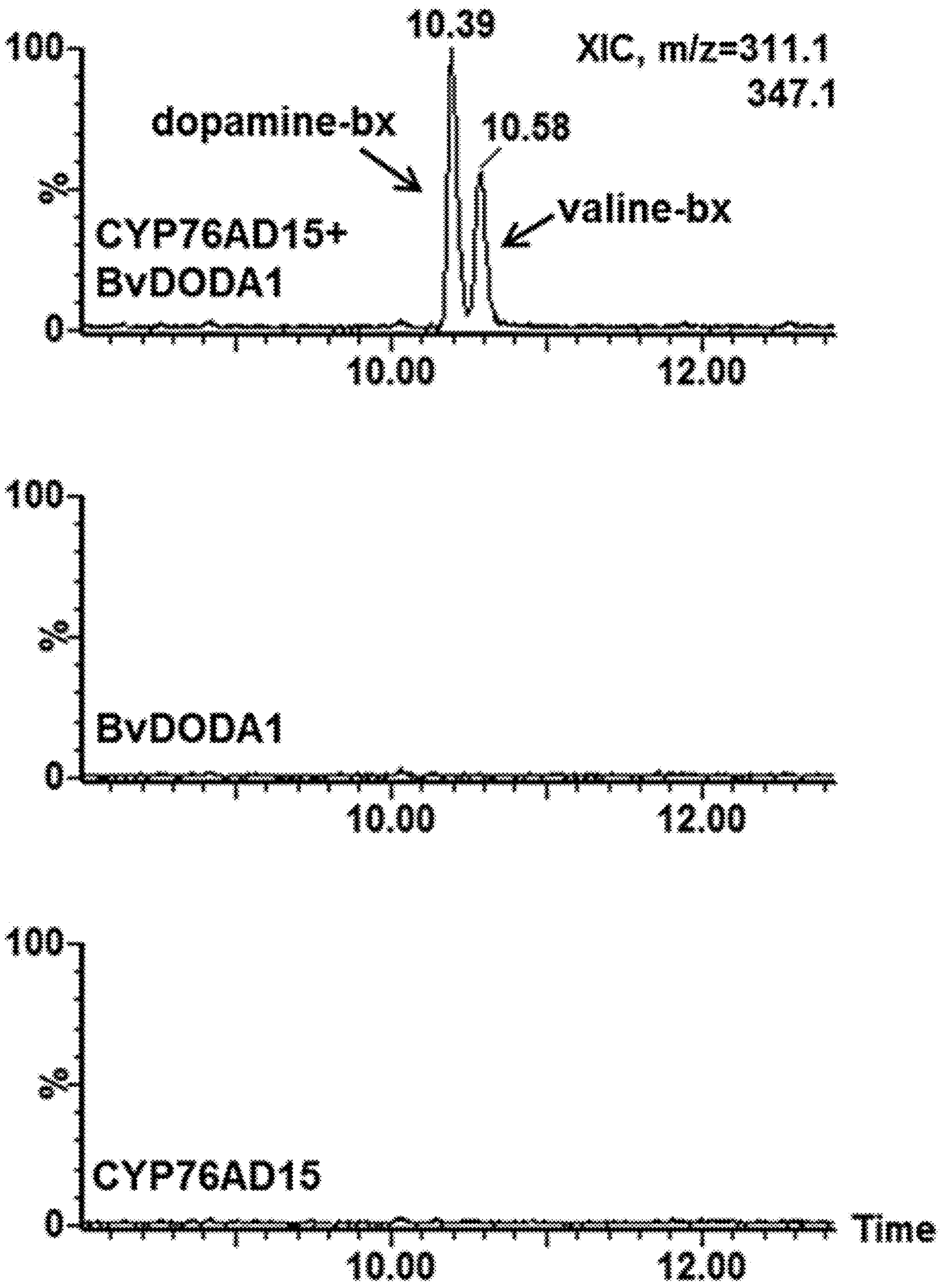
Figure 23C:
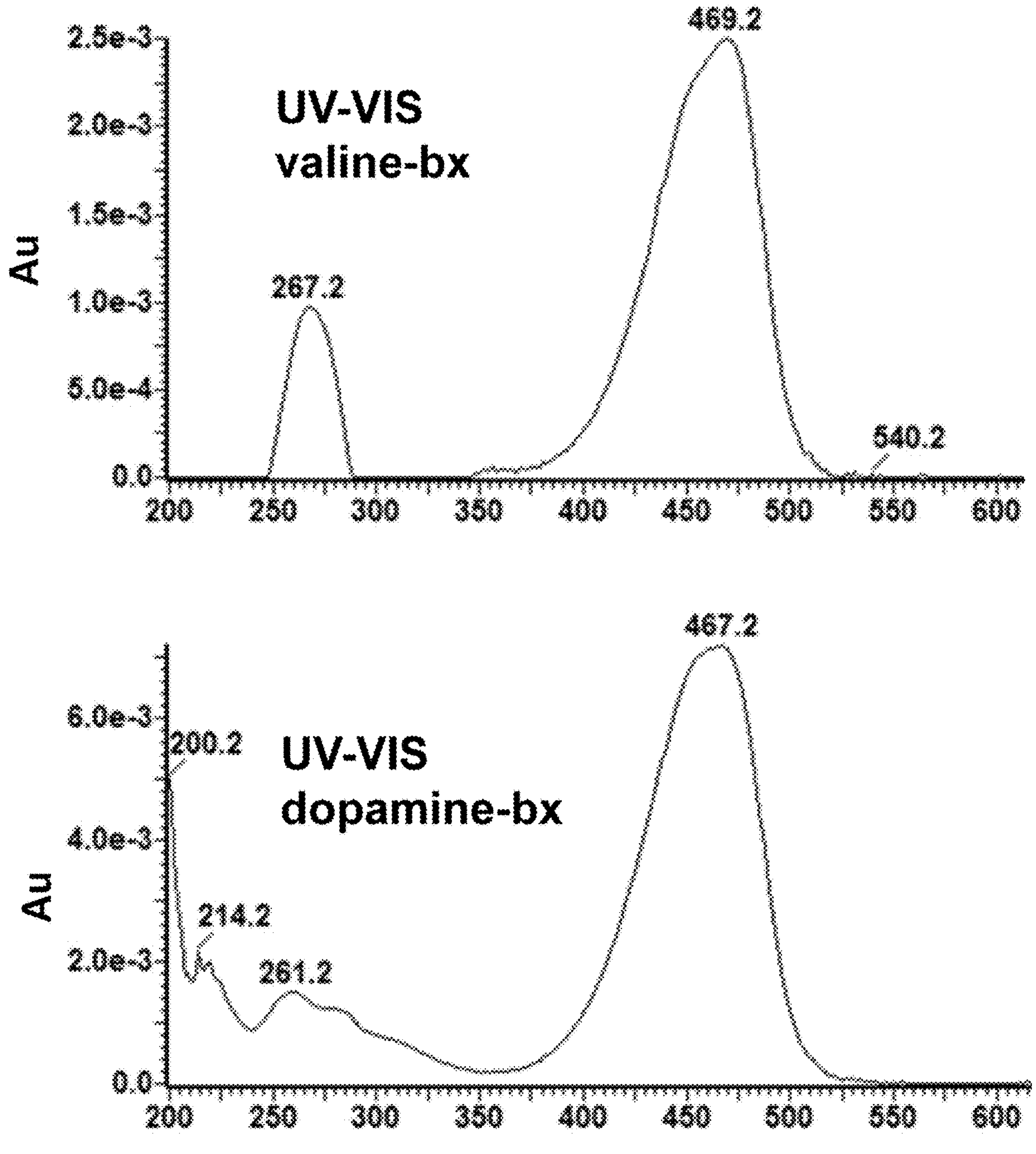
Figure 23D:
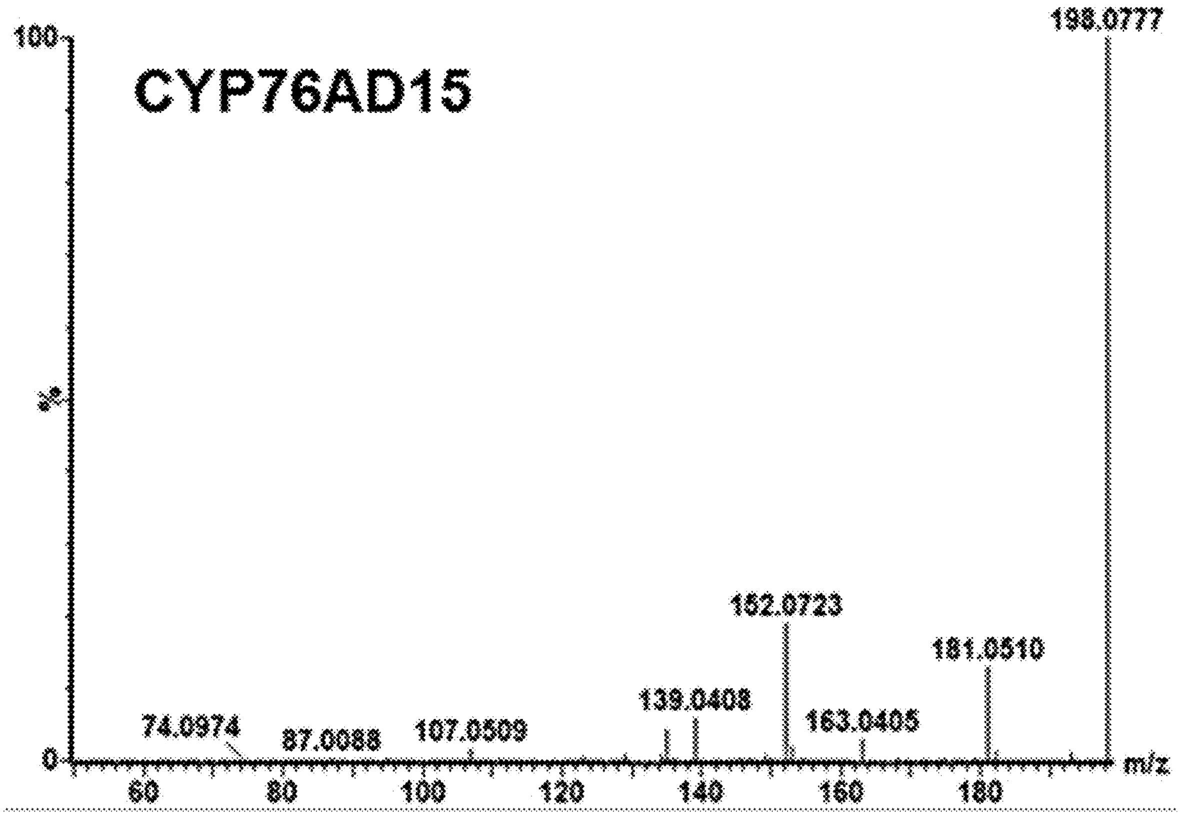

Betalains Confer Resistance to *Botrytis cinerea* Infection in Tobacco Leaves Betalains have previously been suggested to play a role in defense against pathogenic fungi, but evidence for antifungal activity of betalains in scientific literature is scarce. Heterologous betalain production in plants provides an excellent platform for studying antifungal activities of betalains in-planta, and may also be implemented for conferring resistance to phytopathogenic fungi in target crop species. To examine possible antifungal effects of betalains, wildtype and pX11 tobacco plants were subjected to leaf infection by gray mold fungus (*Botrytis cinerea*), a necrotrophic plant pathogen that is responsible for major losses in agricultural produce in both pre-harvest and post-harvest stages. Droplets of *B. cinerea* spore suspension in different concentration were applied on plant leaves, totaling approximately 100, 250 or 500 spores per plant. The degree of *B. cinerea* infection was then estimated by daily measurements of lesion size around the infection points. Leaves of pX11 tobacco exhibited significantly smaller lesion area upon infection compared to wildtype tobacco leaves (FIG. 22). Infected wildtype tobacco leaves also exhibited increased signs of necrosis compared to pX11 leaves within several days post infection (FIG. 22). Together, these results indicate increased resistance towards *B. cinerea* infection of betalain-producing plants.

Example 19

CYP76AD15 is a Functional Ortholog of CYP76AD6 in *Mirabilis jalapa*

Considering the natural occurrence of additional betalain-producing plant species that consist of red or yellow-colored varieties, it is plausible that these species have a molecular mechanism similar to the one observed in red beet, where one cytochrome P450 enzyme catalyzes only tyrosine hydroxylation, while another catalyzes both tyrosine hydroxylation and cyclo-DOPA formation. It is also possible that the functional orthologs of CYP76AD1 and CYP76AD6 are found in the CYP76AD1-α, and the CYP76AD1-β subclades, respectively. However, functional analyses of corresponding genes from additional betalain-producing species are needed to support this hypothesis.

Functional orthologs of CYP76AD1 have previously been identified in several plants, including *Mirabilis jalapa*, where CYP76AD3 was identified based on sequence similarity to CYP76AD1 (Hatlestad et al., 2012). However, CYP76AD6 orthologs were not previously described. In order to assess the occurrence of a CYP76AD6 ortholog in *M. jalapa*, a tBLASTx query was performed in a previously obtained *M. jalapa* transcriptome dataset (Polturak et al., 2016), using the CYP76AD1 nucleotide sequence. This search resulted in the identification of several interrelated genes, including one gene with the highest sequence similarity to CYP76AD6, hereinafter named CYP76AD15. Interestingly, according to the data obtained in the *M. jalapa* transcriptome analysis, CYP76AD15 does not exhibit an expression pattern that parallels betalain accumulation. Instead, a generally constitutive expression pattern was observed for this gene. CYP76AD15 activity was tested by agroinfiltration assays in *N. benthamiana*. Similarly to CYP76AD6, CYP76AD15 was found to allow betaxanthin production in *N. benthamiana* leaves when co-infiltrated with BvDODA1, and L-DOPA production when infiltrated alone (FIG. 23). Occurrence of several betaxanthins was verified by LC-MS analysis, including dopamine-betaxanthin and valine-betaxanthin that were identified based on typical absorption patterns and MS/MS fragmentation. CYP76AD15 was therefore identified as a functional ortholog of CYP76AD6, catalyzing the formation of L-DOPA from tyrosine. Sequence analysis indicates that CYP76AD15 belongs to the CYP76AD1-β subclade together with CYP76AD6, while CYP76AD3 belongs in the CYP76AD1-α clade with CYP76AD1, thereby confirming the association of each of the subclades with a specific catalytic activity.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

The invention claimed is:

1. A method of producing betalains, comprising introducing into a cell a first heterologous polynucleotide that encodes a CYP76AD1-beta clade protein and a second heterologous polynucleotide that encodes a DOPA 4,5-dioxygenase (DOD) protein that converts L-DOPA to betalamic acid, wherein the first heterologous polynucleotide and the second heterologous polynucleotide are each under the control of a promoter active in the cell, wherein the cell is selected from a plant cell, a bacterial cell and a yeast cell, and wherein said CYP76AD1-beta clade protein is a protein with at least 85% sequence identity to at least one of: SEQ ID NO: 10, SEQ ID NO: 11, SEQ ID NO: 12, SEQ ID NO: 13, SEQ ID NO: 18 and SEQ ID NO: 44, and that converts tyrosine to L-DOPA and does not convert L-DOPA to cyclo-DOPA, thereby producing betalains.

2. The method of claim 1, wherein the CYP76AD1-beta clade protein is selected from the group consisting of: SEQ ID NO: 10, SEQ ID NO: 11, SEQ ID NO: 12, SEQ ID NO: 13, SEQ ID NO: 18 and SEQ ID NO: 44.

3. The method of claim 1, wherein the CYP76AD1-beta clade protein is a protein with at least 85% sequence identity to SEQ ID NO: 18, and that converts tyrosine to L-DOPA and does not convert L-DOPA to cyclo-DOPA.

4. The method of claim 1, wherein the DOD protein is SEQ ID NO: 42 or a protein with at least 90% sequence identity to SEQ ID NO: 42 and that converts L-DOPA to betalamic acid.

5. The method of claim 1, wherein the heterologous polynucleotide that encodes the DOD protein comprises a sequence selected from the group consisting of: SEQ ID NO: 3, SEQ ID NO: 33, SEQ ID NO: 39, SEQ ID NO: 40, SEQ ID NO: 41 and a sequence with at least 90% sequence identity to SEQ ID NO: 3, SEQ ID NO: 33, SEQ ID NO: 39, SEQ ID NO: 40, or SEQ ID NO: 41 and that encodes a protein that converts L-DOPA to betalamic acid.

6. The method of claim 1, wherein the betalains are betaxanthins.

7. The method of claim 6, wherein the DOD protein is SEQ ID NO: 42 or a protein with at least 90% sequence identity to SEQ ID NO: 42 and that converts L-DOPA to betalamic acid.

8. The method of claim 6, wherein the heterologous polynucleotide that encodes the DOD protein comprises a sequence selected from the group consisting of: SEQ ID NO: 3, SEQ ID NO: 33, SEQ ID NO: 39, SEQ ID NO: 40, SEQ ID NO: 41 and a sequence with at least 90% sequence identity to SEQ ID NO: 3, SEQ ID NO: 33, SEQ ID NO: 39, SEQ ID NO: 40, or SEQ ID NO: 41 and that encodes a protein that converts L-DOPA to betalamic acid.

9. The method of claim 1, wherein the betalains are betacyanins.

10. The method of claim 9, further comprising introducing into the cell a third heterologous polynucleotide that encodes a CYP76AD1-alpha clade protein, wherein the third heterologous polynucleotide is under the control of a heterologous promoter active in the cell, and wherein the CYP76AD1-alpha clade protein is SEQ ID NO: 14 or a protein with at least 90% sequence identity to SEQ ID NO: 14 and that converts L-DOPA to cyclo-DOPA.

11. The method of claim 1, wherein the betalains are a mix of betaxanthins and betacyanins.

12. The method of claim 11, further comprising introducing into the cell a third heterologous polynucleotide that encodes a CYP76AD1-alpha clade protein, wherein the third heterologous polynucleotide is under the control of a heterologous promoter active in the cell, and wherein the CYP76AD1-alpha clade protein is SEQ ID NO: 14 or a protein with at least 90% sequence identity to SEQ ID NO: 14 and that converts L-DOPA to cyclo-DOPA.

13. The method of claim 12, wherein the DOD protein is SEQ ID NO: 42 or a protein with at least 90% sequence identity to SEQ ID NO: 42 and that converts L-DOPA to betalamic acid.

14. The method of claim 12, wherein the heterologous polynucleotide that encodes a DOD protein comprises a sequence selected from the group consisting of: SEQ ID NO: 3, SEQ ID NO: 33, SEQ ID NO: 39, SEQ ID NO: 40, SEQ ID NO: 41 and a sequence with at least 90% sequence identity to SEQ ID NO: 3, SEQ ID NO: 33, SEQ ID NO: 39, SEQ ID NO: 40, or SEQ ID NO: 41 and that encodes a protein that converts L-DOPA to betalamic acid.

15. The method of claim 1, wherein the cell comprises tyrosine.

16. The method of claim 1, wherein the CYP76AD1-beta clade protein is a protein with at least 90% sequence identity to at least one of: SEQ ID NO: 10, SEQ ID NO: 11, SEQ ID NO: 12, SEQ ID NO: 13, SEQ ID NO: 18 and SEQ ID NO: 44, and that converts tyrosine to L-DOPA and does not convert L-DOPA to cyclo-DOPA.

17. The method of claim 16, wherein the CYP76AD1-beta clade protein is a protein with at least 90% sequence identity to SEQ ID NO: 18 or SEQ ID NO: 44, and that converts tyrosine to L-DOPA and does not convert L-DOPA to cyclo-DOPA.

18. The method of claim 17, wherein the CYP76AD1-beta clade protein is a protein with at least 90% sequence identity to SEQ ID NO: 18, and that converts tyrosine to L-DOPA and does not convert L-DOPA to cyclo-DOPA.

19. The method of claim 3, wherein the DOD protein is SEQ ID NO: 42 or a protein with at least 90% identity to SEQ ID NO: 42 and that converts L-DOPA to betalamic acid.

20. The method of claim 16, wherein the DOD protein is SEQ ID NO: 42 or a protein with at least 90% identity to SEQ ID NO: 42 and that converts L-DOPA to betalamic acid.

* * * * *